US012760047B2

(12) United States Patent
Pape et al.

(10) Patent No.: US 12,760,047 B2
(45) Date of Patent: Oct. 13, 2026

(54) PHOSPHORUS DERIVATIVES AS SOS1 INHIBITORS

(71) Applicant: BAYER AKTIENGESELLSCHAFT, Leverkusen (DE)

(72) Inventors: Felix Pape, Berlin (DE); Steffen Gressies, Berlin (DE); Timo Stellfeld, Berlin (DE); Jeremie Xavier G Mortier, Berlin (DE); Atanas Marinov Kamburov, Berlin (DE); Benjamin Bader, Berlin (DE); Keith Graham, Berlin (DE); Roman Hillig, Highton VIC (AU); Jens Schroder, Weimar (DE); Christoph Philipp Hethey, Berlin (DE); Matthias Arlt, Berlin (DE); Gerhard Siemeister, Berlin (DE); Katrin Nowak-Reppel, Berlin (DE); Michael Erkelenz, Berlin (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 332 days.

(21) Appl. No.: 18/286,809

(22) PCT Filed: Apr. 13, 2022

(86) PCT No.: PCT/EP2022/059857
§ 371 (c)(1),
(2) Date: Oct. 13, 2023

(87) PCT Pub. No.: WO2022/219035
PCT Pub. Date: Oct. 20, 2022

(65) Prior Publication Data

US 2024/0247015 A1 Jul. 25, 2024

(30) Foreign Application Priority Data

Apr. 14, 2021 (EP) .................................... 21168256

(51) Int. Cl.
*C07F 9/6584* (2006.01)
*A61K 31/675* (2006.01)
*A61P 35/00* (2006.01)
*C07F 9/6561* (2006.01)
*C07F 9/6568* (2006.01)

(52) U.S. Cl.
CPC .......... *C07F 9/6584* (2013.01); *A61K 31/675* (2013.01); *A61P 35/00* (2018.01); *C07F 9/6561* (2013.01); *C07F 9/65685* (2013.01)

(58) Field of Classification Search
None
See application file for complete search history.

(56) References Cited

U.S. PATENT DOCUMENTS

| | | | |
|---|---|---|---|
| 5,236,925 | A | 8/1993 | Primeau et al. |
| 2011/0054173 | A1 | 3/2011 | Brewster et al. |

FOREIGN PATENT DOCUMENTS

| | | |
|---|---|---|
| EP | 0326328 | 8/1989 |
| EP | 0326329 | 8/1989 |
| FR | 3066761 | 11/2018 |
| WO | WO93/007124 | 4/1993 |
| WO | WO2003/087098 | 10/2003 |
| WO | WO2004/058267 | 7/2004 |
| WO | WO2018/115380 | 6/2018 |
| WO | WO2018/134685 | 7/2018 |
| WO | WO2018/172250 | 9/2018 |
| WO | W2019/122129 | 6/2019 |
| WO | WO2020/180768 | 9/2020 |
| WO | WO2020/180770 | 9/2020 |
| WO | WO2021/074227 | 4/2021 |
| WO | WO2021/228028 | 11/2021 |
| WO | WO2022/058344 | 3/2022 |

OTHER PUBLICATIONS

Malumbres & Barbacid 2002 Nature Reviews Cancer, DOI doi:10.1038; Mar. 2019; 15 pgs.
Pylayeva-Gupta et al. 2011 Nature Reviews Cancer; Nov. 2011; 14 pgs.
D. Vigil, 2010 Nature Reviews Cancer, DOI: 10.1038; Dec. 2010; 16 pgs.
Rojas et al. 2011, Genes & Cancer 2(3) 298-305: DOI : 10.1177; 9 pgs.
Downward 2002 Nature Reviews Cancer; Jan. 2003; 12 pgs.
Krens et al. 2010 Drug Discovery Today Therapeutic modulation of K-ras signaling in colorectal cancer_DOI_10.1016; 2010; 15 pgs.
Cox et al. 2014 Nature Reviews Drug Discovery; Nov. 2014; 24 pgs.
Spiegel et al. 2014 Nature Chemical Biology, DOI 10.1038; Jun. 2014; 10 pgs.

(Continued)

*Primary Examiner* — Sarah Pihonak
*Assistant Examiner* — Donna M Nestor

(57) ABSTRACT

The present invention covers phosphorus derivatives of general formula (I), in which $R^1$, $R^2$, $R^3$, $R^4$, $R^5$, $R^6$, $X_1$, $X_2$, $X_3$, $X_4$ and Y are as defined herein, methods of preparing said compounds, intermediate compounds useful for preparing said compounds, pharmaceutical compositions and combinations comprising said compounds and the use of said compounds for manufacturing pharmaceutical compositions for the treatment or prophylaxis of diseases, in particular of hyperproliferative disorders, especially diseases associated with SOS1, as a sole agent or in combination with other active ingredients.

(I)

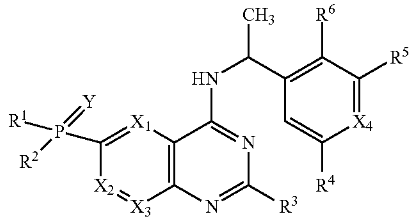

19 Claims, No Drawings

(56) References Cited

OTHER PUBLICATIONS

Hillig et al 2019 PNAS; Feb. 12, 2019; 10 pgs.
Gray et al 2019 Angewandte Chemie; 2019; 25 pgs.
Leshchiner et al. 2015 PNAS; Feb. 15, 2015; 6 pgs.
Hofmann et al., Cancer Discov 2021;11:142-5; Jan. 2021; 16 pgs.
Hillig RC, Bader B. Adv Cancer Res. 2022;153:169-203; 2022; 35 pgs.
Cromm 2015 Angewandte Chemie; 2015; 22 pgs.

PHOSPHORUS DERIVATIVES AS SOS1 INHIBITORS

This application is a U.S. national stage filing under 35 U.S.C. § 371 of International Application No. PCT/EP2022/059857, filed on Apr. 13, 2022, which claims the benefit of, and priority to, European Patent Application No. EP 21168256.2, filed Apr. 14, 2021. The entire disclosures of the above applications are incorporated herein by reference.

The present invention covers novel SOS1 inhibitors of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of hyperproliferative disorders, especially diseases associated with SOS1, as a sole agent or in combination with other active ingredients.

BACKGROUND

The present invention covers phosphorus derivatives of general formula (I)

(I)

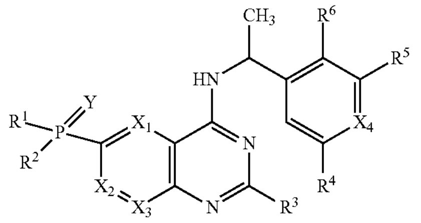

which inhibit the Ras-Sos1 interaction.

US 2011/0054173 A1 discloses certain 1- or 2-(4-(aryloxy)-phenyl)ethylamino-, oxy- or sulfanyl)pteridines and 1- or 2-(4-(heteroaryloxy)-phenyl)ethylamino-, oxy- or sulfanyl)pteridines and their use as agrochemicals and animal health products.

In the 2-position substituted quinazoline compounds are described e.g. in EP 0326328, EP 0326329, WO93/007124, WO2003/087098 and U.S. Pat. No. 5,236,925. These compounds are either not described as pharmaceutically active compounds or, if they are described as pharmacologically active compounds, they are described as compounds having affinity to the Epidermal Growth Factor Receptor (EGFR).

In the majority (45-100%) of patients receiving EGFR inhibitors skin toxicity is a class-specific side effect that is typically manifested as a papulopustular rash. The skin toxicity is related to the inhibition of EGFR in the skin, which is crucial for the normal development and physiology of the epidermis.

However, the state of the art does not describe:

- the phosphorus derivatives of general formula (I) of the present invention as described and defined herein, i.e. derivatives bearing a phosphorus-containing functional group and which effectively and selectively inhibit the Ras-Sos1 interaction.

Ras proteins play an important role in human cancer. Mutations in Ras proteins can be found in 20-30% of all human tumors and are recognized as tumorigenic drivers especially in lung, colorectal and pancreatic cancers (*Malumbres & Barbacid* 2002 *Nature Reviews Cancer*, Pylayeva-Gupta et al. 2011 *Nature Reviews Cancer*). Three human Ras genes are known that encode four different Ras proteins of 21 kDa size: H-Ras, N-Ras, and two splice variants of K-Ras, namely K-Ras 4A and K-Ras-4B. All Ras isoforms are highly conserved within the GTP-binding domain and differ mainly in the hypervariable C-terminal region. The C-termini of the different Ras-isoforms are posttranslationally modified by lipidation (farnesylation, palmitoylation) to facilitate membrane anchorage. The localization of Ras-proteins at the cytoplasmic membrane provides vicinity to transmembrane growth receptors and has been shown to be essential for transmitting growth signals from extracellular growth factor binding to intracellular downstream pathways. A variety of upstream signals may activate Ras proteins depending on the cellular context, such as epidermal growth factor receptor (EGFR), platelet-derived growth factor receptor (PDGFR), nerve growth factor receptor (NGFR) and others. Activated Ras can signal through various downstream pathways, e.g. the Raf-MEK-ERK or the P13K-PDK1-Akt pathways.

On the molecular level, Ras proteins function as molecular switches. By binding GTP and GDP they exist in an active (GTP-bound) and inactive (GDP-bound) state in the cell. Active GTP-loaded Ras recruits other proteins by binding of their cognate Ras-binding domains (RBDs) resulting in activation of the effector protein followed by downstream signalling events of diverse functions, e.g. cytoskeletal rearrangements or transcriptional activation. The activity status of Ras is tightly regulated by guanine nucleotide exchange factors (GEFs) and GTPase activating proteins (GAPs). GEFs function as activators of Ras by promoting the nucleotide exchange from GDP to GTP. GAPs deactivate Ras-GTP by catalyzing the hydrolysis of the bound GTP to GDP. In a cancer cell, point mutations, typically within the GTP-binding region at codon 12, eliminate the ability of RAS to efficiently hydrolyse bound GTP, even in the presence of a GAP. Therefore, cancer cells comprise increased levels of active mutated Ras-GTP, which is thought to be a key factor for driving cancer cell proliferation.

Three main families of RAS-specific GEFs have been identified so far (reviewed in Vigil 2010 *Nature Reviews Cancer*; Rojas et al 2011, *Genes & Cancer* 2(3) 298-305). There are two son of sevenless proteins (SOS1 and SOS2), 4 different isoforms of Ras guanine nucleotide releasing proteins (Ras-GRP1-4) and two Ras guanine nucleotide releasing factors (Ras-GRF1 and 2). The SOS proteins are ubiquitously expressed and are recruited to sites of activated growth factors. Ras-GRFs are expressed mainly in the nervous system, where they are involved in Calcium-dependent activation of Ras. In contrast, Ras GRP proteins are expressed in hematopoietic cells and act in concert with non-receptor tyrosine kinases. In the context of cancer, mainly SOS proteins have been found to be involved.

Targeting Ras for cancer therapy has been a dream since the 1990s (Downward 2002 *Nature Reviews Cancer*, Krens et al. 2010 *Drug Discovery Today*). Due to the compact nature, the high affinity towards GDP and GTP in combination with high intracellular GTP concentrations, the Ras protein itself has always been considered to be undruggable, i.e. the chance to identify small chemical molecules that would bind to and inhibit active Ras was rated extremely low. Alternative approaches have been undertaken to reduce Ras signaling, e.g. by addressing more promising drug targets such as enzymes involved in the posttranslational modification of Ras proteins, especially farnesyltransferase and geranylgeranyltransferase (Berndt 2011 *Nature Reviews*

*Cancer*). Inhibitors of farnesyltransferase (FTIs) were identified and developed with promising antitumor effects in preclinical models. Unexpectedly, in clinical trials these inhibitors have been of limited efficacy. Targeting upstream and downstream kinases involved in Ras signaling pathways has been more successful. Several drugs are and have been in clinical trials that inhibit different kinases, e.g. EGFR, Raf, MEK, Akt, P13K (Takashima & Faller 2013 *Expert Opin. Ther. Targets*). Marketed cancer drugs are available that inhibit Raf, EGFR or MEK.

Nevertheless, there is still a large unmet need for the treatment of Ras-dependent tumors that are resistant against current therapies. Many research groups have been active to identify small molecules that target Ras directly (Ras small molecules have been reviewed in: Cox et al. 2014 *Nature Reviews Drug Discovery*, Spiegel et al. 2014 *Nature Chemical Biology, Cromm* 2015 *Angewandte Chemie*, Marin-Ramos et al *Seminars in Cancer Biology*). One group of inhibitors comprises small molecules that inhibit the interaction of Ras with its effectors Raf or P13K. Another group of compounds acts as covalent inhibitors of a specific cysteine mutant form of K-Ras (glycine to cysteine point mutation G12C). The specific targeting of the Ras-G12C mutant might have the benefit of reduced side effects, as the wildtype Ras proteins should not be affected. Furthermore, several reports show small molecules and peptides that interrupt the GEF assisted activation of Ras (Hillig et al 2019 *PNAS*; Gray et al 2019 *Angewandte Chemie*). There seem to be several different binding sites possible that result in this mode of action. Inhibitors may bind to Ras or to the GEF in an allosteric or orthosteric fashion. All these approaches of direct Ras-targeting are in preclinical research stage. Stabilized peptides have been shown to be active in the nanomolar range. (Leshchiner et al. 2015 *PNAS*). Their usefulness as drugs in a clinical setting has to be awaited.

The Epidermal Growth Factor Receptor (EGFR) is a tyrosine kinase (TK) receptor that is activated upon binding to the Epidermal Growth Factor and other growth factor ligands, triggering several downstream pathways, including RAS/MAPK, P13K/Akt and STAT that regulate different cellular processes, including DNA synthesis and proliferation (Russo A, Oncotarget. 4254, 2015). The family of HER (ErbB) receptor tyrosine kinases consists of four members, ie, epidermal growth factor receptors [EGFR (HER1 or ErbB1), HER2 (ErbB2, neu), HER3 (ErbB3), and HER4 (ErbB4)]. Overexpression, mutation, or aberrant activity of these receptors has been implicated in various types of cancer (Feldinger K, Breast Cancer (Dove Med Press), 2015, 7, 147).

First-Generation Inhibitors

Erlotinib and Gefitinib are small molecule inhibitors of the EGFR/HER-1 (human epidermal growth factor receptor) tyrosine kinase. Erlotinib and Gefitinib were developed as reversible and highly specific small-molecule tyrosine kinase inhibitors that competitively block the binding of adenosine triphosphate to its binding site in the tyrosine kinase domain of EGFR, thereby inhibiting autophosphorylation and blocking downstream signaling (Cataldo V D, *N Engl J Med,* 2011, 364, 947).

Second-Generation Inhibitors

Afatinib is an oral tyrosine kinase inhibitor (TKI) approved for the first-line treatment of patients with NSCLC whose tumors are driven by activating mutations of genes coding for epidermal growth factor receptor (EGFR). Afatinib is also an inhibitor of a specific EGFR mutation (T790M) that causes resistance to first-generation EGFR-targeted TKIs in about half of patients receiving those drugs. (Engle J A, Am J Health Syst Pharm 2014, 71 (22), 1933).

Neratinib, a pan-HER inhibitor, irreversible tyrosine kinase inhibitor binds and inhibits the tyrosine kinase activity of epidermal growth factor receptors, EGFR (or HER1), HER2 and HER4, which leads to reduced phosphorylation and activation of downstream signaling pathways. Neratinib has been shown to be effective against HER2-overexpressing or mutant tumors in vitro and in vivo. Neratinib is currently being investigated in various clinical trials in breast cancers and other solid tumors, including those with HER2 mutation (Feldinger K, Breast Cancer (Dove Med Press), 2015, 7, 147).

Dacomitinib is an irreversible inhibitor of EGFR, HER2, and HER4. In preclinical cell lines and xenograft studies, dacomitinib demonstrated activities against both activating EGFR mutations and EGFR T790M (Liao B C, Curr Opin Oncol. 2015, 27(2), 94).

Third-Generation Inhibitors

The third-generation EGFR-TKIs were designed to inhibit EGFR T790M while sparing wild-type EGFR.

AZD9291 (AstraZeneca, Macclesfield, UK), a mono-anilino-pyrimidine compound, is an irreversible mutant selective EGFR-TKI. This drug is structurally different from the first and second-generation EGFR-TKIs. In preclinical studies, it potently inhibited phosphorylation of EGFR in cell lines with activating EGFR mutations (EGFR del19 and EGFR L858R) and EGFR T790M. AZD9291 also caused profound and sustained tumor regression in tumor xenograft and transgenic mouse models harboring activating EGFR mutations and EGFR T790M. AZD9291 was less potent in inhibiting phosphorylation of wild-type EGFR cell lines (Liao B C, Curr Opin Oncol. 2015, 27(2), 94).

Rociletinib (CO-1686) (Clovis Oncology, Boulder, Colo), a 2,4-disubstituted pyrimidine molecule, is an irreversible mutant selective EGFR-TKI. In preclinical studies, CO-1686 led to tumor regression in cell-lines, xenograft models, and transgenic mouse models harboring activating EGFR mutations and EGFR T790M (Walter A O, Cancer Discov, 2013, 3(12), 1404).

HM61713 (Hanmi Pharmaceutical Company Ltd, Seoul, South Korea) is an orally administered, selective inhibitor for activating EGFR mutations and EGFR T790M. It has low activity against wild-type EGFR (Steuer C E, Cancer. 2015, 121(8), E1).

Hillig et al 2019 PNAS describe compounds like

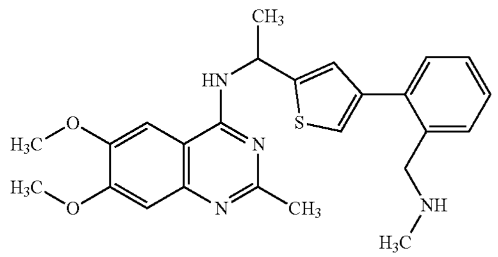 [SMILES: CNCc1ccccc1-c1csc(C(C)Nc2nc(C)nc3cc(OC)c(OC)cc23)c1]

as a potent SOS1 inhibitor and as a tool compound for further investigation of RAS-SOS1 biology in vitro.

FR 3 066 761 (Universite d'Orleans et al) describes compounds like

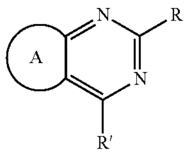

for the treatment of cancer.

WO 2018/134685 (Eisai Management Co. Ltd. et al) describes compounds like

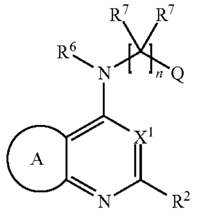

for the treatment and prevention of filarial worm infection.

WO 2018/172250 (Bayer Pharma AG) describes 2-methyl-quinazoline like (I)

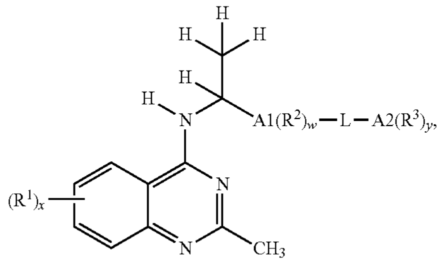

as inhibiting Ras-Sos interaction.

WO 2018/115380 (Boehringer Ingelheim) describes benzylamino substituted quinazolines like

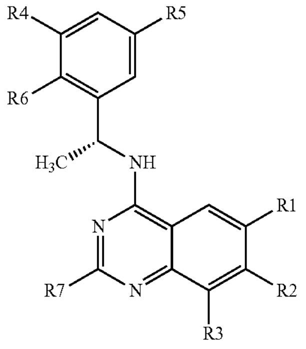

as SOS1 inhibitors.

WO 2019/122129 (Boehringer Ingelheim) describes benzylaminosubstituted pyridopyrimidinones like

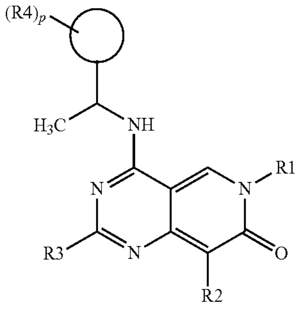

as SOS1 inhibitors.

WO 2020/180768 and WO 2020/180770 (Revolution Medicines) describes compounds of the following formulas:

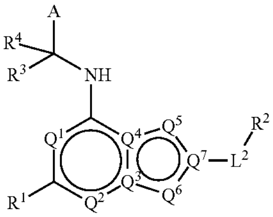

and

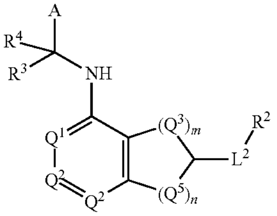

as SOS1 inhibitors.

WO 2021/228028 (Chia Tai Tianqing Pharmaceutical Group Co., Ltd.) describes compounds of the following formula (I)

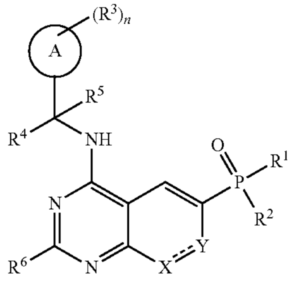

as SOS1 inhibitors.

Further interesting literature is

Hofmann et al., Cancer Discov 2021; 11:142-5 and

Hillig R C, Bader B. Adv Cancer Res. 2022; 153:169-203.

It has now been found, and this constitutes the basis of the present invention, that the compounds of the present invention have surprising and advantageous properties.

In particular, the compounds of the present invention have surprisingly been found to effectively and selectively inhibit the Ras-Sos1 interaction and may therefore be used for the treatment or prophylaxis of hyper-proliferative disorders, in particular cancer.

DESCRIPTION OF THE INVENTION

In accordance with a first aspect, the present invention covers compounds of general formula (I):

(I)

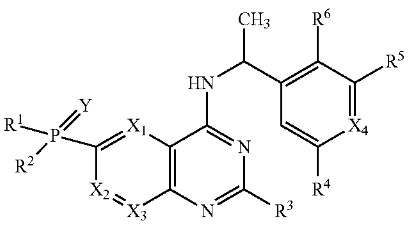

in which $X_1$ represents CH or N;

$X_2$ represents $CR^a$ or N $X_3$ represents $CR^a$ or N $X_4$ represents CH or N Y represents O or S;

$R^1$, $R^2$ is independently of each other selected from $C_{1-4}$ alkyl, $OR^b$ or $NR^cR^d$; or $R^1$, $R^2$ together with the phosphorus atom they are attached to form a 4-7 membered heterocycloalkyl in which one or more carbon atom can be replaced by —O—, —$NR^e$—, —S—, —S(O)—, $S(O)_2$— or —S(O)NRL; and in which each remaining carbon atom can optionally be substituted by one or two $CH_3$ or by one —$CH_2$—$CH_3$, $R^3$ is selected from —H, —OH, —OMe, —CN, —$NR^pR^q$, or $C_{1-2}$-alkyl optionally substituted with OH, OMe, CN or halogen $R^4$ is selected from —F, —C, —Br, —OH, —$NH_2$, —$N(CH_3)H$, —$CH_3$ or —$CF_2H$;

$R^5$ represents -A-B-E in which

A represents —$CR^jR^k$— or absent, and

B represents —$CR^lR^m$— or absent, and

E represents —H, —F, —OH, —$OCH_3$, —$NH_2$, —NH—$CH_3$, —$N(CH_3)_2$, —$N(CH_3)$—$OCH_3$, —CN, —$SO_2$—$CH_3$, —NH—$SO_2$—$CH_3$, —$N(CH_3)$—$SO_2$—$CH_3$, —NH—C(O)—$CH_3$, —$N(CH_3)$—C(O)—$CH_3$, —S(=NH)(=O)—$CH_3$, —S(=N—$CH_3$)(=O)—$CH_3$, —C(O)—$NH_2$, —C(O)—$NH(CH_3)$, —C(O)—$N(CH_3)_2$, or $R^5$ represents —$SO_2$—$NR^nR^o$, $R^6$ is selected from —H, halogen or —$CH_3$;

$R^a$ is selected from —H, halogen, —OH, —$OCH_3$, —CN, cyclopropyl, —$NH_2$, —$NH(CH_3)$, —$N(CH_3)_2$, or $C_{1-2}$ alkyl optionally substituted one or more times by halogen, —OH or —$OCH_3$, —$CH_3$, —$CF_3$, —$NH_2$, —$NH(CH_3)$, —$N(CH_3)_2$, or —CN $R^b$ is selected from —H (under the condition, that if $R^1$ and $R^2$ are both $OR^b$ only one $R^b$ can be H), —$CH_3$, —$CH_2$—$CH_3$, —$CH(CH_3)_2$ or cyclopropyl, $R^c$ is selected from —$CH_3$, —$CH_2$—$CH_3$, —$CH(CH_3)_2$ or cyclopropyl, $R^d$ is selected from —H, —$CH_3$, —$CH_2$—$CH_3$, —CH $(CH_3)_2$ or cyclopropyl, $R^e$ is selected from H, $C_1$-$C_3$-alkyl optionally substituted by one or more F, cyclopropyl, —C(O)—$R^9$, —$SO_2$—$CH_3$ or 5 membered heteroaryl optionally substituted by —$CH_3$, halogen, —$CF_3$ or —$CF_2H$ $R^f$ is selected from H, —$CH_3$, or —$CH_2$—$CH_3$, $R^g$ is selected from $C_{1-4}$ alkyl optionally substituted by —OH, —$OCH_3$, —$CH_3$, halogen; or is selected from 5-membered heteroaryl optionally substituted by —$CH_3$, $CH_2CH_3$, $CF_2H$, $CF_3$ or halogen; or is selected from $NR^hR^i$;

$R^h$ is selected from H or —$CH_3$, and $R^i$ is selected from $C_{1-3}$ alkyl optionally substituted by halogen or from cyclopropyl, $R^j$ and $R^k$ are independently of each other selected from H, F or —$CH_3$, or form together with the carbon atom they are attached to cyclopropyl;

$R^l$ and $R^m$ are independently of each other selected from H, Deuterium, or —$CH_3$, —$CH_2$—$CH_3$, cyclopropyl; or form together with the carbon atom they are attached to cyclopropyl;

$R^n$ and $R^o$ are independently selected from H or $C_{1-4}$ alkyl optionally substituted by —OH, —$OCH_3$, or $R^n$ and $R^o$ form together with the nitrogen they are attached to a 4 to 7 membered heterocycloalkyl optionally containing further heteroatoms selected from N or O, in which carbon atoms of this heterocycloalkyl can be optionally substituted by H or $C_{1-4}$ alkyl and where this $C_{1-4}$ alkyl can again be substituted by halogen, =O, —OH, —$OCH_3$, —$NH_2$, —NH—$CH_3$ or —$N(CH_3)_2$, and in which nitrogen atoms of this heterocycloalkyl can be optionally substituted by —C(O)-cyclopropyl or —C(O)—$C_1$-$C_4$-alkyl, both optionally substituted one or more times with F;

$R^p$ and $R^q$ are independently selected from H, —$CH_3$ or —$CH_2$—$CH_3$;

or a stereoisomer, a tautomer, an N-oxide, a hydrate, a solvate, or a salt thereof, or a mixture of same.

In accordance with a further aspect, the present invention covers compounds of general formula (Ia) (subgroup of formula (I) above)

(Ia)

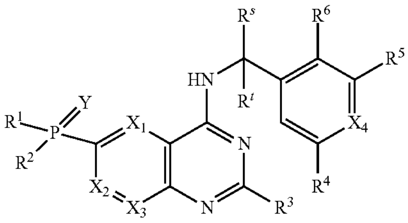

in which $X_1$ represents CH;

$X_2$ represents $CR^a$ or N $X_3$ represents $CR^a$ or N $X_4$ represents CH or N Y represents O;

$R^1$, $R^2$ is independently of each other selected from —$CH_3$, —$CH_2$—$CH_3$ or —$CH(CH_3)_2$; or $R^1$, $R^2$ together with the phosphor atom they are attached to form

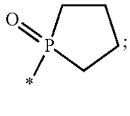; 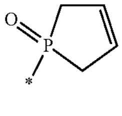 or 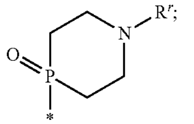

$R^3$ is selected from $—CH_3$, $—CHF_2$, $—CF_3$ or —Cl;

$R^4$ is selected from —H, $—NH_2$ or $—CH_3$;

$R^5$ is selected from

—Br, $—CF_2—H$, $—CF_2—F$, $—CF_2—CH_3$, $—CF_2—CH_2—OH$, $—CF_2—CD_2\text{-}OH$, $—CF_2—CH_2—OCH_3$, $—CF_2—CH(CH_3)—OH$, $—CF_2—CH(CH_2—CH_3)—OH$, $—CF_2—C(CH_3)_2—OH$, $CF_2—C(CH_3)_2—OCH_3$, $—CF_2—CH(CH(CH_3)_2)—OH$, $—CF_2—CH(C(CH_3)_3)—OH$, $—CF_2—C(CH_3)(CH_2—CH_2—CH_2—CH_3)—OH$, $—CF_2—C(=O)—CH(CH_3)_2$, $—CF_2—C(=O)—C(CH_3)_3$, $—CF_2—C(=O)—OH$, $—CF_2—C(=O)—NH_2$, $—CF_2—C(=O)—N(CH_3)_2$, $—CF_2—C(=O)—NH—CH_3$, $—CF_2—C(=O)—NH—CH_2—CH_3$, $—CF_2—C(=O)—NH\text{-cyclopropyl}$, $—CF_2—CH_2—NH—SO_2—CH_3$, $—CF_2—CH_2—N(CH_3)—SO_2—CH_3$, $—CF_2—CH_2—NH—C(=O)—CH_3$ or $—CF_2—CH_2—N(CH_3)$;

$R^6$ is selected from —H, $—CH_3$, —Fl or —Cl;

$R^a$ is selected from —H, $—CH_3$, $—CH_2—CH_3$, $—CF_3$, $—CHF_2$, $—CH_2—OH$, $—CH_2—O—CH_3$, —OH, $—OCH_3$ or cyclopropyl, $R^r$ is selected from —H, $—CH_3$, $—CH(CH_3)_2$, $—CH_2$-phenyl, —C(=O)—H, $—C(=O)—CH_3$, $—C(=O)—CH_2F$, $—C(=O)—CH(CH_3)_2$, $—C(=O)—CH(CH_3)—OH$, $—C(=O)—CH(CH_3)—O—CH_3$,

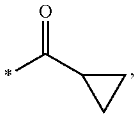, 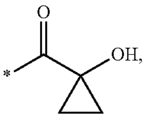, 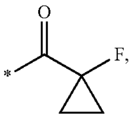, 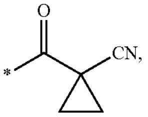, 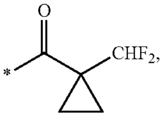, 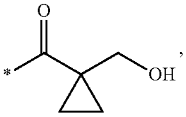, 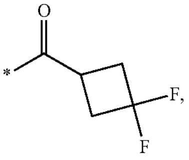, 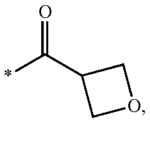, 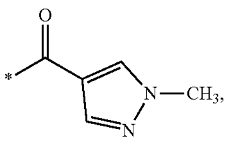

$C(=O)—CH_2—CN$, $—C(=O)—CH_2—O—CH_3$, $—C(=O)—O—C(CH_3)_3$, $—C(=O)—O—CH_2—CH_3$, $—C(=O)—NH_2$, $—C(=O)—N(CH_3)_2$, $—C(=O)—CH_2—CHF_2$, $—C(=O)—NH\text{-cyclopropyl}$, $—C(=S)—CH_3$, $—SO_2—CH_3$,

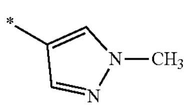 or 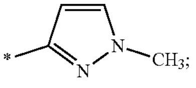

$R^s$ is selected from $—CH_3$ or $—CD_3$;

$R^t$ is selected from —H or D;

or a stereoisomer, a tautomer, an N-oxide, a hydrate, a solvate, or a salt thereof, or a mixture of same.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen or phosphor atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two or three identical or different substituents, particularly with one substituent.

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

Should a composite substituent be composed of more than one parts, e.g. ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of".

If within the present text any item is referred to as "as mentioned herein", it means that it may be mentioned anywhere in the present text.

The terms as mentioned in the present text have the following meanings: The term "halogen atom" means a fluorine, chlorine, bromine or iodine atom, particularly a fluorine, chlorine or bromine atom.

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "$C_1$-$C_5$-hydroxyalkyl" means a linear or branched, saturated, monovalent hydrocarbon group in which the term "$C_1$-$C_5$-alkyl" is defined supra, and in which 1, 2 or 3 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "$C_1$-$C_5$-alkylsulfanyl" means a linear or branched, saturated, monovalent group of formula ($C_1$-$C_6$-alkyl)-S—, in which the term "$C_1$-$C_6$-alkyl" is as defined supra, e.g. a methylsulfanyl, ethylsulfanyl, propylsulfanyl, isopropylsulfanyl, butylsulfanyl, sec-butylsulfanyl, isobutylsulfanyl, tert-butylsulfanyl, pentylsulfanyl, isopentylsulfanyl, hexylsulfanyl group.

The term "$C_1$-$C_5$-haloalkyl" means a linear or branched, saturated, monovalent hydrocarbon group in which the term "$C_1$-$C_5$-alkyl" is as defined supra, and in which one or more of the hydrogen atoms are replaced, identically or differently, with a halogen atom. Particularly, said halogen atom is a fluorine atom. Said $C_1$-$C_5$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_5$-alkoxy" means a linear or branched, saturated, monovalent group of formula ($C_1$-$C_6$-alkyl)-O—, in which the term "$C_1$-$C_6$-alkyl" is as defined supra, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof.

The term "$C_1$-$C_5$-haloalkoxy" means a linear or branched, saturated, monovalent $C_1$-$C_5$-alkoxy group, as defined supra, in which one or more of the hydrogen atoms is replaced, identically or differently, with a halogen atom. Particularly, said halogen atom is a fluorine atom. Said $C_1$-$C_5$-haloalkoxy group is, for example, fluoromethoxy, difluoromethoxy, trifluoromethoxy, 2,2,2-trifluoroethoxy or pentafluoroethoxy.

The term "$C_2$-$C_6$-alkenyl" means a linear or branched, monovalent hydrocarbon group, which contains one or two double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then it is possible for said double bonds to be isolated from, or conjugated with, each other. Said alkenyl group is, for example, an ethenyl (or "vinyl"), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl, 1-(1,1-dimethylethyl)ethenyl, buta-1,3-dienyl, penta-1,4-dienyl or hexa-1,5-dienyl group. Particularly, said group is vinyl or allyl.

The term "$C_2$-$C_6$-alkynyl" means a linear or branched, monovalent hydrocarbon group which contains one triple bond, and which contains 2, 3, 4, 5 or 6 carbon atoms, particularly 2 or 3 carbon atoms ("$C_2$-$C_3$-alkynyl"). Said $C_2$-$C_5$-alkynyl group is, for example, ethynyl, prop-1-ynyl, prop-2-ynyl (or "propargyl"), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl group. Particularly, said alkynyl group is ethynyl, prop-1-ynyl or prop-2-ynyl.

The term "$C_3$-$C_3$-cycloalkyl" means a saturated, monovalent, mono- or bicyclic hydrocarbon ring which contains 3, 4, 5, 6, 7 or 8 carbon atoms ("$C_3$-$C_8$-cycloalkyl"). Said $C_3$-$C_3$-cycloalkyl group is for example, a monocyclic hydrocarbon ring, e.g. a cyclopropyl, cyclobutyl, cyclopentyl, cyclohexyl, cycloheptyl or cyclooctyl group, or a bicyclic hydrocarbon ring, e.g. a bicyclo[4.2.0]octyl or octahydropentalenyl.

The term "$C_4$-$C_3$-cycloalkenyl" means a monovalent, mono- or bicyclic hydrocarbon ring which contains 4, 5, 6, 7 or 8 carbon atoms and one double bond. Particularly, said ring contains 4, 5 or 6 carbon atoms ("$C_4$-$C_6$-cycloalkenyl"). Said $C_4$-$C_3$-cycloalkenyl group is for example, a monocyclic hydrocarbon ring, e.g. a cyclobutenyl, cyclopentenyl, cyclohexenyl, cycloheptenyl or cyclooctenyl group, or a bicyclic hydrocarbon ring, e.g. a bicyclo[2.2.1]hept-2-enyl or bicyclo [2.2.2]oct-2-enyl.

The term "$C_3$-$C_3$-cycloalkoxy" means a saturated, monovalent, mono- or bicyclic group of formula ($C_3$-$C_3$-cycloalkyl)-O—, which contains 3, 4, 5, 6, 7 or 8 carbon atoms, in which the term "$C_3$-$C_3$-cycloalkyl" is defined supra, e.g. a cyclopropyloxy, cyclobutyloxy, cyclopentyloxy, cyclohexyloxy, cycloheptyloxy or cyclooctyloxy group.

The term "spirocycloalkyl" means a saturated, monovalent bicyclic hydrocarbon group in which the two rings share one common ring carbon atom, and wherein said bicyclic hydrocarbon group contains 5, 6, 7, 8, 9, 10 or 11 carbon atoms, it being possible for said spirocycloalkyl group to be attached to the rest of the molecule via any one of the carbon atoms except the spiro carbon atom. Said spirocycloalkyl group is, for example, spiro[2.2]pentyl, spiro[2.3]hexyl, spiro[2.4]heptyl, spiro[2.5]octyl, spiro[2.6]nonyl, spiro[3.3]heptyl, spiro[3.4]octyl, spiro[3.5]nonyl, spiro[3.6]decyl, spiro[4.4]nonyl, spiro[4.5]decyl, spiro[4.6]undecyl or spiro[5.5]undecyl.

The terms "4- to 7-membered heterocycloalkyl" and "4- to 6-membered heterocycloalkyl" mean a monocyclic, saturated heterocycle with 4, 5, 6 or 7 or, respectively, 4, 5 or 6 ring atoms in total, which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example, or a 7-membered ring, such as azepanyl, 1,4-diazepanyl or 1,4-oxazepanyl, for example.

Particularly, "4- to 6-membered heterocycloalkyl" means a 4- to 6-membered heterocycloalkyl as defined supra containing one ring nitrogen atom and optionally one further ring heteroatom from the series: N, O, S. More particularly, "5- or 6-membered heterocycloalkyl" means a monocyclic, saturated heterocycle with 5 or 6 ring atoms in total, containing one ring nitrogen atom and optionally one further ring heteroatom from the series: N, O.

The term "5- to 8-membered heterocycloalkenyl" means a monocyclic, unsaturated, nonaromatic heterocycle with 5, 6, 7 or 8 ring atoms in total, which contains one or two double bonds and one or two identical or different ring heteroatoms from the series: N, O, S; it being possible for said heterocycloalkenyl group to be attached to the rest of the molecule via any one of the carbon atoms or, if present, a nitrogen atom.

Said heterocycloalkenyl group is, for example, 4H-pyranyl, 2H-pyranyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl or 4H-[1,4]thiazinyl.

The term "heterospirocycloalkyl" means a bicyclic, saturated heterocycle with 6, 7, 8, 9, 10 or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxazaspiro[4.3]octyl, azaspiro[4,5]decyl, oxazaspiro [5.5]undecyl, diazaspiro[3.3]heptyl, thiazaspiro[3.3]heptyl, thiazaspiro[4.3]octyl, azaspiro[5.5]undecyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "fused heterocycloalkyl" means a bicyclic, saturated heterocycle with 6, 7, 8, 9 or 10 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom.

Said fused heterocycloalkyl group is, for example, azabicyclo[3.3.0]octyl, azabicyclo[4.3.0]nonyl, diazabicyclo[4.3.0]nonyl, oxazabicyclo[4.3.0]nonyl, thiazabicyclo[4.3.0]nonyl or azabicyclo[4.4.0]decyl.

The term "bridged heterocycloalkyl" means a bicyclic, saturated heterocycle with 7, 8, 9 or 10 ring atoms in total, in which the two rings share two common ring atoms which are not adjacent, which "bridged heterocycloalkyl" contains one or two identical or different ring heteroatoms from the series: N, O, S; it being possible for said bridged heterocycloalkyl group to be attached to the rest of the molecule via any one of the carbon atoms, except the spiro carbon atom, or, if present, a nitrogen atom.

Said bridged heterocycloalkyl group is, for example, azabicyclo[2.2.1]heptyl, oxazabicyclo[2.2.1]heptyl, thiazabicyclo[2.2.1]heptyl, diazabicyclo[2.2.1]heptyl, azabicyclo[2.2.2]octyl, diazabicyclo[2.2.2]octyl, oxazabicyclo[2.2.2]octyl, thiazabicyclo[2.2.2]octyl, azabicyclo[3.2.1]octyl, diazabicyclo[3.2.1]octyl, oxazabicyclo[3.2.1]octyl, thiazabicyclo[3.2.1]octyl, azabicyclo[3.3.1]nonyl, diazabicyclo[3.3.1]nonyl, oxazabicyclo[3.3.1]nonyl, thiazabicyclo[3.3.1]nonyl, azabicyclo[4.2.1]nonyl, diazabicyclo[4.2.1]nonyl, oxazabicyclo[4.2.1]nonyl, thiazabicyclo[4.2.1]nonyl, azabicyclo[3.3.2]decyl, diazabicyclo[3.3.2]decyl, oxazabicyclo[3.3.2]decyl, thiazabicyclo[3.3.2]decyl or azabicyclo[4.2.2]decyl.

The term "heteroaryl" means a monovalent, monocyclic, bicyclic or tricyclic aromatic ring having 5, 6, 8, 9, 10, 11, 12, 13 or 14 ring atoms (a "5- to 14-membered heteroaryl" group), particularly 5, 6, 9 or 10 ring atoms, which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_6$", as used in the present text, e.g. in the context of the definition of "$C_1$-$C_6$-alkyl", "$C_1$-$C_6$-haloalkyl", "$C_1$-$C_6$-hydroxyalkyl", "$C_1$-$C_6$-alkoxy" or "$C_1$-$C_6$-haloalkoxy" means an alkyl group having a finite number of carbon atoms of 1 to 6, i.e. 1, 2, 3, 4, 5 or 6 carbon atoms.

Further, as used herein, the term "$C_3$-$C_8$", as used in the present text, e.g. in the context of the definition of "$C_3$-$C_8$-cycloalkyl", means a cycloalkyl group having a finite number of carbon atoms of 3 to 8, i.e. 3, 4, 5, 6, 7 or 8 carbon atoms.

When a range of values is given, said range encompasses each value and sub-range within said range.

For example:

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_3$-$C_6$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_6$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_6$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_1$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In the context of the present invention, the substituents and residues have the following meanings, unless specified otherwise:

($C_1$-$C_4$)-Alkyl in the context of the invention means a straight-chain or branched alkyl group having 1, 2, 3 or 4 carbon atoms, such as: methyl, ethyl, n-propyl, isopropyl, n-butyl, isobutyl, sec-butyl, and tert-butyl, for example.

($C_1$-$C_4$)-Alkoxy in the context of the invention means a straight-chain or branched alkoxy group having 1, 2, 3 or 4 carbon atoms, such as: methoxy, ethoxy, n-propoxy, isopropoxy, n-butoxy, iso-butoxy, sec-butoxy, and tert-butoxy, for example.

Mono-($C_1$-$C_4$)-alkylamino in the context of the invention means an amino group with one straight-chain or branched alkyl substituent which contains 1, 2, 3 or 4 carbon atoms, such as: methylamino, ethylamino, n-propylamino, isopropylamino, n-butylamino, and tert-butylamino, for example.

Di-($C_1$-$C_4$)-alkylamino in the context of the invention means an amino group with two identical or different straight-chain or branched alkyl substituents which each contain 1, 2, 3 or 4 carbon atoms, such as: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino, and N-tert-butyl-N-methylamino, for example.

($C_1$-$C_4$)-Alkylcarbonyl in the context of the invention means a straight-chain or branched alkyl group having 1, 2, 3 or 4 carbon atoms which is bound to the rest of the molecule via a carbonyl group [—C(═O)—], such as: acetyl, propionyl, n-butyryl, isobutyryl, n-pentanoyl, and pivaloyl, for example.

($C_1$-$C_4$)-Alkoxycarbonyl in the context of the invention means a straight-chain or branched alkoxy group having 1, 2, 3 or 4 carbon atoms which is bound to the rest of the molecule via a carbonyl group [—C(═O)—], such as: methoxycarbonyl, ethoxycarbonyl, n-propoxycarbonyl, isopropoxycarbonyl, n-butoxycarbonyl, and tert-butoxycarbonyl, for example.

Mono-($C_1$-$C_4$)-alkylaminocarbonyl in the context of the invention means an amino group which is bound to the rest of the molecule via a carbonyl group [—C(═O)-] and which has one straight-chain or branched alkyl substituent having 1, 2, 3 or 4 carbon atoms, such as: methylaminocarbonyl, ethylaminocarbonyl, n-propylaminocarbonyl, isopropylaminocarbonyl, n-butylaminocarbonyl, and tert-butylaminocarbonyl, for example.

Di-($C_1$-$C_4$)-alkylaminocarbonyl in the context of the invention means an amino group which is bound to the rest of the molecule via a carbonyl group [—C(═O)-] and which has two identical or different straight-chain or branched alkyl substituents having in each case 1, 2, 3 or 4 carbon atoms, such as: N,N-dimethylaminocarbonyl, N,N-diethylamino-carbonyl, N-ethyl-N-methylaminocarbonyl, N-methyl-N-n-propylaminocarbonyl, N-isopro-pyl-N-methylaminocarbonyl, N,N-diisopropylaminocarbonyl, N-n-butyl-N-methylaminocarbonyl, and N-tert-butyl-N-methylaminocarbonyl, for example.

($C_3$-$C_5$)-Cycloalkyl in the context of the invention means a monocyclic, saturated carbocycle having 3, 4, 5 or 6 ring carbon atoms, such as: cyclopropyl, cyclobutyl, cyclopentyl, and cyclohexyl, for example, particularly cyclopropyl and cyclobutyl, 4- to 7-membered heterocycloalkyl and 4- to 6-membered heterocycloalkyl in the context of the invention mean a monocyclic, saturated heterocycle with 4, 5, 6 or 7 or, respectively, 4, 5 or 6 ring atoms in total, which contains one or two identical or different ring heteroatoms from the series N, O, S, S(O) and $S(O)_2$, and which can be bound via a ring carbon atom or via a ring nitrogen atom (if present), such as: azetidinyl, oxetanyl, thietanyl, pyrrolidinyl, pyrazolidinyl, imidazolidinyl, tetrahydrofuranyl, thiolanyl, 1,1-dioxidothiolanyl, 1,2-oxazolidinyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, 1,2-oxazinanyl, morpholinyl, thiomorpholinyl, 1,1-dioxidothiomorpholinyl, azepanyl, 1,4-diazepanyl, and 1,4-oxazepanyl, for example, in particular a 4- to 6-membered heterocycloalkyl containing one ring nitrogen atom and optionally one further ring heteroatom from the series N, O or $S(O)_2$ and a 5- or 6-membered heterocycloalkyl containing one ring nitrogen atom and optionally one further ring heteroatom from the series N or O: such as: azetidinyl, pyrrolidinyl, pyrazolidinyl, imidazolidinyl, 1,2-oxazolidinyl, 1,3-oxazolidinyl, piperidinyl, piperazinyl, 1,2-oxazinanyl, morpholinyl, and thiomorpholinyl, particularly pyrrolidinyl, piperidinyl, piperazinyl, and morpholinyl.

5-membered aza-heteroaryl in the context of the invention means an aromatic heterocyclic group (heteroaromatic) having 5 ring atoms in total, which contains at least one ring nitrogen atom and optionally one or two further ring heteroatoms selected from N, O and S, and which is bound via a ring carbon atom or optionally via a ring nitrogen atom (if allowed by valency), in particular a 5-membered aza-heteroaryl containing one ring nitrogen atom and one or two further ring heteroatoms selected from N and O, such as: pyrrolyl, pyrazolyl, imidazolyl, oxazolyl, thiazolyl, isoxazolyl, isothiazolyl, triazolyl, oxadiazolyl, and thiadiazolyl, for example, particularly pyrazolyl, imidazolyl, oxazolyl, isoxazolyl, and oxadiazolyl.

An oxo substituent in the context of the invention means an oxygen atom, which is bound to a carbon atom via a double bond.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^{3}H$ or $^{14}C$, are incorporated are useful e.g. in drug and/or substrate tissue distribution studies.

These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$ containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing. A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains an imidazopyridine moiety as a heteroaryl group for example can exist as a 1H tautomer, or a 3H tautomer, or even a mixture in any amount of the two tautomers, namely:

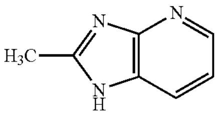

1H tautomer

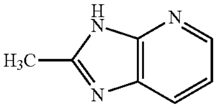

3H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates. Further, it is possible for the compounds of the present invention to exist in free form, e.g.

as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3000H$", "x Na+", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

As used herein, the term "in vivo hydrolysable ester" means an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_5$ alkyl esters, e.g. 1-cyclohexylcarbonyloxyethyl 1,3-dioxolen-2-onylmethyl esters, e.g. 5-methyl-1,3-dioxolen-2-onylmethyl and $C_1$-$C_6$-alkoxycarbonyloxyethyl esters, e.g. 1-methoxycarbonyloxyethyl, it being possible for said esters to be formed at any carboxy group in the compounds of the present invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with another embodiment the present invention covers compounds of general formula (I), wherein only one of $X_1$, $X_2$, $X_3$ or $X_4$ is N or a stereoisomer, a tautomer, an N-oxide, a hydrate, a solvate, or a salt thereof, or a mixture of same.

In accordance with another embodiment the present invention covers compounds of general formula (I), wherein Y represents O or a stereoisomer, a tautomer, an N-oxide, a hydrate, a solvate, or a salt thereof, or a mixture of same.

In accordance with another embodiment the present invention covers compounds of general formula (I), wherein $R^1$ and $R^2$ are selected from $C_{1-4}$ alkyl or a stereoisomer, a tautomer, an N-oxide, a hydrate, a solvate, or a salt thereof, or a mixture of same.

In accordance with another embodiment the present invention covers compounds of general formula (I), wherein $R^1$ and $R^2$ together with the phosphorous atom they are attached to form

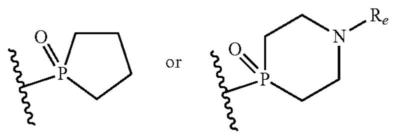

or or a stereoisomer, a tautomer, an N-oxide, a hydrate, a solvate, or a salt thereof, or a mixture of same.

In accordance with another embodiment the present invention covers compounds of general formula (I), wherein $R^3$ is selected from $C_{1-2}$-alkyl optionally substituted with 1 to 3 F or a stereoisomer, a tautomer, an N-oxide, a hydrate, a solvate, or a salt thereof, or a mixture of same.

In accordance with another embodiment the present invention covers compounds of general formula (I), wherein $R^6$ is selected from —F, —Cl, —H or —$CH_3$ or a stereoisomer, a tautomer, an N-oxide, a hydrate, a solvate, or a salt thereof, or a mixture of same.

In accordance with another embodiment the present invention covers compounds of general formula (I), wherein $R^a$ is selected from —H, —Cl, —$CH_3$, —$CF_3$ or —$CF_2H$ or a stereoisomer, a tautomer, an N-oxide, a hydrate, a solvate, or a salt thereof, or a mixture of same.

In accordance with another embodiment the present invention covers compounds of general formula (I), wherein $R^j$ and $R^k$ form together with the carbon atom they are attached to cyclopropyl or are selected from either both —F, both —$CH_3$, or a stereoisomer, a tautomer, an N-oxide, a hydrate, a solvate, or a salt thereof, or a mixture of same.

In accordance with another embodiment the present invention covers compounds of general formula (I), wherein $R^n$ and $R^o$ form together with the nitrogen they are attached to morpholine or N-acetylpiperazine both optionally substituted with 1 or 2 —$CH_3$, —$CF_3$ or —$CF_2H$ or a stereoisomer, a tautomer, an N-oxide, a hydrate, a solvate, or a salt thereof, or a mixture of same.

In accordance with another embodiment the present invention covers compounds of general formula (I), wherein any substituent of the embodiments above can be combined with any other substituent or substituents from one or more of the embodiments above or a stereoisomer, a tautomer, an N-oxide, a hydrate, a solvate, or a salt thereof, or a mixture of same.

In accordance with another embodiment the present invention covers the following compounds:

6-(dimethylphosphoryl)-2-methyl-N-{(1R)-1-[2-methyl-3-(trifluoromethyl)phenyl]ethyl}pyrido[3,4-d]pyrimidin-4-amine N-{(1R)-1-[3-(difluoromethyl)-2-fluorophenyl]ethyl}-6-(dimethylphosphoryl)-2-methylpyrido[3,4-d]pyrimidin-4-amine 1-{3-[(1R)-1-{[6-(dimethylphosphoryl)-2-methylpyrido[3,4-d]pyrimidin-4-yl]amino}ethyl]-2-fluorophenyl}-1,1-difluoro-2-methylpropan-2-ol 1-[4-({(1R)-1-[3-(1,1-difluoro-2-hydroxy-2-methylpropyl)-2-fluorophenyl]ethyl}amino)-2-methylpyrido[3,4-d]pyrimidin-6-yl]-1lambda$^5$-phospholan-1-one 1-benzyl-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-acetyl-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-benzyl-4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one 4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one 1-acetyl-4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one 1-{3-[(1R)-1-{[6-(dimethylphosphoryl)-2,8-dimethylpyrido[3,4-d]pyrimidin-4-yl]amino}ethyl]-2-fluorophenyl}-1,1-difluoro-2-methylpropan-2-ol 1-{3-[(1R)-1-({6-[di(propan-2-yl)phosphoryl]-2-methylpyrido[3,4-d]pyrimidin-4-yl}amino)ethyl]-2-fluorophenyl}-1,1-difluoro-2-methylpropan-2-ol 6-(dimethylphosphoryl)-2-methyl-N-{(1R)-1-[2-methyl-3-(trifluoromethyl)phenyl]ethyl}pyrido[2,3-d]pyrimidin-4-amine 1-{3-[(1R)-1-{[6-(dimethylphosphoryl)-2-methylpyrido[2,3-d]pyrimidin-4-yl]amino}ethyl]-2-fluorophenyl}-1,1-difluoro-2-methylpropan-2-ol 1-{3-[(1R)-1-({6-[di(propan-2-yl)phosphoryl]-2-methylpyrido[2,3-d]pyrimidin-4-yl}amino)ethyl]-2-fluorophenyl}-1,1-difluoro-2-methylpropan-2-ol 1-[4-({(1R)-1-[3-(1,1-difluoro-2-hydroxy-2-methylpropyl)-2-fluorophenyl]ethyl}amino)-2-methylpyrido[2,3-d]pyrimidin-6-yl]-1lambda$^5$-phospholan-1-one 6-(dimethylphosphoryl)-2,7-dimethyl-N-{(1R)-1-[2-methyl-3-(trifluoromethyl)phenyl]ethyl}pyrido[2,3-d]pyrimidin-4-amine N-{(1R)-1-[3-(difluoromethyl)-2-fluorophenyl]ethyl}-6-(dimethylphosphoryl)-2,7-dimethylpyrido[2,3-d]pyrimidin-4-amine 1-{3-[(1R)-1-{[6-(dimethylphosphoryl)-2,7-dimethylpyrido[2,3-d]pyrimidin-4-yl]amino}ethyl]-2-fluorophenyl}-1,1-difluoro-2-methylpropan-2-ol 1-[4-({(1R)-1-[3-(1,1-difluoro-2-hydroxy-2-methylpropyl)-2-fluorophenyl]ethyl}amino)-2,7-dimethylpyrido[2,3-d]pyrimidin-6-yl]-1lambda$^5$-phospholan-1-one 1-{3-[(1R)-1-({6-[di(propan-2-yl)phosphoryl]-2,7-dimethylpyrido[2,3-d]pyrimidin-4-yl}amino)ethyl]-2-fluorophenyl}-1,1-difluoro-2-methylpropan-2-ol 6-(dimethylphosphoryl)-2-methyl-N-{(1R)-1-[2-methyl-3-(trifluoromethyl)phenyl]ethyl}-7-(trifluoromethyl)pyrido[2,3-d]pyrimidin-4-amine (2RS)-1-{3-[(1R)-1-{[6-(dimethylphosphoryl)-2-methylpyrido[3,4-d]pyrimidin-4-yl]amino}ethyl]-2-fluorophenyl}-1,1-difluoro-2-methylhexan-2-ol (mixture of diastereomers)

6-(dimethylphosphoryl)-2-methyl-N-{1-[2-(trifluoromethyl)pyridin-4-yl]ethyl}pyrido[3,4-d]pyrimidin-4-amine (enantiomer 1)

6-(dimethylphosphoryl)-2-methyl-N-{1-[2-(trifluoromethyl)pyridin-4-yl]ethyl}pyrido[3,4-d]pyrimidin-4-amine (enantiomer 2)

4-({(1R)-1-[3-(1,1-difluoro-2-hydroxy-2-methylpropyl)-2-fluorophenyl]ethyl}amino)-6-(dimethylphosphoryl)-2-methylpyrido[3,4-d]pyrimidin-8-ol 1-acetyl-4-[8-hydroxy-2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carbaldehyde 1-ethanethioyl-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 2-{3-[(1R)-1-{[6-(dimethylphosphoryl)-2-methylquinazolin-4-yl]amino}ethyl]-2-fluorophenyl}-2,2-difluoroethan-1-ol 1-acetyl-4-[8-(hydroxymethyl)-2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-acetyl-4-[8-cyclopropyl-2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-acetyl-4-[8-(difluoromethyl)-2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-acetyl-4-[8-(methoxymethyl)-2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one (2RS)-1-{3-[(1R)-1-{[6-(dimethylphosphoryl)-8-ethyl-2-methylpyrido[3,4-d]pyrimidin-4-yl]amino}ethyl]-2-fluorophenyl}-1,1-difluorobutan-2-ol (mixture of diastereomers)

4-[2-methyl-4-({(1R)-1-[2-methyl-3-(trifluoromethyl)phenyl]ethyl}amino)pyrido[3,4-d]pyrimidin-6-yl]-1-(1-methyl-1H-pyrazol-4-yl)-1,4lambda$^5$-azaphosphinan-4-one 4-[2-methyl-4-({(1R)-1-[2-methyl-3-(trifluoromethyl)phenyl]ethyl}amino)pyrido[3,4-d]pyrimidin-6-yl]-1-(1-methyl-1H-pyrazol-3-yl)-1,4lambda$^5$-azaphosphinan-4-one 1-(methanesulfonyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-acetyl-4-[4-({(1R)-1-[3-(1,1-difluoro-2-hydroxyethyl)-2-fluorophenyl]ethyl}amino)-2-methylpyrido[3,4-d]pyrimidin-6-yl]-1,4lambda$^5$-azaphosphinan-4-one {3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}(difluoro)acetic acid 2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-N-cyclopropyl-2,2-difluoroacetamide 2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-2,2-difluoro-N,N-dimethylacetamide 2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-2,2-difluoroacetamide 2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-2,2-difluoro-N-methylacetamide 2-{3-[(1R)-1-{[6-(dimethylphosphoryl)-2-methylpyrido[3,4-d]pyrimidin-4-yl]amino}ethyl]-2-fluorophenyl}-2,2-difluoroacetamide 2-{3-[(1R)-1-{[6-(dimethylphosphoryl)-2-methylpyrido[3,4-d]pyrimidin-4-yl]amino}ethyl]-2-fluorophenyl}-N-ethyl-2,2-difluoroacetamide 2-{3-[(1R)-1-{[6-(dimethylphosphoryl)-2-methylpyrido[3,4-d]pyrimidin-4-yl]amino}ethyl]-2-fluorophenyl}-2,2-difluoro-N,N-dimethylacetamide 2-{3-[(1R)-1-{[6-(dimethylphosphoryl)-2-methylpyrido[3,4-d]pyrimidin-4-yl]amino}ethyl]-2-fluorophenyl}-2,2-difluoro-N-methylacetamide 4-[4-({(1R)-1-[3-(difluoromethyl)-2-fluorophenyl]ethyl}amino)-2-methylpyrido[3,4-d]pyrimidin-6-yl]-1-methyl-1,4lambda$^5$-azaphosphinan-4-one 4-[2-methyl-4-({(1R)-1-[2-methyl-3-(trifluoromethyl)phenyl]ethyl}amino)pyrido[3,4-d]pyrimidin-6-yl]-1-(propan-2-yl)-1,4lambda$^5$-azaphosphinan-4-one 1-benzyl-4-[4-({(1R)-1-[3-(1,1-difluoro-2-hydroxy-2-methylpropyl)-2-fluorophenyl]ethyl}amino)-2-methylpyrido[3,4-d]pyrimidin-6-yl]-1,4lambda$^5$-azaphosphinan-4-one 6-(dimethylphosphoryl)-N-{(1R)-1-[2-fluoro-3-(trifluoromethyl)phenyl]ethyl}-2-methylpyrido[3,4-d]pyrimidin-4-amine N-[(1R)-1-(3-bromo-2-fluorophenyl)ethyl]-6-(dimethylphosphoryl)-2-methylpyrido[3,4-d]pyrimidin-4-amine 1-acetyl-4-[4-({(1R)-1-[3-(difluoromethyl)phenyl]ethyl}amino)-2-methylpyrido[3,4-d]pyrimidin-6-yl]-1,4lambda$^5$-azaphosphinan-4-one 1-acetyl-4-[4-({(1R)-1-[2,5-dimethyl-3-(trifluoromethyl)phenyl]ethyl}amino)-2-methylpyrido[3,4-d]pyrimidin-6-yl]-1,4lambda$^5$-azaphosphinan-4-one 1-[4-({(1R)-1-[3-(1,1-difluoro-2-hydroxyethyl)-2-fluorophenyl]ethyl}amino)-2-methylpyrido[3,4-d]pyrimidin-6-yl]-2,5-dihydro-1H-1lambda$^5$-phosphol-1-one 2-{3-[(1R)-1-{[6-(dimethylphosphoryl)-2-methylpyrido[3,4-d]pyrimidin-4-yl]amino}ethyl]-2-fluorophenyl}-2,2-difluoro($^2H_2$)ethan-1-ol 1-(4-{[(1R)-1-{3-[1,1-difluoro-2-hydroxy($^2$H2)ethyl]-2-fluorophenyl}ethyl]amino}-2-methylpyrido[3,4-d]pyrimidin-6-yl)-1lambda$^5$-phospholan-1-one 2-{3-[(1R)-1-{[6-(dimethylphosphoryl)-2-methylpyrido[3,4-d]pyrimidin-4-yl]amino}ethyl]-2-fluorophenyl}-2,2-difluoroethan-1-ol 1-[4-({(1R)-1-[3-(1,1-difluoro-2-hydroxyethyl)-2-fluorophenyl]ethyl}amino)-2-methylpyrido[3,4-d]pyrimidin-6-yl]-1lambda$^5$-phospholan-1-one 2-{3-[(1R)-1-{[6-(diethylphosphoryl)-2-methylpyrido[3,4-d]pyrimidin-4-yl]amino}ethyl]-2-fluorophenyl}-2,2-difluoroethan-1-ol (2R*)-1-{3-[(1R)-1-{[6-(dimethylphosphoryl)-2-methylpyrido[3,4-d]pyrimidin-4-yl]amino}ethyl]-2-fluorophenyl}-1,1-difluorobutan-2-ol (diastereomer 1)

(2R*)-1-{3-[(1R)-1-{[6-(dimethylphosphoryl)-2-methylpyrido[3,4-d]pyrimidin-4-yl]amino}ethyl]-2-fluorophenyl}-1,1-difluoro-3-methylbutan-2-ol (diastereomer 1)

1-{3-[(1R)-1-({6-[ethyl(methyl)phosphoryl]-2-methylpyrido[3,4-d]pyrimidin-4-yl}amino)ethyl]-2-fluorophenyl}-1,1-difluoro-2-methylpropan-2-ol (mixture of diastereomers)

1-{3-[(1R)-1-({6-[ethyl(methyl)phosphoryl]-2-methylpyrido[3,4-d]pyrimidin-4-yl}amino)ethyl]-2-fluorophenyl}-1,1-difluoro-2-methylpropan-2-ol (diastereomer 1)

1-{3-[(1R)-1-({6-[ethyl(methyl)phosphoryl]-2-methylpyrido[3,4-d]pyrimidin-4-yl}amino)ethyl]-2-fluorophenyl}-1,1-difluoro-2-methylpropan-2-ol (diastereomer 2)

1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}-2-methylpropan-2-ol (mixture of diastereomers)

1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}-2-methylpropan-2-ol (diastereomer 1)

1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}-2-methylpropan-2-ol (diastereomer 2)

(2R*)-1-{3-[(1R)-1-({6-[ethyl(methyl)phosphoryl]-2-methylpyrido[3,4-d]pyrimidin-4-yl}amino)ethyl]-2-fluorophenyl}-1,1-difluoropropan-2-ol (mixture of diastereomers)

(2R*)-1-{3-[(1R)-1-({6-[ethyl(methyl)phosphoryl]-2-methylpyrido[3,4-d]pyrimidin-4-yl}amino)ethyl]-2-fluorophenyl}-1,1-difluoropropan-2-ol (diastereomer 1)

(2R*)-1-{3-[(1R)-1-({6-[ethyl(methyl)phosphoryl]-2-methylpyrido[3,4-d]pyrimidin-4-yl}amino)ethyl]-2-fluorophenyl}-1,1-difluoropropan-2-ol (diastereomer 2)

(2R*)-1-{3-[(1R)-1-({6-[ethyl(methyl)phosphoryl]-2-methylpyrido[3,4-d]pyrimidin-4-yl}amino)ethyl]-2-fluorophenyl}-1,1-difluoropropan-2-ol (mixture of diastereomers)

(2R*)-1-{3-[(1R)-1-({6-[ethyl(methyl)phosphoryl]-2-methylpyrido[3,4-d]pyrimidin-4-yl}amino)ethyl]-2-fluorophenyl}-1,1-difluoropropan-2-ol (diastereomer 3)

(2R*)-1-{3-[(1R)-1-({6-[ethyl(methyl)phosphoryl]-2-methylpyrido[3,4-d]pyrimidin-4-yl}amino)ethyl]-2-fluorophenyl}-1,1-difluoropropan-2-ol (diastereomer 4)

(2R*)-1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}propan-2-ol (mixrure of diastereomers)

(2R*)-1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}propan-2-ol (diastereomer 1)

(2R*)-1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}propan-2-ol (diastereomer 2)

(2R*)-1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}propan-2-ol (2R*)-1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}propan-2-ol (diastereomer 3)

(2R*)-1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}propan-2-ol (diastereomer 4) 1-[4-({(1R)-1-[3-(1,1-difluoro-2-hydroxy-2-methylpropyl)-2-fluorophenyl]ethyl}amino)-2-methylpyrido[3,4-d]pyrimidin-6-yl]-2,5-dihydro-1H-1lambda$^5$-phosphol-1-one (2R*)-1-{3-[(1R)-1-{[6-(dimethylphosphoryl)-2-methylpyrido[3,4-d]pyrimidin-4-yl]amino}ethyl]-2-fluorophenyl}-1,1-difluoropropan-2-ol (2R*)-1-{3-[(1R)-1-{[6-(dimethylphosphoryl)-2-methylpyrido[3,4-d]pyrimidin-4-yl]amino}ethyl]-2-fluorophenyl}-1,1-difluoro-3-methylbutan-2-ol (diastereomer 2)

(2R*)-1-{3-[(1R)-1-{[6-(dimethylphosphoryl)-2-methylpyrido[3,4-d]pyrimidin-4-yl]amino}ethyl]-2-fluorophenyl}-1,1-difluorobutan-2-ol (diastereomer 2)

(2R*)-1-{3-[(1R)-1-{[6-(diethylphosphoryl)-2-methylpyrido[3,4-d]pyrimidin-4-yl]amino}ethyl]-2-fluorophenyl}-1,1-difluoropropan-2-ol (diastereomer 2)

tert-butyl 4-[2,8-dimethyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxylate 6-(diethylphosphoryl)-N-{(1R)-1-[3-(difluoromethyl)-2-fluorophenyl]ethyl}-2-methylpyrido[3,4-d]pyrimidin-4-amine 1-[4-({(1R)-1-[3-(1,1-difluoro-2-methoxyethyl)-2-fluorophenyl]ethyl}amino)-2-methylpyrido[3,4-d]pyrimidin-6-yl]-1lambda$^5$-phospholan-1-one N-{(1R)-1-[3-(1,1-difluoro-2-methoxyethyl)-2-fluorophenyl]ethyl}-6-(dimethylphosphoryl)-2-methylpyrido[3,4-d]pyrimidin-4-amine 1-[4-({(1R)-1-[3-amino-5-(trifluoromethyl)phenyl]ethyl}amino)-2-methylpyrido[3,4-d]pyrimidin-6-yl]-1lambda$^5$-phospholan-1-one 6-(diethylphosphoryl)-2-methyl-N-{(1R)-1-[2-methyl-3-(trifluoromethyl)phenyl]ethyl}pyrido[3,4-d]pyrimidin-4-amine N-{(1R)-1-[3-amino-5-(trifluoromethyl)phenyl]ethyl}-6-(dimethylphosphoryl)-2-methylpyrido[3,4-d]pyrimidin-4-amine 6-[di(propan-2-yl)phosphoryl]-2-methyl-N-{(1R)-1-[2-methyl-3-(trifluoromethyl)phenyl]ethyl}pyrido[3,4-d]pyrimidin-4-amine 1-[2-methyl-4-({(1R)-1-[2-methyl-3-(trifluoromethyl)phenyl]ethyl}amino)pyrido[3,4-d]pyrimidin-6-yl]-1lambda$^5$-phospholan-1-one 1-[2,7-dimethyl-4-({(1R)-1-[2-methyl-3-(trifluoromethyl)phenyl]ethyl}amino)pyrido[2,3-d]pyrimidin-6-yl]-1lambda$^5$-phospholan-1-one 6-(dimethylphosphoryl)-7-methoxy-2-methyl-N-{(1R)-1-[2-methyl-3-(trifluoromethyl)phenyl]ethyl}pyrido[2,3-d]pyrimidin-4-amine 6-[di(propan-2-yl)phosphoryl]-2,7-dimethyl-N-{(1R)-1-[2-methyl-3-(trifluoromethyl)phenyl]ethyl}pyrido[2,3-d]pyrimidin-4-amine 1-{3-[(1R)-1-{[6-(diethylphosphoryl)-2-methylpyrido[2,3-d]pyrimidin-4-yl]amino}ethyl]-2-fluorophenyl}-1,1-difluoro-2-methylpropan-2-ol 1-[2-methyl-4-({(1R)-1-[2-methyl-3-(trifluoromethyl)phenyl]ethyl}amino)quinazolin-6-yl]-1lambda$^5$-phospholan-1-one 1-benzyl-4-[2-methyl-4-({(1R)-1-[2-methyl-3-(trifluoromethyl)phenyl]ethyl}amino)quinazolin-6-yl]-1,4lambda$^5$-azaphosphinan-4-one 6-(dimethylphosphoryl)-2-methyl-N-{(1R)-1-[2-methyl-3-(trifluoromethyl)phenyl]ethyl}quinazolin-4-amine 1-[4-({(1R)-1-[3-(difluoromethyl)-2-fluorophenyl]ethyl}amino)-2-methylpyrido[3,4-d]pyrimidin-6-yl]-1lambda$^5$-phospholan-1-one N-{(1R)-1-[3-(difluoromethyl)-2-fluorophenyl]ethyl}-6-[di(propan-2-yl)phosphoryl]-2-methylpyrido[3,4-d]pyrimidin-4-amine 1-{3-[(1R)-1-{[6-(dimethylphosphoryl)-2-methylpyrido[3,4-d]pyrimidin-4-yl]amino}ethyl]-2-fluorophenyl}-1,1-difluoro-3-methylbutan-2-one 1-{3-[(1R)-1-{[6-(dimethylphosphoryl)-2-methylpyrido[3,4-d]pyrimidin-4-yl]amino}ethyl]-2-fluorophenyl}-1,1-difluoro-3,3-dimethylbutan-2-one 1-(4-{[(1R)-1-{3-[(2R*)-1,1-difluoro-2-hydroxypropyl]-2-fluorophenyl}ethyl]amino}-2-methylpyrido[3,4-d]pyrimidin-6-yl)-1lambda$^5$-phospholan-1-one (diastereomer 1)

1-(4-{[(1R)-1-{3-[(2R*)-1,1-difluoro-2-hydroxypropyl]-2-fluorophenyl}ethyl]amino}-2-methylpyrido[3,4-d]pyrimidin-6-yl)-1lambda$^5$-phospholan-1-one (diastereomer 2)

(2R*)-1-{3-[(1R)-1-{[6-(dimethylphosphoryl)-2-methylpyrido[3,4-d]pyrimidin-4-yl]amino}ethyl]-2-fluorophenyl}-1,1-difluoropropan-2-ol (diastereomer 2)

N-{(1R)-1-[3-(difluoromethyl)-2-fluorophenyl]ethyl}-2-methyl-6-[methyl(propan-2-yl)phosphoryl]pyrido[3,4-d]pyrimidin-4-amine (mixture of diastereomers)

N-{(1R)-1-[3-(difluoromethyl)-2-fluorophenyl]ethyl}-2-methyl-6-[methyl(propan-2-yl)phosphoryl]pyrido[3,4-d]pyrimidin-4-amine (diastereomer 1)

N-{(1R)-1-[3-(difluoromethyl)-2-fluorophenyl]ethyl}-2-methyl-6-[methyl(propan-2-yl)phosphoryl]pyrido[3,4-d]pyrimidin-4-amine (diastereomer 2)

N-{(1R)-1-[3-(difluoromethyl)-2-fluorophenyl]ethyl}-6-[ethyl(methyl)phosphoryl]-2-methylpyrido[3,4-d]pyrimidin-4-amine (mixture of diastereomers)

N-{(1R)-1-[3-(difluoromethyl)-2-fluorophenyl]ethyl}-6-[ethyl(methyl)phosphoryl]-2-methylpyrido[3,4-d]pyrimidin-4-amine (diastereomer 1)

N-{(1R)-1-[3-(difluoromethyl)-2-fluorophenyl]ethyl}-6-[ethyl(methyl)phosphoryl]-2-methylpyrido[3,4-d]pyrimidin-4-amine (diastereomer 2)

N-{(1R)-1-[2-chloro-3-(trifluoromethyl)phenyl]ethyl}-6-(dimethylphosphoryl)-2-methylpyrido[3,4-d]pyrimidin-4-amine N-{(1R)-1-[3-(1,1-difluoro-2-methoxy-2-methylpropyl)-2-fluorophenyl]ethyl}-6-(dimethylphosphoryl)-2-methylpyrido[3,4-d]pyrimidin-4-amine 1-[4-({(1R)-1-[3-(1,1-difluoro-2-methoxy-2-methylpropyl)-2-fluorophenyl]ethyl}amino)-2-methylpyrido[3,4-d]pyrimidin-6-yl]-1lambda$^5$-phospholan-1-one 1-{3-[(1R)-1-{[6-(diethylphosphoryl)-2-methylpyrido[3,4-d]pyrimidin-4-yl]amino}ethyl]-2-fluorophenyl}-1,1-difluoro-2-methylpropan-2-ol 2-{3-[(1R)-1-{[6-(dimethylphosphoryl)-2,8-dimethylpyrido[3,4-d]pyrimidin-4-yl]amino}ethyl]-2-fluorophenyl}-2,2-difluoroethan-1-ol N-{(1R)-1-[3-(difluoromethyl)-2-fluorophenyl]ethyl}-6-(dimethylphosphoryl)-2-methyl-7-(trifluoromethyl)pyrido[2,3-d]pyrimidin-4-amine 1-[4-({(1R)-1-[3-(difluoromethyl)-2-fluorophenyl]ethyl}amino)-2,7-dimethylpyrido[2,3-d]pyrimidin-6-yl]-1lambda$^5$-phospholan-1-one 1-[4-({(1R)-1-[3-(difluoromethyl)-2-fluorophenyl]ethyl}amino)-2-methylquinazolin-6-yl]-1lambda$^5$-phospholan-1-one N-{(1R)-1-[3-(difluoromethyl)-2-fluorophenyl]ethyl}-6-(dimethylphosphoryl)-2-methylquinazolin-4-amine N-{(1R)-1-[3-(difluoromethyl)-2-fluorophenyl]ethyl}-6-[di(propan-2-yl)phosphoryl]-2,7-dimethylpyrido[2,3-d]pyrimidin-4-amine 2-{3-[(1R)-1-({6-[ethyl(methyl)phosphoryl]-2-methylpyrido[3,4-d]pyrimidin-4-yl}amino)ethyl]-2-fluorophenyl}-2,2-difluoroethan-1-ol (mixture of diastereomers)

2-{3-[(1R)-1-({6-[ethyl(methyl)phosphoryl]-2-methylpyrido[3,4-d]pyrimidin-4-yl}amino)ethyl]-2-fluorophenyl}-2,2-difluoroethan-1-ol (diastereomer 1)

2-{3-[(1R)-1-({6-[ethyl(methyl)phosphoryl]-2-methylpyrido[3,4-d]pyrimidin-4-yl}amino)ethyl]-2-fluorophenyl}-2,2-difluoroethan-1-ol (diastereomer 2)

2,2-difluoro-2-{2-fluoro-3-[(1R)-1-({2-methyl-6-[methyl(propan-2-yl)phosphoryl]pyrido[3,4-d]pyrimidin-4-yl}amino)ethyl]phenyl}ethan-1-ol (mixture of diastereomers)

2,2-difluoro-2-{2-fluoro-3-[(1R)-1-({2-methyl-6-[methyl(propan-2-yl)phosphoryl]pyrido[3,4-d]pyrimidin-4-yl}amino)ethyl]phenyl}ethan-1-ol (diastereomer 1)

2,2-difluoro-2-{2-fluoro-3-[(1R)-1-({2-methyl-6-[methyl(propan-2-yl)phosphoryl]pyrido[3,4-d]pyrimidin-4-yl}amino)ethyl]phenyl}ethan-1-ol (diastereomer 2)

(2R*)-1-{3-[(1R)-1-{[6-(dimethylphosphoryl)-2-methylpyrido[3,4-d]pyrimidin-4-yl]amino}ethyl]-2-fluorophenyl}-1,1-difluoro-3,3-dimethylbutan-2-ol (diastereomer 1)

(2R*)-1-{3-[(1R)-1-{[6-(dimethylphosphoryl)-2-methylpyrido[3,4-d]pyrimidin-4-yl]amino}ethyl]-2-fluorophenyl}-1,1-difluoro-3,3-dimethylbutan-2-ol (diastereomer 2)

1-acetyl-4-(2-methyl-4-{[(1S)-1-[2-methyl-3-(trifluoromethyl)phenyl]($^2$H4)ethyl]amino}pyrido[3,4-d]pyrimidin-6-yl)-1,4lambda$^5$-azaphosphinan-4-one 1-acetyl-4-[4-({(1R)-1-[3-(1,1-difluoro-2-methoxyethyl)-2-fluorophenyl]ethyl}amino)-2-methylpyrido[3,4-d]pyrimidin-6-yl]-1,4lambda$^5$-azaphosphinan-4-one 1-acetyl-4-[4-({(1R)-1-[3-(1,1-difluoro-2-methoxy-2-methylpropyl)-2-fluorophenyl]ethyl}amino)-2-methylpyrido[3,4-d]pyrimidin-6-yl]-1,4lambda$^5$-azaphosphinan-4-one 1-acetyl-4-[4-({(1R)-1-[3-(1,1-difluoroethyl)phenyl]ethyl}amino)-2-methylpyrido[3,4-d]pyrimidin-6-yl]-1,4lambda$^5$-azaphosphinan-4-one 1-acetyl-4-[4-({(1R)-1-[2-fluoro-3-(trifluoromethyl)phenyl]ethyl}amino)-2-methylpyrido[3,4-d]pyrimidin-6-yl]-1,4lambda$^5$-azaphosphinan-4-one 1-acetyl-4-[4-({(1R)-1-[3-(1,1-difluoro-2-methoxyethyl)phenyl]ethyl}amino)-2-methylpyrido[3,4-d]pyrimidin-6-yl]-1,4lambda$^5$-azaphosphinan-4-one 1-acetyl-4-[7-methoxy-2-methyl-4-({(1R)-1-[2-methyl-3-(trifluoromethyl)phenyl]ethyl}amino)pyrido[2,3-d]pyrimidin-6-yl]-1,4lambda$^5$-azaphosphinan-4-one 1-acetyl-4-[2,7-dimethyl-4-({(1R)-1-[2-methyl-3-(trifluoromethyl)phenyl]ethyl}amino)pyrido[2,3-d]pyrimidin-6-yl]-1,4lambda$^5$-azaphosphinan-4-one (R)-1-(4-(2,8-dimethyl-4-((1-(2-methyl-3-(trifluoromethyl)phenyl)ethyl)amino)pyrido[3,4-d]pyrimidin-6-yl)-4-oxido-1,4-azaphosphinan-1-yl)ethan-1-one 1-acetyl-4-[2-methyl-4-({(1R)-1-[2-methyl-3-(trifluoromethyl)phenyl]ethyl}amino)pyrido[2,3-d]pyrimidin-6-yl]-1,4lambda$^5$-azaphosphinan-4-one 4-[4-({(1R)-1-[3-(difluoromethyl)-2-fluorophenyl]ethyl}amino)-2-methylpyrido[3,4-d]pyrimidin-6-yl]-1-[(2S)-2-methoxypropanoyl]-1,4lambda$^5$-azaphosphinan-4-one 4-[4-({(1R)-1-[3-(difluoromethyl)-2-fluorophenyl]ethyl}amino)-2-methylpyrido[3,4-d]pyrimidin-6-yl]-1-[(2R)-2-hydroxypropanoyl]-1,4lambda$^5$-azaphosphinan-4-one 4-[4-({(1R)-1-[3-(difluoromethyl)-2-fluorophenyl]ethyl}amino)-2-methylpyrido[3,4-d]pyrimidin-6-yl]-1-(1-fluorocyclopropane-1-carbonyl)-1,4lambda$^5$-azaphosphinan-4-one 1-{4-[4-({(1R)-1-[3-(difluoromethyl)-2-fluorophenyl]ethyl}amino)-2-methylpyrido[3,4-d]pyrimidin-6-yl]-4-oxo-1,4lambda$^5$-azaphosphinane-1-carbonyl}cyclopropane-1-carbonitrile 4-[4-({(1R)-1-[3-(difluoromethyl)-2-fluorophenyl]ethyl}amino)-2-methylpyrido[3,4-d]pyrimidin-6-yl]-1-(2-methylpropanoyl)-1,4lambda$^5$-azaphosphinan-4-one 4-[4-({(1R)-1-[3-(difluoromethyl)-2-fluorophenyl]ethyl}amino)-2-methylpyrido[3,4-d]pyrimidin-6-yl]-1-(methoxyacetyl)-1,4lambda$^5$-azaphosphinan-4-one 4-[4-({(1R)-1-[3-(difluoromethyl)-2-fluorophenyl]ethyl}amino)-2-methylpyrido[3,4-d]pyrimidin-6-yl]-1-[(2R)-2-methoxypropanoyl]-1,4lambda$^5$-azaphosphinan-4-one 4-[4-({(1R)-1-[3-(difluoromethyl)-2-fluorophenyl]ethyl}amino)-2-methylpyrido[3,4-d]pyrimidin-6-yl]-1-(1-hydroxycyclopropane-1-carbonyl)-1,4lambda$^5$-azaphosphinan-4-one 4-[4-({(1R)-1-[3-(difluoromethyl)-2-fluorophenyl]ethyl}amino)-2-methylpyrido[3,4-d]pyrimidin-6-yl]-1-[(2S)-2-hydroxypropanoyl]-1,4lambda$^5$-azaphosphinan-4-one 4-[4-({(1R)-1-[3-(difluoromethyl)-2-fluorophenyl]ethyl}amino)-2-methylpyrido[3,4-d]pyrimidin-6-yl]-1-(oxetane-3-carbonyl)-1,4lambda$^5$-azaphosphinan-4-one 1-[1-(difluoromethyl)cyclopropane-1-carbonyl]-4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one 1-(3,3-difluorocyclobutane-1-carbonyl)-4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one 4-[4-({(1R)-1-[3-(difluoromethyl)-2-fluorophenyl]ethyl}amino)-2-methylpyrido[3,4-d]pyrimidin-6-yl]-1-(1-methyl-1H-pyrazole-4-carbonyl)-1,4lambda$^5$-azaphosphinan-4-one 3-{4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinan-1-yl}-3-oxopropanenitrile 1-(cyclopropanecarbonyl)-4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one 4-[2-methyl-4-({(1R)-1-[2-methyl-3-(trifluoromethyl)phenyl]ethyl}amino)pyrido[3,4-d]pyrimidin-6-yl]-1-(oxetane-3-carbonyl)-1,4lambda$^5$-azaphosphinan-4-one 1-[(2S)-2-hydroxypropanoyl]-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-[(2R)-2-hydroxypropanoyl]-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-{4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carbonyl}cyclopropane-1-carbonitrile 1-(1-fluorocyclopropane-1-carbonyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-[1-(difluoromethyl)cyclopropane-1-carbonyl]-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-(3,3-difluorocyclobutane-1-carbonyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 4-[2-methyl-4-({(1R)-1-[2-methyl-3-(trifluoromethyl)phenyl]ethyl}amino)pyrido[3,4-d]pyrimidin-6-yl]-1-(2-methylpropanoyl)-1,4lambda$^5$-azaphosphinan-4-one 1-(cyclopropanecarbonyl)-4-[4-({(1R)-1-[3-(1,1-difluoro-2-hydroxy-2-methylpropyl)-2-fluorophenyl]ethyl}amino)-2-methylpyrido[3,4-d]pyrimidin-6-yl]-1,4lambda$^5$-azaphosphinan-4-one 1-(1-hydroxycyclopropane-1-carbonyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-(cyclopropanecarbonyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 4-[2-methyl-4-({(1R)-1-[2-methyl-3-(trifluoromethyl)phenyl]ethyl}amino)pyrido[3,4-d]pyrimidin-6-yl]-1-(1-methyl-1H-pyrazole-4-carbonyl)-1,4lambda$^5$-azaphosphinan-4-one 1-[(2S)-2-methoxypropanoyl]-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-(methoxyacetyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-[1-(hydroxymethyl)cyclopropane-1-carbonyl]-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one N-(2-{3-[(1R)-1-({6-[1-(cyclopropanecarbonyl)-4-oxo-1,4lambda$^5$-azaphosphinan-4-yl]-2-methylpyrido[3,4-d]pyrimidin-4-yl}amino)ethyl]-2-fluorophenyl}-2,2-difluoroethyl)methanesulfonamide N-(2-{3-[(1R)-1-({6-[1-(cyclopropanecarbonyl)-4-oxo-1,4lambda$^5$-azaphosphinan-4-yl]-2-methylpyrido[3,4-d]pyrimidin-4-yl}amino)ethyl]-2-fluorophenyl}-2,2-difluoroethyl)acetamide N-(2-{3-[(1R)-1-({6-[1-(cyclopropanecarbonyl)-4-oxo-1,4lambda$^5$-azaphosphinan-4-yl]-2-methylpyrido[3,4-d]pyrimidin-4-yl}amino)ethyl]-2-fluorophenyl}-2,2-difluoroethyl)-N-methylmethanesulfonamide N-(2-{3-[(1R)-1-({6-[1-(cyclopropanecarbonyl)-4-oxo-1,4lambda$^5$-azaphosphinan-4-yl]-2-methylpyrido[3,4-d]pyrimidin-4-yl}amino)ethyl]-2-fluorophenyl}-2,2-difluoroethyl)-N-methylacetamide 4-[4-({(1R)-1-[3-(difluoromethyl)-2-fluorophenyl]ethyl}amino)-2-methylpyrido[3,4-d]pyrimidin-6-yl]-4-oxo-1,4lambda$^5$-azaphosphinane-1-carboxamide N-cyclopropyl-4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxamide N-(2,2-difluoroethyl)-4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxamide 4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxamide ethyl 4-[4-({(1R)-1-[3-(difluoromethyl)-2-fluorophenyl]ethyl}amino)-2-methylpyrido[3,4-d]pyrimidin-6-yl]-4-oxo-1,4lambda$^5$-azaphosphinane-1-carboxylate N,N-dimethyl-4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxamide ethyl 4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxylate 1-acetyl-4-[4-({(1R)-1-[3-(difluoromethyl)-2-methylphenyl]ethyl}amino)-2-methylpyrido[3,4-d]pyrimidin-6-yl]-1,4lambda$^5$-azaphosphinan-4-one 1-acetyl-4-[4-({(1R)-1-[2-chloro-3-(trifluoromethyl)phenyl]ethyl}amino)-2-methylpyrido[3,4-d]pyrimidin-6-yl]-1,4lambda$^5$-azaphosphinan-4-one 1-acetyl-4-[2-methyl-4-({(1R)-1-[3-(trifluoromethyl)phenyl]ethyl}amino)pyrido[3,4-d]pyrimidin-6-yl]-1,4lambda$^5$-azaphosphinan-4-one (R)-1-(4-(4-((1-(3-(1,1-difluoro-2-hydroxy-2-methylpropyl)-2-fluorophenyl)ethyl)amino)-2-methylpyrido[3,4-d]pyrimidin-6-yl)-4-oxido-1,4-azaphosphinan-1-yl)ethan-1-one 1-acetyl-4-[4-({(1R)-1-[2-methyl-3-(trifluoromethyl)phenyl]ethyl}amino)-2-(trifluoromethyl)pyrido[3,4-d]pyrimidin-6-yl]-1,4lambda$^5$-azaphosphinan-4-one 1-acetyl-4-[2-(difluoromethyl)-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-acetyl-4-[2-chloro-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 1-acetyl-4-[2-methyl-4-({(1R)-1-[2-methyl-3-(trifluoromethyl)phenyl]ethyl}amino)quinazolin-6-yl]-1,4lambda$^5$-azaphosphinan-4-one N-(2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-2,2-difluoroethyl)methanesulfonamide N-(2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-2,2-difluoroethyl)acetamide N-(2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-2,2-difluoroethyl)-N-methylmethanesulfonamide N-(2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-2,2-difluoroethyl)-N-methylacetamide N-(2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-2,2-difluoroethyl)-N-cyclopropylacetamide 1-(difluoroacetyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one 4-[4-({(1R)-1-[2-chloro-3-(trifluoromethyl)phenyl]ethyl}amino)-2-methylpyrido[3,4-d]pyrimidin-6-yl]-1-(difluoroacetyl)-1,4lambda$^5$-azaphosphinan-4-one 1-(difluoroacetyl)-4-[2-methyl-4-({(1R)-1-[3-(trifluoromethyl)phenyl]ethyl}amino)pyrido[3,4-d]pyrimidin-6-yl]-1,4lambda$^5$-azaphosphinan-4-one 1-(difluoroacetyl)-4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one 1-(difluoroacetyl)-4-[2-methyl-4-({(1R)-1-[2-methyl-3-(trifluoromethyl)phenyl]ethyl}amino)quinazolin-6-yl]-1,4lambda$^5$-azaphosphinan-4-one or a stereoisomer, a tautomer, an N-oxide, a hydrate, a solvate, or a salt thereof, or a mixture of same.

A further embodiment of the present invention covers compounds of formula (I) or formula (Ia), supra, in which $X_1$ represents CH or a stereoisomer, a tautomer, an N-oxide, a hydrate, a solvate, or a salt thereof, or a mixture of same.

A further embodiment of the present invention covers compounds of formula (I) or formula (Ia), supra, in which $X_2$ represents $CR^a$ or a stereoisomer, a tautomer, an N-oxide, a hydrate, a solvate, or a salt thereof, or a mixture of same.

A further embodiment of the present invention covers compounds of formula (I) or formula (Ia), supra, in which $X_2$ represents N or a stereoisomer, a tautomer, an N-oxide, a hydrate, a solvate, or a salt thereof, or a mixture of same.

A further embodiment of the present invention covers compounds of formula (I) or formula (Ia), supra, in which: $X_3$ represents $CR^a$ or a stereoisomer, a tautomer, an N-oxide, a hydrate, a solvate, or a salt thereof, or a mixture of same.

A further embodiment of the present invention covers compounds of formula (I) or formula (Ia), supra, in which $X_3$ represents N or a stereoisomer, a tautomer, an N-oxide, a hydrate, a solvate, or a salt thereof, or a mixture of same.

A further embodiment of the present invention covers compounds of formula (I) or formula (Ia), supra, in which $X_4$ represents CH or a stereoisomer, a tautomer, an N-oxide, a hydrate, a solvate, or a salt thereof, or a mixture of same.

A further embodiment of the present invention covers compounds of formula (I) or formula (Ia), supra, in which $X_4$ represents N or a stereoisomer, a tautomer, an N-oxide, a hydrate, a solvate, or a salt thereof, or a mixture of same.

A further embodiment of the present invention covers compounds of formula (I) or formula (Ia), supra, in which Y represents O or a stereoisomer, a tautomer, an N-oxide, a hydrate, a solvate, or a salt thereof, or a mixture of same.

A further embodiment of the present invention covers compounds of formula (I) or formula (Ia), supra, in which $R^1$ is $—CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^1$ is $—CH_2—CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^1$ is $—CH(CH_3)_2$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^2$ is $—CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^2$ is $—CH_2—CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^2$ is $—CH(CH_3)_2$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^1$, $R^2$ together with the phosphor atom they are attached to form

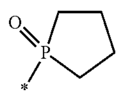

or a stereoisomer, a tautomer, an N-oxide, a hydrate, a solvate, or a salt thereof, or a mixture of same.

A further embodiment of the present invention covers compounds of formula (I) or formula (Ia), supra, in which $R^1$, $R^2$ together with the phosphor atom they are attached to form

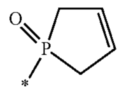 [SMILES: *P1(=O)CC=CC1]

or a stereoisomer, a tautomer, an N-oxide, a hydrate, a solvate, or a salt thereof, or a mixture of same.

A further embodiment of the present invention covers compounds of formula (I) or formula (Ia), supra, in which $R^1$, $R^2$ together with the phosphor atom they are attached to form

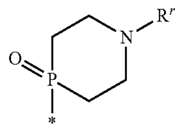

or a stereoisomer, a tautomer, an N-oxide, a hydrate, a solvate, or a salt thereof, or a mixture of same.

A further embodiment of the present invention covers compounds of formula (I) or formula (Ia), supra, in which $R^3$ is $—CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^3$ is $—CHF_2$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^3$ is $—CF_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^3$ is $—C_1$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^4$ is —H or a stereoisomer, a tautomer, an N-oxide, a hydrate, a solvate, or a salt thereof, or a mixture of same.

A further embodiment of the present invention covers compounds of formula (I) or formula (Ia), supra, in which $R^4$ is $—NH_2$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^4$ is $—CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is —Br or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—H$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—F$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—CH_2—OH$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—CD_2\text{-}OH$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—CH_2—OCH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—CH(CH_3)—OH$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—CH(CH_2—CH_3)—OH$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—C(CH_3)_2—OH$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—C(CH_3)_2—OCH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—CH(CH(CH_3)_2)—OH$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—CH(C(CH_3)_3)—OH$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—C(CH_3)(CH_2—CH_2—CH_2—CH_3)—OH$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—C(=O)—CH(CH_3)_2$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—C(=O)—C(CH_3)_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $—CF_2—C(=O)—OH$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $-CF_2-C(=O)-NH_2$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $-CF_2-C(=O)-N(CH_3)_2$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $-CF_2-C(=O)-NH-CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $-CF_2-C(=O)-NH-CH_2-CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $-CF_2-C(=O)-$NH-cyclopropyl or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $-CF_2-CH_2-NH-SO_2-CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $-CF_2-CH_2-N(CH_3)-SO_2-CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $-CF_2-CH_2-NH-C(=O)-CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is $-CF_2-CH_2-N(CH_3)$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^6$ is —H or a stereoisomer, a tautomer, an N-oxide, a hydrate, a solvate, or a salt thereof, or a mixture of same.

A further embodiment of the present invention covers compounds of formula (I) or formula (Ia), supra, in which $R^6$ is $-CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^6$ is —Fl or a stereoisomer, a tautomer, an N-oxide, a hydrate, a solvate, or a salt thereof, or a mixture of same.

A further embodiment of the present invention covers compounds of formula (I) or formula (Ia), supra, in which $R^6$ —Cl or a stereoisomer, a tautomer, an N-oxide, a hydrate, a solvate, or a salt thereof, or a mixture of same.

A further embodiment of the present invention covers compounds of formula (I) or formula (Ia), supra, in which $R^a$ is —H or a stereoisomer, a tautomer, an N-oxide, a hydrate, a solvate, or a salt thereof, or a mixture of same.

A further embodiment of the present invention covers compounds of formula (I) or formula (Ia), supra, in which $R^a$ is $-CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^a$ is $-CH_2-CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^a$ is $-CF_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^a$ is $-CHF_2$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^a$ is $-CH_2-OH$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^a$ is $-CH_2-O-CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^a$ is —OH or a stereoisomer, a tautomer, an N-oxide, a hydrate, a solvate, or a salt thereof, or a mixture of same.

A further embodiment of the present invention covers compounds of formula (I) or formula (Ia), supra, in which $R^a$ is $-OCH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^a$ is -cyclopropyl or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is —H or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is $-CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is $-CH(CH_3)_2$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is $-CH_2$-phenyl or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is $-C(=O)-H$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is $-C(=O)-CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is $-C(=O)-CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is —C(═O)—$CH_2F$ or a stereoisomer, a tautomer, an N-oxide, a hydrate, a solvate, or a salt thereof, or a mixture of same.

A further embodiment of the present invention covers compounds of formula (I) or formula (Ia), supra, in which R′ is —C(═O)—$CH(CH_3)_2$ or a stereoisomer, a tautomer, an N-oxide, a hydrate, a solvate, or a salt thereof, or a mixture of same.

A further embodiment of the present invention covers compounds of formula (I) or formula (Ia), supra, in which R′ is —C(═O)—$CH(CH_3)$—OH or a stereoisomer, a tautomer, an N-oxide, a hydrate, a solvate, or a salt thereof, or a mixture of same.

A further embodiment of the present invention covers compounds of formula (I) or formula (Ia), supra, in which R′ is —C(═O)—$CH(CH_3)$—O—$CH_3$ or a stereoisomer, a tautomer, an N-oxide, a hydrate, a solvate, or a salt thereof, or a mixture of same. A further embodiment of the present invention covers compounds of formula (I) or formula (Ia), supra, in which R′ is

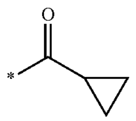 [SMILES: *C(=O)C1CC1]

or a stereoisomer, a tautomer, an N-oxide, a hydrate, a solvate, or a salt thereof, or a mixture of same.

A further embodiment of the present invention covers compounds of formula (I) or formula (Ia), supra, in which R′ is

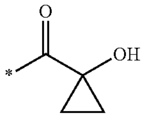

or a stereoisomer, a tautomer, an N-oxide, a hydrate, a solvate, or a salt thereof, or a mixture of same.

A further embodiment of the present invention covers compounds of formula (I) or formula (Ia), supra, in which R′ is

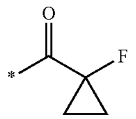 [SMILES: *C(=O)C1(F)CC1]

or a stereoisomer, a tautomer, an N-oxide, a hydrate, a solvate, or a salt thereof, or a mixture of same.

A further embodiment of the present invention covers compounds of formula (I) or formula (Ia), supra, in which R′ is

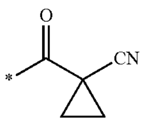 [SMILES: *C(=O)C1(C#N)CC1]

or a stereoisomer, a tautomer, an N-oxide, a hydrate, a solvate, or a salt thereof, or a mixture of same.

A further embodiment of the present invention covers compounds of formula (I) or formula (Ia), supra, in which R′ is

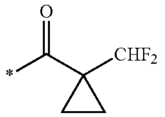 [SMILES: *C(=O)C1(C(F)F)CC1]

or a stereoisomer, a tautomer, an N-oxide, a hydrate, a solvate, or a salt thereof, or a mixture of same.

A further embodiment of the present invention covers compounds of formula (I) or formula (Ia), supra, in which R′ is

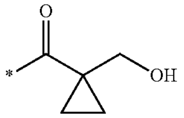 [SMILES: *C(=O)C1(CO)CC1]

or a stereoisomer, a tautomer, an N-oxide, a hydrate, a solvate, or a salt thereof, or a mixture of same.

A further embodiment of the present invention covers compounds of formula (I) or formula (Ia), supra, in which R′ is

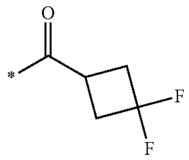 [SMILES: *C(=O)C1CC(F)(F)C1]

or a stereoisomer, a tautomer, an N-oxide, a hydrate, a solvate, or a salt thereof, or a mixture of same.

A further embodiment of the present invention covers compounds of formula (I) or formula (Ia), supra, in which R′ is

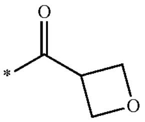 [SMILES: *C(=O)C1COC1]

or a stereoisomer, a tautomer, an N-oxide, a hydrate, a solvate, or a salt thereof, or a mixture of same.

A further embodiment of the present invention covers compounds of formula (I) or formula (Ia), supra, in which R′ is

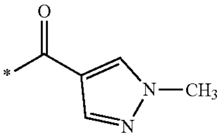 [SMILES: *C(=O)c1cnn(C)c1]

or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is —C(=O)—$CH_2$—CN or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is —C(=O)—$CH_2$—O—$CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is —C(=O)—O—$C(CH_3)_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is —C(=O)—O—$CH_2$—$CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is —C(=O)—$NH_2$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is —C(=O)—$N(CH_3)_2$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is —C(=O)—$CH_2$—$CHF_2$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is —C(=O)—NH-cyclopropyl or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is —C(=S)—$CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is —$SO_2$—$CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is

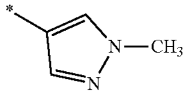

or a stereoisomer, a tautomer, an N-oxide, a hydrate, a solvate, or a salt thereof, or a mixture of same.

A further embodiment of the present invention covers compounds of formula (I) or formula (Ia), supra, in which $R^r$ is

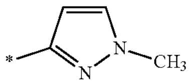 [SMILES: *c1ccn(C)n1]

or a stereoisomer, a tautomer, an N-oxide, a hydrate, a solvate, or a salt thereof, or a mixture of same.

A further embodiment of the present invention covers compounds of formula (I) or formula (Ia), supra, in which $R^s$ is —$CD_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^s$ is —$CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^t$ is —H or a stereoisomer, a tautomer, an N-oxide, a hydrate, a solvate, or a salt thereof, or a mixture of same.

A further embodiment of the present invention covers compounds of formula (I) or formula (Ia), supra, in which $R^t$ is D or a stereoisomer, a tautomer, an N-oxide, a hydrate, a solvate, or a salt thereof, or a mixture of same.

A further embodiment of the present invention covers compounds of formula (I) or formula (Ia), supra, in which both $R^1$ and $R^2$ are —$CH_3$ or a stereoisomer, a tautomer, an N-oxide, a hydrate, a solvate, or a salt thereof, or a mixture of same.

A further embodiment of the present invention covers compounds of formula (I) or formula (Ia), supra, in which $R^5$ is —$CF_3$ and $R^6$ is —F or a stereoisomer, a tautomer, an N-oxide, a hydrate, a solvate, or a salt thereof, or a mixture of same.

A further embodiment of the present invention covers compounds of formula (I) or formula (Ia), supra, in which $X^2$ is N and $X^3$ is CH or a stereoisomer, a tautomer, an N-oxide, a hydrate, a solvate, or a salt thereof, or a mixture of same.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers any sub-combination within any embodiment or aspect of the present invention of intermediate compounds.

The present invention covers the compounds of general formula (I) which are disclosed in the Example Section of this text, infra.

The compounds according to the invention of general formula (I) can be prepared according to the following schemes 1 to 12. The schemes and procedures described below illustrate synthetic routes to the compounds of general formula (I) of the invention and are not intended to be limiting. It is clear to the person skilled in the art that the order of transformations as exemplified in schemes 1 to 12 can be modified in various ways.

The order of transformations exemplified in these schemes is therefore not intended to be limiting. In addition, interconversion of any of the substituents, $R^1$, $R^2$, $R^3$, $R^4$, $R^5$, $R^6$ or Y can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis,* 3rd edition, Wiley 1999). Specific examples are described in the subsequent paragraphs.

Several routes for the preparation of compounds of general formula (I) are described in schemes 1 to 12.

The present invention covers the intermediate compounds which are disclosed in the Example Section of this text, infra.

The present invention covers any sub-combination within any embodiment or aspect of the present invention of intermediate compounds, supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action which could not have been predicted. Compounds of the present invention have surprisingly been found to effectively inhibit SOS1 and it is possible therefore that said compounds be used for the treatment or prophylaxis of diseases, preferably hyperproliferative disorders in humans and animals.

Compounds of the present invention can be utilized to inhibit, block, reduce, decrease, etc., cell proliferation and/or cell division, and/or produce apoptosis. This method comprises administering to a mammal in need thereof, including a human, an amount of a compound of general formula (I) of the present invention, or a pharmaceutically acceptable salt, isomer, polymorph, metabolite, hydrate, solvate or ester thereof, which is effective to treat the disorder.

Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell. Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The present invention also provides methods of treating angiogenic disorders including diseases associated with excessive and/or abnormal angiogenesis.

Inappropriate and ectopic expression of angiogenesis can be deleterious to an organism.

A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480; Peer et al., Lab. Invest., 1995, 72, 638], age-related macular degeneration (AMD) [Lopez et al., Invest. Opththalmol. Vis. Sci., 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing, decreasing, etc. endothelial cell proliferation, or other types involved in angiogenesis, as well as causing cell death or apoptosis of such cell types.

These disorders have been well characterized in humans, but also exist with a similar etiology in other mammals, and can be treated by administering pharmaceutical compositions of the present invention.

The term "treating" or "treatment" as stated throughout this document is used conventionally, for example the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention may be used to sensitize a cell to radiation, i.e. treatment of a cell with a compound of the present invention prior to radiation treatment of the cell renders the cell more susceptible to DNA damage and cell death than the cell would be in the absence of any treatment with a compound of the present invention. In one aspect, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In one aspect, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e. after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g. cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage.

By way of a non-limiting example, a DNA repair pathway in a cell can be inhibited, thereby preventing the repair of DNA damage and resulting in an abnormal accumulation of DNA damage in a cell.

In one aspect of the invention, a compound of general formula (I) of the present invention is administered to a cell prior to the radiation or other induction of DNA damage in the cell. In another aspect of the invention, a compound of general formula (I) of the present invention is administered to a cell concomitantly with the radiation or other induction of DNA damage in the cell. In yet another aspect of the invention, a compound of general formula (I) of the present invention is administered to a cell immediately after radiation or other induction of DNA damage in the cell has begun.

In another aspect, the cell is in vitro. In another embodiment, the cell is in vivo.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular hyperproliferative disorders.

The pharmaceutical activity of the compounds according to the invention can be explained by their activity as SOS1 inhibitor.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular hyperproliferative disorders, especially diseases associated with SOS1.

In accordance with a further aspect, the present invention covers the use of a compound of formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of diseases, in particular hyperproliferative disorders, especially diseases associated with SOS1.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular hyperproliferative disorders, especially diseases associated with SOS1.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular hyperproliferative disorders, especially diseases associated with SOS1.

In accordance with a further aspect, the present invention covers a method of treatment or prophylaxis of diseases, in particular hyperproliferative disorders, especially diseases associated with SOS1, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers),

- plasticizers (for example polyethylene glycols, propylene glycol, glycerol, triacetine, triacetyl citrate, dibutyl phthalate),
- penetration enhancers,
- stabilisers (for example antioxidants such as, for example, ascorbic acid, ascorbyl palmitate, sodium ascorbate, butylhydroxyanisole, butylhydroxytoluene, propyl gallate),
- preservatives (for example parabens, sorbic acid, thiomersal, benzalkonium chloride, chlorhexidine acetate, sodium benzoate),
- colourants (for example inorganic pigments such as, for example, iron oxides, titanium dioxide),
- flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prophylaxis of a hyperproliferative disorder, especially diseases associated with SOS1.

Particularly, the present invention covers a pharmaceutical combination, which comprises:

- one or more first active ingredients, in particular compounds of general formula (I) as defined supra, and
- one or more further active ingredients suitable for treatment of hyperproliferative disorder, especially diseases associated with SOS1.

The term “combination” in the present invention is used as known to persons skilled in the art, it being possible for said combination to be a fixed combination, a non-fixed combination or a kit-of-parts.

A “fixed combination” in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a “fixed combination” is a pharmaceutical composition wherein a first active ingredient and a further active ingredient are present in admixture for simultaneous administration, such as in a formulation. Another example of a “fixed combination” is a pharmaceutical combination wherein a first active ingredient and a further active ingredient are present in one unit without being in admixture.

A non-fixed combination or “kit-of-parts” in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known anti-cancer agents.

Examples of anti-cancer agents include:

131I-chTNT, abarelix, abemaciclib, abiraterone, acalabrutinib, aclarubicin, adalimumab, ado-trastuzumab emtansine, afatinib, aflibercept, aldesleukin, alectinib, alemtuzumab, alendronic acid, alitretinoin, alpharadin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, apalutamide, aprepitant, arcitumomab, arglabin, arsenic trioxide, asparaginase, atezolizumab, avelumab, axicabtagene ciloleucel, axitinib, azacitidine, basiliximab, belotecan, bendamustine, besilesomab, belinostat, bevacizumab, bexarotene, bicalutamide, bisantrene, bleomycin, blinatumomab, bortezomib, bosutinib, buserelin, brentuximab vedotin, brigatinib, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, cemiplimab, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, darolutamide, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, durvalumab, eculizumab, edrecolomab, elliptinium acetate, elotuzumab, eltrombopag, enasidenib, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, inotuzumab ozogamicin, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, lutetium Lu 177 dotatate, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, midostaurin, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, mvasi, nabilone, nabiximols, nafarelin, naloxone+pentazocine, naltrexone, nartograstim, necitumumab, nedaplatin, nelarabine, neratinib, neridronic acid, netupitant/palonosetron, nivolumab, pentetreotide, nilotinib, nilutamide, nimorazole, nimotuzumab, nimustine, nintedanib, niraparib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, ribociclib, risedronic acid, rhenium-186 etidronate, rituximab, rolapitant, romidepsin, romiplostim, romurtide, rucaparib, samarium (153Sm) lexidronam, sargramostim, sarilumab, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tisagenlecleucel, tislelizumab, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Based upon standard laboratory techniques known to evaluate compounds useful for the treatment of hyperproliferativegeneric disorders, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight.

The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

NMR peak forms are stated as they appear in the spectra, possible higher order effects have not been considered.

The $^{1}$H-NMR data of selected compounds are listed in the form of $^{1}$H-NMR peaklists. Therein, for each signal peak the δ value in ppm is given, followed by the signal intensity, reported in round brackets. The δ value-signal intensity pairs from different peaks are separated by commas. Therefore, a peaklist is described by the general form: $\delta_1$ (intensity$_1$), $\delta_2$ (intensity$_2$), . . . , $\delta_i$ (intensity$_i$), . . . , $\delta_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^{1}$H-NMR peaklist is similar to a classical $^{1}$H-NMR readout, and thus usually contains all the peaks listed in a classical NMR interpretation. Moreover, similar to classical $^{1}$H-NMR printouts, peaklists can show solvent signals, signals derived from stereoisomers of the particular target compound, peaks of impurities, 13C satellite peaks, and/or spinning sidebands. The peaks of stereoisomers, and/or peaks of impurities are typically displayed with a lower intensity compared to the peaks of the target compound (e.g., with a purity of >90%). Such stereoisomers and/or impurities may be typical for the particular manufacturing process, and therefore their peaks may help to identify a reproduction of the manufacturing process on the basis of "by-product fingerprints". An expert who calculates the peaks of the target compound by known methods (MestReC, ACD simulation, or by use of empirically evaluated expectation values), can isolate the peaks of the target compound as required, optionally using additional intensity filters. Such an operation would be similar to peak-picking in classical $^{1}$H-NMR interpretation. A detailed description of the reporting of NMR data in the form of peaklists can be found in the publication "Citation of NMR Peaklist Data within Patent Applications". In the peak picking routine, as described in the Research Disclosure Database Number 605005, the parameter "MinimumHeight" can be adjusted between 1% and 4%. However, depending on the chemical structure and/or depending on the concentration of the measured compound it may be reasonable to set the parameter "MinimumHeight"<1%.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

Abbreviations
The following table lists the abbreviations used herein.

| Abbreviation | Meaning |
|---|---|
| $Ac_2O$ | acetic anhydride |
| AcOH | acetic acid (ethanoic acid) |
| aq. | aqueous |
| Boc | tert-butoxycarbonyl |
| BOP | (benzotriazol-1-yloxy)tris(dimethylamino) phosphonium hexafluorophosphate |
| cat. | catalytic |
| conc. | concentrated |
| CI | chemical ionisation |
| DAD | diode array detector |
| DBU | 1,8-diazabicyclo(5.4.0)undec-7-ene |
| DCC | N,N'-dicyclohexylcarbodiimide |
| DCM | dichloromethane |
| DIPEA | diisopropylethylamine |
| DMA | N,N-dimethylacetamide |
| DMF | N,N-dimethylformamide |
| DMSO | dimethylsulfoxide |
| EDC | 1-ethyl-3-(3-dimethylaminopropyl)carbodiimide |
| ELSD | Evaporative Light Scattering Detector |
| EtOAc | ethyl acetate |
| EtOH | ethanol |
| eq. | equivalent |
| ESI | electrospray (ES) ionisation |
| h | hour(s) |
| HATU | 1-[bis(dimethylamino)methylene]-1H-1,2,3-triazolo [4,5-b]pyridinium 3-oxid hexafluorophosphate |
| HCl | hydrochloric acid |
| HPLC | high performance liquid chromatography |
| LC-MS | liquid chromatography mass spectrometry |
| min | minute(s) |
| MeCN | acetonitrile |
| MeOH | methanol |
| MS | mass spectrometry |
| NCS | N-chlorosuccinimide |
| NMR | nuclear magnetic resonance spectroscopy: chemical shifts (δ) are given in ppm. The chemical shifts were corrected by setting the DMSO signal to 2.50 ppm unless otherwise stated. |
| PDA | Photo Diode Array |
| Pd/C | palladium on activated charcoal |
| $PdCl_2$(dppf) | [1,1'-bis(diphenylphosphino)ferrocene]-dichloropalladium(II) |
| $Pd_2(dba)_3$ | tris-(dibenzylidenaceton)-dipalladium(0) |
| PyBOP | (benzotriazol-1-yloxy)tripyrrolidinophosphonium hexafluorophosphate |
| r.t. or rt or RT | room temperature |
| rac | racemic |
| Rt | retention time (as measured either with HPLC or UPLC) in minutes |
| sat. | saturated |
| SM | starting material |
| SPhos | 2-Dicyclohexylphosphino-2',6'-dimethoxybiphenyl |
| SQD | Single-Quadrupole-Detector |
| T3P | propylphosphonic anhydride |
| TEA | triethylamine |
| TFA | trifluoroacetic acid |
| THF | tetrahydrofuran |
| TLC | Thin layer chromatography |
| UPLC | ultra performance liquid chromatography |
| Xantphos | 4,5-Bis(diphenylphosphino)-9,9-dimethylxanthene |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent.

In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Experimental Section—General Procedures

The compounds of the present invention can be prepared as described in the following section. The schemes and the procedures described below illustrate general synthetic routes to the compounds of general formula (I) of the invention and are not intended to be limiting. It is clear to the person skilled in the art that the order of transformations as exemplified in the schemes can be modified in various ways. The order of transformations exemplified in the schemes is therefore not intended to be limiting. In addition, interconversion of any of the substituents can be achieved before and/or after the exemplified transformations. These modifications can be such as the introduction of protecting groups, cleavage of protecting groups, exchange, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example P. G. M. Wuts and T. W. Greene in "Protective Groups in Organic Synthesis", 4th edition, Wiley 2006). Specific examples are described in the subsequent paragraphs. Further, it is possible that two or more successive steps may be performed without work-up being performed between said steps, e.g. a "one-pot" reaction, as is well-known to the person skilled in the art.

The syntheses of the compounds of the present invention are preferably carried out according to the general synthetic sequences, shown in schemes 1-12.

Scheme 1

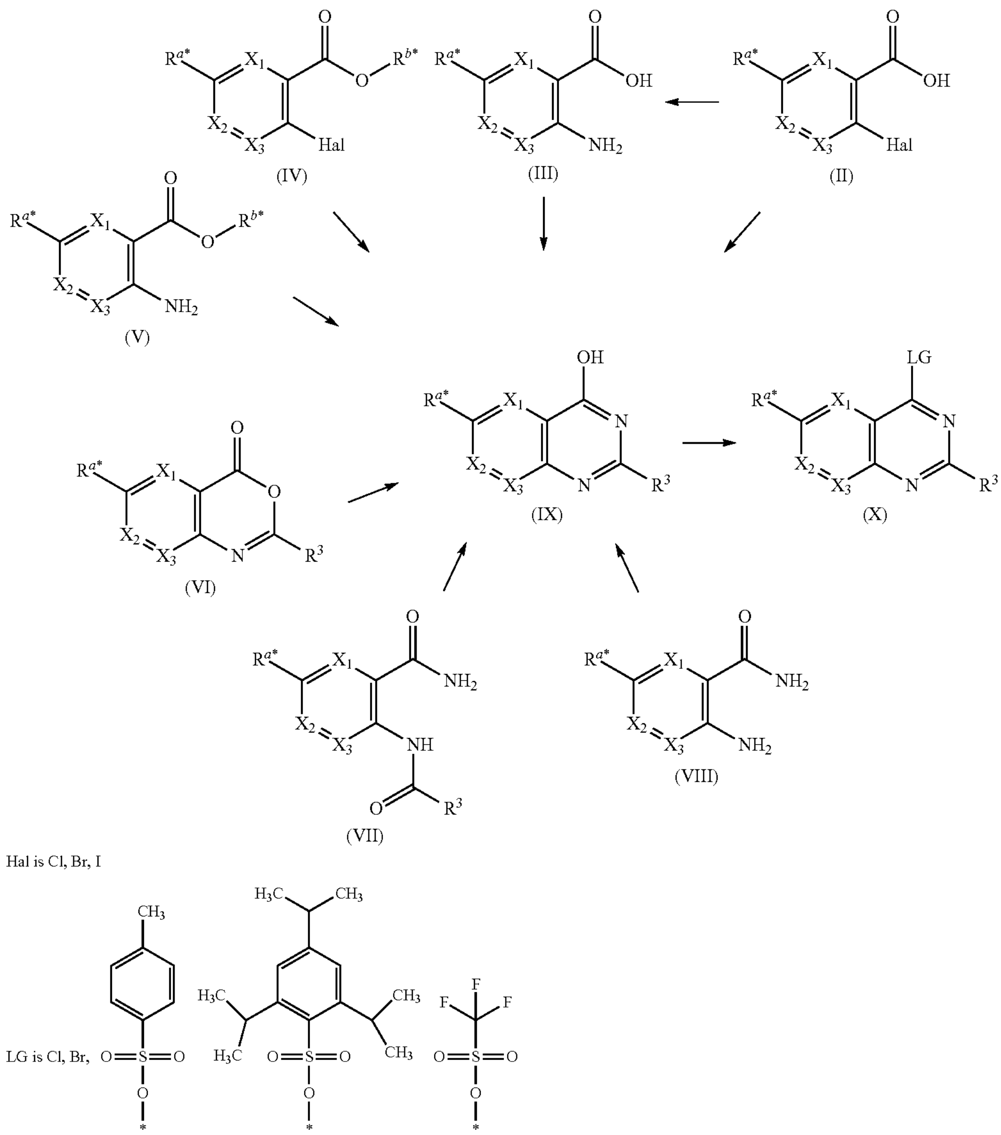

Scheme 1: Synthesis route for the preparation of compounds of general formula (IX), in which $X_1$, $X_2$, $X_3$ have the meaning as given for general formula (I), supra, $R^{a*}$ is a leaving group, for example (not limiting), halide, preferably chloro, bromo and $R^{b*}$ represents a protecting group. $R^{b*}$ could be for example (not-limiting), hydrogen, methyl, ethyl, propyl, isopropyl, butyl, tert-butyl and benzyl. $R^3$ is for example (not limiting) H, (fluorinated) alkyl. LG represents a leaving group, such as, for example, halide, preferably chloro, alkylsulfonyl, alkylsulfonate, and, arylsulfonate, as depicted.

Step 1→General Formula (IX) (Scheme 1)

Bicyclic pyrimidine formation: In the first step halogen substituted benzoic acid derivative of general formula (II) (which could be commercially available or described in the literature) could be converted to the corresponding bicyclic pyrimidine (IX) in analogy to literature procedures. Typically, derivative (II) is reacted with ammonia to form a derivative of general formula (III), preferably under elevated temperatures, optionally under high pressure, in water or an organic solvent or mixture thereof, such as for example, 1,2-dichloroethane, THF, methanol, ethanol. For example, see WO2017069275, US20030199511 and US20030187026 and the references therein. Alternatively, derivative (II) can be converted to the corresponding acid chloride, with for example thionyl chloride, oxalyl chloride, in an organic solvent, optionally with a drop of DMF, optionally at elevated temperature, in an organic solvent. The corresponding acid chloride can be treated with an imidamide or a salt thereof, with an inorganic base such as for example, caesium carbonate, sodium carbonate, potassium carbonate, or an organic base such as for example triethylamine, diisopropylethylamine or pyridine with or without DMAP, optionally using metal-catalyzed reactions, optionally in the presence of a ligand, in an organic solvent such as for example DMF, toluene, 1,4-dioxane/water at elevated temperature. For example, see WO2007134986, *Bioorg. Med. Chem. Lett.,* 2015, 23, 3013 and the references therein.

Step 2→General Formula (IX) (Scheme 1)

Bicyclic pyrimidine formation: Alternatively, amino substituted benzoic acid derivative of general formula (III) (which could be commercially available or described in the literature) could be converted to the corresponding bicyclic pyrimidine (IX) in analogy to literature procedures. Typically, derivative (Ill) is reacted with acetamidine or an imidamide, optionally with a base such as for example potassium carbonate or sodium hydroxide or triethylamine, diisopropylethylamine, 1,8-diazabicyclo[5.4.0]undec-7-ene or pyridine in an organic solvent such as for example DMF at elevated temperature. For example, see WO2004071460, WO2015155306 and *Chem. Med. Chem.,* 2014, 9, 2516.

Step 3→General Formula (IX) (Scheme 1)

Bicyclic pyrimidine formation: Alternatively, halogen substituted benzoic ester derivative of general formula (IV) (which could be commercially available or described in the literature) could be converted to the corresponding bicyclic pyrimidine (IX) in analogy to literature. Typically, derivative (IV) could be reacted with an imidamide or a salt there of, an inorganic base such as for example, caesium carbonate, sodium carbonate, potassium carbonate, or an organic base such as for example, triethylamine, diisopropylethylamine, 1,8-diazabicyclo[5.4.0]undec-7-ene or pyridine with or without DMAP, optionally using a metal-catalyzed reaction, optionally in the presence of a ligand, in an organic solvent such as for example DMF, toluene, 1,4-dioxane/water at elevated temperature. For example, see *Chem. Commun.,* 2008, 6333; *Bioorg. Med. Chem. Lett.,* 2013, 23, 3325; WO2018118735, WO2007134986 and references therein.

Step 4→General Formula (IX) (Scheme 1)

Bicyclic pyrimidine formation: Alternatively, amino substituted benzoic ester derivative of general formula (V) (which could be commercially available or described in the literature) could be converted to the corresponding bicyclic pyrimidine (IX) in analogy to literature procedures. Typically, derivative (V) could be reacted with a nitrile, carboxylic acid chloride, carboxylic acid anhydride, imidamide or a salt there of, in the presence of an acid or a base, in water or an organic solvent, or mixtures thereof, such as for example DMF, toluene, 1,4-dioxane/water at elevated temperature. For example, see *J. Med.* Chem., 2018, 61, 3389; *J. Med. Chem.,* 2019, 62, 9772; WO2004071460, WO2007134986 and references therein.

Step 5→General Formula (IX) (Scheme 1)

Bicyclic pyrimidine formation: Alternatively, benzoxazinone derivative of general formula (VI) (which could be commercially available or could be prepared in analogy to literature procedures) could be converted to the corresponding bicyclic pyrimidine (IX) in analogy to literature procedures. Typically, derivative (VI) could be reacted with ammonium acetate in an organic solvent at elevated temperature. For example, see J. *Med. Chem.,* 2019, 62, 9772; *J. Med. Chem.,* 2011, 54, 6734; *Bioorg. Med. Chem.,* 2014, 22, 5487 or WO2005105760 and references therein.

Step 6→General Formula (IX) (Scheme 1)

Bicyclic pyrimidine formation: Alternatively, benzoic acid amide derivative of general formula (VII) (which could be commercially available or described in the literature) could be converted to the corresponding bicyclic pyrimidine (IX) in analogy to literature procedures. Typically, derivative (VII) could be reacted with a base such as for example sodium hydroxide in a solvent such as for example water at elevated temperature. For example, see Monatshefte FQr Chemie, 1987, 118, 399; WO2007134986, WO2013016999; WO2012028578 and references therein.

Step 7→General Formula (IX) (Scheme 1)

Bicyclic pyrimidine formation: Alternatively, amino benzoic acid amide derivative of general formula (VIII) (which could be commercially available or described in the literature) could be converted to the corresponding bicyclic pyrimidine (IX) in analogy to literature procedures. Typically, derivative (VIII) could be reacted with an organic acid at elevated temperature, an organic acid amide or carboxylic acid anhydrides or using copper-catalyzed reactions, optionally with a base, water or an organic solvent or mixtures thereof, preferably at elevated temperatures. For example, see *Eur. J. Org. Chem.,* 2020, 2730; *Polish Journal of Pharmacology* and Pharmacy, 1985, 37, 541; Heterocycles, 2015, 90, 857; Yakugaku Zasshi, 1977, 97, 1022 and references therein.

Step (IX)→(X) (Scheme 1)

Conversion of Hydroxyl Group into Leaving Group

In the next step (scheme 1) compound (IX) can be converted to the corresponding derivative (X) bearing a leaving group (LG) in analogy to literature procedures.

For LG=chloro or bromo typically with phosphorus oxytrichloride or phosphorus oxytribromide, respectively, with or without N,N-dimethylaniline or N,N-diisopropylethylamine with or without an organic solvent such as for example toluene at elevated temperatures is used. For examples, see US2012/53174; WO2012/30912 or WO2012/66122 and references therein.

For LG=2,4,6-triisopropylbenzenesulfonate typically 2,4,6-triisopropylbenzenesulfonyl chloride, a base such as for example triethylamine and/or DMAP in an organic solvent such as for example dichloromethane is used. For example, see WO2010/99379, US2012/53176 and references therein.

For LG=tosylate typically 4-methylbenzene-1-sulfonyl chloride, a base such as for example triethylamine or potassium carbonate and/or DMAP in an organic solvent such as for example dichloromethane or acetonitrile is used. For examples, see *Org. Lett.*, 2011, 4374 or *Bioorg. Med. Chem. Lett.*, 2013, 2663 and references therein.

For LG=trifluoromethanesulfonate typically N,N-bis(trifluoromethylsulfonyl)aniline or trifluoromethanesulfonic anhydride, a base such as for example triethylamine or 1,8-diazabicyclo[5.4.0]undec-7-ene and/or DMAP in an organic solvent such as for example dichloromethane is used. For examples, see *J. Am. Chem. Soc.*, 2015, 13433 or WO2014/100501 and references therein.

Scheme 2

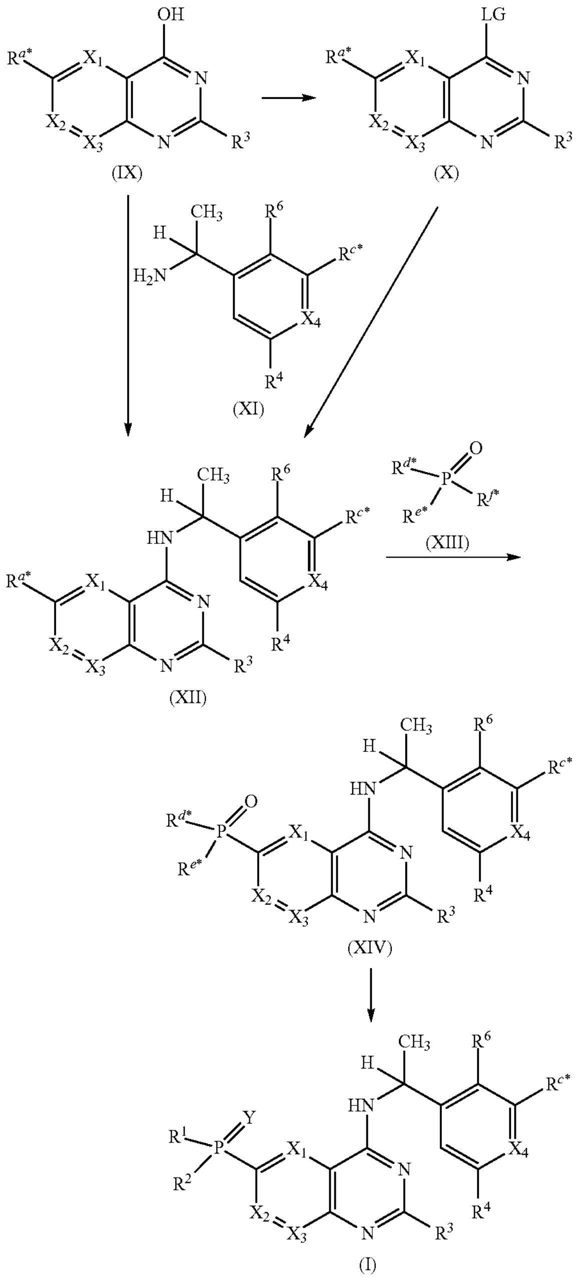

Scheme 2: Synthesis route for the preparation of compounds of general formula (I) in which $R^{a}$* represents a leaving group, for example (not limiting) halide, preferably chloro or bromo and $R^{c}$* represents a protected derivative of $R^5$. $R^{d}$* and $R^{e}$* are $R^1$ and $R^2$ as in general formula (I) or (protected) derivatives thereof. $R^{f}$* is H or a leaving group, such as, for example chloro. LG represents a leaving group, such as, for example, halide, preferably chloro, alkylsulfonyl, alkylsulfonate or arylsulfonate, as depicted in scheme 1. Compounds of general formula (XII) are well known in the public domain and can be formed from compounds of general formula (IX) with compounds of general formula (XI) using dehydrative conjugation methods. Such methods are known using coupling reagents like benzotriazol-1-yloxytris(dimethylamino)phosphonium hexafluorophosphate (BOP) and benzotriazol-1-yl-oxytripyrrolidinophosphonium hexafluorophosphate (pyBOP), see the teachings of *J. Org. Chem.*, 2007, 72, 10194; *Advanced Synthesis & Catalysis*, 2018, 360, 4764; *Bioorg. Med. Chem.*, 2019, 27, 931; WO 2011028741 A1; are in the public domain.

Alternatively, compounds of general formula (XII) can be formed in a two-step process, whereby compounds of general formula (IX) are converted to compounds of general formula (X) using standard well-documented methods, such as, when LG=$C_1$ using phosphorus oxytrichloride, or LG=Br using phosphorus oxytribromide, or LG=tosylate typically 4-methylbenzene-1-sulfonyl chloride, a base such as for example triethylamine or potassium carbonate and/or DMAP in an organic solvent such as for example dichloromethane or acetonitrile. For examples, see *Org. Lett.*, 2011, 4374 or *Bioorg.* Med. *Chem. Lett.*, 2013, 2663 and references therein.

Subsequently the compounds of general formula (X) can be converted to compounds of general formula (XII), using a nucleophilic substitution reaction ($S_NAr$) with compounds of general formula (XI) which are well-documented in the public domain and are known to those skilled in the art.

Compounds of general formula (XIV) can be formed from compounds of general formula (XII), with compounds of general formula (XIII) using literature-known methods. Compounds of general formula (XIII) are well-known in the public domain, commercially available or could be synthesized by known synthetic routes. For example (not-limiting) when $R^{f}$* is H, metal catalyzed reactions could be carried out. For examples, see the teachings of US2019/270704, 2019, A1; US2015/225436, 2015, A1 or *J. Med. Chem.* 2020, 63, 7081 and references therein. When $R^{f}$* is a leaving group (not-limiting), such as, for example, chloro, nucleophilic substitution reactions could be carried out. For examples, see WO2008/110611, 2008, A1 or *J. Med. Chem.* 2020, 63, 7081 and references therein.

Subsequently the compounds of general formula (XIV) can be converted to compounds of general formula (I) by using standard well-documented methods, such as (not-limiting) functional group manipulations. For example (not-limiting) when $R^{o}$* is a protected derivative of $R^5$ in general formula (I), removal of protecting groups can be carried out. Further functional group manipulations for $R^{d}$* and $R^{e}$* can be performed in analogy to the literature, see for example *J. Med. Chem.* 2020, 63, 7081 and references therein. When Y=S, see for example CN109776607, 2019, A or *Synthesis* 2020, 52, 141.

Scheme 3

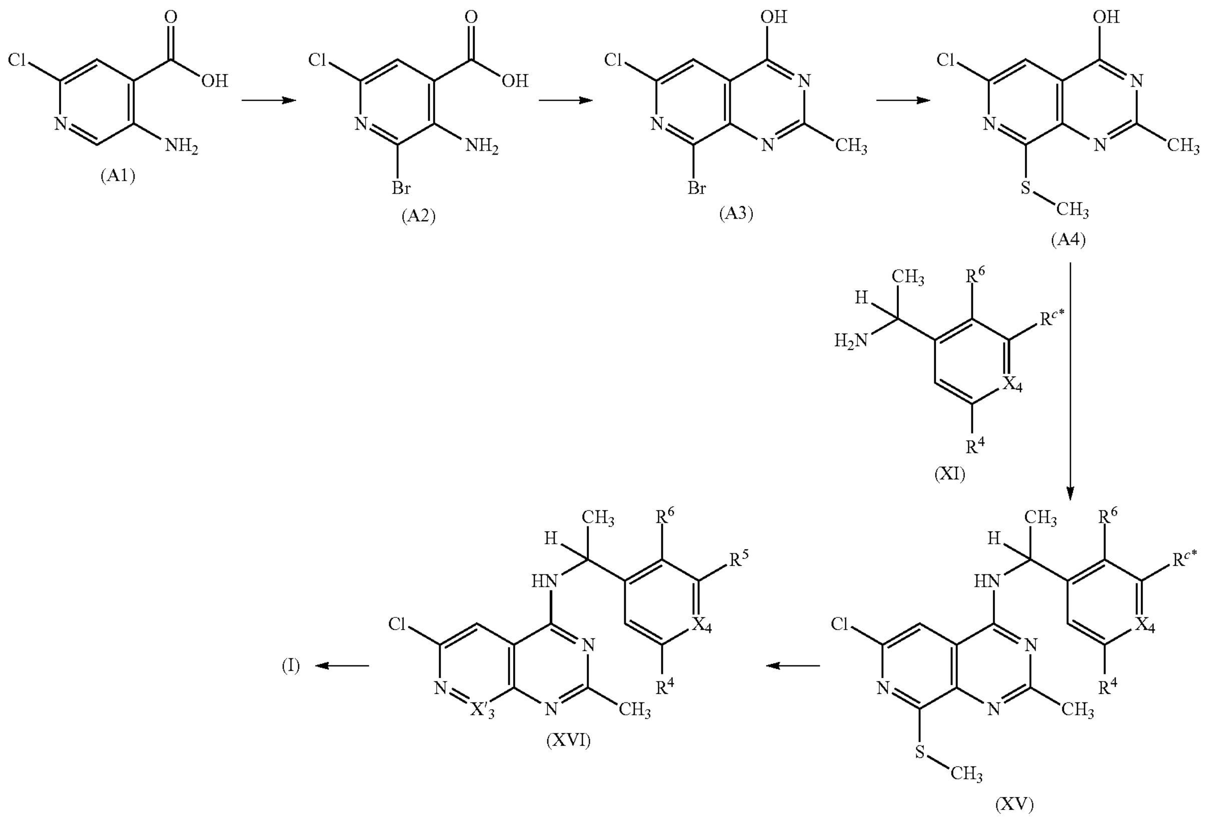

(A1) (A2) (A3) (A4) (XI) (XV) (XVI) (I)

Scheme 3: Synthesis route for the preparation of compounds of general formula (XVI), in which $X'_3$ represents a subset of $X_3$ (where $X_3$ is not N) and $X_4$, $R^4$, $R^5$ and $R^6$ have the meaning as given for general formula (I), supra. $R^{c}*$ is $R^5$ as in general formula (I) or a protected derivative of $R^5$.

The reactions shown in scheme 3 can be performed using different chemistries known to those skilled in the art.

For example, commercially available compound (A1) can be transformed into compound (A2) by a known procedure (for example, see WO2008/130021, 2008, A2). Compound (A2) can be cyclized to compound (A3) as described in scheme 1. Compound (A4) can be obtained from compound (A3) by nucleophilic aromatic substitution (SnAr) with NaSMe in an organic solvent such as for example DMSO at RT (for examples, see US2014/336190, 2014, A1, *Tetrahedron,* 2002, 58, 4931, WO2010/24451, 2010, A1). Compounds of general formula (XV) can be obtained from compound (A4) as described in scheme 2. Compounds of general formula (XV) can be transformed into compounds of general formula (XVI) using different chemistries known to those skilled in the art. For example, palladium-catalyzed reactions (for examples, see WO2012/52167, 2012, A1), nucleophilic aromatic substitutions (for examples, see WO2012/52167, 2012, A1) or oxidation/nucleophilic aromatic substitution sequences (for examples, see KR2016/37198, 2016, A) can be performed. Compounds of general formula (XVI) can be transformed into compounds of general formula (I) as described in scheme 2.

Scheme 4

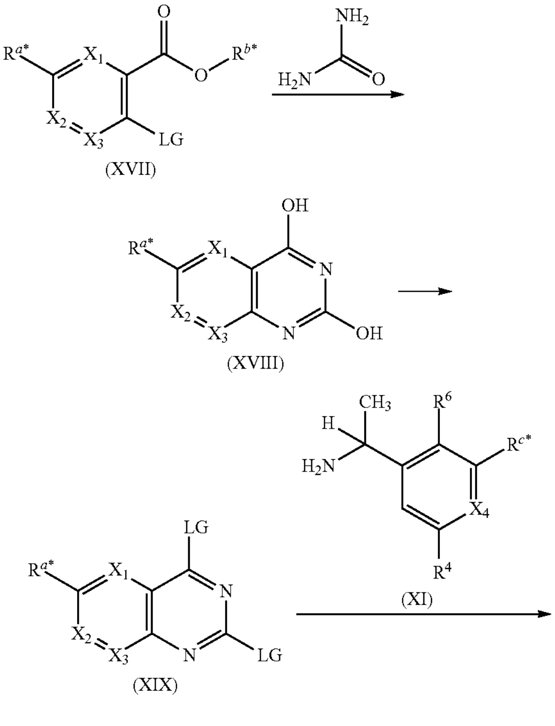

(XVII) (XVIII) (XI) (XIX)

-continued

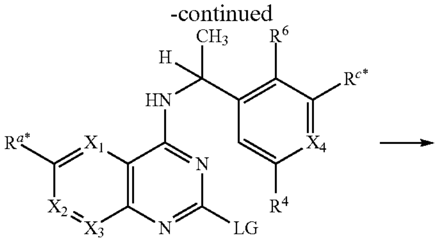

(XX)

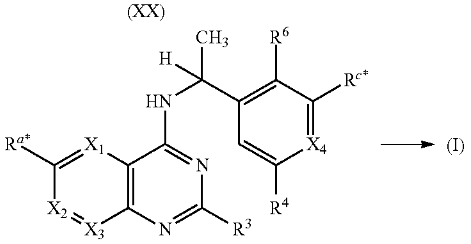

(XII)

Scheme 4: Synthesis route for the preparation of compounds of general formula (XII) in which $R^{a*}$ represents $P(O)R^{d*}R^{e*}$ as depicted in scheme 2 or a leaving group, for example (not limiting), halide, preferably chloro or bromo, and $R^{c*}$ is $R^5$ as in general formula (I), supra, or a protected derivative of $R^5$.

Compounds of general formula (XVIII) are well-known in the public domain, commercially available or could be synthesized by known synthetic routes, for example, via formation of the heteroaromatic ring via a reaction of compounds of general formula (XVII) with urea under different conditions (for example, see the teachings of Luo et al., CN 102584828) or multiple step syntheses as illustrated in the teachings of Brogi et al., *J. Med. Chem.,* 2018, 61, 2124; Bergeron et al., WO 2010014939 A1.

The transformation of compounds of general formula (XVIII) to compounds of general formula (XIX) are well-known in the public domain. For example, when LG=chloro typically trichlorophosphate or thionylchloride, with or without N,N-dimethylaniline or N,N-diisopropylethylamine, with or without an organic solvent such as, for example, toluene at elevated temperatures could be used. For examples, see Cantin et al., *J. Bioorg. Med. Chem. Lett.,* 2012, 2565; Bayrakdarian et al., WO 2008136756 A1; Luo et al., CN 102584828; Zhou et al., *J. Med. Chem.,* 2015, 58, 9480.

For LG=bromo typically phosphorus oxytribromide, with or without base, with or without an organic solvent such as for example toluene at elevated temperatures could be used.

For examples, see Kim et al., *J. Org. Chem.,* 2004, 69, 5638.

The transformation of compounds of general formula (XIX) to compounds of general formula (XX) with compounds of general formula (XI) are well-known in the public domain and are similarly illustrated in scheme 2 for the conversion of (X) to (XII). For example, such nucleophilic substitutions are well-documented, see the teachings of Liwicki et al., WO 2018066718 A1; Gelin et al., WO 2013016197 A1; Jiang, et al., *J. Med. Chem.,* 2016, 59, 10498.

Compounds of general formula (XX) can be converted to compounds of general formula (XII) using different synthetic methods, such as, for example, the Suzuki reaction (Liwicki et al., WO 2018066718 A1; Pulipati, et al., *Synth. Commun.,* 2017, 47, 1142), the Stille reaction (Johnson et al., WO 2011028741 A1; Labadie et al., *Bioorg. Med. Chem. Lett.,* 2013, 23, 5923) or other methods, see the teachings of Finlay et al., *ACS Med. Chem.* Letters, 2016, 7, 831.

The remaining steps from compounds of general formula (XII) to compounds of general formula (I) within scheme 4 follow the same route and methods as described in scheme 2.

Amine Syntheses

Scheme 5

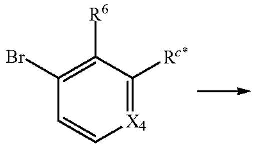

(XXI)

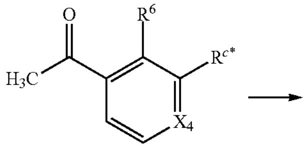

(XXII)

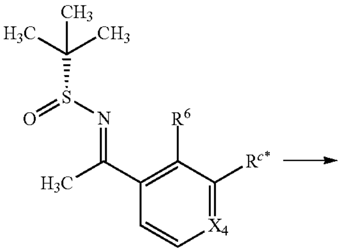

(XXIII)

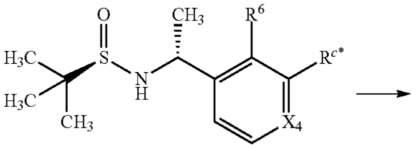

(XXIV)

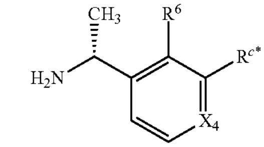

(XXV)

Scheme 5: Synthesis route for the preparation of compounds of general formula (XXV) in which $X_4$ and $R^6$ have the meaning as in the general formula (I), supra, $R^{o*}$ is $R^5$ as in general formula (I), supra, or a protected derivative of $R^5$.

Step (XXI)→(XXII) (Scheme 5)

In the first step (scheme 5) the bromo derivatives (XXI) (which are commercially available or described in the literature) can be converted to the corresponding acetyl compounds (XXII) in analogy to the numerous literature procedures. For example, the reaction can be performed using different chemistries known to those skilled in the art, for example, Grignard chemistry using magnesium in an organic solvent such as for example THF through the addition of the aryl magnesium Grignard reagent to a Weinreb amide; or palladium catalyzed chemistry or Stille chemistry. For such transformations see the teachings of (Grignard: Fillon et al., *Tetahedron* 2003, 59, 8199; Leazer et al., *Org. Synth.* 2005, 82, 115; Palladium: WO2005/5382; Stille: WO2019/122129 and the references therein).

Step (XXII)→(XXIII) (Scheme 5)

Acetyl derivatives (XXII) (which are commercially available or described in the literature or prepared from (XXI) can be converted to the corresponding chiral sulfinimines (XXIII) in analogy to the numerous literature procedures. For example the reaction can be performed at ambient temperature using titanium(IV) ethoxide or titanium(IV) isopropoxide in an organic solvent such as for example THF. For examples, see *Chem. Rev.* 2010, 110, 3600-3740*; Chem. Soc. Rev.* 2009, 38, 1162-1186*; Tetrahedron* 2004, 60, 8003 or WO2019/122129 and the references therein.

Step (XXIII)→(XXIV) (Scheme 5)

The (R)-sulfinimines (XXIII) can be converted to the corresponding (R)-sulfinamides (XXIV) in analogy to the numerous literature procedures. For example, the reaction can be performed using a reducing agent, for example, sodium borohydride or borane-THF, in an organic solvent such as for example ethanol, methanol or THF. Such transformations are known to those skilled in the art, see the teachings of Pan et al., *Tetrahedron Asym.,* 2011, 22, 329; WO2019/122129; Li et al., *Chem. Med. Chem.,* 2018, 13, 1363; Ghosh et al., *Eur. J. Med. Chem.,* 2018, 160, 171. Alternatively, the reaction can be performed using a reducing agent such as for example diisopropylaluminium hydride, in an aprotic solvent, for example, toluene. Such transformations are known to those skilled in the art, see the teachings of WO2017/6282; Lee et al., *Synlett.,* 2019, 30, 401. Alternatively, the (R)-sulfinamides (XXIV) can be obtained from the corresponding (S)-sulfinimines (XXIII) using L-selectride in an organic solvent such as THF. Such transformations are known to those skilled in the art. For examples, see *J. Org. Chem.* 2006, 71, 6859 an/or *J. Org. Chem.* 2007, 72, 626 and the references therein.

Step (XXIV) 4 (XXV) (Step 5):

The (R)-sulfinamides (XXIV) can be converted to the corresponding (R)-amines (XXV) in analogy to the numerous literature procedures. For example, the reaction can be performed using hydrogenchloride (HCl) in an aprotic organic solvent such as dioxane to give the corresponding HCl salts. Basic aqueous work up gives the free $NH_2$ amine. For a review about sulfinimine and sulfonamide chemistry, see for example *Chem. Rev.* 2010, 110, 3600-3740*; Chem. Soc. Rev.* 2009, 38, 1162-1186*; Tetrahedron* 2004, 60, 8003 or WO2013030138 and the references therein.

Scheme 6

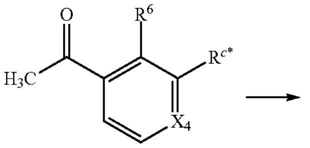

(XXII)

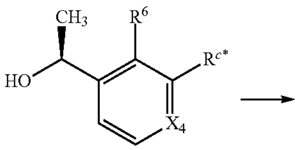

(XXVI)

-continued

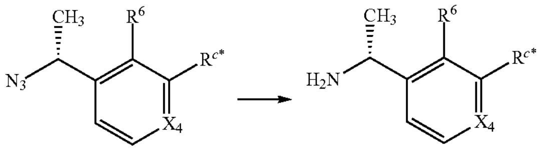

(XXVII) (XXV)

Scheme 6: Alternative synthesis route for the preparation of compounds of the general formula (XXV) in which $X_4$ and $R^6$ have the same meaning as in the general formula (I), supra, and $R^{c}$* is $R^5$ as in general formula (I), supra, or a protected derivative of $R^5$.

Step (XXII) 4 (XXVI) (Scheme 6)

In the first step (scheme 6) ketone derivatives of general formula (XXII) (which are commercially available or described in the literature or prepared as described in scheme 5) can be converted to the corresponding chiral (S)-alcohols (XXVI) in analogy to the numerous literature procedures. For example, the enantioselective reduction can be performed using catalytic hydrogenation, with hydrogen gas under pressure with a catalyst, for example a BINAP-derived catalyst, e.g. (R)- or (S)—RUCY-Xyl-BINAP (see WO2019/122129 page 140 or WO2013/185103 page 81) or using a CBS-Reduction (Corey-Bakshi-Shibata-Reduction) procedure. Such transformations are known to those skilled in the art, for references, see *J. Org. Chem.* 1988, 53, 2861.

Step (XXVI)→(XXVII) (Scheme 6)

The chiral (S)-alcohols (XXVI) can be converted to the corresponding (R)-azides (XXVII) in analogy to the numerous literature procedures. For example, the reaction can be performed using diphenylphosphonic azide and a base, for example, DBU, in an aprotic organic solvent as for example toluene (see the teachings of WO2019/122129 page 144). For a review about azide chemistry see for example *Chem. Rev.* 1988, 88, 297 and the references therein.

Step (XXVII)→(XXV) (Scheme 6)

The (R)-azides (XXVII) can be converted to the corresponding (R)-amines (XXV) in analogy to the numerous literature procedures. For example, the reaction can be performed using the Staudinger reduction conditions, with a phosphine, for example, triphenyl phosphine, in water with various different organic solvents, for example methanol, ethanol or THF. Alternatively, the azide reduction can be carried out using catalytic hydrogenation methods, using a metal catalyst, for example, palladium on charcoal, under a pressurized atmosphere of hydrogen (see the teachings of WO2019/122129 page 144). For a review about azide chemistry see for example Chem. Rev. 1988, 88, 297 and the references therein.

Scheme 7

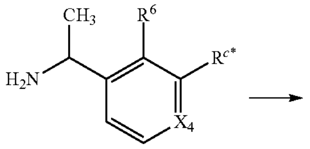

(XXVIII)

-continued

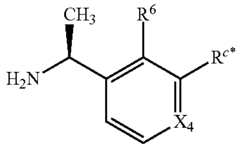

(XXIX)

+

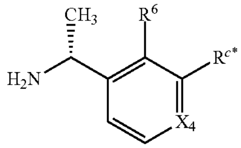

(XXV)

Scheme 7: Alternative synthesis route for the preparation of compounds of the general formula (XXV) in which $X_4$ and $R^6$ have the same meaning as in the general formula (I), supra, and $R^{c*}$ is $R^5$ as in general formula (I), supra, or a protected derivative of $R^5$.

To those skilled in the art it is possible to carry out the chemical reaction described in scheme 7, where the stereoisomers of (XXVIII) can be separated using various methods known to those skilled in the art, such as, for example, separation using chiral HPLC purification. The separation of these stereoisomers can be carried out on compounds of general formula (XXVIII) to obtain compounds with the general structure (XXV).

Scheme 8: Synthetic routes for chiral N-Boc protected amines with various functionalities for the preparation of compounds of the general formula edXXIII to X) in which $X_4$, $R^6$, $R^j$ and $R^k$ have the same meaning as in the general formula (I), supra, and $R^{g*}$ and $R^{h*}$ are independently from each other selected from —$OH_3$ or —H. $R^{i*}$ can be selected from —$CH_3$, —$CH_2CH_3$ or cyclopropyl.

Step (XXX) 4→(XXXI) (Scheme 8)

Acetyl arenes (XXX) (which are commercially available or can be prepared from literature procedures) can be converted to the corresponding chiral (R)-Boc amines (XX) following the synthetic route and procedures as depicted in schemes 5-7.

Step (XXXI) 4→(XXXII) (Scheme 8)

The aryl iodides (XXXI) can be transformed to the esters (XXI) to form a new C—C bond trough literature procedures. Such transformations are known to those skilled in the art as "Ullmann reaction" or "Negishi coupling". For example, the aryl iodides (XXXII) and fluoroalkyl bromide (XXXIa) are reacted in the presence of an excess of Cu(0) powder at elevated temperature. Alternatively, the alkyl bromide can be transformed to the corresponding zinc Scheme 8

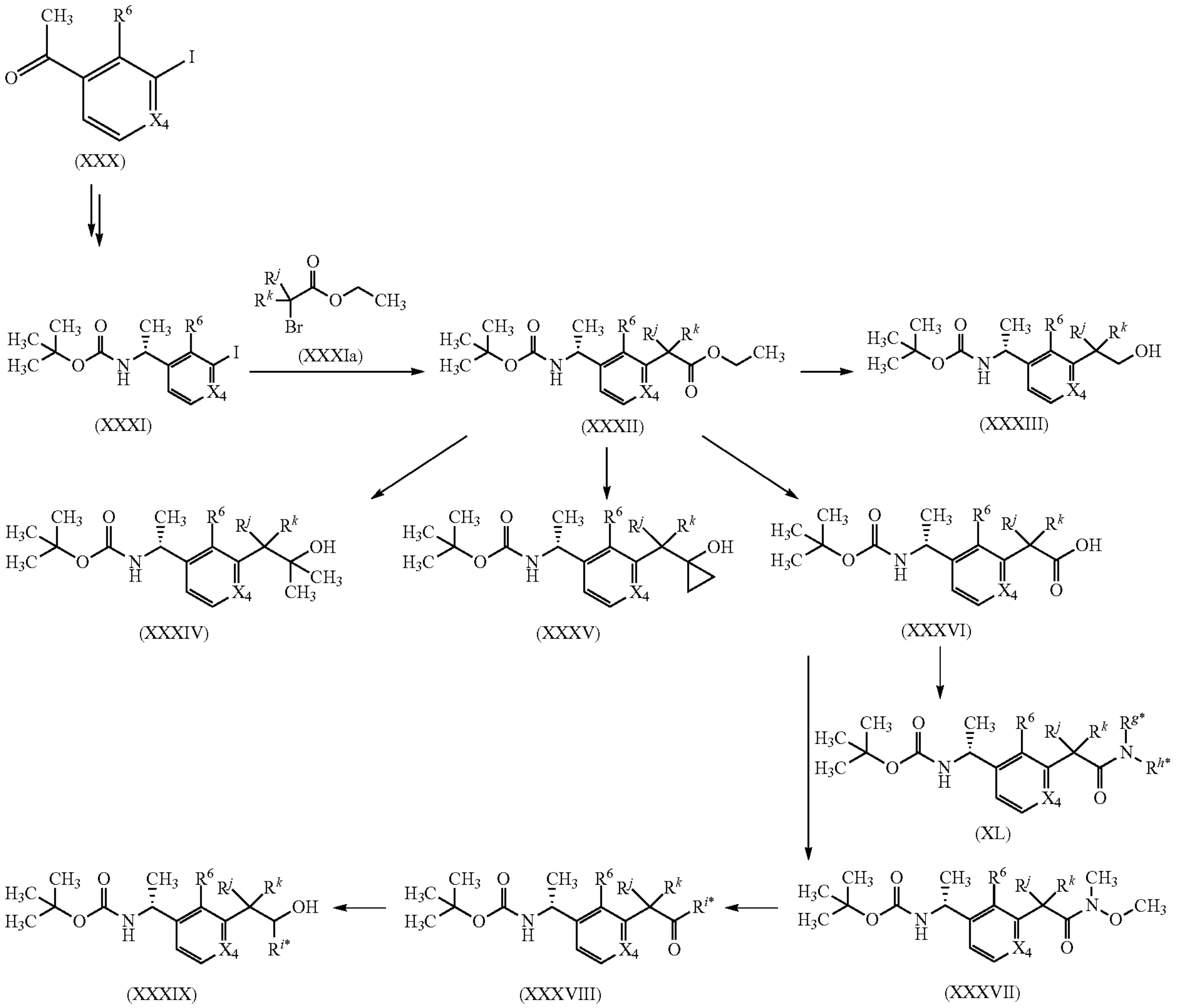

(XXX) (XXXIa) (XXXI) (XXXII) (XXXIII) (XXXIV) (XXXV) (XXXVI) (XL) (XXXIX) (XXXVIII) (XXXVII)

reagent through literature procedures. For example, such transformation can be achieved using zinc powder and the alkyl bromide (XXXIa) in an aprotic organic solvent such as DMA or THF. The coupling of the zinc reagent and the aryl halides (XXXI) can be achieved using standard palladium catalysis conditions. For example, such a transformation can be achieved using tris(dibenzylideneacetone)dipalladium(0) with an appropriate ligand, such as SPhos in an aprotic organic solvent such as DMA or THF at elevated temperatures. For examples, see *Adv. Synth. Catal.* 2018, 360, 1605, *Chem. Commun.* 2012, 48, 7738, E. *J. Org. Chem.* 2016, 33, 5529, *J. Org. Chem* 2013, 78, 8250 and/or *Chem. Lett.* 2015, 44, 818 and the references therein.

Step (XXXII)→(XXXIII) (Scheme 8)

The esters (XXXII) can be reduced to the primary alcohols (XXXIII) using standard literature procedures. Such transformations are known to those skilled in the art, for example, the reaction can be accomplished by using a reducing agent such as sodium borohydride in a protic organic solvent such as methanol or ethanol or in an aprotic organic solvent such as THF. For examples, see *Adv. Synth. Catal.* 2018, 360, 1605 or US2005/54658, 2005, A1, page 18 and/or *Bioorg. Med. Chem.* 2017, 25, 496.

Step (XXXII)→(XXXIV) (Scheme 8)

The esters (XXXII) can be transformed to the tertiary alcohols (XXXIV) using standard literature procedures. Such transformations are known to those skilled in the art, for example, the reaction can be accomplished by using a Grignard reagent such as methyl magnesium bromide or methyl magnesium chloride in an aprotic organic solvent such as THF. For examples, see *J. Am. Chem. Soc.* 2020, 142, 2984 and/or Q. Rev. Chem. Soc. 1967, 21, 259 and the references therein.

Step (XXXII)→(XXXV) (Scheme 8)

The esters (XXXII) can be transformed to the cyclopropyl alcohols (XXXV) using standard literature procedures. Such transformations are known to those skilled in the art under the name "Kulinkovich reaction", for example, the reaction can be accomplished by treating the ester with catalytic amounts of titanium(IV) isopropoxide or titanium(IV) ethoxide and a Grignard reagent such as ethyl magnesium bromide or ethyl magnesium chloride in an aprotic organic solvent such as THF, diethylether or toluene. For references for this chemistry and training and procedures, see *Org. Lett.* 2013, 15, 4968, Adv. Synth. Catal. 2004, 346, 760 and/or *J. Am. Chem. Soc.* 2001, 123, 5777 and the references therein.

Step (XXXII)→(XXXVI) (Scheme 8)

The esters (XXXII) can be hydrolysed to the carboxylic acids (XXXVI) using standard literature procedures. Such transformations are known to those skilled in the art, for example, the reaction can be accomplished by treating the ester with lithium hydroxide in a water and THF or methanol mixture or sodium hydroxide in water and dioxane. For examples, see US2013/303798, 2013, A1 and/or WO2014/153667, A1 and the references therein.

Step (XXXVI)→(XXXVII) (Scheme 8)

The carboxylic acids (XXXVI) can be transformed to the Weinreb amides (XXXVII) using standard literature procedures. Such transformations are known to those skilled in the art. For example, such transformations can be achieved using HATU, DCC, EDC*HCl, T3P, $SOCl_2$ and/or oxalyl chloride in an organic solvent such as dichloromethane or N,N-dimethylformamide, using N,O-dimethylhydroxylamine as coupling partner. For examples, see EP1007514, 2006, B1, E. *J. Org. Chem.* 2017, 25, 3584, *Org. Lett.* 2018, 20, 4691 and/or *Adv. Synth. Catal.* 2020, 362, 1106 and the references therein.

Step (XXXVII)→(XXXVIII) (Scheme 8)

The Weinreb amides (XXXVII) can be transformed to the ketones (XXXVIII) using standard literature procedures. Such transformations are known to those skilled in the art. For example, such a transformation can be achieved by using methyl magnesium bromide or ethyl magnesium chloride or cyclopropyl magnesium chloride in THF. For examples, see *Bioorg. Med. Chem.* 2016, 24, 2707, *Adv. Synth. Catal.* 2020, 362, 1106 and/or CN104803954, 2018, B and the references therein.

Step (XXXVIII)→(XXXIX) (Scheme 8)

The ketones (XXXVIII) can be transformed to the secondary alcohols (XXXIX) using standard literature procedures. Such transformations are known to those skilled in the art. For example, such transformation can be achieved using sodium borohydride in protic organic solvents such as methanol or ethanol or in aprotic organic solvents such as THF. Alternatively, lithium aluminium hydride can be used in aprotic organic solvents such as diethyl ether. For examples, see *Angew. Chem. Int. Ed.* 2019, 58, 17393, *J. Am. Chem.* Soc. 1996, 118, 5952, and/or *J. Org. Chem.* 1989, 54, 661 and the references therein.

Step (XXXVI)→(XL) (Scheme 8)

The carboxylic acids (XXXVI) can be transformed to the amides (XL) using standard literature procedures. Such transformations are known to those skilled in the art. For example, such a transformation can be achieved using HATU, DCC, EDC*HCl, T3P, $SOCl_2$ and/or oxalyl chloride in an organic solvent such as dichloromethane or N,N-dimethylformamide, using a primary or secondary amine or ammonia (derivatives) as coupling partner. For examples, see EP1007514, 2006, 1, E. *J. Org. Chem.* 2017, 25, 3584, *Org. Lett.* 2018, 20, 4691 and/or *Adv. Synth. Catal.* 2020, 362, 1106 and the references therein.

Scheme 9

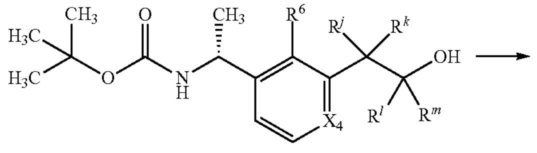

(XLa)

-continued

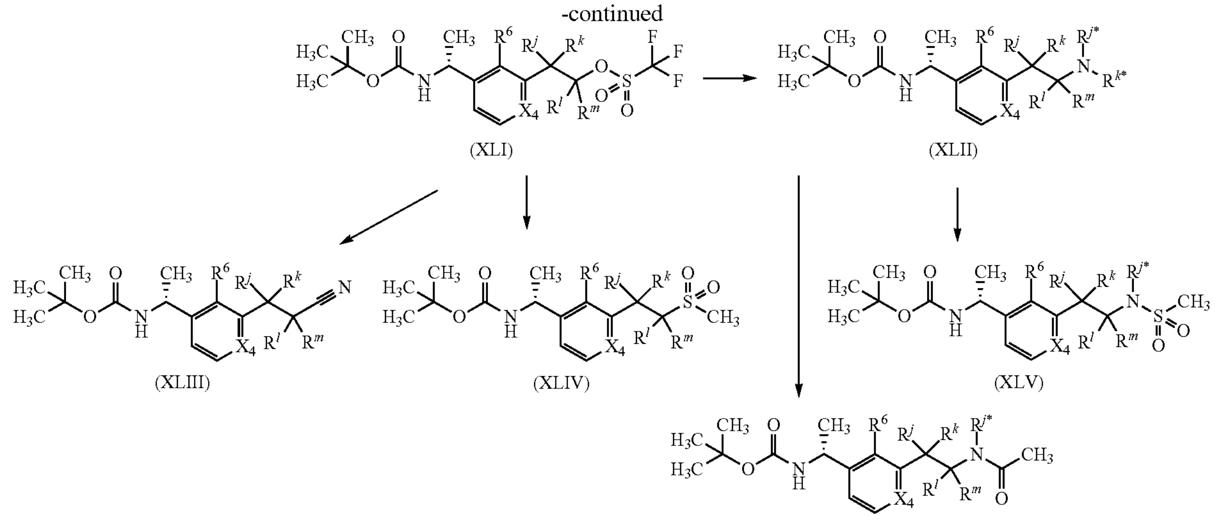

(XLI) (XLII) (XLIII) (XLIV) (XLV) (XLVI)

Scheme 9: Synthetic routes for chiral N-Boc protected amines with various functionalities of the general formula (XLII to XLVI) in which $X_4$, $R^6$, $R^j$, $R^k$, $R^l$ and $R^m$ have the same meaning as in the general formula (I), supra, and $R^{j*}$ and $R^{k*}$ can be independently selected from —H or —$CH_3$.

Step (XLa)→(XLI) (Scheme 9)

The alcohols (XLa), which can be prepared following the synthetic route and procedures as depicted in scheme 8, can be transformed to the triflates (XLI) using standard literature procedures. Such transformations are known to those skilled in the art. For example, the transformation can be achieved using trifluoromethanesulfonic anhydride in combination with triethylamine or pyridine in an aprotic organic solvent such as dichloromethane. For examples, see *Angew. Chem. Int. Ed.* 2014, 53, 6473, *Adv. Synth. Catal.* 2018, 360, 3667 and/or *Org. Lett.* 2020, 22, 6568 and the references therein.

Step (XLI)→(XLII) (Scheme 9)

The triflates (XLI) can be transformed to the amines (XLII) using standard literature procedures. Such transformations are known to those skilled in the art. For example, such transformation can be achieved using the secondary or primary amine or ammonia as nucleophile in a polar organic solvent such as acetonitrile or N,N-dimethylacetamide at elevated temperatures. For examples, see WO2016/49048, 2016, A1; WO2016/44323, 2016, A1 and the references therein.

Step (XLI)→(XLIII) (Scheme 9)

The triflates (XLI) can be transformed to the nitriles (XLIII) using standard literature procedures. Such transformations are known to those skilled in the art. For example, such transformation can be achieved using sodium cyanide as nucleophile in a polar organic solvent such as acetonitrile, N,N-dimethylacetamide or dimethylsulfoxide at elevated temperatures. For examples, see US2014/194431, 2014, A1; WO2016/44429, 2016, A1 and the references therein.

Step (XLI)→(XLIV) (Scheme 9)

The triflates (XLI) can be transformed to the sulfones (XLIV) using standard literature procedures. Such transformations are known to those skilled in the art. For example, such transformation can be achieved using sodium methyl sulfinate as nucleophile in a polar organic solvent such as acetonitrile, N,N-dimethylacetamide or dimethylsulfoxide at elevated temperatures. For examples, see *Green Chem.* 2020, 22, 322 and the references therein.

Step (XLII)→(XLV) (Scheme 9)

For j* or k*=H, the amines (XLII) can be transformed to the sulfonamides (XLV) using standard literature procedures. Such transformations are known to those skilled in the art. For example, the reaction can be achieved using methanesulfonyl chloride or methanesulfonic anhydride in combination with triethylamine or potassium carbonate in an organic solvent such as dichloromethane. For examples, see WO2005/123747, 2005, *A1, ChemMedChem* 2014, 9, 614, *Eur. J. Med. Chem.* 2021, 211, 113053 and the references therein.

Step (XLII)→(XLVI) (Scheme 9)

For j* or k*=H, the amines (XLII) can be transformed to the amides (XLVI) using standard literature procedures. Such transformations are known to those skilled in the art. For example, the reaction can be achieved using acetyl chloride or acetic anhydride in combination with triethylamine or pyridine in an organic solvent such as dichloromethane. For examples, see *Bioorg. Med. Chem. Lett.* 2008, 18, 6429, *Org. Lett.* 2015, 17, 2478; WO2006/45498, 2006, A1 and the references therein.

Scheme 10

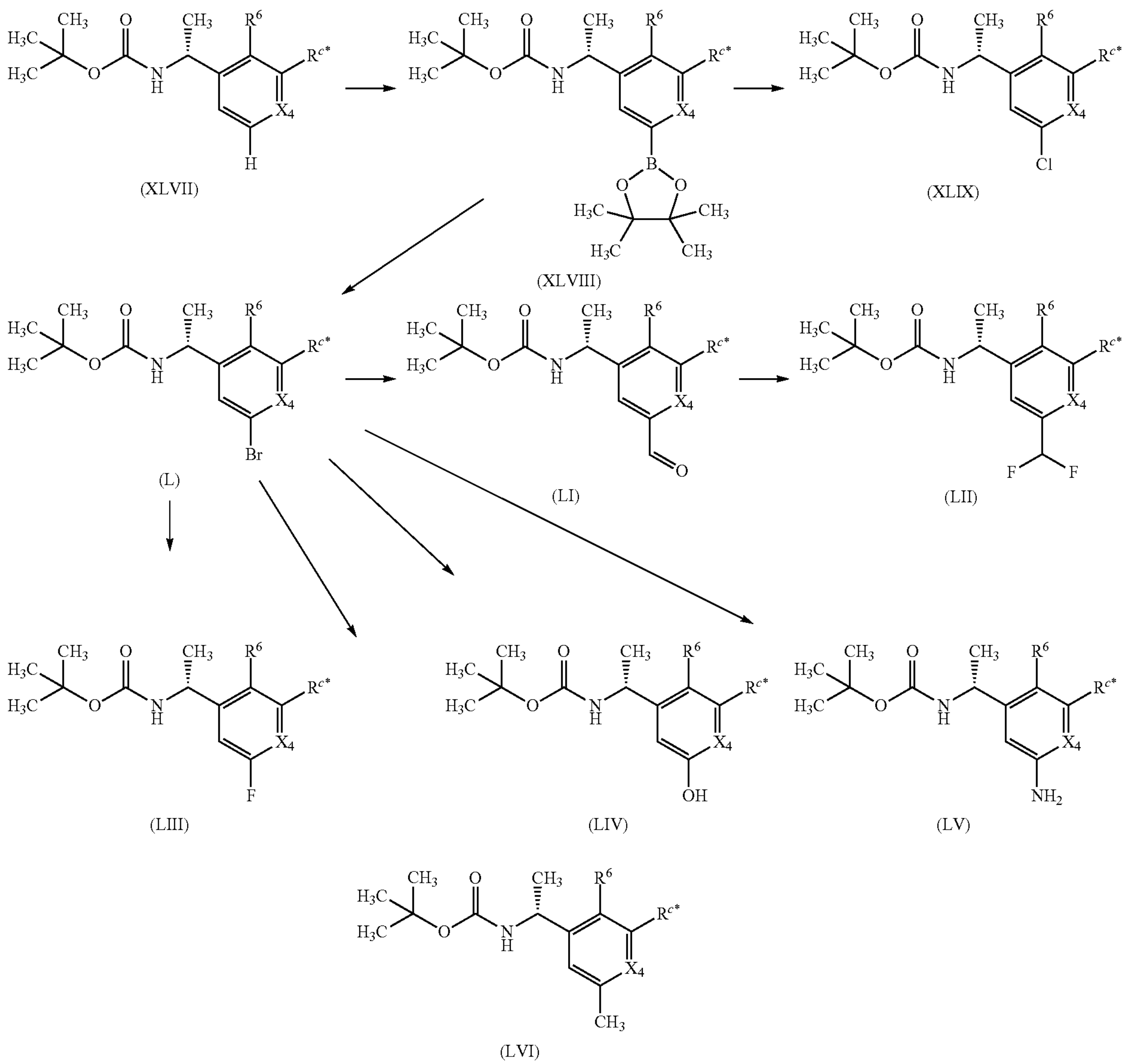

(XLVII) (XLVIII) (XLIX) (L) (LI) (LII) (LIII) (LIV) (LV) (LVI)

Scheme 10: Synthetic routes for chiral N-Boc protected amines of the general formula (XLIX to LVI) in which $X_4$ and $R^6$ have the same meaning as in the general formula (I), supra, and $R^{c*}$ is $R^5$ as in general formula (I), supra, or a protected derivative of $R^5$.

Step (XLVII) 4 (XLVIII) (Scheme 10)

The Boc-protected amines (XLVII), which can be prepared following the synthetic routes and procedures as depicted in schemes 5 and 6 or are commercially available or can be prepared by literature procedures, can be transformed to the borylated compounds (XLVIII) using literature procedures. Such transformations are known to those skilled in the art known as Hartwig-Miyaura-Borylation. For example, the reaction can be achieved using cyclooctadiene iridium methoxide dimer ($[Ir(cod)(OMe)]_2$) as catalyst with an appropriate ligand such as 4,4'-di-tert-butyl-2,2'-dipyridine in combination with bis(pinacolato)diboron in an aprotic organic solvent such as THF at elevated temperatures. For examples, see *J. Am. Chem. Soc.* 2007, 129, 15343, *J. Am. Chem.* Soc. 2002, 124, 390, *Science* 2002, 295, 305 and the references therein.

Step (XLVIII) 4 (XLIX) (Scheme 10)

The borylated compounds (XLVIII) can be transformed to the chlorinated compounds (XLIX) using literature procedures. Such transformations are known to those skilled in the art, for example, the transformation can be achieved using an excess of copper(II)chloride in a mixture of methanol and water at elevated temperatures. For examples, see *J. Am.* Chem. Soc. 2007, 129, 15343 and the references therein.

Step (XLVIII)+(L) (Scheme 10)

The borylated compounds (XLVIII) can be transformed to the brominated compounds (L) using literature procedures. Such transformations are known to those skilled in the art, for example, the transformation can be achieved using an excess of copper(II)bromide in a mixture of methanol and water at elevated temperatures. For examples, see *J. Am.* Chem. Soc. 2007, 129, 15343 and the references therein.

Step (L)+(LI) (Scheme 10)

The brominated compounds (L) can be transformed to the formylated compounds (LI) using literature procedures. Such transformations are known to those skilled in the art. For example, the transformation can be achieved using a halogen-lithium-exchange with an organolithium reagent, such as for example n-butyllithium in an aprotic organic solvent such as THF at low temperatures to create an aryl-lithium species, which is trapped with the Vilsmeier reagent ((chloromethylene)dimethyliminium chloride). For examples, see J. *Organomet. Chem.* 1988, 352, 1 and/or *Org. Prep.* Proc. Int. 2010, 42, 503 and the references therein.

Step (LI) 4 (LII) (Scheme 10)

The formylated compounds (LI) can be transformed to the difluoroalkylated compounds (LII) using literature procedures. Such transformations are known to those skilled in the art. For example, such transformation can be achieved using DAST (N,N-diethylaminosuflur trifluoride) in organic solvents such as dichloromethane. For examples, see *J. Org. Chem.* 1999, 64, 7048, WO2009/121939, 2009*, A*1*; J. Org. Chem.* 1975, 40, 574 and the references therein.

Step (L)+(LIII) (Scheme 10)

The brominated compounds (L) can be transformed to the fluorinated compounds (LIII) using literature procedures. Such transformations are known to those skilled in the art, for example, this transformation can be achieved using a palladium catalyst precursor in combination with a hindered, electron-rich phosphine ligand such as AdBrettPhos (2-(di-1-adamantylphosphino)-3,6-dimethoxy-2',4',6'-tri-i-propyl-1,1'-biphenyl) in an organic solvent such as toluene or cyclohexane and silver fluoride as fluoride source. For examples, see *J. Am. Chem. Soc.* 2014, 136, 3792 and references therein.

Step (L)+(LIV) (Scheme 10)

The brominated compounds (L) can be transformed to the hydroxylated compounds (LIV) using literature procedures. Such transformations are known to those skilled in the art, for example, such transformation can be achieved using a copper catalyst in combination with a phenanthroline ligand and a base in water as solvent. Alternatively, a palladium catalyst such as palladium acetate in combination with a phosphine ligand such as tBuBrettPshos (di-tert-butyl(2',4',6'-triisopropyl-3,6-dimethoxybiphenyl-2-yl)phosphine), a base and boric acid in a polar, aprotic solvent such as NMP can be used. For examples, see *Org. Lett.* 2020, 22, 8470*, J. Org. Chem.* 2013, 78, 5804*, Green Chem.* 2015, 17, 3910 and references therein.

Step (L)+(LV) (Scheme 10)

The brominated compounds (L) can be transformed to the aminated compounds (LV) using literature procedures. Such transformations are known to those skilled in the art. For example, this transformation can be achieved using a palladium catalyst such as $Pd_2dba_3$ (tris(dibenzylideneacetone) dipalladium(0)) and an appropriate phosphine ligand with ammonia in an organic solvent such as dioxane at elevated temperatures. Alternatively, copper-catalyzed transformations can be performed, using for example copper iodide in liquid ammonia. For examples, see *Chem. Eur. J.* 2009, 15, 4528, J. *Org. Chem.* 2012, 77, 7471*, Chem. Soc. Rev.* 2010, 39, 4130 and references therein.

Step (L)+(LVI) (Scheme 10)

The brominated compounds (L) can be transformed to the methylated compounds (LVI) using literature procedures. Such transformations are known to those skilled in the art. For example, such transformations can be achieved by using a palladium catalyst such as ($Pd(PPh_3)_4$) and TMB (Trimethylboroxine) as nucleophile using a base such as potassium carbonate in a mixture of water and an organic solvent such as dioxane. Alternatively, nickel-catalyzed transformations can be performed. For examples, see *Tetrahedron Lett.* 2000, 41, 6237*, Chem. Commun.* 2017, 53, 10183 and references therein.

Scheme 11

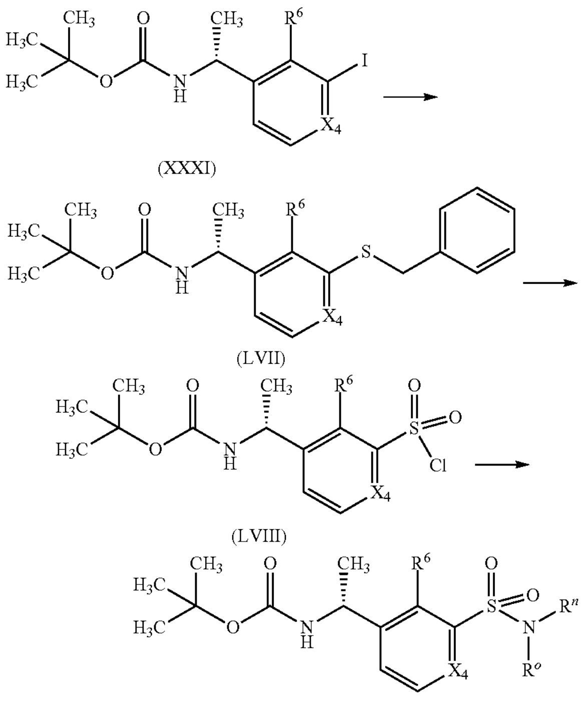

(XXXI)

(LVII)

(LVIII)

(LIX)

Scheme 11: Synthetic route for chiral N-Boc protected amines of the general formula (LIX) in which $X_4$, $R^6$, $R^n$ and $R^o$ have the same meaning as in the general formula (I), supra.

Compounds of general formula (XXXI) can be prepared following literature procedures or following the synthetic routes depicted in the previous schemes.

Step (XXXI)+(LVII) (Scheme 11):

The aryl iodides (XXXI) can be transformed to the thioethers (LVII) using literature procedures. Such transformations are known to those skilled in the art. For example, such transformation can be achieved by using a palladium catalyst such as tris(dibenzylideneacetone)-dipalladium(0) in combination with an appropriate ligand, such as Xantphos with phenylmethanethiol and a base such as DIPEA in an aprotic organic solvent such as dioxane at elevated temperatures. Alternatively, this kind of transformation has also been described using copper catalysis. For examples, see Appl. *Organomet. Chem.* 2013, 27, 501 and *Tetrahedron Lett.* 2006, 47, 5781 and references therein.

Step (LVII)+(LVIII) (Scheme 11)

The thioethers (LVII) can be transformed to the sulfonyl chlorides (LVIII) using literature procedures. Such transformations are known to those skilled in the art. For example, such transformation can be achieved by using an oxidizing agent such as NCS or close analoges thereof, such as 1,3-dichloro-5,5-dimethylhydantoin under acidic conditions using for example acetic acid and water. The sulfonyl chloride (LVIII) can be used in the next step without purification. For examples, see *Tetrahedron Lett.* 2010, 51, 418 and J. *Org. Chem.* 1996, 61, 9289 and references therein.

Step (LVIII)+(LIX) (Scheme 11)

The sulfonyl chlorides (LVIII) can be transformed to the sulfonamides (LIX) using literature procedures. Such transformations are known to those skilled in the art. For example, such transformation can be achieved by using the free primary or secondary amine under basic conditions with an organic base such as DIPEA or TEA in an aprotic organic solvent such as dichloromethane. For examples, see US2014/200277, 2014, *A1; Bioorg. Med. Chem. Lett.* 2006, 16, 1134, *J. Med. Chem.* 2010, 53, 1048 and references therein.

Scheme 12

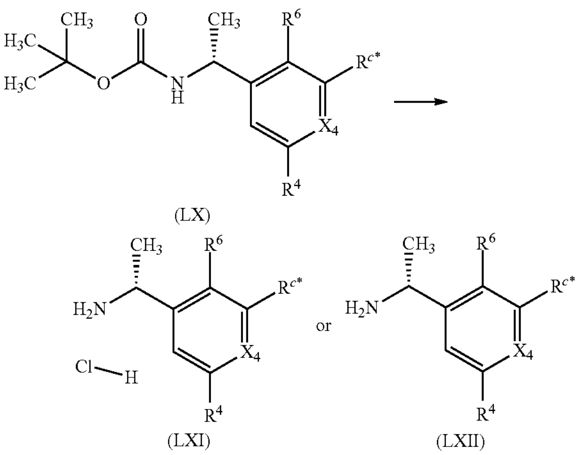

(LX)

(LXI) or (LXII)

Scheme 12: Synthetic route for the deprotection of chiral amines of the general formula (LXI or LXII) in which $X_4$, $R^4$ and $R^6$ have the same meaning as in the general formula (I), supra and $R^{c*}$ is $R^5$ as in general formula (I), supra, or a protected derivative of $R^5$.

The Boc-protected amines (LX) (which can be prepared following the synthetic routes depicted in schemes 5-11) can be transformed to the HCl salt (LXI) or the free amine (LXII) using standard literature procedures. Such transformations are known to those skilled in the art. For example, this transformation can be achieved using a solution of hydrogen chloride in dioxane in an organic solvent such as dioxane. The HCl salts (LXI) can be obtained after removal of the volatiles. Basic aqueous work up delivers the free amines (LXII). Alternatively, trifluoracetic acid in an organic solvent such as dichloromethane can be used for the deprotection. For examples, see *J. Med. Chem.* 2016, 59, 9150, *Eur. J. Med. Chem.* 2018, 145, 413, WO2012/78915, 2012, A1 and the references therein.

General Methods

General Procedure 1:

To a solution of the substrate (1 eq.), the corresponding phosphine oxide (1 eq.) and $Et_3N$ (3.5 eq.) in MeCN (0.2 M) under argon was added $Pd(PPh_3)_4$ (0.15 eq.) and the mixture was heated at 90° C. for the indicated time. The reaction mixture was filtered, concentrated under reduced pressure and purified by preperative HPLC (basic method).

General Procedure 2:

To a solution of 6-bromo-2-methylpyrido[3,4-d]pyrimidin-4-ol (1 eq.) and 2,4,6-tri(propan-2-yl)benzene-1-sulfonyl chloride (1.1 eq.) in DMF (0.2M) was added $Et_3N$ (2.5 eq.) and DMAP (0.15 eq.) and the mixture was stirred for 1 h at rt. Then, the corresponding amine (1.2 eq.) was added and the mixture was stirred until full conv. of the starting material was observed. The mixture was diluted with DCM and $H_2O$, the org. phase was washed with $H_2O$ and brine, dried over $Na_2SO_4$, filtered and concentrated under reduced pressure. The desired product was obtained after purification by flash column chromatography.

General Procedure 3:

To a solution of Boc-protected amine (1 eq.) in DCM (0.2M) was added TFA (10 eq.) and the mixture was stirred at rt until full conversion of the starting material was observed. The mixture was diluted with toluene and concentrated under reduced pressure. The compound was used in the next step without further purification.

General Procedure 4:

To a solution of tert-butyl [(1R)-1-(3-{1,1-difluoro-2-[methoxy(methyl)amino]-2-oxoethyl}-2-fluorophenyl) ethyl]carbamate (1 eq.) in THF (0.1M) was added the corresponding Grignard reagent (3 eq.) at rt. The reaction mixture was stirred at rt until full conv. of the starting material was observed, quenched by slow addition of sat. aq. $NH_4Cl$ sol. and extracted with EtOAc. The org. phase was washed with brine, dried and concentrated under reduced pressure. The residue was purified by flash column chromatography.

General Procedure 5:

To a solution of the alcohol (1 eq.) in DCM (0.2M) was added 2,6-lutidine at 0° C. and the mixture was stirred for 5 min. Then, TESOTf was slowly added and the mixture was stirred at rt overnight. The reaction was quenched by addition of sat. aq. $NaHCO_3$ sol., the org. phase was dried over $Na_2SO_4$ and concentrated under reduced pressure. The residue was purified by flash column chromatography.

General Procedure 6:

To a solution of hydroxypyrimidine derivative (1 eq) and benzylamine (1.1 eq) in DMF (0.2 M) was added PyBOP (1.3 eq) and 1,8-diazabicyclo(5.4.0)undec-7-ene (4 eq) and the mixture was stirred at RT overnight. The mixture was diluted with ethyl acetate, washed twice with water and with saturated aqueous sodium chloride, dried over sodium sulfate, and concentrated. The residue was purified by flash chromatography (silica, hexane, ethyl acetate) to obtain the corresponding N-arylated benzylamine.

General Procedure 7:

To a solution of 1,4lambda$^5$-azaphosphinan-4-one derivative (A, 1.0 eq) in dichloromethane (~1 ml/pmol A) was added N,N-diisopropylethylamine (2.5 eq) and acetic anhydride (1.1 eq) at RT. The mixture was stirred at RT for typically 3 h (until complete reaction, as indicated by analytical HPLC). The mixture was then concentrated, and the residue was purified by preparative HPLC.

General Procedure 8:

To a solution of acid derivative (1.2 eq) in DMF (0.25 M) was added HATU (1.5 eq), and the mixture was stirred at RT for 5 min. Then, amine derivative (1 eq) and N,N-diisopropylethylamine (2.5 eq) were added subsequently, and the mixture was stirred at RT overnight. The mixture was then concentrated and the residue was purified by preparative HPLC.

General Procedure 9:

To a solution of the amine derivative (1 eq) in DMF (0.15 M) was added the respective isocyanate (1.1 eq), and the mixture was stirred at RT overnight. The mixture was concentrated and the residue was purified by preparative HPLC.

General Procedure 10:

To a solution of the amine derivative (1 eq) in DMF (0.15 M) was added N,N-diisopropylethylamine (2.5 eq) and the respective acyl chloride (1 eq), and the mixture was stirred at RT overnight. The mixture was diluted with methanol, concentrated, and the residue was purified by preparative HPLC.

General Procedure 11:

To a solution of difluoroacetic acid (10 eq) in dichloromethane (1 M) was added triethylamine (15 eq), 3-{[(ethylimino)methylen]amino}-N,N-dimethylpropan-1-amine (2.2 eq), and 1-hydroxy-1H-benzotriazol-hydrate (2.2 eq), and the mixture was stirred at RT for 15 min. The respective amine (1 eq) in dichloromethane (0.1 M) was added, and the mixture was stirred at RT overnight. The mixture was concentrated, and the residue was purified by preparative HPLC.

Analytical LC-MS

Method 1:

Instrument: Waters Acquity UPLCMS SingleQuad; Column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method 2:

Instrument: Waters Acquity UPLCMS SingleQuad; Column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

Method 3:

Instrument: Waters Acquity UPLCMS SingleQuad; Column: Acquity UPLC BEH C18 1.7 μm, 50×2.1 mm; eluent A: water+0.2 vol-% aqueous ammonia (32%), eluent B: acetonitrile; gradient: 0-1.7 min 1-45% B, 1.7-1.72 min 45-99% B, 1.72-2.0 min 99% B; flow 0.8 ml/min; temperature: 60° C.; ELSD.

Method 4:

Instrument: Waters Acquity UPLCMS SingleQuad; Column: Acquity UPLC BEH C18 1.7 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm Method 5:

Instrument: Waters Acquity UPLCMS SingleQuad; Colum: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm

Preparative HPLC a) Autopurifier: acidic conditions
- System: Waters Autopurification system: Pump 2545, Sample Manager 2767, CFO, DAD 2996, ELSD 2424, SQD
- Column: XBrigde C18 5.0 μm 100×30 mm
- Solvent: A=$H_2O$+0.1% vol. HCOOH (99%)
  B=acetonitrile
- Gradient: 0-0.5 min 5% B 25 mL/min, 0.51-5.5 min 10-100% B 70 mL/min, 5.51-6.5 min 100% B 70 mL/min
- Temperature: RT
- Solution: max. 250 mg/max. 2.5 mL DMSO or DMF
- Injection: 1×2.5 m L
- Detection: DAD scan range 210-400 nm, MS ESI+, ESI−, scan range 160-1000 m/z b) Autopurifier: basic conditions
- System: Waters Autopurification system: Pump 2545, Sample Manager 2767, CFO, DAD 2996, ELSD 2424, SQD
- Column: XBrigde C18 5.0 μm 100×30 mm
- Solvent: A=$H_2O$+0.2% vol. $NH_3$ (32%)
  B=acetonitrile
- Gradient: 0-0.5 min 5% B 25 mL/min, 0.51-5.5 min 10-100% B 70 mL/min, 5.51-6.5 min 100% B 70 mL/min
- Temperature: RT
- Solution: max. 250 mg/max. 2.5 mL DMSO or DMF
- Injection: 1×2.5 m L
- Detection: DAD scan range 210-400 nm, MS ESI+, ESI−, scan range 160-1000 m/z Intermediate 1

(1R)-1-(3-{1,1-difluoro-2-methyl-2-[(triethylsilyl)oxy]propyl}-2-fluorophenyl)ethan-1-amine

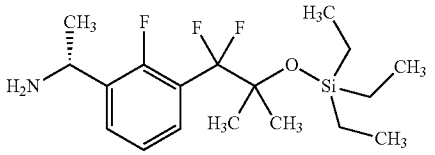 [SMILES: CC[Si](CC)(CC)OC(C)(C)C(F)(F)c1cccc([C@@H](C)N)c1F]

1-{3-[(1R)-1-aminoethyl]-2-fluorophenyl}-1,1-difluoro-2-methylpropan-2-ol-hydrogen chloride (1/1) (5.00 g, 17.6 mmol) was dissolved in dichloromethane (100 mL) and cooled to 0° C. under an atmosphere of argon. 2,6-Dimethylpyridin (14 mL) were added and the suspension was stirred for 5 minutes. Triethylsilyltrifluormethansulfonat (16 ml, 70 mmol) was added dropwise and the mixture was allowed to warm to room temperature and was stirred for 16 hours. At 0° C. the mixture was quenched with aqueous saturated sodium bicarbonate solution. The organic phase was separated and dried over sodium sulfate, which was subsequently filtered off. The solvent was evaporated to give a colorless oil (6.37 g), which was used without further purification.

LC-MS (Method 2): $R_t$=1.65 min; MS $(M+H)^+$: m/z=362

Intermediate 2

6-chloro-2-methylpyrido[3,4-d]pyrimidin-4-ol

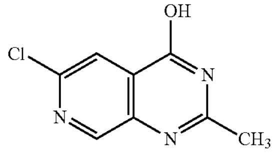

To a solution of 5-amino-2-chloropyridine-4-carboxylic acid (100 g, 579 mmol) and ethanimidamide hydrochloride (164 g, 1.74 mol) in 2-methoxyethanol (1.2 L) was added sodium acetate (143 g, 1.74 mol) at room temperature. The reaction mixture was stirred at 130° C. for 48 hours. The reaction mixture was concentrated to remove about 400 ml 2-methoxyethanol under reduced pressure. The residue was poured into water, brown solid was precipitated. The precipitates were filtered, dried under reduced pressure by oil pump to give 7-chloro-2-methylpyrido[4,3-d]pyrimidin-4-ol as a brown solid (16.6 g, 69%) LC-MS (Method 2): $R_t$=0.64 min; MS $(M+H)^+$: m/z=196 $^1$H-NMR (400 MHz, DMSO-d6) δ[ppm]: 2.384 (16.00), 2.518 (0.89), 2.523 (0.59), 7.928 (4.21), 7.930 (4.17), 8.817 (3.76), 8.819 (3.55).

Intermediate 3

6-bromo-2-methylpyrido[2,3-d]pyrimidin-4-ol

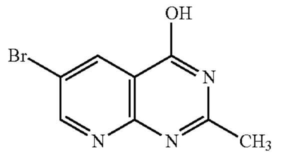

2-amino-5-bromopyridine-3-carboxylic acid (5.00 g, 23.0 mmol) and ethanimidamide-hydrogen chloride (1/1) (7.62 g, 80.6 mmol) were dissolved in 2-methoxyethanol (60 mL). Sodium acetate (6.61 g, 80.6 mmol) was added and the mixture was heated to 150° C. for three days. The mixture was cooled to room temperature and poured on a ice and water mixture. The resulting solids were collected by filtration and were washed with water. The solids were dried to give the title compound as pale brown solids (4.60 g, 83% yield).

LC-MS (method 3): $R_t$=0.43 min; MS (M+H)*: m/z=240

$^1$H-NMR (400 MHz, DMSO-d6) δ[ppm]: 2.392 (16.00), 2.518 (0.46), 8.554 (3.20), 8.561 (3.45), 8.986 (3.45), 8.993 (3.08), 12.659 (0.48).

Intermediate 4 methyl 2-chloro-6-methylpyridine-3-carboxylate

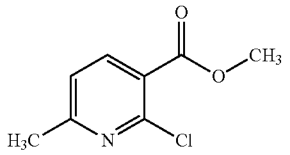

2-chloro-6-methylpyridine-3-carboxylic acid (20.0 g, 117 mmol) and potassium carbonate (43.5 g, 315 mmol) were dissolved in dimethyl formamide (200 mL). The atmosphere was exchanged to argon and methyl iodide (33 ml, 520 mmol) was added. The mixture was stirred at room temperature for 16 hours. The mixture was filtered and the solvent was partially evaporated. Ethyl acetate (200 mL) was added and the resulting organic phase was washed with water, then separated and dried with sodium sulfate to give the title compound as brown oil (21 g, 97% yield).

LC-MS (method 1): $R_t$=0.90 min; MS $(M+H)^+$: m/z=186

$^1$H-NMR (400 MHz, CHLOROFORM-d) 5 [ppm]: 2.590 (10.33), 2.884 (0.62), 2.959 (0.69), 3.941 (16.00), 7.157 (1.41), 7.176 (1.48), 8.078 (2.26), 8.098 (2.17).

Intermediate 5 methyl
2-(tert-butylamino)-6-methylpyridine-3-carboxylate

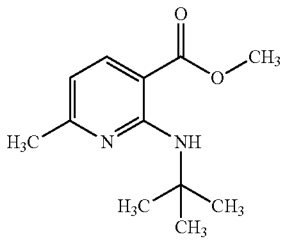

2-(tert-butylamino)-6-methylpyridine-3-carboxylic acid (7.60 g, 36.5 mmol) and potassium carbonate (13.6 g, 98.5 mmol) were dissolved in dimethyl formamide (95 mL) at room temperature under argon. Iodomethane (10 ml, 160 mmol) was added dropwise and the mixture was stirred for 16 hours. The mixture was filtered and ethyl acetate was added. The resulting organic phase was washed with water and brine and then separated and dried with sodium sulfate. The compound was purified by biotage flash column chromatography over silica gel using a mixture of hexane and ethyl acetate as eluent to obtain the title compound (1.75 g, 22% yield).

LC-MS (Method 2): $R_t$=1.55 min; MS (ESIpos): m/z=223 $[M+H]^+$ $^1$H-NMR (400 MHz, DMSO-d6) δ[ppm]: 1.450 (16.00), 2.342 (6.03), 2.518 (0.58), 3.772 (7.79), 6.443 (0.97), 6.464 (1.00), 7.940 (1.22), 7.960 (1.20), 8.007 (0.63).

Intermediate 6 methyl 5-bromo-2-(tert-butylamino)-6-methylpyridine-3-carboxylate

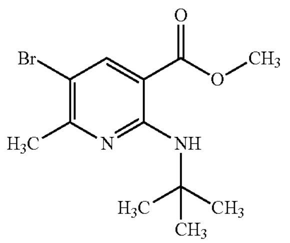

Methyl 2-(tert-butylamino)-6-methylpyridine-3-carboxylate (20.1 g, 90.4 mmol) was dissolved in acetonitrile (450 mL) and cooled to 0° C. under argon. N-Bromsuccinimid (24.1 g, 136 mmol) was added and the mixture was stirred for 1.5 hours. Saturated aqueous sodium thiosulfate solution was added and it was extracted with dichloromethane. The organic phase was dried with sodium sulfate. The compound was purified by biotage flash column chromatography on silica gel using a mixture of hexane and ethyl acetate as eluent to obtain the title compound (12.3 g, 45% yield).

LC-MS (Method 2): $R_t$=1.74 min; MS (ESIpos): m/z=301 $[M+H]^+$ $^1$H-NMR (400 MHz, DMSO-d6) δ[ppm]: 1.440 (16.00), 2.468 (7.06), 2.518 (0.75), 2.523 (0.55), 3.324 (0.46), 3.796 (8.22), 7.957 (0.65), 8.086 (2.37).

Intermediate 7 trifluoroacetic acid-methyl 2-amino-5-bromo-6-methylpyridine-3-carboxylate (1/1)

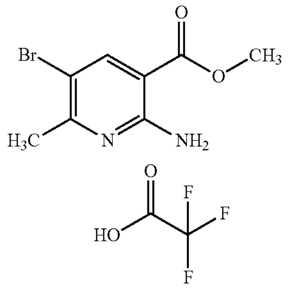

To methyl 5-bromo-2-(tert-butylamino)-6-methylpyridine-3-carboxylate (12.3 g, 40.8 mmol) was added trifluoroacetic acid (120 ml, 1.5 mol) and the mixture was stirred at 120° C. for 45 minutes using a microwave. Toluene was added and the solvent was evaporated to give a crude solid (15.1 g, 103% yield) which was used without further purification.

LC-MS (Method 2): $R_t$=1.10 min; MS (ESIpos): m/z=245 $[M+H]^+$

Intermediate 8

2-amino-5-bromo-6-methylpyridine-3-carboxylic acid

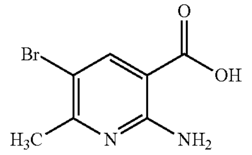

Trifluoroacetic acid-methyl 2-amino-5-bromo-6-methylpyridine-3-carboxylate (1/1) (15.1 g, 92% purity, 38.7 mmol) was dissolved in methanol (180 mL) at room temperature under argon. Sodium hydroxide solution (150 ml, 5 wt %, 190 mmol) was added and the resulting suspension was stirred for 16 hours. Methanol was evaporated, aqueous hydrochloric acid (2.5 M) was added until solids formed. Acetic acid was added until pH of 4 was reached. The solids were filtered off and washed with water and ether and then dried at 70° C. under vacuum to give the title compound (7.5 g, 84% yield).

LC-MS (method 1): $R_t$=0.67 min; MS (ESIpos): m/z=231 $[M+H]^+$ $^1$H-NMR (400 MHz, DMSO-d6) δ[ppm]: 1.907 (0.20), 2.251 (0.08), 2.412 (16.00), 2.518 (1.53), 2.523 (1.06), 2.570 (0.09), 3.324 (0.67), 4.399 (0.08), 7.291 (0.14), 8.042 (6.41).

Intermediate 9

6-bromo-2,7-dimethylpyrido[2,3-d]pyrimidin-4-ol

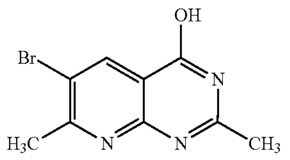

A mixture of the substrate 2-amino-5-bromo-6-methylpyridine-3-carboxylic acid (3.50 g, 15.1 mmol), acetamidine hydrochloride (6.44 g, 68.2 mmol) and sodium acetate (1.24 g, 15.1 mmol) in 2-methoxyethanol (30 mL) was heated at 135° C. for 4 days. Additional 2-methoxyethanol (30 ml) and acetamidine hydrochloride (1.43 g, 15.1 mmol) and sodium acetate (1.24 g, 15.1 mmol) was added, heated at 140° C. for another 2 days. Additional 2-methoxyethanol (20 ml) and acetamidine hydrochloride (2.86 g, 30.3 mmol) and sodium acetate (2.49 g, 30.3 mmol) was added, heated at 140° C. for another day. The reaction mixture was poured into ice water and the resulting suspension was filtered. The residue was washed with water and dried under reduced pressure at 65° C. over three days ti give the title compound as pale brown solids (2.95 g, 77% yield).

LC-MS (method 1): $R_t$=0.70 min; MS (ESIneg): m/z=252 $[M-H]^-$ $^1$H-NMR (400 MHz, DMSO-d6) δ[ppm]: 1.229 (0.08), 1.752 (0.07), 1.899 (0.37), 2.208 (0.08), 2.318 (0.14), 2.322 (0.31), 2.327 (0.42), 2.331 (0.32), 2.336 (0.17), 2.371 (16.00), 2.518 (4.96), 2.522 (3.84), 2.659 (0.25), 2.665 (0.44), 2.669 (0.72), 2.678 (13.68), 2.838 (0.08), 3.239 (0.41), 8.479 (4.79), 12.596 (0.05).

Intermediate 10 methyl 2-acetamido-5-bromo-6-(trifluoromethyl)pyridine-3-carboxylate

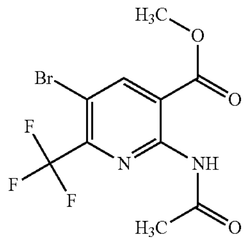 [SMILES: COC(=O)c1cc(Br)c(C(F)(F)F)nc1NC(C)=O]

To a solution of methyl 2-amino-5-bromo-6-(trifluoromethyl)pyridine-3-carboxylate (920 mg, 3.08 mmol) in $Ac_2O$ (61 ml, 650 mmol) was added DMAP (3.76 mg, 30.8 μmol) and the mixture was stirred at 100° C. for 2 days. Then, toluene was added at RT and the mixture was concentrated under reduced pressure. The crude product was dried under vacuum and used in the next step without further purification (1.05 g, 100% yield).

LC-MS (Method 2): $R_t$=1.12 min; MS (ESIpos): m/z=341 $[M+H]^+$

Intermediate 11

6-bromo-2-methyl-7-(trifluoromethyl)pyrido[2,3-d]pyrimidin-4-ol

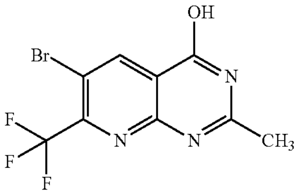 [SMILES: Cc1nc(O)c2cc(Br)c(C(F)(F)F)nc2n1]

A solution of methyl 2-acetamido-5-bromo-6-(trifluoromethyl)pyridine-3-carboxylate (1.05 g, 3.08 mmol) (1.05 g, 3.08 mmol) in aq. $NH_4O$ H-solution (28-30%, 93 ml) was stirred at RT overnight. The mixture was concentrated under reduced pressure, diluted with $H_2O$ and extracted with EtOAc. The combined org. phases were washed with brine, dried over $Na_2SO_4$, filtered and concentrated under reduced pressure. The titled compound (630 mg, 66% yield) was obtained after purification by silica chromatography (hexane/EtOAc).

LC-MS (method 1): $R_t$=0.93 min; MS (ESIpos): m/z=308 $[M+H]^+$ $^1$H-NMR (400 MHz, DMSO-d6) δ[ppm]: 1.810 (0.52), 1.850 (0.73), 1.987 (0.66), 2.422 (16.00), 2.518 (0.95), 2.523 (0.66), 8.827 (2.58), 12.878 (0.47).

Intermediate 12

6-bromo-2-methyl-N-{(1R)-1-[2-methyl-3-(trifluoromethyl)phenyl]ethyl}-7-(trifluoromethyl)pyrido[2,3-d]pyrimidin-4-amine

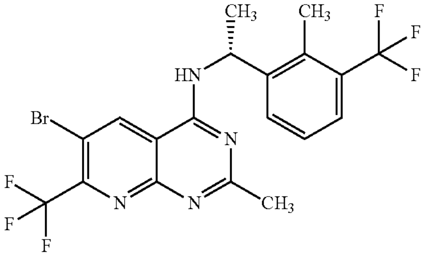 [SMILES: Cc1nc(N[C@H](C)c2cccc(C(F)(F)F)c2C)c2cc(Br)c(C(F)(F)F)nc2n1]

To a solution of 6-bromo-2-methyl-7-(trifluoromethyl)pyrido[2,3-d]pyrimidin-4-ol (250 mg, 812 μmol), (1R)-1-[2-methyl-3-(trifluoromethyl)phenyl]ethan-1-amine (594 mg, 2.92 mmol) and PyBOP (1.65 g, 3.16 mmol) in DMF (6.3 mL) was added 1,8-Diazabicyclo(5.4.0)undec-7-en (1.5 ml, 9.7 mmol) and the reaction mixture was stirred at 50° C. overnight. water was added and the mixture was extracted with ethyl acetate. The combined org. phases were washed with water and brine, dried over $Na_2SO_4$, filtered and concentrated under reduced pressure. The titled compound (258 mg, 64% yield) was obtained after purification by silica chromatography (hexane/EtOAc).

LC-MS (Method 2): $R_t$=1.51 min; MS (ESIpos): m/z=495 $[M+H]^+$ $^1$H-NMR (400 MHz, DMSO-d6) δ[ppm]: 1.154 (0.85), 1.172 (1.60), 1.189 (0.74), 1.562 (4.55), 1.579 (4.46), 1.987 (3.19), 2.323 (0.52), 2.327 (0.73), 2.331 (0.51), 2.406 (16.00), 2.518 (2.67), 2.523 (1.91), 2.605 (5.08), 2.665 (0.53), 2.669 (0.74), 2.673 (0.50), 4.017 (0.63), 4.035 (0.64), 5.687 (0.66), 5.705 (1.02), 5.722 (0.64), 5.759 (0.56), 7.352 (0.57), 7.372 (1.28), 7.391 (0.78), 7.558 (1.39), 7.576 (1.11), 7.754 (1.22), 7.773 (1.09), 9.188 (1.03), 9.206 (1.00), 9.480 (3.55).

Intermediate 13

6-chloro-N-[(1R)-1-(3-{1,1-difluor-2-methyl-2-[(triethylsilyl)oxy]propyl}-2-fluorphenyl)ethyl]-2-methylpyrido[3,4-d]pyrimidin-4-amine

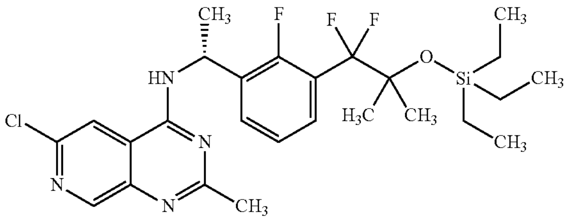 [SMILES: CC[Si](CC)(CC)OC(C)(C)C(F)(F)c1cccc([C@@H](C)Nc2nc(C)nc3cnc(Cl)cc23)c1F]

6-Chlor-2-methylpyrido[3,4-d]pyrimidin-4-ol (2.87 g, 14.7 mmol) was suspended in N,N-Dimethylformamid (29 mL). 2,4,6-Triisopropylbenzensulfonylchlorid (4.89 g, 16.2 mmol) was added, followed by Triethylamin (7.2 ml, 51 mmol) at room temperature. The mixture was stirred for 1 hour. (1R)-1-(3-{1,1-Difluor-2-methyl-2-[(triethylsilyl)oxy]propyl}-2-fluorphenyl)ethanamin (6.37 g, 17.6 mmol) was added and the resulting mixture was stirred at room temperature for 16 hours. The solvent was partially evaporated and the residue was redissolved in dichloromethane and water. The organic phase was washed with water (two times) and brine. The organic phase was dried through hydrophobic filtration. The solvent was evaporated and the compound was purified through flash column chromatography on a Biotage with silica gel and Hexane and ethyl acetate as eluent to give the title compound (6.00 g, 97% purity, 74% yield).

LC-MS (Method 2): $R_t$=1.77 min; MS (ESIneg): m/z=537 $[M-H]^-$ $^1$H-NMR (400 MHz, DMSO-d6) δ[ppm]: 0.382 (1.24), 0.385 (1.24), 0.404 (5.28), 0.424 (7.14), 0.442 (2.59), 0.662 (7.85), 0.672 (0.86), 0.681 (16.00), 0.689 (0.81), 0.701 (5.46), 1.233 (0.41), 1.321 (4.11), 1.329 (4.29), 1.577 (3.02), 1.594 (3.00), 2.332 (1.09), 2.336 (0.51), 2.382 (10.57), 2.518 (7.29), 2.522 (4.80), 2.673 (1.12), 2.678 (0.48), 5.751 (0.46), 5.768 (0.74), 5.786 (0.46), 7.204 (0.43), 7.223 (1.04), 7.242 (0.74), 7.281 (0.48), 7.297 (0.63), 7.622 (0.63), 8.548 (2.57), 8.550 (2.59), 8.835 (2.82), 8.847 (0.79), 8.865 (0.76).

Intermediate 14

6-chloro-N-[(1R)-1-(3-{1,1-difluoro-2-methyl-2-[(triethylsilyl)oxy]propyl}-2-fluorophenyl)ethyl]-2,8-dimethylpyrido[3,4-d]pyrimidin-4-amine

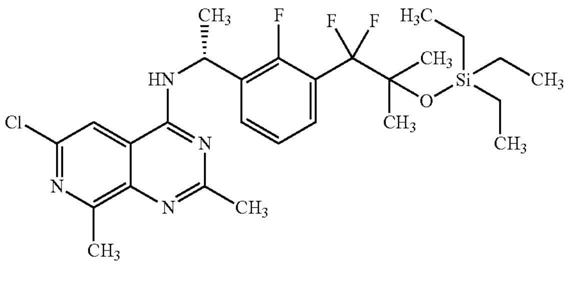 [SMILES: CC[Si](CC)(CC)OC(C)(C)C(F)(F)c1cccc([C@@H](C)Nc2nc(C)nc3c(C)nc(Cl)cc23)c1F]

6-chloro-N-[(1R)-1-(3-{1,1-difluoro-2-methyl-2-[(triethylsilyl)oxy]propyl}-2-fluorophenyl)ethyl]-2-methylpyrido[3,4-d]pyrimidin-4-amine (1.35 g, 2.50 mmol) was dissolved in dimethylsulfoxid (20 mL) in a round flask. 1,8-Diazabicyclo(5.4.0)undec-7-en (750 μl, 5.0 mmol) was added, followed by nitromethane (680 μl, 13 mmol). The mixture was stirred at room temperature for 16 hours. Ethyl acetate and water were added, the phases were separated and the organic phase was dried through hydrophobic filtration. The compound was purified through biotage flash column chromatography on silica gel using hexane and ethyl acetate as eluent to give the title compound (1.00 g, 72% yield).

LC-MS (Method 2): $R_t$=1.91 min; MS (ESIpos): m/z=553 $[M+H]^+$ $^1$H-NMR (400 MHz, DMSO-d6) δ[ppm]: 0.365 (1.71), 0.384 (6.14), 0.404 (7.75), 0.423 (3.26), 0.651 (8.53), 0.670 (16.00), 0.691 (6.74), 1.293 (5.37), 1.305 (5.88), 1.565 (3.47), 1.582 (3.58), 2.361 (9.67), 2.680 (8.64), 5.720 (0.61), 5.737 (0.95), 5.748 (1.31), 5.755 (0.69), 7.165 (0.54), 7.185 (1.29), 7.204 (0.93), 7.246 (0.70), 7.263 (0.95), 7.278 (0.47), 7.567 (0.54), 7.584 (0.92), 7.599 (0.53), 8.319 (2.76), 8.687 (1.06), 8.704 (1.05).

Intermediate 15

6-bromo-2-methyl-N-{(1R)-1-[2-methyl-3-(trifluoromethyl)phenyl]ethyl}pyrido[2,3-d]pyrimidin-4-amine

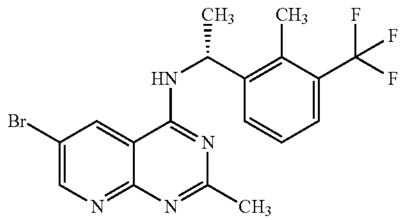

To a solution of 6-bromo-2-methylpyrido[2,3-d]pyrimidin-4-ol (2.00 g, 8.33 mmol), (1R)-1-[2-methyl-3-(trifluoromethyl)phenyl]ethan-1-amine (2.03 g, 10.0 mmol) and PyBOP (5.64 g, 10.8 mmol) in DMF (60 mL) was added DBU (5.0 ml, 33 mmol) and the reaction mixture was stirred at RT overnight. The mixture was concentrated under reduced pressure and the titled compound (1.37 g, 39% yield) was obtained after purification by silica chromatography and subsequent recrystallization from $CH_2Cl_2$/MTBE.

LC-MS (Method 2): $R_t$=1.32 min; MS (ESIpos): m/z=425 $[M+H]^+$ $^1$H-NMR (400 MHz, DMSO-d6) δ[ppm]: 1.154 (1.12), 1.171 (2.50), 1.189 (1.28), 1.470 (1.34), 1.487 (1.36), 1.551 (5.16), 1.569 (5.23), 1.986 (4.69), 2.396 (16.00), 2.448 (1.37), 2.518 (3.22), 2.522 (2.12), 2.606 (5.94), 2.673 (0.56), 4.016 (0.99), 4.034 (0.97), 5.695 (0.73), 5.713 (1.12), 5.730 (0.71), 7.350 (0.66), 7.369 (1.45), 7.389 (0.85), 7.551 (1.60), 7.569 (1.29), 7.756 (1.42), 7.775 (1.29), 9.003 (3.41), 9.009 (3.59), 9.198 (2.97), 9.204 (2.69).

Intermediate 16

6-bromo-N-[(1R)-1-(3-{1,1-difluoro-2-methyl-2-[(triethylsilyl)oxy]propyl}-2-fluorophenyl)ethyl]-2-methylpyrido[2,3-d]pyrimidin-4-amine

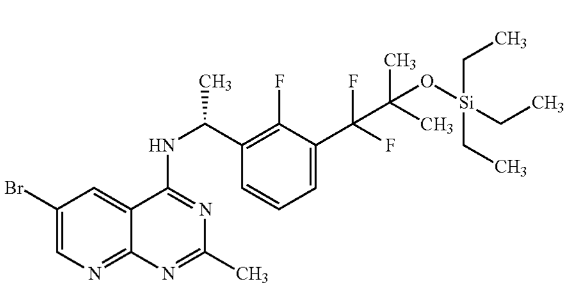 [SMILES: CC[Si](CC)(CC)OC(C)(C)C(F)(F)c1cccc([C@@H](C)Nc2nc(C)nc3ncc(Br)cc23)c1F]

To a solution of 6-bromo-2-methylpyrido[2,3-d]pyrimidin-4-ol (3.89 g, 16.2 mmol), (1R)-1-(3-{1,1-difluoro-2-methyl-2-[(triethylsilyl)oxy]propyl}-2-fluorophenyl)ethan-1-amine (16.1 g, 17.8 mmol) and PyBOP (10.0 g, 17.8 mmol) in DMF (120 mL) was added DBU (9.7 ml, 64.8 mmol) and the reaction mixture was stirred at RT overnight. The mixture was diluted with EtOAc, washed with $H_2O$ (2×) and brine, and dried over $Na_2SO_4$. The mixture was filtered, concentrated under reduced pressure and the titled compound (5.55 g, 59%) was obtained after purification by silica chromatography (basic phase, hexane/EtOAc).

LC-MS (Method 2): $R_t$=1.72 min; MS (ESIpos): m/z=583 $[M+H]^+$ $^1$H-NMR (400 MHz, DMSO-d6) δ[ppm]: 0.384 (1.14), 0.387 (1.21), 0.405 (5.21), 0.417 (0.57), 0.425 (7.62), 0.434 (0.56), 0.444 (2.69), 0.663 (7.57), 0.674 (0.88), 0.682 (16.00), 0.691 (1.14), 0.703 (5.64), 1.323 (3.86), 1.332 (4.28), 1.566 (2.95), 1.584 (2.98), 2.367 (11.84), 2.518 (5.24), 2.523 (3.80), 3.321 (0.48), 5.753 (0.44), 5.770 (0.71), 5.788 (0.46), 7.199 (0.41), 7.218 (1.02), 7.238 (0.73), 7.272 (0.40), 7.276 (0.50), 7.293 (0.64), 7.622 (0.62), 8.790 (0.76), 8.808 (0.74), 8.991 (2.74), 8.998 (2.85), 9.199 (2.02), 9.205 (1.92).

Intermediate 17

1-(3-{(1R)-1-[(6-bromo-2-methylpyrido[2,3-d]pyrimidin-4-yl)amino]ethyl}-2-fluorophenyl)-1,1-difluoro-2-methylpropan-2-ol

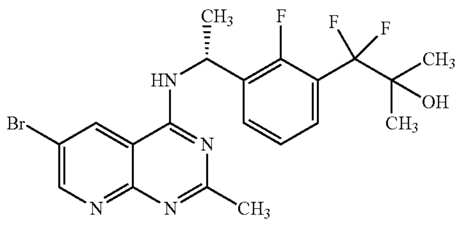

To a solution of 6-bromo-N-[(1R)-1-(3-{1,1-difluoro-2-methyl-2-[(triethylsilyl)oxy]propyl}-2-fluorophenyl)ethyl]-2-methylpyrido[2,3-d]pyrimidin-4-amine (1.00 g, 1.71 mmol) and triethylsilane (27 μl, 170 μmol) in dichloromethane (15 mL) was added trifluoroacetic acid (2.0 ml, 26 mmol) dropwise at room temperature. The mixture was stirred at room temperature overnight. Then, toluene was added and the volatiles were removed under reduced pressure. The titled compound (815 mg, 100% yield) was obtained after purification by silica chromatography (hexane/EtOAc).

LC-MS (Method 2): $R_t$=1.15 min; MS (ESIpos): m/z=469 $[M+H]^+$ $^1$H-NMR (400 MHz, DMSO-d6) δ[ppm]: 1.154 (1.58), 1.171 (3.21), 1.189 (1.98), 1.202 (6.11), 1.226 (6.29), 1.563 (4.70), 1.580 (4.70), 1.986 (5.14), 2.326 (1.01), 2.332 (0.75), 2.368 (16.00), 2.518 (4.79), 2.522 (3.16), 2.669 (1.01), 2.673 (0.75), 4.017 (1.19), 4.034 (1.19), 5.338 (2.24), 5.731 (0.75), 5.748 (1.14), 5.766 (0.70), 7.197 (0.70), 7.216 (1.67), 7.235 (1.05), 7.299 (0.66), 7.303 (0.75), 7.321 (1.05), 7.336 (0.53), 7.340 (0.44), 7.588 (0.62), 7.604 (1.05), 7.620 (0.53), 8.803 (1.23), 8.821 (1.19), 8.995 (3.69), 9.002 (3.65), 9.196 (3.16), 9.202 (2.99).

Intermediate 18

6-bromo-2,7-dimethyl-N-{(1R)-1-[2-methyl-3-(trifluoromethyl)phenyl]ethyl}pyrido[2,3-d]pyrimidin-4-amine

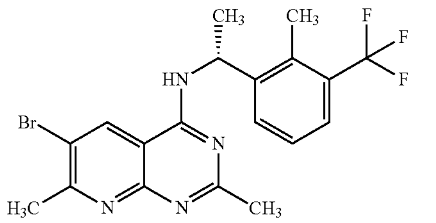

To a solution of 6-bromo-2,7-dimethylpyrido[2,3-d]pyrimidin-4-ol (1.50 g, 5.90 mmol), (1R)-1-[2-methyl-3-(trifluoromethyl)phenyl]ethan-1-amine (1.44 g, 7.08 mmol) and PyBOP (3.99 g, 7.67 mmol) in DMF (46 mL) was added 1,8-diazabicyclo(5.4.0)undec-7-en (3.5 ml, 24 mmol) and the reaction mixture was stirred at room temperature overnight. Water was added and the aq. phase was extracted with dichloromethane. The combined org. phases were washed with brine, dried over sodium sulfate, filtered and concentrated under reduced pressure. The titled compound (1.45 g, 56% yield) was obtained after purification by silica chromatography (hexane/EtOAc).

LC-MS (Method 2): $R_t$=1.37 min; MS (ESIpos): m/z=441 $[M+H]^+$ $^1$H-NMR (400 MHz, DMSO-d6) δ[ppm]: 1.153 (3.17), 1.171 (6.28), 1.189 (3.01), 1.560 (5.52), 1.578 (5.54), 1.986 (12.05), 2.414 (14.52), 2.518 (1.28), 2.523 (0.82), 2.596 (6.89), 2.706 (16.00), 3.998 (0.85), 4.016 (2.49), 4.034 (2.51), 4.052 (0.83), 5.720 (0.79), 5.738 (1.19), 5.758 (1.89), 7.363 (0.74), 7.383 (1.65), 7.402 (0.97), 7.562 (1.81), 7.580 (1.46), 7.758 (1.63), 7.777 (1.46), 9.192 (4.67), 9.315 (0.41).

Intermediate 19

6-bromo-N-{(1R)-1-[3-(difluoromethyl)-2-fluorophenyl]ethyl}-2,7-dimethylpyrido[2,3-d]pyrimidin-4-amine

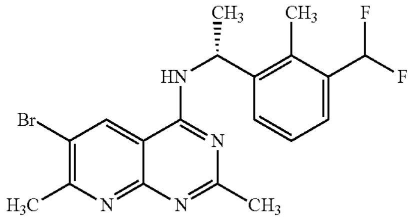 [SMILES: Cc1nc(N[C@H](C)c2cccc(C(F)F)c2C)c2cc(Br)c(C)nc2n1]

To a solution of 6-bromo-2,7-dimethylpyrido[2,3-d]pyrimidin-4-ol (500 mg, 1.97 mmol), (1R)-1-[3-(difluoromethyl)-2-fluorophenyl]ethan-1-amine hydrogen chloride (1/1) (511 mg, 2.26 mmol) and PyBOP (1.33 g, 2.56 mmol) in N,N-Dimethylformamid (17 mL) was added 1,8-Diazabicyclo(5.4.0)undec-7-en (1.2 ml, 7.9 mmol) and the reaction mixture was stirred at room temperature overnight. Water and ethyl acetate were added, the org. phase was washed with water and brine, dried over sodium sulfate, filtered and concentrated under reduced pressure. The titled compound (625 mg, 75% yield) was obtained after purification by silica chromatography (hexane/EtOAc).

LC-MS (Method 2): $R_t$=1.24 min; MS (ESIpos): m/z=427 $[M+H]^+$ $^1$H-NMR (400 MHz, DMSO-d6) δ[ppm]: 1.154 (1.83), 1.172 (3.84), 1.190 (1.87), 1.579 (4.53), 1.597 (4.51), 1.988 (6.18), 2.337 (0.44), 2.364 (16.00), 2.518 (4.31), 2.523 (2.92), 2.673 (0.93), 2.678 (0.58), 2.691 (14.37), 3.999 (0.46), 4.017 (1.37), 4.035 (1.31), 4.053 (0.42), 5.732 (0.68), 5.750 (1.03), 5.767 (0.68), 7.101 (1.05), 7.237 (2.17), 7.275 (0.72), 7.294 (1.57), 7.313 (0.93), 7.373 (0.91), 7.494 (0.54), 7.511 (0.91), 7.529 (0.44), 7.659 (0.52), 7.678 (0.89), 7.695 (0.46), 8.763 (0.48), 8.778 (0.48), 9.144 (4.57).

Intermediate 20

6-bromo-N-[(1R)-1-(3-{1,1-difluoro-2-methyl-2-[(triethylsilyl)oxy]propyl}-2-fluorophenyl)ethyl]-2,7-dimethylpyrido[2,3-d]pyrimidin-4-amine

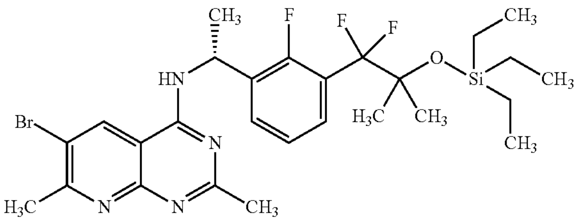 [SMILES: CC[Si](CC)(CC)OC(C)(C)C(F)(F)c1cccc([C@@H](C)Nc2nc(C)nc3nc(C)c(Br)cc23)c1F]

To a solution of 6-bromo-2,7-dimethylpyrido[2,3-d]pyrimidin-4-ol (120 mg, 472 μmol), (1R)-1-(3-{1,1-difluoro-2-methyl-2-[(triethylsilyl)oxy]propyl}-2-fluorophenyl) ethan-1-amine (196 mg, 543 μmol) and PyBOP (320 mg, 614 μmol) in DMF (4.0 mL) was added DBU (280 μl, 1.9 mmol) and the reaction mixture was stirred at RT overnight. The mixture was diluted with $H_2O$ and EtOAc, the org. phase was washed with $H_2O$ (2×) and brine, and dried over $Na_2SO_4$. The mixture was filtered, concentrated under reduced pressure and the titled compound (122 mg, 43%) was obtained after purification by silica chromatography (hexane/EtOAc).

LC-MS (Method 2): $R_t$=1.74 min; MS (ESIpos): m/z=567 $[M+H]^+$ $^1$H-NMR (400 MHz, DMSO-d6) δ[ppm]: 0.388 (1.44), 0.389 (1.44), 0.409 (5.84), 0.429 (7.47), 0.448 (2.94), 0.664 (8.29), 0.683 (16.00), 0.704 (5.90), 1.325 (5.42), 1.331 (5.67), 1.556 (3.40), 1.574 (3.39), 1.987 (0.45), 2.343 (10.70), 2.522 (1.42), 2.684 (9.83), 5.745 (0.54), 5.763 (0.84), 5.781 (0.53), 7.195 (0.49), 7.214 (1.23), 7.233 (0.88), 7.271 (0.61), 7.287 (0.81), 7.591 (0.47), 7.608 (0.79), 7.624 (0.43), 8.711 (0.95), 8.729 (0.91), 9.149 (3.42).

Intermediate 21

1-(3-{(1R)-1-[(6-bromo-2,7-dimethylpyrido[2,3-d]pyrimidin-4-yl)amino]ethyl}-2-fluorophenyl)-1,1-difluoro-2-methylpropan-2-ol

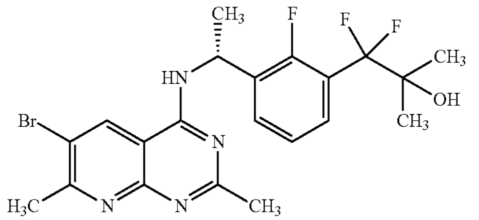 [SMILES: Cc1nc(N[C@H](C)c2cccc(C(F)(F)C(C)(C)O)c2F)c2cc(Br)c(C)nc2n1]

To a solution of 6-bromo-N-[(1R)-1-(3-{1,1-difluoro-2-methyl-2-[(triethylsilyl)oxy]propyl}-2-fluorophenyl)ethyl]-2,7-dimethylpyrido[2,3-d]pyrimidin-4-amine (400 mg, 669 μmol) and triethylsilane (11 μl, 67 μmol) in $CH_2Cl_2$ (5.9 mL) was added TFA (770 μl, 10 mmol) dropwise at RT. The mixture was stirred at RT overnight. Then, toluene was added and the volatiles were removed under reduced pressure. The titled compound (320 mg, 99%) was obtained after purification by silica chromatography (hexane/EtOAc).

LC-MS (Method 2): $R_t$=1.19 min; MS (ESIpos): m/z=485 $[M+H]^+$ $^1$H-NMR (400 MHz, DMSO-d6) δ[ppm]: 1.154 (2.20), 1.172 (4.73), 1.190 (2.99), 1.202 (6.97), 1.217 (6.94), 1.625 (4.90), 1.643 (4.87), 1.907 (0.47), 1.987 (6.92), 2.327 (0.94), 2.331 (0.65), 2.518 (4.10), 2.523 (2.67), 2.669 (0.98), 2.673 (0.65), 2.761 (16.00), 3.999 (0.58), 4.017 (1.68), 4.035 (1.67), 4.053 (0.53), 5.361 (0.81), 5.838 (0.76), 5.856 (1.17), 5.874 (0.73), 7.261 (0.76), 7.280 (1.82), 7.299 (1.17), 7.358 (0.72), 7.362 (0.81), 7.379 (1.15), 7.395 (0.55), 7.399 (0.48), 7.654 (0.64), 7.671 (1.11), 7.686 (0.58), 9.321 (4.32).

Intermediate 22

6-chloro-2-methyl-N-{(1R)-1-[2-methyl-3-(trifluoromethyl)phenyl]ethyl}pyrido[3,4-d]pyrimidin-4-amine

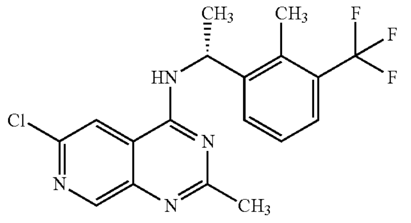

6-chloro-2-methylpyrido[3,4-d]pyrimidin-4-ol (6.00 g, 30.7 mmol) and 2,4,6-tri(propan-2-yl)benzene-1-sulfonyl chloride (10.2 g, 33.7 mmol) were dissolved in N,N-dimethylformamid (60 mL). Triethylamine (11 ml) was added, followed by 4-(Dimethylamino)pyridine (562 mg, 4.60 mmol). The mixture was stirred at room temperature for one hour. Then, (1R)-1-[2-methyl-3-(trifluoromethyl)phenyl]ethan-1-amine (7.48 g, 36.8 mmol) was added and the mixture was stirred for 16 hours. Dichloromethane and water were added, the organic phase was washed with water and brine, dried with sodium sulfate and the solvent was evaporated. The compound was purified by biotage flash column chromatography on silica gel using a mixture of hexane and ethyl acetate as eluent to give the title compound (9.98 g, 85% yield).

LC-MS (Method 2): $R_t$=1.39 min; MS (ESIneg): m/z=379 $[M-H]^-$ $^1$H-NMR (400 MHz, DMSO-d6) δ[ppm]: 1.154 (0.44), 1.171 (0.97), 1.189 (0.51), 1.553 (4.57), 1.570 (4.57), 1.986 (1.77), 2.386 (16.00), 2.518 (1.28), 2.523 (0.86), 2.609 (4.97), 5.668 (0.57), 5.685 (0.88), 5.703 (0.57), 7.343 (0.55), 7.362 (1.24), 7.382 (0.72), 7.544 (1.33), 7.561 (1.07), 7.751 (1.18), 7.770 (1.07), 8.525 (3.73), 8.527 (3.64), 8.818 (3.98), 8.820 (3.79), 8.967 (0.86), 8.984 (0.84).

Intermediate 23

6-chloro-N-{(1R)-1-[3-(difluoromethyl)-2-fluorophenyl]ethyl}-2-methylpyrido[3,4-d]pyrimidin-4-amine

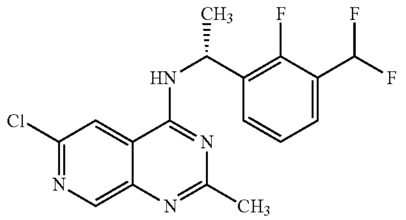

6-chloro-2-methylpyrido[3,4-d]pyrimidin-4-ol (433 mg, 2.22 mmol) and 2,4,6-tri(propan-2-yl)benzene-1-sulfonyl chloride (738 mg, 2.44 mmol) were dissolved in N,N-dimethylformamid (4.3 mL). Triethylamine (770 μl) was added, followed by 4-(Dimethylamino)pyridine (40.6 mg, 332 μmol). The mixture was stirred at room temperature for one hour. (1R)-1-[3-(difluoromethyl)-2-fluorophenyl]ethan-1-amine-hydrogen chloride (1/1) (600 mg, 2.66 mmol) was added and the mixture was stirred for 16 hours. Dichloromethane and water were added, the organic phase was washed with water and brine, dried with sodium sulfate and the solvent was evaporated. The compound was purified by biotage flash column chromatography on silica gel using a mixture of hexane and ethyl acetate as eluent to give the title compound (0.57 g, 70% yield).

LC-MS (Method 2): $R_t$=1.25 min; MS (ESIpos): m/z=367 $[M+H]^+$ $^1$H-NMR (400 MHz, DMSO-d6) δ[ppm]: 1.154 (3.83), 1.172 (7.69), 1.190 (3.67), 1.598 (4.72), 1.615 (4.75), 1.988 (12.40), 2.397 (16.00), 2.518 (1.81), 2.523 (1.25), 4.000 (0.93), 4.017 (2.87), 4.035 (2.88), 4.053 (0.94), 5.732 (0.71), 5.750 (1.11), 5.759 (2.44), 5.768 (0.70), 7.102 (1.04), 7.238 (2.18), 7.280 (0.73), 7.299 (1.60), 7.318 (0.92), 7.373 (0.94), 7.499 (0.54), 7.516 (0.92), 7.534 (0.44), 7.670 (0.50), 7.687 (0.92), 7.706 (0.45), 8.537 (3.84), 8.539 (3.82), 8.841 (4.23), 8.867 (1.04), 8.885 (1.01).

Intermediate 24

N-[(1R)-1-(3-{1,1-difluoro-2-methyl-2-[(triethylsilyl)oxy]propyl}-2-fluorophenyl)ethyl]-6-(dimethylphosphoryl)-2-methylpyrido[3,4-d]pyrimidin-4-amine

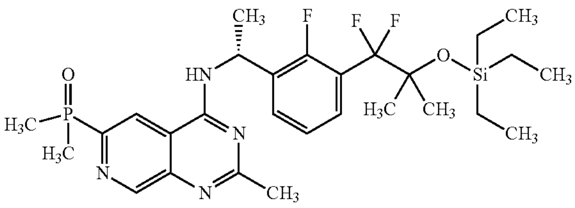 [SMILES: CC[Si](CC)(CC)OC(C)(C)C(F)(F)c1cccc([C@@H](C)Nc2nc(C)nc3cnc(P(C)(C)=O)cc23)c1F]

To a solution of 6-chloro-N-[(1R)-1-(3-{1,1-difluoro-2-methyl-2-[(triethylsilyl)oxy]propyl}-2-fluorophenyl)ethyl]-2-methylpyrido[3,4-d]pyrimidin-4-amine (100 mg, 185 μmol), dimethyl-lambda5-phosphanone (14.5 mg, 185 μmol) and triethylamine (90 μl, 650 μmol; CAS-RN:[121-44-8]) in acetonitrile (1.3 ml) under argon was added tetrakis(triphenylphosphin)palladium(0) (42.9 mg, 37.1 μmol; CAS-RN:[14221-01-3]) and the mixture was heated at 100° C. for two days. The mixture was filtered, concentrated and the crude product directly used for the following step.

LC-MS (Method 2): $R_t$=1.59 min; MS (ESIpos): m/z=581.6 $[M+1]^+$

Intermediate 25

N-[(1R)-1-(3-{1,1-difluoro-2-methyl-2-[(triethylsilyl)oxy]propyl}-2-fluorophenyl)ethyl]-6-(dimethylphosphoryl)-2,8-dimethylpyrido[3,4-d]pyrimidin-4-amine

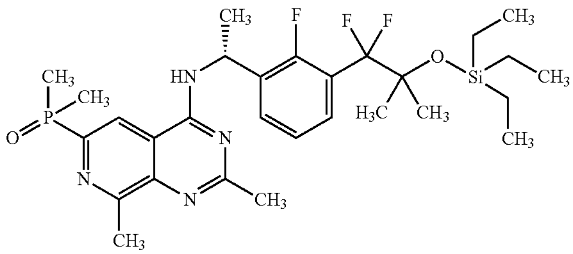 [SMILES: CC[Si](CC)(CC)OC(C)(C)C(F)(F)c1cccc([C@@H](C)Nc2nc(C)nc3c(C)nc(P(C)(C)=O)cc23)c1F]

Following the general procedure 1, 6-chloro-N-[(1R)-1-(3-{1,1-difluoro-2-methyl-2-[(triethylsilyl)oxy]propyl}-2-fluorophenyl)ethyl]-2,8-dimethylpyrido[3,4-d]pyrimidin-4-amine (83.0 mg, 150 μmol) was reacted with dimethyl-lambda$^5$-phosphanone (11.7 mg, 150 μmol), tetrakis (triphenylphosphine)palladium(0) (27.5 mg, 30.0 μmol, 0.20 equiv.) and triethyl amine (73 μl, 530 μmol) in acetonitrile (1.0 mL) at 90° C. for 20 hours. The mixture was cooled to room temperature and ethyl acetate and water were added, the phases were separated and the organic phase was dried through hydrophobic filtration. The solvent was evaporated to give a pale yellow oil, which was not further purified and used as a crude mixture.

LC-MS (Method 2): $R_t$=1.78 min; MS (ESIpos): m/z=595 $[M+H]^+$

Intermediate 26

(S,E)-N-ethylidene-2-methylpropane-2-sulfinamide

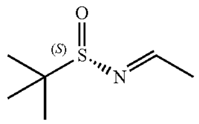

The reactions were performed as two batches in parallel: A mixture of (S)-2-methylpropane-2-sulfinamide (200 g, 1.65 mol), acetaldehyde (500 ml, 5 M in THF) and MgSO4 (750 g, 6.23 mol) in DCM (1.5 L) was stirred for 28 h at 20° C. The two reaction mixture were combined and filtered. The filter cake was washed with DCM (1000 ml×2). The combined filtrate was concentrated in vacuum. The residue was purified by chromatography on silica gel (3% EA in PE) to give (S,E)-N-ethylidene-2-methylpropane-2-sulfinamide (410 g, 84.37% yield) as light yellow oil.

$^1$H NMR (CDCl3 400 MHz) 8.07 (q, 1H), 2.23 (d, 2H), 1.16 (s, 9H)

Intermediate 27

(S)—N—((R)-1-(2-fluoro-3-iodophenyl)ethyl)-2-methylpropane-2-sulfinamide

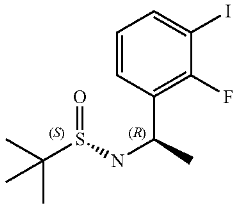

The reactions were performed as four batches in parallel: To a solution n-BuLi (320 ml, 2.5 M in hexane) was added drop-wise N-isopropylpropan-2-amine (120 ml, 849.10 mmol) in THF (300 ml) at −20° C., then it was stirred for 1 h and cooled to −60° C. A solution of 1-fluoro-2-iodo-benzene (180 g, 810.82 mmol) in THF (300 ml) was added drop-wise to the reaction. After stirred for 2 h, a solution of (S,E)-N-ethylidene-2-methylpropane-2-sulfinamide (100 g, 679.17 mmol) in THF (300 ml) was added drop-wise at −60° C. under N2. The mixture was warmed to 20° C. and stirred for 16 h. Each reaction solution was poured into sat. aq. NH4Cl (3 L) and extracted with MTBE (800 ml×3). The combined organic solution was washed with brine (500 ml), dried over Na2SO4, filtered and concentrated in vacuum. The four batches were combined and purified by chromatography on silica gel (PE: EA=10:1 to 1:2) for three times to give the desired product (94 g, 254.58 mmol) as light brown oil (contained ~0.04 eq isomer).

$^1$H NMR (CDCl3 400 MHz) 7.63-7.67 (m, 1H), 7.30-7.33 (m, 1H), 6.86-6.91 (m, 1H), 4.81-4.86 (m, 1H), 3.41 (d, 1H), 1.57 (d, 2H), 1.23 (s, 9H)

Intermediate 28

(R)-1-(2-fluoro-3-iodophenyl)ethanamine hydrochloride

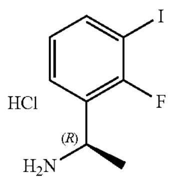

To a solution of (S)—N-[(1R)-1-(2-fluoro-3-iodo-phenyl) ethyl]-2-methyl-propane-2-sulfinamide (94 g, 254.58 mmol) in dioxane (140 ml) was added HCl/dioxane (4 M, 140 ml) at 20° C., then the reaction was stirred for 2 h. TLC (PE: EA=1:1) showed the reaction completed. To the mixture was added MTBE (300 ml) and filtered. The filter cake was washed with MTBE (50 ml×2) and dried in vacuum to give (R)-1-(2-fluoro-3-iodophenyl)ethanamine hydrochloride (67 g, 87.28% yield) as light yellow solid.

$^1$H NMR (DMSO-d6 400 MHz) 8.70 (s, 1H), 7.84-7.88 (m, 1H), 7.66-7.69 (m, 1H), 7.08-7.12 (m, 1H), 4.58-4.61 (m, 1H), 1.52 (d, 3H)

Intermediate 29

(R)-tert-butyl (1-(2-fluoro-3-iodophenyl)ethyl)carbamate

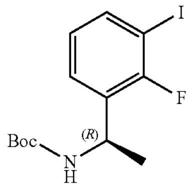

To a solution of (R)-1-(2-fluoro-3-iodophenyl)ethanamine hydrochloride (67 g, 222.20 mmol) in H2O (300 ml) and THF (300 ml) was added $NaHCO_3$ (70 g, 833.27 mmol), then Boc2O (52 g, 238.26 mmol) was added and the reaction was stirred at 25° C. for 1 h. TLC (DCM: MeOH=10:1) showed the reaction completed. The mixture was extracted with MTBE (300 ml×3). The combined organic solution was washed with brine (300 ml), dried over Na2SO4, filtered and concentrated in vacuum. The residue was triturated with PE (100 ml) and filtered. The filter cake was dried in vacuum to give (R)-tert-butyl (1-(2-fluoro-3-iodophenyl)ethyl)carbamate (75 g, 92.43% yield) as light yellow solid.

$^1$H NMR (MeOD 400 MHz) 7.64-7.68 (m, 1H), 7.31-7.35 (m, 1H), 6.90-6.95 (m, 1H), 4.86-4.94 (m, 1H), 1.51 (d, 3H), 1.25 (s, 9H)

Intermediate 30

(R)-ethyl 2-(3-(1-((tert-butoxycarbonyl)amino) ethyl)-2-fluorophenyl)-2,2-difluoroacetate

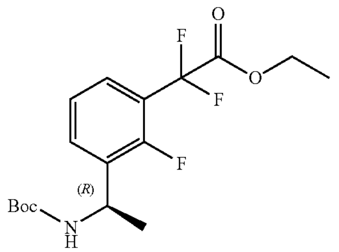

A mixture of ethyl 2-bromo-2,2-difluoro-acetate (40 ml, 311.36 mmol) and Cu (40 g, 629.43 mmol) in DMSO (300 ml) was stirred at 20° C. for 1 h, then (R)-tert-butyl (1-(2-fluoro-3-iodophenyl)ethyl)carbamate (75 g, 205.38 mmol) was added and the reaction was heated to stirred at 80° C. for 5 h. TLC (PE: EA=3:1) showed the reaction completed. The reaction was cooled and directly extracted with MTBE (500 ml×4). The combined MTBE solution was washed with sat. NH4Cl (300 ml×2), dried over Na2SO4, filtered and concentrated in vacuum. The residue was purified by chromatography on silica gel (PE: EA=20:1~5:1) to give (R)-ethyl 2-(3-(1-((tert-butoxycarbonyl)amino)ethyl)-2-fluorophenyl)-2,2-difluoroacetate (45 g, 60.64% yield) as light yellow oil.

$^1$H NMR (CDCl3 400 MHz) 7.52-7.56 (m, 1H), 7.44-7.48 (m, 1H), 7.20-7.25 (m, 1H), 4.97 (br s, 3H), 4.33-4.39 (m, 2H), 1.51 (d, 3H), 1.19-1.45 (m, 12H).

Intermediate 31 tert-butyl (R)-(1-(3-(1,1-difluoro-2-(methoxy (methyl)amino)-2-oxoethyl)-2-fluorophenyl)-ethyl) carbamate

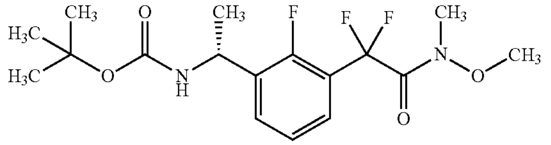 [SMILES: CON(C)C(=O)C(F)(F)c1cccc([C@@H](C)NC(=O)OC(C)(C)C)c1F]

To a solution of ethyl (3-{(1R)-1-[(tert-butoxycarbonyl) amino]ethyl}-2-fluorophenyl)(difluoro)acetate (16.4 g, 45.4 mmol) and N-methoxymethanamine hydrogen chloride (1/1) (6.64 g, 68.1 mmol) in tetrahydrofuran (330 ml) under argon at −15° C. was added N,N-diisopropylethylamine (12 ml), and the solution was stirred for 5 min. Then, 2-propylmagnesiumchloride (2M in THF, 110 ml, 2.0 M, 230 mmol) was added dropwise and the resulting solution was stirred for 1 h. at −15° C. to −10° C. The reaction was quenched with saturated aqueous ammonium chloride solution, and extracted with ethyl acetate. The organic phases were washed with saturated aqueous sodium chloride solution, filter-dried and concentrated. The crude product was purified by flash column chromatography to give the title compound (13.8 g, 81% yield).

$^1$H-NMR (400 MHz, DMSO-d6) δ[ppm]: 1.154 (2.54), 1.172 (5.05), 1.190 (2.60), 1.274 (5.68), 1.291 (5.71), 1.342 (16.00), 1.987 (8.09), 2.327 (0.45), 2.518 (1.66), 2.523 (1.17), 2.669 (0.46), 3.198 (8.59), 3.223 (1.92), 3.999 (0.58), 4.017 (1.73), 4.035 (1.69), 4.053 (0.53), 4.843 (0.49), 4.862 (0.68), 4.880 (0.45), 7.333 (0.89), 7.353 (2.11), 7.372 (1.30), 7.483 (0.91), 7.500 (1.41), 7.516 (0.65), 7.545 (0.77), 7.562 (1.35), 7.584 (1.27), 7.605 (0.76).

Intermediate 32

6-bromo-2-methylpyrido[3,4-d]pyrimidin-4-ol

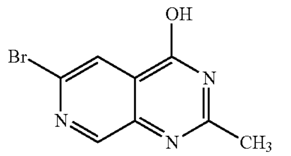

To a solution of 5-amino-2-bromoisonicotinic acid (CAS 1242336-80-6, 50 g, 230 mmol) and ethanimidamide hydrochloride (1:1) (65 g, 691 mmol) in 2-methoxyethanol (300 ml) was added sodium acetate (57 g, 691 mmol) was stirred at 160° C. for 48 hours. The mixture was cooled to room temperature, diluted with water and stirred for 1 hour. The resulting precipitate was filtered off and dried in vacuum to yield the title compound (44 g, 76% yield).

LC-MS (Method 2): $R_t$=0.48 min; MS (ESIpos): m/z=240 $[M+H]^+$

Intermediate 33

2-amino-5-bromo-6-methoxypyridine-3-carboxamide

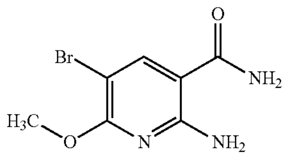

To a solution of 2-amino-6-methoxypyridine-3-carboxamide (19.0 g, 114 mmol) in DMF (160 ml) was added NBS (22.3 g, 125 mmol) and the reaction mixture was stirred at 25° C. for 2 hours. The mixture was concentrated, the residue was triturated with water (200 ml) and the resulting solid was dried under reduced pressure to give the titled compound (20.0 g, 64% yield) as a brown solid which was used without further purification.

Intermediate 34

6-bromo-7-methoxy-2-methylpyrido[2,3-d]pyrimidin-4-ol

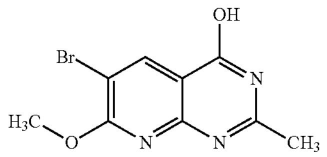

A solution of 2-amino-5-bromo-6-methoxypyridine-3-carboxamide (Intermediate 33, 52 g, 90% purity, 211 mmol) and triethyl orthoacetate (165 g, 1.02 mol) in 2-methoxyethanol (520 ml) was stirred at 120° C. for 2 hours. The resulting suspension was filtered and the precipitate was recrystallized from 2-propanol to give 6-bromo-7-methoxy-2-methylpyrido[2,3-d]pyrimidin-4-ol as a brown solid (27.8 g, 96% purity, 49% yield).

LC-MS (Method 2): $R_t$=0.54 min; MS (ESIpos): m/z=272 $[M+H]^+$ $^1$H NMR (400 MHz, DMSO-$d_6$) δ ppm 12.55 (br s, 1H), 8.45 (s, 1H), 4.00-4.07 (m, 3H), 2.52-2.55 (m, 1H), 2.36 (s, 3H)

Intermediate 35

6-bromo-7-methoxy-2-methyl-N-{(1R)-1-[2-methyl-3-(trifluoromethyl)phenyl]ethyl}-pyrido[2,3-d]pyrimidin-4-amine

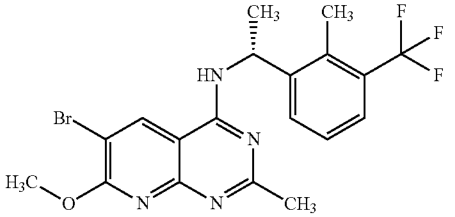 [SMILES: COc1nc2nc(C)nc(N[C@H](C)c3cccc(C(F)(F)F)c3C)c2cc1Br]

According to General Procedure 6, starting from 6-bromo-7-methoxy-2-methylpyrido[2,3-d]pyrimidin-4-ol (Intermediate 34, 900 mg, 3.33 mmol) and (1R)-1-[2-methyl-3-(trifluoromethyl)phenyl]ethan-1-amine hydrogen chloride (1/1) (879 mg, 3.67 mmol), the title compound was obtained (1.22 g, 80% yield).

LC-MS (Method 2): $R_t$=1.40 min; MS (ESIpos): m/z=455 $[M+H]^+$ $^1$H NMR (400 MHz, DMSO-d6) b ppm 1.53 (d, J=6.84 Hz, 3H) 2.33 (s, 3H) 2.60 (s, 3H) 4.00 (s, 3H) 5.57-5.74 (m, 1H) 7.27-7.40 (m, 1H) 7.45-7.60 (m, 1H) 7.71-7.80 (m, 1H) 8.58-8.70 (m, 1H) 9.12 (s, 1H).

Intermediate 36 tert-butyl {(1R)-1-[3-(1,1-difluoro-2-oxopropyl)-2-fluorophenyl]ethyl}carbamate

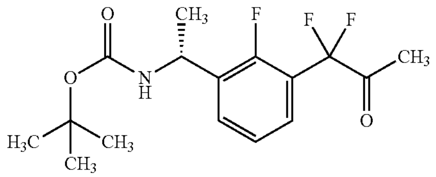 [SMILES: CC(=O)C(F)(F)c1cccc([C@@H](C)NC(=O)OC(C)(C)C)c1F]

Following General Procedure 4: tert-butyl [(1R)-1-(3-{1,1-difluoro-2-[methoxy(methyl)amino]-2-oxoethyl}-2-fluorophenyl)ethyl]carbamate (4.00 g, 10.6 mmol), bromido(methyl)magnesium (32 ml, 1.0 M, 32 mmol) in THF (120 ml) were reacted from −10° C. to 0° C. for 1.5 h. The titled compound (3.63 g, quant.) was obtained after aq. work-up and used in the next step without further purification.

LC-MS (Method 2): $R_t$=1.29 min; MS (ESIpos): m/z=332 $[M+H]^+$ $^1$H-NMR (400 MHz, DMSO-d6) δ[ppm]: 1.154 (0.87), 1.172 (0.63), 1.190 (0.40), 1.272 (6.20), 1.289 (6.20), 1.353 (16.00), 2.443 (8.06), 2.518 (1.59), 2.523 (1.09), 4.851 (0.45), 4.869 (0.62), 4.887 (0.42), 5.759 (0.88), 7.356 (0.72), 7.376 (1.65), 7.395 (1.01), 7.533 (0.89), 7.550 (1.41), 7.566 (0.73), 7.569 (0.74), 7.596 (1.11), 7.614 (1.59), 7.633 (0.67).

Intermediate 37 tert-butyl [(1R)-1-{3-[(2RS)-1,1-difluoro-2-hydroxypropyl]-2-fluorophenyl}ethyl]carbamate

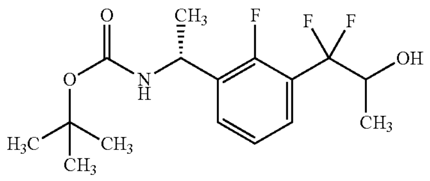 [SMILES: CC(O)C(F)(F)c1cccc([C@@H](C)NC(=O)OC(C)(C)C)c1F]

To a solution of tert-butyl {(1R)-1-[3-(1,1-difluoro-2-oxopropyl)-2-fluorophenyl]ethyl}carbamate (3.63 g, 97% purity, 10.6 mmol) in EtOH (42 ml) was added $NaBH_4$ portionwise at 0° C. The mixture was stirred at rt for 2 h, then poured into a sat. aq. $NH_4Cl$ sol. at 0° C. The mixture was extracted with EtOAc, the org. phase was washed with brine, dried over $Na_2SO_4$ and concentrated under reduced pressure. Purification by flash column chromatography yielded a mixture of diastereomers (3.32 g, 94% yield), which were separated by chiral HPLC.

Prep.-Method: SFC

Instrument: Sepiatec: Prep SFC100; Column: Chiralpak IG 5p 250×30 mm; eluent A: $C_{02}$; eluent B: methanol; isocratic: 10% B; flow: 100 ml/min; temperature: 40° C.; BPR: 150 bar; UV: 210 nm LC-MS (Method 2): $R_t$=1.16 min; MS (ESIpos): m/z=351 $[M+NH_4+]$*

$^1$H-NMR (400 MHz, DMSO-d6) δ[ppm]: 1.135 (3.55), 1.147 (3.69), 1.171 (1.70), 1.189 (1.04), 1.277 (4.65), 1.281 (4.31), 1.294 (4.89), 1.361 (16.00), 1.986 (1.18), 4.126 (0.44), 4.147 (0.63), 4.164 (0.64), 4.183 (0.45), 4.909 (0.69), 5.555 (1.07), 5.571 (1.11), 5.588 (0.80), 5.604 (0.72), 7.247 (0.77), 7.266 (1.87), 7.286 (1.30), 7.348 (1.08), 7.364 (1.60), 7.381 (0.74), 7.493 (0.89), 7.509 (1.57), 7.528 (0.85), 7.547 (0.60), 7.565 (0.90), 7.583 (0.56).

Diastereomer 1: 1.71 g $^1$H NMR (400 MHz, DMSO-$d_6$) δ ppm 1.10-1.23 (m, 4H), 1.29 (d, 4H), 1.36 (s, 8H), 4.16 (td, 1H), 4.91 (br t, 1H), 5.60 (br d, 1H), 7.27 (t, 1H), 7.36 (t, 1H), 7.48-7.61 (m, 2H).

Diastereomer 2: 1.67 g $^1$H NMR (400 MHz, DMSO-$d_6$) δ ppm 1.15 (br d, 5H), 1.29 (d, 4H), 1.36 (s, 7H), 2.52-2.55 (m, 1H), 4.10-4.21 (m, 1H), 4.91 (br t, 1H), 5.56 (d, 1H), 7.17-7.30 (m, 1H), 7.36 (t, 1H), 7.48-7.59 (m, 2H)

Intermediate 38

1-{3-[(1R)-1-aminoethyl]-2-fluorophenyl}-1,1-difluoropropan-2-ol trifluoroacetic acid (1/1) (diastereomer 1)

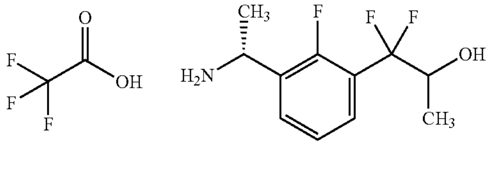 [SMILES: O=C(O)C(F)(F)F ; CC(O)C(F)(F)c1cccc([C@@H](C)N)c1F]

Following General Procedure 3: tert-butyl [(1R)-1-{3-[1,1-difluoro-2-hydroxypropyl]-2-fluorophenyl}ethyl]carbamate (Intermediate 37, diastereomer 1) (1.70 g, 5.10 mmol) and TFA (5.9 ml, 76 mmol) in DCM (30 ml) gave the titled compound (2.07 g) which was used without further purification.

LC-MS (Method 2): $R_t$=0.83 min; MS (ESIpos): m/z=234 $[M+H]^+$ $^1$H-NMR (400 MHz, DMSO-d6) δ[ppm]: 1.145 (11.32), 1.161 (11.34), 1.223 (2.34), 1.394 (1.43), 1.409 (1.41), 1.501 (16.00), 1.519 (15.96), 1.734 (0.86), 2.296 (3.25), 2.518 (3.45), 2.523 (2.51), 4.121 (0.61), 4.139 (0.86), 4.159 (1.08), 4.175 (0.89), 4.196 (0.56), 4.669 (1.26), 4.684 (1.63), 4.699 (1.26), 7.160 (0.67), 7.164 (0.59), 7.180 (0.86), 7.230 (0.74), 7.248 (0.76), 7.388 (2.16), 7.408 (5.07), 7.428 (3.08), 7.478 (0.57), 7.522 (1.72), 7.526 (2.00), 7.544 (2.97), 7.559 (1.42), 7.563 (1.33), 7.693 (1.62), 7.710 (2.85), 7.726 (1.45), 8.383 (4.21).

Intermediate 39

1-{3-[(1R)-1-aminoethyl]-2-fluorophenyl}-1,1-difluoropropan-2-ol trifluoroacetic acid (1/1) (diastereomer 2)

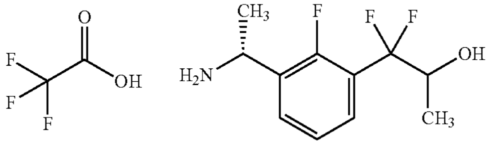 [SMILES: O=C(O)C(F)(F)F ; CC(O)C(F)(F)c1cccc([C@@H](C)N)c1F]

Following General Procedure 3: tert-butyl [(1R)-1-{3-[1,1-difluoro-2-hydroxypropyl]-2-fluorophenyl}ethyl]carbamate (Intermediate 37, diastereomer 2) (1.66 g, 4.98 mmol), TFA (5.8 ml) in DCM (30 ml) gave the titled compound (2.03 g) which was used without further purification.

LC-MS (Method 2): $R_t$=0.82 min; MS (ESIpos): m/z=234 $[M+H]^+$ $^1$H-NMR (400 MHz, DMSO-d6) δ[ppm]: 1.153 (11.70), 1.169 (11.66), 1.223 (2.96), 1.406 (1.47), 1.423 (1.47), 1.491 (2.28), 1.503 (16.00), 1.520 (15.65), 1.734 (1.13), 2.297 (4.13), 2.336 (0.41), 2.518 (4.38), 2.523 (3.26), 2.678 (0.41), 4.132 (0.63), 4.151 (0.96), 4.169 (1.21), 4.188 (0.98), 4.207 (0.59), 4.678 (1.30), 4.695 (1.70), 4.708 (1.36), 7.142 (0.42), 7.162 (0.88), 7.164 (0.80), 7.180 (1.03), 7.185 (0.62), 7.230 (0.91), 7.248 (0.94), 7.391 (2.19), 7.411 (5.20), 7.430 (3.18), 7.484 (0.59), 7.527 (2.00), 7.544 (3.07), 7.560 (1.44), 7.564 (1.36), 7.699 (1.66), 7.716 (2.97), 7.732 (1.51), 8.360 (4.29).

Intermediate 40

(1R)-1-(3-{1,1-difluoro-2-[(triethylsilyl)oxy]propyl}-2-fluorophenyl)ethan-1-amine (diastereomer 1)

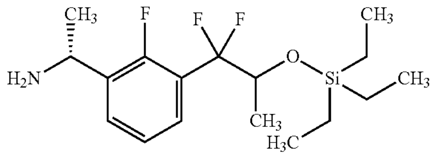 [SMILES: CC[Si](CC)(CC)OC(C)C(F)(F)c1cccc([C@@H](C)N)c1F]

Following General Procedure 5: (1-{3-[(1R)-1-aminoethyl]-2-fluorophenyl}-1,1-difluoropropan-2-ol trifluoroacetic acid (1/1) (Intermediate 38, 1.57 g, 3.84 mmol), triethylsilyl trifluoromethanesulfonate (4.3 ml, 19 mmol), 2,6-lutidine (3.1 ml) in DCM (25 ml) gave the titled compound (1.17 g, 88% yield).

LC-MS (Method 2): $R_t$=1.58 min; MS (ESIpos): m/z=349 $[M+H]^+$ $^1$H-NMR (400 MHz, DMSO-d6) δ[ppm]: 0.362 (0.65), 0.379 (0.91), 0.383 (0.83), 0.400 (2.30), 0.407 (0.91), 0.420 (2.51), 0.427 (2.43), 0.435 (0.77), 0.440 (1.17), 0.447 (2.63), 0.455 (0.72), 0.466 (1.40), 0.484 (0.72), 0.765 (6.97), 0.772 (0.52), 0.776 (0.71), 0.785 (16.00), 0.793 (0.72), 0.804 (5.14), 0.873 (0.60), 0.892 (1.24), 0.913 (0.51), 1.189 (2.09), 1.204 (2.12), 1.248 (3.35), 1.265 (3.31), 2.518 (0.53), 4.241 (0.63), 4.257 (0.62), 7.255 (0.93), 7.274 (0.66), 7.311 (0.43), 7.325 (0.50), 7.329 (0.53), 7.707 (0.51).

Intermediate 41

(1R)-1-(3-{1,1-difluoro-2-[(triethylsilyl)oxy]propyl}-2-fluorophenyl)ethan-1-amine (diastereomer 2)

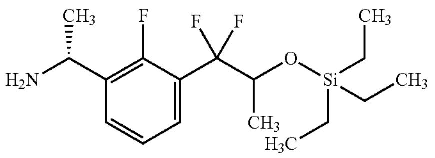 [SMILES: CC[Si](CC)(CC)OC(C)C(F)(F)c1cccc([C@@H](C)N)c1F]

Following General Procedure 3: trifluoroacetic acid/(1-{3-[(1R)-1-aminoethyl]-2-fluorophenyl}-1,1-difluoropropan-2-ol (1/1) (Intermediate 39, 1.53 g, 85% purity, 3.73 mmol), triethylsilyl trifluoromethanesulfonate (4.2 ml, 19 mmol), 2,6-lutidine (3.0 ml) in DCM (25 mL) gave the titled compound (1.14 g, 87% yield).

LC-MS (Method 2): $R_t$=1.58 min; MS (ESIpos): m/z=349 $[M+H]^+$ $^1$H-NMR (400 MHz, DMSO-d6) δ[ppm]: 0.306 (0.93), 0.323 (0.90), 0.326 (1.14), 0.343 (2.11), 0.363 (2.20), 0.383 (1.34), 0.402 (2.03), 0.421 (2.25), 0.436 (0.67), 0.440 (1.43), 0.455 (0.72), 0.459 (1.02), 0.478 (0.46), 0.736 (7.05), 0.748 (0.73), 0.756 (16.00), 0.765 (0.69), 0.776 (5.43), 0.873 (0.54), 0.893 (1.13), 0.913 (0.51), 1.222 (4.18), 1.234 (2.60), 1.238 (3.91), 1.962 (0.54), 2.518 (0.61), 2.523 (0.43), 4.280 (0.61), 4.296 (0.63), 7.261 (0.91), 7.280 (0.68), 7.327 (0.50), 7.747 (0.50).

Intermediate 42

6-bromo-N-[(1R)-1-(3-{1,1-difluoro-2-[(triethylsilyl)oxy]propyl}-2-fluorophenyl)ethyl]-2-methylpyrido[3,4-d]pyrimidin-4-amine (diastereomer 1)

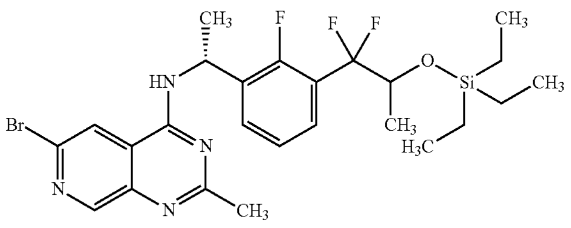

Following General Procedure 2: 6-bromo-2-methylpyrido[3,4-d]pyrimidin-4-ol (350 mg, 1.46 mmol), (1R)-1-(3-{1,1-difluoro-2-[(triethylsilyl)oxy]propyl}-2-fluorophenyl)ethan-1-amine (Intermediate 40, 608 mg, 1.75 mmol), 2,4,6-tri(propan-2-yl)benzene-1-sulfonyl chloride (486 mg, 1.60 mmol), triethylamine (510 μl) and DMAP (26.7 mg, 219 μmol) in DMF (4.4 ml) gave the titled compound (600 mg, 72% yield) after flash column chromatography.

LC-MS (Method 2): $R_t$=1.70 min; MS (ESIpos): m/z=572 $[M+H]^+$ $^1$H-NMR (400 MHz, DMSO-d6) δ[ppm]: 0.244 (0.78), 0.261 (0.83), 0.264 (0.99), 0.282 (2.07), 0.302 (2.20), 0.305 (0.85), 0.322 (1.12), 0.326 (2.11), 0.345 (2.27), 0.364 (1.37), 0.383 (0.88), 0.402 (0.40), 0.639 (6.53), 0.647 (0.50), 0.650 (0.73), 0.658 (16.00), 0.666 (0.70), 0.678 (5.04), 1.172 (0.76), 1.189 (0.41), 1.218 (1.90), 1.234 (1.94), 1.589 (2.23), 1.606 (2.23), 1.987 (1.18), 2.411 (7.93), 2.518 (0.70), 2.523 (0.47), 5.846 (0.52), 7.270 (0.86), 7.289 (0.54), 7.379 (0.49), 7.687 (0.48), 8.658 (1.98), 8.805 (2.35), 8.838 (0.59), 8.857 (0.57).

Intermediate 43

6-bromo-N-[(1R)-1-(3-{1,1-difluoro-2-[(triethylsilyl)oxy]propyl}-2-fluorophenyl)ethyl]-2-methylpyrido[3,4-d]pyrimidin-4-amine (diastereomer 2)

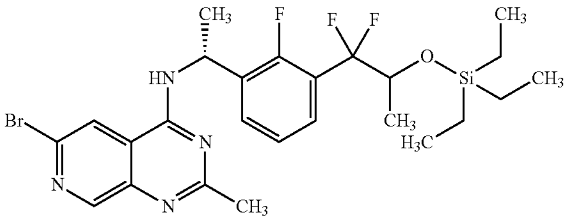 [SMILES: CC[Si](CC)(CC)OC(C)C(F)(F)c1cccc([C@@H](C)Nc2nc(C)nc3cnc(Br)cc23)c1F]

Following General Procedure 2: (1R)-1-(3-{1,1-difluoro-2-[(triethylsilyl)oxy]propyl}-2-fluorophenyl)ethan-1-amine (Intermediate 41, 507 mg, 1.46 mmol), 2,4,6-tri(propan-2-yl)benzene-1-sulfonyl chloride (486 mg, 1.60 mmol), triethylamine (510 μl), DMAP (26.7 mg, 219 μmol) in DMF (3.7 ml) were reacted overnight to give the titled compound (500 mg, 60% yield).

LC-MS (Method 2): $R_t$=1.72 min; MS (ESIpos): m/z=572 $[M+H]^+$ $^1$H-NMR (400 MHz, DMSO-d6) δ[ppm]: 0.211 (0.97), 0.228 (0.82), 0.230 (1.11), 0.248 (1.98), 0.268 (1.99), 0.288 (0.80), 0.296 (0.62), 0.316 (1.76), 0.336 (1.97), 0.354 (1.32), 0.373 (1.00), 0.392 (0.44), 0.645 (6.51), 0.653 (0.40), 0.656 (0.65), 0.665 (16.00), 0.673 (0.67), 0.684 (5.07), 1.223 (1.89), 1.239 (1.86), 1.594 (2.22), 1.612 (2.22), 2.371 (7.61), 2.518 (0.43), 5.669 (0.54), 7.244 (0.85), 7.263 (0.52), 7.371 (0.48), 7.642 (0.47), 8.689 (1.85), 8.797 (2.10), 8.895 (0.54), 8.912 (0.52).

Intermediate 44

(1-(3-{(1R)-1-[(6-bromo-2-methylpyrido[3,4-d]pyrimidin-4-yl)amino]ethyl}-2-fluorophenyl)-1,1-difluoropropan-2-ol (diastereomer 1)

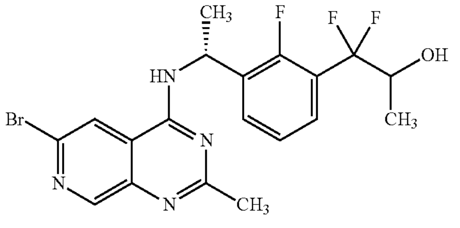 [SMILES: Cc1nc(N[C@H](C)c2cccc(C(F)(F)C(C)O)c2F)c2cc(Br)ncc2n1]

Following General Procedure 3: 6-bromo-N-[(1R)-1-(3-{1,1-difluoro-2-[(triethylsilyl)oxy]propyl}-2-fluorophenyl)ethyl]-2-methylpyrido[3,4-d]pyrimidin-4-amine (Intermediate 42, 125 mg, 219 μmol) and TFA (250 μl) in DCM (1.4 ml) gave the titled compound (99.0 mg, 99% yield) after purification by flash column chromatography.

LC-MS (Method 2): $R_t$=1.14 min; MS (ESIpos): m/z=455 $[M+H]^+$ $^1$H-NMR (400 MHz, DMSO-d6) δ[ppm]: 1.144 (3.59), 1.154 (1.90), 1.161 (3.59), 1.172 (2.26), 1.190 (1.16), 1.578 (4.44), 1.596 (4.37), 1.987 (4.51), 2.399 (16.00), 2.518 (1.66), 2.523 (1.24), 3.320 (0.64), 4.017 (0.96), 4.034 (0.94), 5.563 (2.34), 5.579 (2.28), 5.747 (0.68), 5.758 (6.34), 5.765 (1.06), 5.782 (0.65), 7.230 (0.72), 7.249 (1.65), 7.269 (0.99), 7.363 (0.54), 7.367 (0.61), 7.384 (0.92), 7.400 (0.45), 7.404 (0.41), 7.617 (0.52), 7.634 (0.90), 7.651 (0.45), 8.668 (3.75), 8.670 (3.84), 8.807 (4.39), 8.858 (1.09), 8.875 (1.05).

Intermediate 45

1-(3-{(1R)-1-[(6-bromo-2-methylpyrido[3,4-d]pyrimidin-4-yl)amino]ethyl}-2-fluorophenyl)-1,1-difluoropropan-2-ol (diastereomer 2)

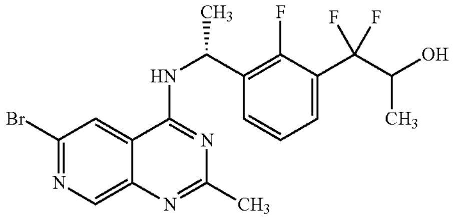 [SMILES: Cc1nc(N[C@H](C)c2cccc(C(F)(F)C(C)O)c2F)c2cc(Br)ncc2n1]

Following General Procedure 3: 6-bromo-N-[(1R)-1-(3-{1,1-difluoro-2-[(triethylsilyl)oxy]propyl}-2-fluorophenyl)ethyl]-2-methylpyrido[3,4-d]pyrimidin-4-amine (Intermediate 43, 490 mg, 860 μmol) and TFA (990 μl) in DCM (5.0 ml) gave the titled compound (351 mg, 90% yield)) after purification by flash column chromatography.

LC-MS (Method 2): $R_t$=1.11 min; MS (ESIpos): m/z=455 $[M+H]^+$ $^1$H-NMR (400 MHz, DMSO-d6) δ[ppm]: 1.131 (3.39), 1.147 (3.45), 1.154 (2.16), 1.171 (3.70), 1.189 (1.77), 1.582 (4.17), 1.600 (4.21), 1.986 (5.52), 2.377 (16.00), 2.518 (1.96), 2.523 (1.38), 4.016 (1.11), 4.034 (1.08), 5.578 (2.44), 5.594 (2.37), 5.703 (0.65), 5.720 (1.01), 5.738 (0.64), 5.756 (2.12), 7.221 (0.70), 7.240 (1.60), 7.259 (0.96), 7.358 (0.51), 7.362 (0.58), 7.380 (0.88), 7.395 (0.44), 7.599 (0.49), 7.615 (0.86), 7.632 (0.44), 8.666 (3.67), 8.668 (3.68), 8.805 (4.24), 8.875 (1.05), 8.893 (1.00).

Intermediate 46

(1R)-1-{3-[2-{[tert-butyl(dimethyl)silyl]oxy}-1,1-difluoropropyl]-2-fluorophenyl}ethan-1-amine (diastereomer 1)

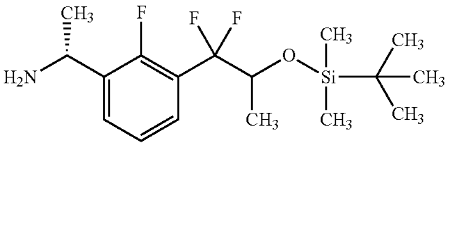 [SMILES: CC(O[Si](C)(C)C(C)(C)C)C(F)(F)c1cccc([C@@H](C)N)c1F]

Following General Procedure 5: 1-{3-[(1R)-1-aminoethyl]-2-fluorophenyl}-1,1-difluoropropan-2-ol trifluoroacetic acid (1/1) (Intermediate 38, 1.93 g, 81% purity, 4.47 mmol), tert-butyl(dimethyl)silyl trifluoromethanesulfonate (4.1 ml, 18 mmol) and 2,6-lutidine (3.6 ml) in DCM (25 ml) gave the titled compound (1.04 g, 67% yield) after purification by flash column chromatography.

LC-MS (Method 2): $R_t$=1.58 min; MS (ESIpos): m/z=349 $[M+H]^+$ $^1$H-NMR (400 MHz, DMSO-d6) δ[ppm]: −0.225 (4.64), 0.718 (1.04), 0.726 (16.00), 0.733 (1.01), 1.209 (1.33), 1.225 (1.36), 1.260 (2.06), 1.276 (2.02), 7.265 (0.56), 7.284 (0.40).

Intermediate 47

6-bromo-N-[(1R)-1-{3-[2-{[tert-butyl(dimethyl)silyl]oxy}-1,1-difluoropropyl]-2-fluorophenyl}ethyl]-2-methylpyrido[3,4-d]pyrimidin-4-amine (diastereomer 1)

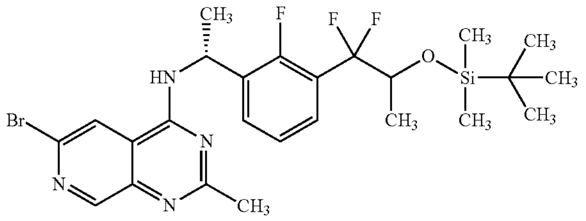 [SMILES: Cc1nc(N[C@H](C)c2cccc(C(F)(F)C(C)O[Si](C)(C)C(C)(C)C)c2F)c2cc(Br)ncc2n1]

Following General Procedure 2: 6-bromo-2-methylpyrido[3,4-d]pyrimidin-4-ol (425 mg, 1.77 mmol), (1R)-1-{3-[2-{[tert-butyl(dimethyl)silyl]oxy}-1,1-difluoropropyl]-2-fluorophenyl}ethan-1-amine (Intermediate 46, 738 mg, 2.12 mmol), 2,4,6-tri(propan-2-yl)benzene-1-sulfonyl chloride (590 mg, 1.95 mmol), $Et_3N$ (620 μl), DMAP (32.4 mg, 266 μmol) in DMF (5.0 ml) gave the titled compound (796 mg, 79% yield).

LC-MS (Method 2): $R_t$=1.73 min; MS (ESIneg): m/z=567 $[M-H]^-$ $^1$H-NMR (400 MHz, DMSO-d6) δ[ppm]: −0.319 (4.72), 0.670 (1.01), 0.678 (16.00), 1.285 (1.28), 1.300 (1.25), 1.643 (1.43), 1.659 (1.43), 2.044 (0.75), 2.460 (5.07), 2.575 (0.79), 2.580 (0.56), 7.320 (0.54), 8.714 (1.25), 8.864 (1.44).

Intermediate 48

(1R)-1-(3-{1,1-difluoro-2-methyl-2-[(triethylsilyl)oxy]propyl}-2-fluorophenyl)ethan-1-amine

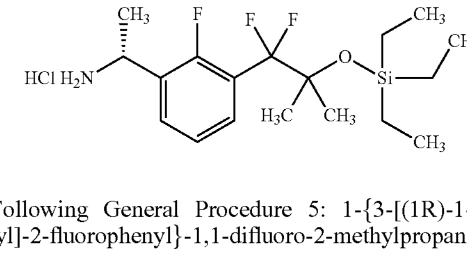

Following General Procedure 5: 1-{3-[(1R)-1-aminoethyl]-2-fluorophenyl}-1,1-difluoro-2-methylpropan-2-ol hydrogen chloride (1/1) [CAS 2569698-46-8] (6.00 g, 21.1 mmol), triethylsilyl trifluoromethanesulfonate (17 ml, 76 mmol), 2,6-lutidine (17 ml) in DCM (140 ml) gave the titled compound (7.29 g, 95% yield).

LC-MS (Method 2): $R_t$=1.66 min; MS (ESIpos): m/z=363 $[M+H]^+$ $^1$H-NMR (400 MHz, CHLOROFORM-d) 5 [ppm]: 0.641 (1.70), 0.662 (6.54), 0.671 (0.47), 0.673 (0.46), 0.682 (7.49), 0.701 (2.64), 0.958 (8.28), 0.969 (0.74), 0.978 (16.00), 0.986 (0.76), 0.998 (6.12), 1.544 (4.94), 1.560 (4.89), 1.699 (2.91), 4.560 (1.04), 4.577 (1.02), 7.251 (0.47), 7.290 (0.64), 7.407 (1.68), 7.438 (0.48), 7.443 (0.52), 7.460 (0.77), 7.475 (0.42), 7.480 (0.41), 7.632 (0.74).

Intermediate 49

6-bromo-N-[(1R)-1-(3-{1,1-difluoro-2-methyl-2-[(triethylsilyl)oxy]propyl}-2-fluorophenyl)ethyl]-2-methylpyrido[3,4-d]pyrimidin-4-amine

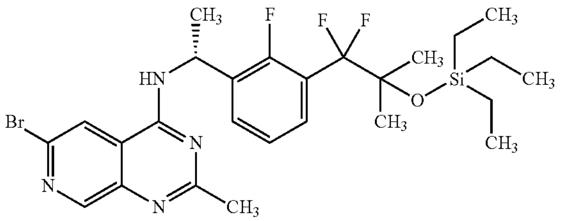 [SMILES: CC[Si](CC)(CC)OC(C)(C)C(F)(F)c1cccc([C@@H](C)Nc2nc(C)nc3cnc(Br)cc23)c1F]

Following General Procedure 2: 6-bromo-2-methylpyrido[3,4-d]pyrimidin-4-ol (2.50 g, 10.4 mmol), (1R)-1-(3-{1,1-difluoro-2-methyl-2-[(triethylsilyl)oxy]propyl}-2-fluorophenyl)ethan-1-amine (Intermediate 48, 4.52 g, 12.5 mmol), 2,4,6-tri(propan-2-yl)benzene-1-sulfonyl chloride (3.47 g, 11.5 mmol), $Et_3N$ (5.1 ml, 36 mmol), DMAP (191 mg, 1.56 mmol) in DMF (25 ml) gave the titled compound (5.30 g, 87% yield).

LC-MS (Method 1): $R_t$=1.79 min; MS (ESIneg): m/z=581, 583 $[M-H]^-$.

$^1$H NMR (400 MHz, DMSO-$d_6$) δ ppm 8.87 (d, 1H), 8.80 (s, 1H), 8.68 (s, 1H), 7.62 (t, 1H), 7.20-7.32 (m, 2H), 5.73-5.80 (m, 1H), 2.52-2.53 (m, 1H), 2.33-2.39 (m, 3H), 1.58 (d, 3H), 1.33 (br d, 6H), 1.23 (br s, 1H), 0.65-0.73 (m, 9H), 0.38-0.48 (m, 6H).

Intermediate 50 tert-butyl {(1R)-1-[3-(1,1-difluoro-3,3-dimethyl-2-oxobutyl)-2-fluorophenyl]ethyl}carbamate

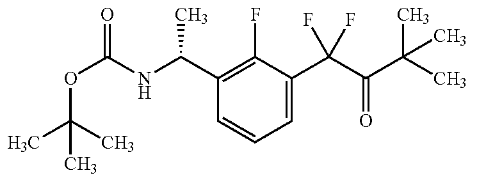 [SMILES: C[C@@H](NC(=O)OC(C)(C)C)c1cccc(C(F)(F)C(=O)C(C)(C)C)c1F]

To a solution of tert-butyl [(1R)-1-(3-{1, 1-difluoro-2-[methoxy(methyl)amino]-2-oxoethyl}-2-fluorophenyl)ethyl]carbamate (Intermediate 31, 4.34 g, 11.5 mmol) in THF (120 ml) was slowly added tert-butyllithium (15 ml, 1.7 M, 25 mmol) at −78° C. The mixture was stirred at −78° C. for 1 h and quenched by addition of sat. aq. $NH_4Cl$ sol. at −78° C. The mixture was diluted with water at rt, extracted with EtOAc, the org. phase was washed with brine, dried over $Na_2SO_4$, filtered and concentrated under reduced pressure. Purification by flash column chromatography gave the titled compound (1.51 g, 35% yield).

LC-MS (Method 2): $R_t$=1.51 min; MS (ESIpos): m/z=374 $[M+H]^+$ $^1$H-NMR (400 MHz, DMSO-d6) δ[ppm]: 0.792 (0.90), 1.154 (0.43), 1.172 (0.79), 1.190 (0.44), 1.264 (16.00), 1.279 (3.14), 1.351 (6.23), 1.987 (0.76), 2.518 (2.00), 2.523 (1.36), 5.758 (1.57), 7.358 (0.71), 7.377 (0.45), 7.520 (0.55), 7.581 (0.59), 7.600 (0.77).

Intermediate 51 tert-butyl 4-ethoxy-4-oxo-1,4lambda$^5$-azaphosphinane-1-carboxylate

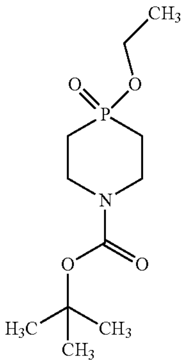

4-Ethoxy-1,4lambda$^5$-azaphosphinan-4-one [CAS 1042425-93-3] (20.8 g, 102 mmol) was dissolved in $CH_2Cl_2$ (300 mL). Triethylamine (43 ml, 310 mmol) was added, followed by di-tert-butyl dicarbonate (26 ml, 110 mmol). The mixture was stirred at RT for one night. The organic phase was washed with sat. aq. $NaHCO_3$ solution and brine. The organic phase was dried, filtered and the solvent was evaporated to give the title compound (30.7 g, quantitative), which was used for the next step without purification.

LC-MS (Method 2): $R_t$=0.86 min; MS (ESIpos): m/z=264 $[M+H]^+$ $^1$H-NMR (400 MHz, DMSO-d6) δ[ppm]: 1.239 (1.89), 1.257 (4.04), 1.275 (1.87), 1.405 (16.00), 3.977 (0.99), 3.994 (1.01), 3.996 (1.06), 4.014 (0.90).

Intermediate 52 tert-butyl 4-oxo-1,4lambda$^5$-azaphosphinane-1-carboxylate

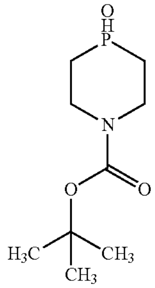

Tert-butyl 4-ethoxy-4-oxo-1,4lambda$^5$-azaphosphinane-1-carboxylate (Intermediate 51, 26.9 g, 102 mmol) was dissolved in THF (300 mL) and cooled to 0° C. Lithium aluminiumhydride (82 ml, 1.0 M in THF, 82 mmol) was added dropwise. The mixture was stirred at 0° C. for 45 minutes. TLC analysis indicated full consumption of the starting material. Half sat. aq. Rochelles salt solution was added dropwise. Ethyl acetate was added and the mixture was stirred at RT for 1 hour. The suspension was filtered and the organic phase was separated. The aq. phase was extracted with additional ethyl acetate. The combined organic phases were dried and the solvent was evaporated. The residue was dissolved in $CH_2Cl_2$ (350 mL) and cooled to 0° C. Hydrogen peroxide (10 ml, 30% purity, 100 mmol) was added dropwise. The mixture was allowed to warm to RT and was stirred for 0.5 hour. The mixture was cooled to 0° C. and $Na_2S_2O_3$ solution (10 wt %) was added slowly. The mixture was stirred at RT for 5 minutes. The organic phase was separated, filtered and the solvent was evaporated. The title compound was purified by flash column chromatography on silica gel using $CH_2Cl_2$/EtOH (0% to 10% EtOH). The title compound was obtained as white solid (21.6 g, 97% yield).

$^1$H NMR (400 MHz, DMSO-d6) b ppm 1.41 (s, 9H) 1.63-1.88 (m, 2H) 2.05-2.27 (m, 2H) 3.00-3.26 (m, 2H) 3.78-4.09 (m, 2H) 6.21-7.59 (m, 1H)

Intermediate 53 tert-butyl [(1R)-1-{3-[(2RS)-1,1-difluoro-2-hydroxy-3,3-dimethylbutyl]-2-fluorophenyl}ethyl] carbamate

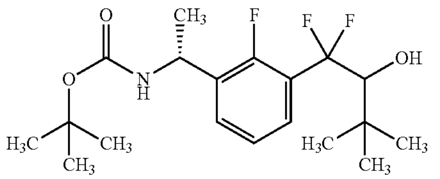 [SMILES: C[C@@H](NC(=O)OC(C)(C)C)c1cccc(C(F)(F)C(O)C(C)(C)C)c1F]

To a solution of tert-butyl {(1R)-1-[3-(1,1-difluoro-3,3-dimethyl-2-oxobutyl)-2-fluorophenyl]ethyl}carbamate (Intermediate 50, 1.24 g, 3.32 mmol) in EtOH (15 ml) was added $NaBH_4$ (159 mg, 4.21 mmol) and the mixture was stirred at rt for 2 h. The mixture was poured into sat. aq. $NH_4Cl$ sol. at 0° C., extracted with EtOAc and the org. phase was washed with brine, dried over $Na_204$, filtered and concentrated under reduced pressure. The diastereomers were separated by flash column chromatography.

Diastereomer 1: 411 mg (33% yield)

LC-MS (Method 2): $R_t$=1.37 min; MS (ESIpos): m/z=393.6 [M+NH$_4$+]*

$^1$H NMR (400 MHz, DMSO-d$_6$) δ ppm 7.59 (br d, 1H), 7.49 (t, 1H), 7.38 (br t, 1H), 7.25 (t, 1H), 5.61 (d, 1H), 4.86-4.96 (m, 1H), 3.66-3.77 (m, 1H), 2.52-2.54 (m, 1H), 1.37 (s, 9H), 1.28 (d, 4H), 0.97-1.23 (m, 2H), 0.94 (s, 9H), 0.73-0.87 (m, 1H)

Diastereomer 2: 554 mg (44% yield)

LC-MS (Method 2): $R_t$=1.36 min; MS (ESIpos): m/z=393.6 [M+NH$_4$+]$^+$ $^1$H NMR (400 MHz, DMSO-d$_6$) δ ppm 7.45-7.56 (m, 2H), 7.36 (br t, 1H), 7.17-7.29 (m, 1H), 5.53 (d, 1H), 4.91 (br t, 1H), 3.66-3.77 (m, 1H), 1.26-1.38 (m, 11H), 1.07-1.22 (m, 2H), 0.96 (s, 9H)

Intermediate 54 trifluoroacetic acid/1-{3-[(1R)-1-aminoethyl]-2-fluorophenyl}-1,1-difluoro-3,3-dimethylbutan-2-ol (1/1) (diastereomer 1)

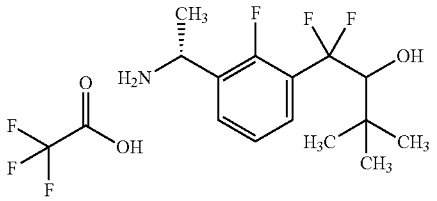

Following GP 3: tert-butyl [(1R)-1-{3-[1,1-difluoro-2-hydroxy-3,3-dimethylbutyl]-2-fluorophenyl}ethyl]carbamate (Intermediate 53 (diastereomer 1), 409 mg, 1.09 mmol) and TFA (1.3 ml, 16 mmol) in DCM (7.0 ml) gave the titled compound (626 mg) which was used without further purification.

LC-MS (Method 2): $R_t$=1.10 min; MS (ESIpos): m/z=276 [M+H]$^+$

Intermediate 55 trifluoroacetic acid/1-{3-[(1R)-1-aminoethyl]-2-fluorophenyl}-1,1-difluoro-3,3-dimethylbutan-2-ol (1/1) (diastereomer 2)

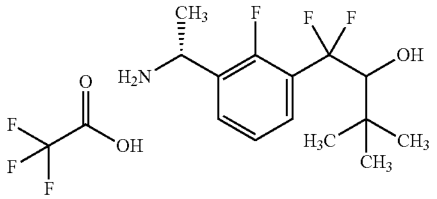

Following General Procedure 3: tert-butyl [(1R)-1-{3-[1,1-difluoro-2-hydroxy-3,3-dimethylbutyl]-2-fluorophenyl}ethyl]carbamate (Intermediate 53 (diastereomer 2), 552 mg, 1.47 mmol) and TFA (1.7 ml, 22 mmol) in DCM (9.0 ml) gave the titled compound (787 mg) which was used without further purification.

LC-MS (Method 2): $R_t$=1.08 min; MS (ESIpos): m/z=276 [M+H]$^+$

Intermediate 56

(1R)-1-(3-{1,1-difluoro-3,3-dimethyl-2-[(triethylsilyl)oxy]butyl}-2-fluorophenyl)ethan-1-amine (diastereomer 1)

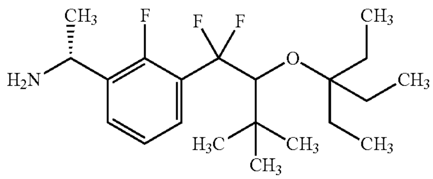 [SMILES: CCC(CC)(CC)OC(C(C)(C)C)C(F)(F)c1cccc([C@@H](C)N)c1F]

Following GP 6: 1-{3-[(1R)-1-aminoethyl]-2-fluorophenyl}-1,1-difluoro-3,3-dimethylbutan-2-ol trifluoroacetic acid (1/1) (Intermediate 54, 626 mg, 1.09 mmol), triethylsilyl trifluoromethanesulfonate (1.2 ml, 5.4 mmol) and 2,6-lutidine (880 μl) in DCM (7.0 ml) gave the titled compound (702 mg) which was used without further purification.

LC-MS (Method 2): $R_t$=1.78 min; MS (ESIpos): m/z=390 $[M+H]^+$

Intermediate 57

(1R)-1-(3-{1,1-difluoro-3,3-dimethyl-2-[(triethylsilyl)oxy]butyl}-2-fluorophenyl)ethan-1-amine (diastereomer 2)

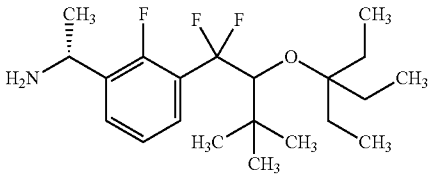 [SMILES: CCC(CC)(CC)OC(C(C)(C)C)C(F)(F)c1cccc([C@@H](C)N)c1F]

Following General Procedure 5: 1-{3-[(1R)-1-aminoethyl]-2-fluorophenyl}-1,1-difluoro-3,3-dimethylbutan-2-ol trifluoroacetic acid (1/1) (Intermediate 55, 787 mg, 1.47 mmol), triethylsilyl trifluoromethanesulfonate (1.7 ml, 7.3 mmol), 2,6-lutidine (1.2 ml) in DCM (10 ml) gave the titled compound (786 mg) which was used without further purification.

LC-MS (Method 2): $R_t$=1.78 min; MS (ESIpos): m/z=390 $[M+H]^+$

Intermediate 58

6-bromo-N-[(1R)-1-(3-{1,1-difluoro-3,3-dimethyl-2-[(triethylsilyl)oxy]butyl}-2-fluorophenyl)ethyl]-2-methylpyrido[3,4-d]pyrimidin-4-amine (diastereomer 1)

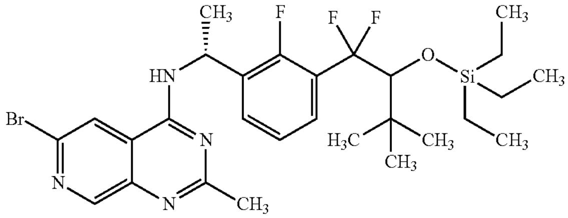 [SMILES: CC[Si](CC)(CC)OC(C(C)(C)C)C(F)(F)c1cccc([C@@H](C)Nc2nc(C)nc3cnc(Br)cc23)c1F]

Following General Procedure 2: (1R)-1-(3-{1,1-difluoro-3,3-dimethyl-2-[(triethylsilyl)oxy]butyl}-2-fluorophenyl) ethan-1-amine (Intermediate 56, 702 mg, 1.08 mmol), 6-bromo-2-methylpyrido[3,4-d]pyrimidin-4-ol (286 mg, 1.19 mmol), 2,4,6-tri(propan-2-yl)benzene-1-sulfonyl chloride (394 mg, 1.30 mmol), $Et_3N$ (380 μl), DMAP (19.9 mg, 163 μmol) in DMF (3.5 ml) gave the titled compound (399 mg, 60% yield).

LC-MS (Method 2): $R_t$=1.89 min; MS (ESIpos): m/z=611 $[M+H]^+$ $^1$H-NMR (400 MHz, DMSO-d6) δ[ppm]: 0.382 (0.45), 0.399 (0.83), 0.419 (2.32), 0.434 (2.46), 0.440 (2.56), 0.453 (2.53), 0.459 (1.07), 0.473 (1.14), 0.491 (0.45), 0.814 (11.81), 0.820 (10.17), 0.831 (1.20), 0.839 (16.00), 0.847 (1.16), 0.859 (5.87), 1.154 (0.64), 1.172 (1.37), 1.190 (0.71), 1.583 (2.69), 1.600 (2.66), 1.987 (2.29), 2.331 (0.66), 2.388 (9.60), 2.518 (2.97), 2.523 (2.15), 2.673 (0.65), 4.017 (0.69), 4.035 (0.62), 4.047 (0.55), 5.746 (0.42), 5.763 (0.64), 5.782 (0.40), 7.261 (0.52), 7.280 (1.12), 7.299 (0.66), 7.446 (0.58), 7.676 (0.58), 8.670 (2.35), 8.809 (2.60), 8.847 (0.71), 8.865 (0.69).

Intermediate 59

6-bromo-N-[(1R)-1-(3-{1,1-difluoro-3,3-dimethyl-2-[(triethylsilyl)oxy]butyl}-2-fluorophenyl)ethyl]-2-methylpyrido[3,4-d]pyrimidin-4-amine (diastereomer 2)

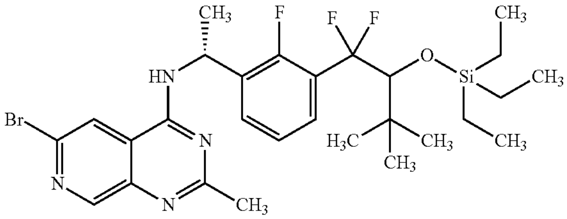 [SMILES: CC[Si](CC)(CC)OC(C(C)(C)C)C(F)(F)c1cccc([C@@H](C)Nc2nc(C)nc3cnc(Br)cc23)c1F]

Following General Procedure 2: (1R)-1-(3-{1,1-difluoro-3,3-dimethyl-2-[(triethylsilyl)oxy]butyl}-2-fluorophenyl) ethan-1-amine (Intermediate 57, 786 mg, 1.47 mmol), 6-bromo-2-methylpyrido[3,4-d]pyrimidin-4-ol (388 mg, 1.62 mmol), 2,4,6-tri(propan-2-yl)benzene-1-sulfonyl chloride (534 mg, 1.76 mmol), $Et_3N$ (510 μl), DMAP (26.9 mg, 220 μmol) in DMF (5.0 ml) gave the titled compound (683 mg, 76% yield).

LC-MS (Method 2): $R_t$=1.89 min; MS (ESIpos): m/z=611 $[M+H]^+$ $^1$H-NMR (400 MHz, DMSO-d6) δ[ppm]: 0.323 (0.62), 0.342 (0.86), 0.360 (2.06), 0.369 (0.83), 0.380 (2.24), 0.389 (2.16), 0.400 (1.00), 0.409 (2.27), 0.428 (1.19), 0.447 (0.71), 0.795 (7.39), 0.807 (1.10), 0.815 (16.00), 0.824 (1.10), 0.835 (6.59), 0.850 (11.81), 1.154 (0.73), 1.172 (1.60), 1.190 (0.83), 1.591 (2.84), 1.609 (2.81), 1.987 (2.97), 2.361 (9.68), 2.518 (2.34), 2.523 (1.67), 4.017 (0.68), 4.035 (0.96), 4.072 (0.56), 5.630 (0.45), 5.648 (0.69), 5.666 (0.44), 7.237 (0.56), 7.256 (1.21), 7.275 (0.71), 7.432 (0.62), 7.641 (0.61), 8.699 (2.47), 8.802 (2.82), 8.915 (0.73), 8.933 (0.71).

Intermediate 60

1-(3-{(1R)-1-[(6-bromo-2-methylpyrido[3,4-d]pyrimidin-4-yl)amino]ethyl}-2-fluorophenyl)-1,1-difluoro-3,3-dimethylbutan-2-ol (diastereomer 1)

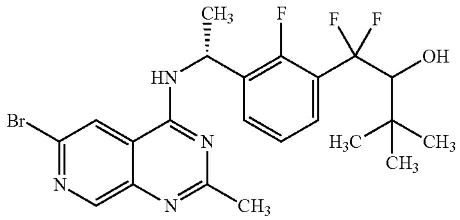 [SMILES: Cc1nc(N[C@H](C)c2cccc(C(F)(F)C(O)C(C)(C)C)c2F)c2cc(Br)ncc2n1]

Following General Procedure 3: 6-bromo-N-[(1R)-1-(3-{1,1-difluoro-3,3-dimethyl-2-[(triethylsilyl)oxy]butyl}-2-fluorophenyl)ethyl]-2-methylpyrido[3,4-d]pyrimidin-4-amine (Intermediate 58, 197 mg, 322 μmol) and TFA (500 μl) in DCM (3.0 ml) gave the titled compound (162 mg, quant.).

LC-MS (Method 2): $R_t$=1.35 min; MS (ESIpos): m/z=497 $[M+H]^+$ $^1$H-NMR (400 MHz, DMSO-d6) δ[ppm]: 0.928 (16.00), 1.154 (1.39), 1.172 (3.14), 1.190 (1.63), 1.572 (3.80), 1.590 (3.78), 1.987 (5.39), 2.382 (0.46), 2.411 (13.54), 2.518 (2.04), 2.523 (1.45), 4.017 (1.23), 4.035 (1.23), 4.053 (0.40), 5.537 (1.83), 5.556 (1.82), 5.749 (0.61), 5.759 (6.90), 5.767 (0.94), 5.784 (0.58), 7.219 (0.68), 7.238 (1.51), 7.258 (0.88), 7.383 (0.52), 7.400 (0.83), 7.416 (0.40), 7.605 (0.45), 7.621 (0.80), 7.638 (0.41), 8.681 (3.21), 8.683 (3.31), 8.811 (3.75), 8.850 (0.98), 8.869 (0.96).

Intermediate 61

1-(3-{(1R)-1-[(6-bromo-2-methylpyrido[3,4-d]pyrimidin-4-yl)amino]ethyl}-2-fluorophenyl)-1,1-difluoro-3,3-dimethylbutan-2-ol (diastereomer 2)

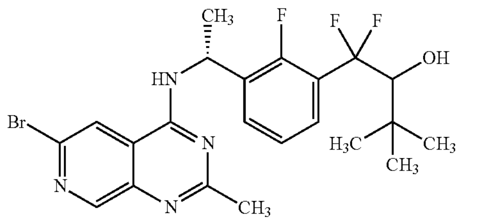

Following General Procedure 3: 6-bromo-N-[(1R)-1-(3-{1,1-difluoro-3,3-dimethyl-2-[(triethylsilyl)oxy]butyl}-2-fluorophenyl)ethyl]-2-methylpyrido[3,4-d]pyrimidin-4-amine (Intermediate 59, 340 mg, 556 μmol) and TFA (860 μl) in DCM (5.0 ml) gave the titled compound (285 mg, quant.).

LC-MS (Method 2): $R_t$=1.34 min; MS (ESIpos): m/z=497 $[M+H]^+$ $^1$H-NMR (400 MHz, DMSO-d6) δ[ppm]: 0.934 (10.60), 1.154 (1.12), 1.172 (2.25), 1.189 (1.06), 1.583 (2.52), 1.600 (2.50), 1.987 (3.85), 2.084 (16.00), 2.382 (8.95), 2.518 (0.89), 2.523 (0.62), 4.016 (0.79), 4.034 (0.76), 5.570 (1.00), 5.589 (0.99), 5.737 (0.56), 5.759 (1.82), 7.203 (0.46), 7.222 (1.01), 7.241 (0.60), 7.398 (0.55), 7.591 (0.53), 8.672 (2.13), 8.805 (2.45), 8.860 (0.61), 8.878 (0.59).

Intermediate 62

1-{3-[(1R)-1-aminoethyl]-2-fluorophenyl}-1,1-difluoro-3,3-dimethylbutan-2-one trifluoroacetic acid (1/1)

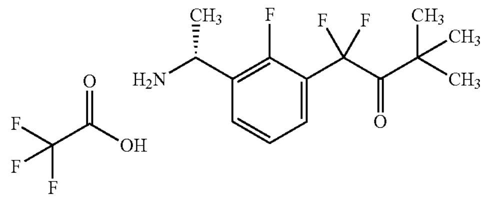 [SMILES: O=C(O)C(F)(F)F ; C[C@@H](N)c1cccc(C(F)(F)C(=O)C(C)(C)C)c1F]

Following General Procedure 3: tert-butyl {(1R)-1-[3-(1,1-difluoro-3,3-dimethyl-2-oxobutyl)-2-fluorophenyl]ethyl}carbamate (Intermediate 50, 200 mg, 536 μmol), TFA (410 μl, 5.4 mmol) in DCM (4 ml) gave the titled compound (284 mg).

LC-MS (Method 2): $R_t$=1.20 min; MS (ESIpos): m/z=274 $[M+H]^+$

Intermediate 63

1-(3-{(1R)-1-[(6-bromo-2-methylpyrido[3,4-d]pyrimidin-4-yl)amino]ethyl}-2-fluorophenyl)-1,1-difluoro-3,3-dimethylbutan-2-one

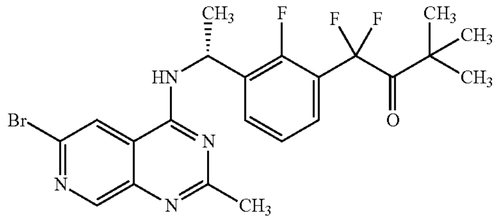 [SMILES: Cc1nc(N[C@H](C)c2cccc(C(F)(F)C(=O)C(C)(C)C)c2F)c2cc(Br)ncc2n1]

Following General Procedure 2: 6-bromo-2-methylpyrido[3,4-d]pyrimidin-4-ol (Intermediate 32, 141 mg, 589 μmol), 1-{3-[(1R)-1-aminoethyl]-2-fluorophenyl}-1,1-difluoro-3,3-dimethylbutan-2-one trifluoroacetic acid (1/1) (Intermediate 62, 284 mg, 535 μmol), 2,4,6-tri(propan-2-yl)benzene-1-sulfonyl chloride (195 mg, 642 μmol), $Et_3N$ (220 μl, 1.6 mmol), DMAP (13.1 mg, 107 μmol) and additional DIPEA (370 μl, 2.1 mmol) in DMF (3 ml) gave the titled compound (217 mg, 74% yield).

LC-MS (Method 2): $R_t$=144.00 min; MS (ESIpos): m/z=495 $[M+H]^+$ $^1$H NMR (400 MHz, DMSO-$d_6$) δ ppm 8.90 (d, 1H), 8.81 (s, 1H), 8.66 (d, 1H), 7.70 (t, 1H), 7.54 (t, 1H), 7.30-7.38 (m, 1H), 5.60-5.72 (m, 1H), 2.52-2.54 (m, 2H), 2.33-2.39 (m, 3H), 1.58 (d, 3H), 1.15-1.28 (m, 9H), 0.73 (s, 1H)

Intermediate 64

2-{(1R)-1-[3-(1,1-difluoro-2-hydroxy-2-methylpropyl)-2-fluorophenyl]ethyl}-1H-isoindole-1,3(2H)-dione

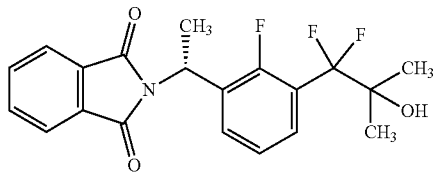 [SMILES: C[C@H](c1cccc(C(F)(F)C(C)(C)O)c1F)N1C(=O)c2ccccc2C1=O]

To a solution of 1-{3-[(1R)-1-aminoethyl]-2-fluorophenyl}-1,1-difluoro-2-methylpropan-2-ol hydrogen chloride (1/1) (500 mg, 1.76 mmol), $Et_3N$ (980 μl, 7.0 mmol) and DMAP (10.8 mg, 0.088 mmol) in THF (50 ml) was added 2-benzofuran-1,3-dione (313 mg, 2.11 mmol). The mixture was stirred at rt overnight and then heated to 70° C. overnight. Then, $Ac_2O$ (170 μl, 1.8 mmol) was added at rt and the mixture was heated to 70° C. for 3 days. The mixture was washed with sat. aq. $NaHCO_3$ sol. and brine, dried over $Na_2SO_4$, filtered and concentrated under reduced pressure. Purification by flash column chromatography gave the titled compound (584 mg, 88% yield).

LC-MS (Method 2): $R_t$=1.21 min; MS (ESIpos): m/z=378 $[M+H]^+$ $^1$H-NMR (400 MHz, DMSO-d6) δ[ppm]: 1.101 (7.88), 1.151 (7.99), 1.172 (2.27), 1.190 (1.14), 1.786 (6.84), 1.804 (6.76), 1.987 (3.89), 2.518 (2.26), 2.523 (1.58), 4.017 (0.90), 4.035 (0.89), 5.311 (9.06), 5.658 (0.42), 5.677 (1.47), 5.694 (1.44), 5.713 (0.41), 5.759 (1.22), 7.280 (0.84), 7.299 (2.09), 7.319 (1.40), 7.365 (0.86), 7.369 (0.98), 7.386 (1.33), 7.402

(0.61), 7.406 (0.57), 7.742 (0.72), 7.759 (1.30), 7.775 (0.66), 7.839 (1.58), 7.848 (16.00), 7.851 (8.12), 7.856 (1.47).

Intermediate 65

2-{(1R)-1-[3-(1,1-difluoro-2-methoxy-2-methylpropyl)-2-fluorophenyl]ethyl}-1H-isoindole-1,3(2H)-dione

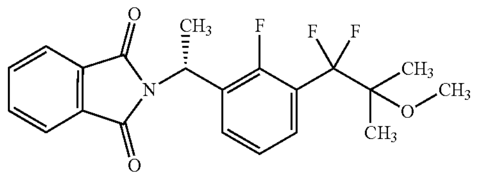 [SMILES: COC(C)(C)C(F)(F)c1cccc([C@@H](C)N2C(=O)c3ccccc3C2=O)c1F]

To a solution of 2-{(1R)-1-[3-(1,1-difluoro-2-hydroxy-2-methylpropyl)-2-fluorophenyl]-ethyl}-1H-isoindole-1,3(2H)-dione (Intermediate 64, 580 mg, 1.54 mmol) in DMF (10 ml) was added NaH (61.5 mg, 60% purity, 1.54 mmol) and the mixture was stirred at rt for 30 min. Iodomethane (190 μl, 3.1 mmol) was added and the reaction was stirred for 1 h. More iodomethane (190 μl, 3.1 mmol) was added and the mixture was stirred at rt overnight. The mixture was concentrated under reduced pressure, the residue was dissolved in DCM, washed with brine, dried over $Na_2SO_4$, filtered and concentrated under reduced pressure. Purification by flash column chromatography gave the titled compound (443 mg, 74% yield).

LC-MS (Method 2): $R_t$=1.39 min; MS (ESIpos): m/z=392 $[M+H]^+$ $^1$H-NMR (400 MHz, DMSO-d6) δ[ppm]: 1.151 (7.38), 1.177 (7.28), 1.190 (0.91), 1.784 (6.43), 1.802 (6.39), 1.987 (1.73), 2.074 (1.51), 2.518 (5.25), 2.523 (3.51), 2.678 (0.40), 3.078 (16.00), 4.017 (0.41), 5.673 (1.28), 5.691 (1.25), 5.759 (2.25), 7.283 (0.72), 7.303 (1.86), 7.322 (1.29), 7.357 (0.80), 7.362 (0.95), 7.379 (1.20), 7.395 (0.55), 7.399 (0.50), 7.747 (0.61), 7.764 (1.13), 7.780 (0.58), 7.838 (1.39), 7.847 (13.01), 7.849 (12.83), 7.851 (7.10), 7.857 (1.46).

Intermediate 66

(1R)-1-[3-(1,1-difluoro-2-methoxy-2-methylpropyl)-2-fluorophenyl]ethan-1-amine

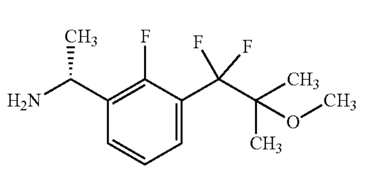 [SMILES: COC(C)(C)C(F)(F)c1cccc([C@@H](C)N)c1F]

To a solution of 2-{(1R)-1-[3-(1,1-difluoro-2-methoxy-2-methylpropyl)-2-fluorophenyl]ethyl}-1H-isoindole-1,3(2H)-dione (Intermediate 65, 440 mg, 1.12 mmol) in EtOH (5.5 ml) and THF (5.5 ml) was added hydrazine hydrate (550 μl, 11 mmol) and the mixture was stirred at rt overnight. The resulting suspension was filtered and the residue was washed with EtOH/DCM. The residue was dissolved in DCM/$H_2O$ and the org. phase was washed with sat. aq. $NaHCO_3$ sol., brine, dried over $Na_2SO_4$, filtered, concentrated under reduced pressure and combined with the concentrated filtrate. Purification by flash column chromatography gave the titled compound (270 mg, 92% yield).

LC-MS (Method 2): $R_t$=1.10 min; MS (ESIpos): m/z=262 $[M+H]^+$ $^1$H-NMR (400 MHz, DMSO-d6) δ[ppm]: 1.225 (15.13), 1.240 (15.59), 2.332 (0.42), 2.518 (1.96), 2.523 (1.37), 2.673 (0.41), 3.185 (16.00), 4.242 (0.44), 4.258 (1.39), 4.275 (1.37), 4.291 (0.43), 7.214 (0.53), 7.233 (1.74), 7.251 (2.39), 7.255 (2.00), 7.265 (1.15), 7.270 (1.36), 7.285 (0.55), 7.290 (0.42), 7.688 (0.53), 7.694 (0.62), 7.705 (1.02), 7.711 (1.05), 7.723 (0.56), 7.728 (0.56).

Intermediate 67

6-bromo-N-{(1R)-1-[3-(1,1-difluoro-2-methoxy-2-methylpropyl)-2-fluorophenyl]ethyl}-2-methylpyrido[3,4-d]pyrimidin-4-amine

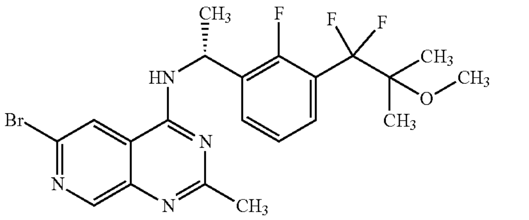 [SMILES: COC(C)(C)C(F)(F)c1cccc([C@@H](C)Nc2nc(C)nc3cnc(Br)cc23)c1F]

Following General Procedure 2: 6-bromo-2-methylpyrido[3,4-d]pyrimidin-4-ol (Intermediate 32, 205 mg, 854 μmol), (1R)-1-[3-(1,1-difluoro-2-methoxy-2-methylpropyl)-2-fluorophenyl]ethan-1-amine (Intermediate 66, 268 mg, 1.02 mmol), 2,4,6-tri(propan-2-yl)benzene-1-sulfonyl chloride (284 mg, 939 μmol), $Et_3N$ (360 μl, 2.6 mmol), DMAP (20.9 mg, 171 μmol) in DMF (3.0 ml) gave the titled compound (285 mg, 69% yield).

LC-MS (Method 2): $R_t$=1.39 min; MS (ESIpos): m/z=483 $[M+H]^+$ $^1$H-NMR (400 MHz, DMSO-d6) δ[ppm]: 1.171 (0.71), 1.247 (5.99), 1.255 (6.17), 1.572 (4.29), 1.589 (4.32), 1.987 (0.99), 2.332 (0.46), 2.370 (16.00), 2.518 (2.44), 2.523 (1.71), 2.673 (0.47), 3.174 (12.80), 3.349 (0.96), 5.704 (0.65), 5.722 (1.03), 5.740 (0.65), 7.202 (0.60), 7.221 (1.45), 7.240 (0.97), 7.291 (0.58), 7.295 (0.68), 7.312 (0.91), 7.328 (0.44), 7.590 (0.50), 7.606 (0.87), 7.622 (0.45), 8.678 (3.74), 8.805 (4.39), 8.877 (1.04), 8.895 (1.00).

Intermediate 68

(1R)-1-[3-(2-{[tert-butyl(dimethyl)silyl]oxy}-1,1-difluoro-2-methylpropyl)-2-fluorophenyl]-ethan-1-amine

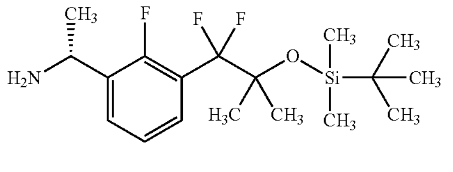 [SMILES: C[C@@H](N)c1cccc(C(F)(F)C(C)(C)O[Si](C)(C)C(C)(C)C)c1F]

1-{3-[(1R)-1-aminoethyl]-2-fluorophenyl}-1,1-difluoro-2-methylpropan-2-ol hydrogen chloride (1/1) (2.00 g, 7.05 mmol) was dissolved in CH2Cl2 (40 mL) and cooled to 0° C. under argon atmosphere. Lutidin (5.7 ml) was added and the resulting mixture was stirred for 5 minutes. tert-butyl (dimethyl)silyl trifluoromethanesulfonate (6.5 ml, 28 mmol) was added dropwise and the mixture was allowed to slowly warm to RT over night. Sat. Aq. NaHCO3 solution was added and the mixture was stirred for 10 minutes. Th organic phase was separated and dried. The solvent was evaporated at elevated temperatures. Toluene was added and the solvent was again evaporated. The title compound was purified by flash column chromatography on silica gel to give the title compound (2.07 g, 81% yield).

LC-MS (Method 2): $R_t$=1.65 min; MS (ESIpos): m/z=363 $[M+H]^+$ $^1$H-NMR (400 MHz, DMSO-d6) δ[ppm]: −0.013 (0.48), 0.766 (1.23), 0.773 (16.00), 0.780 (0.95), 0.839 (1.21), 1.222 (2.07), 1.238 (2.05), 1.316 (3.78), 2.518 (0.79), 2.523 (0.53), 7.229 (0.50), 7.248 (0.42).

Intermediate 69

6-bromo-N-{(1R)-1-[3-(2-{[tert-butyl(dimethyl) silyl]oxy}-1,1-difluoro-2-methylpropyl)-2-fluorophenyl]ethyl}-2-methylpyrido[3,4-d]pyrimidin-4-amine

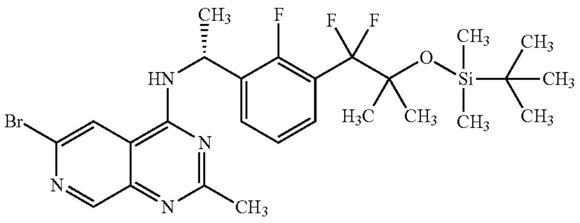 [SMILES: Cc1nc(N[C@H](C)c2cccc(C(F)(F)C(C)(C)O[Si](C)(C)C(C)(C)C)c2F)c2cc(Br)ncc2n1]

6-bromo-2-methylpyrido[3,4-d]pyrimidin-4-ol (Intermediate 32, 200 mg, 833 μmol) and (1R)-1-[3-(2-{[tert-butyl (dimethyl)silyl]oxy}-1,1-difluoro-2-methylpropyl)-2-fluorophenyl]-ethan-1-amine (Intermediate 68, 452 mg, 1.25 mmol) were dissolved in DMF (6.4 mL). PyBop (564 mg, 1.08 mmol) was added, followed by DBU (500 μl, 3.3 mmol) and the resulting mixture was stirred at RT for one night. Ethyl acetate was added. The organic phase was washed with water (two times) and brine and the ndried. The solvent was evaporated. The title compound was purified by flash column chromatography on silica gel to give the title compound (330 mg, 68% yield)

LC-MS (Method 2): $R_t$=1.79 min; MS (ESIpos): m/z=586 $[M+H]^+$ $^1$H-NMR (400 MHz, DMSO-d6) δ[ppm]: 0.804 (1.02), 0.811 (16.00), 0.819 (0.90), 1.249 (0.87), 1.267 (1.83), 1.285 (0.89), 1.434 (2.40), 1.668 (1.48), 1.685 (1.48), 2.083 (3.06), 2.455 (5.25), 2.614 (0.63), 2.618 (0.44), 4.112 (0.67), 4.130 (0.65), 7.310 (0.51), 8.771 (1.25), 8.773 (1.27), 8.897 (1.48).

Intermediate 70

1-(3-{(1R)-1-[(6-bromo-2-methylpyrido[3,4-d]pyrimidin-4-yl)amino]ethyl}-2-fluorophenyl)-1,1-difluoro-2-methylpropan-2-ol

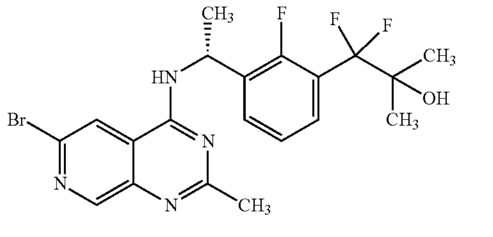 [SMILES: Cc1nc(N[C@H](C)c2cccc(C(F)(F)C(C)(C)O)c2F)c2cc(Br)ncc2n1]

6-bromo-N-[(1R)-1-(3-{1,1-difluoro-2-methyl-2-[(triethylsilyl)oxy]propyl}-2-fluorophenyl)-ethyl]-2-methylpyrido [3,4-d]pyrimidin-4-amine (Intermediate 69, 400 mg, 685 μmol) was dissolved in CH2Cl2 (6 mL) at RT. Triethyl silane (11 μl, 69 μmol) was added, followed by trifluoracetic acid (790 μl, 10 mmol) dropwise. The resulting mixture was stirred at RT for one night. Toluene was added and the solvent was evaporated. The title compound was purified by flash column chromatography on silica gel to give the title compound (340 mg, 106% yield).

LC-MS (Method 2): $R_t$=1.21 min; MS (ESIpos): m/z=471 $[M+H]^+$ $^1$H-NMR (400 MHz, DMSO-d6) δ[ppm]: 1.201 (9.34), 1.221 (9.52), 1.599 (6.66), 1.616 (6.61), 2.442 (16.00), 2.518 (6.01), 2.523 (3.93), 3.165 (6.91), 4.016 (0.42), 4.035 (0.41), 5.759 (8.13), 5.770 (1.06), 5.788 (1.58), 5.806 (1.01), 7.228 (1.02), 7.247 (2.42), 7.266 (1.56), 7.331 (1.09), 7.348 (1.57), 7.363 (0.73), 7.614 (0.88), 7.631 (1.55), 7.646 (0.78), 8.744 (4.93), 8.845 (6.52).

Intermediate 71

6-(dimethylphosphoryl)-2-methylpyrido[3,4-d]pyrimidin-4-ol

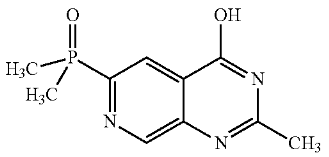

6-chloro-2-methylpyrido[3,4-d]pyrimidin-4-ol (Intermediate 32, 5.00 g, 25.6 mmol) and tetrakis (4.68 g, 5.11 mmol) were dissolved in acetonitrile (130 mL). Triethyl amine (12 ml, 89 mmol) was added, followed by dimethyl-lambda$^5$-phosphanone (2.00 g, 25.6 mmol). The mixture was heated to 90° C. for 48 hours. The formed solids were collected by filtration and washed with MTBE to give the title compound as pale grey solids (6.68 g, 82% purity, 90% yield) LC-MS (Method 1): $R_t$=0.50 min; MS (ESIpos): m/z=238 $[M+H]^+$ $^1$H-NMR (400 MHz, DMSO-d6) δ[ppm]: 1.103 (3.14), 1.675 (15.74), 1.708 (16.00), 2.075 (0.76), 2.426 (14.14), 2.518 (2.02), 2.523 (1.48), 3.073 (1.07), 8.385 (1.83), 8.388 (1.88), 8.400 (1.88), 8.402 (1.79), 9.108 (3.17).

Intermediate 72 tert-butyl {(1R)-1-[3-(1,1-difluoro-2-oxobutyl)-2-fluorophenyl]ethyl}carbamate

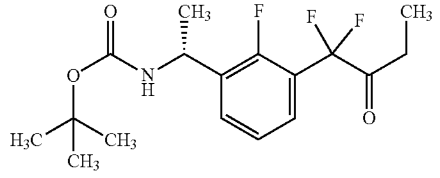 [SMILES: CCC(=O)C(F)(F)c1cccc([C@@H](C)NC(=O)OC(C)(C)C)c1F]

Tert-butyl [(1R)-1-(3-{1,1-difluoro-2-[methoxy(methyl) amino]-2-oxoethyl}-2-fluorophenyl)ethyl]carbamate (Intermediate 31, 501 mg, 1.33 mmol) was dissolved in THF (15 mL) at RT under nitrogen atmosphere. Ethyl magnesium bromide solution (1.2 ml, 3.2 M, 4.0 mmol) was added slowly and the mixture was stirred at RT for 3 hours. Sat. aq.

$NH_4Cl$ solution was added. The mixture was extracted with ethyl acetate. The combined organic phases were washed with brine. The organic phase was dried and the solvent was evaporated to give the title compound as yellow oil (440 mg, 96% yield).

LC-MS (Method 2): $R_t$=1.34 min; MS (ESIpos): m/z=363 $[M+NH_4]^*$

Intermediate 74 tert-butyl [(1R)-1-{3-[(2RS)-1,1-difluoro-2-hydroxybutyl]-2-fluorophenyl}ethyl]carbamate (mixture of diastereomers)

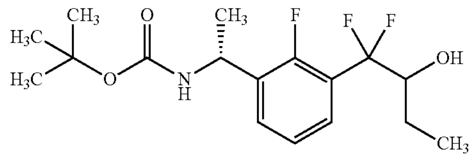 [SMILES: CCC(O)C(F)(F)c1cccc([C@@H](C)NC(=O)OC(C)(C)C)c1F]

tert-butyl {(1R)-1-[3-(1,1-difluoro-2-oxobutyl)-2-fluorophenyl]ethyl}carbamate (2.76 g, 7.99 mmol) was dissolved in ethanol (31 mL). The atmosphere was exchanged to argon and the mixture was cooled to 0° C. Sodium borhydride (453 mg, 12.0 mmol) was added portionwise. The mixture was allowed to warm to RT. The mixture was added to half sat. aq. NH4Cl solution. And stirred at RT for 1 hour. The mixture was extracted with ethyl acetate. The combined organic phases were washed with brine. The organic phase was separated, dried and the solvent was evaporated to give a colorless oil. The title compound was purified by HPLC separation to give a colorless oil (1.09 g, 39% yield).

LC-MS (Method 2): $R_t$=1.24 min; MS (ESIpos): m/z=365 $[M+NH_4]^+$

The two diastereomers of Intermediate 72 were separated by chiral HPLC.

Anal.-Method:

Instrument: Agilent: 1260, Aurora SFC-Modul; Column: Chiralpak IG 3p 100×4.6 mm; eluent A: $C_{02}$; eluent B: methanol+0.2 vol % aqueous ammonia (32%); isocratic: 7% B; gradient: no; flow: 4 ml/min; temperature: 37.5° C.; BPR: 100 bar; UV: 262 nm Prep.-Method: SFC Instrument: Sepiatec: Prep SFC100; Column: Chiralpak IG 5p 250×30 mm; eluentA: $C_{02}$; eluent B: methanol; isocratic: 7% B; gradient: no; flow: 100 ml/min; temperature: 40° C.; BPR: 150 bar; UV: 262 nm Intermediate 73 tert-butyl [(1R)-1-{3-[1,1-difluoro-2-hydroxybutyl]-2-fluorophenyl}ethyl]carbamate (diastereomer 1)

Diastereomer 1 of Intermediate 72:

Rt (analytical method)=0.80 min

Intermediate 75 tert-butyl [(1R)-1-{3-[1,1-difluoro-2-hydroxybutyl]-2-fluorophenyl}ethyl]carbamate (diastereomer 2)

Diastereomer 2 of Intermediate 72:

Rt (analytical method)=1.17 min

Intermediate 76

1-{3-[(1R)-1-aminoethyl]-2-fluorophenyl}-1,1-difluorobutan-2-ol trifluoroacetic acid (1/1) (diastereomer 1)

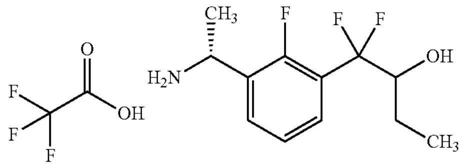 [SMILES: O=C(O)C(F)(F)F ; CCC(O)C(F)(F)c1cccc([C@@H](C)N)c1F]

Tert-butyl [(1R)-1-{3-[1,1-difluoro-2-hydroxybutyl]-2-fluorophenyl}ethyl]carbamate (Intermediate 74, 549 mg, 1.58 mmol) was dissolved in $CH_2Cl_2$ (5 mL) at RT. Trifluor acetic acid (2.0 ml, 26 mmol) was added and the mixture was stirred at RT for 3 hours. Toluene was added and the solvent was evaporated to give a colorless oil (615 mg) which was used without further purification.

LC-MS (Method 2): $R_t$=0.90 min; MS (ESIpos): m/z=248 $[M+H]^+$

Intermediate 77

1-{3-[(1R)-1-aminoethyl]-2-fluorophenyl}-1,1-difluorobutan-2-ol trifluoroacetic acid (1/1) (diastereomer 2)

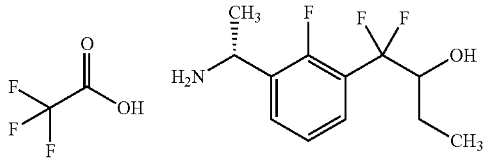 [SMILES: O=C(O)C(F)(F)F ; CCC(O)C(F)(F)c1cccc([C@@H](C)N)c1F]

Tert-butyl [(1R)-1-{3-[1,1-difluoro-2-hydroxybutyl]-2-fluorophenyl}ethyl]carbamate (Intermediate 75, 692 mg, 1.99 mmol) was dissolved in $CH_2Cl_2$ (5 mL). Trifluoracetic acid (2.0 ml, 26 mmol) was added and the mixture was stirred at RT for 3 hours. Toluene was added to the mixture and the solvent was evaporated to give the title compound as a colorless oil (859 mg) which was used without further purification.

LC-MS (Method 2): $R_t$=0.88 min; MS (ESIpos): m/z=248 $[M+H]^+$

Intermediate 78

(1R)-1-(3-{1,1-difluoro-2-[(triethylsilyl)oxy]butyl}-2-fluorophenyl)ethan-1-amine (diastereomer 1)

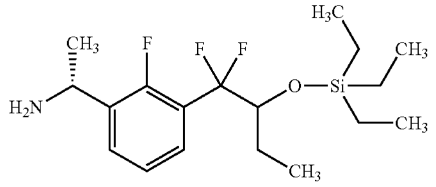 [SMILES: CCC(O[Si](CC)(CC)CC)C(F)(F)c1cccc([C@@H](C)N)c1F]

1-{3-[(1R)-1-Aminoethyl]-2-fluorophenyl}-1,1-difluorobutan-2-ol trifluoroacetic acid (1/1) (Intermediate 76, 615 mg, 1.70 mmol) was dissolved in $CH_2Cl_2$ (7.6 mL) and 2,6-lutidine (1.4 mL) was added. The mixture was stirred for 10 minutes at RT. Triethylsilyl trifluoromethanesulfonate (2.25 g, 8.51 mmol) was added dropwise and the resulting mixture was stirred at RT under nitrogen atmosphere for 6 hours. Sat. aq. $NaHCO_3$ was added. The phases were separated and the organic phase was dried and the solvent was evaporated. Toluene was added and the solvent was again evaporated. This step was repeated. The title compound was purified by flash column chromatography on silica gel using hexane/ethyl acetate (9/1 to 0/10) as eluent. The title compound was obtained as pale yellow oil (387 mg, 63% yield).

LC-MS (Method 2): $R_t$=1.66 min; MS (ESIpos): m/z=362.5 $[M+H]^+$

Intermediate 79

(1R)-1-(3-{1,1-difluoro-2-[(triethylsilyl)oxy]butyl}-2-fluorophenyl)ethan-1-amine (diastereomer 2)

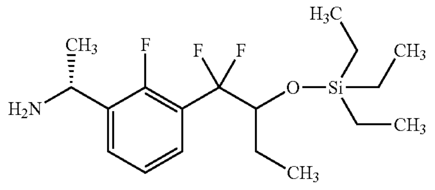

1-{3-[(1R)-1-Aminoethyl]-2-fluorophenyl}-1,1-difluorobutan-2-ol trifluoroacetic acid (1/1) (Intermediate 77, 859 mg, 2.38 mmol) was dissolved in $CH_2Cl_2$ (11 mL). 2,6-Lutidine (1.9 mL) was added. Triethylsilyl trifluoromethanesulfonate (3.14 g, 11.9 mmol) was added dropwise and the mixture was stirred at RT under nitrogen atmosphere for 6 hours. Sat. aq. $NaHCO_3$ solution was added and the mixture was stirred for 10 minutes. The organic phase was separated and dried. The solvent was evaporated. Toluene was added and the solvent was evaporated. The step was repeated again. The title compound was purified by flash column chromatography on silica gel using hexane/ethyl acetate (9/1 to 0/10) as eluent. The title compound was obtained as pale yellow oil (466 mg, 54% yield).

LC-MS (Method 2): $R_t$=1.63 min; MS (ESIpos): m/z=362.9 $[M+H]^+$

Intermediate 80 tert-butyl {(1R)-1-[3-(1,1-difluoro-2-oxohexyl)-2-fluorophenyl]ethyl}carbamate

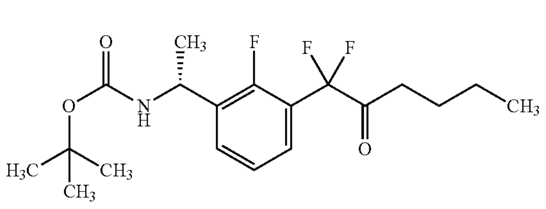 [SMILES: CCCCC(=O)C(F)(F)c1cccc([C@@H](C)NC(=O)OC(C)(C)C)c1F]

n-Butyllithium (1.6 ml, 2.5 M, 4.0 mmol) was diluted in THF (4 mL) under argon and cooled to −78° C. and stirred for 15 minutes. Tert-butyl [(1R)-1-(3-{1,1-difluoro-2-[methoxy(methyl)amino]-2-oxoethyl}-2-fluorophenyl) ethyl]carbamate (Intermediate 31, 500 mg, 1.33 mmol) was dissolved in THF (4 mL) and was added to this solution. The mixture was stirred at −78° C. for 1 hour and then slowly allowed to warm to RT over night. Sat. aq. NH4Cl solution was added dropwise. The mixture was extracted with ethyl acetate two times. The combined organic phases were washed with brine. The organic phase was dried and the solvent was evaporated. The title compound was purified by flash column chromatography on silica gel. The title compound was obtained (300 mg, 60% yield).

LC-MS (Method 2): $R_t$=1.72 min; MS (ESIpos): m/z=490 $[M+H]^+$ $^1$H-NMR (400 MHz, DMSO-d6) δ[ppm]: 0.818 (5.29), 0.836 (13.01), 0.854 (6.33), 1.154 (0.98), 1.212 (0.67), 1.230 (1.83), 1.248 (2.89), 1.253 (1.78), 1.265 (8.18), 1.282 (7.11), 1.305 (0.92), 1.349 (16.00), 1.488 (0.69), 1.505 (1.88), 1.525 (2.29), 1.543 (1.66), 1.560 (0.50), 2.073 (0.65), 2.327 (0.63), 2.331 (0.45), 2.518 (2.99), 2.523 (1.95), 2.669 (0.63), 2.673 (0.45), 2.784 (1.93), 2.801 (3.60), 2.819 (1.77), 4.841 (0.51), 4.859 (0.69), 4.876 (0.47), 7.355 (0.79), 7.374 (1.80), 7.394 (1.12), 7.534 (0.96), 7.551 (1.56), 7.571 (1.07), 7.578 (0.95), 7.595 (1.42), 7.610 (1.61), 7.628 (0.74).

Intermediate 81 tert-butyl [(1R)-1-{3-[(2RS)-1,1-difluoro-2-hydroxy-2-methylhexyl]-2-fluorophenyl}ethyl]carbamate (mixture of diastereomers)

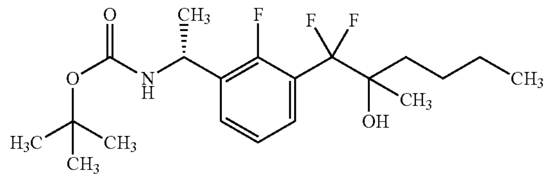 [SMILES: CCCCC(C)(O)C(F)(F)c1cccc([C@@H](C)NC(=O)OC(C)(C)C)c1F]

Tert-butyl {(1R)-1-[3-(1,1-difluoro-2-oxohexyl)-2-fluorophenyl]ethyl}carbamate (Intermediate 80, 297 mg, 795 μmol) was dissolved in THF (12 mL) under argon atmosphere and cooled to 0° C. methyl magnesium bromide solution (700 μl, 3.4 M, 2.4 mmol) was added dropwise. The mixture was stirred at 0° C. for 30 minutes and then slowly allowed to warm to RT over night. The mixture was cooled to 0° C. and sat. aq. $NH_4Cl$ solution was added slowly. The mixture was extracted with ethyl acetate two times. The combined organic phases were washed with brine. The organic phase was dried and the solvent was evaporated. The title compound was purified by flash column chromatography on silica gel. The title compound was obtained (278 mg, 90% yield).

LC-MS (Method 2): $R_t$=1.40 min; MS (ESIpos): m/z=407 [M+H]+NH3$^+$ $^1$H-NMR (400 MHz, DMSO-d6) δ[ppm]: 0.834 (1.53), 0.841 (1.59), 0.852 (4.39), 0.859 (2.93), 0.869 (2.28), 0.876 (1.42), 1.116 (3.42), 1.132 (3.59), 1.154 (0.68), 1.172 (1.35), 1.190 (1.01), 1.232 (1.31), 1.250 (1.90), 1.267 (5.23), 1.284 (4.60), 1.359 (16.00), 1.421 (0.51), 1.461 (0.92), 1.482 (0.74), 1.987 (1.03), 2.518 (2.06), 2.523 (1.39), 4.879 (0.48), 4.897 (0.65), 4.915 (0.44), 5.176 (3.63), 5.185 (2.26), 5.758 (5.62), 7.220 (0.60), 7.239 (1.59), 7.258 (1.29), 7.284 (0.93), 7.299 (1.19), 7.316 (0.51), 7.465 (0.69), 7.480 (1.21), 7.497 (0.65), 7.528 (0.50), 7.538 (0.62), 7.547 (0.60), 7.558 (0.52).

Intermediate 82 trifluoroacetic acid/(2RS)-1-{3-[(1R)-1-aminoethyl]-2-fluorophenyl}-1,1-difluoro-2-methylhexan-2-ol (1/1) (mixture of diastereomers)

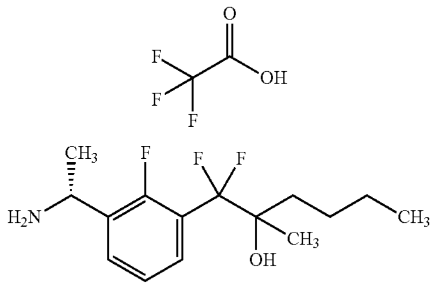

tert-butyl [(1R)-1-{3-[(2RS)-1,1-difluoro-2-hydroxy-2-methylhexyl]-2-fluorophenyl}ethyl]carbamate (50.0 mg, 128 μmol) was dissolved in $CH_2Cl_2$ (1 mL) under argon atmosphere at RT. Trifluoracetic acid (99 μl, 1.3 mmol) was added and the mixture was stirred over night at RT. Toluene was added and the solvent was evaporated. Toluene was added again and the solvent was evaporated to give the title compound (64.0 mg), which was used without further purification.

LC-MS (Method 2): $R_t$=1.14 min; MS (ESIpos): m/z=290 $[M+H]^+$

Intermediate 83 tert-butyl {(1R)-1-[3-(1,1-difluoro-3-methyl-2-oxobutyl)-2-fluorophenyl]ethyl}carbamate

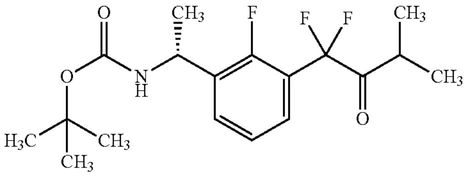 [SMILES: CC(C)C(=O)C(F)(F)c1cccc([C@@H](C)NC(=O)OC(C)(C)C)c1F]

Following General Procedure 4: tert-butyl [(1R)-1-(3-{1,1-difluoro-2-[methoxy(methyl)amino]-2-oxoethyl}-2-fluorophenyl)ethyl]carbamate (Intermediate 31, 2.76 g, 7.34 mmol) and chlorido(propan-2-yl)magnesium (11 ml, 2.0 M, 22 mmol) were reacted for 5 h to give the titled compound (773 mg, 29% yield) as an oil.

LC-MS (Method 2): $R_t$=1.38 min; MS (ESIneg): m/z=358.5 $(M-H)^-$.

$^1$H NMR (400 MHz, CHLOROFORM-d) δ ppm 1.14-1.63 (m, 22H), 3.20-3.38 (m, 1H), 4.81-5.07 (m, 2H), 7.18-7.25 (m, 1H), 7.39-7.47 (m, 1H), 7.48-7.57 (m, 1H).

Intermediate 84 trifluoroacetic acid/1-{3-[(1R)-1-aminoethyl]-2-fluorophenyl}-1,1-difluoro-3-methylbutan-2-one (1/1)

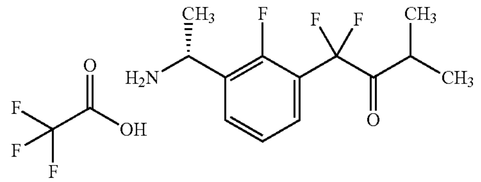

Following General Procedure 3: tert-butyl {(1R)-1-[3-(1,1-difluoro-3-methyl-2-oxobutyl)-2-fluorophenyl]ethyl}carbamate (Intermediate 83, 288 mg, 801 μmol) and TFA (620 μl, 8.0 mmol) gave the titled compound as an oil (312 mg, quant) which was used without further purification.

LC-MS (Method 2): $R_t$=1.17 min; MS (ESIpos): m/z=260.4 $[M+H]^+$.

Intermediate 85

1-(3-{(1R)-1-[(6-bromo-2-methylpyrido[3,4-d]pyrimidin-4-yl)amino]ethyl}-2-fluorophenyl)-1,1-difluoro-3-methylbutan-2-one

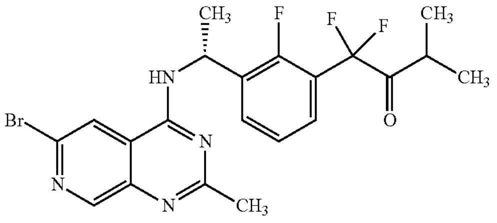 [SMILES: Cc1nc(N[C@H](C)c2cccc(C(F)(F)C(=O)C(C)C)c2F)c2cc(Br)ncc2n1]

Following General Procedure 2: 6-bromo-2-methylpyrido[3,4-d]pyrimidin-4-ol (204 mg, 852 μmol), trifluoroacetic acid/1-{3-[(1R)-1-aminoethyl]-2-fluorophenyl}-1,1-difluoro-3-methylbutan-2-one (1/1) (289 mg, 774 μmol), 2,4,6-tri(propan-2-yl)benzene-1-sulfonyl chloride (281 mg, 929 μmol), DMAP (18.9 mg, 155 μmol) and additional DIPEA (540 μl, 3.1 mmol) in DMF (3.0 ml) gave the titled compound (259.0 mg, 63%) as white solid after purification by flash column chromatography (hexane/EtOAc).

LC-MS (Method 2): $R_t$=1.38 min; MS (ESIpos): m/z=481.5, 483.4 $[M+H]^+$

Intermediate 86 tert-butyl [(1R)-1-{3-[1,1-difluoro-2-hydroxy-3-methylbutyl]-2-fluorophenyl}ethyl]carbamate (diastereomer 1)

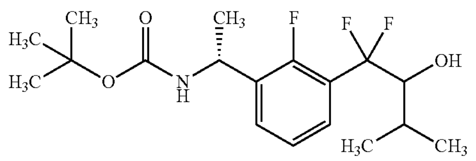 [SMILES: CC(C)C(O)C(F)(F)c1cccc([C@@H](C)NC(=O)OC(C)(C)C)c1F]

tert-butyl {(1R)-1-[3-(1,1-difluoro-3-methyl-2-oxobutyl)-2-fluorophenyl]ethyl}carbamate (Intermediate 85, 5.96 g, 16.6 mmol) was dissolved in ethanol (65 mL). The atmosphere was exchanged to argon and the mixture was cooled to O ° C. $NaBH_4$ (942 mg, 24.9 mmol) was added portionwise. The mixture was allowed to warm to RT. The mixture was added to half sat. aq. $NH_4Cl$ solution and stirred at RT for 1 hour. The mixture was extracted with ethyl acetate. The combined organic phases were washed with brine. The organic phase was separated, dried and the solvent was evaporated to give a colorless oil. The title compound was purified by HPLC separation to give a colorless oil (3.37 g, 56% yield).

The two diastereomers were separated by chiral HPLC. Diastereomer 1 was obtained as the first eluting isomer.

LC-MS (Method 2): $R_t$=1.28 min; MS (ESIpos): m/z=379.6 $[M+NH_4]^+$

Intermediate 87 tert-butyl [(1R)-1-{3-[1,1-difluoro-2-hydroxy-3-methylbutyl]-2-fluorophenyl}ethyl]carbamate (diastereomer 2)

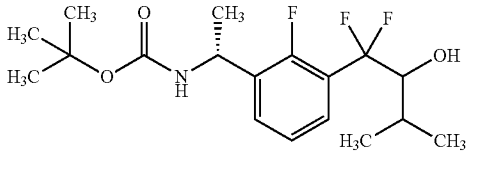

After separation of the two diastereomers of Intermediate 86, diastereomer 2 was obtained as the second eluting isomer.

LC-MS (Method 2): $R_t$=1.26 min; MS (ESIpos): m/z=379.6 $[M+NH_4]^*$

Intermediate 88

1-{3-[(1R)-1-aminoethyl]-2-fluorophenyl}-1,1-difluoro-3-methylbutan-2-ol trifluoroacetic acid (1/1) (diastereomer 1)

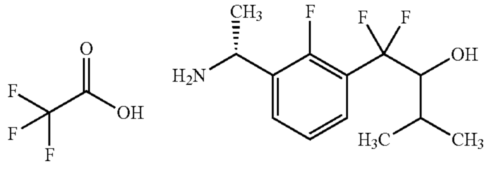 [SMILES: O=C(O)C(F)(F)F ; CC(C)C(O)C(F)(F)c1cccc([C@@H](C)N)c1F]

Tert-butyl [(1R)-1-{3-[1,1-difluoro-2-hydroxy-3-methylbutyl]-2-fluorophenyl}ethyl]-carbamate (Intermediate 86, 286 mg, 791 µmol) was dissolved in $CH_2Cl_2$ (5 mL) at RT.

Trifluoracetic acid (2.0 ml, 26 mmol) was added and the mixture was stirred at RT for 3 hours. Toluene was added and the solvent was evaporated to give the title compound as colorless oil (295 mg, 99% yield).

LC-MS (Method 2): $R_t$=1.01 min; MS (ESIpos): m/z=262.6 $[M+H]^+$

Intermediate 89

1-{3-[(1R)-1-aminoethyl]-2-fluorophenyl}-1,1-difluoro-3-methylbutan-2-ol trifluoroacetic acid (1/1) (diastereomer 2)

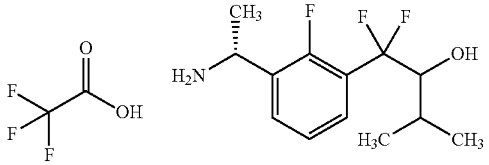 [SMILES: O=C(O)C(F)(F)F ; CC(C)C(O)C(F)(F)c1cccc([C@@H](C)N)c1F]

tert-butyl [(1R)-1-{3-[1,1-difluoro-2-hydroxy-3-methylbutyl]-2-fluorophenyl}ethyl]-carbamate (Intermediate 87, 297 mg, 822 µmol) was dissolved in $CH_2Cl_2$ (5 mL) at RT. Trifluoracetic acid (2.0 ml, 26 mmol) was added and the mixture was stirred for 3 hours. Toluene was added and the solvent was evaporated to give a colorless oil (339 mg) which was used without further purification.

LC-MS (Method 2): $R_t$=0.99 min; MS (ESIpos): m/z=262.6 $[M+H]^+$

Intermediate 90

(1R)-1-(3-{1,1-difluoro-3-methyl-2-[(triethylsilyl)oxy]butyl}-2-fluorophenyl)ethan-1-amine (diastereomer 1)

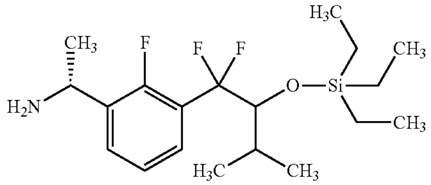 [SMILES: CC[Si](CC)(CC)OC(C(C)C)C(F)(F)c1cccc([C@@H](C)N)c1F]

1-{3-[(1R)-1-Aminoethyl]-2-fluorophenyl}-1,1-difluoro-3-methylbutan-2-ol trifluoroacetic acid (1/1) (Intermediate 88, 295 mg, 786 µmol) was dissolved in $CH_2Cl_2$ (3.5 mL) and 2,6-lutidine (0.64 mL) was added. The mixture was stirred for 10 minutes at RT. Triethylsilyl trifluoromethanesulfonate (1.04 g, 3.93 mmol) was added dropwise and the resulting mixture was stirred at RT under nitrogen atmosphere for 6 hours. Sat. aq. $NaHCO_3$ was added. The phase was separated and the organic phase was dried and the solvent was evaporated. Toluene was added and the solvent was again evaporated. This step was repeated. The title compound was purified by flash column chromatography on silica gel using hexane/ethyl acetate (9/1 to 0/10) as eluent. The title compound was obtained as pale yellow oil (197 mg, 67% yield).

LC-MS (Method 2): $R_t$=1.73 min; MS (ESIpos): m/z=376.9 $[M+H]^+$

Intermediate 91

(1R)-1-(3-{1,1-difluoro-3-methyl-2-[(triethylsilyl)oxy]butyl}-2-fluorophenyl)ethan-1-amine (diastereomer 2)

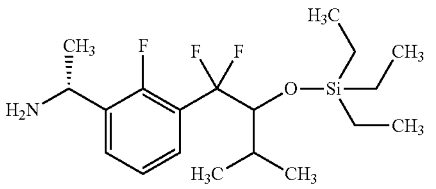 [SMILES: CC[Si](CC)(CC)OC(C(C)C)C(F)(F)c1cccc([C@@H](C)N)c1F]

1-{3-[(1R)-1-Aminoethyl]-2-fluorophenyl}-1,1-difluoro-3-methylbutan-2-ol trifluoroacetic acid (1/1) (Intermediate 89, 339 mg, 903 μmol) was dissolved in CH2Cl2 (4 mL) and Lutidin (0.74 mL) was added. The mixture was stirred for 10 minutes at RT. triethylsilyl trifluoromethanesulfonate (1.19 g, 4.52 mmol) was added dropwise and the resulting mixture was stirred at RT under nitrogen atmosphere for 6 hours. Sat. aq. $NaHCO_3$ was added. The phases were separated and the organic phase was dried and the solvent was evaporated. Toluene was added and the solvent was again evaporated. This step was repeated. The title compound was purified by flash column chromatography on silica gel using hexane/ethyl acetate (9/1 to 0/10) as eluent. The title compound was obtained as pale yellow oil (201 mg, 59% yield).

LC-MS (Method 2): $R_t$=1.72 min; MS (ESIpos): m/z=376.8 $[M+H]^+$

Intermediate 92 tert-butyl {(1R)-1-[3-(1,1-difluoro-2-oxohexyl)-2-fluorophenyl]ethyl}carbamate

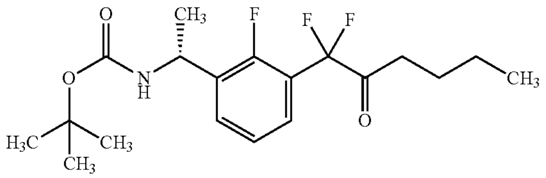 [SMILES: CCCCC(=O)C(F)(F)c1cccc([C@@H](C)NC(=O)OC(C)(C)C)c1F]

To a solution of tert-butyl [(1R)-1-(3-{1,1-difluoro-2-[methoxy(methyl)amino]-2-oxoethyl}-2-fluorophenyl)ethyl]carbamate (500 mg, 1.33 mmol) in THF (8.0 ml) was dropwise added butyllithium (1.6 ml, 2.5 M, 4.0 mmol) at −78° C. The reaction was stirred for 1 h at −78° C. and allowed to warm to RT overnight. The reaction was quenched by addition of aqueous ammonium chloride solution. The mixture was extracted twice with ethyl acetate, the organic phases were washes with saturated aqueous sodium chloride, dried over sodium sulfate and concentrated. The crude product was purified by flash chromatography (silica, hexane, ethyl acetate) to yield the title compound (300 mg, 95% purity, 60% yield).

LC-MS (Method 2): $R_t$=1.72 min; MS (ESIpos): m/z=490 $[M+H]^+$ $^1$H-NMR (400 MHz, DMSO-d6) δ[ppm]: 0.818 (5.29), 0.836 (13.01), 0.854 (6.33), 1.154 (0.98), 1.212 (0.67), 1.230 (1.83), 1.248 (2.89), 1.253 (1.78), 1.265 (8.18), 1.282 (7.11), 1.305 (0.92), 1.349 (16.00), 1.488 (0.69), 1.505 (1.88), 1.525 (2.29), 1.543 (1.66), 1.560 (0.50), 2.073 (0.65), 2.327 (0.63), 2.331 (0.45), 2.518 (2.99), 2.523 (1.95), 2.669 (0.63), 2.673 (0.45), 2.784 (1.93), 2.801 (3.60), 2.819 (1.77), 4.841 (0.51), 4.859 (0.69), 4.876 (0.47), 7.355 (0.79), 7.374 (1.80), 7.394 (1.12), 7.534 (0.96), 7.551 (1.56), 7.571 (1.07), 7.578 (0.95), 7.595 (1.42), 7.610 (1.61), 7.628 (0.74).

Intermediate 93 tert-butyl [(1R)-1-{3-[(2RS)-1,1-difluoro-2-hydroxy-2-methylhexyl]-2-fluorophenyl}ethyl]carbamate (mixture of diastereomers)

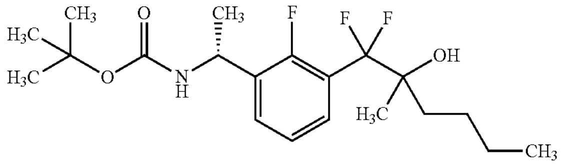 [SMILES: CCCCC(C)(O)C(F)(F)c1cccc([C@@H](C)NC(=O)OC(C)(C)C)c1F]

To a solution of tert-butyl {(1R)-1-[3-(1,1-difluoro-2-oxohexyl)-2-fluorophenyl]ethyl}carbamate (Intermediate 92, 297 mg, 795 μmol) in THF (8.0 ml) was dropwise added bromido(methyl)magnesium (700 μl, 3.4 M, 2.4 mmol) at 0° C. The reaction was stirred for 30 min at 0° C. and allowed to warm to RT overnight. The reaction was cooled again to 0° C. and quenched by addition of aqueous ammonium chloride solution. The mixture was extracted twice with ethyl acetate, the organic phases were washes with saturated aqueous sodium chloride, dried over sodium sulfate and concentrated. The crude product was purified by flash chromatography (silica, hexane, ethyl acetate) to yield the title compound (300 mg, 95% purity, 60% yield).

LC-MS (Method 2): $R_t$=1.40 min; MS (ESIpos): m/z=407 $[M+H]+NH3^+$ $^1$H-NMR (400 MHz, DMSO-d6) δ[ppm]: 0.834 (1.53), 0.841 (1.59), 0.852 (4.39), 0.859 (2.93), 0.869 (2.28), 0.876 (1.42), 1.116 (3.42), 1.132 (3.59), 1.154 (0.68), 1.172 (1.35), 1.190 (1.01), 1.232 (1.31), 1.250 (1.90), 1.267 (5.23), 1.284 (4.60), 1.359 (16.00), 1.421 (0.51), 1.461 (0.92), 1.482 (0.74), 1.987 (1.03), 2.518 (2.06), 2.523 (1.39), 4.879 (0.48), 4.897 (0.65), 4.915 (0.44), 5.176 (3.63), 5.185 (2.26), 5.758 (5.62), 7.220 (0.60), 7.239 (1.59), 7.258 (1.29), 7.284 (0.93), 7.299 (1.19), 7.316 (0.51), 7.465 (0.69), 7.480 (1.21), 7.497 (0.65), 7.528 (0.50), 7.538 (0.62), 7.547 (0.60), 7.558 (0.52).

Intermediate 94 trifluoroacetic acid salt of (2RS)-1-{3-[(1R)-1-aminoethyl]-2-fluorophenyl}-1,1-difluoro-2-methylhexan-2-ol (1/1) (mixture of diastereomers)

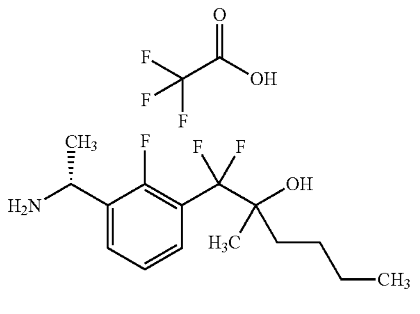

To a solution of tert-butyl [(1R)-1-{3-[(2RS)-1,1-difluoro-2-hydroxy-2-methylhexyl]-2-fluorophenyl}ethyl]carbamate (Intermediate 93, 50.0 mg, 128 μmol) in dichloromethane (1.0 ml) was added trifluoroacetic acid (99 μl, 1.3 mmol) and the mixture was stirred at RT overnight. To the mixture was then twice added toluene and the mixture was concentrated. The crude product was used LC-MS (Method 2): $R_t$=1.14 min; MS (ESIpos): m/z=290 $[M+H]^+$ Intermediate 95

6-bromo-2-methyl-N-{(1RS)-1-[2-(trifluoromethyl)pyridin-4-yl]ethyl}pyrido[3,4-d]pyrimidin-4-amine (Racemate)

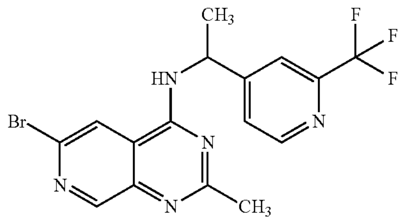 [SMILES: Cc1nc(NC(C)c2ccnc(C(F)(F)F)c2)c2cc(Br)ncc2n1]

Using general method 1, starting from (1RS)-1-[2-(trifluoromethyl)pyridin-4-yl]ethan-1-amine (310 mg, 1.63 mmol) and 6-bromo-2-methylpyrido[3,4-d]pyrimidin-4-ol (Intermediate 32, 587 mg, 2.45 mmol), yielded the title compound 469 mg (95% purity, 66% yield).

$^1$H-NMR (400 MHz, DMSO-d6) δ[ppm]: 1.151 (0.63), 1.169 (1.23), 1.187 (0.59), 1.609 (5.87), 1.627 (5.96), 1.985 (2.66), 2.381 (16.00), 2.518 (1.00), 2.522 (0.67), 4.014 (0.55), 4.032 (0.54), 5.556 (0.67), 5.574 (1.04), 5.591 (0.68), 7.747 (1.29), 7.760 (1.33), 7.984 (2.58), 8.622 (3.74), 8.692 (2.07), 8.704 (1.99), 8.819 (3.71), 8.889 (1.04), 8.906 (1.02).

Intermediate 96

6-bromo-2-methyl-N-{(1S*)-1-[2-(trifluoromethyl)pyridin-4-yl]ethyl}pyrido[3,4-d]pyrimidin-4-amine (Enantiomer 1)

The enantiomers of Intermediate 95 were separated by chiral HPLC:

Analytical Method:

Instrument: Thermo Fisher UltiMate 3000; Column: YMC Cellulose SC 3p, 100×4.6; eluent A: hexane+0.1 vol % diethylamine; eluent B: ethanol; isocratic: 80% A+20% B; flow: 1.4 ml/min; temperature: 25° C.; UV: 280 nm Preparative Method:

Instrument: PrepCon Labomatic HPLC-2; Column: YMC Cellulose SC 10p, 250×50; eluent A: hexane+0.1 vol % diethylamine; eluent B: ethanol; isocratic: 80% A+20% B; flow: 90 ml/min; temperature: 25° C.; UV: 280 nm $R_t$ (analytical method) Enantiomer 1: 1.66 min Intermediate 97

6-bromo-2-methyl-N-{(1R*)-1-[2-(trifluoromethyl)pyridin-4-yl]ethyl}pyrido[3,4-d]pyrimidin-4-amine (Enantiomer 2)

The enantiomers of Intermediate 95 were separated by chiral HPLC:

Analytical Method:

Instrument: Thermo Fisher UltiMate 3000; Column: YMC Cellulose SC 3p, 100×4.6; eluent A: hexane+0.1 vol % diethylamine; eluent B: ethanol; isocratic: 80% A+20% B; flow: 1.4 ml/min; temperature: 25° C.; UV: 280 nm Preparative Method:

Instrument: PrepCon Labomatic HPLC-2; Column: YMC Cellulose SC 10p, 250×50; eluent A: hexane+0.1 vol % diethylamine; eluent B: ethanol; isocratic: 80% A+20% B; flow: 90 ml/min; temperature: 25° C.; UV: 280 nm $R_t$ (analytical method) Enantiomer 1: 2.59 min $^1$H-NMR (400 MHz, DMSO-d6) δ[ppm]: 1.082 (0.49), 1.258 (0.70), 1.609 (4.88), 1.627 (4.92), 2.382 (16.00), 2.518 (1.19), 2.523 (0.83), 5.557 (0.65), 5.575 (1.01), 5.592 (0.65), 7.748 (1.05), 7.761 (1.08), 7.985 (2.13), 8.623 (3.57), 8.692 (1.69), 8.705 (1.63), 8.823 (4.02), 8.889 (1.00), 8.907 (0.97).

Intermediate 98

8-bromo-6-chloro-2-methyl-4H-pyrido[3,4-d][1,3]oxazin-4-one

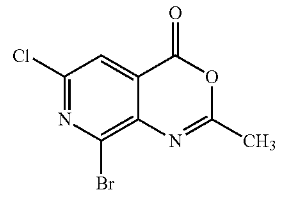

3-Amino-2-bromo-6-chloro-4-pyridinecarboxylic acid (CAS 1073182-69-0.67 g, 85% purity, 226.5 mmol) was added to acetic anhydride (700 ml) at RT. The reaction was then heated at 100° C. for 16 h. The reyction mixture was concentrated and the residue was directly used for the next step.

Intermediate 99

8-bromo-6-chloro-2-methylpyrido[3,4-d]pyrimidin-4-ol

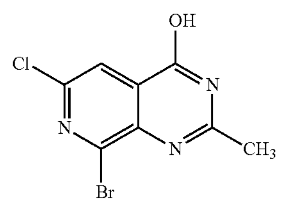

A solution of 8-bromo-6-chloro-2-methyl-4H-pyrido[3,4-d][1,3]oxazin-4-one (70 g, 79% purity, 200.8 mmol) and ammonium acetate (Intermediate 98, 61.9 g, 802 mmol) in 2-methoxyethanol (700 ml) was stirred at 120° C. for 16 h. The reaction mixture was then concentrated and the residue was added to water and stirred at RT for 30 min. The mixture was filtered and concentrated to give the title compound as brown solid, which was directly used for the next reaction.

Intermediate 100

6-chloro-8-[(4-methoxyphenyl)methoxy]-2-methylpyrido[3,4-d]pyrimidin-4-ol

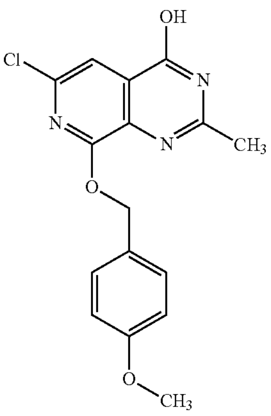 [SMILES: COc1ccc(COc2nc(Cl)cc3c(O)nc(C)nc23)cc1]

To a solution of 8-bromo-6-chloro-2-methylpyrido[3,4-d]pyrimidin-4-ol (Intermediate 99, 12 g, 91% purity, 39.7 mmol) and (4-methoxyphenyl)methanol (11.0 g, 79.6 mmol) in dimethyl sulfoxide was added potassium hydroxide at room temperature. The reaction mixture was stirred at 80° C. for 16 h. The solution was cooled to room temperature, poured into water and yellow solid was precipitated. The mixture was filtered to give a crude solid. The solid was added to a mixture of petroleum ether/ethyl acetate (1:1) and stirred at room temperature for 30 min. The mixture was filtered and dried under reduced pressure by oil pump to give 6-chloro-8-[(4-methoxybenzyl)oxy]-2-methylpyrido[3,4-d]pyrimidin-4-ol as a brown solid. The solid was added to acetonitrile (70 ml) and recrystallized at 70° C. for 30 min. The mixture was filtered and dried under reduced pressure by oil pump to give a brown solid (9.10 g, 90% purity, 62% yield).

LC-MS (Method 1): $R_t$=1.08 min; MS (ESIneg): m/z=330 $[M-H]^-$

Intermediate 101

6-chloro-N-[(1R)-1-(3-{1,1-difluoro-2-methyl-2-[(triethylsilyl)oxy]propyl}-2-fluorophenyl)ethyl]-8-[(4-methoxyphenyl)methoxy]-2-methylpyrido[3,4-d]pyrimidin-4-amine

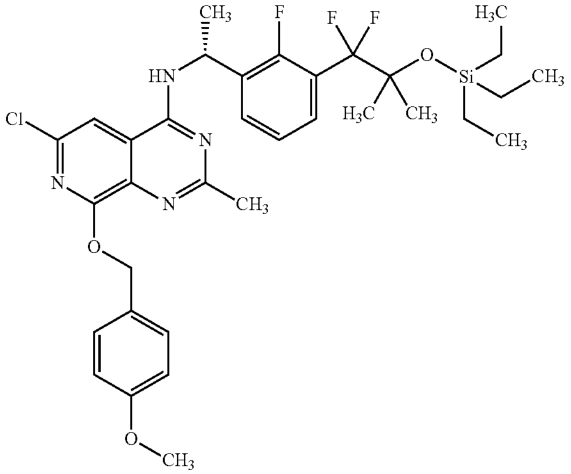 [SMILES: CC[Si](CC)(CC)OC(C)(C)C(F)(F)c1cccc([C@@H](C)Nc2nc(C)nc3c(OCc4ccc(OC)cc4)nc(Cl)cc23)c1F]

Using general method 1, starting from (1R)-1-(3-{1,1-difluoro-2-methyl-2-[(triethylsilyl)oxy]propyl}-2-fluorophenyl)ethan-1-amine (Intermediate 48, 783 mg, 2.17 mmol) and 6-chloro-8-[(4-methoxyphenyl)methoxy]-2-methylpyrido[3,4-d]pyrimidin-4-ol (Intermediate 100, 599 mg, 1.80 mmol), the title compound was obtained as yellow oil (590 mg, 48% yield).

LC-MS (Method 2): $R_t$=1.88 min; MS (ESIpos): m/z=675.6 $[M+H]^+$

Intermediate 102

N-[(1R)-1-(3-{1,1-difluoro-2-methyl-2-[(triethylsilyl)oxy]propyl}-2-fluorophenyl)ethyl]-6-(dimethylphosphoryl)-8-[(4-methoxyphenyl)methoxy]-2-methylpyrido[3,4-d]pyrimidin-4-amine

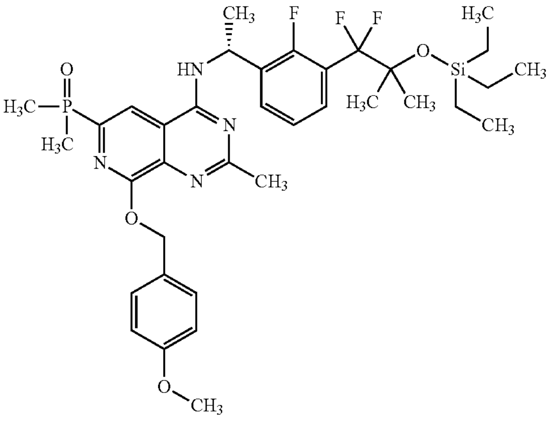 [SMILES: CC[Si](CC)(CC)OC(C)(C)C(F)(F)c1cccc([C@@H](C)Nc2nc(C)nc3c(OCc4ccc(OC)cc4)nc(P(C)(C)=O)cc23)c1F]

To a solution of 6-chloro-N-[(1R)-1-(3-{1,1-difluoro-2-methyl-2-[(triethylsilyl)oxy]propyl}-2-fluorophenyl)ethyl]-8-[(4-methoxyphenyl)methoxy]-2-methylpyrido[3,4-d]pyrimidin-4-amine (Intermediate 101, 300 mg, 444 μmol), tetrakis(triphenylphosphin)palladium(0) (77.0 mg, 66.6 μmol) was added, followed by acetonitrile (5 mL), triethylamine (220 μl, 1.6 mmol) and dimethyl-lambda$^5$-phosphanone (34.7 mg, 444 μmol). The atmosphere was exchanged to argon and the vial was sealed and heated to 90° C. for 24 h. The solvent was evaporated, and the residue was purified by flash chromatography (silica, dichloromethane, methanol) to obtain the title compound (208 mg, 65% yield) as colorless oil.

LC-MS (Method 2): $R_t$=1.73 min; MS (ESIpos): m/z=717.9 $[M+H]^+$

Intermediate 103

6-bromo-2-(trifluoromethyl)pyrido[3,4-d]pyrimidin-4(3H)-one

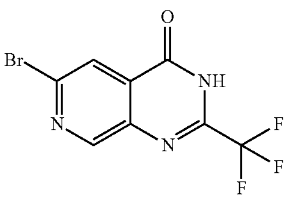 [SMILES: O=c1[nH]c(C(F)(F)F)nc2cnc(Br)cc12]

A solution of 5-amino-2-bromopyridine-4-carboxylic acid (640 mg, 2.95 mmol) and trifluoroethanimidamide (583 mg, 85% purity, 4.42 mmol) in 2-methoxyethanol (9.6 ml) was stirred at 130° C. (reflux) overnight. The mixture was cooled to RT, concentrated, and the residue was purified by flash chromatography (silica, dichloromethane, methanol) to yield the title compound (809 mg, 99% purity, 93% yield) as brown solid.

LC-MS (Method 1): $R_t$=0.92 min; MS (ESIpos): m/z=296 $[M+H]^+$

Intermediate 104

6-bromo-4-chloro-2-(trifluoromethyl)pyrido[3,4-d]pyrimidine

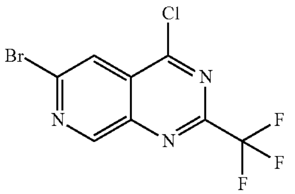 [SMILES: FC(F)(F)c1nc(Cl)c2cc(Br)ncc2n1]

To a suspension of 6-bromo-2-(trifluoromethyl)pyrido[3,4-d]pyrimidin-4(3H)-one (Intermediate 103, 314 mg, 1.07 mmol) in 1,2-dichloroethane (2.9 ml) was added 3 drops of DMF thionyl chloride (230 μl, 3.2 mmol), subsequently, and the mixture was stirred at 100° C. for 3 h. The mixture was then cooled, concentrated, and the residue was purified by flash chromatography (silica, dichloromethane, methanol) to yield the title compound (311 mg, 94% purity, 88% yield) as yellow oil.

LC-MS (Method 1): $R_t$=1.27 min; MS (ESIpos): m/z=310.9 $[M+H]^+$ $^1$H-NMR (400 MHz, DMSO-d6) δ[ppm]: 2.518 (3.31), 2.523 (2.19), 8.077 (0.65), 8.079 (0.63), 8.188 (15.97), 8.190 (16.00), 9.030 (12.25), 9.032 (12.35), 9.063 (0.46), 9.065 (0.44).

Intermediate 105

6-bromo-N-{(1R)-1-[2-methyl-3-(trifluoromethyl)phenyl]ethyl}-2-(trifluoromethyl)pyrido[3,4-d]pyrimidin-4-amine

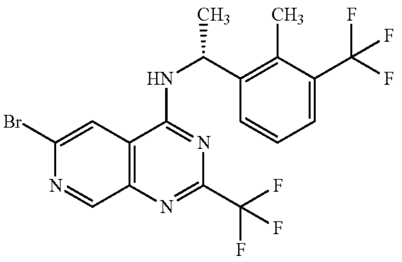 [SMILES: Cc1c([C@@H](C)Nc2nc(C(F)(F)F)nc3cnc(Br)cc23)cccc1C(F)(F)F]

To a solution of 6-bromo-4-chloro-2-(trifluoromethyl)pyrido[3,4-d]pyrimidine (Intermediate 105, 208 mg, 666 μmol) in N,N-dimethylacetamide (2.7 ml) was subsequently added triethylamine (240 μl, 1.7 mmol) and (1R)-1-[2-methyl-3-(trifluoromethyl)phenyl]ethan-1-amine hydrogen chloride (1/1) (168 mg, 699 μmol), and the miture was stirred at RT overnight. The crude mixture was concentrated and the residue was subjected to flash chromatography (silica, hexane, ethyl acetate) to yield the title compound (317 mg, 99% purity, 99% yield) as dark yellow solid.

LC-MS (Method 1): $R_t$=1.55 min; MS (ESIpos): m/z=481 $[M+H]^+$

Intermediate 106

6-bromo-2-(difluoromethyl)pyrido[3,4-d]pyrimidin-4(3H)-one

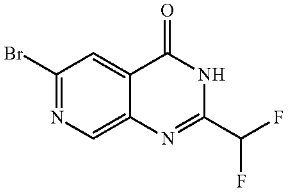 [SMILES: O=c1[nH]c(C(F)F)nc2cnc(Br)cc12]

As described for Intermediate 103, starting from 5-amino-2-bromopyridine-4-carboxylic acid (139 mg, 638 μmol) and difluoroethanimidamide hydrogen chloride (1/1) (100 mg, 766

LC-MS (Method 1): $R_t$=0.78 min; MS (ESIpos): m/z=276 $[M+H]^+$

Intermediate 107

6-bromo-4-chloro-2-(difluoromethyl)pyrido[3,4-d]pyrimidine

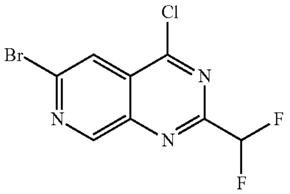 [SMILES: FC(F)c1nc(Cl)c2cc(Br)ncc2n1]

As described for Intermediate 104, starting from 6-bromo-2-(difluoromethyl)pyrido[3,4-d]pyrimidin-4(3H)-one (Intermediate 106, 114 mg, 413 μmol) and thionyl chloride (90 μl, 1.2 mmol), the title LC-MS (Method 1): $R_t$=1.14 min; MS (ESIpos): m/z=296 $[M+H]^+$ Intermediate 108

6-bromo-2-(difluoromethyl)-N-{(1R)-1-[2-methyl-3-(trifluoromethyl)phenyl]ethyl}pyrido[3,4-d]pyrimidin-4-amine

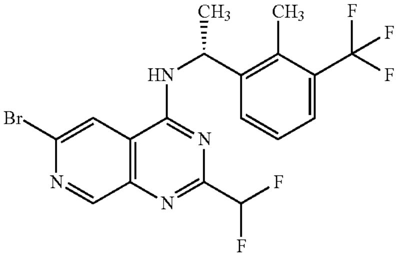 [SMILES: Cc1c([C@@H](C)Nc2nc(C(F)F)nc3cnc(Br)cc23)cccc1C(F)(F)F]

To a solution of 6-bromo-4-chloro-2-(difluoromethyl) pyrido[3,4-d]pyrimidine (Intermediate 107,113 mg, 384 μmol) in N,N-dimethylacetamide (1.5 ml) was added triethylamine (140 μl, 1000 μmol), followed by (1R)-1-[2-methyl-3-(trifluoromethyl)phenyl]ethan-1-amine hydrogen chloride (1/1) (101 mg, 422 μmol), and the mixture was stirred at RT overnight. The mixture was concentrated and the residue was purified by flash chromatography (silica, hexane, ethyl acetate) to yield the title compound (142 mg, 94% purity, 75% yield) as white solid.

LC-MS (Method 1): $R_t$=1.45 min; MS (ESIpos): m/z=463 $[M+H]^+$

Intermediate 109

6-bromopyrido[3,4-d]pyrimidine-2,4 (1H,3H)-dione

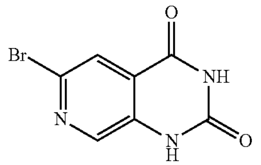 [SMILES: O=c1[nH]c(=O)c2cc(Br)ncc2[nH]1]

A mixture of 5-amino-2-bromopyridine-4-carboxylic acid (488 mg, 2.25 mmol) and urea (540 mg, 8.99 mmol) was stirred at 170° C. overnight. Then cooled, diluted with water and heated to reflux for 40 min. After cooling to RT, the title compound partially precipitated (214 mg, 58% purity, 23% yield) and was collected by filtration. The filtrate was concentrated and purified by flash chromatography (silica, dichloromethane, methanol) to yield another fraction (365 mg, 82% purity, 55% yield) of the title compound.

LC-MS (Method 1): $R_t$=0.60 min; MS (ESIneg): m/z=240 $[M-H]^-$

Intermediate 110

6-bromo-2,4-dichloropyrido[3,4-d]pyrimidine

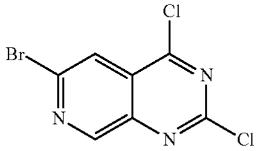 [SMILES: Clc1nc(Cl)c2cc(Br)ncc2n1]

A mixture of 6-bromopyrido[3,4-d]pyrimidine-2,4(1H, 3H)-dione (Intermediate 109, 210 mg, 868 μmol), phosphoryl trichloride (2.1 ml, 23 mmol), and N,N-diisopropylethylamine (760 μl, 4.3 mmol) was stirred at 100° C. overnight. To the mixture was added glacial acetic acid, the resulting mixture was extracted with ethyl acetate, the organic phase was washed with saturated aqueous sodium hydrogen carbonate, dried over sodium sulfate, and concentrated. The crude product was used in the next reaction without purification.

LC-MS (Method 1): $R_t$=1.17 min; MS (ESIpos): m/z=280 $[M+H]^+$

Intermediate 111

6-bromo-2-chloro-N-{(1R)-1-[2-methyl-3-(trifluoromethyl)phenyl]ethyl}pyrido[3,4-d]pyrimidin-4-amine

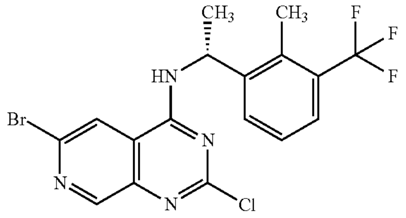 [SMILES: Cc1c([C@@H](C)Nc2nc(Cl)nc3cnc(Br)cc23)cccc1C(F)(F)F]

The reaction was performed as described for Intermediate 108, starting from 6-bromo-2,4-dichloropyrido[3,4-d]pyrimidine (Intermediate 110, 120 mg, 430 μmol) and (1R)-1-[2-methyl-3-(trifluoromethyl)phenyl]ethan-1-amine (96.2 mg, 473 μmol). The title compound (120 mg, 94% purity, 59% yield) was obtained after purification by flash chromatography (silica, hexane, ethyl acetate) as orange oil.

LC-MS (Method 1): $R_t$=1.49 min; MS (ESIpos): m/z=447 $[M+H]^+$

Intermediate 112

6-chloro-8-[(4-methoxyphenyl)methoxy]-2-methyl-N-{(1R)-1-[2-methyl-3-(trifluoromethyl)phenyl] ethyl}pyrido[3,4-d]pyrimidin-4-amine

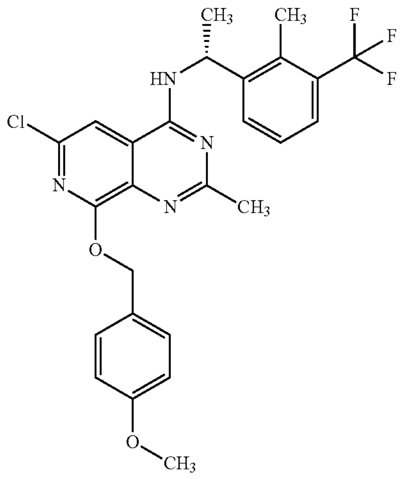 [SMILES: COc1ccc(COc2nc(Cl)cc3c(N[C@H](C)c4cccc(C(F)(F)F)c4C)nc(C)nc23)cc1]

Using general method 1, starting from 6-chloro-8-[(4-methoxyphenyl)methoxy]-2-methylpyrido[3,4-d]pyrimidin-4-ol (Intermediate 116, 1.01 g, 3.05 mmol) and (1R)-1-[2-methyl-3-(trifluoromethyl)phenyl]ethan-1-amine (744 mg, 3.66 mmol), the title compound was LC-MS (Method 2): $R_t$=1.53 min; MS (ESIpos): m/z=517.6 $[M+H]^+$ Intermediate 113 tert-butyl 4-{8-[(4-methoxyphenyl)methoxy]-2-methyl-4-({(1R)-1-[2-methyl-3-(trifluoromethyl)phenyl]ethyl}amino)pyrido[3,4-d]pyrimidin-6-yl}-4-oxo-1,4lambda$^5$-azaphosphinane-1-carboxylate

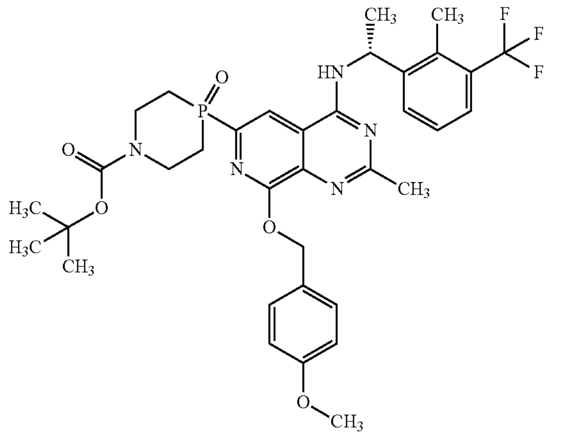 [SMILES: COc1ccc(COc2nc(P3(=O)CCN(C(=O)OC(C)(C)C)CC3)cc3c(N[C@H](C)c4cccc(C(F)(F)F)c4C)nc(C)nc23)cc1]

The reaction was performed as described for Intermediate 102, starting from 6-chloro-8-[(4-methoxyphenyl)methoxy]-2-methyl-N-{(1R)-1-[2-methyl-3-(trifluoromethyl)phenyl]ethyl}-pyrido[3,4-d]pyrimidin-4-amine (Intermediate 112, 409 mg, 791 μmol) and tert-butyl 4-oxo-1,4lambda$^5$-azaphosphinane-1-carboxylate (Intermediate 52, 208 mg, 949 μmol) to obtain the title compound (105 mg, 19% yield) as yellow oil.

LC-MS (Method 2): $R_t$=1.47 min; MS (ESIpos): m/z=701.0 $[M+H]^+$

Intermediate 117

6-bromo-2-methyl-N-{(1R)-1-[2-methyl-3-(trifluoromethyl)phenyl]ethyl}pyrido[3,4-d]pyrimidin-4-amine

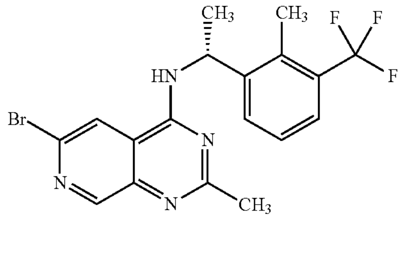 [SMILES: Cc1nc(N[C@H](C)c2cccc(C(F)(F)F)c2C)c2cc(Br)ncc2n1]

The title compound (28.77 g, 81% yield) was prepared as described for Intermediate 22, using 6-bromo-2-methylpyrido[3,4-d]pyrimidin-4-ol (Intermediate 32, 20 g, 83.3 mmol).

LC-MS (Method 2): $R_t$=1.40 min; MS (ESIpos): m/z=425, 427 $[M+H]^+$

Intermediate 118

Ethyl (R)-2-(3-(1-aminoethyl)-2-fluorophenyl)-2,2-difluoroacetate hydrogen chloride

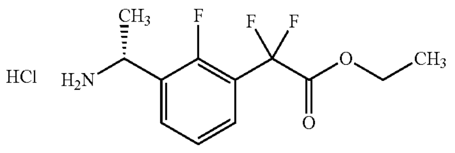 [SMILES: Cl ; CCOC(=O)C(F)(F)c1cccc([C@@H](C)N)c1F]

The reaction was performed as described for Intermediate 28, starting from (R)-ethyl 2-(3-(1-((tert-butoxycarbonyl)amino)ethyl)-2-fluorophenyl)-2,2-difluoroacetate (Intermediate 30, 4.2 g, 11.62 mmol), to obtain the title compound (2.8 g, 95% purity, 76% yield).

LC-MS (Method 2): $R_t$=1.07 min; MS (ESIpos): m/z=262.3 $[M+H]^+$

Intermediate 130 tert-butyl {(1R)-1-[3-(1,1-difluoro-2-hydroxyethyl)-2-fluorophenyl]ethyl}carbamate

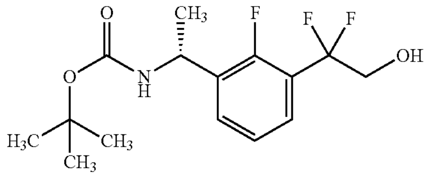 [SMILES: C[C@@H](NC(=O)OC(C)(C)C)c1cccc(C(F)(F)CO)c1F]

To a solution of ethyl (3-{(1R)-1-[(tert-butoxycarbonyl)amino]ethyl}-2-fluorophenyl)(difluoro)acetate (15.1 g, 41.7 mmol) in tetrahydrofuran (1.2.ml) was added sodium tetrahydridoborate (3.31 g, 87.6 mmol) portionwise, and the resulting mixture was stirred at RT overnight. To the mixture was added aqueous hydrochloric acid (1 M), until the solution has reached ~pH6, and the mixture was stirred for 15 min. The mixture was then extracted with ethyl acetate, the organic phases were washed with saturated aqueous sodium chloride, dried over sodium sulfate and concentrated. The residue was used for the next reaction without purification.

$^1$H-NMR (400 MHz, CHLOROFORM-d) 5 [ppm]: 1.116 (0.42), 1.133 (0.81), 1.151 (0.43), 1.243 (0.69), 1.249 (5.05), 1.261 (0.77), 1.267 (10.29), 1.285 (5.04), 1.429 (10.00), 1.439 (8.97), 1.451 (7.32), 1.468 (5.81), 1.496 (0.41), 1.861 (0.54), 2.054 (16.00), 3.753 (0.45), 4.065 (2.36), 4.102 (4.56), 4.120 (3.70), 4.138 (4.61), 4.155 (1.17), 5.005 (0.87), 7.179 (1.53), 7.198 (3.18), 7.218 (1.84), 7.405 (1.36), 7.423 (1.95), 7.442 (0.95), 7.454 (1.47), 7.458 (1.30), 7.473 (2.13), 7.490 (1.15), 7.495 (1.00).

Intermediate 131

2-{3-[(1R)-1-aminoethyl]-2-fluorophenyl}-2,2-difluoroethan-1-ol trifluoroacetic acid (1/1)

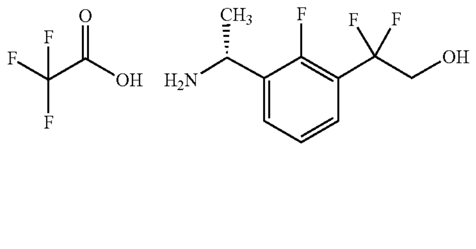

To a solution of tert-butyl {(1R)-1-[3-(1,1-difluoro-2-hydroxyethyl)-2-fluorophenyl]-ethyl}carbamate (Intermediate 130, 14.3 g, 44.8 mmol) in dichloromethane (530 ml) was added trifluoroacetic acid (52 ml, 670 mmol), and the mixture was stirred at RT for 2 h. The mixture was concentrated and subsequently diluted with toluene and concentrated two times to yield the crude title compound (17.6 g, 91% purity, quantitative), which was used for the next step without purification.

LC-MS (Method 2): $R_t$=0.74 min; MS (ESIpos): m/z=220 $[M+H]^+$

Intermediate 132

(1R)-1-[3-(2-{[tert-butyl(dimethyl)silyl]oxy}-1,1-difluoroethyl)-2-fluorophenyl]ethan-1-amine

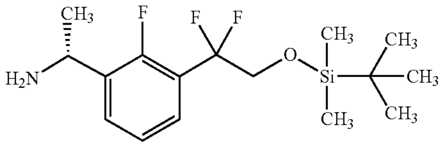 [SMILES: C[C@@H](N)c1cccc(C(F)(F)CO[Si](C)(C)C(C)(C)C)c1F]

To a solution of 2-{3-[(1R)-1-aminoethyl]-2-fluorophenyl}-2,2-difluoroethan-1-ol trifluoroacetic acid (1/1) (Intermediate 131, 17.6 g, 91% purity, 48.1 mmol) in dichloromethane (270 ml) at 0° C. was added 2,6-dimethylpyridine (39 ml), followed by tert-butyl(dimethyl)silyl trifluoromethanesulfonate (44 ml, 190 mmol), and the mixture was stirred at RT for 3 h. The mixture was quenched with saturated aqueous sodium hydrogen carbonate solution, the organic phase was separated, dried with sodium sulfate, and concentrated. The residue was purified by flash chromatography (silica, hexane, ethyl acetate) to give the title compound (9.09 g, 60% yield) as yellow oil.

LC-MS (Method 2): $R_t$=1.50 min; MS (ESIpos): m/z=335 $[M+H]^+$ $^1$H-NMR (400 MHz, CHLOROFORM-d) 5 [ppm]: −0.008 (3.80), 0.787 (0.44), 0.791 (0.79), 0.799 (16.00), 0.806 (0.60), 1.414 (1.58), 1.430 (1.56), 4.108 (0.68), 4.111 (0.66).

Intermediate 133 tert-butyl [(1R)-1-{3-[1,1-difluoro-2-hydroxy($^2$H2)ethyl]-2-fluorophenyl}ethyl]carbamate

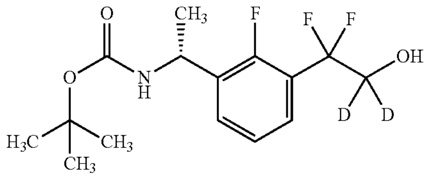 [SMILES: [2H]C([2H])(O)C(F)(F)c1cccc([C@@H](C)NC(=O)OC(C)(C)C)c1F]

The reaction was performed as described for Intermediate 141, using sodium tetradeuterioborate (982 mg, 23.5 mmol), to yield the title compound (2.79 g, 92% yield) LC-MS (Method 2): $R_t$=1.26 min; MS (ESIpos): m/z=339.4 $[M+H_2O+H]^+$ Intermediate 134

6-bromo-N-[(1R)-1-{3-[2-{[tert-butyl(dimethyl)silyl]oxy}-1,1-difluoro($^2H_2$)ethyl]-2-fluorophenyl}ethyl]-2-methylpyrido[3,4-d]pyrimidin-4-amine

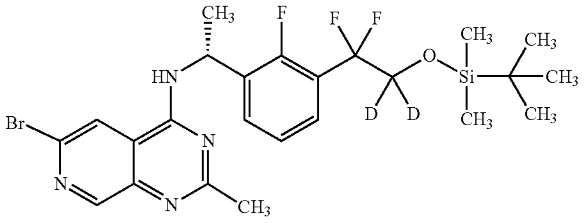 [SMILES: [2H]C([2H])(O[Si](C)(C)C(C)(C)C)C(F)(F)c1cccc([C@@H](C)Nc2nc(C)nc3cnc(Br)cc23)c1F]

Intermediate 134 was prepared in two steps as described for the isotopomer Intermediate 117, starting from deuterated Intermediate 133. The title compound was obtained as yellow solid (741 mg, 66% yield).

LC-MS (Method 2): $R_t$=1.67 min; MS (ESIpos): m/z=557.5 $[M+H]^+$ $^1$H NMR (400 MHz, DMSO-d6) b ppm −0.14-0.07 (m, 6H) 0.68 (s, 9H) 1.55-1.64 (m, 3H) 2.38 (s, 3H) 5.64-5.80 (m, 1H) 7.22-7.31 (m, 1H) 7.36-7.46 (m, 1H) 7.59-7.72 (m, 1H) 8.64-8.68 (m, 1H) 8.79-8.81 (m, 1H) 8.84-8.90 (m, 1H).

Intermediate 135

1-[2-methyl-3-(trifluoromethyl)phenyl]($^2$H3)ethan-1-one

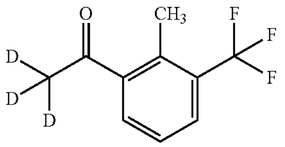 [SMILES: [2H]C([2H])([2H])C(=O)c1cccc(C(F)(F)F)c1C]

To a solution of 1-[2-methyl-3-(trifluoromethyl)phenyl]ethan-1-one (2.50 g, 12.4 mmol) in 1,4-dioxane (19 ml) and deuterium oxide (19 ml, 1.0 mol) was added pyrrolidine (100 μl, 1.2 mmol), and the mixture was stirred at RT overnight. The mixture was extracted with methyl-tert-butyl ether, washed with saturated aqueous sodium chloride, dried over sodium sulfate, and concentrated. The crude product (2.37 g, 93% yield) was used for the next reaction without purification.

$^1$H-NMR (400 MHz, DMSO-d6) δ[ppm]: 2.417 (16.00), 2.421 (15.91), 2.518 (1.50), 2.523 (0.98), 7.499 (1.87), 7.519 (4.13), 7.538 (2.36), 7.817 (4.10), 7.837 (3.58), 7.928 (3.82), 7.948 (3.49).

Intermediate 136

6-bromo-2-methyl-N-[(1S)-1-[2-methyl-3-(trifluoromethyl)phenyl]($^2H_4$)ethyl]pyrido[3,4-d]pyrimidin-4-amine

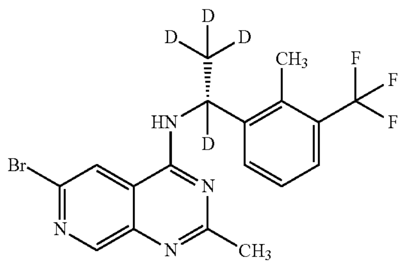 [SMILES: [2H]C([2H])([2H])[C@]([2H])(Nc1nc(C)nc2cnc(Br)cc12)c1cccc(C(F)(F)F)c1C]

The title compound was prepared as described for its isotopomer Intermediate 117, starting from deuterated Intermediate 135, using literature known procedures, to obtain the title compound (143 mg, 81% yield).

LC-MS (Method 2): $R_t$=1.39 min; MS (ESIpos): m/z=429 $[M+H]^+$ $^1$H-NMR (400 MHz, DMSO-d6) δ[ppm]: 1.171 (0.66), 1.517 (0.48), 1.986 (1.40), 2.379 (16.00), 2.518 (1.13), 2.523 (0.81), 2.606 (4.93), 7.345 (0.56), 7.364 (1.26), 7.383 (0.73), 7.544 (1.32), 7.561 (1.05), 7.746 (1.18), 7.766 (1.06), 8.649 (3.33), 8.651 (3.52), 8.785 (3.92), 8.787 (4.04), 8.967 (1.85).

Intermediate 137 tert-butyl 4-(4-hydroxy-2-methylpyrido[3,4-d]pyrimidin-6-yl)-4-oxo-1,4lambda$^5$-azaphosphinane-1-carboxylate

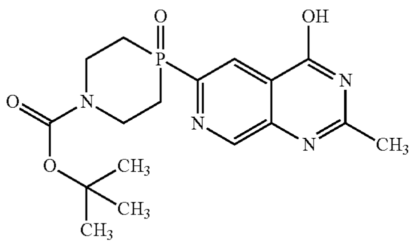 [SMILES: Cc1nc(O)c2cc(P3(=O)CCN(C(=O)OC(C)(C)C)CC3)ncc2n1]

A mixture of 6-bromo-2-methylpyrido[3,4-d]pyrimidin-4-ol (Intermediate 32, 5.00 g, 95% purity, 19.8 mmol), tert-butyl 4-oxo-1,4lambda$^5$-azaphosphinane-1-carboxylate (Intermediate 52, 4.34 g, 19.8 mmol), tetrakis(triphenylphosphin)palladium(0) (3.62 g, 3.96 mmol) and triethylamine (9.7 ml, 69 mmol) in acetonitrile (100 ml) was stirred at 90° C. for 22 h. The mixture was then cooled, filtered, and concentrated to yield the title compound (7.63 g, 86% purity, 88% yield), which was used for the next step without purification.

LC-MS (Method 2): $R_t$=0.58 min; MS (ESIpos): m/z=379.5 $[M+H]^+$ $^1$H-NMR (400 MHz, DMSO-d6) δ[ppm]: 1.438 (16.00), 2.074 (2.99), 2.432 (5.35), 2.518 (0.81), 2.523 (0.53), 8.434 (0.71), 8.436 (0.73), 8.449 (0.72), 8.451 (0.71), 9.128 (1.42).

Intermediate 138

4-(4-hydroxy-2-methylpyrido[3,4-d]pyrimidin-6-yl)-1,4lambda-azaphosphinan-4-one-hydrogen chloride (1/1)

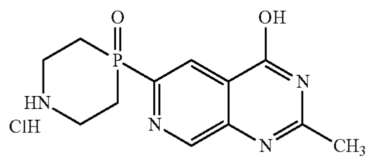 [SMILES: Cl ; Cc1nc(O)c2cc(P3(=O)CCNCC3)ncc2n1]

To a solution of tert-butyl 4-(4-hydroxy-2-methylpyrido[3,4-d]pyrimidin-6-yl)-4-oxo-1,4lambda$^5$-azaphosphinane-1-carboxylate (Intermediate 137, 2.50 g, 86% purity, 5.68 mmol) in 1,4-dioxane (15 ml) was added hydrogen chloride in 1,4-dioxane (4 M in 1,4-dioxane, 15 ml, 85 mmol) and the mixture was stirred at RT for 22 h. The mixture was concentrated, and the residue was stirred in methyl-tert-butyl ether (50 ml) at RT. The resulting suspension was filtered and solid collected to obtain the title compound (2.34 g, 90% purity, quantitative) as light-brown solid, which was used for the next reaction without purification.

LC-MS (Method 1): $R_t$=1.09 min; MS (ESIpos): m/z=279.5 $[M+H]^+$

Intermediate 139

1-acetyl-4-(4-hydroxy-2-methylpyrido[3,4-d]pyrimidin-6-yl)-1,4lambda$^5$-azaphosphinan-4-one

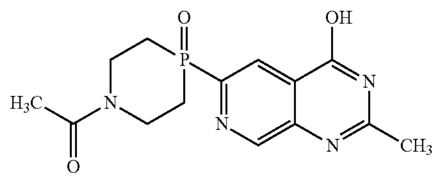 [SMILES: CC(=O)N1CCP(=O)(c2cc3c(O)nc(C)nc3cn2)CC1]

Using general procedure 7, starting from 4-(4-hydroxy-2-methylpyrido[3,4-d]pyrimidin-6-yl)-1,4lambda$^5$-azaphosphinan-4-one hydrogen chloride (1/1) (Intermediate 138, 2.34 g, 7.44 mmol), the title compound (3.46 g, 84% purity, 122% yield) was obtained as brown solid, which was used for the next reaction without purification.

LC-MS (Method 1): $R_t$=0.50 min; MS (ESIneg): m/z=319.5 $[M-H]^-$

Intermediate 140

6-bromo-2,8-dimethyl-N-{(1R)-1-[2-methyl-3-(trifluoromethyl)phenyl]ethyl}pyrido[3,4-d]pyrimidin-4-amine

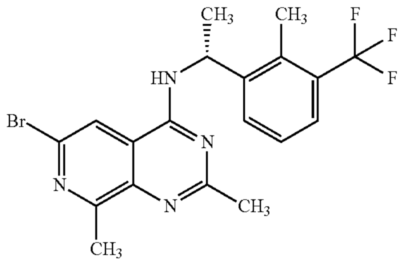 [SMILES: Cc1nc(N[C@H](C)c2cccc(C(F)(F)F)c2C)c2cc(Br)nc(C)c2n1]

To a mixture of 6-bromo-2-methyl-N-{(1R)-1-[2-methyl-3-(trifluoromethyl)phenyl]ethyl}-pyrido[3,4-d]pyrimidin-4-amine (Intermediate 117, 200 mg, 470 μmol) in DMSO (3.3 ml) was added 1,8-diazabicyclo(5.4.0)undec-7-ene (140 μl, 940 μmol), and the mixture was stirred at RT overnight. The mixture was then diluted with water, extracted with dichloromethane, and the organic phases were separated, dried with sodium sulfate, and concentrated. The crude product was purified by preparative TLC (silica, hexane, ethyl acetate) to give the title compound (170 mg, 82% yield).

LC-MS (Method 2): $R_t$=1.52 min; MS (ESIpos): m/z=439 $[M+H]^+$ $^1$H-NMR (400 MHz, DMSO-d6) δ[ppm]: 1.543 (4.55), 1.560 (4.58), 2.327 (0.48), 2.385 (16.00), 2.518 (1.89), 2.523 (1.30), 2.605 (5.15), 2.669 (0.52), 2.702 (11.32), 5.651 (0.67), 5.668 (1.04), 5.686 (0.65), 5.758 (1.26), 7.338 (0.58), 7.357 (1.28), 7.377 (0.74), 7.538 (1.38), 7.555 (1.11), 7.736 (1.23), 7.755 (1.10), 8.472 (3.27), 8.857 (1.05), 8.874 (1.00).

Intermediate 141

2-(3-{(1R)-1-[(6-bromo-2-methylpyrido[3,4-d]pyrimidin-4-yl)amino]ethyl}-2-fluorophenyl)-2,2-difluoroethan-1-ol

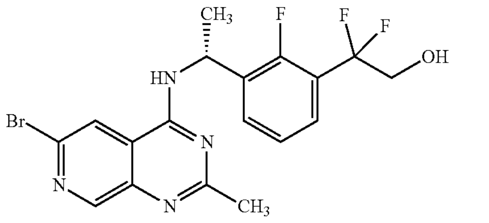 [SMILES: Cc1nc(N[C@H](C)c2cccc(C(F)(F)CO)c2F)c2cc(Br)ncc2n1]

To a solution of 6-bromo-N-{(1R)-1-[3-(2-{[tert-butyl(dimethyl)silyl]oxy}-1,1-difluoroethyl)-2-fluorophenyl]ethyl}-2-methylpyrido[3,4-d]pyrimidin-4-amine (Intermediate 131, 300 mg, 540 μmol) in dichloromethane (2.0 ml) was added trifluoroacetic acid (620 μl, 8.1 mmol), and the mixture was stirred at RT overnight. The mixture was then diluted with toluene and concentrated. The residue was purified by flash chromatography (Biotage® Sfar Amino, hexane, ethyl acetate) to obtain the title compound (208 mg, 87% yield).

LC-MS (Method 2): $R_t$=1.07 min; MS (ESIpos): m/z=441 $[M+H]^+$ $^1$H-NMR (400 MHz, DMSO-d6) δ[ppm]: 1.153 (1.80), 1.171 (3.55), 1.189 (1.70), 1.586 (4.91), 1.603 (4.85), 1.986 (6.51), 2.332 (0.41), 2.395 (16.00), 2.518 (2.20), 2.523 (1.49), 3.358 (1.84), 3.372 (0.44), 3.888 (0.48), 3.903 (0.53), 3.924 (0.95), 3.939 (0.98), 3.960 (0.48), 3.974 (0.45), 3.998 (0.50), 4.016 (1.48), 4.034 (1.47), 4.052 (0.48), 5.706 (0.66), 5.722 (1.62), 5.727 (1.17), 5.737 (0.77), 5.745 (1.26), 5.756 (0.78), 5.763 (0.75), 7.241 (0.83), 7.261 (1.87), 7.280 (1.08), 7.411 (0.68), 7.428 (1.09), 7.444 (0.53), 7.630 (0.59), 7.648 (1.06), 7.665 (0.53), 8.665 (4.08), 8.805 (4.52), 8.868 (1.23), 8.886 (1.17).

Intermediate 142

2-(3-{(1R)-1-[(6-bromo-2,8-dimethylpyrido[3,4-d]pyrimidin-4-yl)amino]ethyl}-2-fluorophenyl)-2,2-difluoroethan-1-ol

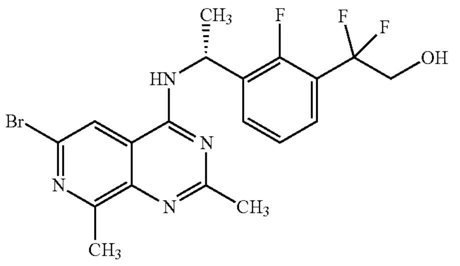 [SMILES: Cc1nc(N[C@H](C)c2cccc(C(F)(F)CO)c2F)c2cc(Br)nc(C)c2n1]

The reaction was perormed as described for Intermediate 140, starting from 2-(3-{(1R)-1-[(6-bromo-2-methylpyrido[3,4-d]pyrimidin-4-yl)amino]ethyl}-2-fluorophenyl)-2,2-difluoroethan-1-ol (Intermediate 141, 200 mg, 453 μmol). The product (208 mg, quantitative) was used for the next reaction without purification.

LC-MS (Method 2): $R_t$=1.21 min; MS (ESIpos): m/z=455 $[M+H]^+$ $^1$H-NMR (400 MHz, DMSO-d6) δ[ppm]: 1.154 (0.96), 1.171 (2.06), 1.189 (1.00), 1.577 (4.34), 1.594 (4.37), 1.986 (3.33), 2.402 (16.00), 2.518 (2.69), 2.523 (2.11), 2.718 (11.43), 3.359 (1.74), 3.385 (0.49), 3.886 (0.48), 3.901 (0.52), 3.922 (0.94), 3.938 (1.00), 3.957 (0.45), 3.974 (0.45), 4.016 (0.68), 4.034 (0.64), 5.704 (1.16), 5.720 (3.01), 5.736 (2.02), 5.756 (2.21), 7.234 (0.76), 7.254 (1.69), 7.273 (0.98), 7.404 (0.59), 7.422 (0.93), 7.438 (0.47), 7.613 (0.52), 7.630 (0.91), 7.646 (0.46), 8.481 (3.26), 8.756 (1.11), 8.774 (1.06).

Intermediate 143

2-(3-{(1R)-1-[(6-bromo-2-methylpyrido[3,4-d]pyrimidin-4-yl)amino]ethyl}-2-fluorophenyl)-2,2-difluoroethyl trifluoromethanesulfonate

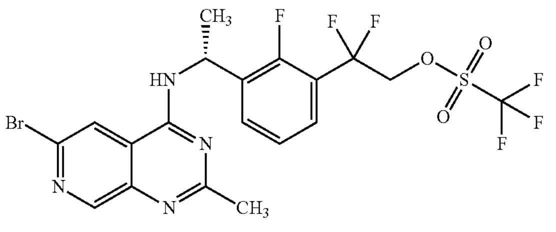 [SMILES: Cc1nc(N[C@H](C)c2cccc(C(F)(F)COS(=O)(=O)C(F)(F)F)c2F)c2cc(Br)ncc2n1]

To a solution of 2-(3-{(1R)-1-[(6-bromo-2-methylpyrido[3,4-d]pyrimidin-4-yl)amino]ethyl}-2-fluorophenyl)-2,2-difluoroethan-1-ol (Intermediate 141, 757 mg, 1.72 mmol) in dichloromethane (8.5 ml) was added at 0° C. triethylamine (960 μl, 6.9 mmol) and trifluoromethanesulfonic anhydride (410 μl, 2.4 mmol), and the mixture was stirred at RT for 2 h. Further trifluoromethanesulfonic anhydride (145 μl) was added, and the mixture was stirred at RT overnight. The mixture was then diluted with dichloromethane (60 ml), washed with water, and the organic phases were separated, filtered through a separation funnel and concentrated. The residue was subjected to flash chromatography (silica, hexane, ethyl acetate) to yield the title compound (577 mg, 80% purity, 47% yield) LC-MS (Method 2): $R_t$=1.43 min; MS (ESIpos): m/z=573.5 $[M+H]^+$ $^1$H-NMR (400 MHz, DMSO-d6) δ[ppm]: 1.154 (5.16), 1.172 (10.62), 1.189 (5.94), 1.206 (0.47), 1.580 (0.54), 1.597 (3.00), 1.614 (2.64), 1.986 (16.00), 2.370 (1.69), 2.381 (8.60), 2.518 (1.73), 2.523 (1.19), 3.999 (1.27), 4.016 (3.86), 4.034 (3.80), 4.052 (1.21), 5.366 (0.54), 5.404 (0.52), 5.700 (0.44), 5.717 (0.64), 5.735 (0.41), 7.325 (0.52), 7.344 (1.06), 7.364 (0.60), 7.503 (0.67), 7.523 (0.57), 7.731 (0.43), 7.748 (0.57), 8.664 (2.61), 8.809 (3.33), 8.897 (0.61), 8.913 (0.59).

Intermediate 144

2-{(1R)-1-[3-(2-{[tert-butyl(dimethyl)silyl]oxy}-1,1-difluoroethyl)-2-fluorophenyl]ethyl}-1H-isoindole-1,3(2H)-dione

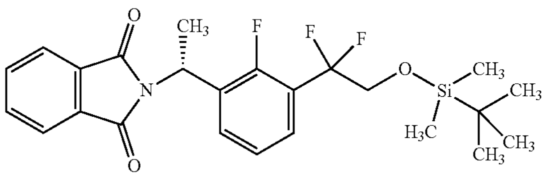 [SMILES: C[C@H](c1cccc(C(F)(F)CO[Si](C)(C)C(C)(C)C)c1F)N1C(=O)c2ccccc2C1=O]

To a solution of (1R)-1-[3-(2-{[tert-butyl(dimethyl)silyl]oxy}-1,1-difluoroethyl)-2-fluorophenyl]-ethan-1-amine (Intermediate 132, 750 mg, 2.25 mmol), triethylamine (940 μl, 6.7 mmol) and 4-(dimethylamino)pyridine (54 mg, 0.45 mmol) in tetrahydrofuran (50 ml) was added 2-benzofuran-1,3-dione (400 mg, 2.70 mmol), and the mixture was stirred at 80° C. overnight. Then, acetic anhydride (320 μl, 3.4 mmol) was added, and stirring was continued overnight at 80° C. The mixture was cooled, and saturated aqueous sodium hydrogen carbonate was added. The organic phase was separated, washed with saturated aqueous sodium chloride, dried with sodium sulfate, and concentrated. The residue was subjected to flash chromatography (silica, hexane, ethyl acetate) to obtain the title compound (833 mg, 80% yield).

LC-MS (Method 2): $R_t$=1.67 min; MS (ESIpos): m/z=464 $[M+H]^+$ $^1$H-NMR (400 MHz, DMSO-d6) δ[ppm]: −0.242 (4.60), −0.173 (4.75), 0.587 (0.83), 0.595 (16.00), 0.602 (0.84), 1.791 (1.45), 1.809 (1.44), 2.518 (0.72), 2.523 (0.49), 4.042 (0.40), 7.347 (0.47), 7.842 (6.00).

Intermediate 145

2-{(1R)-1-[3-(1,1-difluoro-2-hydroxyethyl)-2-fluorophenyl]ethyl}-1H-isoindole-1,3(2H)-dione

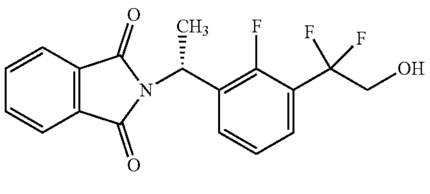 [SMILES: C[C@H](c1cccc(C(F)(F)CO)c1F)N1C(=O)c2ccccc2C1=O]

To a solution of 2-{(1R)-1-[3-(2-{[tert-butyl(dimethyl)silyl]oxy}-1,1-difluoroethyl)-2-fluorophenyl]-ethyl}-1H-isoindole-1,3(2H)-dione (Intermediate 144, 830 mg, 1.79 mmol) in dichloromethane (10 ml) was added trifluoroacetic acid (2.8 ml) and the mixture was stirred at RT overnight. The mixture was concentrated, diluted with dichloromethane (2 ml), and stirred for further 3 h. The mixture was then diluted with toluene, concentrated, and the crude product was purified by flash chromatography (silica, hexane, ethyl acetate) to yield the title compound (472 mg, 75% yield).

LC-MS (Method 1): $R_t$=1.12 min; MS (ESIpos): m/z=350 $[M+H]^+$ $^1$H-NMR (400 MHz, DMSO-d6) δ[ppm]: 1.791 (9.26), 1.809 (9.13), 2.518 (2.54), 2.523 (1.80), 3.811 (0.72), 3.821 (0.77), 3.847 (1.44), 3.858 (1.45), 3.883 (0.74), 3.893 (0.70), 5.658 (1.80), 5.674 (1.09), 5.693 (1.92), 5.711 (1.85), 5.729 (0.53), 5.758 (2.00), 7.316 (1.30), 7.335 (2.94), 7.355 (1.73), 7.472 (0.96), 7.476 (1.09), 7.493 (1.75), 7.509 (0.84), 7.512 (0.79), 7.792 (0.93), 7.809 (1.71), 7.827 (1.36), 7.829 (1.47), 7.837 (0.79), 7.842 (2.05), 7.851 (15.68), 7.853 (16.00), 7.857 (6.30), 7.862 (2.01), 7.866 (0.76), 7.872 (0.45), 7.875 (0.63), 7.877 (0.52).

Intermediate 146

2-{(1R)-1-[3-(1,1-difluoro-2-methoxyethyl)-2-fluorophenyl]ethyl}-1H-isoindole-1,3(2H)-dione

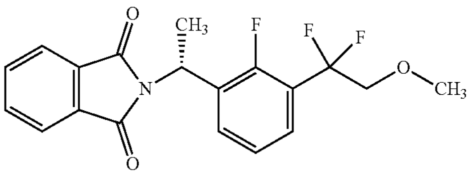 [SMILES: COCC(F)(F)c1cccc([C@@H](C)N2C(=O)c3ccccc3C2=O)c1F]

To a solution of 2-{(1R)-1-[3-(1,1-difluoro-2-hydroxyethyl)-2-fluorophenyl]ethyl}-1H-isoindole-1,3(2H)-dione (Intermediate 145, 470 mg, 1.35 mmol) in DMF (8.0 ml) was added sodium hydride (108 mg, 60% purity, 2.69 mmol), and the mixture was stirred at RT for 30 min. Then, iodomethane (420 μl, 6.7 mmol) was added and stirring was continued for 1 h. Further iodomethane (420 μl, 6.7 mmol) was added and stirring was continued overnight. The mixture was then concentrated and the residue was purified by flash chromatography (silica, hexane, ethyl acetate) to yield the title compound (386 mg, 79% yield).

LC-MS (Method 1): $R_t$=1.31 min; MS (ESIpos): m/z=364 $[M+H]^+$ $^1$H-NMR (400 MHz, DMSO-d6) δ[ppm]: 1.789 (5.17), 1.807 (5.22), 2.518 (2.09), 2.523 (1.40), 3.272 (16.00), 3.865 (1.14), 3.900 (2.03), 3.935 (0.99), 5.696 (1.03), 5.714 (1.01), 5.758 (1.19), 7.331 (0.71), 7.350 (1.61), 7.370 (0.95), 7.493 (0.60), 7.511 (0.97), 7.526 (0.47), 7.530 (0.44), 7.808 (0.52), 7.826 (1.23), 7.828 (1.11), 7.837 (0.52), 7.842 (1.47), 7.851 (9.53), 7.852 (9.56), 7.856 (3.87), 7.861 (1.16).

Intermediate 147

(1R)-1-[3-(1,1-difluoro-2-methoxyethyl)-2-fluorophenyl]ethan-1-amine

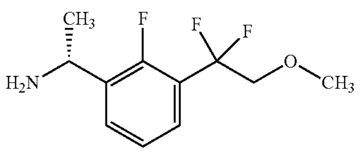 [SMILES: COCC(F)(F)c1cccc([C@@H](C)N)c1F]

To a solution of 2-{(1R)-1-[3-(1,1-difluoro-2-methoxyethyl)-2-fluorophenyl]ethyl}-1H-isoindole-1,3(2H)-dione (Intermediate 146, 384 mg, 1.06 mmol) in THF (5.0 ml) and ethanol (5.0 ml) was added hydrazine hydrate (510 μl, 11 mmol), and the mxture was stirred at RT overnight. The mixture was filtered, and the solid was washed with ethanol.

The solid was taken up in dichloromethane and water, the organic phase was separated and washed with saturated aqueous sodium hydrogen carbonate, washed with saturated aqueous sodium chloride, dried over sodium sulfate, and concentrated. The residue was purified by flash chromatography (silica, hexane, ethyl acetate) to obtain the title compound (231 mg, 94% yield).

LC-MS (Method 2): $R_t$=0.95 min; MS (ESIpos): m/z=234 $[M+H]^+$ $^1$H-NMR (400 MHz, DMSO-d6) δ[ppm]: 1.037 (0.43), 1.045 (0.86), 1.064 (0.45), 1.236 (16.00), 1.253 (15.56), 1.717 (1.32), 1.725 (0.44), 1.914 (0.50), 2.024 (1.31), 2.225 (0.42), 2.518 (3.20), 2.523 (2.21), 3.350 (1.22), 3.908 (3.02), 3.911 (2.99), 3.944 (6.20), 3.946 (5.96), 3.979 (2.95), 3.982 (2.86), 4.258 (0.86), 4.274 (2.69), 4.291 (2.65), 4.308 (0.83), 7.263 (1.66), 7.282 (4.00), 7.301 (2.53), 7.372 (1.44), 7.377 (1.60), 7.391 (2.23), 7.395 (2.31), 7.410 (1.11), 7.414 (1.06), 7.741 (1.22), 7.758 (2.18), 7.775 (1.10), 7.778 (1.07).

Intermediate 148

4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one

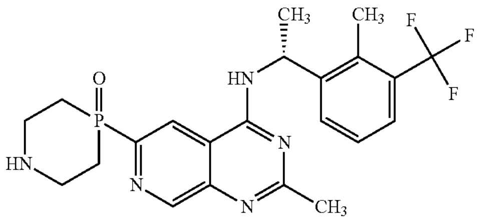 [SMILES: Cc1nc(N[C@H](C)c2cccc(C(F)(F)F)c2C)c2cc(P3(=O)CCNCC3)ncc2n1]

4-[2-methyl-4-({(1R)-1-[2-methyl-3-(trifluoromethyl) phenyl]ethyl}amino)pyrido[3,4-d]pyrimidin-6-yl]-1,4lambda$^5$-azaphosphinan-4-one hydrogen chloride (1/1) (Intermediate 164, 1.20 g, 81% purity, 1.94 mmol) was purified by flash chromatography (SNAP NH 55 g, hexane, ethyl acetate) to obtain the title compound 831 mg (92% yield) as free base.

LC-MS (Method 2): $R_t$=1.08 min; MS (ESIpos): m/z=464 $[M+H]^+$ $^1$H-NMR (400 MHz, DMSO-d6) δ[ppm]: 1.572 (5.11), 1.590 (5.12), 1.753 (0.44), 1.795 (0.87), 1.835 (0.49), 2.256 (0.52), 2.270 (0.76), 2.280 (1.01), 2.292 (0.81), 2.304 (1.02), 2.318 (0.98), 2.323 (1.13), 2.327 (1.47), 2.331 (1.14), 2.336 (0.76), 2.416 (16.00), 2.518 (4.05), 2.523 (2.72), 2.622 (6.51), 2.665 (0.73), 2.669 (0.99), 2.673 (0.69), 3.008 (0.56), 3.023 (0.89), 3.034 (0.76), 3.056 (0.60), 3.070 (1.11), 3.102 (0.79), 3.110 (0.77), 3.133 (0.72), 3.140 (0.71), 5.701 (0.80), 5.718 (1.24), 5.736 (0.79), 7.346 (0.74), 7.365 (1.60), 7.385 (0.92), 7.542 (1.73), 7.559 (1.40), 7.783 (1.55), 7.802 (1.40), 8.948 (1.84), 8.963 (1.83), 9.091 (4.44), 9.329 (1.32), 9.346 (1.27).

Intermediate 149

N-{(1R)-1-[3-(2-amino-1,1-difluoroethyl)-2-fluorophenyl]ethyl}-6-bromo-2-methylpyrido[3,4-d]pyrimidin-4-amine

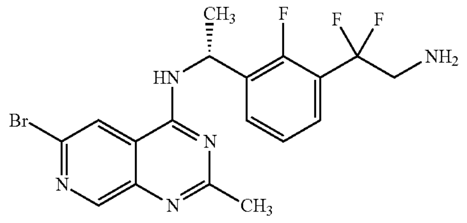 [SMILES: Cc1nc(N[C@H](C)c2cccc(C(F)(F)CN)c2F)c2cc(Br)ncc2n1]

To a solution of ammonia (1.9 ml, 7.0 M in methanol, 13 mmol) was added a solution of 2-(3-{(1R)-1-[(6-bromo-2-methylpyrido[3,4-d]pyrimidin-4-yl)amino]ethyl}-2-fluorophenyl)-2,2-difluoroethyl trifluoromethanesulfonate (Intermediate 143, 750 mg, 1.31 mmol) in acetonitrile (17 ml) and the mixture was stirred at 50° C. for 2 h. The mixture was concentrated, diluted with dichloromethane, and washed with water. The phases were separated, and the aqueous phase was extracted with ethyl acetate. The combined organic phases were concentrated, and the residue was purified by flash chromatography (silica, hexane, ethyl acetate, ethanol) to obtain the title compound 300 mg (90% purity, 47% yield).

LC-MS (Method 2): $R_t$=1.09 min; MS (ESIpos): m/z=440 $[M+H]^+$ $^1$H-NMR (400 MHz, DMSO-d6) δ[ppm]: 1.154 (4.17), 1.172 (8.19), 1.189 (3.89), 1.586 (3.23), 1.603 (3.18), 1.987 (16.00), 2.213 (0.52), 2.393 (10.67), 2.518 (2.96), 2.523 (1.98), 3.186 (0.72), 3.224 (1.39), 3.262 (0.66), 3.999 (1.09), 4.017 (3.32), 4.035 (3.36), 4.053 (1.11), 5.724 (0.50), 5.741 (0.75), 5.759 (0.48), 7.236 (0.59), 7.255 (1.25), 7.275 (0.70), 7.403 (0.44), 7.421 (0.69), 7.635 (0.67), 8.665 (2.63), 8.807 (2.93), 8.865 (0.76), 8.883 (0.73).

Intermediate 150

N-[2-(3-{(1R)-1-[(6-bromo-2-methylpyrido[3,4-d]pyrimidin-4-yl)amino]ethyl}-2-fluorophenyl)-2,2-difluoroethyl]methanesulfonamide

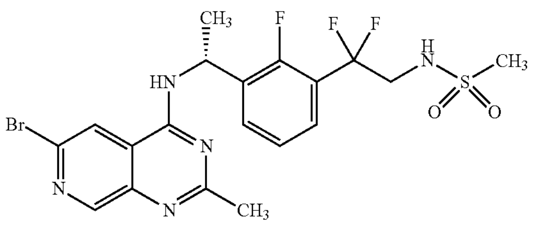 [SMILES: Cc1nc(N[C@H](C)c2cccc(C(F)(F)CNS(C)(=O)=O)c2F)c2cc(Br)ncc2n1]

To a solution of N-{(1R)-1-[3-(2-amino-1,1-difluoroethyl)-2-fluorophenyl]ethyl}-6-bromo-2-methylpyrido[3,4-d]pyrimidin-4-amine (Intermediate 149, 150 mg, 341 μmol) in 1,2-dichloroethane (3.1 ml) was added triethylamine (240 μl, 1.7 mmol) and DMAP (420 μg, 3.4 μmol), followed by methanesulfonyl chloride (32 μl, 410 μmol), and the mixture was stirred at RT for 1 h. The mixture was diluted with water, extracted with dichloromethane, and the organic phase was washed with saturated aqueous sodium hydrogen carbonate, saturated aqueous sodium sulfate, and concentrated. The crude product (158 mg, 85%

LC-MS (Method 2): $R_t$=1.09 min; MS (ESIpos): m/z=518 $[M+H]^+$ $^1$H-NMR (500 MHz, DMSO-d6) δ[ppm]: 1.587 (1.92), 1.601 (1.91), 2.398 (5.48), 2.514 (0.66), 2.518 (0.62), 2.522 (0.50), 2.820 (0.56), 2.829 (6.29), 2.976 (0.62), 3.212 (0.44), 3.349 (1.07), 3.403 (0.59), 3.901 (16.00), 5.749 (0.46), 7.284 (0.73), 7.300 (0.41), 7.781 (0.59), 8.671 (1.58), 8.808 (1.20), 8.870 (0.46), 8.884 (0.45).

Intermediate 151

N-[2-(3-{(1R)-1-[(6-bromo-2-methylpyrido[3,4-d]pyrimidin-4-yl)amino]ethyl}-2-fluorophenyl)-2,2-difluoroethyl]acetamide

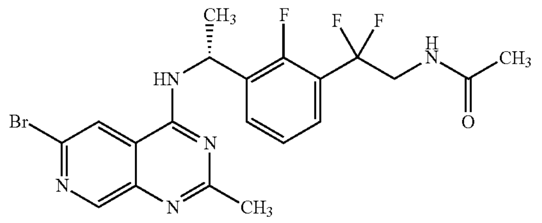 [SMILES: CC(=O)NCC(F)(F)c1cccc([C@@H](C)Nc2nc(C)nc3cnc(Br)cc23)c1F]

According to general procedure 7, starting from N-{(1R)-1-[3-(2-amino-1,1-difluoroethyl)-2-fluorophenyl]ethyl}-6-bromo-2-methylpyrido[3,4-d]pyrimidin-4-amine (Intermediate 149, 150 mg, 341 μmol), the title compound was obtained (170 mg, 85%

LC-MS (Method 2): $R_t$=1.07 min; MS (ESIpos): m/z=482 $[M+H]^+$ $^1$H-NMR (500 MHz, DMSO-d6) δ[ppm]: 0.959 (1.07), 1.044 (0.55), 1.058 (0.51), 1.114 (0.47), 1.128 (0.47), 1.157 (0.50), 1.171 (0.73), 1.186 (0.54), 1.229 (0.43), 1.484 (0.42), 1.586 (5.06), 1.600 (4.97), 1.788 (16.00), 1.796 (1.45), 1.905 (3.25), 1.986 (0.79), 2.215 (3.41), 2.218 (0.86), 2.397 (15.68), 2.514 (2.47), 2.518 (2.14), 2.522 (1.70), 3.852 (0.42), 3.869 (0.44), 3.934 (0.44), 5.731 (0.81), 5.746 (1.21), 5.760 (0.80), 7.236 (0.99), 7.252 (1.96), 7.267 (1.14), 7.385 (0.68), 7.399 (1.09), 7.412 (0.55), 7.632 (0.62), 7.646 (1.06), 7.660 (0.55), 8.328 (0.69), 8.340 (1.37), 8.353 (0.68), 8.674 (3.98), 8.806 (4.43), 8.863 (1.04), 8.878 (1.04).

Intermediate 152

6-bromo-N-[(1R)-1-{3-[1,1-difluoro-2-(methylamino)ethyl]-2-fluorophenyl}ethyl]-2-methylpyrido[3,4-d]pyrimidin-4-amine

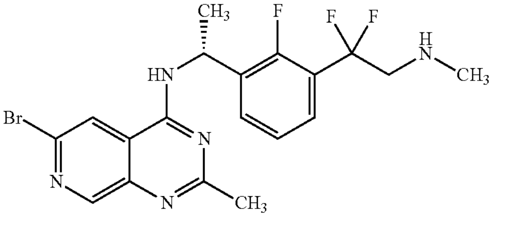 [SMILES: CNCC(F)(F)c1cccc([C@@H](C)Nc2nc(C)nc3cnc(Br)cc23)c1F]

The title compound was prepared as described for Intermediate 149, starting from 2-(3-{(1R)-1-[(6-bromo-2-methylpyrido[3,4-d]pyrimidin-4-yl)amino]ethyl}-2-fluorophenyl)-2,2-difluoroethyl trifluoromethanesulfonate (Intermediate 143, 570 mg, 994 μmol): 290 mg ( LC-MS (Method 2): $R_t$=1.18 min; MS (ESIpos): m/z=454 $[M+H]^+$ $^1$H-NMR (400 MHz, DMSO-d6) δ[ppm]: 1.052 (1.00), 1.069 (0.87), 1.153 (3.66), 1.171 (7.33), 1.189 (3.56), 1.582 (5.32), 1.600 (5.27), 1.986 (14.81), 2.249 (12.32), 2.384 (16.00), 2.518 (1.36), 2.523 (0.94), 3.183 (0.73), 3.191 (0.66), 3.221 (1.31), 3.228 (1.32), 3.258 (0.64), 3.266 (0.73), 3.998 (1.08), 4.016 (3.28), 4.034 (3.24), 4.052 (1.04), 5.718 (0.82), 5.736 (1.26), 5.753 (0.80), 7.225 (0.90), 7.244 (1.98), 7.264 (1.18), 7.398 (0.73), 7.416 (1.19), 7.431 (0.58), 7.607 (0.65), 7.624 (1.16), 7.641 (0.59), 8.667 (4.24), 8.804 (4.09), 8.865 (1.24), 8.883 (1.21).

Intermediate 153

N-[2-(3-{(1R)-1-[(6-bromo-2-methylpyrido[3,4-d]pyrimidin-4-yl)amino]ethyl}-2-fluorophenyl)-2,2-difluoroethyl]-N-methylmethanesulfonamide

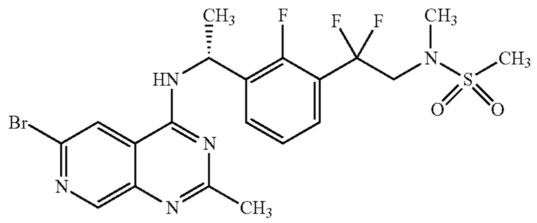 [SMILES: Cc1nc(N[C@H](C)c2cccc(C(F)(F)CN(C)S(C)(=O)=O)c2F)c2cc(Br)ncc2n1]

The title compound was obtained as described for Intermediate 150, starting from 6-bromo-N-[(1R)-1-{3-[1,1-difluoro-2-(methylamino)ethyl]-2-fluorophenyl}ethyl]-2-methylpyrido[3,4-d]pyrimidin-4-amine (Intermediate 152, 145 mg, 319 μmol): 187 mg (95% purity, quantitative).

LC-MS (Method 2): $R_t$=1.20 min; MS (ESIpos): m/z=532 $[M+H]^+$ $^1$H-NMR (400 MHz, DMSO-d6) δ[ppm]: 1.578 (1.98), 1.596 (1.96), 2.386 (6.74), 2.518 (1.84), 2.523 (1.32), 2.854 (9.21), 2.956 (0.90), 3.350 (0.44), 3.903 (16.00), 5.730 (0.47), 5.758 (0.50), 7.281 (0.79), 7.300 (0.45), 7.454 (0.43), 7.665 (0.43), 8.677 (1.70), 8.810 (1.93), 8.867 (0.52), 8.884 (0.49).

Intermediate 154

N-[2-(3-{(1R)-1-[(6-bromo-2-methylpyrido[3,4-d]pyrimidin-4-yl)amino]ethyl}-2-fluorophenyl)-2,2-difluoroethyl]-N-methylacetamide

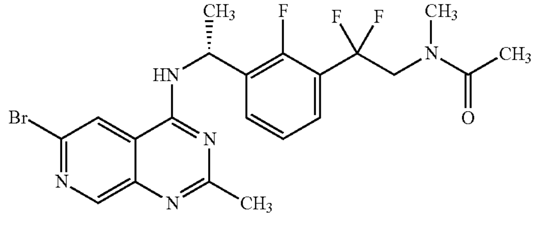 [SMILES: CC(=O)N(C)CC(F)(F)c1cccc([C@@H](C)Nc2nc(C)nc3cnc(Br)cc23)c1F]

The title compound was prepared as described for Intermediate 151, starting from 6-bromo-N-[(1R)-1-{3-[1,1-difluoro-2-(methylamino)ethyl]-2-fluorophenyl}ethyl]-2-methylpyrido[3,4-d]pyrimidin-4-amine (Intermediate 152, 145 mg, 319 μmol): 130 mg (95% purity, 78% yield).

LC-MS (Method 2): $R_t$=1.16 min; MS (ESIpos): m/z=496 $[M+H]^+$ $^1$H-NMR (400 MHz, DMSO-d6) δ[ppm]: 1.224 (1.30), 1.241 (4.54), 1.256 (6.01), 1.272 (3.08), 1.582 (4.92), 1.590 (4.51), 1.600 (5.16), 1.608 (4.27), 1.838 (0.55), 1.912 (10.22), 1.924 (15.66), 1.938 (0.41), 2.216 (1.87), 2.337 (0.83), 2.385 (13.71), 2.391 (16.00), 2.518 (9.91), 2.523 (7.14), 2.679 (0.84), 2.838 (7.49), 3.019 (10.10), 3.125 (0.40), 3.136 (0.41), 3.143 (0.44), 4.014 (0.47), 4.056 (0.48), 4.114 (0.52), 4.130 (0.46), 4.153 (0.75), 4.166 (0.81), 4.183 (0.59), 4.206 (0.51), 4.216 (0.72), 4.258 (0.54), 5.710 (1.04), 5.727 (1.59), 5.744 (1.02), 5.759 (2.82), 7.223 (0.80), 7.243 (1.77), 7.262 (1.06), 7.287 (0.68), 7.307 (1.48), 7.326 (0.89), 7.379 (0.64), 7.396 (1.00), 7.412 (0.52), 7.436 (0.56), 7.452 (0.85), 7.469 (0.43), 7.616 (0.56), 7.634 (0.98), 7.649 (0.51), 7.675 (0.48), 7.692 (0.84), 7.710 (0.42), 8.679 (6.80), 8.809 (4.68), 8.812 (4.06), 8.855 (1.12), 8.873 (1.13), 8.893 (1.00), 8.911 (0.92).

Intermediate 155

2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-2,2-difluoroethyl trifluoromethanesulfonate

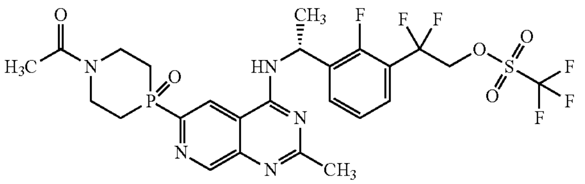 [SMILES: CC(=O)N1CCP(=O)(c2cc3c(N[C@H](C)c4cccc(C(F)(F)COS(=O)(=O)C(F)(F)F)c4F)nc(C)nc3cn2)CC1]

The title compound was obtained as described for Intermediate 143, starting from 1-acetyl-4-[4-({(1R)-1-[3-(1,1-difluoro-2-hydroxyethyl)-2-fluorophenyl]ethyl}amino)-2-methylpyrido[3,4-d]pyrimidin-6-yl]-1,4lambda$^5$-azaphosphinan-4-one (Example 42, 320 mg, 614 μmol): 94.0 mg (22% purity, 5% yield).

LC-MS (Method 2): $R_t$=1.11 min; MS (ESIpos): m/z=654 $[M+H]^+$

Intermediate 156

1-acetyl-4-(4-{[(1R)-1-{3-[2-(cyclopropylamino)-1,1-difluoroethyl]-2-fluorophenyl}ethyl]amino}-2-methylpyrido[3,4-d]pyrimidin-6-yl)-1,4lambda$^5$-azaphosphinan-4-one

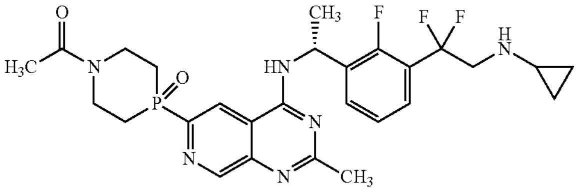 [SMILES: CC(=O)N1CCP(=O)(c2cc3c(N[C@H](C)c4cccc(C(F)(F)CNC5CC5)c4F)nc(C)nc3cn2)CC1]

The title compound was obtained as described for Intermediate 149, starting from 2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-2,2-difluoroethyl trifluoromethanesulfonate (Intermediate 155, 90.0 mg, 138 μmol): 7.00 mg (95% purity, 9% yield)

LC-MS (Method 2): $R_t$=0.99 min; MS (ESIpos): m/z=561.6 $[M+H]^+$

Intermediate 157 tert-butyl 4-[4-({(1R)-1-[3-(2-ethoxy-1,1-difluoro-2-oxoethyl)-2-fluorophenyl]ethyl}amino)-2-methylpyrido[3,4-d]pyrimidin-6-yl]-4-oxo-1,4lambda$^5$-azaphosphinane-1-carboxylate

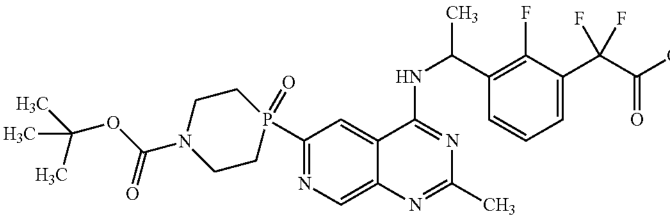

The title compound was prepared as described for Intermediate 102, starting from ethyl (3-{(1R)-1-[(6-bromo-2-methylpyrido[3,4-d]pyrimidin-4-yl)amino]ethyl}-2-fluorophenyl)(difluoro)acetate (Intermediate 174, 1.68 g, 3.88 mmol), and tert-butyl 4-oxo-1,4lambda$^5$-azaphosphinane-1-carboxylate (Intermediate 52, 850 mg, 3.88 mmol): 1.45 g (80% purity, 48% yield).

LC-MS (Method 2): $R_t$=1.22 min; MS (ESIpos): m/z=622.5 $[M+H]^+$

Intermediate 158 ethyl difluoro{2-fluoro-3-[(1R)-1-{[2-methyl-6-(4-oxo-1,4lambda$^5$-azaphosphinan-4-yl)pyrido[3,4-d]pyrimidin-4-yl]amino}ethyl]phenyl}acetate hydrogen chloride (1/1)

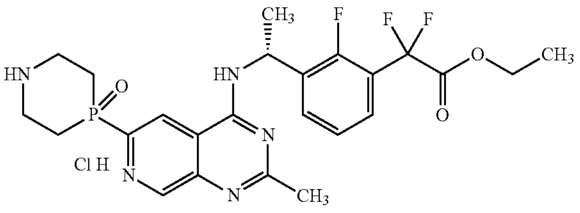

The reaction was performed as described for Intermediate 138, starting from tert-butyl 4-[4-({(1R)-1-[3-(2-ethoxy-1,1-difluoro-2-oxoethyl)-2-fluorophenyl]ethyl}amino)-2-methylpyrido[3,4-d]pyrimidin-6-yl]-4-oxo-1,4lambda$^5$-azaphosphinane-1-carboxylate LC-MS (Method 2): $R_t$=1.01 min; MS (ESIpos): m/z=522.5 [M+H]$^+$ Intermediate 159 ethyl {3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}(difluoro)acetate

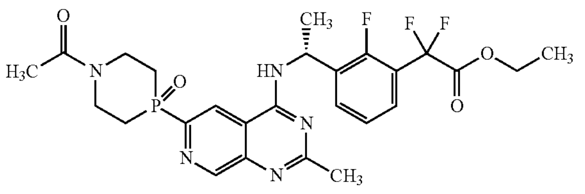 [SMILES: CCOC(=O)C(F)(F)c1cccc([C@@H](C)Nc2nc(C)nc3cnc(P4(=O)CCN(C(C)=O)CC4)cc23)c1F]

The title compound was prepared according to general procedure 7, starting from ethyl difluoro{2-fluoro-3-[(1R)-1-{[2-methyl-6-(4-oxo-1,4lambda$^5$-azaphosphinan-4-yl)pyrido[3,4-d]pyrimidin-4-yl]amino}ethyl]phenyl}acetate hydrogen chloride (1/1) (Intermediate 158, 1.34 g, 2.40 mmol), to obtain 622 mg (80% purity, 37% yield).

LC-MS (Method 2): $R_t$=1.03 min; MS (ESIpos): m/z=564.5 [M+H]$^+$ $^1$H-NMR (400 MHz, DMSO-d6) δ[ppm]: 1.034 (0.73), 1.052 (1.52), 1.069 (0.74), 1.085 (1.28), 1.102 (1.28), 1.149 (0.78), 1.170 (3.29), 1.187 (6.72), 1.205 (3.21), 1.605 (3.17), 1.623 (3.13), 2.118 (9.00), 2.323 (0.47), 2.327 (0.51), 2.392 (9.43), 2.518 (1.30), 2.523 (0.95), 3.159 (16.00), 3.172 (14.99), 3.439 (0.43), 3.452 (0.49), 3.895 (0.44), 4.087 (1.27), 4.099 (3.87), 4.113 (3.84), 4.126 (1.23), 4.320 (0.56), 4.323 (0.60), 4.338 (1.53), 4.342 (1.61), 4.347 (0.50), 4.356 (1.55), 4.360 (2.00), 4.373 (0.71), 4.377 (0.48), 5.724 (0.51), 5.741 (0.78), 5.758 (6.79), 6.939 (0.46), 7.326 (0.56), 7.345 (1.21), 7.365 (0.69), 7.565 (0.48), 7.582 (0.80), 7.730 (0.40), 7.749 (0.73), 9.166 (0.71), 9.183 (0.67), 9.260 (1.74), 9.267 (1.56), 9.272 (1.37), 9.297 (0.71).

Intermediate 160

{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}(difluoro)acetyl chloride

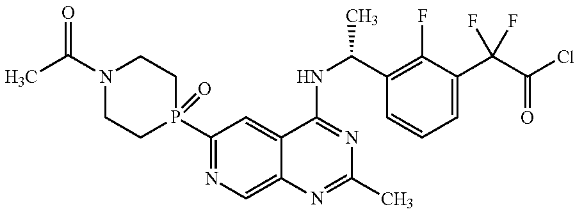 [SMILES: CC(=O)N1CCP(=O)(c2cc3c(N[C@H](C)c4cccc(C(F)(F)C(=O)Cl)c4F)nc(C)nc3cn2)CC1]

To a solution of {3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}(difluoro)acetic acid (Example 43, 133 mg, 248 μmol) in dichloromethane (6.9 ml) at 0° C. was added ethanedioyl dichloride (84 μl, 990 μmol), and DMF (0.38 μl), and the mixture was stirred at RT 2 h. The acid chloride solution was directly used for the next reactions.

Intermediate 161 ethyl {3-[(1R)-1-{[6-(dimethylphosphoryl)-2-methylpyrido[3,4-d]pyrimidin-4-yl]amino}ethyl]-2-fluorophenyl}(difluoro)acetate

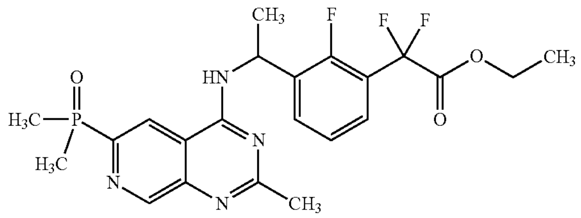 [SMILES: CCOC(=O)C(F)(F)c1cccc(C(C)Nc2nc(C)nc3cnc(P(C)(C)=O)cc23)c1F]

The reaction was performed according to general procedure 1, starting from 6-(dimethylphosphoryl)-2-methylpyrido[3,4-d]pyrimidin-4-ol (Intermediate 71, 172 mg, 725 μmol) and ethyl {3-[(1R)-1-aminoethyl]-2-fluorophenyl}(difluoro)acetate trifluoroacetic acid (1/1) (Intermediate 321 mg, 855 μmol) to obtain the title compound (417 mg, quantitative).

LC-MS (Method 2): $R_t$=1.08 min; MS (ESIpos): m/z=481.5 [M+H]$^+$

Intermediate 162 tert-butyl [(1R)-1-{3-[1,1-difluoro-2-(methylamino)-2-oxoethyl]-2-fluorophenyl}ethyl]-carbamate

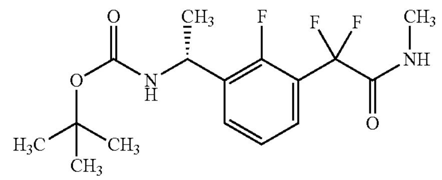 [SMILES: CNC(=O)C(F)(F)c1cccc([C@@H](C)NC(=O)OC(C)(C)C)c1F]

To ethyl (3-{(1R)-1-[(tert-butoxycarbonyl)amino]ethyl}-2-fluorophenyl)(difluoro)acetate (935 mg, 2.59 mmol) was added methylamine (6.5 ml, 2.0 M in methanol, 13 mmol), and the mixture was stirred at RT for 3 h. The mixture was concentrated, and the residue was suspended in tert-butyl-methyl ether. The solid was filtered off and dried to yield the title compound (768 mg, 86% yield) as off-white solid.

LC-MS (Method 1): $R_t$=1.08 min; MS (ESIpos): m/z=364.7 [M+$NH_4$]*

Intermediate 163

2-{3-[(1R)-1-aminoethyl]-2-fluorophenyl}-2,2-difluoro-N-methylacetamide-hydrogen chloride (1/1)

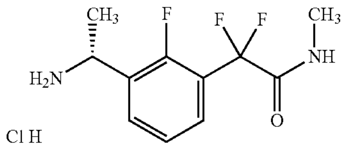 [SMILES: "Cl H" ; CNC(=O)C(F)(F)c1cccc([C@@H](C)N)c1F]

The reaction was performed as described for Intermediate 138, starting from tert-butyl [(1R)-1-{3-[1,1-difluoro-2-(methylamino)-2-oxoethyl]-2-fluorophenyl}ethyl]carbamate (Intermediate 162, 768 mg, 2.22 mmol), to obtain the title compound (600 mg, 96% yield).

LC-MS (Method 2): $R_t$=0.74 min; MS (ESIpos): m/z=247 $[M+H]^+$

Intermediate 164

4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one-hydrogen chloride (1/1)

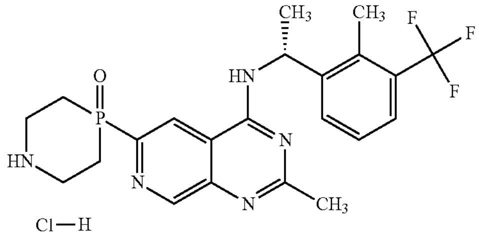

The reaction was performed as described for Intermediate 138, starting from tert-butyl 4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxylate (Intermediate 187, 400 mg, 710 μmol), to obtain the title compound (430 mg, 121% yield).

LC-MS (Method 2): $R_t$=1.10 min; MS (ESIpos): m/z=464.5 $[M+H]^+$

The intermediates shown in Table 1 were prepared according to general procedure 2 from the respective pyrimidin-4-ol derivatives and the respective amines.

Intermediates Table 1

| No. | Structure<br>IUPAC-Name<br>Analytical Data | Starting Materials Yield |
|---|---|---|
| 165 | 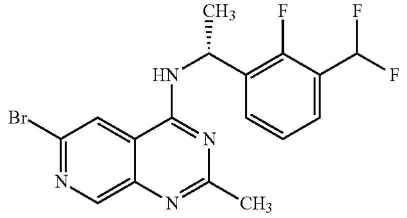<br>6-bromo-N-{(1R)-1-[3-(difluoromethyl)-2-fluorophenyl]ethyl}-2-methylpyrido[3,4-d]pyrimidin-4-amine<br>$^1$H-NMR (400 MHz, DMSO-d6) δ [ppm]: 1.596 (4.78), 1.613 (4.78), 1.986 (0.66), 2.389 (16.00), 2.518 (1.02), 2.523 (0.77), 5.727 (0.70), 5.744 (1.09), 5.761 (0.70), 7.102 (1.07), 7.237 (2.22), 7.280 (0.73), 7.298 (1.61), 7.318 (0.94), 7.373 (0.95), 7.499 (0.54), 7.516 (0.92), 7.533 (0.45), 7.667 (0.49), 7.685 (0.92), 7.703 (0.46), 8.666 (3.67), 8.807 (3.93), 8.875 (1.03), 8.893 (1.01).<br>LC-MS (Method 2): $R_t$ = 1.25 min; MS (ESIpos): m/z = 413 $[M + H]^+$ | Intermediate 32 and CAS 1389852-29-2<br>5.20 g (87% yield) |
| 166 | 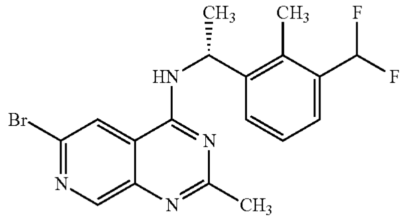<br>6-bromo-N-{(1R)-1-[3-(difluoromethyl)-2-methylphenyl]ethyl}-2-methylpyrido[3,4-d]pyrimidin-4-amine<br>$^1$H-NMR (400 MHz, DMSO-d6) δ [ppm]: 1.153 (0.96), 1.171 (2.00), 1.189 (0.96), 1.534 (4.60), 1.551 (4.56), 1.955 (10.11), 1.986 (3.29), 2.397 (15.94), 2.518 (0.73), 2.523 (0.66), 2.781 (9.53), 2.940 (16.00), 4.016 (0.68), 4.034 (0.69), 5.691 (0.67), 5.708 (1.05), 5.726 | Intermediate 32 and CAS 2230840-56-7<br>1.10 g (81% yield) |

-continued

Intermediates Table 1

| No. | Structure<br>IUPAC-Name<br>Analytical Data | Starting<br>Materials<br>Yield |
|---|---|---|
| | (0.67), 7.076 (0.86), 7.214 (1.83), 7.282 (0.59), 7.301 (1.43), 7.321 (0.95), 7.351 (0.77), 7.390 (1.39), 7.408 (0.93), 7.632 (1.12), 7.651 (0.98), 8.658 (3.73), 8.783 (4.30), 8.914 (1.03), 8.932 (1.00).<br>LC-MS (Method 2): $R_t$ = 1.30 min; MS (ESIpos): m/z = 408 $[M + H]^+$ | |
| 167 | 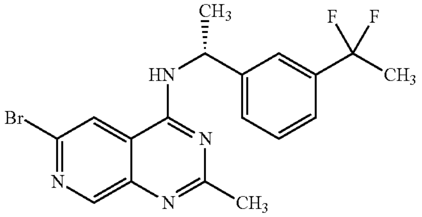 [SMILES: Cc1nc(N[C@H](C)c2cccc(C(C)(F)F)c2)c2cc(Br)ncc2n1]<br>6-bromo-N-{(1R)-1-[3-(1,1-difluoroethyl)phenyl]ethyl}-2-methylpyrido[3,4-d]pyrimidin-4-amine<br>$^1$H-NMR (400 MHz, DMSO-d6) δ [ppm]: 1.154 (4.12), 1.172 (8.62), 1.189 (4.23), 1.591 (4.87), 1.609 (4.85), 1.912 (4.39), 1.959 (8.40), 1.987 (15.25), 2.006 (3.83), 2.331 (0.40), 2.430 (16.00), 2.518 (2.36), 2.523 (1.67), 2.673 (0.40), 3.999 (1.10), 4.016 (3.30), 4.034 (3.21), 4.052 (1.01), 5.579 (0.67), 5.596 (1.00), 5.615 (0.65), 7.434 (2.45), 7.436 (3.49), 7.443 (1.19), 7.451 (1.65), 7.563 (0.93), 7.575 (0.66), 7.578 (0.82), 7.664 (1.89), 8.626 (3.66), 8.798 (4.04), 8.819 (1.07), 8.838 (1.04).<br>LC-MS (Method 2): $R_t$ = 1.31 min; MS (ESIpos): m/z = 407 $[M + H]^+$ | Intermediate 32 and CAS 2359690-78-9<br>92.0 mg (31% yield) |
| 168 | 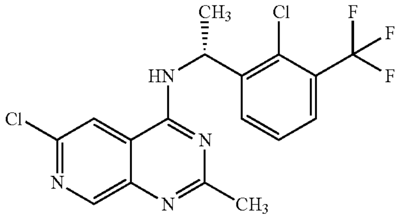<br>6-chloro-N-{(1R)-1-[2-chloro-3-(trifluoromethyl)phenyl]ethyl}-2-methylpyrido[3,4-d]pyrimidin-4-amine<br>LC-MS (Method 2): $R_t$ = 1.39 min; MS (ESIpos): m/z = 303 $[M + H]^+$ | Intermediate 2 and CAS 1213555-38-4<br>1.11 g (90% yield) |
| 16 | 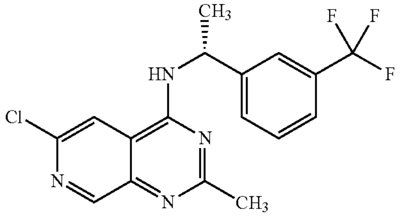 [SMILES: Cc1nc(N[C@H](C)c2cccc(C(F)(F)F)c2)c2cc(Cl)ncc2n1]<br>6-chloro-2-methyl-N-{(1R)-1-[3-(trifluoromethyl)phenyl]ethyl}pyrido[3,4-d]pyrimidin-4-amine<br>$^1$H NMR (400 MHz, DMSO-d6) δ ppm 1.52-1.67 (m, 3 H) 2.42 (s, 3 H) 5.43-5.68 (m, 1 H) 7.48-7.65 (m, 2 H) 7.72-7.78 (m, 1 H) 7.80-7.86 (m, 1 H) 8.46 (s, 1 H) 8.81 (s, 2 H) | Intermediate 2 and CAS 127852-30-6<br>26.0 g (97% purity, 47% yield) |
| 170 | 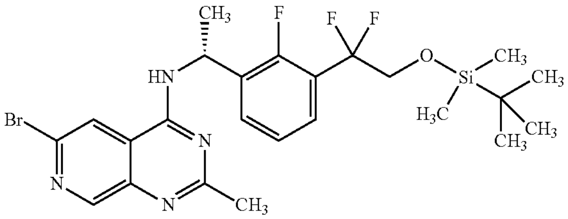 [SMILES: Cc1nc(N[C@H](C)c2cccc(C(F)(F)CO[Si](C)(C)C(C)(C)C)c2F)c2cc(Br)ncc2n1]<br>6-bromo-N-{(1R)-1-[3-(2-{[tert-butyl(dimethyl)silyl]oxy}-1,1-difluoroethyl)-2-fluorophenyl]ethyl}-2-methylpyrido[3,4- | Intermediate 32 and Intermediate 132<br>2.72 g (64% yield) |

-continued

Intermediates Table 1

| No. | Structure<br>IUPAC-Name<br>Analytical Data | Starting<br>Materials<br>Yield |
|---|---|---|
| | d]pyrimidin-4-amine<br>$^{1}$H-NMR (400 MHz, CHLOROFORM-d) δ [ppm]: −0.079 (4.14), −0.062 (4.05), 0.727 (0.75), 0.735 (16.00), 0.743 (0.67), 1.249 (0.47), 1.266 (0.90), 1.285 (0.45), 1.714 (1.28), 1.731 (1.26), 2.056 (1.73), 2.589 (4.87), 4.112 (0.63), 4.140 (0.44), 5.306 (1.43), 7.186 (0.44), 7.485 (0.41), 7.720 (0.83), 8.948 (0.98). | |
| 171 | 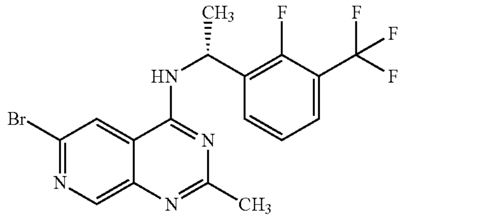<br>6-bromo-N-{(1R)-1-[2-fluoro-3-(trifluoromethyl)phenyl]ethyl}-2-methylpyrido[3,4-d]pyrimidin-4-amine<br>LC-MS (Method 2): $R_t$ = 1.37 min; MS (ESIpos): m/z = 429 [M + H]$^+$ | Intermediate 32 and CAS 1079656-93-1<br>442 mg (85% yield) |
| 172 | 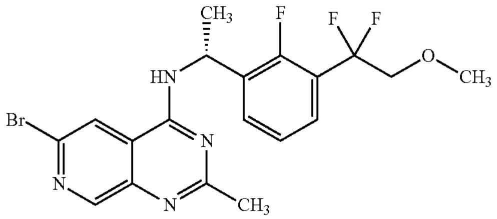<br>6-bromo-N-{(1R)-1-[3-(1,1-difluoro-2-methoxyethyl)-2-fluorophenyl]ethyl}-2-methylpyrido[3,4-d]pyrimidin-4-amine<br>$^{1}$H-NMR (400 MHz, DMSO-d6) δ [ppm]: 1.585 (3.87), 1.603 (3.86), 1.715 (0.69), 2.331 (0.57), 2.383 (13.23), 2.518 (3.27), 2.523 (2.20), 2.673 (0.56), 3.331 (16.00), 3.374 (0.54), 3.947 (0.96), 3.982 (1.82), 4.016 (0.89), 5.709 (0.58), 5.726 (0.91), 5.744 (0.59), 7.250 (0.66), 7.270 (1.45), 7.289 (0.84), 7.425 (0.52), 7.443 (0.84), 7.459 (0.41), 7.641 (0.46), 7.659 (0.80), 7.674 (0.40), 8.667 (3.23), 8.807 (3.62), 8.883 (0.93), 8.901 (0.89).<br>LC-MS (Method 2): $R_t$ = 1.28 min; MS (ESIpos): m/z = 455 [M + H]$^+$ | Intermediate 32 and Intermediate 147<br>362 mg (97% yield) |
| 173 | 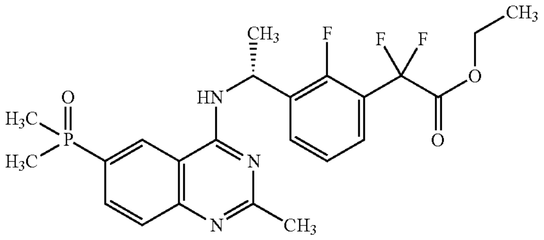 [SMILES: CCOC(=O)C(F)(F)c1cccc([C@@H](C)Nc2nc(C)nc3ccc(P(C)(C)=O)cc23)c1F]<br>ethyl {3-[(1R)-1-{[6-(dimethylphosphoryl)-2-methylquinazolin-4-yl]amino}ethyl]-2-fluorophenyl}(difluoro)acetate<br>$^{1}$H-NMR (400 MHz, DMSO-d6) δ [ppm]: 1.035 (2.26), 1.052 (4.77), 1.070 (2.65), 1.087 (16.00), 1.104 (15.81), 1.151 (9.60), 1.158 (1.01), 1.168 (10.19), 1.172 (3.11), 1.190 (4.59), 1.208 (2.16), 1.600 (1.93), 1.617 (1.91), 1.724 (6.51), 1.757 (6.37), 2.323 (0.42), 2.327 (0.59), 2.331 (0.49), 2.346 (5.96), 2.518 (2.34), 2.523 (1.48), 2.669 (0.54), 2.774 (0.50), 2.791 (0.66), 2.808 (0.48), 3.422 (1.08), 3.435 (1.12), 3.440 (0.95), 3.452 (0.98), 4.337 (0.90), 4.341 (0.96), 4.347 (0.84), 4.354 (0.96), 4.360 (2.18), 4.372 (0.97), 4.553 (1.07), 4.570 (1.45), 4.587 (1.04), 5.758 (0.48), 6.942 (5.50), 7.336 (0.79), 7.355 (0.45), 7.564 (0.48), 7.650 (0.55), 7.657 (0.56), 7.672 (0.61), 7.678 (0.61), 7.755 (0.45), 8.014 (0.66), 8.018 (0.41), 8.802 (0.51), 8.805 (0.51), 8.834 (0.53), 8.836 (0.53), 8.859 (0.45), 8.877 (0.43). | Intermediate 183 and Intermediate 118<br>92.0 mg (85% purity, 11% yield) |

-continued

Intermediates Table 1

| No. | Structure<br>IUPAC-Name<br>Analytical Data | Starting<br>Materials<br>Yield |
|---|---|---|
| 174 | 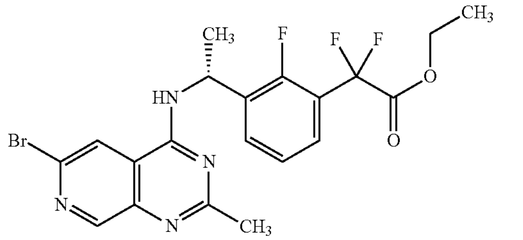 [SMILES: CCOC(=O)C(F)(F)c1cccc([C@@H](C)Nc2nc(C)nc3cnc(Br)cc23)c1F]<br>ethyl (3-{(1R)-1-[(6-bromo-2-methylpyrido[3,4-d]pyrimidin-4-yl)amino]ethyl}-2-fluorophenyl)(difluoro)acetate<br>$^1$H-NMR (400 MHz, DMSO-d6) δ [ppm]: 1.085 (0.99), 1.102 (1.00), 1.147 (0.66), 1.151 (1.48), 1.165 (0.86), 1.170 (5.44), 1.189 (10.57), 1.206 (4.89), 1.580 (4.76), 1.598 (4.75), 1.984 (5.40), 2.366 (16.00), 2.518 (0.68), 2.523 (0.51), 2.735 (0.45), 3.996 (0.41), 4.014 (1.22), 4.032 (1.20), 4.317 (0.69), 4.322 (0.72), 4.334 (2.09), 4.339 (2.12), 4.352 (2.11), 4.357 (2.06), 4.370 (0.72), 4.375 (0.64), 5.664 (0.75), 5.682 (1.16), 5.699 (0.74), 7.319 (0.89), 7.339 (1.92), 7.358 (1.09), 7.557 (0.58), 7.561 (0.67), 7.578 (1.10), 7.594 (0.54), 7.598 (0.52), 7.714 (0.58), 7.732 (1.06), 7.750 (0.54), 8.654 (4.01), 8.802 (4.50), 8.893 (1.20), 8.910 (1.15). | Intermediate 183 and Intermediate 118<br>2.20 g (90% purity, 49% yield) |
| 175 | 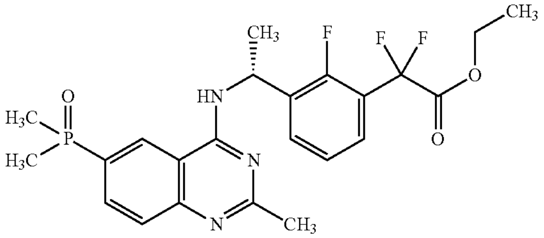 [SMILES: CCOC(=O)C(F)(F)c1cccc([C@@H](C)Nc2nc(C)nc3ccc(P(C)(C)=O)cc23)c1F]<br>ethyl {3-[(1R)-1-{[6-(dimethylphosphoryl)-2-methylquinazolin-4-yl]amino}ethyl]-2-fluorophenyl}(difluoro)acetate<br>$^1$H-NMR (400 MHz, DMSO-d6) δ [ppm]: 1.035 (2.26), 1.052 (4.77), 1.070 (2.65), 1.087 (16.00), 1.104 (15.81), 1.151 (9.60), 1.158 (1.01), 1.168 (10.19), 1.172 (3.11), 1.190 (4.59), 1.208 (2.16), 1.600 (1.93), 1.617 (1.91), 1.724 (6.51), 1.757 (6.37), 2.323 (0.42), 2.327 (0.59), 2.331 (0.49), 2.346 (5.96), 2.518 (2.34), 2.523 (1.48), 2.669 (0.54), 2.774 (0.50), 2.791 (0.66), 2.808 (0.48), 3.422 (1.08), 3.435 (1.12), 3.440 (0.95), 3.452 (0.98), 4.337 (0.90), 4.341 (0.96), 4.347 (0.84), 4.354 (0.96), 4.360 (2.18), 4.372 (0.97), 4.553 (1.07), 4.570 (1.45), 4.587 (1.04), 5.758 (0.48), 6.942 (5.50), 7.336 (0.79), 7.355 (0.45), 7.564 (0.48), 7.650 (0.55), 7.657 (0.56), 7.672 (0.61), 7.678 (0.61), 7.755 (0.45), 8.014 (0.66), 8.018 (0.41), 8.802 (0.51), 8.805 (0.51), 8.834 (0.53), 8.836 (0.53), 8.859 (0.45), 8.877 (0.43). | Intermediate<br>92.0 mg (85% purity, 11% yield) |
| 176 | 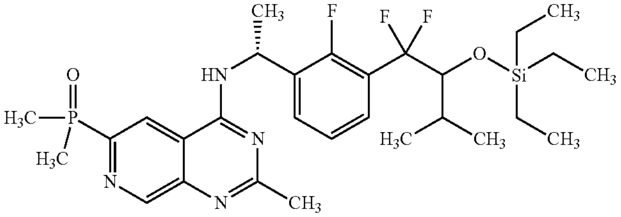 [SMILES: CC[Si](CC)(CC)OC(C(C)C)C(F)(F)c1cccc([C@@H](C)Nc2nc(C)nc3cnc(P(C)(C)=O)cc23)c1F]<br>N-[(1R)-1-(3-{(2R*)-1,1-difluoro-3-methyl-2-[(triethylsilyl)oxy]butyl}-2-fluorophenyl)ethyl]-6-(dimethylphosphoryl)-2-methylpyrido[3,4-d]pyrimidin-4-amine (diastereomer 1)<br>LC-MS (Method 1): $R_t$ = 1.69 min; MS (ESIpos): m/z = 596 [M + H]$^+$ | Intermediate 71 and Intermediate 90<br>115 mg (48% purity, 100% yield) |

-continued

Intermediates Table 1

| No. | Structure<br>IUPAC-Name<br>Analytical Data | Starting<br>Materials<br>Yield |
|---|---|---|
| 177 | 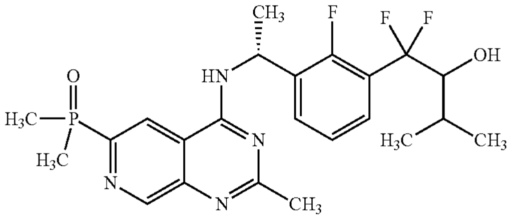<br>N-[(1R)-1-(3-{(2R*)-1,1-difluoro-3-methyl-2-[(triethylsilyl)oxy]butyl}-2-fluorophenyl)ethyl]-6-(dimethylphosphoryl)-2-methylpyrido[3,4-d]pyrimidin-4-amine (diastereomer 2)<br>LC-MS (Method 1): $R_t$ = 1.68 min; MS (ESIpos): m/z = 596 $[M + H]^+$ | Intermediate 71 and Intermediate 91<br>90.0 mg (61% purity, 100% yield) |
| 178 | 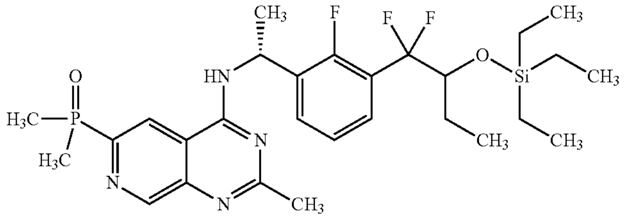 [SMILES: CCC(O[Si](CC)(CC)CC)C(F)(F)c1cccc([C@@H](C)Nc2nc(C)nc3cnc(P(C)(C)=O)cc23)c1F]<br>N-[(1R)-1-(3-{(2R*)-1, 1-difluoro-2-[(triethylsilyl)oxy]butyl}-2-fluorophenyl)ethyl]-6-(dimethylphosphoryl)-2-methylpyrido[3,4-d]pyrimidin-4-amine (diastereomer 1)<br>LC-MS (Method 1): $R_t$ = 1.59 min; MS (ESIpos): m/z = 582 $[M + H]^+$ | Intermediate 71 and Intermediate 78<br>95.0 mg (58% purity, 99% yield) |
| 179 | 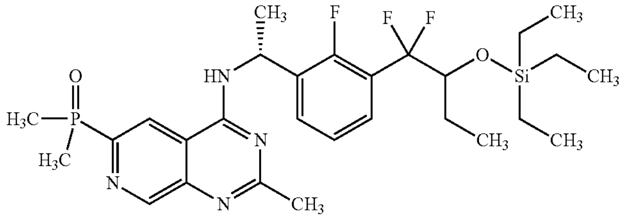 [SMILES: CCC(O[Si](CC)(CC)CC)C(F)(F)c1cccc([C@@H](C)Nc2nc(C)nc3cnc(P(C)(C)=O)cc23)c1F]<br>N-[(1R)-1-(3-{(2R*)-1,1-difluoro-2-[(triethylsilyl)oxy]butyl}-2-fluorophenyl)ethyl]-6-(dimethylphosphoryl)-2-methylpyrido[3,4-d]pyrimidin-4-amine (diastereomer 2)<br>LC-MS (Method 1): $R_t$ = 1.59 min; MS (ESIpos): m/z = 582 $[M + H]^+$ | Intermediate 71 and Intermediate 79<br>90.0 mg (62% purity, 100% yield) |

The intermediates shown in Table 2 were prepared according to general procedure 6 from the respective pyrimidin-4-ol derivatives and the respective amines.

Intermediates Table 2

| No. | Structure<br>IUPAC-Name<br>Analytical Data | Starting<br>Materials<br>Yield |
|---|---|---|
| 180 | 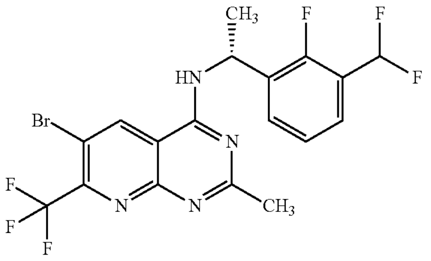 [SMILES: Cc1nc(N[C@H](C)c2cccc(C(F)F)c2F)c2cc(Br)c(C(F)(F)F)nc2n1] | Intermediate 11 and CAS 1389852-29-2 |
| | 6-bromo-N-{(1R)-1-[3-(difluoromethyl)-2-fluorophenyl]ethyl}-2-methyl-7-(trifluoromethyl)pyrido[2,3-d]pyrimidin-4-amine<br>$^1$H-NMR (400 MHz, DMSO-d6) δ [ppm]: 1.154 (4.68), 1.172 (9.71), 1.190 (4.72), 1.607 (4.41), 1.624 (4.39), 1.988 (16.00), 2.331 (0.79), 2.415 (14.99), 2.518 (3.72), 2.523 (2.44), 2.673 (0.77), 3.999 (1.20), 4.017 (3.59), 4.035 (3.50), 4.053 (1.11), 5.744 (0.67), 5.759 (2.95), 5.779 (0.66), 7.107 (1.01), 7.243 (2.09), 7.285 (0.71), 7.305 (1.55), 7.324 (0.89), 7.379 (0.89), 7.511 (0.54), 7.528 (0.92), 7.547 (0.50), 7.687 (0.49), 7.704 (0.89), 7.723 (0.45), 9.109 (1.02), 9.126 (0.98), 9.497 (3.52).<br>LC-MS (Method 2): $R_t$ = 1.36 min; MS (ESIpos): m/z = 479 $[M + H]^+$ | 270 mg<br>(87% yield) |
| 181 | 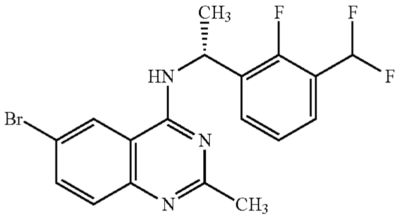 [SMILES: Cc1nc(N[C@H](C)c2cccc(C(F)F)c2F)c2cc(Br)ccc2n1] | CAS 5426-59-5 and CAS 1389852-29-2 |
| | 6-bromo-N-{(1R)-1-[3-(difluoromethyl)-2-fluorophenyl]ethyl}-2-methylquinazolin-4-amine<br>$^1$H-NMR (400 MHz, DMSO-d6) δ [ppm]: 1.154 (0.51), 1.172 (1.07), 1.190 (0.53), 1.584 (4.65), 1.602 (4.63), 1.988 (1.72), 2.318 (0.45), 2.323 (0.99), 2.327 (1.45), 2.331 (1.34), 2.338 (16.00), 2.518 (4.41), 2.523 (3.05), 2.665 (0.91), 2.669 (1.26), 2.673 (0.86), 5.753 (0.68), 5.770 (1.05), 5.788 (0.66), 7.101 (1.04), 7.237 (2.17), 7.270 (0.71), 7.289 (1.57), 7.308 (0.90), 7.373 (0.93), 7.482 (0.52), 7.498 (0.89), 7.523 (3.02), 7.545 (3.32), 7.662 (0.48), 7.679 (0.89), 7.697 (0.44), 7.836 (1.90), 7.842 (2.02), 7.858 (1.61), 7.864 (1.78), 8.562 (1.04), 8.580 (1.01), 8.721 (2.42), 8.727 (2.37).<br>LC-MS (Method 2): $R_t$ = 1.35 min; MS (ESIpos): m/z = 410 $[M + H]^+$ | 388 mg<br>(90% yield) |
| 182 | 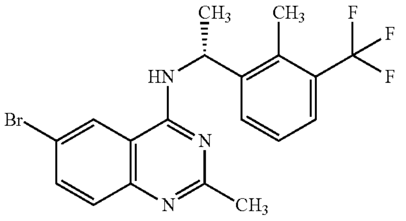 [SMILES: Cc1nc(N[C@H](C)c2cccc(C(F)(F)F)c2C)c2cc(Br)ccc2n1] | CAS 5426-59-5 and CAS 1212862-77-5 |
| | 6-bromo-2-methyl-N-{(1R)-1-[2-methyl-3-(trifluoromethyl)phenyl]ethyl}quinazolin-4-amine<br>$^1$H-NMR (400 MHz, DMSO-d6) δ [ppm]: 1.536 (5.07), 1.554 (5.06), 2.326 (16.00), 2.616 (5.95), 5.670 (0.76), 5.687 (1.17), 5.704 (0.75), 7.322 (0.67), 7.341 (1.46), 7.361 (0.86), 7.495 (3.08), 7.517 (4.78), 7.533 (1.31), 7.759 (1.43), 7.778 (1.28), 7.806 (1.97), 7.811 (2.05), 7.828 (1.66), 7.834 (1.79), 8.659 (1.13), 8.677 (1.10), 8.705 (2.60), 8.711 (2.66).<br>LC-MS (Method 2): $R_t$ = 1.50 min; MS (ESIpos): m/z = 425 $[M + H]^+$ | 3.90 g<br>(88% yield) |

Intermediates Table 3

| No. | Structure<br>IUPAC-Name<br>Analytical Data | Starting<br>Materials<br>Yield |
|---|---|---|
| 183 | 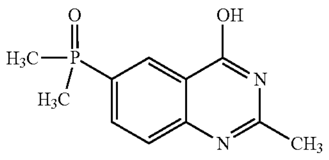<br>6-(dimethylphosphoryl)-2-methylquinazolin-4-ol<br>$^{1}H$-NMR (400 MHz, DMSO-d6) δ [ppm]: 1.035 (1.94), 1.052 (3.81), 1.069 (2.10), 1.357 (0.48), 1.390 (0.48), 1.683 (15.94), 1.716 (16.00), 2.376 (13.54), 2.518 (1.08), 2.523 (0.71), 3.422 (1.00), 3.434 (1.03), 3.439 (0.87), 3.452 (0.91), 4.345 (0.74), 4.357 (1.44), 4.370 (0.71), 7.656 (1.08), 7.661 (1.07), 7.677 (1.19), 7.682 (1.16), 8.069 (0.82), 8.074 (0.82), 8.090 (0.78), 8.095 (1.55), 8.099 (0.83), 8.116 (0.74), 8.120 (0.75), 8.439 (1.15), 8.443 (1.13), 8.469 (1.16), 8.473 (1.11), 12.397 (0.67).<br>LC-MS (): $R_t$ = min; MS (): m/z = | CAS 5426-59-5<br>94.0 mg<br>(19% yield) |
| 184 | 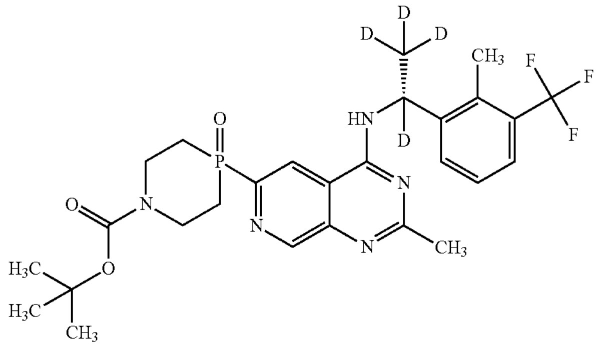 [SMILES: [2H]C([2H])([2H])[C@]([2H])(Nc1nc(C)nc2cnc(P3(=O)CCN(C(=O)OC(C)(C)C)CC3)cc12)c1cccc(C(F)(F)F)c1C]<br>tert-butyl 4-(2-methyl-4-{[(1S)-1-[2-methyl-3-(trifluoromethyl)phenyl]($^{2}H_4$)ethyl]amino}pyrido[3,4-d]pyrimidin-6-yl)-4-oxo-1,4lambda$^5$-azaphosphinane-1-carboxylate<br>$^{1}H$-NMR (400 MHz, DMSO-d6) δ [ppm]: 1.447 (16.00), 2.327 (0.41), 2.422 (4.78), 2.518 (1.14), 2.523 (0.80), 2.621 (1.97), 7.367 (0.52), 7.542 (0.53), 7.559 (0.43), 7.785 (0.48), 7.804 (0.43), 9.000 (0.55), 9.016 (0.54), 9.087 (1.29), 9.373 (0.75).<br>LC-MS (Method 2): $R_t$ = 135.00 min; MS (ESIpos): m/z = 568 $[M + H]^+$ | Intermediate 136 and Intermediate 52<br>169 mg<br>(91% yield) |
| 185 | 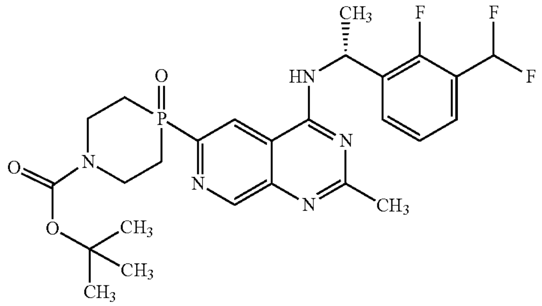 [SMILES: Cc1nc(N[C@H](C)c2cccc(C(F)F)c2F)c2cc(P3(=O)CCN(C(=O)OC(C)(C)C)CC3)ncc2n1]<br>tert-butyl 4-[4-({(1R)-1-[3-(difluoromethyl)-2-fluorophenyl]ethyl}amino)-2-methylpyrido[3,4-d]pyrimidin-6-yl]-4-oxo-1,4lambda$^5$-azaphosphinane-1-carboxylate<br>$^{1}H$-NMR (400 MHz, DMSO-d6) δ [ppm]: 1.446 (16.00), 1.615 (1.79), 1.633 (1.78), 2.432 (4.24), 2.518 (0.83), 2.523 (0.55), 5.756 (0.89), 5.795 (0.40), 7.103 (0.43), 7.238 (0.89), 7.303 (0.67), 7.514 (0.41), 9.002 (0.57), 9.019 (0.57), 9.106 (1.37), 9.285 (0.40).<br>LC-MS (Method 2): $R_t$ = 1.24 min; MS (ESIpos): m/z = 550 $[M + H]^+$ | Intermediate 165 and Intermediate 52<br>2.09 g<br>(89% yield) |

-continued

Intermediates Table 3

| No. | Structure<br>IUPAC-Name<br>Analytical Data | Starting<br>Materials<br>Yield |
|---|---|---|
| 186 | 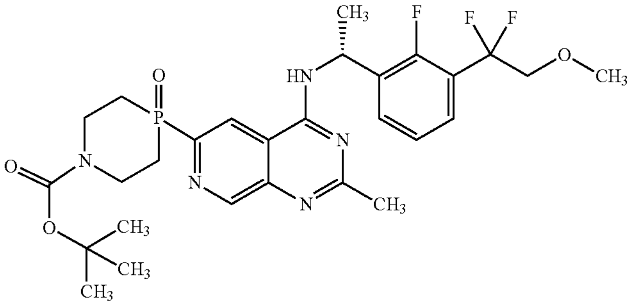 [SMILES: COCC(F)(F)c1cccc([C@@H](C)Nc2nc(C)nc3cnc(P4(=O)CCN(C(=O)OC(C)(C)C)CC4)cc23)c1F]<br>tert-butyl 4-[4-({(1R)-1-[3-(1,1-difluoro-2-methoxyethyl)-2-fluorophenyl]ethyl}amino)-2-methylpyrido[3,4-d]pyrimidin-6-yl]-4-oxo-1,4lambda$^5$-azaphosphinane-1-carboxylate<br>LC-MS (Method 2): $R_t$ = 1.25 min; MS (ESIpos): m/z = 595 [M + H]$^+$ | Intermediate 172 and Intermediate 52<br>192 mg<br>(147% yield) |
| 187 | 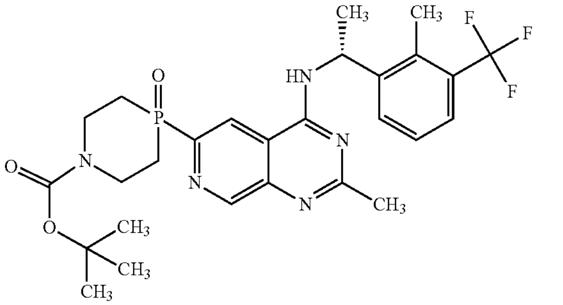 [SMILES: Cc1nc(N[C@H](C)c2cccc(C(F)(F)F)c2C)c2cc(P3(=O)CCN(C(=O)OC(C)(C)C)CC3)ncc2n1]<br>tert-butyl 4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxylate<br>LC-MS (Method 2): $R_t$ = 1.38 min; MS (ESIpos): m/z = 564.5 [M + H]$^+$ | Intermediate 117 and Intermediate 52<br>290 mg<br>(crude, 87% yield) |
| 188 | 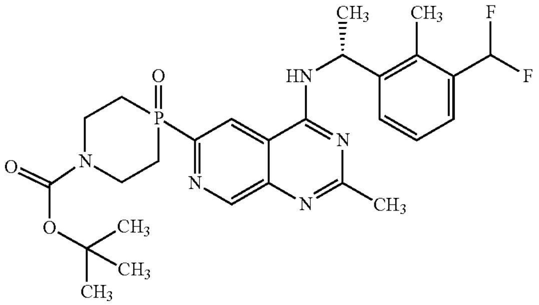 [SMILES: Cc1nc(N[C@H](C)c2cccc(C(F)F)c2C)c2cc(P3(=O)CCN(C(=O)OC(C)(C)C)CC3)ncc2n1]<br>tert-butyl 4-[4-({(1R)-1-[3-(difluoromethyl)-2-methylphenyl]ethyl}amino)-2-methylpyrido[3,4-d]pyrimidin-6-yl]-4-oxo-1,4lambda$^5$-azaphosphinane-1-carboxylate<br>LC-MS (Method 2): $R_t$ = 1.26 min; MS (ESIpos): m/z = 546.7 [M + H]$^+$ | Intermediate 166 and Intermediate 52<br>210 mg<br>(crude, 105% yield) |

-continued

Intermediates Table 3

| No. | Structure<br>IUPAC-Name<br>Analytical Data | Starting Materials<br>Yield |
|---|---|---|
| 189 | 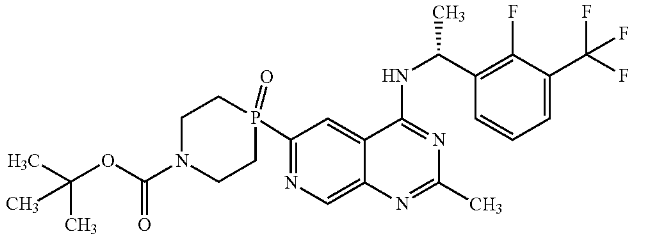 [SMILES: Cc1nc(N[C@H](C)c2cccc(C(F)(F)F)c2F)c2cc(P3(=O)CCN(C(=O)OC(C)(C)C)CC3)ncc2n1]<br>tert-butyl 4-[4-({(1R)-1-[2-fluoro-3-(trifluoromethyl)phenyl]ethyl}amino)-2-methylpyrido[3,4-d]pyrimidin-6-yl]-4-oxo-1,4lambda$^5$-azaphosphinane-1-carboxylate<br>$^1$H-NMR (400 MHz, DMSO-d6) δ [ppm]: 1.448 (16.00), 1.631 (1.99), 1.649 (1.98), 2.323 (0.51), 2.327 (0.58), 2.331 (0.45), 2.414 (5.37), 2.522 (1.57), 2.669 (0.41), 5.758 (0.49), 7.369 (0.69), 7.659 (0.52), 7.834 (0.51), 9.001 (0.72), 9.017 (0.72), 9.109 (1.77), 9.324 (0.55), 9.341 (0.55).<br>LC-MS (Method 2): $R_t$ = 1.34 min; MS (ESIpos): m/z = 568 $[M + H]^+$ | Intermediate 171 and Intermediate 52<br>108 mg<br>(95% purity, 39% yield) |
| 190 | 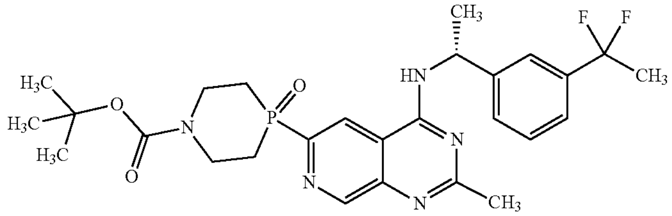 [SMILES: Cc1nc(N[C@H](C)c2cccc(C(C)(F)F)c2)c2cc(P3(=O)CCN(C(=O)OC(C)(C)C)CC3)ncc2n1]<br>tert-butyl 4-[4-{{(1R)-1-[3-(1,1-difluoroethyl)phenyl]ethyl}amino)-2-methylpyrido[3,4-d]pyrimidin-6-yl]-4-oxo-1,4lambda$^5$-azaphosphinane-1-carboxylate<br>LC-MS (Method 2): $R_t$ = 1.28 min; MS (ESIpos): m/z = 546.5 $[M + H]^+$ | Intermediate 167 and Intermediate 52<br>190 mg<br>(crude) |
| 191 | 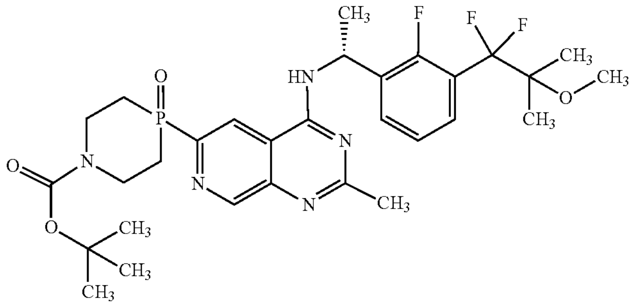 [SMILES: COC(C)(C)C(F)(F)c1cccc([C@@H](C)Nc2nc(C)nc3cnc(P4(=O)CCN(C(=O)OC(C)(C)C)CC4)cc23)c1F]<br>tert-butyl 4-[4-({(1R)-1-[3-(1,1-difluoro-2-methoxy-2-methylpropyl)-2-fluorophenyl]ethyl}amino)-2-methylpyrido[3,4-d]pyrimidin-6-yl]-4-oxo-1,4lambda$^5$-azaphosphinane-1-carboxylate<br>$^1$H-NMR (400 MHz, DMSO-d6) δ [ppm]: 1.250 (2.57), 1.258 (2.72), 1.410 (0.58), 1.448 (16.00), 1.593 (1.64), 1.610 (1.65), 2.323 (0.48), 2.327 (0.59), 2.331 (0.46), 2.413 (4.44), 2.518 (1.75), 2.523 (1.19), 2.669 (0.45), 3.174 (5.17), 5.759 (2.91), 5.772 (0.41), 7.225 (0.61), 7.245 (0.41), 7.595 (0.46), 7.608 (0.44), 7.612 (0.58), 7.621 (0.58), 7.625 (0.71), 7.641 (0.40), 7.645 (0.44), 9.014 (0.58), 9.029 (0.57), 9.105 (1.34), 9.282 (0.41).<br>LC-MS (Method 2): $R_t$ = 1.35 min; MS (ESIpos): m/z = 622 $[M + H]^+$ | Intermediate 67 and Intermediate 52<br>185 mg<br>(115% yield) |

-continued

Intermediates Table 3

| No. | Structure<br>IUPAC-Name<br>Analytical Data | Starting<br>Materials<br>Yield |
|---|---|---|
| 192 | 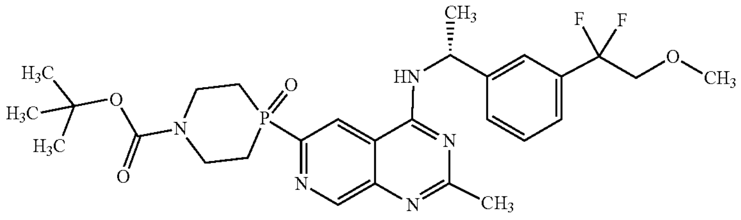 [SMILES: COCC(F)(F)c1cccc([C@@H](C)Nc2nc(C)nc3cnc(P4(=O)CCN(C(=O)OC(C)(C)C)CC4)cc23)c1]<br>tert-butyl 4-[4-{{(1R)-1-[3-(1,1-difluoro-2-methoxyethyl)phenyl]ethyl}amino)-2-methylpyrido[3,4-d]pyrimidin-6-yl]-4-oxo-1,4lambda$^5$-azaphosphinane-1-carboxylate<br>LC-MS (Method 2): $R_t$ = 1.25 min; MS (ESIpos): m/z = 576.5 $[M + H]^+$ | Intermediate 172 and Intermediate 52<br>!No TS! |
| 193 | 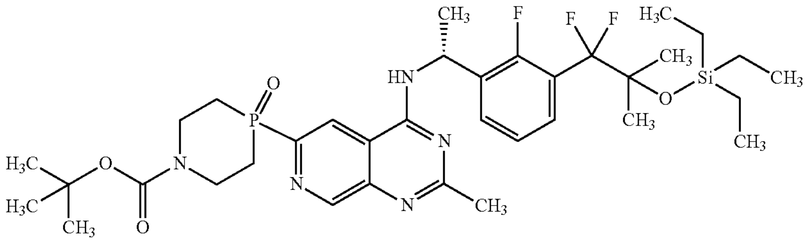 [SMILES: CC[Si](CC)(CC)OC(C)(C)C(F)(F)c1cccc([C@@H](C)Nc2nc(C)nc3cnc(P4(=O)CCN(C(=O)OC(C)(C)C)CC4)cc23)c1F]<br>tert-butyl 4-(4-{[(1R)-1-(3-{1,1-difluoro-2-methyl-2-[(triethylsilyl)oxy]propyl}-2-fluorophenyl)ethyl]amino}-2-methylpyrido[3,4-d]pyrimidin-6-yl)-4-oxo-1,4lambda$^5$-azaphosphinane-1-carboxylate<br>LC-MS (Method 2): $R_t$ = 1.76 min; MS (ESIpos): m/z = 722 $[M + H]^+$ | Intermediate 49 and Intermediate 52<br>300 mg<br>(81% yield) |
| 194 | 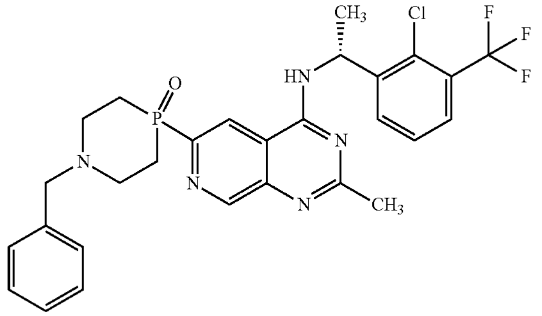 [SMILES: Cc1nc(N[C@H](C)c2cccc(C(F)(F)F)c2Cl)c2cc(P3(=O)CCN(Cc4ccccc4)CC3)ncc2n1]<br>1-benzyl-4-[4-({(1R)-1-[2-chloro-3-(trifluoromethyl)phenyl]ethyl}amino)-2-methylpyrido[3,4-d]pyrimidin-6-yl]-1,4lambda$^5$-azaphosphinan-4-one<br>$^1$H-NMR (400 MHz, DMSO-d6) δ [ppm]: 1.052 (0.41), 1.070 (0.51), 1.592 (5.16), 1.610 (5.24), 1.874 (0.41), 1.914 (0.81), 1.955 (0.47), 2.322 (0.60), 2.327 (0.85), 2.332 (0.75), 2.336 (0.52), 2.385 (16.00), 2.518 (3.45), 2.523 (2.29), 2.665 (0.55), 2.669 (0.81), 2.673 (0.57), 2.807 (0.90), 2.838 (0.98), 2.928 (0.61), 2.942 (0.46), 2.959 (0.46), 2.971 (0.53), 2.983 (0.62), 2.997 (0.46), 3.014 (0.41), 3.660 (6.09), 5.758 (1.08), 5.860 (0.84), 5.877 (1.28), 5.895 (0.82), 7.250 (0.50), 7.257 (0.65), 7.265 (1.02), 7.270 (0.72), 7.273 (0.87), 7.280 (0.90), 7.287 (0.71), 7.326 (0.84), 7.328 (0.66), 7.331 (0.48), 7.340 (0.64), 7.346 (4.32), 7.354 (4.56), 7.361 (11.58), 7.374 (0.62), 7.487 (0.85), 7.507 (1.78), 7.526 (1.02), 7.725 (1.40), 7.728 (1.59), 7.744 (1.27), 7.747 (1.25), 7.846 (1.35), 7.849 (1.36), 7.867 (1.22), 9.005 (1.69), 9.020 (1.67), 9.126 (4.27), 9.128 (4.20), 9.387 (1.32), 9.404 (1.27).<br>LC-MS (Method 2): $R_t$ = 1.39 min; MS (ESIpos): m/z = 574 $[M + H]^+$ | Intermediate 168<br>270 mg<br>(94% yield) |

-continued

| Intermediates Table 3 | | |
|---|---|---|
| No. | Structure<br>IUPAC-Name<br>Analytical Data | Starting<br>Materials<br>Yield |
| 195 | 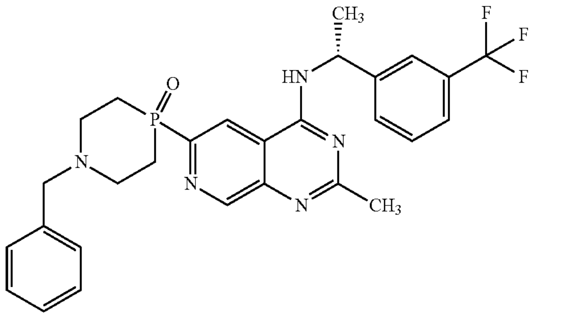 [SMILES: Cc1nc(N[C@H](C)c2cccc(C(F)(F)F)c2)c2cc(P3(=O)CCN(Cc4ccccc4)CC3)ncc2n1]<br>1-benzyl-4-[2-methyl-4-({(1R)-1-[3-(trifluoromethyl)phenyl]ethyl}amino)pyrido[3,4-d]pyrimidin-6-yl]-1,4lambda$^5$-azaphosphinan-4-one<br>$^1$H-NMR (400 MHz, DMSO-d6) δ [ppm]: 1.052 (0.52), 1.070 (0.60), 1.234 (0.45), 1.384 (1.85), 1.619 (5.89), 1.637 (5.94), 1.867 (0.50), 1.909 (0.98), 1.946 (0.57), 2.322 (0.90), 2.327 (1.24), 2.332 (1.11), 2.336 (0.71), 2.367 (0.84), 2.377 (0.83), 2.461 (16.00), 2.518 (4.38), 2.523 (2.96), 2.664 (0.71), 2.669 (1.03), 2.673 (0.73), 2.798 (1.06), 2.829 (1.17), 2.856 (0.48), 2.908 (0.71), 2.922 (0.55), 2.941 (0.57), 2.952 (0.62), 2.962 (0.73), 2.977 (0.53), 2.994 (0.47), 3.651 (7.31), 5.638 (0.88), 5.656 (1.32), 5.674 (0.88), 7.248 (0.57), 7.254 (0.76), 7.261 (1.22), 7.268 (0.94), 7.270 (0.92), 7.276 (1.02), 7.283 (0.80), 7.321 (0.89), 7.324 (0.78), 7.327 (0.54), 7.341 (5.32), 7.348 (5.59), 7.356 (12.47), 7.369 (0.70), 7.549 (0.60), 7.569 (1.83), 7.587 (2.27), 7.596 (2.46), 7.615 (0.75), 7.759 (1.58), 7.778 (1.24), 7.844 (2.59), 8.929 (1.96), 8.944 (1.94), 9.121 (4.75), 9.214 (1.50), 9.233 (1.44).<br>LC-MS (Method 2): $R_t$ = 1.33 min; MS (ESIneg): m/z = 538 [M − H]$^-$ | Intermediate 169<br>296 mg<br>(101% yield) |
| 196 | 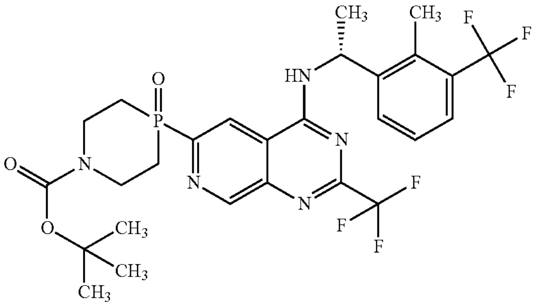 [SMILES: Cc1c([C@@H](C)Nc2nc(C(F)(F)F)nc3cnc(P4(=O)CCN(C(=O)OC(C)(C)C)CC4)cc23)cccc1C(F)(F)F]<br>tert-butyl 4-[4-({(1R)-1-[2-methyl-3-(trifluoromethyl)phenyl]ethyl}amino)-2-(trifluoromethyl)pyrido[3,4-d]pyrimidin-6-yl]-4-oxo-1,4lambda$^5$-azaphosphinane-1-carboxylate<br>LC-MS (Method 1): $R_t$ = 1.49 min; MS (ESIpos): m/z = 619 [M + H]$^+$ | Intermediate 105 and Intermediate 52<br>537 mg<br>(71% purity, 93% yield) |
| 197 | 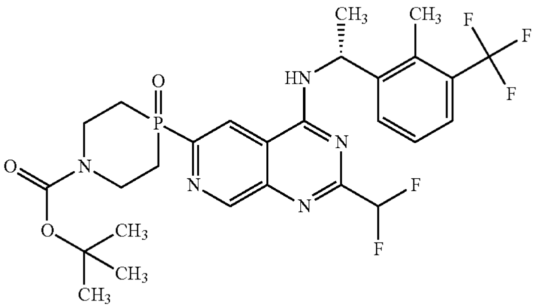 [SMILES: Cc1c([C@@H](C)Nc2nc(C(F)F)nc3cnc(P4(=O)CCN(C(=O)OC(C)(C)C)CC4)cc23)cccc1C(F)(F)F]<br>tert-butyl 4-[2-(difluoromethyl)-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxylate<br>LC-MS (Method 1): $R_t$ = 1.42 min; MS (ESIpos): m/z = 601 [M + H]$^+$ | Intermediate 108 and Intermediate 52<br>252 mg<br>(70% purity, 96% yield) |

-continued

| Intermediates Table 3 | | |
|---|---|---|
| No. | Structure<br>IUPAC-Name<br>Analytical Data | Starting<br>Materials<br>Yield |
| 198 | 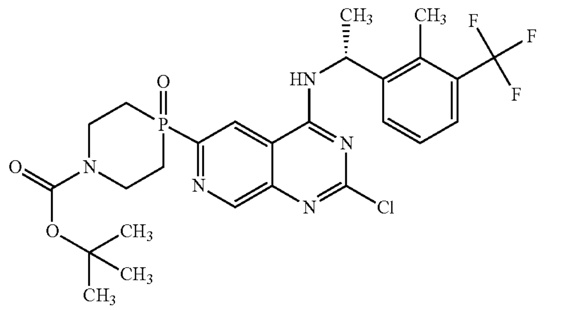 [SMILES: Cc1c([C@@H](C)Nc2nc(Cl)nc3cnc(P4(=O)CCN(C(=O)OC(C)(C)C)CC4)cc23)cccc1C(F)(F)F]<br>tert-butyl 4-[2-chloro-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxylate<br>LC-MS (Method 1): $R_t$ = 1.46 min; MS (ESIpos): m/z = 585 $[M + H]^+$ | Intermediate 111 and Intermediate 52<br>162 mg<br>(29% purity, 30% yield) |
| 199 | 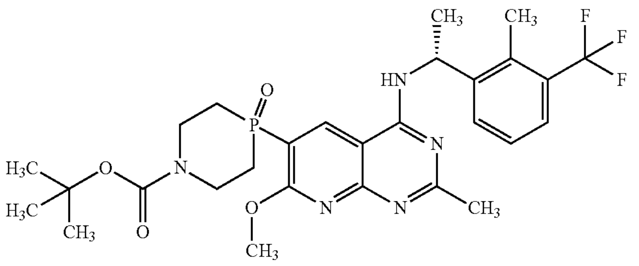 [SMILES: COc1nc2nc(C)nc(N[C@H](C)c3cccc(C(F)(F)F)c3C)c2cc1P1(=O)CCN(C(=O)OC(C)(C)C)CC1]<br>tert-butyl 4-[7-methoxy-2-methyl-4-({(1R)-1-[2-methyl-3-(trifluoromethyl)phenyl]ethyl}amino)pyrido[2,3-d]pyrimidin-6-yl]-4-oxo-1,4lambda$^5$-azaphosphinane-1-carboxylate<br>LC-MS (Method 2): $R_t$ = 1.30 min; MS (ESIpos): m/z = 595 $[M + H]^+$ | Intermediate 35 and Intermediate 52<br>180 mg<br>(110% yield) |
| 200 | 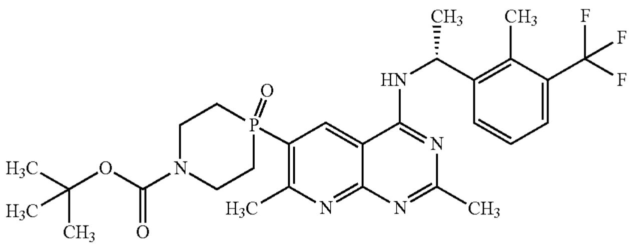 [SMILES: Cc1nc(N[C@H](C)c2cccc(C(F)(F)F)c2C)c2cc(P3(=O)CCN(C(=O)OC(C)(C)C)CC3)c(C)nc2n1]<br>tert-butyl 4-[2,7-dimethyl-4-({(1R)-1-[2-methyl-3-(trifluoromethyl)phenyl]ethyl}amino)pyrido[2,3-d]pyrimidin-6-yl]-4-oxo-1,4lambda$^5$-azaphosphinane-1-carboxylate<br>$^1$H-NMR (400 MHz, DMSO-d6) δ [ppm]: 1.153 (1.92), 1.172 (3.98), 1.189 (1.95), 1.407 (4.02), 1.429 (16.00), 1.470 (0.83), 1.487 (0.82), 1.589 (1.89), 1.607 (1.84), 2.323 (0.49), 2.327 (0.62), 2.331 (0.50), 2.394 (3.56), 2.449 (1.03), 2.518 (2.71), 2.523 (1.67), 2.601 (2.61), 2.669 (0.50), 2.866 (3.74), 3.084 (0.62), 3.095 (0.64), 3.102 (0.66), 3.113 (0.60), 7.375 (0.58), 7.557 (0.68), 7.575 (0.54), 7.749 (0.59), 7.769 (0.53), 8.843 (0.49), 8.875 (0.48).<br>LC-MS (Method 2): $R_t$ = 1.29 min; MS (ESIpos): m/z = 578 $[M + H]^+$ | Intermediate 18 and Intermediate 52<br>247 mg<br>(75% yield) |

-continued

Intermediates Table 3

| No. | Structure<br>IUPAC-Name<br>Analytical Data | Starting<br>Materials<br>Yield |
|---|---|---|
| 201 | 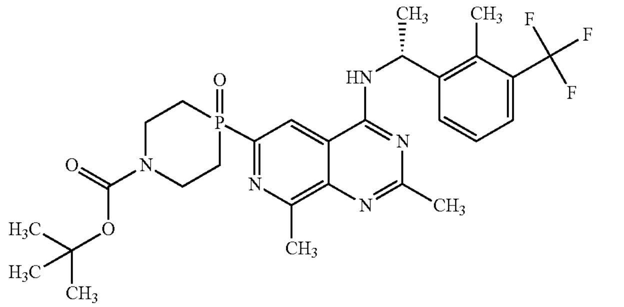 [SMILES: Cc1nc(N[C@H](C)c2cccc(C(F)(F)F)c2C)c2cc(P3(=O)CCN(C(=O)OC(C)(C)C)CC3)nc(C)c2n1]<br>tert-butyl 4-[2,8-dimethyl-4-{{(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxylate<br>LC-MS (Method 2): $R_t$ = 1.50 min; MS (ESIpos): m/z = 578 $[M + H]^+$ | Intermediate 140 and Intermediate 52<br>201 mg<br>(153% yield) |
| 202 | 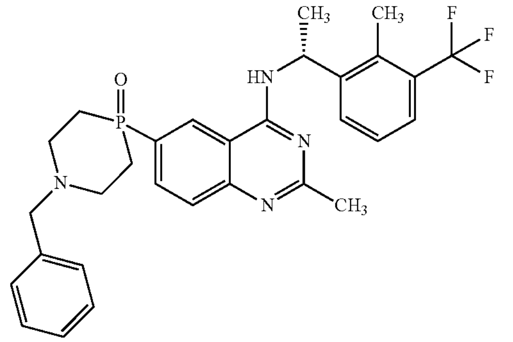 [SMILES: Cc1nc(N[C@H](C)c2cccc(C(F)(F)F)c2C)c2cc(P3(=O)CCN(Cc4ccccc4)CC3)ccc2n1]<br>1-benzyl-4-[2-methyl-4-({(1R)-1-[2-methyl-3-(trifluoromethyl)phenyl]ethyl}amino)quinazolin-6-yl]-1,4lambda$^5$-azaphosphinan-4-one<br>$^1$H-NMR (400 MHz, DMSO-d6) δ [ppm]: 0.797 (0.54), 0.814 (0.53), 0.821 (0.58), 0.904 (0.60), 1.052 (0.46), 1.070 (0.60), 1.155 (7.41), 1.173 (16.00), 1.191 (7.85), 1.581 (5.66), 1.598 (5.67), 1.751 (1.02), 1.907 (0.76), 1.955 (0.72), 1.971 (0.79), 2.011 (0.50), 2.323 (1.24), 2.327 (1.71), 2.332 (1.42), 2.336 (1.00), 2.368 (13.09), 2.411 (0.41), 2.518 (5.36), 2.523 (3.68), 2.629 (7.53), 2.660 (0.46), 2.665 (0.96), 2.669 (1.34), 2.673 (0.97), 2.678 (0.45), 2.727 (0.82), 2.781 (0.70), 2.819 (0.70), 2.888 (1.42), 2.941 (0.88), 3.065 (0.84), 3.077 (0.92), 3.083 (2.57), 3.095 (2.34), 3.102 (2.61), 3.113 (2.21), 3.119 (0.96), 3.131 (0.71), 3.660 (1.36), 5.725 (0.79), 5.742 (1.22), 5.758 (1.42), 7.283 (0.83), 7.342 (1.56), 7.362 (6.15), 7.369 (6.39), 7.381 (1.98), 7.535 (2.04), 7.554 (1.65), 7.662 (1.26), 7.668 (1.29), 7.684 (1.42), 7.689 (1.38), 7.777 (1.80), 7.796 (1.64), 8.039 (0.53), 8.062 (0.92), 8.084 (0.47), 8.824 (1.12), 8.855 (1.18).<br>LC-MS (Method 2): $R_t$ = 1.34 min; MS (ESIpos): m/z = 553 $[M + H]^+$ | Intermediate 182<br>234 mg<br>(120% yield) |
| 203 | 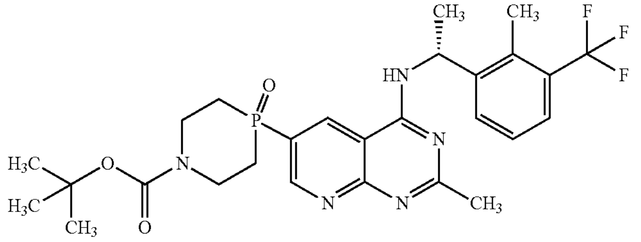 [SMILES: Cc1nc(N[C@H](C)c2cccc(C(F)(F)F)c2C)c2cc(P3(=O)CCN(C(=O)OC(C)(C)C)CC3)cnc2n1]<br>tert-butyl 4-[2-methyl-4-({(1R)-1-[2-methyl-3-(trifluoromethyl)phenyl]ethyl}amino)pyrido[2,3-d]pyrimidin-6-yl]-4-oxo-1,4lambda$^5$-azaphosphinane-1-carboxylate<br>$^1$H-NMR (400 MHz, DMSO-d6) δ [ppm]: 1.444 (16.00), 1.574 (1.91), 1.592 (1.93), 2.323 (0.43), 2.327 (0.59), 2.331 (0.50), 2.378 (0.45), | Intermediate 15 and Intermediate 52<br>257 mg<br>(97% yield) |

-continued

Intermediates Table 3

| No. | Structure<br>IUPAC-Name<br>Analytical Data | Starting<br>Materials<br>Yield |
|---|---|---|
| | 2.406 (2.88), 2.518 (2.31), 2.523 (1.49), 2.618 (2.56), 2.669 (0.48), 5.758 (0.97), 7.369 (0.57), 7.549 (0.70), 7.568 (0.57), 7.765 (0.68), 7.784 (0.57), 9.218 (0.78), 9.224 (0.60), 9.229 (0.57), 9.240 (0.44).<br>LC-MS (Method 2): $R_t$ = 1.26 min; MS (ESIpos): m/z = 564 [M + H]$^+$ | |
| 204 | 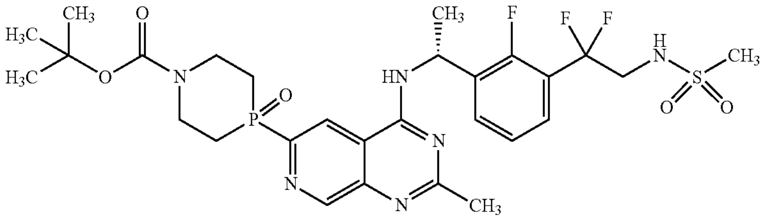 [SMILES: Cc1nc(N[C@H](C)c2cccc(C(F)(F)CNS(C)(=O)=O)c2F)c2cc(P3(=O)CCN(C(=O)OC(C)(C)C)CC3)ncc2n1]<br>tert-butyl 4-(4-{[(1R)-1-(3-{1,1-difluoro-2-[(methanesulfonyl)amino]ethyl}-2-fluorophenyl)ethyl]amino}-2-methylpyrido[3,4-d]pyrimidin-6-yl)-4-oxo-1,4lambda$^5$-azaphosphinane-1-carboxylate<br>$^1$H-NMR (400 MHz, DMSO-d6) δ [ppm]: 1.035 (1.74), 1.052 (3.64), 1.070 (1.68), 1.410 (1.13), 1.448 (16.00), 1.605 (1.65), 1.623 (1.60), 2.318 (0.44), 2.323 (0.67), 2.327 (0.86), 2.331 (0.64), 2.441 (4.54), 2.518 (3.23), 2.523 (2.14), 2.665 (0.50), 2.669 (0.71), 2.673 (0.50), 2.829 (5.62), 3.422 (0.54), 3.435 (0.55), 3.440 (0.52), 3.452 (0.52), 4.358 (0.49), 5.800 (0.41), 7.289 (0.71), 7.309 (0.42), 7.445 (0.40), 7.782 (0.63), 9.007 (0.59), 9.023 (0.58), 9.110 (1.40), 9.271 (0.41), 9.288 (0.40). | Intermediate 150 and Intermediate 52<br>136 mg<br>(90% purity, 62% yield) |
| 205 | 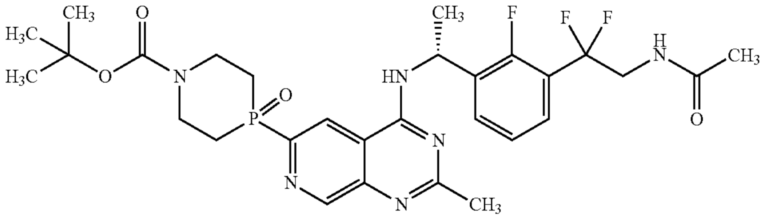 [SMILES: CC(=O)NCC(F)(F)c1cccc([C@@H](C)Nc2nc(C)nc3cnc(P4(=O)CCN(C(=O)OC(C)(C)C)CC4)cc23)c1F]<br>tert-butyl 4-[4-({(1R)-1-[3-(2-acetamido-1,1-difluoroethyl)-2-fluorophenyl]ethyl}amino)-2-methylpyrido[3,4-d]pyrimidin-6-yl]-4-oxo-1,4lambda$^5$-azaphosphinane-1-carboxylate<br>LC-MS (Method 2): $R_t$ = 1.09 min; MS (ESIpos): m/z = 621.8 [M + H]$^+$ | Intermediate 151 and Intermediate 52<br>168 mg<br>(90% purity, 70% yield) |
| 206 | 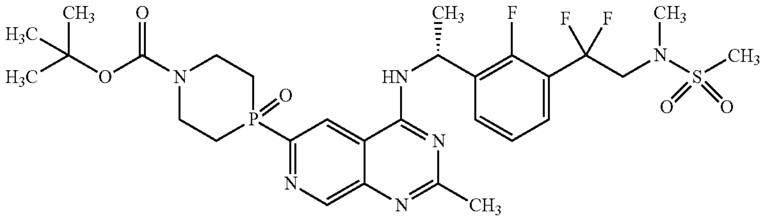 [SMILES: Cc1nc(N[C@H](C)c2cccc(C(F)(F)CN(C)S(C)(=O)=O)c2F)c2cc(P3(=O)CCN(C(=O)OC(C)(C)C)CC3)ncc2n1]<br>tert-butyl 4-(4-{[(1R)-1-(3-{1,1-difluoro-2-[(methanesulfonyl)(methyl)amino]ethyl}-2-fluorophenyl)ethyl]amino}-2-methylpyrido[3,4-d]pyrimidin-6-yl)-4-oxo-1,4lambda$^5$-azaphosphinane-1-carboxylate<br>$^1$H-NMR (400 MHz, DMSO-d6) δ [ppm]: 1.053 (1.02), 1.071 (0.96), 1.159 (0.46), 1.409 (0.83), 1.448 (16.00), 1.599 (1.59), 1.617 (1.59), 2.323 (0.40), 2.327 (0.45), 2.430 (3.95), 2.518 (1.22), 2.523 (0.84), 2.855 (8.91), 3.363 (0.66), 7.286 (0.69), 7.305 (0.40), 9.012 (0.57), 9.029 (0.56), 9.110 (1.21). | Intermediate 153 and Intermediate 52<br>182 mg<br>(95% purity, 81% yield) |

-continued

Intermediates Table 3

| No. | Structure<br>IUPAC-Name<br>Analytical Data | Starting Materials Yield |
| --- | --- | --- |
| 207 | 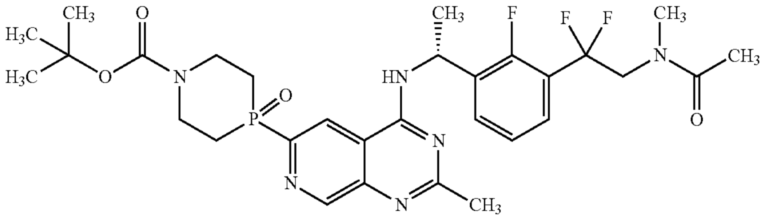 [SMILES: CC(=O)N(C)CC(F)(F)c1cccc([C@@H](C)Nc2nc(C)nc3cnc(P4(=O)CCN(C(=O)OC(C)(C)C)CC4)cc23)c1F]<br>tert-butyl 4-(4-{[(1R)-1-(3-{2-[acetyl(methyl)amino]-1,1-difluoroethyl}-2-fluorophenyl)ethyl]amino}-2-methylpyrido[3,4-d]pyrimidin-6-yl)-4-oxo-1,4lambda$^5$-azaphosphinane-1-carboxylate<br>$^1$H-NMR (400 MHz, DMSO-d6) δ [ppm]: 1.052 (0.99), 1.070 (0.69), 1.159 (0.55), 1.165 (0.67), 1.408 (2.69), 1.447 (16.00), 1.602 (1.03), 1.610 (0.96), 1.620 (1.06), 1.628 (0.87), 1.915 (2.46), 1.926 (3.60), 2.323 (0.46), 2.327 (0.54), 2.332 (0.41), 2.428 (2.47), 2.433 (2.88), 2.518 (1.45), 2.523 (1.02), 2.840 (1.67), 3.020 (2.21), 9.013 (0.62), 9.029 (0.61), 9.107 (0.95). | Intermediate 154 and Intermediate 52<br>139 mg<br>(95% purity, 81% yield) |
| 208 | 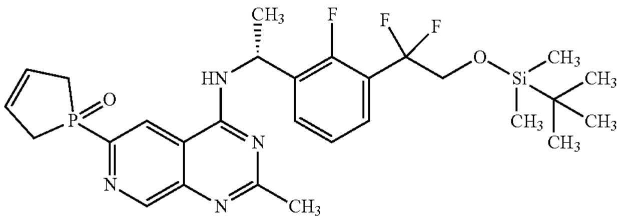 [SMILES: Cc1nc(N[C@H](C)c2cccc(C(F)(F)CO[Si](C)(C)C(C)(C)C)c2F)c2cc(P3(=O)CC=CC3)ncc2n1]<br>1-[4-{{(1R)-1-[3-(2-{[tert-butyl(dimethyl)silyl]oxy}-1,1-difluoroethyl)-2-fluorophenyl]ethyl}amino)-2-methylpyrido[3,4-d]pyrimidin-6-yl]-2,5-dihydro-1H-1lambda$^5$-phosphol-1-one<br>LC-MS (Method 2): $R_t$ = 1.53 min; MS (ESIpos): m/z = 577.7 [M + H]$^+$ | Intermediate 170<br>120 mg<br>(116% yield) |
| 209 | 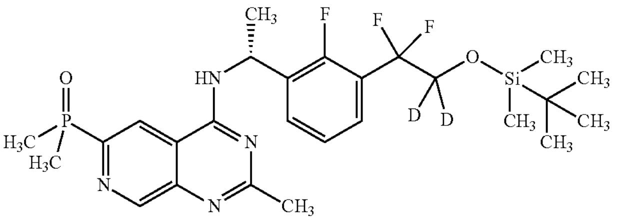 [SMILES: [2H]C([2H])(O[Si](C)(C)C(C)(C)C)C(F)(F)c1cccc([C@@H](C)Nc2nc(C)nc3cnc(P(C)(C)=O)cc23)c1F]<br>N-[(1R)-1-{3-[2-{[tert-butyl(dimethyl)silyl]oxy}-1,1-difluoro($^2H_2$)ethyl]-2-fluorophenyl}ethyl]-6-(dimethylphosphoryl)-2-methylpyrido[3,4-d]pyrimidin-4-amine<br>LC-MS (Method 2): $R_t$ = 1.48 min; MS (ESIpos): m/z = 555 [M + H]$^+$ | Intermediate 135<br>121 mg<br>(122% yield) |
| 210 | 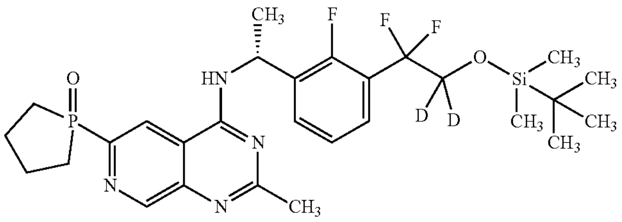 [SMILES: [2H]C([2H])(O[Si](C)(C)C(C)(C)C)C(F)(F)c1cccc([C@@H](C)Nc2nc(C)nc3cnc(P4(=O)CCCC4)cc23)c1F]<br>1-(4-{[(1R)-1-{3-[2-{[tert-butyl(dimethyl)silyl]oxy}-1,1-difluoro($^2H_2$)ethyl]-2-fluorophenyl}ethyl]amino}-2-methylpyrido[3,4-d]pyrimidin-6-yl)-1lambda$^5$-phospholan-1-one<br>LC-MS (Method 2): $R_t$ = 1.60 min; MS (ESIpos): m/z = 581 [M + H]$^+$ | Intermediate 134<br>157 mg<br>(151% yield) |

-continued

Intermediates Table 3

| No. | Structure<br>IUPAC-Name<br>Analytical Data | Starting<br>Materials<br>Yield |
|---|---|---|
| 211 | 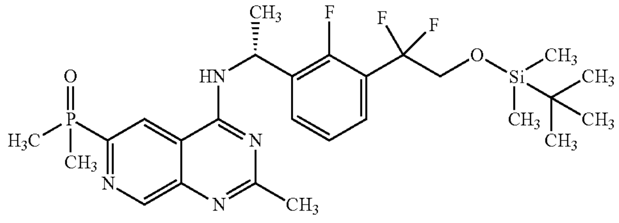 [SMILES: Cc1nc(N[C@H](C)c2cccc(C(F)(F)CO[Si](C)(C)C(C)(C)C)c2F)c2cc(P(C)(C)=O)ncc2n1]<br>N-{(1R)-1-[3-(2-{[tert-butyl(dimethyl)silyl]oxy}-1,1-difluoroethyl)-2-fluorophenyl]ethyl}-6-(dimethylphosphoryl)-2-methylpyrido[3,4-d]pyrimidin-4-amine<br>LC-MS (Method 2): $R_t$ = 1.49 min; MS (ESIpos): m/z = 553 $[M + H]^+$ | Intermediate 170<br>65.0 mg<br>(131% yield) |
| 212 | 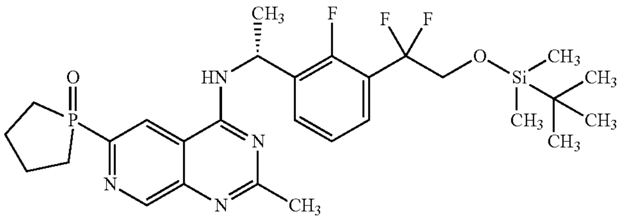 [SMILES: Cc1nc(N[C@H](C)c2cccc(C(F)(F)CO[Si](C)(C)C(C)(C)C)c2F)c2cc(P3(=O)CCCC3)ncc2n1]<br>1-[4-{{(1R)-1-[3-(2-{[tert-butyl(dimethyl)silyl]oxy}-1,1-difluoroethyl)-2-fluorophenyl]ethyl}amino)-2-methylpyrido[3,4-d]pyrimidin-6-yl]-1lambda5-phospholan-1-one<br>LC-MS (Method 2): $R_t$ = 1.57 min; MS (ESIpos): m/z = 579 $[M + H]^+$ | Intermediate 170<br>113 mg<br>(145% yield) |
| 213 | 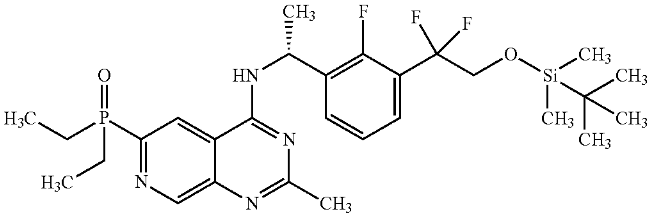 [SMILES: CCP(=O)(CC)c1cc2c(N[C@H](C)c3cccc(C(F)(F)CO[Si](C)(C)C(C)(C)C)c3F)nc(C)nc2cn1]<br>N-{(1R)-1-[3-(2-{[tert-butyl(dimethyl)silyl]oxy}-1,1-difluoroethyl)-2-fluorophenyl]ethyl}-6-(diethylphosphoryl)-2-methylpyrido[3,4-d]pyrimidin-4-amine<br>LC-MS (Method 2): $R_t$ = 1.57 min; MS (ESIpos): m/z = 581 $[M + H]^+$ | Intermediate 170<br>115 mg<br>(147% yield) |
| 216 | 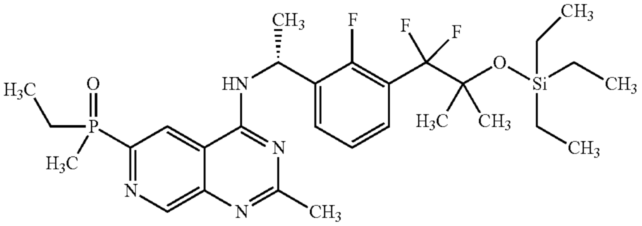 [SMILES: CC[Si](CC)(CC)OC(C)(C)C(F)(F)c1cccc([C@@H](C)Nc2nc(C)nc3cnc(P(C)(=O)CC)cc23)c1F]<br>N-[(1R)-1-(3-{1,1-difluoro-2-methyl-2-[(triethylsilyl)oxy]propyl}-2-fluorophenyl)ethyl]-6-[ethyl(methyl)phosphoryl]-2-methylpyrido[3,4-d]pyrimidin-4-amine (mixture of diastereomers)<br>LC-MS (Method 1): $R_t$ = 1.64 min; MS (ESIpos): m/z = 596 $[M + H]^+$ | Intermediate 49<br>240 mg<br>(112% yield) |

-continued

Intermediates Table 3

| No. | Structure<br>IUPAC-Name<br>Analytical Data | Starting<br>Materials<br>Yield |
| --- | --- | --- |
| 219 | 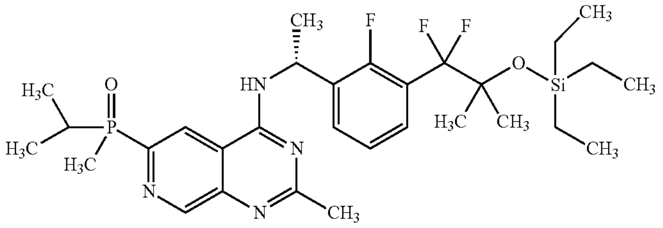 [SMILES: CC[Si](CC)(CC)OC(C)(C)C(F)(F)c1cccc([C@@H](C)Nc2nc(C)nc3cnc(P(C)(=O)C(C)C)cc23)c1F]<br>N-[(1R)-1-(3-{1,1-difluoro-2-methyl-2-[(triethylsilyl)oxy]propyl}-2-fluorophenyl)ethyl]-2-methyl-6-[methyl(propan-2-yl)phosphoryl]pyrido[3,4-d]pyrimidin-4-amine (mixture of diastereomers)<br>LC-MS (Method 1): $R_t$ = 1.68 min; MS (ESIpos): m/z = 610 $[M + H]^+$ | Intermediate 49<br>270 mg<br>(114% yield) |
| 220 | 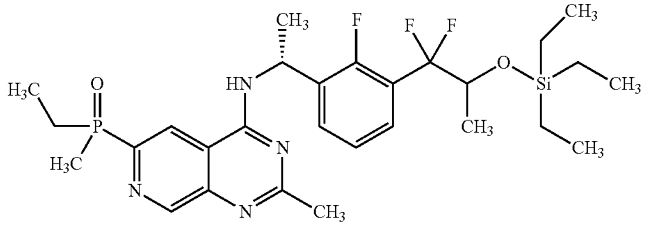 [SMILES: CC[Si](CC)(CC)OC(C)C(F)(F)c1cccc([C@@H](C)Nc2nc(C)nc3cnc(P(C)(=O)CC)cc23)c1F]<br>N-[(1R)-1-(3-{(2R*)-1,1-difluoro-2-[(triethylsilyl)oxy]propyl}-2-fluorophenyl)ethyl]-6-[ethyl(methyl)phosphoryl]-2-methylpyrido[3,4-d]pyrimidin-4-amine<br>Used without purification. | Intermediate 42<br>260 mg<br>(102% yield) |
| 221 | 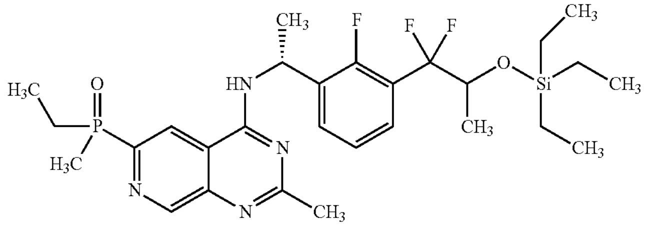 [SMILES: CC[Si](CC)(CC)OC(C)C(F)(F)c1cccc([C@@H](C)Nc2nc(C)nc3cnc(P(C)(=O)CC)cc23)c1F]<br>N-[(1R)-1-(3-{(2R*)-1,1-difluoro-2-[(triethylsilyl)oxy]propyl}-2-fluorophenyl)ethyl]-6-[ethyl(methyl)phosphoryl]-2-methylpyrido[3,4-d]pyrimidin-4-amine (mixture of diastereomers)<br>Used without purification. | Intermediate 43<br>230 mg<br>(103% yield) |
| 222 | 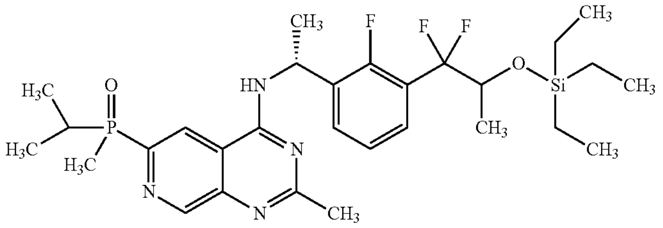 [SMILES: CC[Si](CC)(CC)OC(C)C(F)(F)c1cccc([C@@H](C)Nc2nc(C)nc3cnc(P(C)(=O)C(C)C)cc23)c1F]<br>N-[(1R)-1-(3-{(2R*)-1,1-difluoro-2-[(triethylsilyl)oxy]propyl}-2-fluorophenyl)ethyl]-2-methyl-6-[methyl(propan-2-yl)phosphoryl]pyrido[3,4-d]pyrimidin-4-amine (mixture of diastereomers 1.1 and 1.2)<br>Used without purification. | Intermediate 42<br>265 mg<br>(102% yield) |

-continued

Intermediates Table 3

| No. | Structure<br>IUPAC-Name<br>Analytical Data | Starting<br>Materials<br>Yield |
|---|---|---|
| 223 | 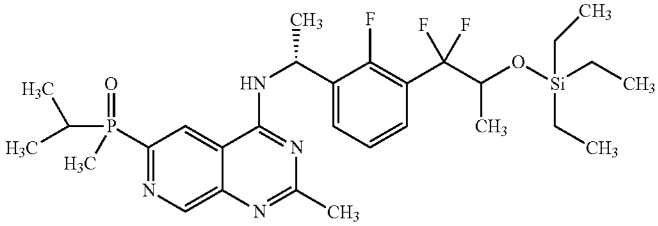 [SMILES: CC[Si](CC)(CC)OC(C)C(F)(F)c1cccc([C@@H](C)Nc2nc(C)nc3cnc(P(C)(=O)C(C)C)cc23)c1F]<br>N-[(1R)-1-(3-{(2R*)-1,1-difluoro-2-[(triethylsilyl)oxy]propyl}-2-fluorophenyl)ethyl]-2-methyl-6-[methyl(propan-2-yl)phosphoryl]pyrido[3,4-d]pyrimidin-4-amine (mixture of diastereomers 2.1 and 2.2)<br>Used without purification. | Intermediate 43<br>240 mg<br>(104% yield) |
| 224 | 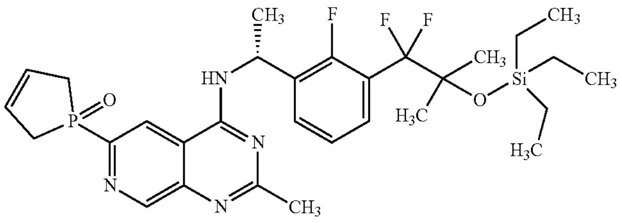 [SMILES: CC[Si](CC)(CC)OC(C)(C)C(F)(F)c1cccc([C@@H](C)Nc2nc(C)nc3cnc(P4(=O)CC=CC4)cc23)c1F]<br>1-(4-{[(1R)-1-(3-{1,1-difluoro-2-methyl-2-[(triethylsilyl)oxy]propyl}-2-fluorophenyl)ethyl]amino}-2-methylpyrido[3,4-d]pyrimidin-6-yl)-2,5-dihydro-1H-1lambda$^5$-phosphol-1-one<br>LC-MS (Method 2): $R_t$ = 1.66 min; MS (ESIpos): m/z = 605 $[M + H]^+$ | Intermediate 49<br>350 mg<br>(169% yield) |
| 225 | 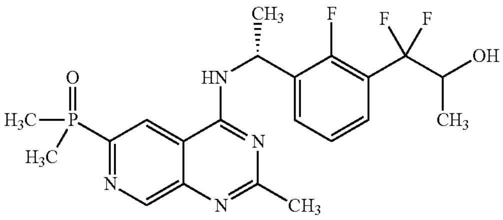<br>N-[(1R)-1-{3-[(2R*)-2-{[tert-butyl(dimethyl)silyl]oxy}-1,1-difluoropropyl]-2-fluorophenyl}ethyl]-6-(dimethylphosphoryl)-2-methylpyrido[3,4-d]pyrimidin-4-amine (diastereomer 1)<br>LC-MS (Method 2): $R_t$ = 1.56 min; MS (ESIpos): m/z = 567 $[M + H]^+$ | Intermediate 47<br>150 mg<br>(151% yield) |

The intermediates shown in Table 4 were prepared according to general procedure 3 from the respective N-Boc protected derivatives derivatives and the respective amines.

Intermediates Table 4

| No. | Structure<br>IUPAC-Name<br>Analytical Data | Starting<br>Materials<br>Yield |
|---|---|---|
| 226 | 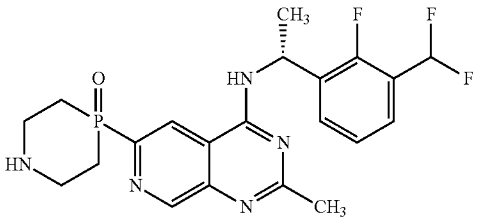 [SMILES: Cc1nc(N[C@H](C)c2cccc(C(F)F)c2F)c2cc(P3(=O)CCNCC3)ncc2n1] | Intermediate 185<br>1.23 g (95% purity, 90% yield) |

-continued

Intermediates Table 4

| No. | Structure<br>IUPAC-Name<br>Analytical Data | Starting<br>Materials<br>Yield |
|---|---|---|
| | 4-[4-{{(1R)-1-[3-(difluoromethyl)-2-fluorophenyl]ethyl}amino)-2-methylpyrido[3,4-d]pyrimidin-6-yl]-1,4lambda$^5$-azaphosphinan-4-one<br>$^1$H-NMR (400 MHz, DMSO-d6) δ [ppm]: 1.617 (5.02), 1.635 (5.00), 1.758 (0.40), 1.797 (0.80), 1.838 (0.44), 2.284 (0.81), 2.296 (0.81), 2.309 (0.86), 2.318 (1.10), 2.322 (1.33), 2.327 (1.44), 2.331 (1.23), 2.428 (16.00), 2.518 (3.30), 2.523 (2.24), 2.665 (0.59), 2.669 (0.83), 2.673 (0.58), 3.013 (0.70), 3.070 (0.75), 3.079 (0.71), 3.094 (0.49), 3.103 (0.70), 3.112 (0.72), 3.119 (0.66), 3.134 (0.68), 3.142 (0.66), 5.775 (0.78), 5.793 (1.20), 5.811 (0.76), 7.104 (1.18), 7.240 (2.45), 7.284 (0.86), 7.303 (1.89), 7.322 (1.08), 7.376 (1.04), 7.496 (0.64), 7.513 (1.08), 7.531 (0.53), 7.685 (0.59), 7.702 (1.07), 7.721 (0.54), 8.949 (1.75), 8.965 (1.76), 9.111 (4.36), 9.240 (1.26), 9.257 (1.21).<br>LC-MS (Method 2): $R_t$ = 0.98 min; MS (ESIpos): m/z = 451 [M + H]$^+$ | |
| 227 | 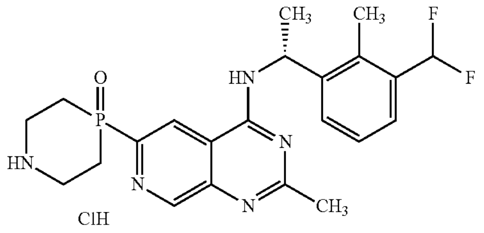 [SMILES: Cc1nc(N[C@H](C)c2cccc(C(F)F)c2C)c2cc(P3(=O)CCNCC3)ncc2n1 ; Cl]<br>4-[4-{{(1R)-1-[3-(difluoromethyl)-2-methylphenyl]ethyl}amino)-2-methylpyrido[3,4-d]pyrimidin-6-yl]-1,4lambda$^5$-azaphosphinan-4-one hydrogen chloride (1/1)<br>LC-MS (Method 2): $R_t$ = 0.98 min; MS (ESIpos): m/z = 446.6 [M + H]$^+$ | Intermediate 188<br>210 mg<br>(113% yield) |
| 228 | 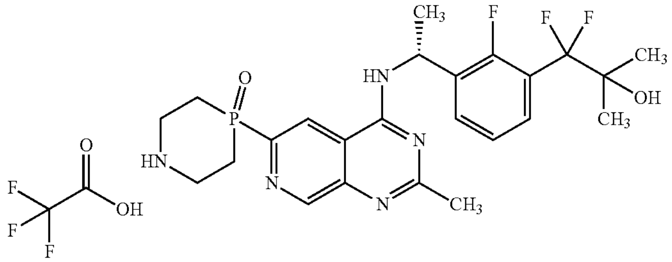 [SMILES: O=C(O)C(F)(F)F ; Cc1nc(N[C@H](C)c2cccc(C(F)(F)C(C)(C)O)c2F)c2cc(P3(=O)CCNCC3)ncc2n1]<br>trifluoroacetic acid 4-[4-({(1R)-1-[3-(1,1-difluoro-2-hydroxy-2-methylpropyl)-2-fluorophenyl]ethyl}amino)-2-methylpyrido[3,4-d]pyrimidin-6-yl]-1,4lambda$^5$-azaphosphinan-4-one (1/1)<br>LC-MS (Method 2): $R_t$ = 0.93 min; MS (ESIpos): m/z = 508 [M + H]$^+$ | Intermediate 193<br>154 mg<br>(102% yield) |
| 229 | 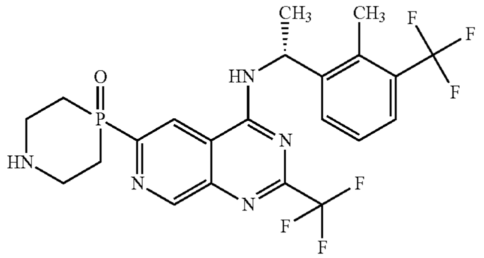 [SMILES: Cc1c([C@@H](C)Nc2nc(C(F)(F)F)nc3cnc(P4(=O)CCNCC4)cc23)cccc1C(F)(F)F]<br>4-[4-{{(1R)-1-[2-methyl-3-(trifluoromethyl)phenyl]ethyl}amino)-2-(trifluoromethyl)pyrido[3,4-d]pyrimidin-6-yl]-1,4lambda$^5$-azaphosphinan-4-one<br>LC-MS (Method 2): $R_t$ = 1.35 min; MS (ESIneg): m/z = 516 [M − H]$^-$ | Intermediate 196<br>690 mg<br>(153% yield) |

-continued

Intermediates Table 4

| No. | Structure<br>IUPAC-Name<br>Analytical Data | Starting<br>Materials<br>Yield |
|---|---|---|
| 230 | 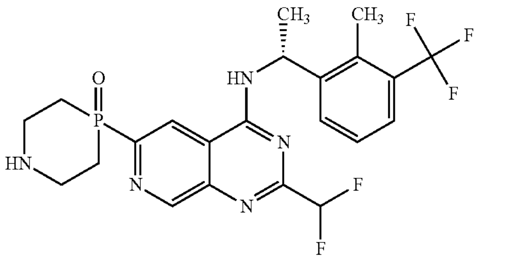 [SMILES: Cc1c([C@@H](C)Nc2nc(C(F)F)nc3cnc(P4(=O)CCNCC4)cc23)cccc1C(F)(F)F]<br>4-[2-(difluoromethyl)-4-({(1R)-1-[2-methyl-3-(trifluoromethyl)phenyl]ethyl}amino)pyrido[3,4-d]pyrimidin-6-yl]-1,4lambda$^5$-azaphosphinan-4-one<br>LC-MS (Method 2): $R_t$ = 1.26 min; MS (ESIneg): m/z = 498 $[M - H]^-$ | Intermediate 197<br>316 mg<br>(151% yield) |
| 231 | 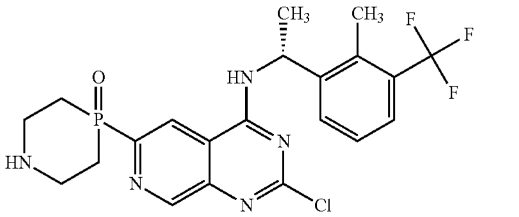 [SMILES: Cc1c([C@@H](C)Nc2nc(Cl)nc3cnc(P4(=O)CCNCC4)cc23)cccc1C(F)(F)F]<br>4-[2-chloro-4-({(1R)-1-[2-methyl-3-(trifluoromethyl)phenyl]ethyl}amino)pyrido[3,4-d]pyrimidin-6-yl]-1,4lambda$^5$-azaphosphinan-4-one<br>LC-MS (Method 2): $R_t$ = 1.18 min; MS (ESIpos): m/z = 485 $[M + H]^+$ | Intermediate 198<br>134 mg<br>(50% purity,<br>50% yield) |
| 232 | 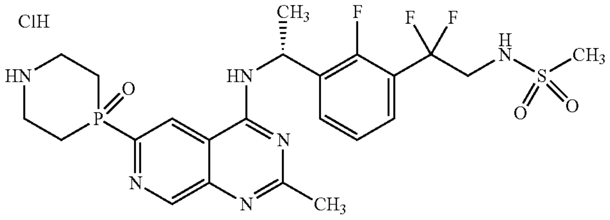 [SMILES: Cc1nc(N[C@H](C)c2cccc(C(F)(F)CNS(C)(=O)=O)c2F)c2cc(P3(=O)CCNCC3)ncc2n1 ; Cl]<br>N-(2,2-difluoro-2-{2-fluoro-3-[(1R)-1-{[2-methyl-6-(4-oxo-1,4lambda$^5$-azaphosphinan-4-yl)pyrido[3,4-d]pyrimidin-4-yl]amino}ethyl]phenyl}ethyl)methanesulfonamide hydrogen chloride (1/1)<br>$^1$H-NMR (400 MHz, DMSO-d6) δ [ppm]: 1.662 (3.40), 1.679 (3.15), 2.336 (1.47), 2.518 (11.64), 2.523 (7.39), 2.559 (5.10), 2.827 (16.00), 3.164 (5.95), 3.232 (1.17), 3.312 (1.23), 3.385 (3.70), 3.469 (10.73), 3.565 (5.13), 3.643 (1.54), 3.650 (1.07), 3.662 (0.99), 3.674 (0.94), 3.699 (0.84), 3.713 (0.84), 3.724 (1.04), 3.740 (1.02), 3.759 (1.29), 3.776 (1.30), 3.796 (0.83), 3.813 (0.78), 4.132 (0.44), 5.759 (2.21), 5.872 (0.56), 5.889 (0.76), 5.906 (0.48), 7.308 (0.70), 7.327 (1.57), 7.346 (0.93), 7.462 (0.66), 7.479 (1.11), 7.496 (0.54), 7.757 (0.61), 7.771 (1.54), 7.787 (2.15), 7.804 (0.90), 9.250 (2.18). | Intermediate 204<br>129 mg<br>(90% purity,<br>96% yield) |
| 233 | 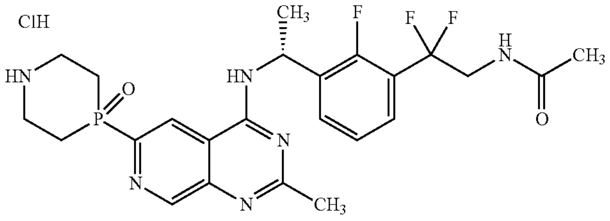 [SMILES: CC(=O)NCC(F)(F)c1cccc([C@@H](C)Nc2nc(C)nc3cnc(P4(=O)CCNCC4)cc23)c1F ; Cl]<br>N-(2,2-difluoro-2-{2-fluoro-3-[(1R)-1-{[2-methyl-6-(4-oxo-1,4lambda$^5$-azaphosphinan-4-yl)pyrido[3,4-d]pyrimidin-4-yl]amino}ethyl]phenyl}ethyl)acetamide hydrogen chloride (1/1) | Intermediate 205<br>152 mg<br>(90% purity,<br>92% yield) |

-continued

Intermediates Table 4

| No. | Structure<br>IUPAC-Name<br>Analytical Data | Starting<br>Materials<br>Yield |
|---|---|---|
| | $^{1}$H-NMR (400 MHz, DMSO-d6) δ [ppm]: 1.184 (0.82), 1.201 (0.43), 1.248 (3.55), 1.265 (3.95), 1.273 (2.95), 1.289 (2.49), 1.675 (2.55), 1.692 (1.95), 1.764 (9.37), 2.331 (1.98), 2.336 (1.23), 2.518 (10.05), 2.523 (6.21), 2.589 (2.73), 2.673 (1.97), 2.706 (0.69), 3.114 (0.51), 3.124 (0.53), 3.132 (0.53), 3.142 (0.54), 3.164 (16.00), 3.232 (0.67), 3.311 (0.94), 3.384 (3.19), 3.565 (7.78), 3.643 (2.28), 3.662 (1.60), 3.674 (1.40), 3.699 (1.13), 3.709 (0.94), 3.713 (0.95), 3.838 (0.62), 3.860 (0.68), 3.882 (0.76), 3.898 (0.87), 3.911 (0.81), 3.928 (0.50), 3.951 (0.43), 5.759 (2.99), 5.885 (0.48), 5.903 (0.55), 7.280 (0.52), 7.300 (1.16), 7.320 (0.66), 7.419 (0.58), 7.436 (0.96), 7.453 (0.45), 7.765 (0.56), 8.335 (0.64), 8.351 (1.33), 8.366 (0.63), 9.285 (1.36). | |
| 234 | 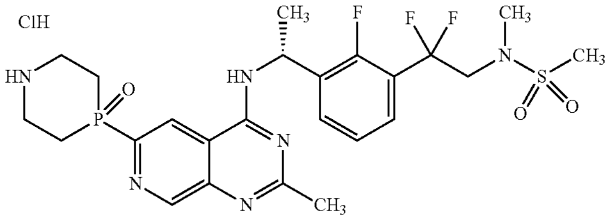 [SMILES: Cc1nc(N[C@H](C)c2cccc(C(F)(F)CN(C)S(C)(=O)=O)c2F)c2cc(P3(=O)CCNCC3)ncc2n1 ; Cl]<br>N-(2,2-difluoro-2-{2-fluoro-3-[(1R)-1-{[2-methyl-6-(4-oxo-1,4lambda$^{5}$-azaphosphinan-4-yl)pyrido[3,4-d]pyrimidin-4-yl]amino}ethyl]phenyl}ethyl)-N-methylmethanesulfonamide hydrogen chloride (1/1)<br>$^{1}$H-NMR (400 MHz, DMSO-d6) δ [ppm]: 1.672 (3.33), 1.689 (3.25), 2.318 (0.48), 2.322 (0.92), 2.327 (1.25), 2.332 (1.01), 2.336 (0.61), 2.373 (0.61), 2.413 (0.40), 2.518 (3.31), 2.523 (2.39), 2.580 (5.80), 2.665 (0.75), 2.669 (1.08), 2.673 (0.80), 2.678 (0.45), 2.724 (0.66), 2.747 (0.62), 2.841 (16.00), 2.854 (12.11), 3.164 (2.28), 3.232 (0.75), 3.311 (0.84), 3.384 (2.03), 3.441 (0.87), 3.446 (0.96), 3.452 (1.01), 3.457 (1.32), 3.459 (1.17), 3.463 (1.02), 3.468 (1.38), 3.469 (1.45), 3.479 (0.99), 3.486 (1.64), 3.488 (1.56), 3.490 (1.44), 3.496 (1.46), 3.499 (1.55), 3.501 (1.34), 3.510 (1.19), 3.514 (1.16), 3.597 (1.34), 3.604 (1.30), 3.644 (2.41), 3.651 (1.34), 3.658 (1.33), 3.662 (1.55), 3.667 (1.50), 3.675 (1.56), 3.677 (1.70), 3.690 (1.17), 3.699 (1.57), 3.701 (1.59), 3.709 (1.40), 3.713 (1.49), 3.717 (1.24), 3.724 (1.18), 3.729 (1.12), 3.731 (1.05), 3.834 (0.64), 3.872 (0.99), 3.903 (1.24), 3.939 (1.33), 3.974 (0.77), 4.018 (0.61), 4.132 (0.84), 5.882 (0.53), 5.900 (0.77), 5.917 (0.49), 7.310 (0.76), 7.330 (1.64), 7.350 (0.95), 7.478 (0.61), 7.494 (1.03), 7.511 (0.51), 7.782 (0.50), 7.798 (0.81), 7.816 (0.42), 9.301 (1.90), 9.354 (1.40). | Intermediate 206<br>175 mg (90% purity, 96% yield) |
| 235 | 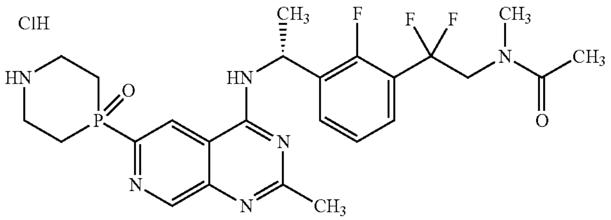 [SMILES: CC(=O)N(C)CC(F)(F)c1cccc([C@@H](C)Nc2nc(C)nc3cnc(P4(=O)CCNCC4)cc23)c1F ; Cl]<br>N-(2,2-difluoro-2-{2-fluoro-3-[(1R)-1-{[2-methyl-6-(4-oxo-1,4lambda$^{5}$-azaphosphinan-4-yl)pyrido[3,4-d]pyrimidin-4-yl]amino}ethyl]phenyl}ethyl)-N-methylacetamide hydrogen chloride (1/1)<br>$^{1}$H-NMR (400 MHz, DMSO-d6) δ [ppm]: 1.103 (0.71), 1.166 (3.50), 1.185 (7.34), 1.203 (3.76), 1.249 (1.23), 1.266 (1.35), 1.275 (0.83), 1.290 (0.76), 1.671 (2.63), 1.686 (3.26), 1.897 (16.00), 2.318 (0.85), 2.322 (1.53), 2.327 (2.11), 2.332 (1.69), 2.336 (1.06), 2.370 (0.88), 2.518 (5.71), 2.523 (3.98), 2.573 (2.70), 2.660 (0.60), 2.665 (1.29), 2.669 (1.87), 2.673 (1.40), 2.678 (0.78), 2.732 (0.90), 2.836 (6.00), 3.029 (9.03), 3.058 (1.37), 3.070 (1.74), 3.072 (1.51), 3.076 (1.37), 3.088 (1.41), 3.105 (0.51), 3.164 (0.89), 3.232 (0.95), 3.242 (0.56), 3.247 (0.71), 3.299 (0.62), 3.311 (1.36), 3.384 (5.55), 3.441 (2.06), 3.446 (2.23), 3.452 (2.44), 3.457 (3.16), 3.459 (2.88), 3.468 (3.49), 3.469 (3.64), 3.486 (4.19), 3.488 (4.02), 3.497 (3.96), 3.499 (4.31), 3.504 (3.84), 3.510 (4.01), 3.514 (4.11), 3.644 (3.23), 3.651 (2.71), 3.658 (2.59), 3.662 (2.96), 3.667 (2.77), 3.674 (2.82), 3.677 (2.96), 3.698 | Intermediate 207<br>142 mg (90% purity, 102% yield) |

-continued

Intermediates Table 4

| No. | Structure<br>IUPAC-Name<br>Analytical Data | Starting<br>Materials<br>Yield |
|---|---|---|
| | (2.54), 3.701 (2.50), 3.708 (2.07), 3.713 (2.25), 3.717 (1.73), 3.724 (1.54), 3.728 (1.44), 3.840 (0.58), 3.860 (0.54), 4.018 (0.71), 4.033 (0.59), 4.076 (0.64), 4.114 (0.51), 4.133 (0.88), 4.150 (0.97), 4.171 (0.79), 4.183 (1.02), 4.204 (0.54), 4.223 (0.61), 5.881 (0.71), 5.897 (0.70), 7.268 (0.48), 7.287 (1.07), 7.307 (0.65), 7.356 (0.62), 7.418 (0.52), 7.436 (0.86), 7.455 (0.42), 7.496 (0.59), 7.750 (0.44), 9.273 (1.16), 9.311 (1.32). | |
| 236 | 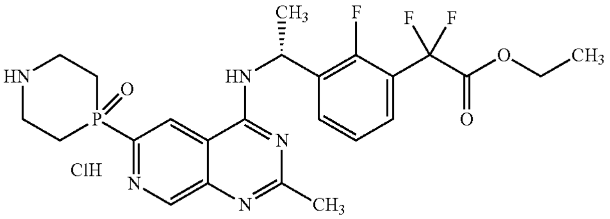 [SMILES: CCOC(=O)C(F)(F)c1cccc([C@@H](C)Nc2nc(C)nc3cnc(P4(=O)CCNCC4)cc23)c1F ; Cl]<br>ethyl difluoro{2-fluoro-3-[(1R)-1-{[2-methyl-6-(4-oxo-1,4lambda$^5$-azaphosphinan-4-yl)pyrido[3,4-d]pyrimidin-4-yl]amino}ethyl]phenyl}acetate hydrogen chloride (1/1)<br>LC-MS (Method 2): $R_t$ = 1.01 min; MS (ESIpos): m/z = 522.5 [M + H]$^+$ | Intermediate 157<br>1.34 g<br>(103% yield) |

The intermediates shown in Table 5 were prepared from their respective N-benzyl derivatives by hydrogenation: The N-benzyl compound (1 eq) was solved in ethanol (0.1 M), Pd/C (10% Pd, 0.9 eq) was added, and the mixture was stirred under a hydrogen atmosphere at RT overnight. The mixture was filtered, concentrated, and the obtained crude product was used for the next reaction without purification.

Intermediates Table 5

| No. | Structure<br>IUPAC-Name<br>Analytical Data | Starting<br>Materials<br>Yield |
|---|---|---|
| 237 | 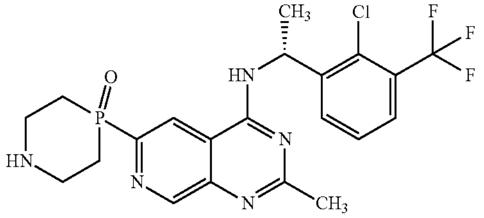 [SMILES: Cc1nc(N[C@H](C)c2cccc(C(F)(F)F)c2Cl)c2cc(P3(=O)CCNCC3)ncc2n1]<br>4-[4-{{(1R)-1-[2-chloro-3-(trifluoromethyl)phenyl]ethyl}amino)-2-methylpyrido[3,4-d]pyrimidin-6-yl]-1,4lambda$^5$-azaphosphinan-4-one<br>LC-MS (Method 2): $R_t$ = 1.10 min; MS (ESIpos): m/z = 484 [M + H]$^+$ | Intermediate 194<br>218 mg<br>(97% yield) |
| 238 | 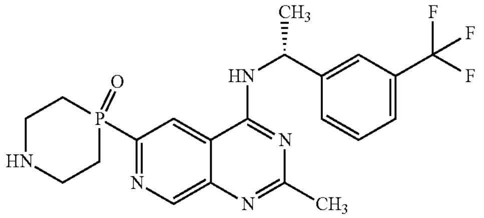 [SMILES: Cc1nc(N[C@H](C)c2cccc(C(F)(F)F)c2)c2cc(P3(=O)CCNCC3)ncc2n1]<br>4-[2-methyl-4-({(1R)-1-[3-(trifluoromethyl)phenyl]ethyl}amino)pyrido[3,4-d]pyrimidin-6-yl]-1,4lambda$^5$-azaphosphinan-4-one<br>LC-MS (Method 2): $R_t$ = 1.03 min; MS (ESIneg): m/z = 448 [M − H]$^-$ | Intermediate 195<br>235 mg<br>(96% yield) |

-continued

Intermediates Table 5

| No. | Structure<br>IUPAC-Name<br>Analytical Data | Starting<br>Materials<br>Yield |
|---|---|---|
| 239 | 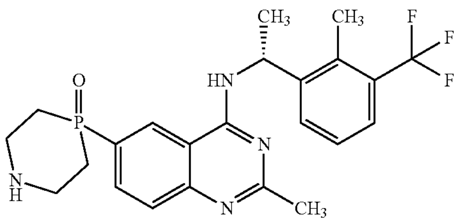 [SMILES: Cc1nc(N[C@H](C)c2cccc(C(F)(F)F)c2C)c2cc(P3(=O)CCNCC3)ccc2n1]<br>4-[2-methyl-4-({(1R)-1-[2-methyl-3-(trifluoromethyl)phenyl]ethyl}amino)quinazolin-6-yl]-1,4lambda$^5$-azaphosphinan-4-one<br>LC-MS (Method 2): $R_t$ = 1.10 min; MS (ESIneg): m/z = 461 $[M-H]^-$ | Intermediate 202<br>207 mg<br>(111% yield) |

Intermediate 240

(2R*)-1-(3-{(1R)-1-[(6-bromo-2-methylpyrido[3,4-d]pyrimidin-4-yl)amino]ethyl}-2-fluorophenyl)-1,1-difluoropropan-2-ol (diastereomer 2)

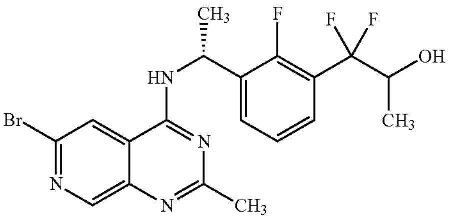 [SMILES: Cc1nc(N[C@H](C)c2cccc(C(F)(F)C(C)O)c2F)c2cc(Br)ncc2n1]

The title compound was prepared from intermediate 43 as described for Intermediate 141, to obtain 351 mg (90% yield).

LC-MS (Method 2): $R_t$=1.11 min; MS (ESIpos): m/z=455 $[M+H]^+$ $^1$H-NMR (400 MHz, DMSO-d6) δ[ppm]: 1.131 (3.39), 1.147 (3.45), 1.154 (2.16), 1.171 (3.70), 1.189 (1.77), 1.582 (4.17), 1.600 (4.21), 1.986 (5.52), 2.377 (16.00), 2.518 (1.96), 2.523 (1.38), 4.016 (1.11), 4.034 (1.08), 5.578 (2.44), 5.594 (2.37), 5.703 (0.65), 5.720 (1.01), 5.738 (0.64), 5.756 (2.12), 7.221 (0.70), 7.240 (1.60), 7.259 (0.96), 7.358 (0.51), 7.362 (0.58), 7.380 (0.88), 7.395 (0.44), 7.599 (0.49), 7.615 (0.86), 7.632 (0.44), 8.666 (3.67), 8.668 (3.68), 8.805 (4.24), 8.875 (1.05), 8.893 (1.00).

Intermediate 241

(R)—N-(1-(3-amino-5-(trifluoromethyl)phenyl)ethyl)-6-bromo-2-methylpyrido[3,4-d]pyrimidin-4-amine

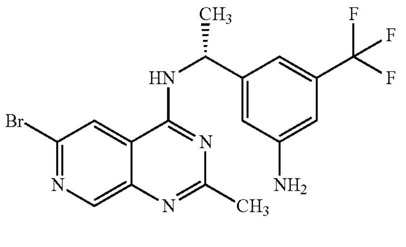 [SMILES: Cc1nc(N[C@H](C)c2cc(N)cc(C(F)(F)F)c2)c2cc(Br)ncc2n1]

The title compound was prepared according to General Procedure 2, starting from Intermediate 32 (1.0 g, 4.2 mmol) and (R)-3-Amino-α-methyl-5-(trifluoromethyl)benzenemethanamine (CAS 1213552-98-7, 1.2 g, 5.0 mmol)) to obtain the title compound (1.47 g, 82% yield).

LC-MS (Method 2): $R_t$=1.21 min; MS (ESIpos): m/z=426 $[M+H]^+$

Intermediate 242 tert-Butyl (R)-(1-(2-methyl-3-(trifluoromethyl)phenyl)ethyl)carbamate

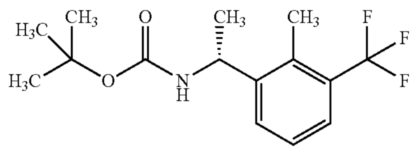 [SMILES: Cc1c([C@@H](C)NC(=O)OC(C)(C)C)cccc1C(F)(F)F]

To a suspension of (R)-1-(2-methyl-3-(trifluoromethyl)phenyl)ethan-1-amine hydrochloride (2.0 g, 9.84 mmol) in dichloromethane (50 ml) was added N,N-diisopropylethylamine (3.43 ml, 19.6 mmol), followed by di-tert-butyldicarbonat (2.58 g, 11.8 mmol), and the mixture was stirred at RT for 20 h. The mixture was diluted with saturated aqueous sodium chloride and extracted with ethyl acetate. The organic phases were dried and concentrated, and the residue was re-dissolved in ethanol, imidazole (335 mg) was added, and the mixture was stirred at RT for 2 h. The mixture was then diluted with saturated aqueous sodium chloride and extracted with ethyl acetate. The organic phases were dried and concentrated, and the residue was purified by flash chromatography (silica, hexane, ethyl acetate) to yield the title compound (2.78 g, 92% yield).

$^1$H NMR (400 MHz, CHLOROFORM-d) b ppm 1.40 (br s, 12H) 2.46 (s, 3H) 4.70-5.26 (m, 2H) 7.20-7.34 (m, 1H) 7.39-7.57 (m, 2H).

Intermediate 243 tert-Butyl (R)-(1-(5-bromo-2-methyl-3-(trifluoromethyl)phenyl)ethyl)carbamate

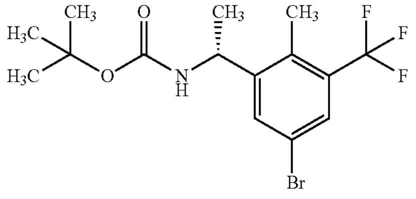 [SMILES: Cc1c([C@@H](C)NC(=O)OC(C)(C)C)cc(Br)cc1C(F)(F)F]

To a solution of bis(1,5-cyclooctadiene)dimethoxydiiridium (49 mg, 74 μmol) and 4,4'-di-tert-butyl-2,2'-bipyridine (39 mg, 148 μmol) in tetrahydrofuran (15 ml) was added tert-butyl (R)-(1-(2-methyl-3-(trifluoromethyl)phenyl)ethyl)carbamate (Intermediate 242, 1.5 g, 4.95 mmol) and bis(pinacolato)diboron (1.26 g, 4.95 mmol), and the mixture was stirred at 80° C. for 20 h. The mixture was then concentrated and the residue was re-dissolved in methanol (60 ml). To the mixture was then added copper(II)bromide (3.31 g, 14.8 mmol) in water (60 ml), and the resulting mixture was heated at 90° C. for 6 h. The mixture was then cooled, diluted with saturated aqueous sodium hydrogen carbonate, and extracted with ethyl acetate. The organic phases were dried and concentrated, to yield the title compound (1.31 g, 69% yield).

LC-MS (Method 2): $R_t$=1.51 min; MS (ESIneg): m/z=380 $[M-H]^-$

Intermediate 244 tert-Butyl (R)-(1-(2,5-dimethyl-3-(trifluoromethyl)phenyl)ethyl)carbamate

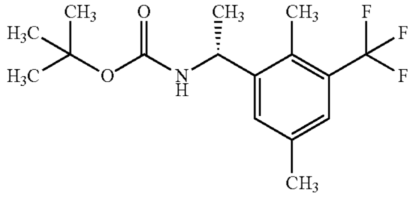 [SMILES: Cc1cc([C@@H](C)NC(=O)OC(C)(C)C)c(C)c(C(F)(F)F)c1]

A mixture of tert-butyl (R)-(1-(5-bromo-2-methyl-3-(trifluoromethyl)phenyl)ethyl)-carbamate (crude Intermediate 243, 300 mg, 784 μmol), caesium carbonate (511 mg, 1.57 mmol), trimethylboroxine (147 mg, 1.18 mmol), and [1,1'bis(diphenylphosphino)ferrocene]dichloropalladium(II) (57.4 mg, 78.5 μmol) was heated to 110° C. for 20 h. The mixture was cooled, concentrated, and the residue was purified by flash chromatography (silica, hexane, ethyl acetate) to yield the title compound (180 mg, 72% yield).

LC-MS (Method 2): $R_t$=1.49 min; MS (ESIneg): m/z=316 $[M-H]^-$

Intermediate 245

(R)-1-(2,5-Dimethyl-3-(trifluoromethyl)phenyl)ethan-1-amine hydrochloride

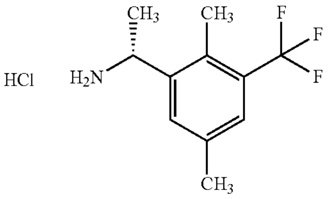

The title compound was prepared as described for Intermediate 28, starting from tert-butyl (R)-(1-(2,5-dimethyl-3-(trifluoromethyl)phenyl)ethyl)carbamate (intermediate 244, 180 mg, 567 μmol) to yield the title compound (105 mg, 72% yield).

$^1$H NMR (400 MHz, DMSO-d6) b ppm 1.41-1.53 (m, 3H) 2.38 (m, 6H) 4.49-4.85 (m, 1H) 7.44-7.59 (m, 1H) 7.60-7.79 (m, 1H) 8.13-8.66 (m, 3H).

Example 1

6-(dimethylphosphoryl)-2-methyl-N-{(1R)-1-[2-methyl-3-(trifluoromethyl)phenyl]ethyl}pyrido[3,4-d]pyrimidin-4-amine

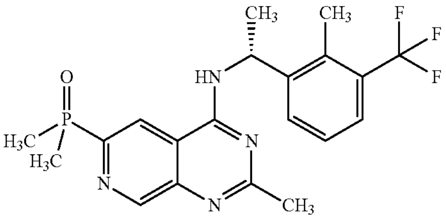 [SMILES: Cc1nc(N[C@H](C)c2cccc(C(F)(F)F)c2C)c2cc(P(C)(C)=O)ncc2n1]

Following general procedure 1, a solution of 6-chloro-2-methyl-N-{(1R)-1-[2-methyl-3-(trifluoromethyl)phenyl]ethyl}pyrido[3,4-d]pyrimidin-4-amine (60.0 mg, 158 μmol), dimethyl-lambda5-phosphanone (12.3 mg, 158 μmol) and triethylamine (77 μl, 550 μmol) in acetonitrile (800 μl) under argon was added tetrakis(triphenylphosphin)palladium(0) (28.9 mg, 31.5 μmol) and the mixture was heated at 90° C. overnight. The mixture was filtered, concentrated and purified by HPLC (basic method), to yield the title compound (17 mg, 95% purity, 24% yield).

LC-MS (Method 2): $R_t$=1.17 min; MS (ESIneg): m/z=421 $[M-H]^-$

1H-NMR (400 MHz, DMSO-d6): 5 [ppm]=1.58 (d, 3H), 1.68-1.73 (m, 6H), 2.42 (s, 3H), 2.63 (s, 3H), 5.72 (t, 1H), 7.37 (t, 1H), 7.55 (d, 1H), 7.81 (d, 1H), 8.96 (dd, 1H), 9.07 (s, 1H), 9.38 (d, 1H).

Example 2

N-{(1R)-1-[3-(difluoromethyl)-2-fluorophenyl]ethyl}-6-(dimethylphosphoryl)-2-methylpyrido[3,4-d]pyrimidin-4-amine

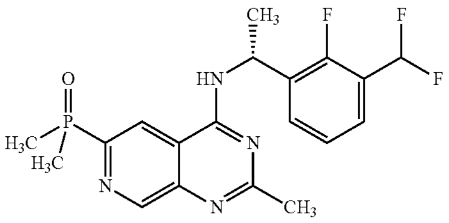 [SMILES: Cc1nc(N[C@H](C)c2cccc(C(F)F)c2F)c2cc(P(C)(C)=O)ncc2n1]

To a solution of 6-chloro-N-{(1R)-1-[3-(difluoromethyl)-2-fluorophenyl]ethyl}-2-methylpyrido[3,4-d]pyrimidin-4-amine (70.0 mg, 191 μmol), dimethyl-lambda5-phosphanone (14.9 mg, 191 μmol) and triethylamine (93 μl, 670 μmol) in acetonitrile (970 μl) under argon was added tetrakis (triphenylphosphin)palladium(0) (35.0 mg, 38.2 μmol) and the mixture was heated at 90° C. overnight. The mixture was filtered, concentrated and purified by HPLC (basic method). The fractions containing the title compound were concentrated and was further purified by preparative thin layer chromatography (silica gel, CH2Cl2/EtOH 95:5) to yield the title compound as white solid (35 mg, 95% purity, 43% yield).

LC-MS (Method 2): $R_t$=1.01 min; MS (ESIneg): m/z=407 $[M-H]^-$

1H NMR (DMSO-d6) δ: 9.30 (d, J=7.4 Hz, 1H), 9.09 (s, 1H), 8.96 (d, J=6.1 Hz, 1H), 7.71 (s, 1H), 7.42-7.57 (m, 1H), 7.09-7.39 (m, 2H), 5.70-5.87 (m, 1H), 2.43 (s, 3H), 1.67-1.75 (m, 6H), 1.59-1.65 (m, 3H) CL Example 3

1-{3-[(1R)-1-{[6-(dimethylphosphoryl)-2-methylpyrido[3,4-d]pyrimidin-4-yl]amino}ethyl]-2-fluorophenyl}-1,1-difluoro-2-methylpropan-2-ol

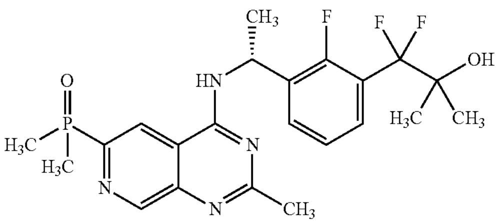 [SMILES: Cc1nc(N[C@H](C)c2cccc(C(F)(F)C(C)(C)O)c2F)c2cc(P(C)(C)=O)ncc2n1]

To a solution of N-[(1R)-1-(3-{1,1-difluoro-2-methyl-2-[(triethylsilyl)oxy]propyl}-2-fluorophenyl)ethyl]-6-(dimethylphosphoryl)-2-methylpyrido[3,4-d]pyrimidin-4-amine (107 mg, 184 μmol) and triethylsilane (2.9 μl, 18 μmol) in dichlormethane, trifluoroacetic acid (210 μl, 2.8 mmol) was added dropwise at RT and the mixture was stirred overnight. Then, further trifluoroacetic acid (210 μl, 2.8 mmol) was added and tehreaction mixture was stirred again overnight, then the mixture was diluted with toluene, concentrated and purified by preparative HPLC (acidic method) to yield the title compound (16 mg, 98% purity, 18% yield)

LC-MS (Method 4): $R_t$=0.82 min; MS (ESIpos): m/z=467.46 $[M+H]^+$

1H NMR (DMSO-d6) δ: 9.21-9.35 (m, 1H), 9.09 (s, 1H), 8.98 (d, J=6.6 Hz, 1H), 7.54-7.73 (m, 1H), 7.30-7.40 (m, 1H), 7.14-7.26 (m, 1H), 5.71-5.85 (m, 1H), 5.34 (s, 1H), 2.39-2.43 (m, 3H), 1.68-1.75 (m, 6H), 1.57-1.63 (m, 3H), 1.18-1.25 (m, 7H)

Example 4

1-[4-({(1R)-1-[3-(1,1-difluoro-2-hydroxy-2-methylpropyl)-2-fluorophenyl]ethyl}amino)-2-methylpyrido[3,4-d]pyrimidin-6-yl]-1lambda$^5$-phospholan-1-one

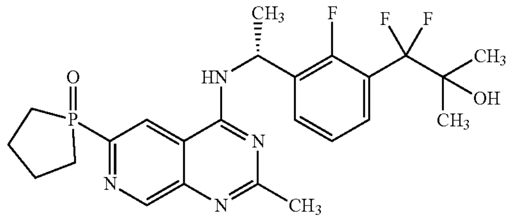 [SMILES: Cc1nc(N[C@H](C)c2cccc(C(F)(F)C(C)(C)O)c2F)c2cc(P3(=O)CCCC3)ncc2n1]

To a solution of 1-(3-{(1R)-1-[(6-bromo-2-methylpyrido[3,4-d]pyrimidin-4-yl)amino]ethyl}-2-fluorophenyl)-1,1-difluoro-2-methylpropan-2-ol (80.0 mg, 170 μmol), 1lambda5-phospholan-1-one (17.7 mg, 170 μmol) and triethylamine (83 μl, 600 μmol; CAS-RN:[121-44-8]) in acetonitrile (1.8 ml) under Argon was added tetrakis(triphenylphosphin)palladium(0) (29.5 mg, 25.6 μmol; CAS-RN: [14221-01-3]) and the mixture was stirred at 90° C. overnight. The mixture was cooled, filtered and concentrated. The residue was purified by preparative thin layer chromatography (silica gel, dichloromethane, ethanol 9:1) to yield the title compound (60.7 mg, 95% purity, 69% yield)

LC-MS (Method 2): $R_t$=1.07 min; MS (ESIpos): m/z=493 $[M+H]^+$

1H NMR (DMSO-d6) δ: 9.32 (d, J=7.4 Hz, 1H), 9.07-9.12 (m, 1H), 9.00-9.06 (m, 1H), 7.59-7.67 (m, 1H), 7.27-7.36 (m, 1H), 7.18-7.26 (m, 1H), 5.76-5.86 (m, 1H), 5.27-5.39 (m, 1H), 2.41 (s, 3H), 1.93-2.21 (m, 6H), 1.75-1.90 (m, 2H), 1.53-1.63 (m, 3H), 1.12-1.32 (m, 6H)

Example 5

1-benzyl-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one

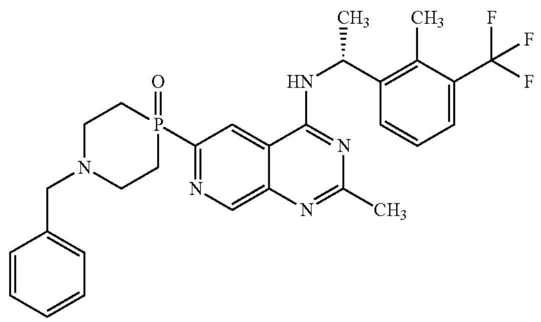 [SMILES: Cc1nc(N[C@H](C)c2cccc(C(F)(F)F)c2C)c2cc(P3(=O)CCN(Cc4ccccc4)CC3)ncc2n1]

To a solution of the substrate 6-bromo-2-methyl-N-{(1R)-1-[2-methyl-3-(trifluoromethyl)phenyl]ethyl}pyrido[3,4-d]pyrimidin-4-amine (100 mg, 235 μmol), 1-benzyl-1,4lambda5-azaphosphinan-4-one (49.2 mg, 235 μmol) and triethylamine (110 μl, 820 μmol) in acetonitrile (1.2 ml) under argon was added tetrakis(triphenylphosphin)palladium(0) (43.1 mg, 47.0 μmol) and the mixture was heated at 90° C. overnight. The mixture was then cooled, filtered, concentrated and purified by HPLC (basic method) to yield the title compound as white solid (71 mg, 95% purity, 52% yield).

LC-MS (Method 2): $R_t$=1.39 min; MS (ESIpos): m/z=554 $[M+H]^+$ $^1$H-NMR (400 MHz, DMSO-d6) δ[ppm]: 1.566 (5.04), 1.584 (5.07), 1.867 (0.43), 1.906 (0.85), 1.947 (0.48), 2.322 (0.81), 2.326 (1.14), 2.332 (0.91), 2.336 (0.67), 2.361 (0.78), 2.372 (0.71), 2.381 (0.76), 2.418 (16.00), 2.518 (3.76), 2.522 (2.40), 2.620 (6.37), 2.664 (0.64), 2.669 (0.90), 2.673 (0.64), 2.801 (0.93), 2.831 (1.02), 2.860 (0.40), 2.917 (0.62), 2.931 (0.48), 2.950 (0.47), 2.961 (0.54), 2.972 (0.66), 2.985 (0.47), 3.003 (0.41), 3.655 (6.52), 5.698 (0.78), 5.715 (1.21), 5.733 (0.76), 7.249 (0.50), 7.255 (0.66), 7.263 (1.07), 7.268 (0.78), 7.271 (0.85), 7.277 (0.91), 7.284 (0.72), 7.323 (0.79), 7.329 (0.48), 7.343 (5.16), 7.350 (5.04), 7.358 (12.53), 7.371 (0.67), 7.380 (0.98), 7.538 (1.74), 7.556 (1.40), 7.779 (1.54), 7.798 (1.38), 8.977 (1.78), 8.992 (1.74), 9.104 (4.69), 9.350 (1.33), 9.368 (1.28).

Example 6

4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one

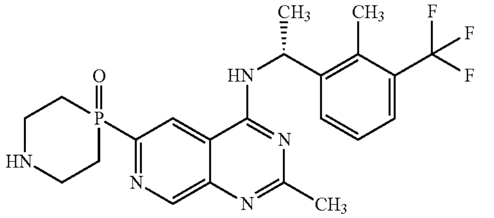

To a solution of 1-benzyl-4-[2-methyl-4-({(1R)-1-[2-methyl-3-(trifluoromethyl)phenyl]ethyl}amino)pyrido[3,4-d]pyrimidin-6-yl]-1,4lambda5-azaphosphinan-4-one (130 mg, 235 μmol) in ethanol (2.0 ml) was added Pd/C 10% (50.0 mg, 47.0 μmol). The flask was evacuated and backfilled with argon (3×). Then, the flask was purged with hydrogen and the mixture stirred at RT under hydrogen atmosphere for two days. The mixture was then filtered, concentrated under reduced pressure and purified by column chromatography (silica gel, dichloromethane/ethanol). The combined fractions were concentrated to yield the title compound 35.0 mg (32% yield).

LC-MS (Method 2): $R_t$=1.10 min; MS (ESIneg): m/z=462 $[M-H]^-$

1H NMR (DMSO-d6) δ: 9.28-9.43 (m, 1H), 9.09 (s, 1H), 8.89-9.01 (m, 1H), 7.74-7.87 (m, 1H), 7.48-7.60 (m, 1H), 7.26-7.44 (m, 1H), 5.61-5.84 (m, 1H), 2.96-3.23 (m, 5H), 2.62 (s, 3H), 2.42 (s, 3H), 2.27-2.37 (m, 3H), 1.75-1.88 (m, 2H), 1.54-1.62 (m, 3H)

Example 7

1-acetyl-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one

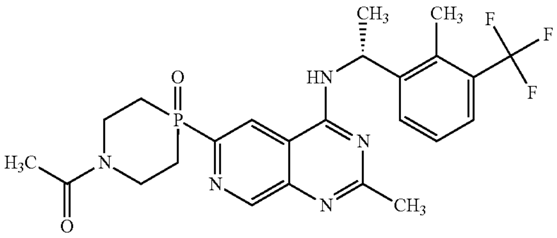 [SMILES: CC(=O)N1CCP(=O)(c2cc3c(N[C@H](C)c4cccc(C(F)(F)F)c4C)nc(C)nc3cn2)CC1]

To a solution of 4-[2-methyl-4-({(1R)-1-[2-methyl-3-(trifluoromethyl)phenyl]ethyl}amino)pyrido[3,4-d]pyrimidin-6-yl]-1,4lambda5-azaphosphinan-4-one (33.0 mg, 71% purity, 50.2 μmol) in dichloromethane (530 μl) at RT was added N,N-diisopropylethylamine (10 μl, 60 μmol) and acetic anhydride (5.2 μl, 55 μmol) and the mixture was stirred overnight at RT. The mixture was then titurated with toluene, concentrated and purified by HPLC (basic method) to yield the title compound (21.5 mg, 95% purity, 80% yield).

LC-MS (Method 2): $R_t$=1.13 min; MS (ESIneg): m/z=504 $[M-H]^-$ $^1$H-NMR (400 MHz, DMSO-d6) δ[ppm]: 1.574 (4.69), 1.591 (4.67), 2.054 (0.40), 2.116 (16.00), 2.254 (0.43), 2.274 (0.40), 2.327 (1.12), 2.332 (0.83), 2.382 (0.42), 2.420 (12.71), 2.518 (4.41), 2.523 (3.04), 2.623 (6.24), 2.669 (1.14), 2.673 (0.82), 3.859 (0.59), 3.872 (0.59), 3.885 (0.49), 3.916 (0.41), 5.708 (0.48), 5.724 (0.68), 5.739 (0.45), 7.348 (0.72), 7.367 (1.57), 7.387 (0.90), 7.543 (1.68), 7.561 (1.36), 7.787 (1.50), 7.806 (1.35), 9.010 (1.53), 9.026 (1.52), 9.094 (3.72), 9.375 (0.88), 9.389 (0.84).

Example 8

1-benzyl-4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one

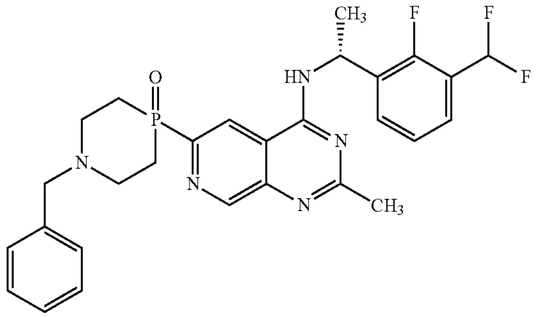 [SMILES: Cc1nc(N[C@H](C)c2cccc(C(F)F)c2F)c2cc(P3(=O)CCN(Cc4ccccc4)CC3)ncc2n1]

Following general procedure 1, a solution of 6-bromo-N-{(1R)-1-[3-(difluoromethyl)-2-fluorophenyl]ethyl}-2-methylpyrido[3,4-d]pyrimidin-4-amine (300 mg, 730 μmol), 1-benzyl-1,4lambda$^5$-azaphosphinan-4-one (153 mg, 730 μmol) and triethylamine (360 μl, 2.6 mmol) in acetonitrile (3.6 mL) under argon was added tetrakis(triphenylphosphin) palladium(0) (126 mg, 109 μmol) and the mixture was heated at 90° C. for 16 hours. The mixture was filtered and concentrated and purified by Biotage-Selekt. flash column chromatography using CH2Cl2/Ethanol (9/1) as eluent to give the title compound 1-benzyl-4-[4-({(1R)-1-[3-(difluoromethyl)-2-fluorophenyl]ethyl}amino)-2-methylpyrido[3,4-d]pyrimidin-6-yl]-1,4lambda5-azaphosphinan-4-one (366 mg, 95% purity, 88% yield).

LC-MS (Method 2): $R_t$=1.28 min; MS (ESIpos): m/z=541 $[M+H]^+$ $^1$H-NMR (400 MHz, DMSO-d6) δ[ppm]: 1.035 (0.64), 1.052 (1.44), 1.070 (0.77), 1.234 (0.73), 1.611 (5.60), 1.629 (5.58), 1.870 (0.47), 1.914 (0.90), 1.951 (0.54), 2.323 (0.48), 2.327 (0.73), 2.332 (0.69), 2.370 (0.86), 2.380 (0.76), 2.390 (0.84), 2.401 (0.82), 2.430 (16.00), 2.518 (2.19), 2.523 (1.64), 2.665 (0.45), 2.669 (0.64), 2.673 (0.44), 2.803 (0.98), 2.834 (1.09), 2.860 (0.46), 2.911 (0.69), 2.925 (0.54), 2.943 (0.54), 2.954 (0.60), 2.965 (0.71), 2.980 (0.52), 2.997 (0.45), 3.654 (6.72), 4.356 (0.44), 5.758 (0.41), 5.774 (0.88), 5.792 (1.35), 5.810 (0.87), 7.102 (1.35), 7.238 (2.86), 7.249 (0.59), 7.255 (0.73), 7.263 (1.15), 7.271 (0.92), 7.278 (1.74), 7.284 (0.89), 7.298 (2.23), 7.309 (0.68), 7.317 (1.36), 7.323 (1.06), 7.329 (0.56), 7.343 (4.87), 7.350 (5.10), 7.358 (12.04), 7.374 (1.47), 7.493 (0.73), 7.510 (1.23), 7.528 (0.61), 7.681 (0.67), 7.699 (1.20), 7.717 (0.60), 8.979 (1.85), 8.995 (1.85), 9.124 (4.59), 9.262 (1.39), 9.280 (1.36).

Example 9

4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one

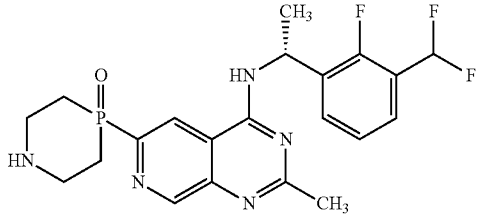 [SMILES: Cc1nc(N[C@H](C)c2cccc(C(F)F)c2F)c2cc(P3(=O)CCNCC3)ncc2n1]

To a solution of 1-benzyl-4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one (100 mg, 185 μmol) in ethanol (1.6 mL) was added palladium on carbon (10 wt %, 158 mg, 148 μmol). The flask was evacuated and backfilled with argon (repeat three times). Then the flask was purged with hydrogen gas and the mixture stirred at room temperature under hydrogen atmosphere for 16 hours. The crude mixture was then filtered and concentrated under reduced pressure. The compound was purified by biotage flash column chromatography on silica gel using dichloromethane and ethanol (9/1) as eluent. The title compound was obtained (31.0 mg, 37% yield).

LC-MS (Method 2): $R_t$=0.97 min; MS (ESIpos): m/z=450 $[M+H]^+$ $^1$H-NMR (400 MHz, DMSO-d6) δ[ppm]: 1.074 (10.08), 1.094 (0.53), 1.236 (0.48), 1.617 (4.46), 1.635 (4.38), 1.808 (0.72), 1.846 (0.40), 1.955 (11.30), 2.169 (0.61), 2.297 (0.66), 2.318 (1.09), 2.323 (1.67), 2.327 (2.15), 2.332 (1.51), 2.336 (0.88), 2.429 (13.03), 2.518 (6.66), 2.523 (4.59), 2.660 (0.56), 2.665 (1.17), 2.669 (1.65), 2.673 (1.17), 2.678 (0.56), 2.781 (10.75), 2.942 (16.00), 3.029 (0.64), 3.081 (0.80), 3.090 (0.72), 3.113 (0.66), 3.122 (0.64), 3.129 (0.61), 3.144 (0.61), 3.153 (0.61), 5.777 (0.69), 5.794 (1.06), 5.812 (0.69), 7.105 (1.03), 7.240 (2.15), 7.284 (0.80), 7.303 (1.65), 7.322 (0.96), 7.376 (0.90), 7.497 (0.58), 7.514 (0.96), 7.532 (0.48), 7.686 (0.53), 7.703 (0.96), 7.721 (0.48), 8.954 (1.51), 8.969 (1.51), 9.112 (3.69), 9.242 (1.09), 9.259 (1.06).

Example 10

1-acetyl-4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one

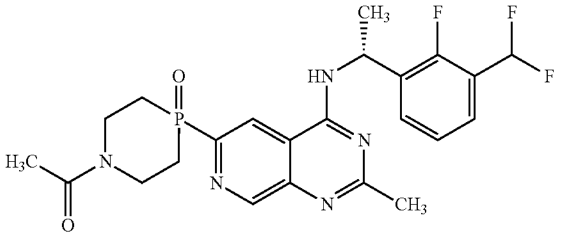 [SMILES: CC(=O)N1CCP(=O)(c2cc3c(N[C@H](C)c4cccc(C(F)F)c4F)nc(C)nc3cn2)CC1]

4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one (33.0 mg, 73.4 μmol) was dissolved in dichloromethane (0.78 mL) at room temperature. N,N-diisopropylethylamine (15 μl, 88 μmol) was added, followed by acetic anhydride (7.6 μl, 81 μmol). The mixture was stirred for 16 hours. Toluene was added and the mixture was partially evaporated. The compound was purified by HPLC (basic method) to give the title compound (23 mg, 95% purity, 61% yield).

LC-MS (Method 2): $R_t$=1.00 min; MS (ESIpos): m/z=492 $[M+H]^+$ $^1$H-NMR (400 MHz, DMSO-d6) δ[ppm]: 1.232 (0.11), 1.352 (0.11), 1.619 (2.10), 1.636 (2.04), 1.908 (0.17), 2.058 (0.22), 2.118 (6.62), 2.327 (3.48), 2.331 (2.48), 2.433 (5.63), 2.518 (16.00), 2.523 (10.32), 2.669 (3.42), 2.673 (2.43), 2.678 (1.16), 3.707 (0.17), 3.866 (0.33), 4.037 (0.17), 5.784 (0.28), 5.799 (0.39), 5.817 (0.28), 7.106 (0.50), 7.241 (0.99), 7.287 (0.33), 7.306 (0.77), 7.325 (0.44), 7.377 (0.44), 7.500 (0.33), 7.516 (0.50), 7.534 (0.22), 7.688 (0.28), 7.706 (0.50), 7.725 (0.22), 9.014 (0.72), 9.031 (0.77), 9.118 (1.82), 9.282 (0.55), 9.300 (0.50).

Example 11

1-{3-[(1R)-1-{[6-(dimethylphosphoryl)-2,8-dimethylpyrido[3,4-d]pyrimidin-4-yl]amino}ethyl]-2-fluorophenyl}-1,1-difluoro-2-methylpropan-2-ol

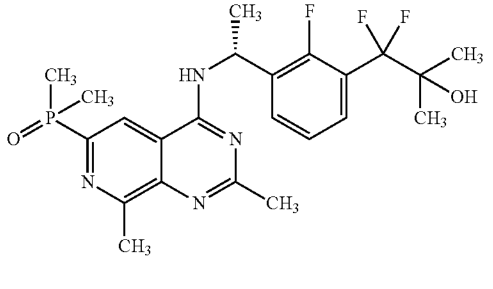 [SMILES: Cc1nc(N[C@H](C)c2cccc(C(F)(F)C(C)(C)O)c2F)c2cc(P(C)(C)=O)nc(C)c2n1]

N-[(1R)-1-(3-{1,1-difluoro-2-methyl-2-[(triethylsilyl)oxy]propyl}-2-fluorophenyl)ethyl]-6-(dimethylphosphoryl)-2,8-dimethylpyrido[3,4-d]pyrimidin-4-amine (100 mg, 168 μmol) was dissolved in dichloromethane (2 mL) at room temperature. Triethylsilan (2.7 μl, 17 μmol) was added, followed by trifluoroacetic acid (190 μl, 2.5 mmol). The resulting mixture was stirred at room temperature for 20 h. Water and ethyl acetate were added to the mixture and the phases were separated. The organic phase was dried through hydrophobic filtration. The solvent was evaporated. The compound was purified by HPLC (basic method) and subsequent preparative thin layer chromatography using dichloromethane and ethanol as eluents to give the title compound (12.0 mg, 15% yield).

LC-MS (Method 2): $R_t$=1.12 min; MS (ESIpos): m/z=481 $[M+H]^+$ $^1$H-NMR (400 MHz, DMSO-d6) δ[ppm]: 1.202 (6.15), 1.229 (6.43), 1.582 (4.64), 1.599 (4.66), 1.671 (6.95), 1.674 (7.40), 1.705 (7.13), 1.708 (7.21), 2.416 (16.00), 2.518 (0.97), 2.523 (0.64), 2.770 (13.42), 5.335 (7.89), 5.757 (3.57), 5.768 (0.76), 5.786 (1.17), 5.803 (0.74), 7.195 (0.74), 7.214 (1.75), 7.233 (1.13), 7.291 (0.66), 7.295 (0.77), 7.312 (1.09), 7.328 (0.51), 7.332 (0.47), 7.601 (0.61), 7.617 (1.06), 7.633 (0.55), 8.794 (1.93), 8.810 (1.91), 9.162 (1.32), 9.181 (1.26).

Example 12

1-{3-[(1R)-1-({6-[di(propan-2-yl)phosphoryl]-2-methylpyrido[3,4-d]pyrimidin-4-yl}amino)ethyl]-2-fluorophenyl}-1,1-difluoro-2-methylpropan-2-ol

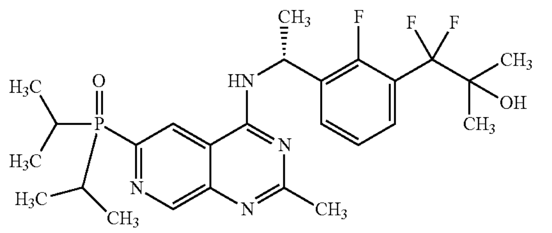 [SMILES: Cc1nc(N[C@H](C)c2cccc(C(F)(F)C(C)(C)O)c2F)c2cc(P(=O)(C(C)C)C(C)C)ncc2n1]

Following the general procedure 1, 1-(3-{(1R)-1-[(6-Brom-2-methylpyrido[3,4-d]pyrimidin-4-yl)amino]ethyl}-2-fluorphenyl)-1,1-difluor-2-methylpropan-2-ol (80.0 mg, 170 μmol) was reacted with diisopropylphosphinoxid (22.9 mg, 170 μmol) at 90° C. for 16 hours. After that, additional tetrakis(triphenylphosphine)palladium(0) (19.7 mg, 17.0 μmol) were added and the mixture was stirred for additional 16 hours at 90° C. The mixture was then cooled to room temperature and filtered. The compound was purified by preparative thin layer chromatography on silica gel plates using dichloromethane and ethanol as solvent to give the title compound (20.1 mg, 95% purity, 21% yield).

LC-MS (Method 2): $R_t$=1.19 min; MS (ESIpos): m/z=523 $[M+H]^+$ $^1$H-NMR (400 MHz, DMSO-d6) δ[ppm]: 0.922 (3.58), 0.929 (3.65), 0.939 (3.78), 0.947 (3.71), 0.960 (3.71), 0.968 (3.78), 0.978 (3.71), 0.986 (3.51), 1.052 (0.95), 1.065 (0.95), 1.070 (1.01), 1.083 (0.95), 1.097 (1.22), 1.105 (3.78), 1.115 (4.25), 1.123 (4.25), 1.133 (3.71), 1.143 (3.65), 1.153 (3.71), 1.161 (3.71), 1.171 (3.51), 1.195 (6.82), 1.222 (7.02), 1.593 (4.86), 1.611 (4.86), 2.318 (0.47), 2.409 (16.00), 2.426 (0.88), 2.444 (1.35), 2.452 (1.15), 2.461 (1.82), 2.470 (2.30), 2.518 (6.75), 2.523 (4.66), 3.378 (0.41), 5.333 (2.23), 5.758 (9.92), 5.769 (0.88), 5.787 (1.28), 5.805 (0.81), 7.211 (0.74), 7.230 (1.82), 7.249 (1.22), 7.300 (0.88), 7.317 (1.22), 7.333 (0.54), 7.618 (0.68), 7.634 (1.15), 7.650 (0.61), 8.898 (1.96), 8.912 (1.89), 9.079 (4.86), 9.081 (4.79), 9.357 (1.42), 9.375 (1.35).

Example 13

6-(dimethylphosphoryl)-2-methyl-N-{(1R)-1-[2-methyl-3-(trifluoromethyl)phenyl]ethyl}pyrido[2,3-d]pyrimidin-4-amine

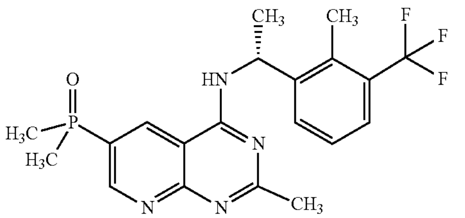 [SMILES: Cc1nc(N[C@H](C)c2cccc(C(F)(F)F)c2C)c2cc(P(C)(C)=O)cnc2n1]

Following the general procedure 1: 6-bromo-2-methyl-N-{(1R)-1-[2-methyl-3-(trifluoromethyl)phenyl]ethyl}pyrido[2,3-d]pyrimidin-4-amine (60.0 mg, 141 μmol) and dimethylphosphine oxide (11.0 mg, 141 μmol) gave the titled compound (25.1 mg, 40%) after purification by preperative TLC ($CH_2Cl_2$/EtOH 8:1).

LC-MS (Method 2): $R_t$=1.08 min; MS (ESIpos): m/z=423 $[M+H]^+$ $^1$H-NMR (400 MHz, DMSO-d6) δ[ppm]: 1.565 (4.57), 1.583 (4.65), 1.782 (14.54), 1.815 (13.99), 2.399 (16.00), 2.518 (3.22), 2.522 (2.15), 2.623 (5.45), 2.673 (0.50), 5.713 (0.69), 5.730 (1.07), 5.748 (0.69), 7.346 (0.63), 7.366 (1.38), 7.385 (0.80), 7.542 (1.46), 7.560 (1.18), 7.784 (1.29), 7.803 (1.18), 9.175 (1.57), 9.180 (1.76), 9.186 (1.60), 9.192 (1.73), 9.230 (1.13), 9.244 (1.98), 9.249 (2.01), 9.274 (1.46), 9.279 (1.24).

Example 14

1-{3-[(1R)-1-{[6-(dimethylphosphoryl)-2-methylpyrido[2,3-d]pyrimidin-4-yl]amino}ethyl]-2-fluorophenyl}-1,1-difluoro-2-methylpropan-2-ol

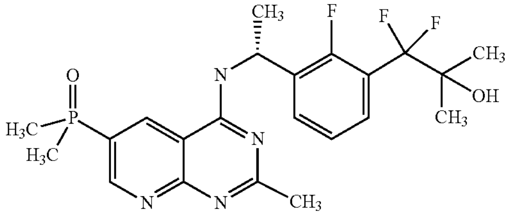

Following the general procedure 1: 1-(3-{(1R)-1-[(6-bromo-2-methylpyrido[2,3-d]pyrimidin-4-yl)amino]ethyl}-2-fluorophenyl)-1,1-difluoro-2-methylpropan-2-ol (60.0 mg, 128 μmol) and dimethylphosphine oxide (9.98 mg, 128 μmol) gave the titled compound (30.0 mg, 48%) after purification by preperative HPLC (basic method).

LC-MS (Method 5): $R_t$=0.87 min; MS (ESIpos): m/z=467 $[M+H]^+$

$^1$H-NMR (400 MHz, DMSO-d6) δ[ppm]: 1.205 (5.76), 1.230 (6.07), 1.588 (4.46), 1.606 (4.51), 1.786 (8.48), 1.819 (8.44), 2.396 (16.00), 2.518 (8.50), 2.523 (6.25), 5.340 (6.99), 5.782 (0.71), 5.800 (1.11), 5.817 (0.72), 7.206 (0.69), 7.225 (1.64), 7.244 (1.08), 7.306 (0.72), 7.323 (1.03), 7.338 (0.50), 7.606 (0.55), 7.622 (0.99), 7.637 (0.53), 9.125 (1.22), 9.143 (1.18), 9.188 (1.57), 9.193 (1.97), 9.200 (1.71), 9.205 (1.81), 9.250 (1.44), 9.255 (1.28), 9.280 (1.41), 9.285 (1.28).

Example 15

1-{3-[(1R)-1-({6-[di(propan-2-yl)phosphoryl]-2-methylpyrido[2,3-d]pyrimidin-4-yl}amino)ethyl]-2-fluorophenyl}-1,1-difluoro-2-methylpropan-2-ol

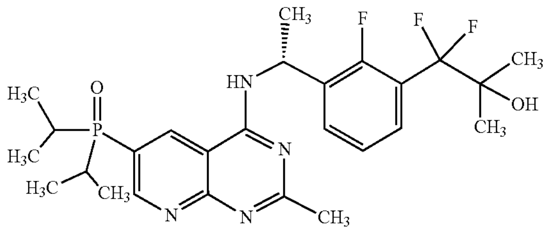 [SMILES: Cc1nc(N[C@H](C)c2cccc(C(F)(F)C(C)(C)O)c2F)c2cc(P(=O)(C(C)C)C(C)C)cnc2n1]

Following the general procedure 1: 1-(3-{(1R)-1-[(6-bromo-2-methylpyrido[2,3-d]pyrimidin-4-yl)amino]ethyl}-2-fluorophenyl)-1,1-difluoro-2-methylpropan-2-ol (100 mg, 213 μmol), di(propan-2-yl)-lambda[5]-phosphanone (28.6 mg, 213 μmol) and tetrakis(triphenylphosphin)palladium(0) (61.5 mg, 53.3 μmol) were heated at 90° C. for 2 days. The titled compound (52.6 mg, 45%) was obtained after purification by preperative HPLC (basic method).

LC-MS (Method 2): $R_t$=1.04 min; MS (ESIneg): m/z=521 $[M-H]^-$

$^1$H-NMR (400 MHz, DMSO-d6) δ[ppm]: 0.925 (3.35), 0.928 (3.47), 0.942 (3.57), 0.946 (3.47), 0.965 (3.47), 0.969 (3.52), 0.982 (3.54), 0.987 (3.37), 1.088 (2.86), 1.103 (3.69), 1.106 (3.84), 1.120 (3.32), 1.126 (3.30), 1.141 (3.76), 1.143 (3.84), 1.158 (2.93), 1.193 (5.98), 1.219 (6.16), 1.600 (4.45), 1.617 (4.40), 2.397 (16.00), 2.518 (3.84), 2.523 (2.49), 5.335 (4.35), 5.758 (1.91), 5.777 (0.73), 5.795 (1.12), 5.813 (0.71), 7.210 (0.71), 7.229 (1.71), 7.248 (1.10), 7.299 (0.66), 7.304 (0.76), 7.320 (1.05), 7.336 (0.51), 7.341 (0.44), 7.598 (0.59), 7.614 (1.03), 7.629 (0.54), 9.073 (1.47), 9.078 (1.91), 9.080 (1.83), 9.085 (1.49), 9.174 (1.27), 9.179 (1.17), 9.199 (1.27), 9.204 (1.12), 9.241 (1.25), 9.259 (1.20).

Example 16

1-[4-({(1R)-1-[3-(1,1-difluoro-2-hydroxy-2-methylpropyl)-2-fluorophenyl]ethyl}amino)-2-methylpyrido[2,3-d]pyrimidin-6-yl]-1lambda[5]-phospholan-1-one

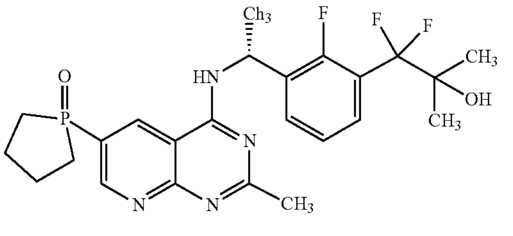

Following the general procedure 1: 1-(3-{(1R)-1-[(6-bromo-2-methylpyrido[2,3-d]pyrimidin-4-yl)amino]ethyl}-2-fluorophenyl)-1,1-difluoro-2-methylpropan-2-ol (100 mg, 213 μmol) and phospholane 1-oxide (22.2 mg, 213 μmol) gave the titled compound (66.6 mg, 60%) after purification by preperative TLC ($CH_2Cl_2$/EtOH 9:1).

LC-MS (Method 2): $R_t$=0.95 min; MS (ESIneg): m/z=491 $[M-H]^-$

$^1$H-NMR (400 MHz, DMSO-d6) δ[ppm]: 1.205 (6.62), 1.230 (6.90), 1.591 (5.00), 1.609 (4.97), 1.892 (0.48), 1.910 (0.63), 1.947 (1.32), 1.973 (1.37), 1.986 (1.06), 2.017 (1.06), 2.037 (0.99), 2.059 (0.91), 2.077 (0.58), 2.161 (0.48), 2.180 (0.71), 2.195 (0.89), 2.209 (0.89), 2.223 (0.53), 2.327 (0.91), 2.331 (0.66), 2.397 (16.00), 2.518 (3.65), 2.523 (2.48), 2.669 (0.91), 2.673 (0.63), 5.342 (6.39), 5.759 (8.98), 5.784 (0.81), 5.802 (1.24), 5.820 (0.79), 7.202 (0.79), 7.221 (1.85), 7.241 (1.19), 7.300 (0.74), 7.305 (0.84), 7.322 (1.17), 7.337 (0.58), 7.341 (0.53), 7.606 (0.66), 7.622 (1.14), 7.638 (0.61), 9.114 (1.70), 9.119 (1.93), 9.124 (1.80), 9.130 (1.72), 9.177 (1.37), 9.195 (1.29), 9.243 (1.50), 9.248 (1.37), 9.272 (1.50), 9.277 (1.37).

Example 17

6-(dimethylphosphoryl)-2,7-dimethyl-N-{(1R)-1-[2-methyl-3-(trifluoromethyl)phenyl]ethyl}pyrido[2,3-d]pyrimidin-4-amine

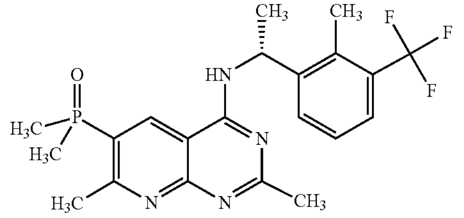 [SMILES: Cc1nc(N[C@H](C)c2cccc(C(F)(F)F)c2C)c2cc(P(C)(C)=O)c(C)nc2n1]

Following the general procedure 1: 6-bromo-2,7-dimethyl-N-{(1R)-1-[2-methyl-3-(trifluoromethyl)phenyl]ethyl}pyrido[2,3-d]pyrimidin-4-amine (100 mg, 228 μmol), dimethylphosphine oxide (35.5 mg, 455 μmol) and tetrakis(triphenylphosphin)palladium(0) (52.6 mg, 45.5 μmol) gave the titled compound (24.0 mg, 23%) after purification by preperative HPLC (basic method).

LC-MS (Method 2): $R_t$=1.10 min; MS (ESIneg): m/z=435 $[M-H]^-$

$^1$H-NMR (400 MHz, DMSO-d6) δ[ppm]: 1.564 (4.64), 1.582 (4.69), 1.838 (16.00), 1.872 (15.74), 2.336 (0.46), 2.364 (15.23), 2.518 (5.56), 2.523 (3.92), 2.613 (5.61), 2.678 (0.44), 2.832 (12.47), 5.705 (0.71), 5.722 (1.08), 5.739 (0.69), 7.342 (0.64), 7.362 (1.39), 7.381 (0.80), 7.541 (1.51), 7.559 (1.22), 7.765 (1.35), 7.785 (1.20), 8.926 (2.19), 8.958 (2.17), 9.037 (1.17), 9.054 (1.11).

Example 18

N-{(1R)-1-[3-(difluoromethyl)-2-fluorophenyl]ethyl}-6-(dimethylphosphoryl)-2,7-dimethylpyrido[2,3-d]pyrimidin-4-amine

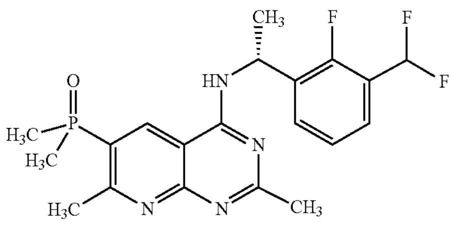 [SMILES: Cc1nc(N[C@H](C)c2cccc(C(F)F)c2F)c2cc(P(C)(C)=O)c(C)nc2n1]

Following the general procedure 1: 6-bromo-N-{(1R)-1-[3-(difluoromethyl)-2-fluorophenyl]ethyl}-2,7-dimethylpyrido[2,3-d]pyrimidin-4-amine (100 mg, 235 μmol), dimethylphosphine oxide (36.7 mg, 470 μmol) and tetrakis(triphenylphosphine)palladium(0) (54.3 mg, 47.0 μmol) gave the titled compound (31.0 mg, 30%) after purification by preperative HPLC (basic method).

LC-MS (Method 2): $R_t$=0.96 min; MS (ESIpos): m/z=423 $[M+H]^+$ $^1$H-NMR (400 MHz, DMSO-d6) δ[ppm]: 1.611 (4.86), 1.629 (4.84), 1.839 (13.82), 1.872 (13.83), 2.331 (0.48), 2.376 (16.00), 2.518 (2.60), 2.523 (1.81), 2.673 (0.46), 2.845 (13.08), 5.789 (0.74), 5.808 (1.14), 5.825 (0.72), 7.107 (1.09), 7.243 (2.31), 7.280 (0.82), 7.299 (1.78), 7.319 (1.01), 7.379 (0.96), 7.497 (0.61), 7.514 (1.02), 7.532 (0.50), 7.671 (0.56), 7.688 (1.01), 7.706 (0.50), 8.923 (2.23), 8.951 (1.42), 8.956 (2.52), 8.969 (1.21).

Example 19

1-{3-[(1R)-1-{[6-(dimethylphosphoryl)-2,7-dimethylpyrido[2,3-d]pyrimidin-4-yl]amino}ethyl]-2-fluorophenyl}-1,1-difluoro-2-methylpropan-2-ol

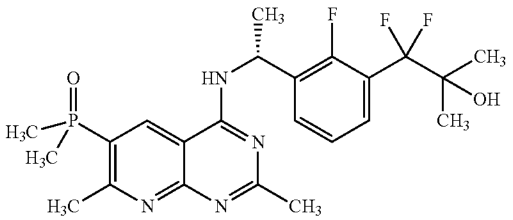 [SMILES: Cc1nc(N[C@H](C)c2cccc(C(F)(F)C(C)(C)O)c2F)c2cc(P(C)(C)=O)c(C)nc2n1]

Following the general procedure 1: 1-(3-{(1R)-1-[(6-bromo-2,7-dimethylpyrido[2,3-d]pyrimidin-4-yl)amino]ethyl}-2-fluorophenyl)-1,1-difluoro-2-methylpropan-2-ol (100 mg, 207 μmol), dimethylphosphine oxide (16.1 mg, 207 μmol) and tetrakis(triphenylphosphine)palladium(0) (59.8 mg, 51.7 μmol) gave the titled compound (40.0 mg, 38%) after purification by preperative HPLC (basic method).

LC-MS (Method 2): $R_t$=0.92 min; MS (ESIneg): m/z=479 $[M-H]^-$ $^1$H-NMR (400 MHz, DMSO-d6) δ[ppm]: 0.928 (0.41), 1.205 (5.87), 1.229 (6.09), 1.588 (4.60), 1.605 (4.60), 1.839 (12.73), 1.873 (12.58), 2.074 (0.63), 2.331 (1.63), 2.337 (0.74), 2.363 (16.00), 2.518 (8.76), 2.523 (6.16), 2.669 (2.30), 2.673 (1.56), 2.678 (0.71), 2.846 (12.96), 5.344 (7.94), 5.779 (0.71), 5.797 (1.11), 5.815 (0.71), 7.202 (0.71), 7.221 (1.67), 7.240 (1.08), 7.305 (0.74), 7.322 (1.04), 7.338 (0.48), 7.591 (0.56), 7.607 (1.00), 7.624 (0.52), 8.924 (2.30), 8.938 (1.34), 8.957 (3.12).

Example 20

1-[4-({(1R)-1-[3-(1,1-difluoro-2-hydroxy-2-methylpropyl)-2-fluorophenyl]ethyl}amino)-2,7-dimethylpyrido[2,3-d]pyrimidin-6-yl]-1lambda$^5$-phospholan-1-one

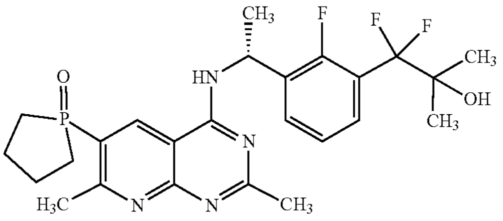 [SMILES: Cc1nc(N[C@H](C)c2cccc(C(F)(F)C(C)(C)O)c2F)c2cc(P3(=O)CCCC3)c(C)nc2n1]

Following the general procedure 1: 1-(3-{(1R)-1-[(6-bromo-2,7-dimethylpyrido[2,3-d]pyrimidin-4-yl)amino]ethyl}-2-fluorophenyl)-1,1-difluoro-2-methylpropan-2-ol (104 mg, 215 μmol), 1lambda$^5$-phospholan-1-one (22.4 mg, 215 μmol) and tetrakis(triphenylphosphine)palladium(0) (62.2 mg, 53.8 μmol) gave the titled compound (23.8 mg, 21%) after purification by preperative HPLC (basic method).

LC-MS (Method 2): $R_t$=0.97 min; MS (ESIpos): m/z=507 $[M+H]^+$ $^1$H-NMR (400 MHz, DMSO-d6) δ[ppm]: 1.202 (6.28), 1.226 (6.50), 1.601 (4.85), 1.619 (4.83), 1.797 (0.56), 1.806 (0.53), 1.820 (0.65), 1.837 (0.60), 1.847 (0.66), 1.863 (0.47), 1.948 (0.55), 1.968 (0.73), 1.983 (0.78), 2.012 (1.21), 2.047 (0.61), 2.064 (0.56), 2.074 (0.50), 2.327 (0.80), 2.332 (0.60), 2.366 (16.00), 2.426 (0.47), 2.444 (0.47), 2.518 (3.71), 2.523 (2.54), 2.669 (0.83), 2.673 (0.58), 2.828 (13.23), 5.344 (5.12), 5.782 (0.76), 5.800 (1.18), 5.817 (0.75), 7.202 (0.75), 7.221 (1.78), 7.240 (1.13), 7.302 (0.66), 7.306 (0.76), 7.323 (1.10), 7.339 (0.53), 7.343 (0.48), 7.584 (0.61), 7.600 (1.08), 7.616 (0.55), 8.907 (2.08), 8.938 (3.17), 8.956 (1.30).

Example 21

1-{3-[(1R)-1-({6-[di(propan-2-yl)phosphoryl]-2,7-dimethylpyrido[2,3-d]pyrimidin-4-yl}amino)ethyl]-2-fluorophenyl}-1,1-difluoro-2-methylpropan-2-ol

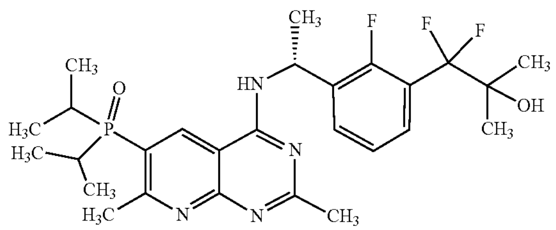 [SMILES: Cc1nc(N[C@H](C)c2cccc(C(F)(F)C(C)(C)O)c2F)c2cc(P(=O)(C(C)C)C(C)C)c(C)nc2n1]

Following the general procedure 1: 1-(3-{(1R)-1-[(6-bromo-2,7-dimethylpyrido[2,3-d]pyrimidin-4-yl)amino]

ethyl}-2-fluorophenyl)-1,1-difluoro-2-methylpropan-2-ol (104 mg, 215 µmol), di(propan-2-yl)-lambda$^5$-phosphanone (28.9 mg, 215 µmol) and tetrakis(triphenylphosphine)palladium(0) (99.5 mg, 86.1 µmol) were heated at 90° C. for 3 days. The titled compound (20.5 mg, 17%) was obtained after purification by preperative TLC ($CH_2Cl_2$/EtOH 9:1).

LC-MS (Method 2): $R_t$=1.05 min; MS (ESIpos): m/z=537 $[M+H]^+$ $^1$H-NMR (400 MHz, DMSO-d6) δ[ppm]: 0.878 (2.79), 0.894 (3.73), 0.896 (3.80), 0.911 (3.03), 0.918 (3.01), 0.934 (3.75), 0.935 (3.73), 0.951 (2.72), 1.021 (0.63), 1.040 (0.76), 1.050 (0.45), 1.052 (0.67), 1.058 (0.83), 1.070 (0.43), 1.077 (1.06), 1.095 (0.61), 1.158 (2.76), 1.176 (6.18), 1.185 (6.61), 1.193 (5.28), 1.213 (9.15), 1.231 (3.30), 1.608 (4.49), 1.626 (4.45), 2.331 (0.99), 2.337 (0.45), 2.367 (16.00), 2.518 (5.28), 2.523 (3.75), 2.558 (0.72), 2.567 (1.08), 2.575 (0.99), 2.584 (0.70), 2.593 (0.92), 2.610 (0.52), 2.673 (0.97), 2.678 (0.43), 2.834 (10.52), 5.331 (6.47), 5.759 (1.84), 5.776 (0.72), 5.794 (1.10), 5.812 (0.70), 7.209 (0.70), 7.229 (1.66), 7.248 (1.12), 7.301 (0.65), 7.305 (0.76), 7.322 (1.03), 7.338 (0.52), 7.342 (0.45), 7.557 (0.56), 7.573 (1.01), 7.589 (0.52), 8.817 (1.10), 8.844 (1.10), 8.988 (1.01), 9.006 (0.99).

Example 22

6-(dimethylphosphoryl)-2-methyl-N-{(1R)-1-[2-methyl-3-(trifluoromethyl)phenyl]ethyl}-7-(trifluoromethyl)pyrido[2,3-d]pyrimidin-4-amine

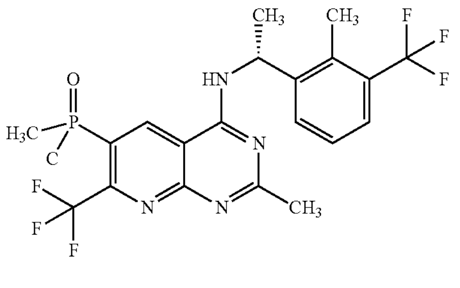 [SMILES: Cc1nc(N[C@H](C)c2cccc(C(F)(F)F)c2C)c2cc(P(C)(C)=O)c(C(F)(F)F)nc2n1]

Following the general procedure 1: 6-bromo-2-methyl-N-{(1R)-1-[2-methyl-3-(trifluoromethyl)phenyl]ethyl}-7-(trifluoromethyl)pyrido[2,3-d]pyrimidin-4-amine (70.0 mg, 142 µmol), dimethylphosphine oxide (15.5 mg, 199 µmol) and tetrakis(triphenylphosphin)palladium(0) (73.8 mg, 63.4 µmol) were heated at 90° C. for 2 days. The titled compound (10.0 mg, 14%) was obtained after purification by preparative HPLC (basic method).

LC-MS (Method 2): $R_t$=1.24 min; MS (ESIpos): m/z=491 $[M+H]^+$ 1H-NMR (400 MHz, DMSO-d6) δ[ppm]: 1.065 (4.29), 1.154 (0.53), 1.172 (0.53), 1.232 (0.71), 1.590 (3.65), 1.607 (3.65), 1.861 (3.88), 1.895 (3.88), 2.327 (3.41), 2.331 (2.47), 2.430 (11.71), 2.518 (16.00), 2.523 (10.65), 2.618 (4.82), 2.669 (3.53), 2.673 (2.53), 5.730 (0.59), 5.747 (1.00), 5.760 (10.35), 7.353 (0.53), 7.373 (1.12), 7.393 (0.65), 7.556 (1.41), 7.575 (1.18), 7.792 (1.12), 7.811 (1.00), 9.463 (1.35), 9.495 (1.29), 9.575 (0.59), 9.593 (0.59).

Example 23

(2RS)-1-{3-[(1R)-1-{[6-(dimethylphosphoryl)-2-methylpyrido[3,4-d]pyrimidin-4-yl]amino}ethyl]-2-fluorophenyl}-1,1-difluoro-2-methylhexan-2-ol (Mixture of Diastereomers)

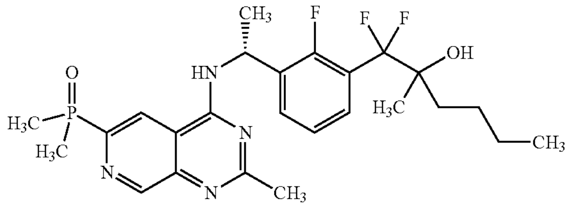 [SMILES: CCCCC(C)(O)C(F)(F)c1cccc([C@@H](C)Nc2nc(C)nc3cnc(P(C)(C)=O)cc23)c1F]

Using general procedure 6, starting from trifluoroacetic acid salt of (2RS)-1-{3-[(1R)-1-aminoethyl]-2-fluorophenyl}-1,1-difluoro-2-methylhexan-2-ol (1/1) (mixture of diastereomers, intermddiate 82, 64.0 mg, 81% purity, 128 µmol) and 6-(dimethylphosphoryl)-2-methylpyrido[3,4-d]pyrimidin-4-ol (33.5 mg, 141 µmol) (intermediate 71). Purification by preparative thin layer chromatography (silica gel plates 20×20 cm, dichloromethane, ethanol), to obtain 15.5 mg (95% purity, 23% yield) of the title compound.

LC-MS (Method 2): $R_t$=1.18 min; MS (ESIpos): m/z=509 $[M+H]^+$ $^1$H-NMR (400 MHz, DMSO-d6) δ[ppm]: 0.791 (2.29), 0.802 (3.24), 0.809 (6.54), 0.819 (7.45), 0.827 (3.42), 0.837 (3.37), 1.135 (5.66), 1.154 (5.70), 1.176 (1.10), 1.194 (1.96), 1.212 (2.28), 1.228 (2.28), 1.268 (0.77), 1.286 (0.72), 1.299 (0.72), 1.313 (0.68), 1.330 (0.80), 1.346 (0.74), 1.358 (0.80), 1.376 (0.67), 1.413 (0.60), 1.452 (1.14), 1.465 (0.96), 1.481 (1.10), 1.492 (1.09), 1.516 (0.52), 1.586 (6.82), 1.603 (6.76), 1.689 (16.00), 1.723 (15.99), 2.084 (0.45), 2.332 (1.50), 2.336 (0.64), 2.411 (14.13), 2.423 (13.61), 2.518 (7.82), 2.523 (5.56), 2.673 (1.51), 2.678 (0.64), 5.174 (4.52), 5.191 (4.24), 5.758 (2.39), 5.765 (0.68), 5.782 (1.10), 5.801 (1.02), 5.821 (1.05), 5.839 (0.65), 7.200 (0.69), 7.207 (0.70), 7.220 (1.69), 7.226 (1.66), 7.239 (1.16), 7.245 (1.08), 7.295 (0.74), 7.312 (1.17), 7.322 (1.09), 7.338 (0.52), 7.605 (0.90), 7.623 (1.55), 7.641 (0.86), 8.963 (1.72), 8.970 (1.78), 8.979 (1.76), 8.984 (1.75), 9.089 (6.35), 9.263 (1.15), 9.282 (2.12), 9.301 (1.16).

Example 24

6-(dimethylphosphoryl)-2-methyl-N-{1-[2-(trifluoromethyl)pyridin-4-yl]ethyl}pyrido[3,4-d]pyrimidin-4-amine (enantiomer 1)

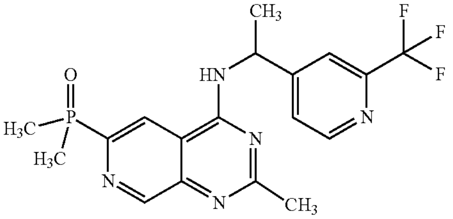 [SMILES: Cc1nc(NC(C)c2ccnc(C(F)(F)F)c2)c2cc(P(C)(C)=O)ncc2n1]

To a solution of 6-bromo-2-methyl-N-{(1S*)-1-[2-(trifluoromethyl)pyridin-4-yl]ethyl}pyrido[3,4-d]pyrimidin-4-amine (Enantiomer 1) (Intermediate 96, 50 mg, 121.3 μmol) tetrakis(triphenylphosphin)palladium(0) (21.0 mg, 18.2 μmol) was added, followed by acetonitrile (2 mL), triethylamine (59 μl, 420 μmol) and dimethyl-lambda$^5$-phosphanone (11 μl, 150 μmol). The atmosphere was exchanged to argon and the vial was sealed and heated to 90° C. for 24 h. The solvent was evaporated, the residue was redissolved in DMSO (2.5 mL) and filtered and then submitted to HPLC purification (basic method) to obtain the title compound 22.0 mg (98% purity, 43% yield) as white solid.

LC-MS (Method 2): $R_t$=1.02 min; MS (ESIpos): m/z=410.4 $[M+H]^+$ $^1$H-NMR (400 MHz, DMSO-d6) δ[ppm]: 1.627 (5.33), 1.645 (5.36), 1.689 (5.99), 1.696 (6.11), 1.723 (6.04), 1.730 (5.97), 2.427 (16.00), 2.518 (1.11), 2.522 (0.71), 5.611 (0.73), 5.629 (1.13), 5.647 (0.72), 7.761 (1.25), 7.770 (1.26), 7.773 (1.27), 8.004 (2.54), 8.699 (2.00), 8.711 (1.95), 8.919 (1.74), 8.920 (1.80), 8.935 (1.80), 8.937 (1.78), 9.108 (4.03), 9.275 (1.20), 9.293 (1.17).

Example 25

6-(dimethylphosphoryl)-2-methyl-N-{1-[2-(trifluoromethyl)pyridin-4-yl]ethyl}pyrido[3,4-d]pyrimidin-4-amine (enantiomer 2)

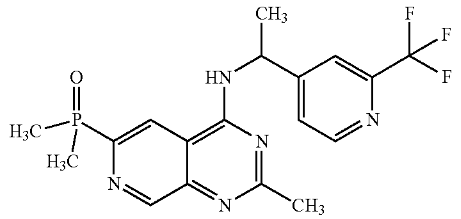 [SMILES: Cc1nc(NC(C)c2ccnc(C(F)(F)F)c2)c2cc(P(C)(C)=O)ncc2n1]

To a solution of 6-bromo-2-methyl-N-{(1R*)-1-[2-(trifluoromethyl)pyridin-4-yl]ethyl}pyrido[3,4-d]pyrimidin-4-amine (Enantiomer 2) (Intermediate 97, 50 mg, 121.3 μmol) Tetrakis(triphenylphosphin)palladium(0) (21.0 mg, 18.2 μmol) was added, followed by acetonitrile (2 mL), triethylamine (59 μl, 420 μmol) and dimethyl-lambda$^5$-phosphanone (11 μl, 150 μmol). The atmosphere was exchanged to argon and the vial was sealed and heated to 90° C. for 24 h. The solvent was evaporated, the residue was redissolved in DMSO (2.5 mL) and filtered and then submitted to HPLC purification (basic method) to obtain the title compound 17.0 mg (98% purity, 34% yield) as white solid.

LC-MS (Method 2): $R_t$=1.01 min; MS (ESIpos): m/z=410.4 $[M+H]^+$ $^1$H-NMR (400 MHz, DMSO-d6) δ[ppm]: 1.61-1.66 (m, 3H) 1.68-1.71 (m, 3H) 1.71-1.75 (m, 3H) 2.41-2.45 (m, 3H) 5.43-5.74 (m, 1H) 7.69-7.84 (m, 1H) 7.95-8.13 (m, 1H) 8.61-8.77 (m, 1H) 8.85-9.00 (m, 1H) 9.04-9.18 (m, 1H) 9.24-9.39 (m, 1H)

Example 26

4-({(1R)-1-[3-(1,1-difluoro-2-hydroxy-2-methylpropyl)-2-fluorophenyl]ethyl}amino)-6-(dimethylphosphoryl)-2-methylpyrido[3,4-d]pyrimidin-8-ol

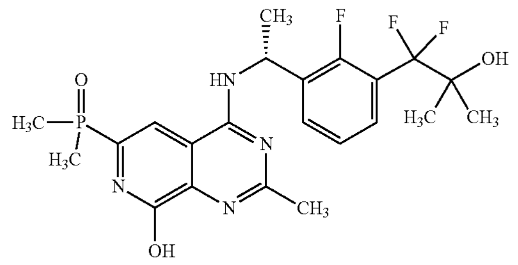 [SMILES: Cc1nc(N[C@H](C)c2cccc(C(F)(F)C(C)(C)O)c2F)c2cc(P(C)(C)=O)nc(O)c2n1]

To a solution of N-[(1R)-1-(3-{1,1-difluoro-2-methyl-2-[(triethylsilyl)oxy]propyl}-2-fluorophenyl)ethyl]-6-(dimethylphosphoryl)-8-[(4-methoxyphenyl)methoxy]-2-methylpyrido[3,4-d]pyrimidin-4-amine (Intermediate 102, 208 mg, 290 μmol) in dichloromethane (3.0 ml) was slowly added trifluoroacetic acid (3.0 ml) and the mixture was stirred at RT for 2 h. The reaction mixture was concentrated and the residue was subjected to preparative HPLC (Instrument: Waters Autopurificationsystem; Column: XBrigde C18 5p, 100×30 mm; eluent A: water+0.2 vol % aqueous ammonia (32%); eluent B: acetonitril; gradient: 0.0-0.5 min 9% B (35-70 ml/min), 0.5-5.5 min 9-29% B; flow: 70 ml/min; temperature: RT; DAD scan: 210-400 nm) to yield the title compound (52 mg, 99% purity, 37% yield) as white solid.

LC-MS (Method 2): $R_t$=0.75 min; MS (ESIpos): m/z=483.7 $[M+H]^+$ $^1$H NMR (400 MHz, DMSO-d6) b ppm 1.17-1.27 (m, 6H) 1.50-1.61 (m, 3H) 1.69-1.82 (m, 6H) 2.34 (s, 3H) 5.21-5.44 (m, 1H) 5.63-5.79 (m, 1H) 7.16-7.25 (m, 1H) 7.27-7.34 (m, 1H) 7.47-7.71 (m, 2H) 8.72 (d, J=7.35 Hz, 1H) 11.22-12.25 (m, 1H)

Example 30

1-acetyl-4-[8-hydroxy-2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one

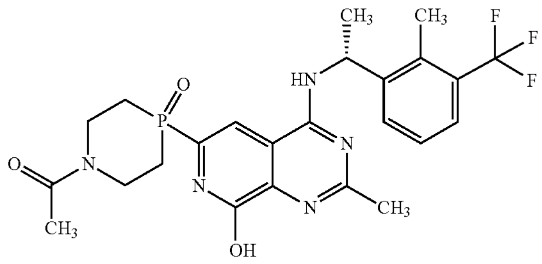 [SMILES: CC(=O)N1CCP(=O)(c2cc3c(N[C@H](C)c4cccc(C(F)(F)F)c4C)nc(C)nc3c(O)n2)CC1]

Following General Procedure 3, starting from tert-butyl 4-{8-[(4-methoxyphenyl)methoxy]-2-methyl-4-({(1R)-1-[2-methyl-3-(trifluoromethyl)phenyl]ethyl}amino)-pyrido[3,4-d]pyrimidin-6-yl}-4-oxo-1,4lambda$^5$-azaphosphinane-1-carboxylate (Intermediate 113, 105 mg, 150 μmol), after purification by preparative HPLC (basic method), the title compound (10.0 mg, 98% purity, 13% yield) was obtained as white solid.

LC-MS (Method 2): $R_t$=0.74 min; MS (ESIpos): m/z=522 $[M+H]^+$ $^1$H-NMR (400 MHz, DMSO-d6) δ[ppm]: 0.851 (0.42), 1.232 (1.72), 1.315 (0.43), 1.527 (5.25), 1.545 (5.24), 1.844 (1.36), 1.850 (0.63), 1.870 (0.57), 1.908 (0.56), 2.074 (1.44), 2.101 (16.00), 2.259 (0.44), 2.291 (0.60), 2.318 (1.17), 2.323 (2.23), 2.327 (3.04), 2.331 (2.40), 2.344 (14.10), 2.518 (9.95), 2.523 (6.86), 2.603 (7.23), 2.660 (0.81), 2.665 (1.84), 2.669 (2.56), 2.673 (1.79), 2.678 (0.81), 3.234 (0.52), 3.262 (0.63), 3.659 (0.47), 3.685 (0.49), 5.616 (0.60), 5.633 (0.87), 5.646 (0.57), 6.549 (0.51), 7.339 (0.80), 7.358 (1.78), 7.377 (1.06), 7.529 (1.97), 7.547 (1.61), 7.602 (0.56), 7.625 (0.54), 7.768 (1.72), 7.787 (1.56), 8.850 (0.80).

Example 31

4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carbaldehyde

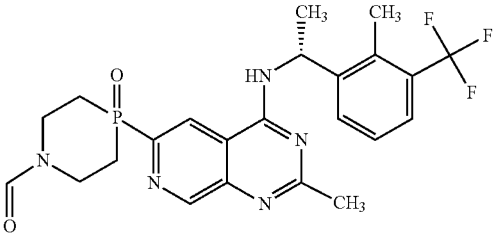 [SMILES: Cc1nc(N[C@H](C)c2cccc(C(F)(F)F)c2C)c2cc(P3(=O)CCN(C=O)CC3)ncc2n1]

To a solution of 4-[2-methyl-4-({(1R)-1-[2-methyl-3-(trifluoromethyl)phenyl]ethyl}amino)-pyrido[3,4-d]pyrimidin-6-yl]-1,4lambda$^5$-azaphosphinan-4-one (Intermediate 148, 50.0 mg, 108 μmol) in ethanol (1 ml) was added posattium carbonate (14.9 mg, 108 μmol) and ethyl formate (70 μl, 860 μmol), and the mixture was stirred at RT overnight. The mixture was diluted with dichloromethane, filtered, and concentrated. The residue was purified by preparative TLC (silica, dichloromethane, ethanol) to obtain the title compound (29.1 mg, 95% purity, 52% yield).

LC-MS (Method 2): $R_t$=1.11 min; MS (ESIpos): m/z=492 $[M+H]^+$ $^1$H-NMR (400 MHz, DMSO-d6) δ[ppm]: 1.229 (0.49), 1.575 (6.11), 1.593 (6.07), 1.955 (0.63), 2.061 (0.66), 2.100 (0.40), 2.258 (0.71), 2.281 (0.61), 2.361 (0.53), 2.374 (0.79), 2.396 (0.85), 2.422 (16.00), 2.623 (8.90), 3.659 (0.64), 3.694 (0.68), 3.774 (0.57), 3.785 (0.57), 3.808 (1.03), 3.821 (1.02), 3.834 (0.80), 3.867 (0.70), 3.879 (0.41), 3.939 (0.43), 3.974 (0.61), 3.987 (0.61), 5.707 (0.89), 5.723 (1.34), 5.741 (0.88), 7.349 (0.96), 7.368 (2.03), 7.388 (1.19), 7.544 (2.27), 7.563 (1.86), 7.786 (2.04), 7.806 (1.85), 8.115 (5.54), 9.015 (2.28), 9.032 (2.25), 9.089 (5.45), 9.373 (1.56), 9.389 (1.50).

Example 32

1-ethanethioyl-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one

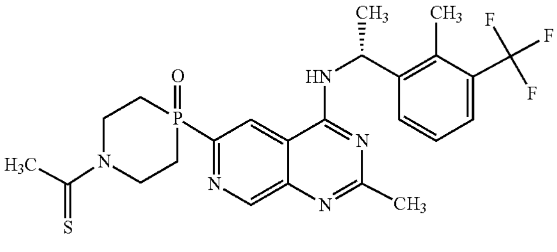 [SMILES: CC(=S)N1CCP(=O)(c2cc3c(N[C@H](C)c4cccc(C(F)(F)F)c4C)nc(C)nc3cn2)CC1]

To a solution of 1-acetyl-4-[2-methyl-4-({(1R)-1-[2-methyl-3-(trifluoromethyl)phenyl]ethyl}-amino)pyrido[3,4-d]pyrimidin-6-yl]-1,4lambda$^5$-azaphosphinan-4-one (Example 7, 100 mg, 198 μmol) in dichloromethane (1.3 ml) was added Lawesson's reagent ([CAS 38078-09-0], 80.0 mg, 198 μmol), and the mixture was stirred at 0° C. for 2 h and at RT overnight. The mixture was filtered, concentrated, and the residue was purified by preparative TLC (silica, hexane, methanol) to obtain the title compound (26.5 mg, 95% purity, 24% yield).

LC-MS (Method 2): $R_t$=1.22 min; MS (ESIpos): m/z=522 $[M+H]^+$ $^1$H-NMR (400 MHz, DMSO-d6) δ[ppm]: 1.229 (0.56), 1.575 (5.41), 1.593 (5.45), 2.107 (0.70), 2.116 (0.52), 2.137 (0.44), 2.173 (0.47), 2.336 (0.42), 2.423 (12.40), 2.425 (12.89), 2.518 (5.66), 2.523 (3.88), 2.624 (7.27), 2.678 (0.56), 2.696 (16.00), 4.143 (0.45), 4.151 (0.41), 4.177 (0.51), 4.299 (0.58), 4.325 (0.71), 4.362 (0.58), 5.706 (0.54), 5.712 (0.58), 5.724 (0.86), 5.729 (0.87), 5.741 (0.59), 5.747 (0.57), 5.758 (11.06), 7.350 (0.80), 7.369 (1.75), 7.389 (1.01), 7.545 (1.93), 7.563 (1.56), 7.789 (1.74), 7.809 (1.57), 9.041 (1.99), 9.059 (1.96), 9.105 (5.48), 9.400 (1.16), 9.415 (1.12).

Example 33

2-{3-[(1R)-1-{[6-(dimethylphosphoryl)-2-methylquinazolin-4-yl]amino}ethyl]-2-fluorophenyl}-2,2-difluoroethan-1-ol

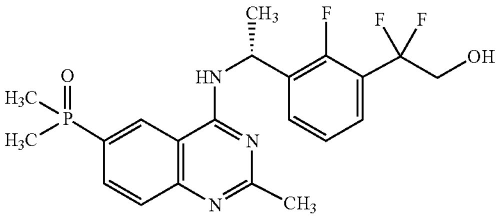 [SMILES: Cc1nc(N[C@H](C)c2cccc(C(F)(F)CO)c2F)c2cc(P(C)(C)=O)ccc2n1]

To a solution of ethyl {3-[(1R)-1-{[6-(dimethylphosphoryl)-2-methylquinazolin-4-yl]amino}ethyl]-2-fluorophenyl}(difluoro)acetate (Intermediate 173, 90.0 mg, 188 μmol) in tetrahydrofuran (1.2.ml) was added sodium tetrahydridoborate (35.5 mg, 939 μmol) portionwise, and the resulting mixture was stirred at RT for 1 h. To the mixture was added aqueous hydrochloric acid (1 M), until the solution has reached ~pH6, and the mixture was stirred for 15 min. The mixture was then extracted with ethyl acetate, the organic phases were washed with saturated aqueous sodium chloride, filtered through a separation funnel and concentrated. The residue was purified by preparative HPLC (basic method) to yield the title compound (25.0 mg, 95% purity, 29% yield).

LC-MS (Method 2): $R_t$=0.85 min; MS (ESIpos): m/z=438.4 $[M+H]^+$ $^1$H-NMR (400 MHz, DMSO-d6) δ[ppm]: 1.605 (4.77), 1.623 (4.90), 1.725 (13.70), 1.759 (13.80), 2.372 (16.00), 2.518 (1.60), 2.523 (1.18), 3.895 (0.50), 3.912 (0.55), 3.932 (0.94), 3.948 (0.98), 3.967 (0.47), 3.983 (0.45), 5.709 (0.81), 5.725 (1.91), 5.741 (0.76), 5.806 (0.73), 5.824 (1.13), 5.842 (0.72), 7.235 (0.87), 7.254 (1.91), 7.273 (1.11), 7.396 (0.68), 7.414 (1.05), 7.429 (0.53), 7.649 (1.63), 7.656 (1.91), 7.671 (2.47), 7.677 (2.04), 7.689 (0.52), 7.986 (0.91), 7.990 (0.91), 8.008 (0.86), 8.011 (1.67), 8.015 (0.96), 8.033 (0.76), 8.036 (0.79), 8.806 (1.24), 8.809 (1.22), 8.829 (1.33), 8.837 (1.44), 8.841 (1.44), 8.848 (1.25).

Example 34

1-acetyl-4-[8-(hydroxymethyl)-2-methyl-4-({(1R)-1-[2-methyl-3-(trifluoromethyl)phenyl]ethyl}amino) pyrido[3,4-d]pyrimidin-6-yl]-1,4lambda$^5$-azaphosphinan-4-one

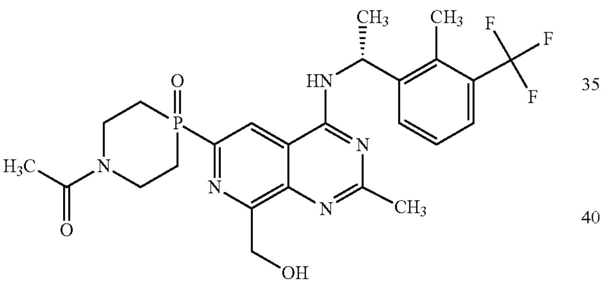

Ina microwave vial, 1-acetyl-4-[2-methyl-4-({(1R)-1-[2-methyl-3-(trifluoromethyl)phenyl]-ethyl}amino)pyrido[3,4-d]pyrimidin-6-yl]-1,4lambda$^5$-azaphosphinan-4-one (Example 7, 100 mg, 70% purity, 138 μmol) was dissolved in methanol (700 μl) and the mixture was irradiated with UV light (370 nm) for 5 days. The mixture was concentrated and the residue was purified by preparative TLC (silica, dichloromethane, methanol) to yield the title compound (5 mg, 95% purity, 6% yield).

LC-MS (Method 2): $R_t$=1.15 min; MS (ESIpos): m/z=537 $[M+H]^+$ $^1$H-NMR (400 MHz, DMSO-d6) δ[ppm]: 0.852 (0.76), 1.233 (2.80), 1.572 (2.33), 1.590 (2.33), 2.121 (7.80), 2.318 (1.51), 2.422 (7.26), 2.518 (16.00), 2.523 (11.33), 2.621 (3.04), 2.678 (1.33), 2.687 (0.93), 3.304 (0.77), 5.007 (0.64), 5.013 (0.85), 5.025 (2.33), 5.047 (1.05), 5.059 (1.28), 5.064 (0.62), 5.721 (0.45), 7.364 (0.76), 7.383 (0.47), 7.540 (0.84), 7.559 (0.66), 7.782 (0.75), 7.801 (0.65), 8.911 (0.92), 8.928 (0.91), 9.335 (0.51), 9.352 (0.50).

Example 35

1-acetyl-4-[8-cyclopropyl-2-methyl-4-({(1R)-1-[2-methyl-3-(trifluoromethyl)phenyl]ethyl}amino) pyrido[3,4-d]pyrimidin-6-yl]-1,4lambda$^5$-azaphosphinan-4-one

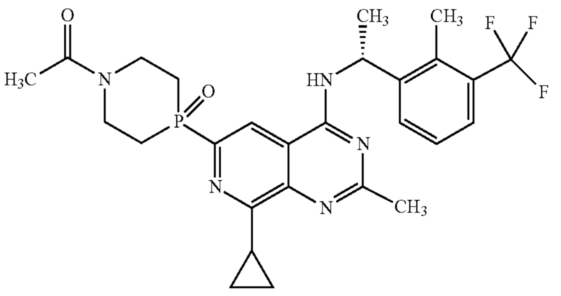 [SMILES: CC(=O)N1CCP(=O)(c2cc3c(N[C@H](C)c4cccc(C(F)(F)F)c4C)nc(C)nc3c(C3CC3)n2)CC1]

A mixture of 1-acetyl-4-[2-methyl-4-({(1R)-1-[2-methyl-3-(trifluoromethyl)phenyl]ethyl}-amino)pyrido[3,4-d]pyrimidin-6-yl]-1,4lambda5-azaphosphinan-4-one (Example 7, 125 mg, 247 μmol), cyclopropanecarboxylic acid (39 μl, 490 μmol), ammonium persulfate ([CAS 7727-54-0], 282 mg, 1.24 mmol) and silver nitrate (168 mg, 989 μmol) in acetonitrile (1.8 ml) and water (750 μl) was heated to 80° C. for 24 h. The mixture was then cooled to RT, diluted with water and extracted with ethyl acetate. The organic phases were separated, dried, and concentrated. The residue was subjected to preparative HPLC (basic method) to obtain the title compound (12 mg, 95% purity, 8% yield) as white solid.

LC-MS (Method 2): $R_t$=1.35 min; MS (ESIpos): m/z=546.5 $[M+H]^+$ $^1$H-NMR (400 MHz, DMSO-d6) δ[ppm]: 0.996 (0.72), 1.009 (0.90), 1.024 (0.83), 1.109 (1.30), 1.125 (1.28), 1.565 (4.60), 1.582 (4.63), 2.053 (0.57), 2.062 (0.54), 2.084 (3.60), 2.113 (16.00), 2.284 (0.42), 2.322 (1.24), 2.327 (1.65), 2.332 (1.27), 2.449 (12.76), 2.518 (5.27), 2.523 (3.44), 2.625 (5.99), 2.660 (0.43), 2.664 (0.92), 2.669 (1.31), 2.673 (0.94), 3.306 (0.86), 3.779 (0.63), 3.909 (0.60), 5.706 (0.52), 5.722 (0.76), 5.737 (0.51), 7.341 (0.70), 7.361 (1.54), 7.380 (0.88), 7.540 (1.64), 7.558 (1.33), 7.778 (1.45), 7.798 (1.31), 8.725 (2.00), 8.742 (1.98), 9.217 (1.03), 9.234 (0.97).

Example 36

1-acetyl-4-[8-(difluoromethyl)-2-methyl-4-({(1R)-1-[2-methyl-3-(trifluoromethyl)phenyl]ethyl}amino) pyrido[3,4-d]pyrimidin-6-yl]-1,4lambda$^5$-azaphosphinan-4-one

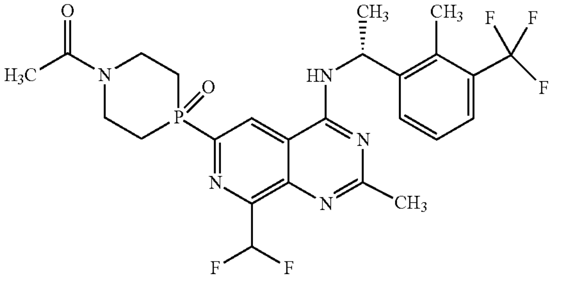 [SMILES: CC(=O)N1CCP(=O)(c2cc3c(N[C@H](C)c4cccc(C(F)(F)F)c4C)nc(C)nc3c(C(F)F)n2)CC1]

To a mixture of 1-acetyl-4-[2-methyl-4-({(1R)-1-[2-methyl-3-(trifluoromethyl)phenyl]ethyl}-amino)pyrido[3,4-d]pyrimidin-6-yl]-1,4lambda$^5$-azaphosphinan-4-one (example 7, 200 mg, 396 μmol) and zinc bis(difluoromethanesulfinate) (665 mg, 95% purity, 2.14 mmol) in dichloromethane (1.6 ml) and water (650 μl) was added trifluoroacetic acid (61 μl, 790 μmol), followed by dropwise addition of 2-methylpropane-2-peroxol ([CAS 75-91-2], 570 μl, 70% purity, 4.0 mmol), and the mixture was stirred at 40° C. for 22 h. Further zinc bis(difluoromethanesulfinate) (665 mg, 95% purity, 2.14 mmol) and 2-methylpropane-2-peroxol (570 μl, 70% purity, 4.0 mmol) were added and stirring was continued for 2 days at RT. The mixture was diluted with saturated aqueous sodium hydrogen carbonate solution, extracted with dichloromethane, and the organic phases were filtered through a separation funnel and concentrated. Purification of the residue by preparative HPLC (basic method) gave the title compound (29.0 mg, 99% purity, 13% yield) as white solid.

LC-MS (Method 2): $R_t$=1.30 min; MS (ESIpos): m/z=556.2 [M+H]$^+$ $^1$H-NMR (400 MHz, DMSO-d6) δ[ppm]: 1.586 (4.96), 1.604 (4.97), 1.960 (0.40), 2.101 (0.44), 2.121 (16.00), 2.151 (0.43), 2.280 (0.48), 2.291 (0.44), 2.318 (0.64), 2.323 (1.06), 2.327 (1.37), 2.331 (1.08), 2.336 (0.64), 2.360 (0.43), 2.452 (14.03), 2.518 (4.99), 2.523 (3.43), 2.619 (6.67), 2.665 (0.80), 2.669 (1.12), 2.673 (0.81), 3.835 (0.43), 3.861 (0.51), 3.873 (0.58), 3.892 (0.79), 3.905 (0.83), 3.949 (0.71), 3.992 (0.46), 5.720 (0.64), 5.737 (0.96), 5.755 (0.63), 7.355 (0.75), 7.374 (1.64), 7.394 (0.95), 7.522 (1.02), 7.553 (1.78), 7.571 (1.43), 7.657 (2.24), 7.782 (1.64), 7.792 (1.02), 7.801 (1.47), 9.180 (1.76), 9.195 (1.75), 9.558 (1.13), 9.575 (1.09).

Example 37

1-acetyl-4-[8-(methoxymethyl)-2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one

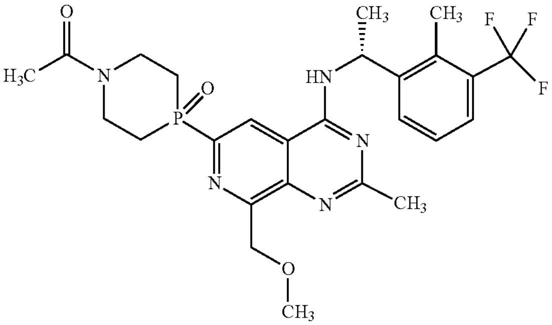 [SMILES: COCc1nc(P2(=O)CCN(C(C)=O)CC2)cc2c(N[C@H](C)c3cccc(C(F)(F)F)c3C)nc(C)nc12]

The reaction was performed as described for Example 35, starting from 1-acetyl-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one (Example 7, 125 mg, 247 μmol) and methoxyacetic acid (38 μl, 490 μmol). Purification by preparative HPLC (basic method) gave the title compound (23.0

LC-MS (Method 2): $R_t$=1.22 min; MS (ESIpos): m/z=550.2 [M+H]$^+$ $^1$H-NMR (400 MHz, DMSO-d6) δ[ppm]: 1.572 (2.87), 1.589 (2.88), 2.098 (0.41), 2.118 (9.38), 2.283 (0.51), 2.322 (0.44), 2.327 (0.53), 2.332 (0.45), 2.422 (7.73), 2.518 (1.44), 2.523 (0.94), 2.619 (3.95), 3.366 (16.00), 3.373 (1.71), 3.896 (0.68), 3.908 (0.68), 3.920 (0.70), 3.929 (0.75), 3.949 (0.71), 4.967 (5.28), 5.718 (0.50), 7.342 (0.45), 7.362 (0.97), 7.381 (0.56), 7.539 (1.07), 7.558 (0.87), 7.779 (0.95), 7.799 (0.88), 8.946 (1.09), 8.962 (1.06), 9.337 (0.62), 9.354 (0.58).

Example 38

(2RS)-1-{3-[(1R)-1-{[6-(dimethylphosphoryl)-8-ethyl-2-methylpyrido[3,4-d]pyrimidin-4-yl]amino}ethyl]-2-fluorophenyl}-1,1-difluorobutan-2-ol (mixture of diastereomers)

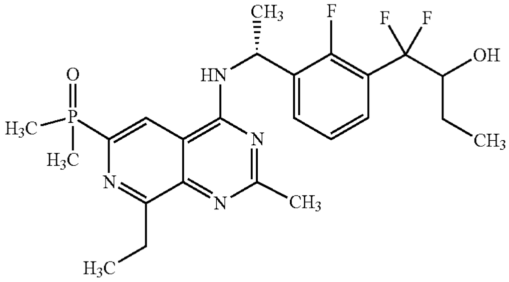 [SMILES: CCc1nc(P(C)(C)=O)cc2c(N[C@H](C)c3cccc(C(F)(F)C(O)CC)c3F)nc(C)nc12]

To a solution of ethyl {3-[(1R)-1-{[6-(dimethylphosphoryl)-2-methylpyrido[3,4-d]pyrimidin-4-yl]amino}ethyl]-2-fluorophenyl}(difluoro)acetate (Intermediate 173, 270 mg, 75% purity, 421 μmol) in tetrahydrofuran (2.0 ml) was added bromo(ethyl)magnesium (530 μl, 3.2 M, 1.7 mmol) at −78° C., the cooling bath was removed, and the mixture was stirred for 3 h. The reaction was then quenched by slow addition of ethanol at RT and concentrated under reduced pressure. Purification of the crude product by preparative HPLC (basic method) and subsequent purification by preparative TLC (silica, dichloromethane, ethanol) gave the title compound (9 mg, 90% purity, 4% yield).

LC-MS (Method 2): $R_t$=1.22 min; MS (ESIpos): m/z=495 [M+H]$^+$ $^1$H NMR (400 MHz, DMSO-d6) b ppm 0.88-0.97 (m, 3H) 1.27 (d, J=1.52 Hz, 3H) 1.33-1.45 (m, 1H) 1.47-1.63 (m, 4H) 1.65-1.74 (m, 6H) 2.39-2.45 (m, 3H) 3.16-3.28 (m, 2H) 3.75-3.97 (m, 1H) 5.49-5.63 (m, 1H) 5.70-5.87 (m, 1H) 7.15-7.31 (m, 1H) 7.33-7.44 (m, 1H) 7.56-7.76 (m, 1H) 8.72-8.85 (m, 1H) 9.08-9.22 (m, 1H).

Example 39

4-[2-methyl-4-({(1R)-1-[2-methyl-3-(trifluoromethyl)phenyl]ethyl}amino)pyrido[3,4-d]pyrimidin-6-yl]-1-(1-methyl-1H-pyrazol-4-yl)-1,4lambda$^5$-azaphosphinan-4-one

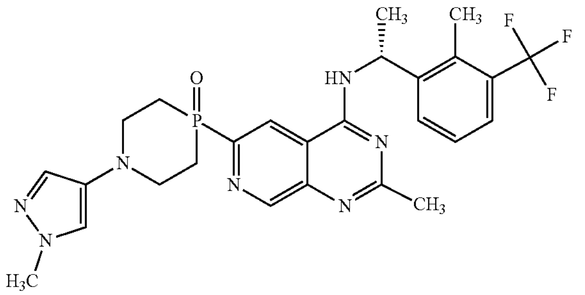

To a solution of 4-[2-methyl-4-({(1R)-1-[2-methyl-3-(trifluoromethyl)phenyl]ethyl}-amino)pyrido[3,4-d]pyrimidin-6-yl]-1,4lambda$^5$-azaphosphinan-4-one (Intermediate 148, 75.0 mg, 162 μmol) and 4-bromo-1-methyl-1H-pyrazole (33 μl, 320 μmol) in toluene (1.5 ml) under argon atmosphere was added sodium tert-butoxide (23.3 mg, 243 μmol), DavePhos [CAS 213697-53-1] (24 mg, 65 μmol), and tris (benzylideneaceton)-dipalladium(0) (37.0 mg, 40.5 μmol), and the mixture was stirred at 120° C. overnight. The mixture was then cooled to RT, filtered, and concentrated. The residue was purified by preparstive TLC (silica, dichloromethane, methanol) to yield the title compound (1.30 mg, 95% purity, 1% yield).

LC-MS (Method 2): $R_t$=1.16 min; MS (ESIneg): m/z=542 $[M-H]^-$ $^1$H-NMR (400 MHz, DMSO-d6) δ[ppm]: 1.231 (0.76), 1.572 (4.16), 1.590 (4.11), 1.840 (0.40), 1.878 (0.76), 1.918 (0.47), 2.318 (0.41), 2.323 (0.93), 2.327 (1.32), 2.331 (0.94), 2.337 (0.58), 2.344 (0.62), 2.362 (0.74), 2.382 (0.80), 2.414 (13.02), 2.465 (0.56), 2.470 (0.83), 2.518 (4.05), 2.523 (2.85), 2.622 (5.18), 2.665 (0.81), 2.669 (1.12), 2.673 (0.76), 3.517 (1.35), 3.547 (1.00), 3.560 (1.46), 3.576 (0.90), 3.752 (16.00), 5.703 (0.65), 5.720 (0.98), 5.737 (0.63), 7.221 (3.67), 7.223 (3.63), 7.347 (0.62), 7.367 (1.34), 7.383 (4.03), 7.385 (4.21), 7.542 (1.42), 7.561 (1.14), 7.788 (1.25), 7.807 (1.13), 8.993 (1.43), 9.009 (1.41), 9.067 (3.86), 9.364 (1.08), 9.382 (1.03).

Example 40

4-[2-methyl-4-({(1R)-1-[2-methyl-3-(trifluoromethyl)phenyl]ethyl}amino)pyrido[3,4-d]pyrimidin-6-yl]-1-(1-methyl-1H-pyrazol-3-yl)-1,4lambda$^5$-azaphosphinan-4-one

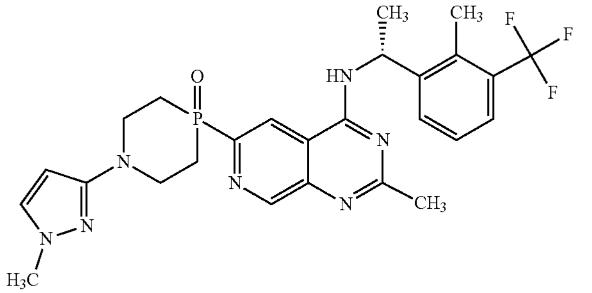 [SMILES: Cc1nc(N[C@H](C)c2cccc(C(F)(F)F)c2C)c2cc(P3(=O)CCN(c4ccn(C)n4)CC3)ncc2n1]

The reaction was performed as described for Example 39, starting from 4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one (Intermediate 148, 75.0 mg, 162 μmol) and 3-bromo-1-methyl-1H-pyrazole (52.1 mg, 324 μmol), to obtain the title compound (60 mg, 95%

LC-MS (Method 2): $R_t$=1.17 min; MS (ESIpos): m/z=544 $[M+H]^+$ $^1$H-NMR (400 MHz, DMSO-d6) δ[ppm]: 1.571 (4.35), 1.589 (4.28), 1.872 (0.76), 1.910 (0.43), 2.304 (0.56), 2.316 (0.82), 2.322 (0.71), 2.327 (0.80), 2.332 (0.76), 2.337 (0.77), 2.351 (0.52), 2.411 (14.18), 2.518 (0.95), 2.523 (0.69), 2.619 (5.51), 3.686 (16.00), 3.727 (0.98), 3.739 (1.25), 3.769 (0.97), 3.779 (1.03), 5.698 (0.67), 5.715 (1.03), 5.733 (0.66), 5.779 (3.76), 5.784 (3.72), 7.343 (0.64), 7.362 (1.37), 7.382 (0.80), 7.490 (2.98), 7.495 (2.91), 7.538 (1.50), 7.556 (1.20), 7.789 (1.33), 7.809 (1.20), 8.995 (1.55), 9.011 (1.50), 9.060 (4.13), 9.374 (1.11), 9.391 (1.06).

Example 41

1-(methanesulfonyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one

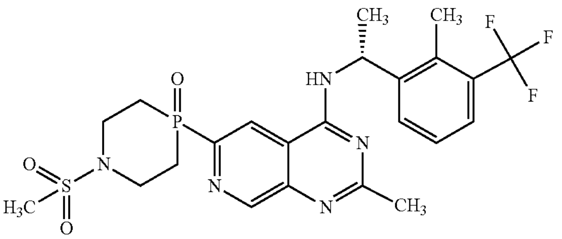 [SMILES: Cc1nc(N[C@H](C)c2cccc(C(F)(F)F)c2C)c2cc(P3(=O)CCN(S(C)(=O)=O)CC3)ncc2n1]

To a solution of 4-[2-methyl-4-({(1R)-1-[2-methyl-3-(trifluoromethyl)phenyl]ethyl}-amino)pyrido[3,4-d]pyrimidin-6-yl]-1,4lambda$^5$-azaphosphinan-4-one (Intermediate 148, 50.0 mg, 108 μmol) in dichloromethane (1.0 ml) at RT was added N,N-diisopropylethylamine (38 μl, 220 μmol), followed by methanesulfonic anhydride (20.7 mg, 119 μmol), and the mixture was stirred at RT overnight. The mixture was diluted with toluene and concentrated. The residue was purified by preparative HPLC (basic method) to obtain the title compound (37.3 mg, 95% purity, 61% yield).

LC-MS (Method 2): $R_t$=1.14 min; MS (ESIpos): m/z=542 $[M+H]^+$ $^1$H-NMR (400 MHz, DMSO-d6) δ[ppm]: 1.575 (4.39), 1.592 (4.37), 2.085 (0.71), 2.425 (14.72), 2.455 (1.14), 2.518 (4.72), 2.523 (3.36), 2.623 (5.50), 3.015 (16.00), 3.301 (0.60), 3.599 (0.76), 3.632 (0.83), 3.723 (0.53), 3.738 (0.42), 3.759 (0.63), 3.771 (0.69), 3.787 (0.41), 5.708 (0.68), 5.725 (1.06), 5.742 (0.66), 7.350 (0.64), 7.369 (1.38), 7.388 (0.80), 7.545 (1.50), 7.563 (1.20), 7.785 (1.32), 7.804 (1.19), 9.022 (1.57), 9.038 (1.53), 9.101 (4.11), 9.103 (3.96), 9.368 (1.17), 9.385 (1.10).

Example 42

1-acetyl-4-[4-({(1R)-1-[3-(1,1-difluoro-2-hydroxyethyl)-2-fluorophenyl]ethyl}amino)-2-methylpyrido[3,4-d]pyrimidin-6-yl]-1,4lambda-azaphosphinan-4-one

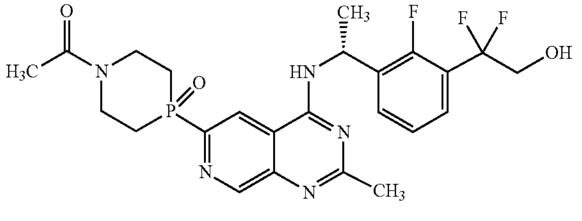 [SMILES: CC(=O)N1CCP(=O)(c2cc3c(N[C@H](C)c4cccc(C(F)(F)CO)c4F)nc(C)nc3cn2)CC1]

Example 42 was obtained as a by-product of Intermediate 156, which was separated by preparative HPLC: 4.00 mg (95% purity, 5% yield).

LC-MS (Method 2): $R_t$=0.81 min; MS (ESIpos): m/z=522.7 $[M+H]^+$ $^1$H NMR (400 MHz, DMSO-d6) b ppm 1.58-1.66 (m, 3H) 1.87-2.39 (m, 2H) 2.12 (s, 4H) 2.27-2.38 (m, 1H) 2.53-2.55 (m, 5H) 3.44-3.58 (m, 1H) 3.70-3.84 (m, 1H) 3.93 (br s, 3H) 4.15-4.34 (m, 1H) 5.73 (s, 1H) 5.76-5.86 (m, 1H) 7.23-7.30 (m, 1H) 7.40-7.48 (m, 1H) 7.64-7.72 (m, 1H) 9.18 (br d, J=7.10 Hz, 1H) 9.26 (br d, J=4.31 Hz, 2H).

Example 43

{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}(difluoro)acetic acid

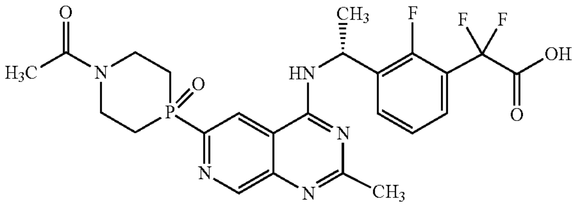 [SMILES: CC(=O)N1CCP(=O)(c2cc3c(N[C@H](C)c4cccc(C(F)(F)C(=O)O)c4F)nc(C)nc3cn2)CC1]

To a solution of ethyl {3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}(difluoro)acetate (Intermediate 159, 150 mg, 266 μmol) in ethanol (450 μl) was added aqueous potassium hydroxide (670 μl, 2.0 M, 1.3 mmol), and the mixture was stirred at RT for 20 min. The mixture was concentrated, diluted with water and purified by solid phase extraction chromatography (C18 SPE, water, methanol) to obtain the title compound (135 mg, 90% purity, 85% yield).

LC-MS (Method 2): $R_t$=0.56 min; MS (ESIpos): m/z=536.5 $[M+H]^+$ $^1$H-NMR (400 MHz, DMSO-d6) δ[ppm]: 1.085 (1.87), 1.103 (1.99), 1.151 (1.16), 1.168 (1.21), 1.235 (0.44), 1.617 (4.70), 1.635 (4.71), 2.008 (0.48), 2.117 (16.00), 2.318 (0.66), 2.323 (0.77), 2.327 (1.04), 2.331 (0.75), 2.337 (0.43), 2.456 (13.46), 2.518 (2.45), 2.523 (1.78), 2.665 (0.46), 2.669 (0.61), 2.673 (0.44), 3.165 (1.88), 3.376 (0.65), 3.442 (0.77), 3.502 (0.97), 3.530 (0.58), 3.754 (0.62), 3.783 (0.65), 3.953 (0.42), 5.793 (0.71), 5.810 (1.08), 5.828 (0.69), 6.940 (0.65), 7.280 (0.84), 7.299 (1.80), 7.319 (1.03), 7.502 (0.73), 7.519 (1.20), 7.535 (0.58), 7.678 (0.60), 7.697 (1.05), 7.715 (0.55), 9.289 (1.31), 9.294 (1.74), 9.300 (1.47), 9.305 (1.55), 9.328 (1.24), 9.333 (1.01), 9.357 (1.20), 9.362 (1.01), 9.601 (0.40).

Example 44

2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-N-cyclopropyl-2,2-difluoroacetamide

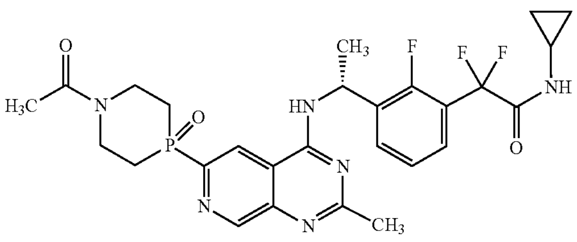 [SMILES: CC(=O)N1CCP(=O)(c2cc3c(N[C@H](C)c4cccc(C(F)(F)C(=O)NC5CC5)c4F)nc(C)nc3cn2)CC1]

To a solution of cyclopropanamine (42 μl, 600 μmol) was added a solution of {3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}(difluoro)acetyl chloride (Intermediate 160, equivalent of 33.3 mg, 60.0 μmol) and the mixture was stirred at RT for 10 min. The mixture was concentrated and purified by preparative HPLC (basic method) to obtain the title compound (10.4 mg, 95% purity, 29% yield).

LC-MS (Method 2): $R_t$=0.87 min; MS (ESIpos): m/z=575.6 $[M+H]^+$ $^1$H-NMR (400 MHz, DMSO-d6) δ[ppm]: 0.561 (0.44), 0.572 (1.02), 0.575 (1.09), 0.582 (1.63), 0.590 (1.99), 0.601 (0.74), 0.663 (0.74), 0.674 (1.37), 0.681 (1.49), 0.693 (1.86), 0.697 (1.04), 0.712 (0.49), 1.107 (16.00), 1.599 (3.42), 1.617 (3.42), 2.117 (10.44), 2.318 (0.51), 2.322 (0.83), 2.327 (0.98), 2.332 (0.72), 2.336 (0.42), 2.414 (11.46), 2.518 (3.11), 2.523 (2.13), 2.664 (0.54), 2.669 (0.75), 2.673 (0.54), 2.762 (0.40), 2.770 (0.62), 2.781 (0.62), 2.789 (0.40), 4.190 (1.06), 5.741 (0.55), 5.758 (1.01), 5.776 (0.55), 7.283 (0.60), 7.302 (1.32), 7.322 (0.76), 7.469 (0.51), 7.487 (0.85), 7.503 (0.41), 7.689 (0.42), 7.707 (0.75), 9.051 (0.94), 9.062 (0.92), 9.147 (0.69), 9.164 (0.67), 9.256 (2.50), 9.262 (1.44), 9.268 (1.40), 9.288 (0.75).

Example 45

2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-2,2-difluoro-N,N-dimethylacetamide

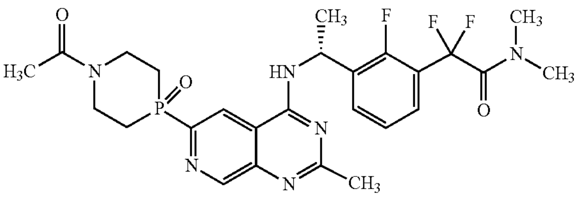 [SMILES: CC(=O)N1CCP(=O)(c2cc3c(N[C@H](C)c4cccc(C(F)(F)C(=O)N(C)C)c4F)nc(C)nc3cn2)CC1]

The reaction was performed as described for Example 44, using Intermediate 160 and N-methylmethanamine (300 μl, 2.0 M, 600 μmol), to obtain the title compound (19.6 mg, 95% purity, 55% yield).

LC-MS (Method 2): $R_t$=0.88 min; MS (ESIpos): m/z=563.6 $[M+H]^+$ $^1$H NMR (400 MHz, DMSO-d6) b ppm 1.61 (d, J=7.10 Hz, 3H) 1.95-2.09 (m, 1H) 2.12 (s, 4H) 2.24-2.38 (m, 1H) 2.40 (s, 3H) 2.94-2.99 (m, 6H) 3.42-3.55 (m, 1H) 3.77 (q, J=11.83 Hz, 1H) 3.86-4.00 (m, 1H) 4.18-4.32 (m, 1H) 5.71-5.78 (m, 1H) 7.31 (t, J=7.73 Hz, 1H) 7.49 (t, J=6.72 Hz, 1H) 7.71 (br t, J=7.22 Hz, 1H) 9.17 (br d, J=6.84 Hz, 1H) 9.24-9.31 (m, 2H).

Example 46

2-{3-[(1R)-1-{[6-(1-acetyl-4-oxo-1,4lambda$^5$-aza-phosphinan-4-yl)-2-methylpyrido[3,4-d]pyrimidin-4-yl]amino}ethyl]-2-fluorophenyl}-2,2-difluoroacetamide

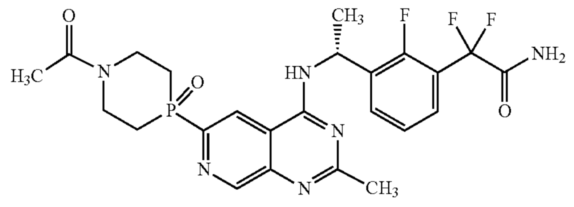 [SMILES: CC(=O)N1CCP(=O)(c2cc3c(N[C@H](C)c4cccc(C(F)(F)C(N)=O)c4F)nc(C)nc3cn2)CC1]

The reaction was performed as described for Example 44, using Intermediate 160 and ammonia (86 µl, 7.0 M, 600 µmol), to obtain the title compound (19.6 mg, 95% purity, 55% yield).

LC-MS (Method 2): $R_t$=0.77 min; MS (ESIpos): m/z=535.6 $[M+H]^+$ $^1$H-NMR (400 MHz, DMSO-d6) δ[ppm]: 0.798 (0.88), 0.802 (0.50), 0.814 (0.96), 0.821 (0.99), 0.840 (0.50), 0.886 (0.50), 0.904 (1.01), 0.923 (0.46), 1.035 (3.23), 1.052 (6.84), 1.070 (3.26), 1.160 (0.44), 1.232 (1.86), 1.602 (4.96), 1.619 (4.95), 1.907 (0.48), 2.005 (0.51), 2.117 (14.61), 2.318 (1.36), 2.323 (2.42), 2.327 (3.20), 2.331 (2.34), 2.336 (1.20), 2.414 (16.00), 2.518 (12.04), 2.523 (8.26), 2.660 (0.93), 2.665 (2.03), 2.669 (2.84), 2.673 (2.01), 2.678 (0.91), 3.159 (0.75), 3.171 (0.80), 3.364 (0.81), 3.404 (0.68), 3.417 (0.64), 3.422 (1.61), 3.435 (1.70), 3.439 (1.62), 3.452 (1.72), 3.457 (0.76), 3.469 (0.71), 3.484 (0.59), 3.511 (0.58), 3.754 (0.53), 3.785 (0.58), 4.347 (1.10), 4.360 (2.10), 4.372 (1.05), 5.758 (10.50), 5.775 (1.27), 5.793 (0.79), 7.282 (0.86), 7.301 (1.87), 7.320 (1.07), 7.483 (0.74), 7.500 (1.26), 7.516 (0.61), 7.686 (0.62), 7.704 (1.12), 7.723 (0.57), 8.137 (1.70), 8.408 (1.98), 9.145 (1.09), 9.162 (1.04), 9.251 (1.00), 9.256 (2.56), 9.262 (2.93), 9.267 (2.52), 9.292 (1.20).

Example 47

2-{3-[(1R)-1-{[6-(1-acetyl-4-oxo-1,4lambda$^5$-aza-phosphinan-4-yl)-2-methylpyrido[3,4-d]pyrimidin-4-yl]amino}ethyl]-2-fluorophenyl}-2,2-difluoro-N-methylacetamide

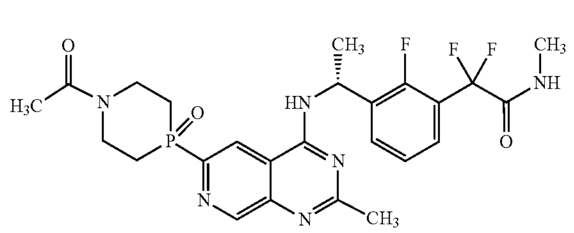 [SMILES: CNC(=O)C(F)(F)c1cccc([C@@H](C)Nc2nc(C)nc3cnc(P4(=O)CCN(C(C)=O)CC4)cc23)c1F]

The reaction was performed as described for Example 44, using Intermediate 160 and ammonia (86 µl, 7.0 M, 600 µmol), to obtain the title compound (19.6 mg, 95% purity, 55% yield).

LC-MS (Method 2): $R_t$=0.78 min; MS (ESIpos): m/z=549.5 $[M+H]^+$ $^1$H NMR (400 MHz, DMSO-d6) b ppm 1.61 (d, J=6.84 Hz, 3H) 1.95-2.08 (m, 1H) 2.12 (s, 4H) 2.27-2.37 (m, 1H) 2.41 (s, 3H) 2.73 (d, J=4.56 Hz, 3H) 3.43-3.55 (m, 1H) 3.77 (q, J=12.00 Hz, 1H) 3.86-3.99 (m, 1H) 4.19-4.31 (m, 1H) 5.71-5.78 (m, 1H) 7.30 (t, J=7.86 Hz, 1H) 7.50 (t, J=6.84 Hz, 1H) 7.71 (br t, J=7.35 Hz, 1H) 8.99 (br d, J=4.56 Hz, 1H) 9.16 (br d, J=6.84 Hz, 1H) 9.24-9.30 (m, 2H).

Example 48

2-{3-[(1R)-1-{[6-(dimethylphosphoryl)-2-methylpyrido[3,4-d]pyrimidin-4-yl]amino}ethyl]-2-fluorophenyl}-2,2-difluoroacetamide

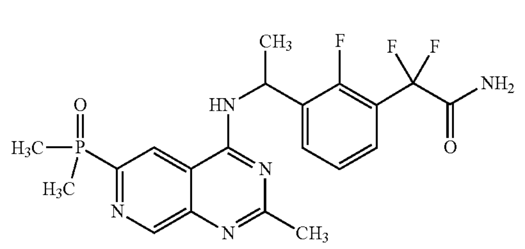 [SMILES: Cc1nc(NC(C)c2cccc(C(F)(F)C(N)=O)c2F)c2cc(P(C)(C)=O)ncc2n1]

As described for Intermediate 162, reacting ethyl {3-[(1R)-1-{[6-(dimethylphosphoryl)-2-methylpyrido[3,4-d]pyrimidin-4-yl]amino}ethyl]-2-fluorophenyl}(difluoro)acetate (Intermediate 161, 142 mg, 296 µmol) and ammonia (300 µl, 7.0 M, 2.1 mmol) gave the title compound (16.0 mg, 91% purity, 11% yield).

LC-MS (Method 2): $R_t$=0.78 min; MS (ESIpos): m/z=452.6 $[M+H]^+$ $^1$H-NMR (400 MHz, DMSO-d6) δ[ppm]: 1.593 (5.12), 1.610 (5.07), 1.688 (7.43), 1.692 (7.59), 1.722 (7.62), 1.726 (7.34), 2.427 (16.00), 2.518 (0.90), 2.523 (0.62), 5.750 (0.84), 5.767 (1.30), 5.785 (0.83), 7.279 (1.02), 7.298 (2.17), 7.317 (1.23), 7.477 (0.76), 7.494 (1.28), 7.511 (0.63), 7.693 (0.68), 7.710 (1.22), 7.728 (0.62), 8.137 (1.66), 8.407 (1.91), 8.949 (1.98), 8.965 (2.00), 9.087 (4.77), 9.284 (1.47), 9.302 (1.39).

Example 49

2-{3-[(1R)-1-{[6-(dimethylphosphoryl)-2-methylpyrido[3,4-d]pyrimidin-4-yl]amino}ethyl]-2-fluorophenyl}-N-ethyl-2,2-difluoroacetamide

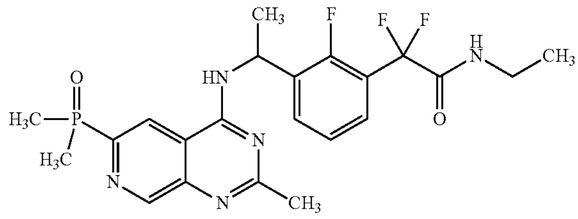 [SMILES: CCNC(=O)C(F)(F)c1cccc(C(C)Nc2nc(C)nc3cnc(P(C)(C)=O)cc23)c1F]

As described for Intermediate 162, reacting ethyl {3-[(1R)-1-{[6-(dimethylphosphoryl)-2-methylpyrido[3,4-d]pyrimidin-4-yl]amino}ethyl]-2-fluorophenyl}(difluoro)acetate (Intermediate 161, 142 mg, 296 µmol) and ethanamine (520 µl, 2.0 M, 1.0 mmol) gave the title compound (19 mg, 95% purity, 19% yield).

LC-MS (Method 2): $R_t$=0.90 min; MS (ESIpos): m/z=480.2 $[M+H]^+$ $^1$H-NMR (400 MHz, DMSO-d6) δ[ppm]: 0.964 (1.05), 1.045 (1.37), 1.064 (3.26), 1.081 (1.48), 1.105 (16.00), 1.142 (0.68), 1.639 (1.40), 1.657 (1.40), 1.714 (2.83), 1.747 (2.80), 3.185 (0.43), 3.203 (0.61), 3.221 (0.42), 7.341 (0.61), 9.221 (0.89).

Example 50

2-{3-[(1R)-1-{[6-(dimethylphosphoryl)-2-methylpyrido[3,4-d]pyrimidin-4-yl]amino}ethyl]-2-fluorophenyl}-2,2-difluoro-N,N-dimethylacetamide

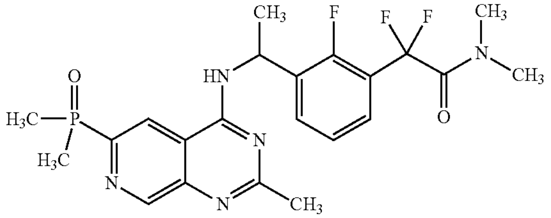

As described for Intermediate 162, reacting ethyl {3-[(1R)-1-{[6-(dimethylphosphoryl)-2-methylpyrido[3,4-d]pyrimidin-4-yl]amino}ethyl]-2-fluorophenyl}(difluoro)acetate (Intermediate 161, 142 mg, 296 μmol) and dimethylamine (540 μl, 2.0 M, 1.1 mmol) gave the title compound (8.00 mg, 96% purity, 7% yield).

LC-MS (Method 2): $R_t$=0.93 min; MS (ESIpos): m/z=480.5 $[M+H]^+$ $^1$H-NMR (400 MHz, DMSO-d6) δ[ppm]: 0.826 (0.64), 0.852 (0.75), 0.967 (1.01), 1.107 (1.04), 1.144 (0.68), 1.232 (2.61), 1.372 (0.57), 1.496 (0.46), 1.605 (3.58), 1.623 (3.54), 1.692 (5.83), 1.694 (5.88), 1.726 (5.94), 1.729 (5.83), 2.331 (3.23), 2.337 (1.41), 2.439 (6.28), 2.518 (16.00), 2.523 (11.18), 2.673 (3.18), 2.678 (1.38), 2.960 (8.48), 2.971 (6.31), 5.743 (0.45), 5.761 (0.70), 5.778 (0.47), 7.301 (0.66), 7.320 (1.41), 7.340 (0.85), 7.478 (0.58), 7.495 (0.93), 7.512 (0.48), 7.710 (0.49), 7.730 (0.83), 8.979 (0.91), 8.995 (0.93), 9.108 (2.71).

Example 51

2-{3-[(1R)-1-{[6-(dimethylphosphoryl)-2-methylpyrido[3,4-d]pyrimidin-4-yl]amino}ethyl]-2-fluorophenyl}-2,2-difluoro-N-methylacetamide

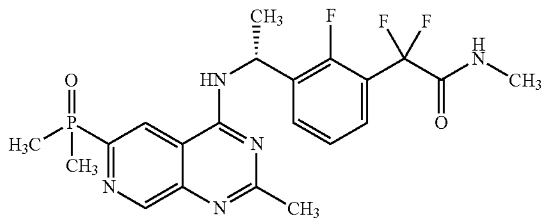

According to general procedure 6, starting from 6-(dimethylphosphoryl)-2-methylpyrido-[3,4-d]pyrimidin-4-ol (Intermediate 71, 49.0 mg, 207 μmol) and 2-{3-[(1R)-1-aminoethyl]-2-fluorophenyl}-2,2-difluoro-N-methylacetamide hydrogen chloride (1/1) (Intermediate 163, 70.1 mg, 248 μmol), the title compound was obtained (5.00 mg, 5% yield).

LC-MS (Method 2): $R_t$=0.88 min; MS (ESIpos): m/z=466.6 $[M+H]^+$ $^1$H-NMR (400 MHz, DMSO-d6) δ[ppm]: 1.107 (16.00), 1.232 (0.56), 1.590 (1.36), 1.608 (1.34), 1.686 (1.92), 1.690 (1.96), 1.720 (1.91), 1.724 (1.89), 2.331 (1.12), 2.336 (0.51), 2.420 (4.42), 2.518 (6.16), 2.523 (4.16), 2.673 (1.12), 2.678 (0.51), 2.723 (1.64), 2.735 (1.58), 4.191 (1.18), 7.301 (0.54), 8.946 (0.52), 8.962 (0.56), 9.092 (1.16).

Example 52

4-[4-({(1R)-1-[3-(difluoromethyl)-2-fluorophenyl]ethyl}amino)-2-methylpyrido[3,4-d]pyrimidin-6-yl]-1-methyl-1,4lambda$^5$-azaphosphinan-4-one

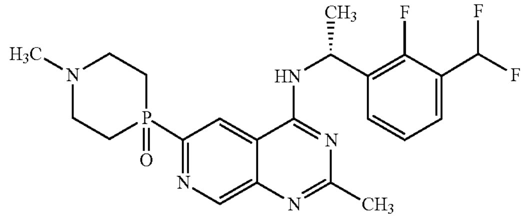 [SMILES: Cc1nc(N[C@H](C)c2cccc(C(F)F)c2F)c2cc(P3(=O)CCN(C)CC3)ncc2n1]

To a solution of 4-[4-({(1R)-1-[3-(difluoromethyl)-2-fluorophenyl]ethyl}amino)-2-methylpyrido[3,4-d]pyrimidin-6-yl]-1,4lambda-azaphosphinan-4-one (Intermediate 226, 51.7 mg, 115 μmol), N,N,N-tributylbutane-1-aminium-bromide (1.85 mg, 5.75 μmol), and (S)-(−)-proline (660 μg, 5.8 μmol) in dimethyl carbonate (0.5 ml) was stirred at 90° C. for 2 d. The residue was concentrated and purified by flash chromatography (silica, dichloromethane, methanol) to give the title compound (21.0 mg, 98% purity, 39% yield).

LC-MS (Method 2): $R_t$=1.02 min; MS (ESIneg): m/z=462 $[M-H]^-$

1H NMR (400 MHz, DMSO-d6) b ppm 1.62 (d, J=7.10 Hz, 3H) 1.84-1.99 (m, 2H) 2.29 (s, 3H) 2.43 (s, 5H) 2.69-2.94 (m, 4H) 5.63-5.86 (m, 1H) 7.08-7.39 (m, 2H) 7.47-7.56 (m, 1H) 7.66-7.76 (m, 1H) 8.92-9.01 (m, 1H) 9.11 (s, 1H) 9.23-9.30 (m, 1H).

Example 53

4-[2-methyl-4-({(1R)-1-[2-methyl-3-(trifluoromethyl)phenyl]ethyl}amino)pyrido[3,4-d]pyrimidin-6-yl]-1-(propan-2-yl)-1,4lambda$^5$-azaphosphinan-4-one

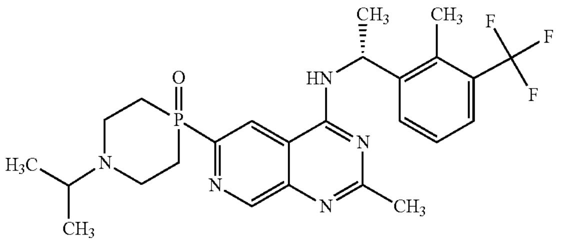 [SMILES: Cc1nc(N[C@H](C)c2cccc(C(F)(F)F)c2C)c2cc(P3(=O)CCN(C(C)C)CC3)ncc2n1]

To a solution of 4-[2-methyl-4-({(1R)-1-[2-methyl-3-(trifluoromethyl)phenyl]ethyl}amino)-pyrido[3,4-d]pyrimidin-6-yl]-1,4lambda$^5$-azaphosphinan-4-one hydrogen chloride (1/1) (Intermediate 164, 430 mg, 860 μmol) in ethanol (8.0 ml) was added acetone (12 ml), followed by sodium cyanoborohydride (81.1 mg, 1.29 mmol) and acetic acid (120 μl), and the mixture was stirred at RT overnight. Then, aqeous sodium hydroxide (1 M) was added, the mixture was diluted with water and extracted with dichloromethane. The organic phases were concentrated and the residue was diluted with DMSO. The formed solid was filtered and dried to give the title compound (275 mg, 90% purity, 57% yield).

LC-MS (Method 2): $R_t$=1.24 min; MS (ESIpos): m/z=507 $[M+H]^+$ $^1$H NMR (400 MHz, DMSO-d6) b ppm 1.04-1.15 (m, 6H) 1.53-1.63 (m, 3H) 1.92-2.14 (m, 1H) 2.42 (s, 3H) 2.62 (s, 4H) 3.01-3.15 (m, 1H) 3.51-3.86 (m, 2H) 4.59-4.77 (m, 1H) 5.65-5.79 (m, 1H) 7.30-7.41 (m, 1H) 7.49-7.60 (m, 1H) 7.74-7.84 (m, 1H) 8.99-9.03 (m, 1H) 9.04-9.06 (m, 1H) 9.37-9.46 (m, 1H).

Example 54

1-benzyl-4-[4-({(1R)-1-[3-(1,1-difluoro-2-hydroxy-2-methylpropyl)-2-fluorophenyl]ethyl}amino)-2-methylpyrido[3,4-d]pyrimidin-6-yl]-1,4lambda$^5$-azaphosphinan-4-one

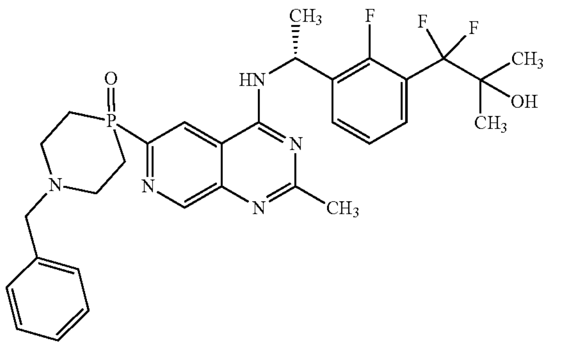 [SMILES: Cc1nc(N[C@H](C)c2cccc(C(F)(F)C(C)(C)O)c2F)c2cc(P3(=O)CCN(Cc4ccccc4)CC3)ncc2n1]

To a solution of 1-benzyl-4-[4-({(1R)-1-[3-(2-{[tert-butyl(dimethyl)silyl]oxy}-1,1-difluoro-2-methylpropyl)-2-fluorophenyl]ethyl}amino)-2-methylpyrido[3,4-d]pyrimidin-6-yl]-1,4lambda$^5$-azaphosphinan-4-one (150 mg, 211 μmol) in THF (1.5 ml) was added tetrabutylammoniumfluoride (840 μl, 1.0 M in THF, 840 μmol), and the mixture was stirred at 40° C. overnight. The mixture was concentrated and the residue was purified by flash chromatography (silica, hexane, ethyl acetate, dichloromethane, ethanol) to obtain the title compound (130 mg, 90% purity, 93% yield).

LC-MS (Method 2): $R_t$=1.23 min; MS (ESIpos): m/z=599 $[M+H]^+$ $^1$H-NMR (400 MHz, DMSO-d6) δ[ppm]: 0.914 (0.40), 0.932 (0.67), 1.153 (0.81), 1.171 (1.59), 1.189 (1.47), 1.199 (6.51), 1.224 (6.70), 1.233 (1.48), 1.251 (0.40), 1.587 (4.89), 1.605 (4.81), 1.876 (0.44), 1.907 (1.12), 1.953 (0.48), 1.986 (2.75), 2.322 (0.49), 2.326 (0.68), 2.332 (0.58), 2.336 (0.43), 2.373 (0.82), 2.415 (16.00), 2.518 (1.88), 2.522 (1.24), 2.664 (0.42), 2.668 (0.58), 2.805 (0.92), 2.836 (1.03), 2.863 (0.45), 2.904 (0.65), 2.917 (0.52), 2.958 (0.67), 2.973 (0.50), 2.989 (0.44), 3.158 (0.84), 3.171 (0.78), 3.653 (6.02), 4.016 (0.57), 4.034 (0.57), 4.212 (0.43), 4.216 (0.44), 4.489 (0.44), 4.494 (0.43), 5.334 (8.36), 5.758 (5.35), 5.767 (0.82), 5.785 (1.24), 5.803 (0.79), 7.199 (0.78), 7.219 (1.81), 7.238 (1.25), 7.249 (0.56), 7.255 (0.67), 7.263 (1.07), 7.271 (0.84), 7.278 (0.93), 7.284 (0.72), 7.297 (0.84), 7.301 (0.88), 7.309 (0.79), 7.319 (1.30), 7.322 (1.39), 7.329 (0.72), 7.343 (4.65), 7.350 (4.87), 7.358 (11.05), 7.371 (0.62), 7.480 (0.43), 7.498 (0.40), 7.525 (0.49), 7.553 (0.63), 7.569 (0.43), 7.600 (0.69), 7.617 (1.16), 7.632 (0.62), 8.986 (1.61), 9.002 (1.60), 9.120 (4.22), 9.254 (1.32), 9.272 (1.26).

The examples shown in Table 6 were prepared according to general procedure 6 from the respective pyrimidin-4-ol derivatives and the respective amines.

TABLE 6

| Examples | |
|---|---|
| Ex. | Structure; IUPAC-Name; Analytical Data; Starting Materials; Yield |
| 55 | 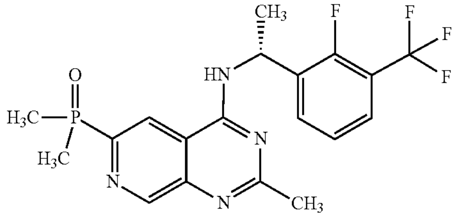 [SMILES: Cc1nc(N[C@H](C)c2cccc(C(F)(F)F)c2F)c2cc(P(C)(C)=O)ncc2n1]<br>6-(dimethylphosphoryl)-N-{(1R)-1-[2-fluoro-3-(trifluoromethyl)phenyl]ethyl}-2-methylpyrido[3,4-d]pyrimidin-4-amine<br>$^1$H-NMR (400 MHz, DMSO-d6) δ [ppm]: 1.628 (5.30), 1.646 (5.28), 1.690 (10.69), 1.724 (10.64), 2.412 (16.00), 2.518 (2.92), 2.523 (2.03), 5.747 (0.78), 5.765 (1.22), 5.782 (0.77), 7.351 (0.76), 7.370 (1.62), 7.390 (0.89), 7.641 (0.66), 7.659 (1.15), 7.676 (0.55), 7.823 (0.61), 7.840 (1.12), 7.858 (0.56), 8.953 (1.85), 8.955 (1.87), 8.970 (1.84), 8.972 (1.79), 9.096 (4.24), 9.334 (0.69), 9.350 (0.67).<br>LC-MS (Method 2): $R_t$ = 1.11 min; MS (ESIneg): m/z = 425 $[M - H]^-$<br>Intermediate 71<br>35.0 mg (95% purity, 12% yield) |

TABLE 6-continued

| Examples | |
|---|---|
| Ex. | Structure; IUPAC-Name; Analytical Data; Starting Materials; Yield |
| 56 | 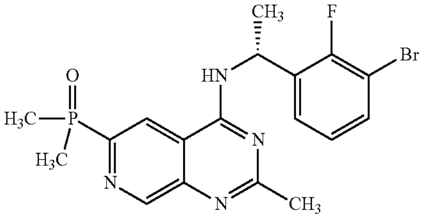 [SMILES: Cc1nc(N[C@H](C)c2cccc(Br)c2F)c2cc(P(C)(C)=O)ncc2n1]<br>N-[(1R)-1-(3-bromo-2-fluorophenyl)ethyl]-6-(dimethylphosphoryl)-2-methylpyrido[3,4-d]pyrimidin-4-amine<br>$^1$H-NMR (400 MHz, DMSO-d6) δ [ppm]: 1.598 (5.02), 1.616 (4.95), 1.689 (7.94), 1.691 (8.11), 1.722 (7.98), 1.724 (7.88), 2.327 (1.00), 2.331 (0.71), 2.433 (16.00), 2.518 (3.47), 2.523 (2.43), 2.669 (1.00), 2.673 (0.69), 5.751 (0.77), 5.769 (1.21), 5.787 (0.76), 7.109 (0.96), 7.129 (2.05), 7.148 (1.13), 7.496 (0.66), 7.500 (0.81), 7.517 (1.28), 7.533 (0.66), 7.536 (0.68), 7.560 (0.92), 7.564 (0.88), 7.576 (1.00), 7.580 (1.57), 7.583 (0.85), 7.596 (0.88), 7.600 (0.74), 8.957 (1.80), 8.958 (1.84), 8.973 (1.80), 8.975 (1.77), 9.096 (4.05), 9.280 (1.20), 9.298 (1.17).<br>LC-MS (Method 2): $R_t$ = 1.09 min; MS (ESIpos): m/z = 439 $[M + H]^+$<br>Intermediate 71<br>33.0 mg (95% purity, 11% yield) |
| 57 | 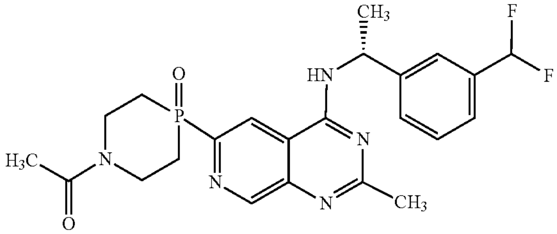 [SMILES: CC(=O)N1CCP(=O)(c2cc3c(N[C@H](C)c4cccc(C(F)F)c4)nc(C)nc3cn2)CC1]<br>1-acetyl-4-[4-{{(1R)-1-[3-(difluoromethyl)phenyl]ethyl}amino)-2-methylpyrido[3,4-d]pyrimidin-6-yl]-1,4lambda$^5$-azaphosphinan-4-one<br>$^1$H-NMR (400 MHz, DMSO-d6) δ [ppm]: 1.615 (4.95), 1.633 (4.93), 2.115 (16.00), 2.318 (0.59), 2.469 (14.23), 2.518 (6.48), 2.523 (4.67), 2.679 (0.52), 3.845 (0.50), 3.857 (0.64), 3.882 (0.45), 5.645 (0.69), 5.663 (1.04), 5.682 (0.68), 6.891 (1.32), 7.031 (2.62), 7.171 (1.18), 7.430 (0.69), 7.449 (1.60), 7.469 (1.27), 7.488 (1.78), 7.507 (0.72), 7.630 (1.17), 7.649 (0.96), 7.681 (1.95), 8.978 (1.58), 8.994 (1.59), 9.110 (4.11), 9.233 (1.12), 9.252 (1.09).<br>LC-MS (Method 1): $R_t$ = 0.86 min; MS (ESIpos): m/z = 474 $[M + H]^+$<br>Intermediate 139<br>29.9 mg (95% purity, 16% yield) |
| 58 | 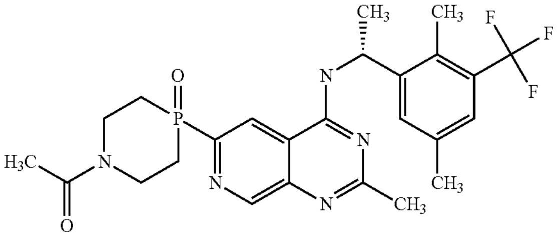<br>1-acetyl-4-[4-{{(1R)-1-[2,5-dimethyl-3-(trifluoromethyl)phenyl]ethyl}amino)-2-methylpyrido[3,4-d]pyrimidin-6-yl]-1,4lambda$^5$-azaphosphinan-4-one<br>$^1$H NMR (400 MHz, DMSO-d6) δ ppm 1.56 (d, J = 7.10 Hz, 3 H) 1.83-1.98 (m, 1 H) 1.99-2.14 (m, 4 H) 2.20-2.36 (m, 5 H) 2.42-2.44 (m, 3 H) 2.54-2.59 (m, 3 H) 3.63-4.12 (m, 4 H) 5.62-5.79 (m, 1 H) 7.37 (s, 1 H) 7.61 (s, 1 H) 8.98-9.04 (m, 1 H) 9.09 (s, 1 H) 9.28-9.40 (m, 1 H).<br>LC-MS (Method 2): Rt = 1.18 min; MS (ESIpos): m/z = 520 $[M + H]^+$<br>Intermediate 139 and Intermediate 245<br>35.0 mg (95% purity, 19% yield) |

The examples shown in Table 7 were prepared as described for Example 4 from the respective silyl protected alcohol derivatives.

TABLE 7

| Ex. | Examples<br>Structure; IUPAC-Name; Analytical Data; Starting Materials; Yield |
|---|---|
| 59 | 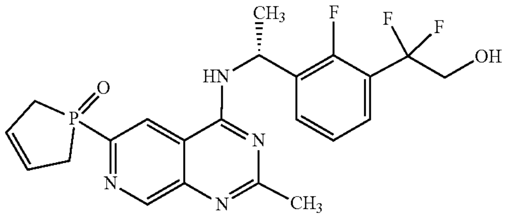 [SMILES: Cc1nc(N[C@H](C)c2cccc(C(F)(F)CO)c2F)c2cc(P3(=O)CC=CC3)ncc2n1]<br>1-[4-{{(1R)-1-[3-(1,1-difluoro-2-hydroxyethyl)-2-fluorophenyl]ethyl}amino)-2-methylpyrido[3,4-d]pyrimidin-6-yl]-2,5-dihydro-1H-1lambda$^5$-phosphol-1-one<br>$^1$H-NMR (400 MHz, DMSO-d6) δ [ppm]: 1.606 (4.88), 1.624 (4.87), 2.322 (0.86), 2.327 (1.16), 2.332 (0.86), 2.436 (16.00), 2.518 (4.93), 2.523 (3.23), 2.558 (0.69), 2.601 (1.22), 2.645 (0.92), 2.660 (0.44), 2.664 (0.91), 2.669 (1.22), 2.673 (0.88), 2.878 (1.00), 2.885 (1.00), 2.931 (0.75), 3.892 (0.56), 3.908 (0.63), 3.928 (1.13), 3.944 (1.20), 3.964 (0.55), 3.980 (0.54), 5.704 (1.08), 5.720 (2.61), 5.736 (1.04), 5.783 (0.80), 5.801 (1.23), 5.819 (0.77), 6.008 (2.57), 6.079 (2.54), 7.245 (0.90), 7.264 (2.00), 7.283 (1.15), 7.409 (0.71), 7.426 (1.13), 7.442 (0.55), 7.656 (0.61), 7.674 (1.11), 7.690 (0.56), 9.058 (1.86), 9.074 (2.01), 9.083 (4.72), 9.307 (1.32), 9.325 (1.25).<br>LC-MS (Method 2): $R_t$ = 0.91 min; MS (ESIneg): m/z = 461 $[M - H]^-$<br>Intermediate 208<br>54.7 mg (95% purity, 63% yield) |
| 60 | 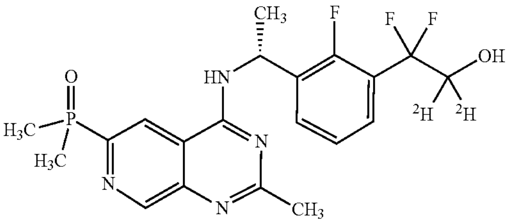 [SMILES: [2H]C([2H])(O)C(F)(F)c1cccc([C@@H](C)Nc2nc(C)nc3cnc(P(C)(C)=O)cc23)c1F]<br>2-{3-[(1R)-1-{[6-(dimethylphosphoryl)-2-methylpyrido[3,4-d]pyrimidin-4-yl]amino}ethyl]-2-fluorophenyl}-2,2-difluoro($^2H_2$)ethan-1-ol<br>$^1$H-NMR (400 MHz, DMSO-d6) δ [ppm]: 1.602 (4.77), 1.620 (4.73), 1.688 (6.65), 1.692 (6.78), 1.722 (6.79), 1.726 (6.68), 1.890 (0.41), 2.432 (16.00), 2.442 (0.85), 2.518 (2.84), 2.523 (2.16), 5.684 (4.34), 5.758 (6.52), 5.782 (0.76), 5.800 (1.16), 5.817 (0.73), 7.245 (0.87), 7.264 (1.91), 7.284 (1.11), 7.408 (0.69), 7.426 (1.10), 7.442 (0.54), 7.656 (0.59), 7.674 (1.02), 7.691 (0.52), 8.955 (1.72), 8.957 (1.76), 8.971 (1.74), 8.973 (1.68), 9.091 (4.08), 9.276 (1.26), 9.294 (1.17).<br>LC-MS (Method 2): $R_t$ = 0.86 min; MS (ESIpos): m/z = 441 $[M + H]^+$<br>Intermediate 135<br>49.4 mg (95% purity, 60% yield) |
| 61 | 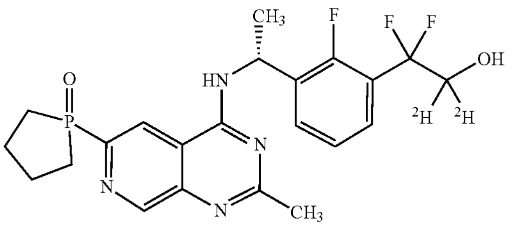 [SMILES: [2H]C([2H])(O)C(F)(F)c1cccc([C@@H](C)Nc2nc(C)nc3cnc(P4(=O)CCCC4)cc23)c1F]<br>1-(4-{[(1R)-1-{3-[1,1-difluoro-2-hydroxy($^2H_2$)ethyl]-2-fluorophenyl}ethyl]amino}-2-methylpyrido[3,4-d]pyrimidin-6-yl)-1lambda$^5$-phospholan-1-one<br>LC-MS (Method 2): $R_t$ = 0.94 min; MS (ESIpos): m/z = 467 $[M + H]^+$<br>Intermediate 210<br>36.9 mg (95% purity, 42% yield) |

TABLE 7-continued

| Examples | |
|---|---|
| Ex. | Structure; IUPAC-Name; Analytical Data; Starting Materials; Yield |
| 62 | 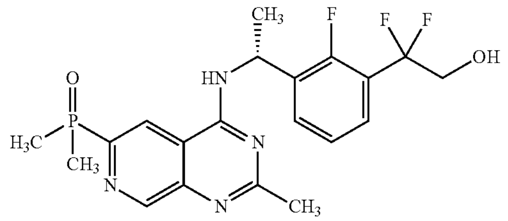 [SMILES: Cc1nc(N[C@H](C)c2cccc(C(F)(F)CO)c2F)c2cc(P(C)(C)=O)ncc2n1]<br>2-{3-[(1R)-1-{[6-(dimethylphosphoryl)-2-methylpyrido[3,4-d]pyrimidin-4-yl]amino}ethyl]-2-fluorophenyl}-2,2-difluoroethan-1-ol<br>$^1$H-NMR (400 MHz, DMSO-d6) δ [ppm]: 1.601 (5.28), 1.619 (5.30), 1.689 (8.01), 1.692 (8.24), 1.723 (8.15), 1.726 (8.05), 2.332 (0.40), 2.431 (16.00), 2.518 (2.71), 2.522 (1.77), 3.891 (0.64), 3.907 (0.71), 3.927 (1.27), 3.943 (1.34), 3.963 (0.63), 3.979 (0.60), 5.711 (1.12), 5.727 (2.51), 5.743 (1.08), 5.779 (0.87), 5.797 (1.33), 5.815 (0.85), 7.244 (0.95), 7.263 (2.13), 7.283 (1.24), 7.407 (0.80), 7.424 (1.29), 7.440 (0.62), 7.655 (0.71), 7.672 (1.26), 7.688 (0.63), 8.952 (1.99), 8.967 (1.97), 9.088 (4.67), 9.276 (1.30), 9.293 (1.25).<br>LC-MS (Method 2): $R_t$ = 0.90 min; MS (ESIpos): m/z = 439 $[M + H]^+$<br>Intermediate 211<br>32.5 mg (95% purity, 52% yield) |
| 63 | 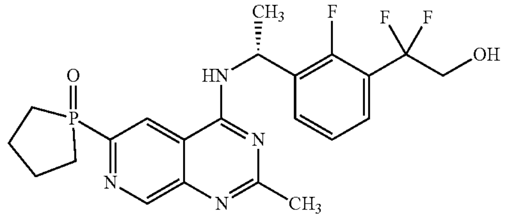 [SMILES: Cc1nc(N[C@H](C)c2cccc(C(F)(F)CO)c2F)c2cc(P3(=O)CCCC3)ncc2n1]<br>1-[4-{{(1R)-1-[3-(1,1-difluoro-2-hydroxyethyl)-2-fluorophenyl]ethyl}amino)-2-methylpyrido[3,4-d]pyrimidin-6-yl]-1lambda$^5$-phospholan-1-one<br>$^1$H-NMR (400 MHz, DMSO-d6) δ [ppm]: 1.601 (5.28), 1.619 (5.26), 1.794 (0.47), 1.813 (0.66), 1.832 (0.81), 1.846 (0.70), 1.867 (0.56), 1.959 (0.58), 1.976 (0.90), 1.995 (1.12), 2.012 (1.24), 2.035 (1.03), 2.053 (0.92), 2.069 (0.66), 2.090 (1.04), 2.101 (0.91), 2.118 (1.06), 2.136 (1.00), 2.153 (0.68), 2.437 (16.00), 2.518 (3.71), 2.522 (2.46), 2.673 (0.73), 3.903 (0.53), 3.938 (0.99), 3.967 (0.50), 5.726 (0.66), 5.782 (0.84), 5.800 (1.28), 5.818 (0.80), 7.242 (0.96), 7.261 (2.16), 7.280 (1.24), 7.407 (0.77), 7.424 (1.20), 7.440 (0.58), 7.655 (0.67), 7.672 (1.16), 7.688 (0.59), 9.012 (1.84), 9.027 (1.82), 9.096 (4.77), 9.351 (0.48).<br>LC-MS (Method 2): $R_t$ = 0.99 min; MS (ESIpos): m/z = 465 $[M + H]^+$<br>Intermediate 212<br>35.3 mg (95% purity, 53% yield) |
| 64 | 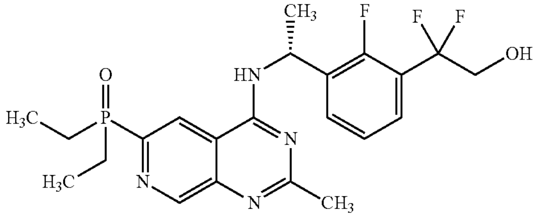 [SMILES: CCP(=O)(CC)c1cc2c(N[C@H](C)c3cccc(C(F)(F)CO)c3F)nc(C)nc2cn1]<br>2-{3-[(1R)-1-{[6-(diethylphosphoryl)-2-methylpyrido[3,4-d]pyrimidin-4-yl]amino}ethyl]-2-fluorophenyl}-2,2-difluoroethan-1-ol<br>$^1$H-NMR (400 MHz, DMSO-d6) δ [ppm]: 0.911 (1.76), 0.930 (4.84), 0.947 (5.16), 0.953 (2.29), 0.966 (2.41), 0.972 (4.79), 0.990 (4.83), 1.009 (1.82), 1.603 (4.72), 1.621 (4.68), 1.952 (0.45), 1.962 (1.11), 1.971 (1.27), 1.981 (1.93), 1.990 (1.80), 1.997 (1.27), 2.000 (1.67), 2.006 (1.56), 2.008 (1.61), 2.022 (1.12), 2.024 (1.19), 2.031 (0.93), 2.040 (0.41), 2.332 (0.64), 2.430 (16.00), 2.518 (3.29), 2.522 (2.15), 2.673 (0.66), 3.312 (0.66), 3.316 (0.67), 3.369 (2.64), 3.385 (0.43), 3.391 (0.41), 3.393 (0.52), 3.401 (0.54), 3.891 (0.52), 3.907 (0.57), 3.927 (1.03), 3.943 (1.09), 3.962 (0.50), 3.978 (0.49), 5.709 (1.07), 5.725 (2.51), 5.741 (1.02), 5.774 (0.76), 5.792 |

TABLE 7-continued

| Ex. | Examples<br>Structure; IUPAC-Name; Analytical Data; Starting Materials; Yield |
| --- | --- |
| | (1.15), 5.810 (0.73), 7.248 (0.86), 7.268 (1.90), 7.287 (1.12), 7.407 (0.68), 7.424 (1.07), 7.440 (0.52), 7.662 (0.58), 7.679 (1.03), 7.696 (0.52), 8.931 (1.74), 8.945 (1.73), 9.087 (4.40), 9.312 (1.26), 9.330 (1.20).<br>LC-MS (Method 2): $R_t$ = 0.99 min; MS (ESIpos): m/z = 467 $[M + H]^+$<br>Intermediate 213<br>33.1 mg (95% purity, 50% yield) |
| 65 | 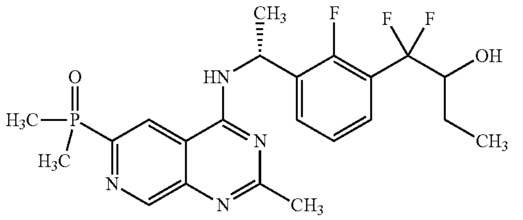 [SMILES: CCC(O)C(F)(F)c1cccc([C@@H](C)Nc2nc(C)nc3cnc(P(C)(C)=O)cc23)c1F]<br>(2R*)-1-{3-[(1R)-1-{[6-(dimethylphosphoryl)-2-methylpyrido[3,4-d]pyrimidin-4-yl]amino}ethyl]-2-fluorophenyl}-1,1-difluorobutan-2-ol (diastereomer 1)<br>$^1$H-NMR (400 MHz, DMSO-d6) δ [ppm]: 0.899 (2.80), 0.917 (6.56), 0.935 (3.22), 1.358 (0.45), 1.375 (0.54), 1.383 (0.49), 1.393 (0.47), 1.399 (0.55), 1.533 (0.51), 1.552 (0.56), 1.562 (0.53), 1.593 (5.26), 1.610 (5.21), 1.689 (8.38), 1.691 (8.47), 1.723 (8.51), 1.726 (8.39), 2.437 (16.00), 2.518 (4.52), 2.523 (3.08), 3.372 (0.93), 3.858 (0.45), 5.556 (2.71), 5.574 (2.64), 5.797 (0.84), 5.815 (1.28), 5.833 (0.83), 7.232 (0.91), 7.251 (2.09), 7.270 (1.31), 7.358 (0.81), 7.375 (1.24), 7.391 (0.59), 7.638 (0.67), 7.655 (1.21), 7.671 (0.63), 8.956 (1.94), 8.971 (1.97), 9.092 (4.73), 9.259 (1.43), 9.276 (1.39).<br>LC-MS (Method 2): $R_t$ = 0.98 min; MS (ESIpos): m/z = 467 $[M + H]^+$<br>Intermediate 178<br>20.0 mg (100% purity, 45% yield) |
| 66 | 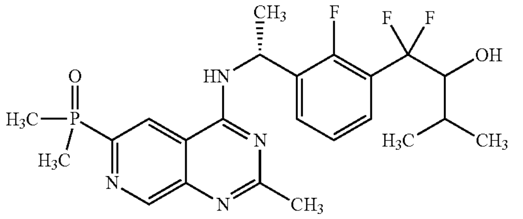 [SMILES: Cc1nc(N[C@H](C)c2cccc(C(F)(F)C(O)C(C)C)c2F)c2cc(P(C)(C)=O)ncc2n1]<br>(2R*)-1-{3-[(1R)-1-{[6-(dimethylphosphoryl)-2-methylpyrido[3,4-d]pyrimidin-4-yl]amino}ethyl]-2-fluorophenyl}-1,1-difluoro-3-methylbutan-2-ol (diastereomer 1)<br>$^1$H-NMR (400 MHz, DMSO-d6) δ [ppm]: 0.863 (5.11), 0.880 (5.28), 0.903 (5.75), 0.920 (5.91), 1.593 (5.16), 1.610 (5.20), 1.691 (9.95), 1.724 (9.94), 1.769 (0.61), 1.779 (0.60), 1.786 (0.72), 1.795 (0.72), 1.803 (0.54), 1.812 (0.52), 2.434 (16.00), 2.518 (4.58), 2.523 (3.23), 3.828 (0.40), 3.846 (0.44), 3.856 (0.44), 5.523 (2.88), 5.541 (2.78), 5.788 (0.84), 5.805 (1.30), 5.823 (0.83), 7.234 (0.96), 7.253 (2.16), 7.273 (1.28), 7.384 (0.79), 7.402 (1.25), 7.418 (0.64), 7.636 (0.74), 7.653 (1.25), 7.670 (0.66), 8.958 (1.95), 8.973 (1.97), 9.092 (4.74), 9.260 (1.45), 9.278 (1.39).<br>LC-MS (Method 2): $R_t$ = 1.05 min; MS (ESIpos): m/z = 481 $[M + H]^+$<br>Intermediate 176<br>17.0 mg (100% purity, 38% yield) |
| 67 | 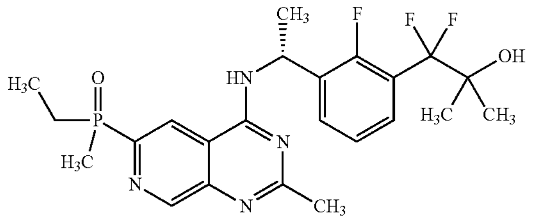 [SMILES: CCP(C)(=O)c1cc2c(N[C@H](C)c3cccc(C(F)(F)C(C)(C)O)c3F)nc(C)nc2cn1]<br>1-{3-[(1R)-1-{{6-[ethyl(methyl)phosphoryl]-2-methylpyrido[3,4-d]pyrimidin-4-yl}amino)ethyl]-2-fluorophenyl}-1,1-difluoro-2-methylpropan-2-ol (mixture of diastereomers)<br>$^1$H-NMR (400 MHz, DMSO-d6) δ [ppm]: 0.935 (1.40), 0.948 (1.53), 0.954 (3.29), 0.967 (3.37), 0.973 (1.78), 0.979 (1.63), 0.986 (1.70), 0.991 (1.70), 0.997 (3.42), 1.010 (3.25), 1.016 (1.65), 1.029 (1.40), 1.201 (8.48), 1.227 (8.51), 1.589 (6.39), 1.607 (6.39), 1.657 (5.35), 1.665 (5.63), 1.690 (5.42), 1.698 (5.43), 1.953 (0.43), 1.963 (0.73), 1.973 (1.14), 1.978 (0.99), 1.981 (1.02), 1.992 (1.52), 1.998 (1.18), 2.005 |

TABLE 7-continued

| Ex. | Examples<br>Structure; IUPAC-Name; Analytical Data; Starting Materials; Yield |
|---|---|
| | (0.93), 2.010 (1.33), 2.018 (0.80), 2.024 (0.74), 2.028 (0.83), 2.331 (0.90), 2.410 (15.83), 2.412 (16.00), 2.518 (4.67), 2.523 (3.22), 2.673 (0.89), 5.336 (9.13), 5.777 (0.76), 5.790 (1.10), 5.795 (1.13), 5.808 (0.74), 5.812 (0.70), 7.203 (0.59), 7.210 (0.62), 7.222 (1.42), 7.229 (1.41), 7.241 (0.94), 7.248 (0.89), 7.301 (1.03), 7.319 (1.56), 7.336 (0.70), 7.610 (0.52), 7.624 (1.01), 7.637 (0.95), 7.652 (0.46), 8.953 (1.37), 8.965 (1.94), 8.979 (1.40), 9.087 (6.40), 9.293 (0.98), 9.310 (1.84), 9.328 (0.97).<br>LC-MS (Method 2): $R_t$ = 1.00 min; MS (ESIpos): m/z = 481 $[M + H]^+$<br>Intermediate 216<br>103 mg (95% purity, 50% yield) |

The diastereomers of example 67 were separated according to the following method.
Anal.-Method:
Instrument: Thermo Fisher UltiMate 3000; Column: YMC Cellulose SB 3μ, 100 x 4.6; eluent A: methyl tert-butyl ether + 0.1 vol % diethylamine; eluent B: acetonitrile; isocratic: 90% A + 10% B; flow: 1.4 ml/min; temperature: 25° C.; UV: 280 nm
Prep.-Method:
Instrument: PrepCon Labomatic HPLC-2; Column: YMC Cellulose SB 5μ, 250 x 30; eluent A: methyl tert-butyl ether + 0.1 vol % diethylamine; eluent B: acetonitrile; isocratic: 90% A + 10% B; flow: 50 ml/min; temperature: 25° C.; UV: 280 nm

| | |
|---|---|
| 68 | 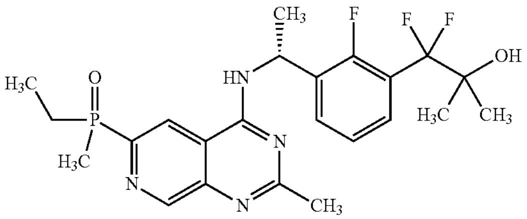 [SMILES: CCP(C)(=O)c1cc2c(N[C@H](C)c3cccc(C(F)(F)C(C)(C)O)c3F)nc(C)nc2cn1]<br>1-{3-[(1R)-1-{{6-[ethyl(methyl)phosphoryl]-2-methylpyrido[3,4-d]pyrimidin-4-yl}amino)ethyl]-2-fluorophenyl}-1,1-difluoro-2-methylpropan-2-ol (diastereomer 1)<br>$^1$H-NMR (400 MHz, DMSO-d6) δ [ppm]: 0.851 (0.48), 0.935 (1.92), 0.954 (4.32), 0.973 (2.24), 0.979 (2.10), 0.997 (4.51), 1.016 (2.06), 1.203 (6.64), 1.229 (8.08), 1.590 (4.91), 1.608 (4.87), 1.665 (7.23), 1.698 (7.32), 1.954 (0.45), 1.963 (0.81), 1.973 (1.27), 1.982 (0.93), 1.992 (1.65), 2.005 (1.07), 2.011 (1.09), 2.024 (0.86), 2.029 (0.42), 2.336 (0.49), 2.411 (16.00), 2.518 (6.41), 2.523 (4.34), 2.678 (0.51), 5.336 (7.12), 5.777 (0.78), 5.795 (1.22), 5.813 (0.76), 7.203 (0.77), 7.222 (1.82), 7.242 (1.18), 7.298 (0.71), 7.301 (0.81), 7.319 (1.12), 7.334 (0.55), 7.611 (0.62), 7.626 (1.11), 7.643 (0.58), 8.965 (1.82), 8.979 (1.82), 9.088 (4.10), 9.311 (1.14), 9.330 (1.09).<br>LC-MS (Method 2): $R_t$ = 1.00 min; MS (ESIpos): m/z = 482 $[M + H]^+$<br>Example 67<br>28.0 mg (95% purity)<br>Rt (analytical method) = 4.92 min; de >99% |
| 69 | 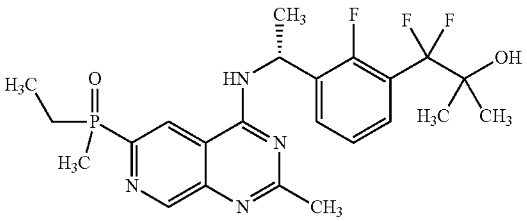 [SMILES: CCP(C)(=O)c1cc2c(N[C@H](C)c3cccc(C(F)(F)C(C)(C)O)c3F)nc(C)nc2cn1]<br>1-{3-[(1R)-1-{{6-[ethyl(methyl)phosphoryl]-2-methylpyrido[3,4-d]pyrimidin-4-yl}amino)ethyl]-2-fluorophenyl}-1,1-difluoro-2-methylpropan-2-ol (diastereomer 2)<br>$^1$H-NMR (400 MHz, DMSO-d6) δ [ppm]: 0.948 (1.97), 0.967 (4.53), 0.986 (2.30), 0.991 (2.19), 1.011 (4.48), 1.030 (2.18), 1.200 (7.17), 1.225 (7.80), 1.588 (5.17), 1.606 (5.12), 1.657 (7.30), 1.690 (7.30), 1.959 (0.41), 1.970 (0.93), 1.978 (1.12), 1.989 (1.15), 1.998 (1.45), 2.009 (1.16), 2.018 (1.01), 2.029 (0.86), 2.331 (1.67), 2.413 (16.00), 2.518 (9.55), 2.523 (6.26), 2.673 (1.67), 5.335 (7.66), 5.772 (0.84), 5.790 (1.29), 5.808 (0.82), 7.210 (0.80), 7.230 (1.88), 7.249 (1.24), 7.304 (0.87), 7.321 (1.22), 7.336 (0.56), 7.621 (0.68), 7.638 (1.18), 7.653 (0.61), 8.953 (1.92), 8.967 (1.94), 9.087 (4.40), 9.293 (1.40), 9.311 (1.39).<br>LC-MS (Method 2): $R_t$ = 1.00 min; MS (ESIpos): m/z = 482 $[M + H]^+$<br>Example 67<br>25.0 mg (95% purity)<br>Rt (analytical method) = 6.23 min; de 97% |

TABLE 7-continued

| Examples | |
|---|---|
| Ex. | Structure; IUPAC-Name; Analytical Data; Starting Materials; Yield |
| 70 | 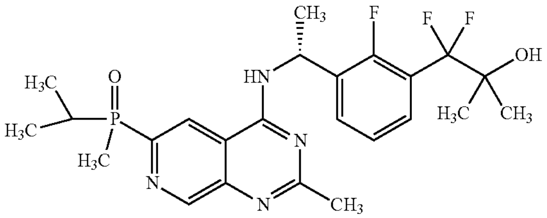 [SMILES: Cc1nc(N[C@H](C)c2cccc(C(F)(F)C(C)(C)O)c2F)c2cc(P(C)(=O)C(C)C)ncc2n1] |

1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}-2-methylpropan-2-ol (mixture of diastereomers)

$^1$H-NMR (400 MHz, DMSO-d6) δ [ppm]: 0.851 (0.54), 0.894 (3.68), 0.902 (4.07), 0.911 (3.97), 0.920 (3.99), 0.934 (3.82), 0.942 (4.12), 0.952 (3.82), 0.960 (3.86), 1.143 (6.03), 1.161 (6.38), 1.184 (7.02), 1.201 (16.00), 1.224 (10.33), 1.594 (9.29), 1.612 (9.20), 1.655 (8.16), 1.663 (8.27), 1.687 (8.19), 1.695 (8.12), 2.182 (0.62), 2.192 (0.70), 2.199 (1.01), 2.204 (0.81), 2.210 (0.99), 2.216 (1.09), 2.223 (0.94), 2.228 (0.80), 2.233 (1.01), 2.240 (0.66), 2.251 (0.59), 2.327 (2.50), 2.331 (1.76), 2.337 (0.79), 2.418 (15.48), 2.423 (15.72), 2.518 (9.17), 2.523 (6.29), 2.673 (1.70), 2.678 (0.76), 5.335 (2.76), 5.779 (1.16), 5.798 (1.75), 5.814 (1.15), 7.206 (0.85), 7.217 (0.97), 7.225 (1.97), 7.237 (2.07), 7.245 (1.40), 7.256 (1.40), 7.304 (1.60), 7.322 (2.35), 7.340 (1.16), 7.609 (0.81), 7.626 (1.86), 7.641 (1.78), 7.657 (0.65), 8.949 (1.72), 8.965 (3.14), 8.981 (1.65), 9.092 (8.46), 9.399 (0.53).

LC-MS (Method 1): $R_t$ = 0.95 min; MS (ESIpos): m/z = 496 [M + H]$^+$

Intermediate 219

68.0 mg (95% purity, 29% yield)

The diastereomers of example 70 were separated according to the following method.

Anal.-Method:

Instrument: Thermo Fisher UltiMate 3000; Column: YMC Cellulose SB 3 μ, 100 × 4.6; eluent A: methyl tert-butyl ether + 0.1 vol % diethylamine; eluent B: acetonitrile; isocratic: 70% A + 30% B; flow: 1.4 ml/min; temperature: 25° C.; UV: 280 nm;

Prep.-Method:

Instrument: PrepCon Labomatic HPLC-2; Column: YMC Cellulose SB 5 μ, 250 × 30; eluent A: methyl tert-butyl ether + 0.1 vol % diethylamine; eluent B: acetonitrile; isocratic: 70% A + 30% B; flow: 50 ml/min; temperature: 25° C.; UV: 280 nm;

71

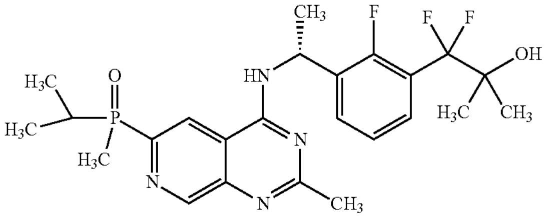 [SMILES: Cc1nc(N[C@H](C)c2cccc(C(F)(F)C(C)(C)O)c2F)c2cc(P(C)(=O)C(C)C)ncc2n1]

1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}-2-methylpropan-2-ol (diastereomer 1)

$^1$H-NMR (400 MHz, DMSO-d6) δ [ppm]: 0.892 (3.47), 0.911 (3.52), 0.933 (3.55), 0.951 (3.51), 1.144 (3.48), 1.161 (3.64), 1.184 (3.76), 1.201 (10.20), 1.229 (7.56), 1.590 (5.08), 1.608 (5.11), 1.662 (7.62), 1.694 (7.63), 2.181 (0.58), 2.199 (0.79), 2.204 (0.67), 2.217 (0.64), 2.222 (0.80), 2.240 (0.52), 2.331 (0.95), 2.336 (0.44), 2.409 (16.00), 2.518 (5.18), 2.523 (3.37), 2.673 (0.93), 2.678 (0.42), 5.335 (8.16), 5.774 (0.83), 5.792 (1.28), 5.810 (0.81), 7.202 (0.81), 7.221 (1.91), 7.240 (1.27), 7.296 (0.76), 7.300 (0.87), 7.317 (1.23), 7.333 (0.59), 7.606 (0.69), 7.622 (1.23), 7.638 (0.64), 8.955 (1.97), 8.970 (1.96), 9.085 (4.85), 9.329 (1.47), 9.347 (1.37).

LC-MS (Method 2): $R_t$ = 1.06 min; MS (ESIpos): m/z = 496 [M + H]$^+$

Example 70

20.0 mg (95% purity, 9% yield)

Rt (analytical method) = 2.03 min; de 99%

72

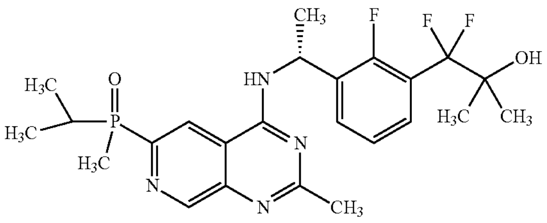 [SMILES: Cc1nc(N[C@H](C)c2cccc(C(F)(F)C(C)(C)O)c2F)c2cc(P(C)(=O)C(C)C)ncc2n1]

TABLE 7-continued

| Ex. | Examples<br>Structure; IUPAC-Name; Analytical Data; Starting Materials; Yield |
|---|---|
| | 1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}-2-methylpropan-2-ol (diastereomer 2)<br>$^1$H-NMR (400 MHz, DMSO-d6) δ [ppm]: 0.902 (3.43), 0.920 (3.48), 0.942 (3.53), 0.960 (3.46), 1.142 (3.45), 1.160 (3.61), 1.182 (3.94), 1.199 (8.10), 1.222 (6.94), 1.589 (4.96), 1.607 (4.95), 1.653 (7.38), 1.685 (7.32), 2.192 (0.53), 2.210 (0.77), 2.216 (0.65), 2.228 (0.59), 2.233 (0.76), 2.252 (0.56), 2.331 (1.07), 2.336 (0.47), 2.413 (16.00), 2.518 (5.52), 2.523 (3.69), 2.673 (1.05), 2.678 (0.48), 5.333 (7.65), 5.770 (0.81), 5.788 (1.25), 5.805 (0.78), 7.214 (0.76), 7.233 (1.85), 7.252 (1.22), 7.299 (0.73), 7.303 (0.85), 7.320 (1.14), 7.336 (0.55), 7.622 (0.66), 7.638 (1.14), 7.654 (0.58), 8.938 (1.90), 8.952 (1.90), 9.084 (4.68), 9.305 (1.38), 9.323 (1.32).<br>LC-MS (Method 2): $R_t$ = 1.05 min; MS (ESIpos): m/z = 496 $[M + H]^+$<br>Example 70<br>20.0 mg (95% purity, 9% yield)<br>Rt (analytical method) = 2.50 min; de 98% |
| 73 | 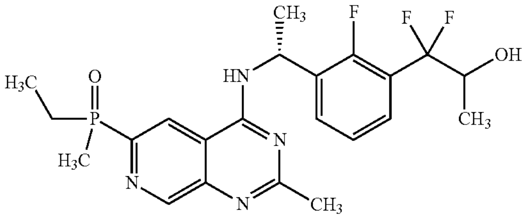 [SMILES: CCP(C)(=O)c1cc2c(N[C@H](C)c3cccc(C(F)(F)C(C)O)c3F)nc(C)nc2cn1]<br>(2R*)-1-{3-[(1R)-1-{{6-[ethyl(methyl)phosphoryl]-2-methylpyrido[3,4-d]pyrimidin-4-yl}amino)ethyl]-2-fluorophenyl}-1,1-difluoropropan-2-ol (mixture of diastereomers)<br>$^1$H-NMR (400 MHz, DMSO-d6) δ [ppm]: 0.934 (1.06), 0.948 (1.21), 0.953 (2.61), 0.968 (2.63), 0.972 (1.38), 0.978 (1.18), 0.987 (1.28), 0.992 (1.33), 0.997 (2.65), 1.011 (2.55), 1.016 (1.29), 1.030 (1.07), 1.131 (3.89), 1.148 (3.90), 1.601 (4.35), 1.619 (4.36), 1.655 (4.08), 1.663 (4.27), 1.688 (4.01), 1.696 (4.10), 1.962 (0.52), 1.972 (0.95), 1.978 (0.69), 1.981 (0.75), 1.991 (1.23), 1.997 (0.75), 2.000 (0.79), 2.009 (1.02), 2.019 (0.56), 2.023 (0.56), 2.028 (0.62), 2.413 (16.00), 2.518 (2.18), 2.523 (1.60), 4.194 (0.41), 4.210 (0.42), 5.579 (2.69), 5.595 (2.63), 5.749 (0.49), 5.756 (0.54), 5.767 (0.77), 5.774 (0.78), 5.785 (0.52), 5.791 (0.47), 7.223 (0.50), 7.229 (0.51), 7.242 (1.15), 7.249 (1.13), 7.261 (0.70), 7.268 (0.68), 7.357 (0.71), 7.374 (1.15), 7.392 (0.52), 7.641 (0.70), 8.945 (1.02), 8.956 (1.26), 8.959 (1.20), 8.970 (1.03), 9.086 (4.67), 9.294 (0.73), 9.311 (1.31), 9.328 (0.69).<br>LC-MS (Method 2): $R_t$ = 0.95 min; MS (ESIpos): m/z = 468 $[M + H]^+$<br>Intermediate 221<br>142 mg (95% purity, 65% yield)<br>The diastereomers of example 73 were separated according to the following method.<br>Anal.-Method:<br>Instrument: Thermo Fisher UltiMate 3000; Column: YMC Cellulose SB 3μ, 100 × 4.6; eluent A: methyl tert-butyl ether + 0.1 vol % diethylamine; eluent B: acetonitrile; isocratic: 70% A + 30% B; flow: 1.4 ml/min; temperature: 25° C.; UV: 280 nm;<br>Prep.-Method:<br>Instrument: PrepCon Labomatic HPLC-3; Column: YMC Cellulose SB 10 μ, 250 × 50; eluent A: methyl tert-butyl ether + 0.1 vol % diethylamine; eluent B: acetonitrile; isocratic: 70% A + 30 % B; flow: 120 mL/min; temperature: 25° C.; UV: 280 nm; |
| 74 | 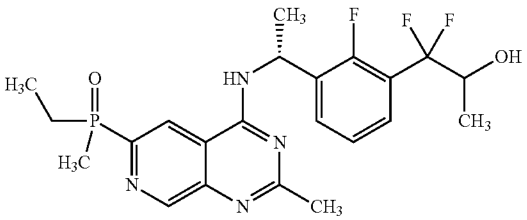 [SMILES: CCP(C)(=O)c1cc2c(N[C@H](C)c3cccc(C(F)(F)C(C)O)c3F)nc(C)nc2cn1]<br>(2R*)-1-{3-[(1R)-1-{{6-[ethyl(methyl)phosphoryl]-2-methylpyrido[3,4-d]pyrimidin-4-yl}amino)ethyl]-2-fluorophenyl}-1,1-difluoropropan-2-ol (diastereomer 1)<br>$^1$H-NMR (400 MHz, DMSO-d6) δ [ppm]: 0.934 (1.86), 0.953 (4.55), 0.972 (2.21), 0.977 (2.07), 0.996 (4.42), 1.016 (1.99), 1.133 (4.29), 1.149 (4.32), 1.232 (1.33), 1.352 (0.63), 1.602 (4.85), 1.619 (4.88), 1.663 (7.45), 1.696 (7.38), 1.953 (0.40), 1.962 (0.76), 1.972 (1.17), 1.981 (0.84), 1.991 (1.60), 2.004 (0.91), 2.010 (1.06), 2.023 (0.79), 2.332 (0.81), 2.413 (16.00), 2.518 (4.50), 2.523 (2.95), 2.673 (0.82), 4.209 (0.41), 5.578 (3.24), 5.594 (3.13), 5.756 (0.80), 5.774 (1.21), 5.791 (0.77), 7.223 (0.87), 7.242 (2.00), 7.261 (1.18), 7.354 (0.64), 7.357 (0.73), 7.374 (1.10), 7.390 |

TABLE 7-continued

| Ex. | Examples<br>Structure; IUPAC-Name; Analytical Data; Starting Materials; Yield |
|---|---|
| | (0.53), 7.623 (0.61), 7.641 (1.08), 7.656 (0.54), 8.955 (1.84), 8.969 (1.82), 8.971 (1.78), 9.086 (4.37), 9.310 (1.32), 9.328 (1.24).<br>LC-MS (Method 2): $R_t$ = 0.95 min; MS (ESIpos): m/z = 468 $[M + H]^+$<br>Example 73<br>48.9 mg (99% purity, 23% yield)<br>Rt (analytical method) = 3.57 min; de >99 % |
| 75 | 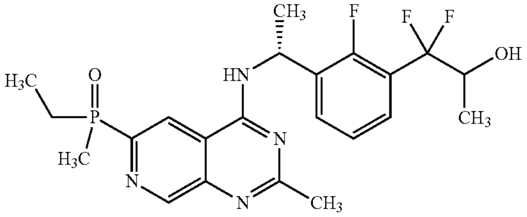 [SMILES: CCP(C)(=O)c1cc2c(N[C@H](C)c3cccc(C(F)(F)C(C)O)c3F)nc(C)nc2cn1]<br>(2R*)-1-{3-[(1R)-1-{{6-[ethyl(methyl)phosphoryl]-2-methylpyrido[3,4-d]pyrimidin-4-yl}amino)ethyl]-2-fluorophenyl}-1,1-difluoropropan-2-ol (diastereomer 2)<br>$^1$H-NMR (400 MHz, DMSO-d6) δ [ppm]: 0.948 (1.90), 0.967 (4.31), 0.987 (2.15), 0.992 (2.04), 1.011 (4.42), 1.030 (2.01), 1.130 (4.44), 1.146 (4.50), 1.232 (0.94), 1.600 (5.04), 1.617 (5.04), 1.655 (7.22), 1.688 (7.24), 1.971 (0.86), 1.978 (0.98), 1.990 (1.08), 1.997 (1.16), 2.009 (1.11), 2.019 (0.88), 2.028 (0.83), 2.414 (16.00), 2.518 (4.27), 2.522 (2.88), 4.195 (0.41), 4.210 (0.42), 5.580 (3.25), 5.595 (3.15), 5.749 (0.80), 5.767 (1.25), 5.784 (0.79), 7.229 (0.89), 7.249 (2.04), 7.268 (1.22), 7.359 (0.76), 7.376 (1.17), 7.392 (0.55), 7.632 (0.64), 7.649 (1.14), 7.666 (0.57), 8.945 (1.90), 8.959 (1.88), 9.085 (4.53), 9.293 (1.35), 9.312 (1.32).<br>LC-MS (Method 2): $R_t$ = 0.95 min; MS (ESIpos): m/z = 468 $[M + H]^+$<br>Example 73<br>42.2 mg (99% purity, 20% yield)<br>Rt (analytical method) = 4.46 min; de 97.5% |
| 76 | 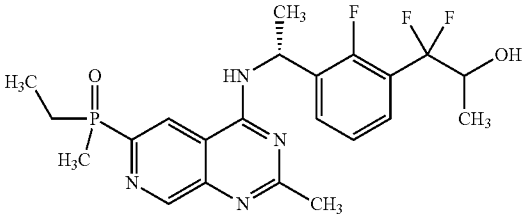 [SMILES: CCP(C)(=O)c1cc2c(N[C@H](C)c3cccc(C(F)(F)C(C)O)c3F)nc(C)nc2cn1]<br>(2R*)-1-{3-[(1R)-1-({6-[ethyl(methyl)phosphoryl]-2-methylpyrido[3,4-d]pyrimidin-4-yl}amino)ethyl]-2-fluorophenyl}-1,1-difluoropropan-2-ol (mixture of diastereomers)<br>$^1$H-NMR (400 MHz, DMSO-d6) δ [ppm]: 0.933 (1.07), 0.944 (1.17), 0.952 (2.49), 0.964 (2.34), 0.971 (1.40), 0.976 (1.35), 0.983 (1.38), 0.988 (1.30), 0.996 (2.49), 1.007 (2.31), 1.015 (1.21), 1.026 (1.01), 1.143 (4.61), 1.159 (4.54), 1.600 (4.69), 1.617 (4.65), 1.658 (4.08), 1.664 (4.40), 1.691 (4.03), 1.697 (4.33), 1.963 (0.60), 1.973 (0.93), 1.977 (0.83), 1.981 (0.82), 1.992 (1.21), 1.997 (0.95), 2.005 (0.83), 2.009 (0.96), 2.017 (0.63), 2.024 (0.63), 2.028 (0.63), 2.069 (0.51), 2.441 (16.00), 4.175 (0.46), 5.587 (0.53), 5.796 (0.51), 5.804 (0.59), 5.814 (0.79), 5.822 (0.81), 5.832 (0.55), 5.839 (0.50), 7.231 (0.62), 7.235 (0.60), 7.250 (1.36), 7.254 (1.29), 7.270 (0.84), 7.273 (0.78), 7.364 (0.84), 7.381 (1.28), 7.397 (0.61), 7.400 (0.56), 7.644 (0.59), 7.648 (0.54), 7.661 (0.99), 7.674 (0.48), 7.679 (0.51), 8.132 (1.44), 8.957 (1.01), 8.968 (1.33), 8.971 (1.26), 8.982 (1.04), 9.086 (4.52), 9.386 (0.48), 9.403 (0.80), 9.420 (0.48).<br>LC-MS (Method 2): $R_t$ = 0.95 min; MS (ESIpos): m/z = 468 $[M + H]^+$<br>Intermediate 220<br>61.0 mg (95% purity, 31% yield) |

The diastereomers of example 76 were separated according to the following method.

Anal.-Method:

Instrument: Thermo Fisher UltiMate 3000; Column: YMC Cellulose SB 3 μ, 100 × 4.6; eluent A: methyl tert-butyl ether + 0.1 vol % diethylamine; eluent B: acetonitrile; isocratic: 90% A + 10% B; flow: 1.4 ml/min; temperature: 25° C.; UV: 280 nm Prep.-Method:

Instrument: PrepCon Labomatic HPLC-3; Column: YMC Cellulose SB 10 μ, 250 × 50; eluent A: methyl tert-butyl ether + 0.1 vol % diethylamine; eluent B: acetonitrile; isocratic: 90% A + 10% B; flow: 100 mL/min; temperature: 25° C.; UV: 280 nm TABLE 7-continued

| Ex. | Examples<br>Structure; IUPAC-Name; Analytical Data; Starting Materials; Yield |
| --- | --- |
| 77 | 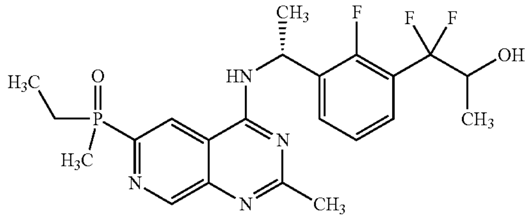 [SMILES: CCP(C)(=O)c1cc2c(N[C@H](C)c3cccc(C(F)(F)C(C)O)c3F)nc(C)nc2cn1]<br>(2R*)-1-{3-[(1R)-1-{{6-[ethyl(methyl)phosphoryl]-2-methylpyrido[3,4-d]pyrimidin-4-yl}amino)ethyl]-2-fluorophenyl}-1,1-difluoropropan-2-ol (diastereomer 3)<br>LC-MS (Method 2): $R_t$ = 0.96 min; MS (ESIpos): m/z = 468 $[M + H]^+$<br>Intermediate<br>15.0 mg (95% purity, 8% yield)<br>Rt (analytical method) = 6.05 min; de >99% |
| 78 | 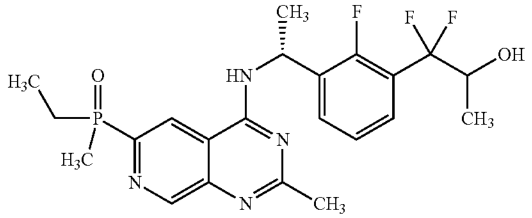 [SMILES: CCP(C)(=O)c1cc2c(N[C@H](C)c3cccc(C(F)(F)C(C)O)c3F)nc(C)nc2cn1]<br>(2R*)-1-{3-[(1R)-1-{{6-[ethyl(methyl)phosphoryl]-2-methylpyrido[3,4-d]pyrimidin-4-yl}amino)ethyl]-2-fluorophenyl}-1,1-difluoropropan-2-ol (diastereomer 4)<br>LC-MS (Method 2): $R_t$ = 0.95 min; MS (ESIpos): m/z = 468 $[M + H]^+$<br>Intermediate<br>17.0 mg (95% purity, 9% yield)<br>Rt (analytical method) = 7.76 min; de 98% |
| 79 | 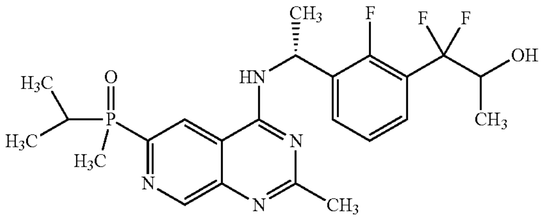 [SMILES: Cc1nc(N[C@H](C)c2cccc(C(F)(F)C(C)O)c2F)c2cc(P(C)(=O)C(C)C)ncc2n1]<br>(2R*)-1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}propan-2-ol<br>(mixrure of diastereomers)<br>$^1$H-NMR (400 MHz, DMSO-d6) δ [ppm]: 0.892 (2.49), 0.904 (2.78), 0.910 (2.81), 0.922 (2.67), 0.932 (2.64), 0.944 (2.76), 0.950 (2.74), 0.962 (2.48), 1.131 (4.24), 1.143 (8.70), 1.161 (5.10), 1.183 (4.88), 1.201 (4.81), 1.601 (5.44), 1.619 (5.42), 1.650 (5.69), 1.659 (5.82), 1.683 (5.71), 1.691 (5.75), 2.180 (0.43), 2.198 (0.70), 2.204 (0.53), 2.212 (0.65), 2.217 (0.76), 2.221 (0.68), 2.230 (0.49), 2.236 (0.68), 2.254 (0.46), 2.332 (0.62), 2.413 (16.00), 2.518 (3.00), 2.523 (2.21), 2.673 (0.61), 4.173 (0.42), 4.194 (0.54), 4.210 (0.56), 5.578 (2.81), 5.581 (2.82), 5.594 (2.77), 5.597 (2.69), 5.747 (0.68), 5.753 (0.72), 5.765 (1.05), 5.770 (1.05), 5.782 (0.71), 5.787 (0.66), 7.221 (0.65), 7.231 (0.71), 7.240 (1.50), 7.251 (1.51), 7.259 (0.95), 7.270 (0.88), 7.355 (0.96), 7.373 (1.54), 7.392 (0.72), 7.620 (0.47), 7.634 (1.12), 7.651 (1.07), 7.667 (0.42), 8.931 (1.35), 8.946 (2.60), 8.960 (1.34), 9.082 (6.42), 9.307 (0.92), 9.328 (1.22), 9.347 (0.87).<br>LC-MS (Method 2): $R_t$ = 1.02 min; MS (ESIpos): m/z = 481.6 $[M + H]^+$<br>Intermediate 223<br>140 mg (95% purity, 62% yield) |

The diastereomers of example 79 were separated according to the following method.

Anal.-Method:

Instrument: Waters Acquity UPC2 QDA; Column: Chiral Art Amylose-SA 3 μ 100 × 4.6 mm; eluent A: CO2; eluent B: 2-propanol + 0.4 vol % diethylamin; isocratic: 10% B; gradient: no; flow: 4 ml/min; temperature: 40.0° C.; BPR: 1800 psi; UV: 220 nm Prep.-Method:

Instrument: Sepiatec: Prep SFC100; Column: Chiral Art Amylose-SA 5 μ 250 × 30mm; eluent A: CO2; eluent B: 2-propanol + 0.4 vol % diethylamin; isocratic: 10% B; gradient: no; flow: 100 ml/min; temperature: 40° C.; BPR: 150 bar; UV: 215 nm TABLE 7-continued

| Ex. | Examples<br>Structure; IUPAC-Name; Analytical Data; Starting Materials; Yield |
| --- | --- |
| 80 | 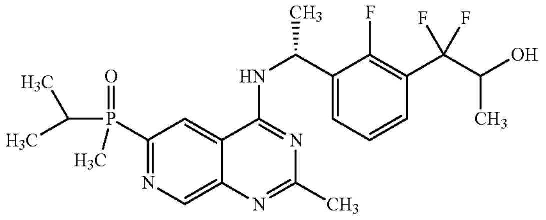 [SMILES: Cc1nc(N[C@H](C)c2cccc(C(F)(F)C(C)O)c2F)c2cc(P(C)(=O)C(C)C)ncc2n1]<br>(2R*)-1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}propan-2-ol (diastereomer 1)<br>LC-MS (Method 2): $R_t$ = 1.01 min; MS (ESIpos): m/z = 482 $[M + H]^+$<br>Example 79<br>23.0 mg (95% purity)<br>Rt (analytical method) = 2.41 min; de 98% |
| 81 | 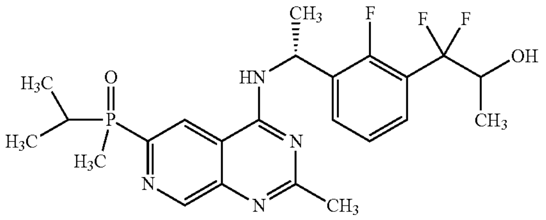 [SMILES: Cc1nc(N[C@H](C)c2cccc(C(F)(F)C(C)O)c2F)c2cc(P(C)(=O)C(C)C)ncc2n1]<br>(2R*)-1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}propan-2-ol (diastereomer 2)<br>Example 79<br>25.1 mg (95% purity)<br>Rt (analytical method) = 3.07 min; de 95% |
| 82 | 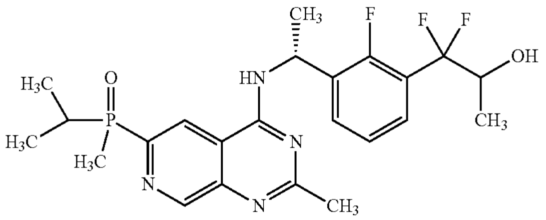 [SMILES: Cc1nc(N[C@H](C)c2cccc(C(F)(F)C(C)O)c2F)c2cc(P(C)(=O)C(C)C)ncc2n1]<br>(2R*)-1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}propan-2-ol<br>$^1$H-NMR (400 MHz, DMSO-d6) δ [ppm]: 0.889 (2.10), 0.895 (2.05), 0.907 (2.20), 0.913 (2.06), 0.930 (2.16), 0.936 (2.10), 0.948 (2.18), 0.953 (2.00), 1.135 (3.61), 1.143 (4.61), 1.153 (4.63), 1.159 (4.71), 1.175 (3.29), 1.192 (3.18), 1.601 (4.54), 1.619 (4.48), 1.652 (4.21), 1.658 (4.79), 1.684 (4.23), 1.690 (4.72), 2.071 (1.36), 2.193 (0.58), 2.198 (0.44), 2.205 (0.49), 2.211 (0.64), 2.216 (0.54), 2.230 (0.54), 2.441 (16.00), 3.458 (0.60), 4.176 (0.42), 5.583 (0.52), 5.796 (0.46), 5.805 (0.55), 5.813 (0.73), 5.822 (0.79), 5.831 (0.52), 5.839 (0.49), 7.230 (0.55), 7.237 (0.53), 7.249 (1.28), 7.256 (1.15), 7.269 (0.79), 7.275 (0.70), 7.359 (0.73), 7.362 (0.84), 7.380 (1.30), 7.396 (0.62), 7.400 (0.58), 7.639 (0.42), 7.655 (0.80), 7.668 (0.72), 8.134 (3.43), 8.947 (0.96), 8.962 (1.96), 8.977 (1.06), 9.086 (5.10), 9.421 (0.61), 9.440 (0.42).<br>LC-MS (Method 2): $R_t$ = 1.00 min; MS (ESIpos): m/z = 482 $[M + H]^+$<br>Intermediate 222<br>69.0 mg (95% purity, 34% yield) |

The diastereomers of example 82 were separated according to the following method.

Anal.-Method:

Instrument: Waters Acquity UPC2 QDA; Column: Chiral Art Amylose-SA 3 μ 100 × 4.6 mm; eluent A: CO2; eluent B: 2-propanol + 0.4 vol % diethylamin; isocratic: 10% B; gradient: no; flow: 4 ml/min; temperature: 40.0° C.; BPR: 1800 psi; UV: 220 nm Prep.-Method:

Instrument: Sepiatec: Prep SFC100; Column: Chiral Art Amylose-SA 5 μ 250 × 30 mm; eluent A: CO2; eluent B: 2-propanol + 0.4 vol % diethylamin; isocratic: 10% B; gradient: no; flow: 100 ml/min; temperature: 40° C.; BPR: 150 bar; UV: 215 nm TABLE 7-continued

| Examples | |
|---|---|
| Ex. | Structure; IUPAC-Name; Analytical Data; Starting Materials; Yield |
| 83 | 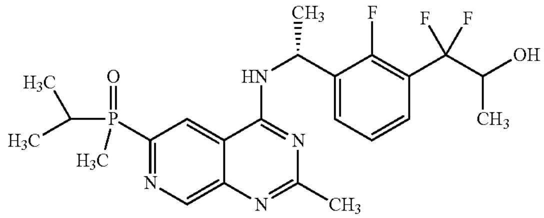 [SMILES: Cc1nc(N[C@H](C)c2cccc(C(F)(F)C(C)O)c2F)c2cc(P(C)(=O)C(C)C)ncc2n1]<br>(2R*)-1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}propan-2-ol (diastereomer 3)<br>$^1$H-NMR (400 MHz, DMSO-d6) δ [ppm]: 0.893 (3.20), 0.911 (3.21), 0.934 (3.27), 0.952 (3.21), 1.027 (2.57), 1.042 (2.66), 1.094 (0.52), 1.112 (1.03), 1.131 (0.67), 1.144 (6.29), 1.161 (7.38), 1.183 (3.30), 1.201 (3.27), 1.596 (4.68), 1.614 (4.62), 1.659 (7.38), 1.691 (7.35), 1.906 (0.50), 2.181 (0.45), 2.198 (0.70), 2.204 (0.58), 2.217 (0.52), 2.222 (0.67), 2.240 (0.44), 2.332 (2.08), 2.336 (0.87), 2.434 (16.00), 2.518 (9.68), 2.523 (6.99), 2.678 (0.84), 5.563 (3.11), 5.578 (2.95), 5.798 (0.74), 5.816 (1.12), 5.833 (0.72), 7.231 (0.83), 7.250 (1.92), 7.270 (1.15), 7.361 (0.72), 7.378 (1.07), 7.395 (0.51), 7.637 (0.60), 7.653 (1.04), 7.670 (0.54), 8.947 (1.72), 8.961 (1.67), 9.087 (4.34), 9.089 (4.33), 9.312 (1.25), 9.331 (1.19).<br>LC-MS (Method 2): $R_t$ = 1.01 min; MS (ESIpos): m/z = 482 $[M + H]^+$<br>Example 82<br>24.0 mg (95% purity, 12% yield)<br>Rt (analytical method) = 1.92 min; de 98% |
| 84 | 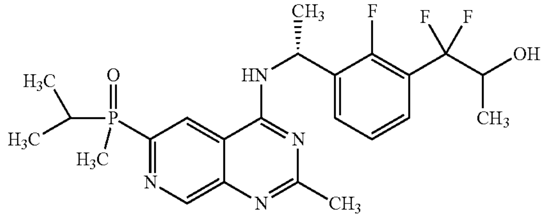 [SMILES: Cc1nc(N[C@H](C)c2cccc(C(F)(F)C(C)O)c2F)c2cc(P(C)(=O)C(C)C)ncc2n1]<br>(2R*)-1,1-difluoro-1-{2-fluoro-3-[(1R)-1-({2-methyl-6-[methyl(propan-2-yl)phosphoryl]pyrido[3,4-d]pyrimidin-4-yl}amino)ethyl]phenyl}propan-2-ol (diastereomer 4)<br>$^1$H-NMR (400 MHz, DMSO-d6) δ [ppm]: 0.904 (3.41), 0.922 (3.49), 0.945 (3.38), 0.962 (3.39), 1.027 (6.87), 1.042 (7.04), 1.079 (0.77), 1.097 (1.59), 1.115 (0.84), 1.143 (7.54), 1.161 (6.59), 1.183 (3.52), 1.201 (3.50), 1.594 (4.81), 1.612 (4.80), 1.650 (7.53), 1.683 (7.56), 2.197 (0.52), 2.214 (0.73), 2.220 (0.60), 2.232 (0.53), 2.238 (0.72), 2.256 (0.46), 2.336 (0.63), 2.435 (16.00), 2.518 (6.66), 2.523 (5.10), 2.679 (0.62), 4.343 (0.81), 4.354 (0.72), 5.561 (2.83), 5.576 (2.74), 5.791 (0.75), 5.808 (1.17), 5.826 (0.74), 7.240 (0.87), 7.259 (1.93), 7.278 (1.16), 7.362 (0.74), 7.380 (1.12), 7.396 (0.52), 7.649 (0.64), 7.666 (1.05), 7.684 (0.53), 8.933 (1.72), 8.947 (1.79), 9.087 (4.64), 9.291 (1.29), 9.309 (1.20).<br>LC-MS (Method 2): $R_t$ = 1.00 min; MS (ESIpos): m/z = 482 $[M + H]^+$<br>Example 82<br>22.0 mg (95% purity, 11% yield)<br>Rt (analytical method) = 2.49 min; de 96% |
| 85 | 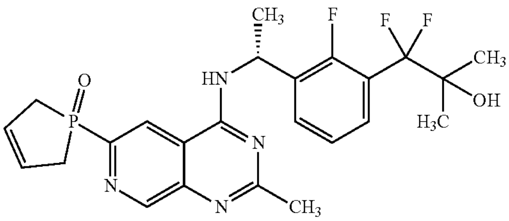 [SMILES: Cc1nc(N[C@H](C)c2cccc(C(F)(F)C(C)(C)O)c2F)c2cc(P3(=O)CC=CC3)ncc2n1]<br>1-[4-({(1R)-1-[3-(1,1-difluoro-2-hydroxy-2-methylpropyl)-2-fluorophenyl]ethyl}amino)-2-methylpyrido[3,4-d]pyrimidin-6-yl]-2,5-dihydro-1H-1lambda$^5$-phosphol-1-one<br>$^1$H-NMR (400 MHz, DMSO-d6) δ [ppm]: 1.154 (0.48), 1.172 (1.03), 1.190 (0.79), 1.205 (6.19), 1.230 (6.40), 1.592 (4.70), 1.610 (4.72), 1.987 (1.42), 2.415 (16.00), 2.518 (3.30), 2.523 (2.38), 2.562 (0.75), 2.604 (1.18), 2.646 (1.03), 2.880 (1.03), 2.889 (0.99), 2.925 (0.73), 2.934 (0.76), 5.336 (7.64), 5.759 (0.91), 5.779 (0.76), 5.796 (1.18), 5.814 (0.75), 6.008 (2.47), 6.081 (2.48), 7.204 (0.74), 7.223 (1.77), 7.243 |

TABLE 7-continued

| Ex. | Examples<br>Structure; IUPAC-Name; Analytical Data; Starting Materials; Yield |
|---|---|
| | (1.13), 7.300 (0.66), 7.304 (0.78), 7.321 (1.08), 7.336 (0.52), 7.341 (0.47), 7.613 (0.61), 7.629 (1.05), 7.645 (0.55), 9.069 (1.94), 9.082 (7.89), 9.312 (1.28), 9.330 (1.23).<br>LC-MS (Method 2): $R_t$ = 1.02 min; MS (ESIpos): m/z = 492 $[M + H]^+$<br>Intermediate 224<br>88.0 mg (95% purity, 49% yield) |
| 86 | 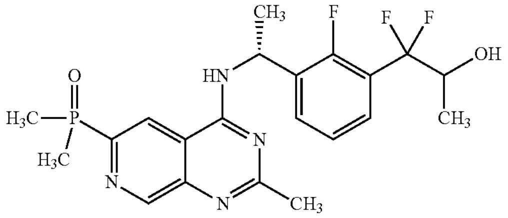 [SMILES: Cc1nc(N[C@H](C)c2cccc(C(F)(F)C(C)O)c2F)c2cc(P(C)(C)=O)ncc2n1]<br>(2R*)-1-{3-[(1R)-1-{[6-(dimethylphosphoryl)-2-methylpyrido[3,4-d]pyrimidin-4-yl]amino}ethyl]-2-fluorophenyl}-1,1-difluoropropan-2-ol<br>$^1$H-NMR (400 MHz, DMSO-d6) δ [ppm]: 1.146 (4.82), 1.162 (4.81), 1.594 (5.34), 1.611 (5.34), 1.688 (7.55), 1.693 (7.82), 1.722 (7.69), 1.727 (7.64), 2.436 (16.00), 2.518 (5.63), 2.523 (3.58), 4.167 (0.45), 4.183 (0.46), 5.568 (2.56), 5.584 (2.49), 5.758 (0.45), 5.800 (0.87), 5.818 (1.32), 5.836 (0.85), 7.234 (0.94), 7.253 (2.14), 7.272 (1.30), 7.363 (0.83), 7.380 (1.29), 7.397 (0.62), 7.641 (0.72), 7.659 (1.29), 7.676 (0.67), 8.958 (2.01), 8.974 (2.00), 9.092 (4.83), 9.272 (1.07), 9.290 (1.05).<br>LC-MS (Method 2): $R_t$ = 0.93 min; MS (ESIneg): m/z = 451 $[M - H]^-$<br>Intermediate 225<br>42.0 mg (95% purity, 50% yield) |
| 87 | 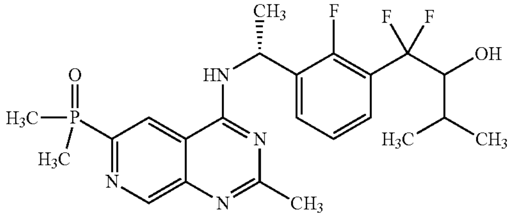 [SMILES: Cc1nc(N[C@H](C)c2cccc(C(F)(F)C(O)C(C)C)c2F)c2cc(P(C)(C)=O)ncc2n1]<br>(2R*)-1-{3-[(1R)-1-{[6-(dimethylphosphoryl)-2-methylpyrido[3,4-d]pyrimidin-4-yl]amino}ethyl]-2-fluorophenyl}-1,1-difluoro-3-methylbutan-2-ol (diastereomer 2)<br>$^1$H-NMR (400 MHz, DMSO-d6) δ [ppm]: 0.851 (4.84), 0.868 (5.03), 0.912 (5.48), 0.929 (5.67), 1.596 (5.03), 1.614 (5.03), 1.691 (9.50), 1.724 (9.67), 1.739 (0.75), 1.749 (0.63), 1.756 (0.72), 1.766 (0.70), 1.773 (0.52), 1.783 (0.48), 2.405 (16.00), 2.518 (4.24), 2.523 (2.97), 3.895 (0.40), 5.547 (2.82), 5.565 (2.75), 5.742 (0.81), 5.760 (1.26), 5.777 (0.80), 7.220 (0.97), 7.240 (2.14), 7.258 (1.26), 7.387 (0.74), 7.404 (1.20), 7.420 (0.60), 7.610 (0.66), 7.627 (1.19), 7.644 (0.62), 8.958 (1.94), 8.975 (1.98), 9.089 (4.67), 9.290 (1.41), 9.308 (1.36).<br>LC-MS (Method 2): $R_t$ = 1.03 min; MS (ESIpos): m/z = 481 $[M + H]^+$<br>Intermediate 177<br>19.0 mg (100% purity, 43% yield) |
| 89 | 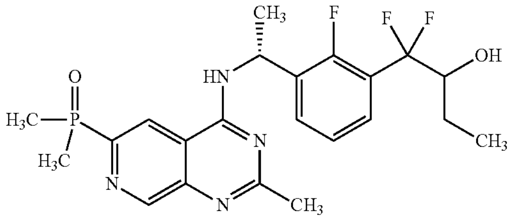 [SMILES: CCC(O)C(F)(F)c1cccc([C@@H](C)Nc2nc(C)nc3cnc(P(C)(C)=O)cc23)c1F]<br>(2R*)-1-{3-[(1R)-1-{[6-(dimethylphosphoryl)-2-methylpyrido[3,4-d]pyrimidin-4-yl]amino}ethyl]-2-fluorophenyl}-1,1-difluorobutan-2-ol (diastereomer 2)<br>$^1$H-NMR (400 MHz, DMSO-d6) δ [ppm]: 0.899 (2.58), 0.918 (6.07), 0.937 (2.99), 1.342 (0.40), 1.359 (0.51), 1.367 (0.45), 1.377 (0.45), 1.384 (0.52), 1.511 (0.44), 1.517 (0.48), 1.529 (0.55), 1.535 (0.55), 1.545 (0.46), 1.597 (5.07), 1.615 (5.12), 1.691 (9.06), 1.724 (9.11), 2.408 (16.00), 2.518 (3.82), 2.523 (2.70), 3.903 (0.42), 5.577 (2.69), 5.595 (2.65), 5.744 (0.83), 5.762 (1.29), 5.780 (0.83), 7.218 (0.93), 7.237 (2.10), 7.256 (1.29), 7.351 (0.79), 7.369 (1.23), 7.384 (0.60), 7.615 (0.67), 7.633 (1.20), 7.649 (0.63), 8.956 (1.95), 8.972 (2.01), 9.087 (4.71), 9.288 (1.42), 9.306 (1.37). |

TABLE 7-continued

| Ex. | Examples<br>Structure; IUPAC-Name; Analytical Data; Starting Materials; Yield |
|---|---|
| | LC-MS (Method 2): $R_t$ = 0.97 min; MS (ESIpos): m/z = 468 $[M + H]^+$<br>Intermediate 179<br>20.0 mg (100% purity, 45% yield) |

The examples shown in Table 8 were prepared according to General Procedure 1 from the respective halo aryl derivative and the respective phosphinoxide.

TABLE 8

| Ex. | Examples<br>Structure; IUPAC-Name; Analytical Data; Starting Materials; Yield |
|---|---|
| 90 | 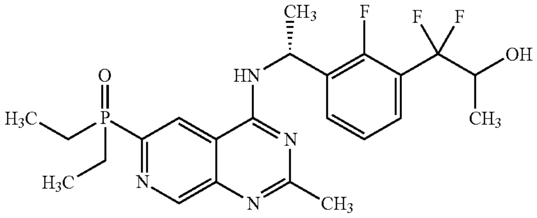 [SMILES: CCP(=O)(CC)c1cc2c(N[C@H](C)c3cccc(C(F)(F)C(C)O)c3F)nc(C)nc2cn1]<br>(2R*)-1-{3-[(1R)-1-{[6-(diethylphosphoryl)-2-methylpyrido[3,4-d]pyrimidin-4-yl]amino}ethyl]-2-fluorophenyl}-1,1-difluoropropan-2-ol (diastereomer 2)<br>$^1$H-NMR (400 MHz, DMSO-d6) δ [ppm]: 0.912 (1.79), 0.931 (4.64), 0.948 (4.96), 0.953 (2.30), 0.967 (2.45), 0.973 (4.95), 0.990 (4.97), 1.009 (1.95), 1.130 (4.04), 1.145 (4.08), 1.603 (4.59), 1.620 (4.57), 1.952 (0.46), 1.962 (1.08), 1.971 (1.29), 1.981 (1.84), 1.990 (1.83), 1.997 (1.26), 2.000 (1.62), 2.005 (1.54), 2.009 (1.56), 2.024 (1.25), 2.031 (0.96), 2.041 (0.43), 2.332 (0.44), 2.413 (16.00), 2.518 (2.20), 2.523 (1.56), 5.588 (0.85), 5.599 (0.88), 5.749 (0.74), 5.767 (1.15), 5.785 (0.73), 7.228 (0.84), 7.247 (1.91), 7.267 (1.16), 7.358 (0.70), 7.375 (1.06), 7.391 (0.51), 7.395 (0.48), 7.634 (0.58), 7.651 (1.02), 7.667 (0.52), 8.936 (1.76), 8.950 (1.74), 9.086 (4.33), 9.325 (1.25), 9.342 (1.19).<br>LC-MS (Method 1): $R_t$ = 0.89 min; MS (ESIpos): m/z = 481 $[M + H]^+$<br>Intermediate 45<br>62.7 mg (95% purity, 56% yield) |
| 91 | 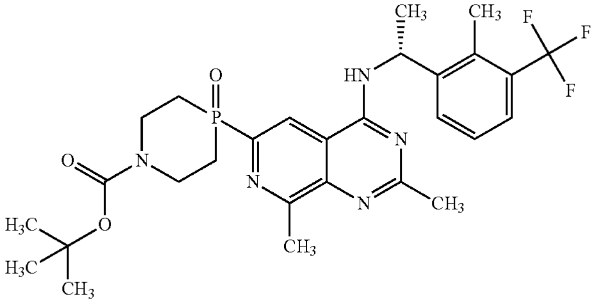 [SMILES: Cc1nc(N[C@H](C)c2cccc(C(F)(F)F)c2C)c2cc(P3(=O)CCN(C(=O)OC(C)(C)C)CC3)nc(C)c2n1]<br>tert-butyl 4-[2,8-dimethyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxylate<br>LC-MS (Method 2): $R_t$ = 1.50 min; MS (ESIpos): m/z = 578 $[M + H]^+$<br>Intermediate 140<br>201 mg (153% yield) |
| 92 | 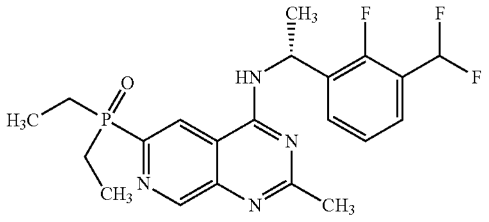 [SMILES: CCP(=O)(CC)c1cc2c(N[C@H](C)c3cccc(C(F)F)c3F)nc(C)nc2cn1] |

TABLE 8-continued

| Ex. | Examples<br>Structure; IUPAC-Name; Analytical Data; Starting Materials; Yield |
|---|---|
| | 6-(diethylphosphoryl)-N-{(1R)-1-[3-(difluoromethyl)-2-fluorophenyl]ethyl}-2-methylpyrido[3,4-d]pyrimidin-4-amine<br>$^1$H-NMR (400 MHz, DMSO-d6) δ [ppm]: 0.911 (1.80), 0.930 (5.37), 0.948 (5.63), 0.953 (2.38), 0.967 (2.59), 0.972 (5.44), 0.990 (5.65), 1.009 (1.95), 1.106 (4.58), 1.143 (0.48), 1.230 (0.76), 1.613 (4.88), 1.631 (4.86), 1.951 (0.45), 1.961 (1.20), 1.970 (1.23), 1.980 (1.98), 1.988 (1.76), 2.000 (1.78), 2.007 (1.99), 2.011 (1.21), 2.021 (1.10), 2.026 (1.24), 2.031 (0.95), 2.426 (16.00), 2.518 (2.23), 2.522 (1.44), 5.779 (0.74), 5.797 (1.14), 5.815 (0.72), 7.105 (1.14), 7.241 (2.41), 7.289 (0.81), 7.308 (1.78), 7.327 (1.02), 7.377 (1.00), 7.495 (0.59), 7.512 (1.00), 7.528 (0.51), 7.700 (0.55), 7.717 (1.00), 7.735 (0.49), 8.087 (0.49), 8.936 (1.74), 8.950 (1.76), 8.952 (1.71), 9.091 (4.19), 9.326 (1.17), 9.344 (1.13).<br>LC-MS (Method 2): $R_t$ = 1.13 min; MS (ESIneg): m/z = 435 $[M - H]^-$<br>Intermediate 165<br>53.1 mg (90% purity, 90% yield) |
| 93 | 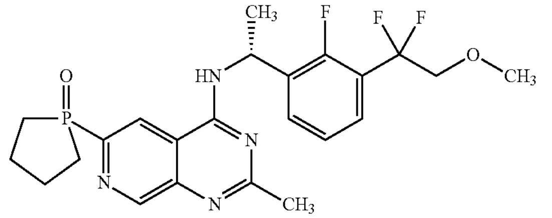 [SMILES: COCC(F)(F)c1cccc([C@@H](C)Nc2nc(C)nc3cnc(P4(=O)CCCC4)cc23)c1F]<br>1-[4-{{(1R)-1-[3-(1,1-difluoro-2-methoxyethyl)-2-fluorophenyl]ethyl}amino)-2-methylpyrido[3,4-d]pyrimidin-6-yl]-1lambda$^5$-phospholan-1-one<br>$^1$H-NMR (500 MHz, DMSO-d6) δ [ppm]: 1.602 (4.89), 1.616 (4.95), 1.799 (0.41), 1.816 (0.59), 1.827 (0.75), 1.843 (0.64), 1.858 (0.47), 1.967 (0.51), 1.981 (0.70), 2.003 (0.75), 2.017 (0.88), 2.035 (0.77), 2.051 (0.76), 2.065 (0.53), 2.073 (0.43), 2.099 (0.61), 2.118 (0.75), 2.132 (0.68), 2.144 (0.50), 2.365 (0.81), 2.422 (16.00), 2.514 (3.33), 2.518 (3.29), 2.522 (2.58), 3.957 (1.12), 3.986 (2.16), 4.014 (0.99), 5.765 (0.79), 5.778 (1.20), 5.793 (0.76), 7.253 (0.88), 7.269 (1.95), 7.284 (1.08), 7.422 (0.62), 7.435 (1.04), 7.449 (0.52), 7.667 (0.56), 7.681 (1.00), 7.694 (0.52), 9.011 (1.69), 9.022 (1.68), 9.095 (4.00), 9.317 (1.27), 9.331 (1.20).<br>LC-MS (Method 2): $R_t$ = 1.13 min; MS (ESIpos): m/z = 479 $[M + H]^+$<br>Intermediate 172<br>42.8 mg (95% purity, 77% yield) |
| 94 | 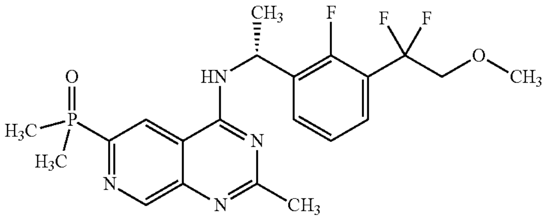<br>N-{(1R)-1-[3-(1,1-difluoro-2-methoxyethyl)-2-fluorophenyl]ethyl}-6-(dimethylphosphoryl)-2-methylpyrido[3,4-d]pyrimidin-4-amine<br>$^1$H-NMR (500 MHz, DMSO-d6) δ [ppm]: 1.603 (3.58), 1.618 (3.54), 1.692 (4.65), 1.695 (4.76), 1.719 (4.74), 1.722 (4.66), 2.421 (11.48), 2.514 (1.30), 2.518 (1.29), 2.522 (1.00), 3.333 (16.00), 3.957 (0.80), 3.986 (1.55), 4.014 (0.69), 5.765 (0.56), 5.778 (0.85), 5.793 (0.55), 7.257 (0.64), 7.273 (1.39), 7.289 (0.77), 7.424 (0.45), 7.438 (0.75), 7.682 (0.72), 8.957 (1.22), 8.969 (1.23), 9.090 (2.87), 9.288 (0.89), 9.303 (0.85).<br>LC-MS (Method 2): $R_t$ = 1.04 min; MS (ESIpos): m/z = 453 $[M + H]^+$<br>Intermediate 172<br>44.4 mg (95% purity, 71% yield) |
| 95 | 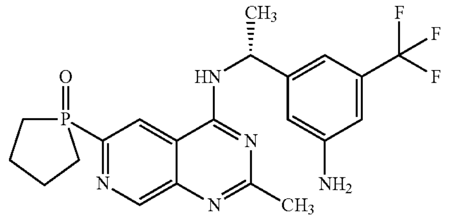 [SMILES: Cc1nc(N[C@H](C)c2cc(N)cc(C(F)(F)F)c2)c2cc(P3(=O)CCCC3)ncc2n1] |

TABLE 8-continued

| Ex. | Examples<br>Structure; IUPAC-Name; Analytical Data; Starting Materials; Yield |
|---|---|
| | 1-[4-{{(1R)-1-[3-amino-5-(trifluoromethyl)phenyl]ethyl}amino)-2-methylpyrido[3,4-d]pyrimidin-6-yl]-1lambda$^5$-phospholan-1-one<br>$^1$H-NMR (400 MHz, DMSO-d6) δ [ppm]: 1.549 (6.34), 1.567 (6.32), 1.790 (0.64), 1.807 (0.90), 1.825 (1.05), 1.860 (0.70), 1.956 (0.78), 1.974 (1.22), 1.991 (1.51), 2.009 (1.53), 2.031 (1.37), 2.049 (1.21), 2.065 (0.85), 2.088 (1.21), 2.106 (1.14), 2.125 (1.24), 2.141 (1.02), 2.158 (0.60), 2.475 (16.00), 2.518 (3.00), 2.523 (2.09), 5.515 (0.98), 5.534 (1.51), 5.553 (1.55), 5.566 (3.69), 6.700 (3.11), 6.853 (2.86), 6.908 (3.15), 8.977 (2.27), 8.992 (2.23), 9.092 (4.34), 9.201 (1.47), 9.220 (1.41).<br>LC-MS (Method 1): $R_t$ = 0.90 min; MS (ESIpos): m/z = 450 [M + H]$^+$<br>Intermediate 241<br>119 mg (95% purity, 72% yield) |
| 96 | 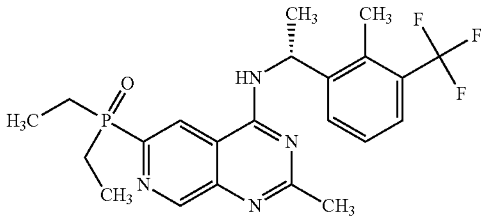 [SMILES: CCP(=O)(CC)c1cc2c(N[C@H](C)c3cccc(C(F)(F)F)c3C)nc(C)nc2cn1]<br>6-(diethylphosphoryl)-2-methyl-N-{(1R)-1-[2-methyl-3-(trifluoromethyl)phenyl]ethyl}pyrido[3,4-d]pyrimidin-4-amine<br>$^1$H-NMR (400 MHz, DMSO-d6) δ [ppm]: 0.911 (1.25), 0.927 (1.57), 0.931 (3.06), 0.946 (3.36), 0.950 (1.83), 0.953 (1.55), 0.965 (2.05), 0.969 (1.83), 0.972 (3.27), 0.988 (3.28), 0.991 (1.66), 1.007 (1.34), 1.107 (16.00), 1.230 (0.52), 1.570 (3.29), 1.588 (3.31), 1.959 (0.74), 1.970 (0.79), 1.974 (0.86), 1.978 (1.24), 1.989 (1.05), 1.992 (0.88), 1.997 (1.00), 2.002 (1.33), 2.005 (0.95), 2.008 (1.03), 2.021 (1.15), 2.027 (0.71), 2.415 (10.76), 2.518 (1.99), 2.523 (1.32), 2.632 (3.96), 4.189 (1.17), 5.704 (0.50), 5.722 (0.77), 5.739 (0.49), 7.352 (0.45), 7.371 (0.99), 7.390 (0.57), 7.540 (1.08), 7.558 (0.85), 7.808 (0.94), 7.827 (0.85), 8.087 (0.40), 8.934 (1.19), 8.936 (1.23), 8.949 (1.19), 8.951 (1.18), 9.071 (2.90), 9.412 (0.80), 9.430 (0.78).<br>LC-MS (Method 2): $R_t$ = 1.28 min; MS (ESIneg): m/z = 449 [M − H]$^-$<br>Intermediate 117<br>44.1 mg (99% purity, 82% yield) |
| 97 | 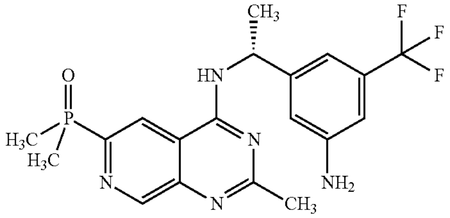 [SMILES: Cc1nc(N[C@H](C)c2cc(N)cc(C(F)(F)F)c2)c2cc(P(C)(C)=O)ncc2n1]<br>N-{(1R)-1-[3-amino-5-(trifluoromethyl)phenyl]ethyl}-6-(dimethylphosphoryl)-2-methylpyrido[3,4-d]pyrimidin-4-amine<br>$^1$H-NMR (400 MHz, DMSO-d6) δ [ppm]: 1.552 (4.76), 1.570 (4.79), 1.683 (6.10), 1.689 (6.28), 1.716 (6.20), 1.723 (6.12), 2.475 (16.00), 2.518 (2.58), 2.523 (1.80), 5.519 (0.71), 5.537 (1.10), 5.556 (1.08), 5.568 (3.76), 5.759 (2.22), 6.703 (2.24), 6.856 (2.06), 6.910 (2.28), 8.920 (1.77), 8.922 (1.80), 8.936 (1.78), 8.938 (1.72), 9.088 (4.14), 9.169 (1.28), 9.188 (1.23).<br>LC-MS (Method 2): $R_t$ = 0.99 min; MS (ESIpos): m/z = 424 [M + H]$^+$<br>Intermediate 241<br>27.0 mg (95% purity, 14% yield) |
| 98 | 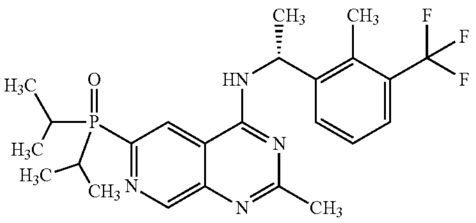 [SMILES: Cc1nc(N[C@H](C)c2cccc(C(F)(F)F)c2C)c2cc(P(=O)(C(C)C)C(C)C)ncc2n1]<br>6-[di(propan-2-yl)phosphoryl]-2-methyl-N-{(1R)-1-[2-methyl-3-(trifluoromethyl)phenyl]ethyl}pyrido[3,4-d]pyrimidin-4-amine<br>$^1$H-NMR (400 MHz, DMSO-d6) δ [ppm]: 0.920 (3.58), 0.926 (3.57), 0.937 (3.77), 0.944 |

TABLE 8-continued

| Ex. | Examples<br>Structure; IUPAC-Name; Analytical Data; Starting Materials; Yield |
|---|---|
| | (3.68), 0.958 (3.68), 0.965 (3.64), 0.976 (3.68), 0.982 (3.53), 1.105 (3.25), 1.116 (3.61), 1.123 (3.73), 1.134 (3.57), 1.142 (3.48), 1.154 (3.66), 1.160 (3.60), 1.172 (3.28), 1.573 (4.99), 1.590 (4.92), 2.413 (16.00), 2.439 (1.02), 2.447 (1.14), 2.465 (2.09), 2.518 (9.24), 2.523 (6.80), 2.636 (6.09), 2.678 (0.84), 5.700 (0.77), 5.718 (1.18), 5.735 (0.76), 7.355 (0.71), 7.374 (1.52), 7.393 (0.89), 7.539 (1.67), 7.557 (1.31), 7.807 (1.48), 7.827 (1.32), 8.895 (1.86), 8.907 (1.82), 9.066 (4.30), 9.068 (4.32), 9.451 (1.26), 9.468 (1.22).<br>LC-MS (Method 2): $R_t$ = 1.39 min; MS (ESIneg): m/z = 477 $[M - H]^-$<br>Intermediate 117<br>26.0 mg (95% purity, 22% yield) |
| 99 | 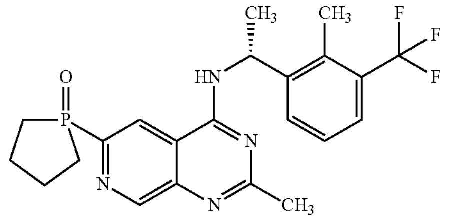 [SMILES: Cc1nc(N[C@H](C)c2cccc(C(F)(F)F)c2C)c2cc(P3(=O)CCCC3)ncc2n1]<br>1-[2-methyl-4-{{(1R)-1-[2-methyl-3-(trifluoromethyl)phenyl]ethyl}amino)pyrido[3,4-d]pyrimidin-6-yl]-1lambda$^5$-phospholan-1-one<br>$^1$H-NMR (400 MHz, DMSO-d6) δ [ppm]: 1.567 (5.03), 1.584 (5.07), 1.793 (0.42), 1.809 (0.60), 1.829 (0.77), 1.842 (0.63), 1.863 (0.48), 1.960 (0.50), 1.977 (0.78), 1.993 (0.99), 2.010 (1.12), 2.033 (0.92), 2.051 (0.85), 2.067 (0.64), 2.087 (0.98), 2.101 (0.79), 2.119 (0.74), 2.125 (0.73), 2.136 (0.64), 2.154 (0.44), 2.331 (0.83), 2.417 (16.00), 2.518 (4.43), 2.523 (3.13), 2.626 (6.06), 2.673 (0.84), 5.705 (0.77), 5.722 (1.21), 5.739 (0.75), 7.342 (0.69), 7.361 (1.51), 7.381 (0.87), 7.538 (1.63), 7.556 (1.31), 7.796 (1.45), 7.815 (1.31), 9.007 (1.79), 9.009 (1.84), 9.022 (1.80), 9.024 (1.81), 9.078 (3.98), 9.402 (1.24), 9.420 (1.20).<br>LC-MS (Method 2): $R_t$ = 1.27 min; MS (ESIpos): m/z = 449 $[M + H]^+$<br>Intermediate 117<br>80.0 mg (95% purity, 72% yield) |
| 100 | 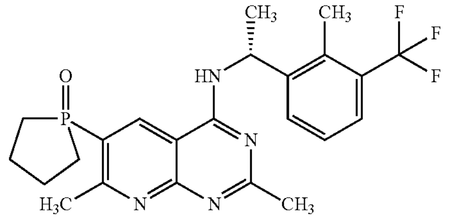 [SMILES: Cc1nc(N[C@H](C)c2cccc(C(F)(F)F)c2C)c2cc(P3(=O)CCCC3)c(C)nc2n1]<br>1-[2,7-dimethyl-4-{{(1R)-1-[2-methyl-3-(trifluoromethyl)phenyl]ethyl}amino)pyrido[2,3-d]pyrimidin-6-yl]-1lambda$^5$-phospholan-1-one<br>$^1$H-NMR (400 MHz, DMSO-d6) δ [ppm]: 1.576 (4.85), 1.593 (4.82), 1.805 (0.53), 1.830 (0.61), 1.847 (0.57), 1.855 (0.58), 1.873 (0.40), 1.975 (0.65), 2.014 (1.02), 2.052 (0.59), 2.069 (0.53), 2.337 (0.63), 2.366 (16.00), 2.418 (0.57), 2.436 (0.48), 2.518 (7.74), 2.523 (5.54), 2.612 (5.77), 2.678 (0.61), 2.816 (12.58), 5.708 (0.72), 5.725 (1.13), 5.743 (0.73), 7.343 (0.65), 7.362 (1.43), 7.383 (0.84), 7.543 (1.62), 7.561 (1.34), 7.749 (1.39), 7.769 (1.26), 8.906 (2.01), 8.938 (1.95), 9.026 (1.22), 9.042 (1.16).<br>LC-MS (Method 2): $R_t$ = 1.15 min; MS (ESIpos): m/z = 463 $[M + H]^+$<br>Intermediate 18<br>50.0 mg (95% purity, 45% yield) |
| 101 | 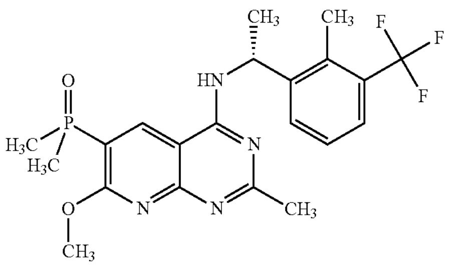 [SMILES: COc1nc2nc(C)nc(N[C@H](C)c3cccc(C(F)(F)F)c3C)c2cc1P(C)(C)=O] |

TABLE 8-continued

| Ex. | Examples<br>Structure; IUPAC-Name; Analytical Data; Starting Materials; Yield |
|---|---|
| | 6-(dimethylphosphoryl)-7-methoxy-2-methyl-N-{(1R)-1-[2-methyl-3-(trifluoromethyl)phenyl]ethyl}pyrido[2,3-d]pyrimidin-4-amine<br>$^1$H-NMR (400 MHz, DMSO-d6) δ [ppm]: 1.530 (3.90), 1.548 (3.93), 1.698 (6.62), 1.733 (6.52), 2.332 (0.92), 2.337 (0.52), 2.349 (13.88), 2.518 (4.84), 2.523 (3.40), 2.618 (4.73), 2.673 (0.83), 4.008 (16.00), 5.688 (0.60), 5.706 (0.93), 5.723 (0.60), 7.336 (0.54), 7.356 (1.20), 7.376 (0.70), 7.528 (1.30), 7.546 (1.04), 7.801 (1.14), 7.820 (1.03), 9.139 (2.24), 9.156 (1.07), 9.171 (2.77).<br>LC-MS (Method 2): $R_t$ = 1.13 min; MS (ESIpos): m/z = 453 $[M + H]^+$<br>Intermediate 35<br>43.0 mg (95% purity, 41% yield) |
| 102 | 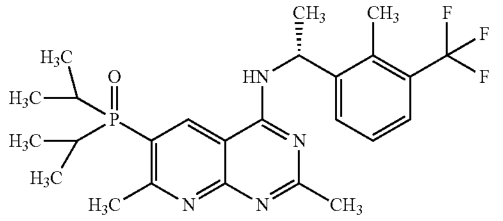 [SMILES: Cc1nc(N[C@H](C)c2cccc(C(F)(F)F)c2C)c2cc(P(=O)(C(C)C)C(C)C)c(C)nc2n1]<br>6-[di(propan-2-yl)phosphoryl]-2,7-dimethyl-N-{(1R)-1-[2-methyl-3-(trifluoromethyl)phenyl]ethyl}pyrido[2,3-d]pyrimidin-4-amine<br>$^1$H-NMR (400 MHz, DMSO-d6) δ [ppm]: 0.877 (0.98), 0.895 (1.97), 0.913 (1.26), 0.917 (1.28), 0.934 (1.96), 0.953 (1.04), 1.165 (0.99), 1.185 (1.41), 1.203 (1.97), 1.222 (1.48), 1.240 (1.16), 1.580 (1.70), 1.598 (1.71), 2.337 (1.24), 2.362 (5.93), 2.518 (16.00), 2.523 (11.18), 2.564 (0.43), 2.609 (2.12), 2.674 (2.90), 2.679 (1.30), 2.819 (3.80), 7.366 (0.52), 7.540 (0.57), 7.559 (0.47), 7.723 (0.49), 7.744 (0.43), 8.832 (0.42), 8.860 (0.42).<br>LC-MS (Method 2): $R_t$ = 1.24 min; MS (ESIneg): m/z = 491 $[M - H]^-$<br>Intermediate 18<br>7.00 mg (95% purity, 6% yield) |
| 103 | 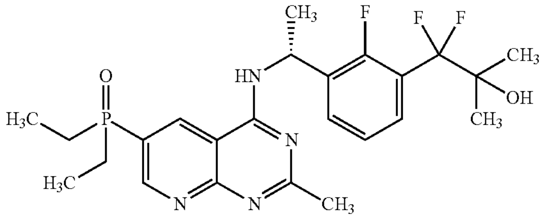<br>1-{3-[(1R)-1-{[6-(diethylphosphoryl)-2-methylpyrido[2,3-d]pyrimidin-4-yl]amino}ethyl]-2-fluorophenyl}-1,1-difluoro-2-methylpropan-2-ol<br>$^1$H-NMR (400 MHz, DMSO-d6) δ [ppm]: 0.943 (1.87), 0.952 (2.00), 0.962 (4.51), 0.971 (4.36), 0.981 (2.35), 0.986 (2.39), 0.990 (2.44), 0.995 (2.23), 1.004 (4.41), 1.014 (4.47), 1.023 (2.05), 1.033 (1.96), 1.200 (6.32), 1.226 (6.50), 1.591 (4.69), 1.609 (4.67), 1.998 (0.52), 2.007 (0.58), 2.017 (0.82), 2.026 (0.92), 2.032 (0.74), 2.036 (0.86), 2.041 (1.16), 2.045 (1.06), 2.051 (0.99), 2.061 (1.37), 2.066 (1.07), 2.070 (0.92), 2.079 (1.19), 2.085 (0.96), 2.092 (0.86), 2.098 (1.17), 2.104 (0.63), 2.111 (0.82), 2.117 (1.04), 2.123 (0.40), 2.130 (0.55), 2.135 (0.58), 2.395 (16.00), 2.518 (2.34), 2.523 (1.61), 5.340 (2.52), 5.776 (0.76), 5.794 (1.16), 5.812 (0.73), 7.208 (0.75), 7.228 (1.80), 7.247 (1.16), 7.301 (0.69), 7.305 (0.80), 7.322 (1.10), 7.338 (0.52), 7.342 (0.46), 7.609 (0.61), 7.626 (1.07), 7.641 (0.55), 9.118 (1.48), 9.123 (1.79), 9.127 (1.64), 9.132 (1.56), 9.179 (1.30), 9.197 (1.24), 9.215 (1.36), 9.220 (1.25), 9.242 (1.33), 9.247 (1.19).<br>LC-MS (Method 2): $R_t$ = 0.98 min; MS (ESIpos): m/z = 496 $[M + H]^+$<br>Intermediate 17<br>33.0 mg (95% purity, 40% yield) |
| 104 | 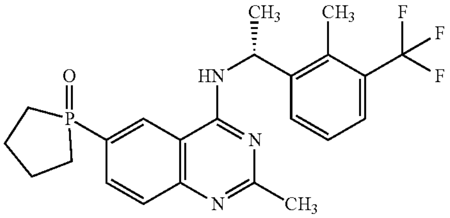 [SMILES: Cc1nc(N[C@H](C)c2cccc(C(F)(F)F)c2C)c2cc(P3(=O)CCCC3)ccc2n1] |

TABLE 8-continued

| Ex. | Examples<br>Structure; IUPAC-Name; Analytical Data; Starting Materials; Yield |
|---|---|
| | 1-[2-methyl-4-{{(1R)-1-[2-methyl-3-(trifluoromethyl)phenyl]ethyl}amino)quinazolin-6-yl]-1lambda$^5$-phospholan-1-one<br>$^1$H-NMR (400 MHz, DMSO-d6) δ [ppm]: 1.571 (4.98), 1.588 (5.03), 1.857 (0.43), 1.872 (0.58), 1.893 (0.78), 1.912 (0.78), 1.928 (1.05), 1.946 (0.81), 1.970 (0.63), 2.017 (0.55), 2.033 (0.71), 2.050 (0.81), 2.063 (0.99), 2.086 (1.34), 2.102 (0.92), 2.124 (0.60), 2.331 (0.90), 2.336 (0.46), 2.357 (16.00), 2.518 (3.88), 2.523 (2.60), 2.635 (6.07), 2.673 (0.85), 5.720 (0.76), 5.737 (1.17), 5.755 (0.75), 7.332 (0.70), 7.351 (1.51), 7.371 (0.86), 7.526 (1.64), 7.543 (1.31), 7.645 (1.33), 7.652 (1.33), 7.667 (1.54), 7.673 (1.51), 7.809 (1.44), 7.829 (1.33), 7.880 (0.87), 7.884 (0.90), 7.905 (1.49), 7.908 (1.03), 7.926 (0.72), 7.929 (0.76), 8.819 (1.23), 8.822 (1.24), 8.850 (1.25), 8.853 (1.22), 9.009 (1.25), 9.026 (1.20).<br>LC-MS (Method 2): $R_t$ = 1.23 min; MS (ESIneg): m/z = 446 [M − H]$^-$<br>Intermediate 182<br>53.0 mg (95% purity, 48% yield) |
| 105 | 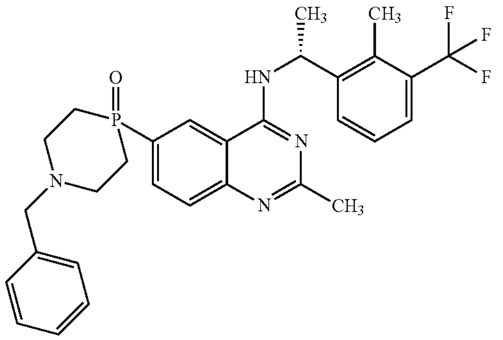 [SMILES: Cc1nc(N[C@H](C)c2cccc(C(F)(F)F)c2C)c2cc(P3(=O)CCN(Cc4ccccc4)CC3)ccc2n1]<br>1-benzyl-4-[2-methyl-4-({(1R)-1-[2-methyl-3-(trifluoromethyl)phenyl]ethyl}amino)quinazolin-6-yl]-1,4lambda$^5$-azaphosphinan-4-one<br>$^1$H-NMR (400 MHz, DMSO-d6) δ [ppm]: 0.798 (0.78), 0.814 (0.87), 0.821 (0.84), 0.840 (0.41), 0.886 (0.42), 0.904 (0.90), 0.923 (0.50), 0.951 (0.50), 1.035 (1.10), 1.052 (2.48), 1.070 (1.41), 1.154 (5.91), 1.172 (12.30), 1.190 (6.08), 1.218 (0.47), 1.236 (1.07), 1.253 (0.48), 1.579 (8.04), 1.597 (8.01), 1.751 (1.80), 1.907 (3.01), 1.927 (0.84), 1.964 (1.55), 2.003 (0.92), 2.323 (3.18), 2.327 (4.27), 2.331 (3.51), 2.336 (2.34), 2.364 (16.00), 2.518 (12.96), 2.523 (8.33), 2.631 (11.72), 2.660 (1.42), 2.665 (2.70), 2.669 (3.56), 2.673 (2.62), 2.783 (1.77), 2.812 (1.87), 2.841 (0.88), 2.884 (1.19), 2.941 (1.19), 3.065 (0.93), 3.084 (2.76), 3.096 (2.81), 3.102 (2.81), 3.114 (2.58), 3.133 (0.83), 3.423 (0.46), 3.435 (0.48), 3.452 (0.42), 3.576 (0.47), 3.652 (7.00), 5.722 (1.14), 5.739 (1.68), 5.756 (1.11), 7.277 (1.58), 7.291 (1.52), 7.298 (1.30), 7.311 (1.35), 7.358 (9.04), 7.365 (12.01), 7.380 (2.43), 7.535 (3.03), 7.553 (2.50), 7.659 (1.62), 7.664 (1.68), 7.679 (1.84), 7.685 (1.78), 7.774 (2.73), 7.795 (2.45), 8.036 (0.76), 8.058 (1.31), 8.080 (0.69), 8.816 (1.51), 8.846 (1.55), 8.969 (0.48).<br>LC-MS (Method 2): $R_t$ = 1.37 min; MS (ESIpos): m/z = 554 [M + H]$^+$<br>Intermediate 182<br>144 mg (95% purity, 81% yield) |
| 106 | 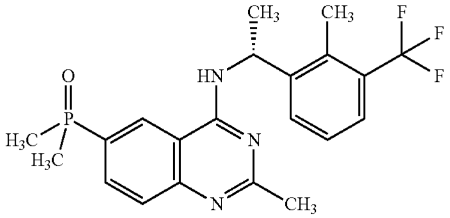 [SMILES: Cc1nc(N[C@H](C)c2cccc(C(F)(F)F)c2C)c2cc(P(C)(C)=O)ccc2n1]<br>6-(dimethylphosphoryl)-2-methyl-N-{(1R)-1-[2-methyl-3-(trifluoromethyl)phenyl]ethyl}quinazolin-4-amine<br>$^1$H-NMR (400 MHz, DMSO-d6) δ [ppm]: 1.570 (4.80), 1.587 (4.73), 1.723 (15.57), 1.756 (16.00), 2.323 (0.50), 2.327 (0.70), 2.331 (0.52), 2.356 (15.45), 2.518 (2.15), 2.523 (1.46), 2.635 (5.71), 2.665 (0.52), 2.669 (0.68), 2.673 (0.47), 5.720 (0.72), 5.737 (1.11), 5.755 (0.71), 7.336 (0.66), 7.356 (1.42), 7.375 (0.82), 7.528 (1.54), 7.546 (1.23), 7.631 (1.30), 7.637 (1.30), 7.652 (1.46), 7.659 (1.42), 7.805 (1.36), 7.824 |

TABLE 8-continued

| Ex. | Structure; IUPAC-Name; Analytical Data; Starting Materials; Yield |
|---|---|
| | (1.23), 7.973 (0.86), 7.976 (0.88), 7.993 (0.86), 7.997 (1.65), 8.001 (0.96), 8.018 (0.75), 8.023 (0.75), 8.806 (1.20), 8.809 (1.18), 8.838 (1.20), 8.841 (1.16), 8.934 (1.18), 8.952 (1.15).<br>LC-MS (Method 2): $R_t$ = 1.17 min; MS (ESIneg): m/z = 420 $[M - H]^-$<br>Intermediate 182<br>47.0 mg (95% purity, 45% yield) |
| 107 | 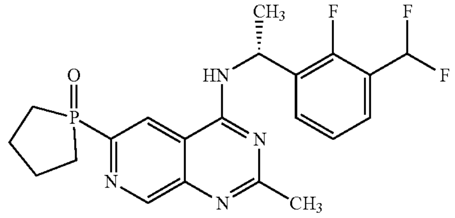 [SMILES: Cc1nc(N[C@H](C)c2cccc(C(F)F)c2F)c2cc(P3(=O)CCCC3)ncc2n1]<br>1-[4-{{(1R)-1-[3-(difluoromethyl)-2-fluorophenyl]ethyl}amino)-2-methylpyrido[3,4-d]pyrimidin-6-yl]-1lambda$^5$-phospholan-1-one<br>$^1$H-NMR (400 MHz, DMSO-d6) δ [ppm]: 1.609 (4.96), 1.627 (4.90), 1.791 (0.40), 1.812 (0.55), 1.831 (0.72), 1.843 (0.60), 1.864 (0.46), 1.961 (0.51), 1.978 (0.79), 1.994 (1.02), 2.012 (1.06), 2.019 (0.93), 2.035 (0.91), 2.053 (0.82), 2.068 (0.59), 2.090 (0.94), 2.103 (0.76), 2.120 (0.76), 2.132 (0.67), 2.138 (0.67), 2.150 (0.50), 2.156 (0.44), 2.331 (0.41), 2.428 (16.00), 2.518 (2.21), 2.523 (1.54), 2.673 (0.41), 2.727 (3.08), 2.729 (2.92), 2.888 (3.75), 5.759 (0.73), 5.783 (0.75), 5.801 (1.15), 5.819 (0.74), 7.104 (1.17), 7.240 (2.39), 7.280 (0.84), 7.299 (1.82), 7.319 (1.04), 7.376 (1.02), 7.493 (0.61), 7.510 (1.04), 7.527 (0.50), 7.690 (0.56), 7.708 (1.03), 7.726 (0.51), 7.950 (0.44), 9.009 (1.70), 9.011 (1.76), 9.025 (1.74), 9.027 (1.73), 9.097 (4.09), 9.315 (1.20), 9.333 (1.16).<br>LC-MS (Method 2): $R_t$ = 1.12 min; MS (ESIpos): m/z = 435 $[M + H]^+$<br>Intermediate 165<br>76.0 mg (95% purity, 68% yield) |
| 108 | 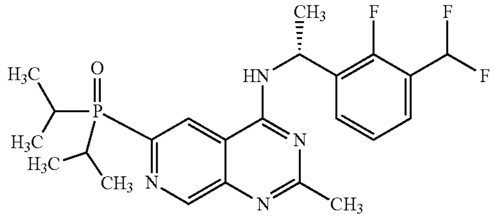 [SMILES: Cc1nc(N[C@H](C)c2cccc(C(F)F)c2F)c2cc(P(=O)(C(C)C)C(C)C)ncc2n1]<br>N-{(1R)-1-[3-(difluoromethyl)-2-fluorophenyl]ethyl}-6-[di(propan-2-yl)phosphoryl]-2-methylpyrido[3,4-d]pyrimidin-4-amine<br>$^1$H-NMR (400 MHz, DMSO-d6) δ [ppm]: 0.920 (3.14), 0.932 (3.45), 0.938 (3.59), 0.950 (3.39), 0.959 (3.36), 0.971 (3.51), 0.977 (3.55), 0.989 (3.16), 1.103 (3.07), 1.120 (5.80), 1.138 (4.35), 1.158 (5.85), 1.175 (3.12), 1.615 (4.82), 1.633 (4.77), 2.154 (0.53), 2.423 (16.00), 2.437 (1.00), 2.445 (0.80), 2.450 (0.86), 2.455 (1.01), 2.463 (1.30), 2.468 (1.52), 2.518 (4.58), 2.523 (3.26), 5.775 (0.75), 5.793 (1.15), 5.810 (0.73), 7.106 (1.16), 7.242 (2.35), 7.291 (0.83), 7.310 (1.80), 7.329 (1.03), 7.377 (1.01), 7.493 (0.60), 7.511 (1.01), 7.529 (0.49), 7.695 (0.55), 7.713 (1.01), 7.731 (0.50), 8.893 (1.72), 8.895 (1.74), 8.908 (1.76), 8.910 (1.72), 9.085 (4.40), 9.087 (4.30), 9.364 (1.21), 9.382 (1.16).<br>LC-MS (Method 2): $R_t$ = 1.25 min; MS (ESIneg): m/z = 463 $[M - H]^-$<br>Intermediate 165<br>28.0 mg (95% purity, 24% yield) |
| 109 | 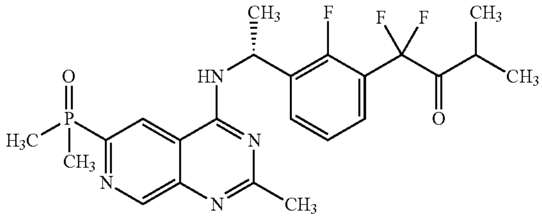 [SMILES: Cc1nc(N[C@H](C)c2cccc(C(F)(F)C(=O)C(C)C)c2F)c2cc(P(C)(C)=O)ncc2n1] |

TABLE 8-continued

| Examples | |
|---|---|
| Ex. | Structure; IUPAC-Name; Analytical Data; Starting Materials; Yield |
| | 1-{3-[(1R)-1-{[6-(dimethylphosphoryl)-2-methylpyrido[3,4-d]pyrimidin-4-yl]amino}ethyl]-2-fluorophenyl}-1,1-difluoro-3-methylbutan-2-one<br>LC-MS (Method 2): $R_t$ = 1.17 min; MS (ESIpos): m/z = 479.6 [M + H]$^+$<br>Intermediate 85<br>246 mg (96% yield) |
| 110 | 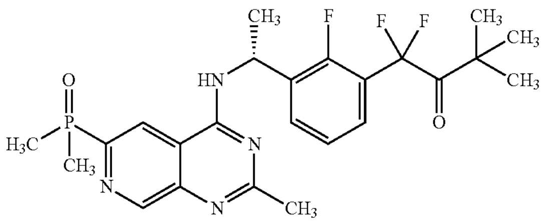 [SMILES: Cc1nc(N[C@H](C)c2cccc(C(F)(F)C(=O)C(C)(C)C)c2F)c2cc(P(C)(C)=O)ncc2n1]<br>1-{3-[(1R)-1-{[6-(dimethylphosphoryl)-2-methylpyrido[3,4-d]pyrimidin-4-yl]amino}ethyl]-2-fluorophenyl}-1,1-difluoro-3,3-dimethylbutan-2-one<br>LC-MS (Method 2): $R_t$ = 1.23 min; MS (ESIpos): m/z = 493 [M + H]$^+$<br>Intermediate 63<br>142 mg (95% purity, 63% yield) |
| 111 | 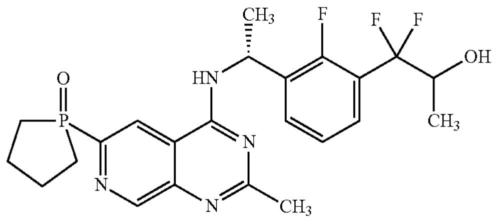 [SMILES: Cc1nc(N[C@H](C)c2cccc(C(F)(F)C(C)O)c2F)c2cc(P3(=O)CCCC3)ncc2n1]<br>1-(4-{[(1R)-1-{3-[(2R*)-1,1-difluoro-2-hydroxypropyl]-2-fluorophenyl}ethyl]amino}-2-methylpyrido[3,4-d]pyrimidin-6-yl)-1lambda$^5$-phospholan-1-one (diastereomer 1)<br>$^1$H-NMR (400 MHz, DMSO-d6) δ [ppm]: 1.146 (4.48), 1.163 (4.52), 1.231 (0.42), 1.592 (5.06), 1.610 (5.04), 1.792 (0.51), 1.811 (0.68), 1.830 (0.84), 1.844 (0.72), 1.865 (0.57), 1.961 (0.61), 1.978 (0.94), 1.995 (1.18), 2.013 (1.23), 2.036 (1.06), 2.054 (0.94), 2.069 (0.66), 2.091 (1.02), 2.102 (0.96), 2.119 (1.08), 2.137 (1.04), 2.155 (0.72), 2.332 (0.90), 2.336 (0.40), 2.437 (16.00), 2.518 (4.97), 2.523 (3.26), 4.183 (0.41), 5.566 (1.93), 5.582 (1.91), 5.758 (6.16), 5.800 (0.80), 5.817 (1.24), 5.834 (0.79), 7.229 (0.90), 7.248 (2.03), 7.268 (1.23), 7.361 (0.77), 7.378 (1.18), 7.394 (0.56), 7.640 (0.65), 7.656 (1.15), 7.674 (0.59), 9.011 (1.88), 9.025 (1.86), 9.096 (4.56), 9.296 (1.39), 9.314 (1.32).<br>LC-MS (Method 2): $R_t$ = 1.02 min; MS (ESIneg): m/z = 477 [M − H]$^-$<br>Intermediate 44<br>22.0 mg (95% purity, 25% yield) |
| 112 | 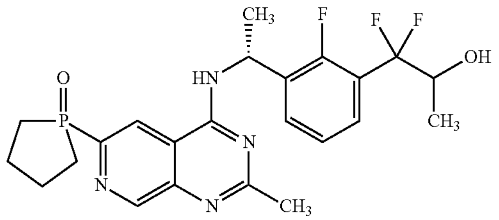 [SMILES: Cc1nc(N[C@H](C)c2cccc(C(F)(F)C(C)O)c2F)c2cc(P3(=O)CCCC3)ncc2n1]<br>1-(4-{[(1R)-1-{3-[(2R*)-1,1-difluoro-2-hydroxypropyl]-2-fluorophenyl}ethyl]amino}-2-methylpyrido[3,4-d]pyrimidin-6-yl)-1lambda$^5$-phospholan-1-one (diastereomer 2)<br>$^1$H-NMR (400 MHz, DMSO-d6) δ [ppm]: 1.133 (4.42), 1.149 (4.48), 1.228 (0.58), 1.598 (5.01), 1.616 (4.97), 1.793 (0.51), 1.811 (0.69), 1.831 (0.85), 1.844 (0.72), 1.865 (0.59), 1.961 (0.59), 1.977 (0.92), 1.995 (1.17), 2.013 (1.26), 2.036 (1.06), 2.053 (0.95), 2.069 (0.68), 2.084 (0.84), 2.090 (1.07), 2.102 (0.93), 2.119 (1.00), 2.137 (0.91), 2.153 (0.62), 2.415 (16.00), 2.435 (0.48), 2.518 (1.78), 2.523 (1.22), 4.194 (0.41), 4.211 (0.41), 5.580 (1.76), 5.595 (1.69), 5.758 (6.77), 5.772 (1.25), 5.789 (0.79), 7.219 (0.90), 7.238 (2.05), 7.257 (1.24), 7.355 (0.76), 7.373 (1.19), 7.388 (0.57), 7.623 (0.64), 7.641 (1.15), 7.657 (0.60), 9.010 (1.93), 9.025 (1.88), 9.091 (4.57), 9.312 (1.37), 9.330 (1.30).<br>LC-MS (Method 2): $R_t$ = 1.01 min; MS (ESIpos): m/z = 479 [M + H]$^+$<br>Intermediate 45<br>6.20 mg (95% purity, 7% yield) |

TABLE 8-continued

| Ex. | Structure; IUPAC-Name; Analytical Data; Starting Materials; Yield |
|---|---|
| | Examples |
| 113 | 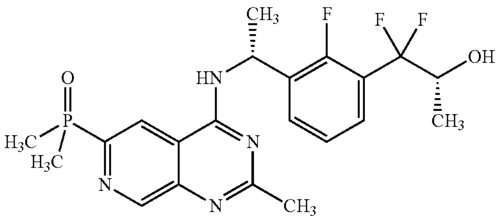 [SMILES: Cc1nc(N[C@H](C)c2cccc(C(F)(F)[C@@H](C)O)c2F)c2cc(P(C)(C)=O)ncc2n1] (2R*)-1-{3-[(1R)-1-{[6-(dimethylphosphoryl)-2-methylpyrido[3,4-d]pyrimidin-4-yl]amino}ethyl]-2-fluorophenyl}-1,1-difluoropropan-2-ol (diastereomer 2) $^1$H-NMR (400 MHz, DMSO-d6) δ [ppm]: 1.134 (5.25), 1.150 (5.30), 1.602 (5.83), 1.620 (5.82), 1.690 (9.02), 1.693 (9.26), 1.724 (9.16), 1.727 (9.08), 2.331 (0.72), 2.420 (16.00), 2.441 (0.55), 2.518 (4.62), 2.523 (2.99), 2.673 (0.70), 4.208 (0.46), 5.581 (0.93), 5.596 (0.90), 5.758 (1.24), 5.778 (1.42), 5.796 (0.91), 7.227 (1.02), 7.246 (2.35), 7.265 (1.42), 7.361 (0.90), 7.378 (1.42), 7.395 (0.68), 7.627 (0.79), 7.644 (1.40), 7.660 (0.76), 8.964 (2.14), 8.980 (2.12), 9.092 (5.14), 9.340 (0.52). LC-MS (Method 2): $R_t$ = 0.92 min; MS (ESIneg): m/z = 451 [M − H]$^-$ Intermediate 45 23.3 mg (95% purity, 28% yield) |
| 114 | 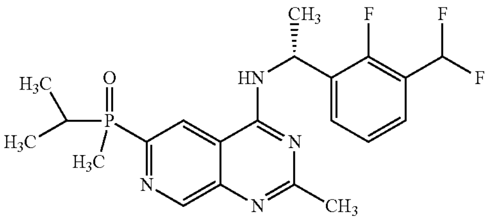 [SMILES: Cc1nc(N[C@H](C)c2cccc(C(F)F)c2F)c2cc(P(C)(=O)C(C)C)ncc2n1] N-{(1R)-1-[3-(difluoromethyl)-2-fluorophenyl]ethyl}-2-methyl-6-[methyl(propan-2-yl)phosphoryl]pyrido[3,4-d]pyrimidin-4-amine (mixture of diastereomers) $^1$H-NMR (400 MHz, DMSO-d6) δ [ppm]: 0.893 (1.22), 0.905 (2.54), 0.910 (1.54), 0.923 (2.43), 0.932 (1.35), 0.946 (2.59), 0.950 (1.54), 0.964 (2.41), 1.144 (3.41), 1.161 (3.52), 1.183 (3.41), 1.201 (3.37), 1.610 (3.95), 1.627 (4.01), 1.648 (5.47), 1.657 (2.97), 1.681 (5.42), 1.689 (2.90), 2.198 (0.60), 2.216 (0.68), 2.222 (0.66), 2.235 (0.46), 2.240 (0.65), 2.425 (16.00), 2.518 (1.82), 2.523 (1.29), 5.775 (0.57), 5.793 (0.88), 5.800 (0.55), 5.811 (0.58), 7.106 (0.92), 7.242 (1.91), 7.291 (0.61), 7.301 (0.73), 7.310 (1.31), 7.321 (0.44), 7.329 (0.75), 7.378 (0.82), 7.494 (0.61), 7.511 (1.05), 7.528 (0.51), 7.703 (0.52), 7.716 (0.78), 8.933 (1.24), 8.934 (1.27), 8.948 (1.63), 8.950 (1.36), 8.960 (0.67), 8.962 (0.65), 9.088 (4.55), 9.311 (0.86), 9.329 (1.01), 9.350 (0.44). LC-MS (Method 2): Rt = 1.12 min; MS (ESIpos): m/z = 438 [M + H]$^+$ Intermediate 165 12.0 mg (95% purity, 7% yield) |

The diastereomers of example 114 were separated according to the following method.
Anal.-Method:
Instrument: Thermo Fisher UltiMate 3000; Column: YMC Cellulose SB 3 μ, 100 × 4.6; eluent A: methyl tert-butyl ether + 0.1 vol % diethylamine; eluent B: acetonitrile; isocratic: 90% A + 10% B; flow: 1.4 ml/min; temperature: 25° C.; UV: 280 nm;
Prep.-Method:
Instrument: PrepCon Labomatic HPLC-2; Column: YMC Cellulose SB 10 μ, 250 × 50; eluent A: methyl tert-butyl ether + 0.1 vol % diethylamine; eluent B: acetonitrile; isocratic: 90% A + 10% B; flow: 70 ml/min; temperature: 25° C.; UV: 280 nm;

| | |
|---|---|
| 115 | 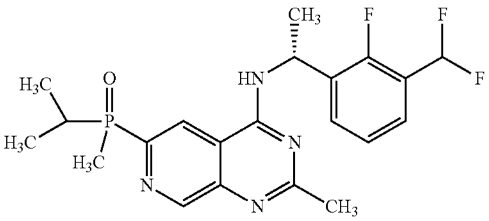 [SMILES: Cc1nc(N[C@H](C)c2cccc(C(F)F)c2F)c2cc(P(C)(=O)C(C)C)ncc2n1] |

TABLE 8-continued

| Examples | |
|---|---|
| Ex. | Structure; IUPAC-Name; Analytical Data; Starting Materials; Yield |
| | N-{(1R)-1-[3-(difluoromethyl)-2-fluorophenyl]ethyl}-2-methyl-6-[methyl(propan-2-yl)phosphoryl]pyrido[3,4-d]pyrimidin-4-amine (diastereomer 1)<br>LC-MS (Method 2): $R_t$ = 1.12 min; MS (ESIpos): m/z = 438 $[M + H]^+$<br>Example 114<br>20.0 mg (95% purity)<br>Rt (analytical Method) = 3.40 min (de = >99%) |
| 116 | 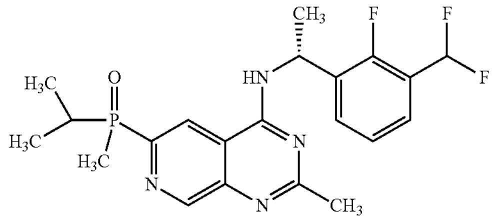 [SMILES: Cc1nc(N[C@H](C)c2cccc(C(F)F)c2F)c2cc(P(C)(=O)C(C)C)ncc2n1]<br>N-{(1R)-1-[3-(difluoromethyl)-2-fluorophenyl]ethyl}-2-methyl-6-[methyl(propan-2-yl)phosphoryl]pyrido[3,4-d]pyrimidin-4-amine (diastereomer 2)<br>$^1$H-NMR (400 MHz, DMSO-d6) δ [ppm]: 0.906 (2.00), 0.924 (2.04), 0.946 (2.03), 0.964 (1.99), 1.144 (1.97), 1.162 (2.12), 1.184 (2.08), 1.202 (2.08), 1.232 (1.07), 1.352 (4.07), 1.609 (2.94), 1.627 (3.02), 1.648 (4.31), 1.681 (4.24), 2.181 (0.60), 2.217 (0.44), 2.241 (0.44), 2.336 (0.66), 2.426 (9.21), 2.518 (16.00), 2.522 (10.76), 2.678 (0.66), 5.775 (0.46), 5.793 (0.70), 5.810 (0.47), 7.106 (0.69), 7.242 (1.39), 7.292 (0.48), 7.311 (1.08), 7.331 (0.65), 7.378 (0.60), 7.512 (0.64), 7.716 (0.67), 8.934 (1.07), 8.950 (1.07), 9.090 (2.46), 9.312 (0.72), 9.330 (0.73).<br>LC-MS (Method 2): Rt = 1.11 min; MS (ESIneg): m/z = 435 $[M - H]^-$<br>Example 114<br>24.0 mg (95% purity)<br>Rt (analytical Method) = 4.90 min (de = 97%) |
| 117 | 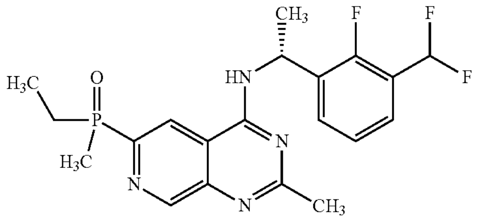 [SMILES: CCP(C)(=O)c1cc2c(N[C@H](C)c3cccc(C(F)F)c3F)nc(C)nc2cn1]<br>N-{(1R)-1-[3-(difluoromethyl)-2-fluorophenyl]ethyl}-6-[ethyl(methyl)phosphoryl]-2-methylpyrido[3,4-d]pyrimidin-4-amine (mixture of diastereomers)<br>$^1$H-NMR (400 MHz, DMSO-d6) δ [ppm]: 0.934 (0.99), 0.950 (1.15), 0.954 (2.52), 0.969 (2.24), 0.973 (1.39), 0.978 (1.16), 0.989 (1.04), 0.994 (1.24), 0.997 (2.58), 1.013 (2.27), 1.016 (1.32), 1.032 (0.92), 1.612 (3.71), 1.630 (3.71), 1.654 (3.47), 1.662 (4.13), 1.687 (3.40), 1.694 (4.16), 1.963 (0.46), 1.973 (0.97), 1.978 (0.59), 1.982 (0.65), 1.991 (1.25), 1.997 (0.62), 2.003 (0.76), 2.010 (0.94), 2.023 (0.61), 2.029 (0.55), 2.427 (16.00), 2.518 (3.53), 2.523 (2.45), 5.786 (0.50), 5.796 (0.63), 5.803 (0.72), 5.814 (0.43), 5.821 (0.44), 7.105 (0.92), 7.241 (1.87), 7.284 (0.49), 7.289 (0.44), 7.303 (1.08), 7.308 (0.93), 7.322 (0.62), 7.328 (0.52), 7.377 (0.84), 7.495 (0.59), 7.512 (1.00), 7.530 (0.49), 7.694 (0.42), 7.711 (0.76), 8.945 (0.84), 8.947 (0.87), 8.954 (1.06), 8.956 (1.08), 8.960 (0.93), 8.969 (1.00), 8.971 (0.95), 9.092 (4.04), 9.300 (0.58), 9.316 (1.11), 9.333 (0.65).<br>LC-MS (Method 2): $R_t$ = 1.06 min; MS (ESIpos): m/z = 424 $[M + H]^+$<br>Intermediate 165<br>58.0 mg (95% purity, 36% yield) |

The diastereomers of example 117 were separated according to the following method.
Anal.-Method:
Instrument: Thermo Fisher UltiMate 3000; Column: YMC Cellulose SB 3 μ, 100 x 4.6; eluent A: methyl tert-butyl ether + 0.1 vol % diethylamine; eluent B: acetonitrile; isocratic:
90% A + 10% B; flow: 1.4 ml/min; temperature: 25° C; UV: 280 nm;
Prep.-Method:
Instrument: PrepCon Labomatic HPLC-2; Column: YMC Cellulose SB 10 μ, 250 x 50; eluent A: methyl tert-butyl ether + 0.1 vol % diethylamine; eluent B: acetonitrile; isocratic:
90% A + 10% B; flow: 70 ml/min; temperature: 25° C.; UV: 280 nm;

TABLE 8-continued

| Ex. | Structure; IUPAC-Name; Analytical Data; Starting Materials; Yield |
|---|---|
| 118 | 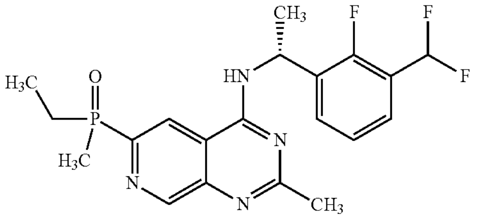 [SMILES: CCP(C)(=O)c1cc2c(N[C@H](C)c3cccc(C(F)F)c3F)nc(C)nc2cn1]<br>N-{(1R)-1-[3-(difluoromethyl)-2-fluorophenyl]ethyl}-6-[ethyl(methyl)phosphoryl]-2-methylpyrido[3,4-d]pyrimidin-4-amine (diastereomer 1)<br>$^{1}$H-NMR (400 MHz, DMSO-d6) δ [ppm]: 0.934 (1.96), 0.953 (4.50), 0.972 (2.19), 0.977 (2.12), 0.997 (4.54), 1.016 (2.13), 1.232 (1.15), 1.613 (5.29), 1.631 (5.38), 1.661 (7.54), 1.694 (7.56), 1.963 (0.78), 1.973 (1.21), 1.981 (0.88), 1.991 (1.65), 2.004 (0.98), 2.010 (1.13), 2.023 (0.84), 2.336 (0.58), 2.427 (16.00), 2.522 (11.51), 2.659 (0.65), 5.786 (0.82), 5.803 (1.28), 5.820 (0.83), 7.104 (1.21), 7.240 (2.50), 7.284 (0.88), 7.303 (1.96), 7.322 (1.16), 7.376 (1.07), 7.495 (0.66), 7.512 (1.17), 7.530 (0.60), 7.691 (0.62), 7.709 (1.16), 7.727 (0.61), 8.955 (1.89), 8.969 (1.94), 9.092 (4.43), 9.315 (1.32), 9.333 (1.28).<br>LC-MS (Method 2): $R_t$ = 1.07 min; MS (ESIneg): m/z = 421 $[M - H]^-$<br>Example 117<br>21.0 mg (95% purity)<br>Rt (analytical Method) = 4.69 min (de = 99%) |
| 119 | 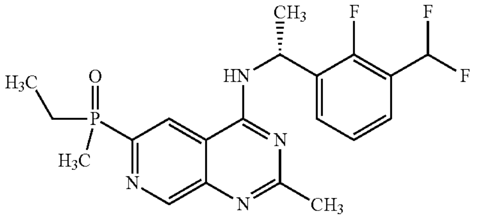 [SMILES: CCP(C)(=O)c1cc2c(N[C@H](C)c3cccc(C(F)F)c3F)nc(C)nc2cn1]<br>N-{(1R)-1-[3-(difluoromethyl)-2-fluorophenyl]ethyl}-6-[ethyl(methyl)phosphoryl]-2-methylpyrido[3,4-d]pyrimidin-4-amine (diastereomer 2)<br>$^{1}$H-NMR (400 MHz, DMSO-d6) δ [ppm]: 0.850 (0.40), 0.950 (1.88), 0.969 (4.42), 0.988 (2.20), 0.993 (2.16), 1.013 (4.28), 1.032 (2.07), 1.231 (1.31), 1.610 (5.20), 1.628 (5.29), 1.654 (7.19), 1.687 (7.19), 1.972 (0.88), 1.978 (0.99), 1.991 (1.12), 1.997 (1.12), 2.002 (1.08), 2.009 (1.16), 2.021 (0.90), 2.028 (0.90), 2.074 (5.04), 2.427 (16.00), 2.522 (7.40), 5.777 (0.79), 5.795 (1.23), 5.814 (0.80), 7.106 (1.17), 7.242 (2.40), 7.289 (0.85), 7.309 (1.87), 7.328 (1.12), 7.377 (1.05), 7.497 (0.64), 7.514 (1.15), 7.531 (0.59), 7.698 (0.61), 7.716 (1.15), 7.735 (0.60), 8.946 (1.81), 8.960 (1.84), 9.092 (4.20), 9.299 (1.24), 9.317 (1.28).<br>LC-MS (Method 2): $R_t$ = 1.06 min; MS (ESIneg): m/z = 421 $[M - H]^-$<br>Example 117<br>13.0 mg (95% purity)<br>Rt (analytical Method) = 6.09 min (de = 95%) |
| 120 | 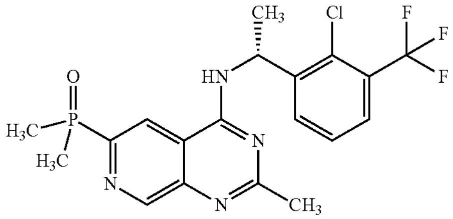 [SMILES: Cc1nc(N[C@H](C)c2cccc(C(F)(F)F)c2Cl)c2cc(P(C)(C)=O)ncc2n1]<br>N-{(1R)-1-[2-chloro-3-(trifluoromethyl)phenyl]ethyl}-6-(dimethylphosphoryl)-2-methylpyrido[3,4-d]pyrimidin-4-amine<br>$^{1}$H-NMR (400 MHz, DMSO-d6) δ [ppm]: 1.229 (0.53), 1.593 (5.52), 1.610 (5.49), 1.622 (0.56), 1.693 (6.41), 1.699 (6.47), 1.727 (6.62), 1.733 (6.46), 2.327 (1.27), 2.331 (0.90), 2.337 (0.41), 2.385 (16.00), 2.518 (5.28), 2.523 (3.67), 2.669 (1.28), 2.673 (0.89), 3.159 (2.38), 3.171 (2.40), 4.099 (0.42), 5.758 (0.51), 5.872 (0.85), 5.890 (1.31), 5.907 (0.83), 7.495 (0.84), 7.514 (1.83), 7.534 (1.07), 7.728 (1.46), 7.731 (1.62), 7.748 (1.31), 7.751 (1.27), 7.862 (1.37), 7.865 (1.37), 7.882 (1.25), 8.984 (1.85), 8.998 (1.84), 9.000 (1.82), 9.095 (4.21), 9.413 (1.29), 9.430 (1.25).<br>LC-MS (Method 2): $R_t$ = 1.16 min; MS (ESIpos): m/z = 444 $[M + H]^+$<br>Intermediate 168<br>15.0 mg (95% purity, 17% yield) |

TABLE 8-continued

| Ex. | Structure; IUPAC-Name; Analytical Data; Starting Materials; Yield |
|---|---|
| | Examples |
| 121 | 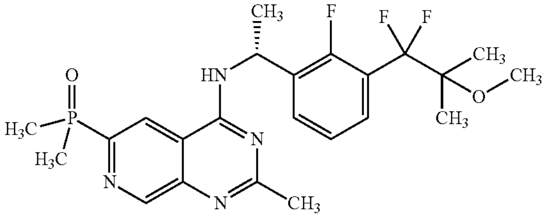 N-{(1R)-1-[3-(1,1-difluoro-2-methoxy-2-methylpropyl)-2-fluorophenyl]ethyl}-6-(dimethylphosphoryl)-2-methylpyrido[3,4-d]pyrimidin-4-amine $^{1}$H-NMR (400 MHz, DMSO-d6) δ [ppm]: 1.251 (7.88), 1.259 (8.21), 1.588 (5.18), 1.605 (5.21), 1.692 (8.85), 1.724 (8.78), 2.406 (16.00), 2.518 (3.58), 2.523 (2.37), 3.174 (15.82), 5.758 (4.86), 5.775 (1.29), 5.793 (0.81), 7.205 (0.76), 7.224 (1.86), 7.243 (1.26), 7.287 (0.75), 7.292 (0.88), 7.308 (1.18), 7.324 (0.55), 7.329 (0.50), 7.617 (0.65), 7.633 (1.15), 7.648 (0.60), 8.965 (1.96), 8.981 (1.98), 9.088 (4.73), 9.285 (1.37), 9.303 (1.32). LC-MS (Method 2): $R_t$ = 1.15 min; MS (ESIpos): m/z = 481 [M + H]$^+$ Intermediate 67 42.4 mg (95% purity, 68% yield) |
| 122 | 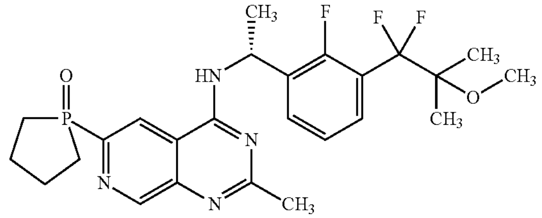 [SMILES: COC(C)(C)C(F)(F)c1cccc([C@@H](C)Nc2nc(C)nc3cnc(P4(=O)CCCC4)cc23)c1F] 1-[4-({(1R)-1-[3-(1,1-difluoro-2-methoxy-2-methylpropyl)-2-fluorophenyl]ethyl}amino)-2-methylpyrido[3,4-d]pyrimidin-6-yl]-1lambda$^5$-phospholan-1-one $^{1}$H-NMR (400 MHz, DMSO-d6) δ [ppm]: 1.231 (0.96), 1.251 (8.36), 1.259 (8.52), 1.586 (5.16), 1.603 (5.17), 1.795 (0.56), 1.812 (0.74), 1.832 (0.90), 1.846 (0.74), 1.867 (0.62), 1.907 (0.40), 1.960 (0.59), 1.978 (0.93), 1.995 (1.18), 2.014 (1.27), 2.036 (1.07), 2.054 (0.95), 2.070 (0.69), 2.091 (1.08), 2.104 (0.91), 2.119 (0.96), 2.137 (0.88), 2.154 (0.60), 2.407 (16.00), 2.518 (4.46), 2.523 (2.97), 3.174 (15.82), 5.758 (4.37), 5.775 (1.29), 5.793 (0.81), 7.200 (0.77), 7.219 (1.87), 7.239 (1.25), 7.285 (0.73), 7.289 (0.86), 7.306 (1.19), 7.322 (0.55), 7.326 (0.51), 7.615 (0.66), 7.631 (1.16), 7.647 (0.61), 9.019 (1.94), 9.034 (1.94), 9.093 (4.74), 9.313 (1.38), 9.331 (1.33). LC-MS (Method 2): $R_t$ = 1.23 min; MS (ESIpos): m/z = 507 [M + H]$^+$ Intermediate 67 44.3 mg (95% purity, 80% yield) |
| 123 | 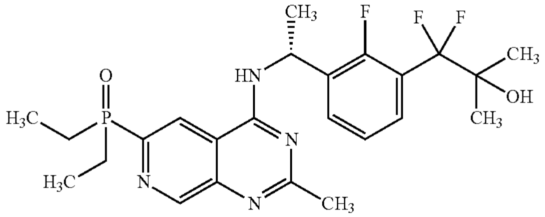 [SMILES: CCP(=O)(CC)c1cc2c(N[C@H](C)c3cccc(C(F)(F)C(C)(C)O)c3F)nc(C)nc2cn1] 1-{3-[(1R)-1-{[6-(diethylphosphoryl)-2-methylpyrido[3,4-d]pyrimidin-4-yl]amino}ethyl]-2-fluorophenyl}-1,1-difluoro-2-methylpropan-2-ol $^{1}$H-NMR (400 MHz, DMSO-d6) δ [ppm]: 0.913 (2.00), 0.928 (2.69), 0.932 (4.85), 0.948 (5.09), 0.951 (3.05), 0.955 (2.60), 0.967 (2.80), 0.970 (3.03), 0.974 (4.81), 0.989 (4.86), 0.993 (2.59), 1.008 (2.02), 1.199 (7.13), 1.225 (7.50), 1.591 (5.20), 1.609 (5.13), 1.947 (0.46), 1.965 (1.18), 1.973 (1.69), 1.977 (1.56), 1.983 (1.85), 1.992 (2.40), 2.005 (2.33), 2.012 (2.15), 2.024 (1.86), 2.031 (1.20), 2.043 (0.63), 2.327 (1.10), 2.331 (0.78), 2.411 (16.00), 2.518 (3.45), 2.523 (2.27), 2.669 (1.09), 2.674 |

TABLE 8-continued

| Ex. | Structure; IUPAC-Name; Analytical Data; Starting Materials; Yield |
|---|---|
| | (0.77), 5.334 (7.02), 5.759 (6.85), 5.772 (0.88), 5.791 (1.32), 5.808 (0.84), 7.210 (0.83), 7.229 (1.95), 7.248 (1.26), 7.299 (0.78), 7.303 (0.90), 7.320 (1.24), 7.336 (0.59), 7.339 (0.53), 7.621 (0.70), 7.638 (1.23), 7.653 (0.64), 8.943 (2.03), 8.957 (2.01), 9.088 (4.80), 9.321 (1.47), 9.339 (1.39).<br>LC-MS (Method 2): $R_t$ = 1.07 min; MS (ESIneg): m/z = 493 $[M - H]^-$<br>Intermediate 70<br>33.0 mg (95% purity, 40% yield) |
| 124 | 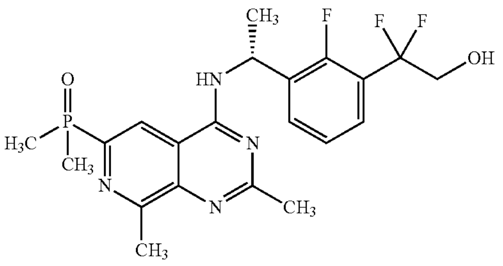 [SMILES: Cc1nc(N[C@H](C)c2cccc(C(F)(F)CO)c2F)c2cc(P(C)(C)=O)nc(C)c2n1]<br>2-{3-[(1R)-1-{[6-(dimethylphosphoryl)-2,8-dimethylpyrido[3,4-d]pyrimidin-4-yl]amino}ethyl]-2-fluorophenyl}-2,2-difluoroethan-1-ol<br>$^1$H-NMR (400 MHz, DMSO-d6) δ [ppm]: 1.595 (4.71), 1.613 (4.66), 1.668 (6.38), 1.672 (6.60), 1.702 (6.60), 1.707 (6.49), 2.075 (0.56), 2.440 (16.00), 2.518 (2.80), 2.523 (2.04), 2.775 (13.05), 3.891 (0.49), 3.906 (0.55), 3.927 (0.98), 3.943 (1.03), 3.963 (0.48), 3.979 (0.48), 5.703 (0.88), 5.719 (2.03), 5.735 (0.85), 5.775 (0.75), 5.793 (1.14), 5.810 (0.73), 7.238 (0.85), 7.257 (1.90), 7.277 (1.10), 7.402 (0.67), 7.419 (1.06), 7.435 (0.52), 7.646 (0.58), 7.663 (1.03), 7.679 (0.52), 8.784 (1.83), 8.801 (1.82), 9.160 (1.26), 9.178 (1.22).<br>LC-MS (Method 1): $R_t$ = 0.87 min; MS (ESIpos): m/z = 453 $[M + H]^+$<br>Intermediate 142<br>65.2 mg (95% purity, 62% yield) |
| 125 | 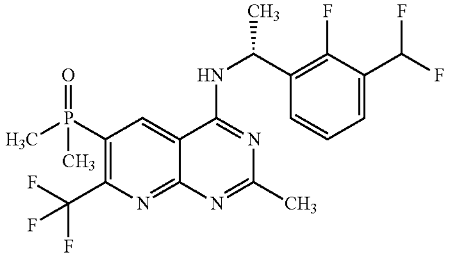 [SMILES: Cc1nc(N[C@H](C)c2cccc(C(F)F)c2F)c2cc(P(C)(C)=O)c(C(F)(F)F)nc2n1]<br>N-{(1R)-1-[3-(difluoromethyl)-2-fluorophenyl]ethyl}-6-(dimethylphosphoryl)-2-methyl-7-(trifluoromethyl)pyrido[2,3-d]pyrimidin-4-amine<br>$^1$H-NMR (600 MHz, DMSO-d6) δ [ppm]: 1.637 (1.64), 1.649 (1.66), 1.870 (1.75), 1.892 (1.75), 2.441 (4.75), 3.317 (5.26), 7.237 (0.65), 7.304 (0.62), 8.310 (16.00), 9.467 (0.53), 9.488 (0.52).<br>LC-MS (Method 2): $R_t$ = 1.10 min; MS (ESIpos): m/z = 477 $[M + H]^+$<br>Intermediate 180<br>5.00 mg (95% purity, 7% yield) |
| 126 | 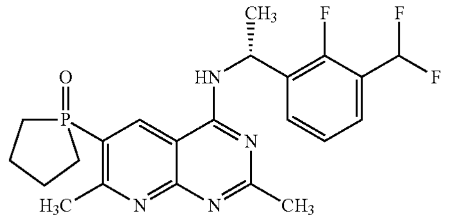 [SMILES: Cc1nc(N[C@H](C)c2cccc(C(F)F)c2F)c2cc(P3(=O)CCCC3)c(C)nc2n1]<br>1-[4-{{(1R)-1-[3-(difluoromethyl)-2-fluorophenyl]ethyl}amino)-2,7-dimethylpyrido[2,3-d]pyrimidin-6-yl]-1lambda$^5$-phospholan-1-one<br>$^1$H-NMR (400 MHz, DMSO-d6) δ [ppm]: 1.232 (0.81), 1.625 (4.85), 1.643 (4.83), 1.801 (0.51), 1.825 (0.57), 1.841 (0.53), 1.850 (0.56), 1.949 (0.49), 1.969 (0.69), 1.986 (0.79), 2.012 (1.03), 2.049 (0.54), 2.064 (0.49), 2.332 (1.20), 2.336 (0.52), 2.378 (16.00), 2.421 (0.40), 2.518 (6.56), 2.522 (4.55), 2.673 (1.24), 2.678 (0.54), 2.828 (12.47), 5.759 (1.50), 5.790 (0.72), 5.808 (1.11), 5.825 (0.70), 7.107 (1.08), 7.243 (2.35), 7.280 (0.80), 7.299 (1.74), 7.318 (0.98), 7.378 (0.95), 7.497 (0.58), 7.514 |

TABLE 8-continued

| Ex. | Examples<br>Structure; IUPAC-Name; Analytical Data; Starting Materials; Yield |
|---|---|
| | (0.97), 7.532 (0.48), 7.663 (0.53), 7.682 (0.97), 7.700 (0.48), 8.908 (2.00), 8.940 (2.52), 8.961 (1.16).<br>LC-MS (Method 2): $R_t$ = 1.01 min; MS (ESIpos): m/z = 449 [M + H]$^+$<br>Intermediate 19<br>37.0 mg (95% purity, 33% yield) |
| 127 | 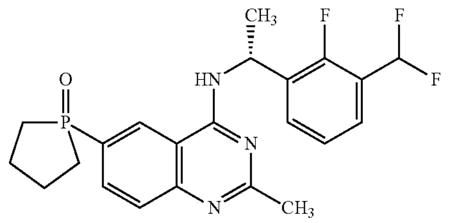 [SMILES: Cc1nc(N[C@H](C)c2cccc(C(F)F)c2F)c2cc(P3(=O)CCCC3)ccc2n1]<br>1-[4-{{(1R)-1-[3-(difluoromethyl)-2-fluorophenyl]ethyl}amino)-2-methylquinazolin-6-yl]-1lambda$^5$-phospholan-1-one<br>$^1$H-NMR (400 MHz, DMSO-d6) δ [ppm]: 1.616 (4.97), 1.633 (4.94), 1.857 (0.40), 1.874 (0.54), 1.895 (0.73), 1.905 (0.75), 1.913 (0.69), 1.928 (1.03), 1.936 (0.95), 1.949 (0.72), 1.954 (0.71), 1.976 (0.65), 1.993 (0.52), 2.017 (0.60), 2.034 (0.69), 2.057 (0.75), 2.073 (0.96), 2.088 (1.19), 2.110 (0.84), 2.129 (0.60), 2.332 (0.65), 2.367 (16.00), 2.518 (2.63), 2.523 (1.92), 5.759 (6.49), 5.812 (0.76), 5.829 (1.16), 5.847 (0.73), 7.105 (1.17), 7.241 (2.40), 7.271 (0.84), 7.290 (1.82), 7.309 (1.04), 7.376 (1.01), 7.480 (0.63), 7.497 (1.02), 7.514 (0.48), 7.666 (1.31), 7.672 (1.33), 7.687 (2.07), 7.693 (1.70), 7.706 (1.02), 7.723 (0.50), 7.901 (0.92), 7.905 (0.89), 7.922 (0.91), 7.925 (1.46), 7.929 (0.95), 7.946 (0.74), 7.950 (0.74), 8.813 (1.22), 8.817 (1.20), 8.844 (1.21), 8.848 (1.17), 8.915 (1.23), 8.933 (1.17).<br>LC-MS (Method 2): $R_t$ = 1.09 min; MS (ESIpos): m/z = 434 [M + H]$^+$<br>Intermediate 181<br>37.0 mg (95% purity, 44% yield) |
| 128 | 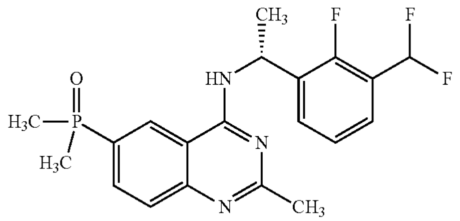<br>N-{(1R)-1-[3-(difluoromethyl)-2-fluorophenyl]ethyl}-6-(dimethylphosphoryl)-2-methylquinazolin-4-amine<br>$^1$H-NMR (400 MHz, DMSO-d6) δ [ppm]: 0.923 (0.41), 1.614 (4.93), 1.632 (4.90), 1.724 (15.61), 1.758 (15.54), 2.332 (1.08), 2.336 (0.50), 2.366 (16.00), 2.518 (4.91), 2.522 (3.39), 2.673 (1.09), 2.678 (0.48), 5.808 (0.73), 5.825 (1.14), 5.843 (0.72), 7.105 (1.15), 7.241 (2.36), 7.275 (0.81), 7.294 (1.77), 7.314 (1.02), 7.377 (1.00), 7.483 (0.59), 7.500 (1.01), 7.517 (0.49), 7.651 (1.32), 7.657 (1.32), 7.672 (1.50), 7.679 (1.50), 7.687 (0.58), 7.705 (1.00), 7.723 (0.50), 7.988 (0.90), 7.992 (0.92), 8.009 (0.86), 8.013 (1.66), 8.017 (0.96), 8.034 (0.74), 8.038 (0.78), 8.806 (1.20), 8.808 (1.18), 8.837 (2.27), 8.856 (1.15).<br>LC-MS (Method 2): $R_t$ = 1.02 min; MS (ESIpos): m/z = 408 [M + H]$^+$<br>Intermediate 181<br>36.0 mg (90% purity, 44% yield) |
| 129 | 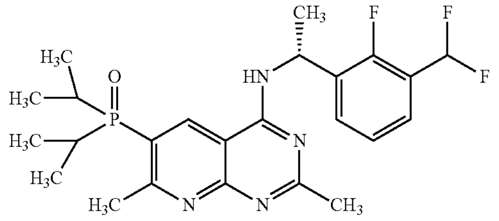 [SMILES: Cc1nc(N[C@H](C)c2cccc(C(F)F)c2F)c2cc(P(=O)(C(C)C)C(C)C)c(C)nc2n1]<br>N-{(1R)-1-[3-(difluoromethyl)-2-fluorophenyl]ethyl}-6-[di(propan-2-yl)phosphoryl]-2,7-dimethylpyrido[2,3-d]pyrimidin-4-amine<br>$^1$H-NMR (400 MHz, DMSO-d6) δ [ppm]: 0.887 (2.33), 0.892 (2.40), 0.905 (2.45), 0.910 (2.43), 0.927 (2.38), 0.932 (2.40), 0.945 (2.40), 0.950 (2.28), 1.168 (2.06), 1.180 (2.47), 1.185 (2.49), 1.198 (2.32), 1.205 (2.28), 1.218 (2.54), 1.222 (2.60), 1.235 (2.41), 1.625 (3.64), 1.643 (3.56), 2.332 (2.97), 2.336 (1.35), 2.356 (1.22), 2.370 |

TABLE 8-continued

| Ex. | Examples<br>Structure; IUPAC-Name; Analytical Data; Starting Materials; Yield |
|---|---|
| | (12.34), 2.518 (16.00), 2.522 (11.33), 2.569 (0.81), 2.586 (1.41), 2.673 (3.03), 2.678 (1.31), 2.829 (7.84), 5.759 (0.99), 5.774 (0.62), 5.792 (0.91), 5.810 (0.57), 7.098 (0.90), 7.234 (1.86), 7.283 (0.70), 7.302 (1.38), 7.321 (0.79), 7.370 (0.81), 7.493 (0.46), 7.508 (0.77), 7.628 (0.42), 7.646 (0.77), 7.665 (0.42), 8.835 (0.84), 8.863 (0.85), 8.996 (0.69), 9.014 (0.68).<br>LC-MS (Method 2): $R_t$ = 1.11 min; MS (ESIneg): m/z = 477 $[M - H]^-$<br>Intermediate 19<br>9.00 mg (95% purity, 8% yield) |
| 130 | 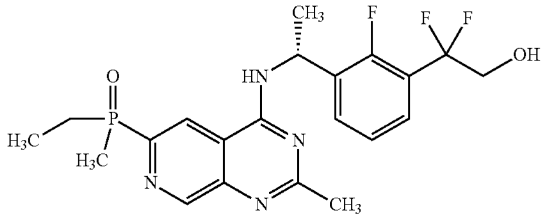 [SMILES: CCP(C)(=O)c1cc2c(N[C@H](C)c3cccc(C(F)(F)CO)c3F)nc(C)nc2cn1]<br>2-{3-[(1R)-1-{{6-[ethyl(methyl)phosphoryl]-2-methylpyrido[3,4-d]pyrimidin-4-yl}amino)ethyl]-2-fluorophenyl}-2,2-difluoroethan-1-ol (mixture of diastereomers)<br>$^1$H-NMR (400 MHz, DMSO-d6) δ [ppm]: 0.934 (0.91), 0.949 (1.18), 0.953 (2.33), 0.969 (2.44), 0.972 (1.25), 0.977 (1.04), 0.988 (1.19), 0.993 (1.28), 0.997 (2.31), 1.012 (2.50), 1.016 (1.17), 1.031 (1.05), 1.603 (3.92), 1.620 (3.94), 1.655 (3.87), 1.663 (3.72), 1.688 (3.92), 1.696 (3.72), 1.962 (0.44), 1.972 (0.93), 1.978 (0.64), 1.982 (0.66), 1.991 (1.20), 1.997 (0.68), 2.002 (0.77), 2.010 (0.96), 2.021 (0.58), 2.028 (0.57), 2.431 (16.00), 2.518 (1.97), 2.523 (1.49), 3.377 (0.40), 3.891 (0.54), 3.907 (0.60), 3.927 (1.07), 3.943 (1.12), 3.963 (0.51), 3.979 (0.51), 5.708 (1.12), 5.724 (2.71), 5.741 (1.08), 5.774 (0.46), 5.780 (0.47), 5.792 (0.72), 5.799 (0.68), 5.810 (0.48), 5.816 (0.42), 7.244 (0.47), 7.249 (0.50), 7.263 (1.05), 7.268 (1.09), 7.282 (0.62), 7.287 (0.63), 7.406 (0.64), 7.424 (1.06), 7.441 (0.50), 7.658 (0.42), 7.675 (0.73), 8.942 (0.98), 8.952 (1.02), 8.956 (1.06), 8.958 (1.01), 8.965 (0.89), 9.087 (4.31), 9.285 (0.69), 9.303 (1.20), 9.320 (0.62).<br>LC-MS (Method 1): $R_t$ = 0.80 min; MS (ESIpos): m/z = 454 $[M + H]^+$<br>Intermediate 141<br>133 mg (95% purity, 59% yield) |
| | The diastereomers of example 130 were separated according to the following method.<br>Prep.-Method:<br>Instrument: PrepCon Labomatic HPLC-2; Column: YMC Cellulose SB 5 μ, 250 x 30; eluent A: methyl tert-butyl ether + 0.1 vol % diethylamine; eluent B: acetonitrile; isocratic: 80% A + 20% B; flow: 30 ml/min; temperature: 25° C.; UV: 280 nm;<br>Anal.-Method:<br>Instrument: Thermo Fisher UltiMate 3000; YMC Cellulose SB 3 μ, 100 x 4.6; eluent A: methyl tert-butyl ether + 0.1 vol % diethylamine; eluent B: acetonitrile; isocratic: 80% A + 20% B; flow: 1.4 ml/min; temperature: 25° C.; UV: 280 nm; |
| 131 | 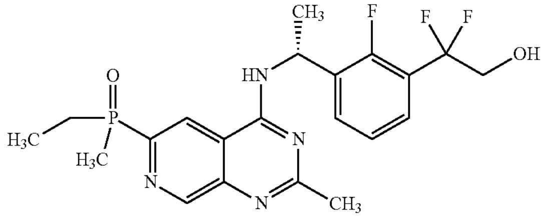 [SMILES: CCP(C)(=O)c1cc2c(N[C@H](C)c3cccc(C(F)(F)CO)c3F)nc(C)nc2cn1]<br>2-{3-[(1R)-1-{{6-[ethyl(methyl)phosphoryl]-2-methylpyrido[3,4-d]pyrimidin-4-yl}amino)ethyl]-2-fluorophenyl}-2,2-difluoroethan-1-ol (diastereomer 1)<br>$^1$H-NMR (400 MHz, DMSO-d6) δ [ppm]: 0.935 (1.78), 0.954 (4.33), 0.973 (2.10), 0.978 (1.99), 0.997 (4.14), 1.016 (1.90), 1.231 (0.58), 1.604 (4.79), 1.622 (4.77), 1.663 (6.99), 1.696 (7.12), 1.954 (0.40), 1.963 (0.76), 1.973 (1.16), 1.981 (0.86), 1.991 (1.57), 2.003 (0.94), 2.010 (1.03), 2.023 (0.80), 2.331 (0.51), 2.432 (16.00), 2.518 (2.67), 2.523 (1.82), 2.673 (0.51), 3.892 (0.56), 3.908 (0.61), 3.927 (1.10), 3.944 (1.17), 3.963 (0.53), 3.980 (0.52), 5.704 (1.16), 5.720 (2.77), 5.736 (1.11), 5.782 (0.75), 5.801 (1.16), 5.819 (0.73), 7.244 (0.88), 7.263 (1.91), 7.282 (1.12), 7.407 (0.69), 7.424 (1.08), 7.440 (0.53), 7.655 (0.60), 7.672 (1.06), 7.690 (0.53), 8.953 (1.75), 8.955 (1.75), 8.969 (1.77), 9.089 (4.30), 9.305 (1.28), 9.323 (1.22).<br>LC-MS (Method 1): $R_t$ = 0.81 min; MS (ESIpos): m/z = 454 $[M + H]^+$<br>Example 130<br>28.0 mg (95% purity, 12% yield)<br>Rt (analytical Method) = 3.28 min (de = >99%) |

TABLE 8-continued

| Examples | |
|---|---|
| Ex. | Structure; IUPAC-Name; Analytical Data; Starting Materials; Yield |
| 132 | 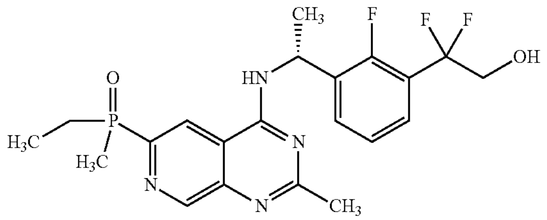 [SMILES: CCP(C)(=O)c1cc2c(N[C@H](C)c3cccc(C(F)(F)CO)c3F)nc(C)nc2cn1]<br>2-{3-[(1R)-1-{{6-[ethyl(methyl)phosphoryl]-2-methylpyrido[3,4-d]pyrimidin-4-yl}amino)ethyl]-2-fluorophenyl}-2,2-difluoroethan-1-ol (diastereomer 2)<br>$^1$H-NMR (400 MHz, DMSO-d6) δ [ppm]: 0.950 (1.81), 0.969 (4.47), 0.988 (2.08), 0.993 (2.12), 1.013 (4.32), 1.032 (1.93), 1.137 (0.45), 1.232 (0.51), 1.602 (4.68), 1.619 (4.68), 1.655 (6.94), 1.688 (6.79), 1.972 (0.81), 1.978 (0.93), 1.990 (1.03), 1.998 (1.05), 2.001 (1.00), 2.009 (1.06), 2.020 (0.81), 2.029 (0.78), 2.336 (0.44), 2.432 (16.00), 2.518 (5.33), 2.523 (3.70), 2.678 (0.44), 3.892 (0.54), 3.908 (0.58), 3.929 (1.04), 3.944 (1.10), 3.963 (0.51), 3.980 (0.50), 5.703 (1.16), 5.718 (2.72), 5.735 (1.12), 5.776 (0.74), 5.794 (1.15), 5.812 (0.72), 7.250 (0.84), 7.269 (1.88), 7.289 (1.09), 7.409 (0.68), 7.427 (1.05), 7.442 (0.52), 7.664 (0.58), 7.681 (1.02), 7.697 (0.52), 8.943 (1.70), 8.945 (1.70), 8.959 (1.70), 9.089 (4.17), 9.288 (1.21), 9.306 (1.16).<br>LC-MS (Method 1): $R_t$ = 0.80 min; MS (ESIpos): m/z = 454 [M + H]$^+$<br>Example 130<br>33.0 mg (95% purity, 15% yield)<br>Rt (analytical Method) = 4.07 min (de = 97%) |
| 133 | 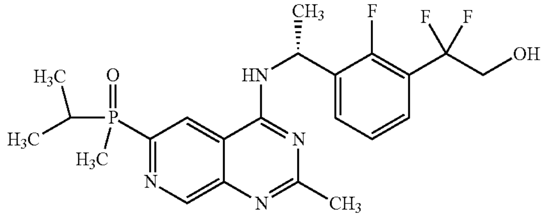 [SMILES: Cc1nc(N[C@H](C)c2cccc(C(F)(F)CO)c2F)c2cc(P(C)(=O)C(C)C)ncc2n1]<br>2,2-difluoro-2-{2-fluoro-3-[(1R)-1-({2-methyl-6-[methyl(propan-2-yl)phosphoryl]pyrido[3,4-d]pyrimidin-4-yl}amino)ethyl]phenyl}ethan-1-ol (mixture of diastereomers)<br>LC-MS (Method 1): $R_t$ = 0.85 min; MS (ESIpos): m/z = 467.6 [M + H]$^+$<br>Intermediate 141<br>68.0 mg (31% yield)<br>The diastereomers of example 133 were separated according to the following method.<br>Anal.-Method:<br>Instrument: Waters Acquity UPC2 QDA; Column: Chiral Art Amylose-SA 3 μ 100 × 4.6 mm; eluent A: CO2; eluent B: 2-propanol + 0.4 vol % diethylamin; isocratic: 10% B; gradient: no; flow: 4 ml/min; temperature: 40.0° C.; BPR: 100 bar; UV: 215 nm<br>Prep.-Method:<br>Instrument: Sepiatec: Prep SFC100; Column: Chiral Art Amylose-SA 5 μ 250 × 30 mm; eluent A: CO2; eluent B: 2-propanol + 0.4 vol % diethylamin; isocratic: 10% B; gradient: no; flow: 100 ml/min; temperature: 40° C.; BPR: 150 bar; UV: 215 nm |
| 134 | 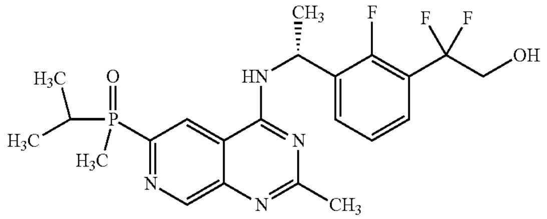 [SMILES: Cc1nc(N[C@H](C)c2cccc(C(F)(F)CO)c2F)c2cc(P(C)(=O)C(C)C)ncc2n1]<br>2,2-difluoro-2-{2-fluoro-3-[(1R)-1-({2-methyl-6-[methyl(propan-2-yl)phosphoryl]pyrido[3,4-d]pyrimidin-4-yl}amino)ethyl]phenyl}ethan-1-ol (diastereomer 1)<br>$^1$H-NMR (400 MHz, DMSO-d6) δ [ppm]: 0.893 (3.44), 0.910 (3.53), 0.933 (3.41), 0.951 (3.43), 1.144 (3.47), 1.161 (3.59), 1.183 (3.60), 1.201 (3.51), 1.605 (5.17), 1.622 (5.18), 1.659 (7.63), 1.691 (7.64), 2.075 (0.44), 2.181 (0.54), 2.198 (0.76), 2.204 (0.64), 2.217 (0.61), 2.222 (0.78), 2.240 (0.50), 2.337 (0.47), 2.430 (16.00), 2.518 (5.69), 2.523 (4.04), 2.673 (1.08), 2.678 (0.47), 3.891 (0.62), 3.906 (0.68), 3.927 (1.23), 3.943 (1.31), 3.962 (0.60), 3.979 (0.60), 5.701 (1.24), 5.717 (3.03), 5.734 |

TABLE 8-continued

| Examples | |
|---|---|
| Ex. | Structure; IUPAC-Name; Analytical Data; Starting Materials; Yield |
| | (1.22), 5.779 (0.84), 5.797 (1.29), 5.815 (0.82), 7.243 (0.90), 7.262 (2.06), 7.282 (1.24), 7.405 (0.77), 7.423 (1.24), 7.439 (0.60), 7.652 (0.64), 7.669 (1.17), 7.686 (0.63), 8.945 (1.92), 8.960 (1.86), 9.087 (4.45), 9.323 (1.38), 9.340 (1.32).<br>LC-MS (Method 1): $R_t$ = 0.85 min; MS (ESIpos): m/z = 468 $[M + H]^+$<br>Example 133<br>55.6 mg (95% purity, 24% yield)<br>Rt (analytical Method) = 2.37 min (de = >99%) |
| 135 | 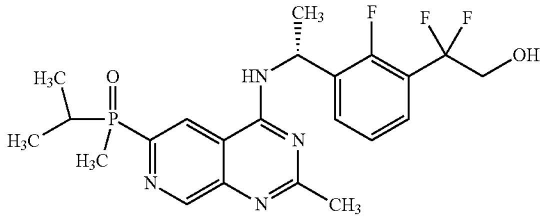<br>2,2-difluoro-2-{2-fluoro-3-[(1R)-1-({2-methyl-6-[methyl(propan-2-yl)phosphoryl]pyrido[3,4-d]pyrimidin-4-yl}amino)ethyl]phenyl}ethan-1-ol (diastereomer 2)<br>$^1$H-NMR (400 MHz, DMSO-d6) δ [ppm]: 0.905 (3.95), 0.922 (3.96), 0.945 (4.03), 0.963 (3.96), 1.038 (0.44), 1.058 (0.41), 1.075 (0.43), 1.144 (3.95), 1.162 (4.36), 1.184 (4.25), 1.202 (4.12), 1.603 (5.81), 1.621 (5.82), 1.650 (8.59), 1.683 (8.60), 2.197 (0.59), 2.215 (0.86), 2.221 (0.72), 2.233 (0.67), 2.238 (0.86), 2.257 (0.56), 2.336 (0.58), 2.435 (16.00), 2.518 (6.98), 2.523 (4.90), 2.679 (0.55), 3.893 (0.59), 3.905 (0.63), 3.929 (1.12), 3.943 (1.16), 3.964 (0.58), 3.978 (0.56), 5.701 (0.61), 5.717 (1.19), 5.733 (0.61), 5.776 (0.90), 5.794 (1.39), 5.812 (0.90), 7.254 (1.02), 7.273 (2.31), 7.292 (1.36), 7.409 (0.85), 7.426 (1.37), 7.443 (0.66), 7.665 (0.75), 7.681 (1.30), 7.698 (0.68), 8.935 (1.94), 8.950 (1.99), 9.089 (5.00), 9.333 (0.52).<br>LC-MS (Method 1): $R_t$ = 0.83 min; MS (ESIpos): m/z = 468 $[M + H]^+$<br>Example 133<br>33.5 mg (95% purity, 14% yield)<br>Rt (analytical Method) = 2.95 min (de = 97%) |
| 136 | 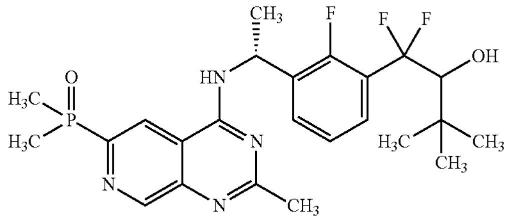 [SMILES: Cc1nc(N[C@H](C)c2cccc(C(F)(F)C(O)C(C)(C)C)c2F)c2cc(P(C)(C)=O)ncc2n1]<br>(2R*)-1-{3-[(1R)-1-{[6-(dimethylphosphoryl)-2-methylpyrido[3,4-d]pyrimidin-4-yl]amino}ethyl]-2-fluorophenyl}-1,1-difluoro-3,3-dimethylbutan-2-ol (diastereomer 1)<br>$^1$H-NMR (400 MHz, DMSO-d6) δ [ppm]: 0.929 (16.00), 1.588 (3.55), 1.605 (3.54), 1.692 (7.77), 1.725 (7.69), 2.448 (11.77), 2.518 (0.87), 2.523 (0.63), 5.541 (1.39), 5.560 (1.37), 5.803 (0.56), 5.821 (0.85), 5.839 (0.54), 7.222 (0.68), 7.242 (1.49), 7.261 (0.87), 7.380 (0.51), 7.397 (0.82), 7.628 (0.45), 7.645 (0.81), 7.661 (0.40), 8.969 (1.30), 8.984 (1.30), 9.092 (3.30), 9.261 (0.96), 9.280 (0.92).<br>Intermediate 60<br>65.0 mg (95% purity, 62% yield) |
| 137 | 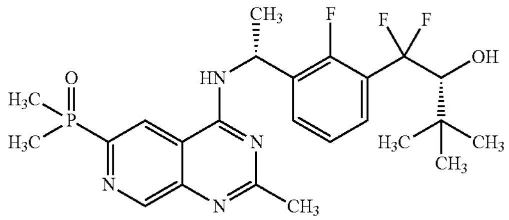 [SMILES: Cc1nc(N[C@H](C)c2cccc(C(F)(F)[C@H](O)C(C)(C)C)c2F)c2cc(P(C)(C)=O)ncc2n1]<br>(2R*)-1-{3-[(1R)-1-{[6-(dimethylphosphoryl)-2-methylpyrido[3,4-d]pyrimidin-4-yl]amino}ethyl]-2-fluorophenyl}-1,1-difluoro-3,3-dimethylbutan-2-ol (diastereomer 2)<br>$^1$H-NMR (400 MHz, DMSO-d6) δ [ppm]: 0.934 (16.00), 1.600 (3.60), 1.618 (3.59), 1.691 (7.97), 1.724 (7.93), 2.421 (12.38), 2.518 (1.69), 2.523 (1.28), 5.573 (1.86), |

TABLE 8-continued

| Ex. | Examples<br>Structure; IUPAC-Name; Analytical Data; Starting Materials; Yield |
|---|---|
| | 5.592 (1.82), 5.774 (0.57), 5.792 (0.88), 5.810 (0.56), 7.207 (0.70), 7.226 (1.52), 7.245 (0.90), 7.376 (0.50), 7.393 (0.83), 7.602 (0.45), 7.620 (0.80), 7.636 (0.41), 8.961 (1.36), 8.976 (1.36), 8.978 (1.34), 9.088 (3.30), 9.267 (0.98), 9.286 (0.94).<br>Intermediate 61<br>70.0 mg (95% purity, 67% yield) |

The examples shown in Table 9 were prepared according to General Procedure 3 followed by direct conversion of the crude intermediates by General Procedure 7 from the respective N-Boc protected derivatives.

TABLE 9

| Ex. | Examples<br>Structure; IUPAC-Name; Analytical Data; Starting Materials; Yield |
|---|---|
| 138 | 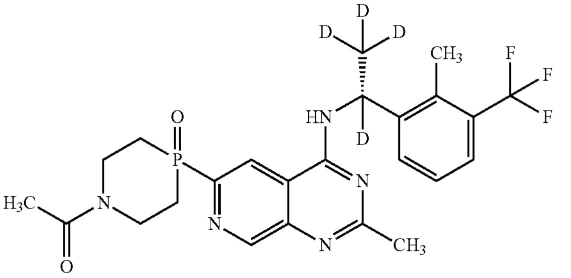 [SMILES: [2H]C([2H])([2H])[C@]([2H])(Nc1nc(C)nc2cnc(P3(=O)CCN(C(C)=O)CC3)cc12)c1cccc(C(F)(F)F)c1C]<br>1-acetyl-4-(2-methyl-4-{[(1S)-1-[2-methyl-3-(trifluoromethyl)phenyl]($^2H_4$)ethyl]amino}pyrido[3,4-d]pyrimidin-6-yl)-1,4lambda$^5$-azaphosphinan-4-one<br>$^1$H-NMR (400 MHz, DMSO-d6) δ [ppm]: 0.929 (0.41), 0.946 (0.42), 1.541 (0.72), 2.055 (0.41), 2.116 (16.00), 2.254 (0.44), 2.275 (0.44), 2.332 (0.58), 2.382 (0.42), 2.422 (14.00), 2.518 (3.35), 2.523 (2.25), 2.622 (6.56), 2.673 (0.61), 3.320 (0.82), 3.848 (0.41), 3.860 (0.60), 3.873 (0.58), 3.886 (0.49), 3.918 (0.43), 7.348 (0.77), 7.368 (1.69), 7.388 (0.97), 7.543 (1.74), 7.561 (1.39), 7.785 (1.57), 7.805 (1.41), 9.006 (1.80), 9.023 (1.78), 9.094 (4.93), 9.096 (4.61), 9.371 (1.95).<br>LC-MS (Method 2): $R_t$ = 1.10 min; MS (ESIpos): m/z = 510 [M + H]$^+$<br>Intermediate 184<br>60.6 mg (95% purity, 64% yield) |
| 139 | 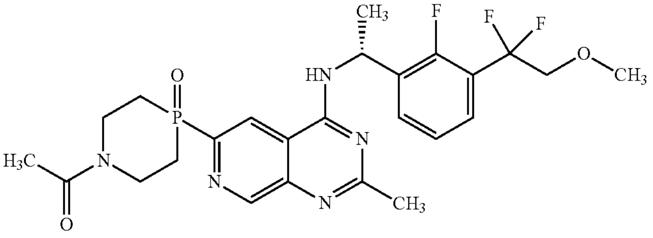 [SMILES: COCC(F)(F)c1cccc([C@@H](C)Nc2nc(C)nc3cnc(P4(=O)CCN(C(C)=O)CC4)cc23)c1F]<br>1-acetyl-4-[4-({(1R)-1-[3-(1,1-difluoro-2-methoxyethyl)-2-fluorophenyl]ethyl}amino)-2-methylpyrido[3,4-d]pyrimidin-6-yl]-1,4lambda$^5$-azaphosphinan-4-one<br>$^1$H-NMR (400 MHz, DMSO-d6) δ [ppm]: 1.609 (0.48), 1.627 (0.48), 2.118 (1.77), 2.425 (1.27), 3.332 (2.08), 3.341 (16.00), 9.112 (0.46).<br>LC-MS (Method 2): $R_t$ = 1.01 min; MS (ESIpos): m/z = 536 [M + H]$^+$<br>Intermediate 186<br>68.4 mg (95% purity, 55% yield) |
| 140 | 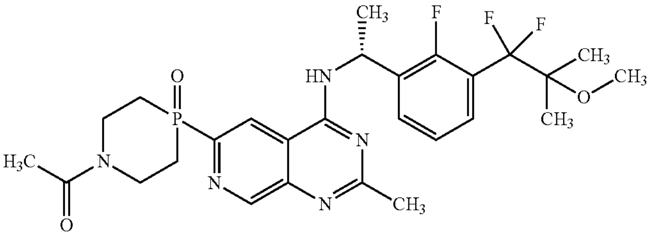 [SMILES: COC(C)(C)C(F)(F)c1cccc([C@@H](C)Nc2nc(C)nc3cnc(P4(=O)CCN(C(C)=O)CC4)cc23)c1F] |

TABLE 9-continued

| Ex. | Structure; IUPAC-Name; Analytical Data; Starting Materials; Yield |
|---|---|
| | 1-acetyl-4-[4-({(1R)-1-[3-(1,1-difluoro-2-methoxy-2-methylpropyl)-2-fluorophenyl]ethyl}amino)-2-methylpyrido[3,4-d]pyrimidin-6-yl]-1,4lambda$^5$-azaphosphinan-4-one<br>$^1$H-NMR (400 MHz, DMSO-d6) δ [ppm]: 1.251 (6.79), 1.258 (7.05), 1.596 (4.28), 1.614 (4.27), 2.118 (16.00), 2.318 (0.67), 2.387 (0.40), 2.413 (12.45), 2.518 (7.52), 2.523 (5.16), 3.175 (13.87), 3.865 (0.66), 3.899 (0.46), 5.757 (0.52), 5.775 (0.78), 5.791 (0.51), 7.208 (0.66), 7.227 (1.60), 7.247 (1.08), 7.296 (0.73), 7.313 (1.02), 7.329 (0.47), 7.612 (0.57), 7.629 (0.99), 7.646 (0.51), 9.022 (1.56), 9.039 (1.55), 9.113 (4.13), 9.279 (1.02), 9.297 (0.99).<br>LC-MS (Method 1): $R_t$ = 1.01 min; MS (ESIpos): m/z = 564 [M + H]$^+$<br>Intermediate 191<br>21.6 mg (95% purity, 14% yield) |
| 141 | 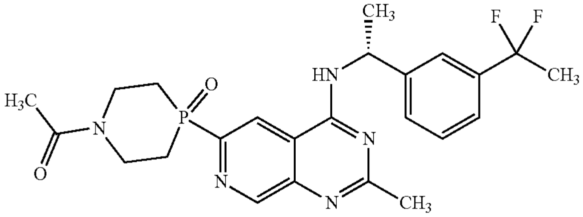<br>1-acetyl-4-[4-({(1R)-1-[3-(1,1-difluoroethyl)phenyl]ethyl}amino)-2-methylpyrido[3,4-d]pyrimidin-6-yl]-1,4lambda$^5$-azaphosphinan-4-one<br>$^1$H-NMR (400 MHz, DMSO-d6) δ [ppm]: 1.615 (4.89), 1.632 (4.93), 1.911 (4.08), 1.958 (7.61), 2.005 (3.52), 2.055 (0.40), 2.082 (0.72), 2.113 (16.00), 2.473 (14.64), 2.518 (0.70), 2.523 (0.50), 3.842 (0.50), 3.853 (0.64), 3.866 (0.49), 3.881 (0.45), 3.891 (0.46), 5.635 (0.69), 5.653 (1.03), 5.672 (0.68), 7.436 (3.94), 7.452 (1.80), 7.471 (0.48), 7.578 (1.10), 7.591 (0.71), 7.595 (1.02), 7.691 (2.04), 8.969 (1.59), 8.985 (1.58), 9.101 (4.33), 9.217 (1.09), 9.236 (1.05).<br>LC-MS (): $R_t$ = min; MS (): m/z =<br>Intermediate 190<br>54.2 mg (95% purity, 47% yield) |
| 142 | 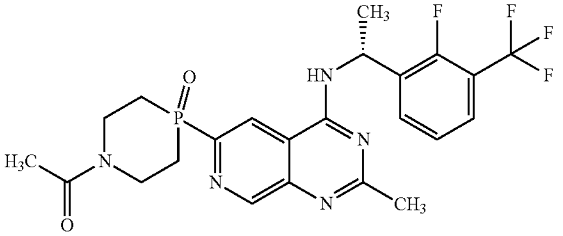 [SMILES: CC(=O)N1CCP(=O)(c2cc3c(N[C@H](C)c4cccc(C(F)(F)F)c4F)nc(C)nc3cn2)CC1]<br>1-acetyl-4-[4-{{(1R)-1-[2-fluoro-3-(trifluoromethyl)phenyl]ethyl}amino)-2-methylpyrido[3,4-d]pyrimidin-6-yl]-1,4lambda$^5$-azaphosphinan-4-one<br>$^1$H-NMR (400 MHz, DMSO-d6) δ [ppm]: 1.635 (4.58), 1.653 (4.55), 2.057 (0.42), 2.118 (16.00), 2.256 (0.44), 2.277 (0.43), 2.318 (0.44), 2.323 (0.78), 2.327 (1.01), 2.331 (0.72), 2.415 (11.01), 2.518 (3.31), 2.523 (2.16), 2.665 (0.69), 2.669 (0.96), 2.673 (0.67), 3.851 (0.43), 3.861 (0.59), 3.873 (0.61), 3.887 (0.52), 3.917 (0.42), 5.744 (0.54), 5.762 (0.81), 5.779 (0.52), 7.351 (0.73), 7.370 (1.55), 7.390 (0.86), 7.643 (0.64), 7.661 (1.11), 7.679 (0.55), 7.819 (0.60), 7.837 (1.07), 7.855 (0.54), 9.012 (1.62), 9.028 (1.60), 9.118 (3.89), 9.327 (1.12), 9.344 (1.09).<br>LC-MS (Method 2): $R_t$ = 1.09 min; MS (ESIpos): m/z = 510 [M + H]$^+$<br>Intermediate 189<br>53.0 mg (95% purity, 56% yield) |
| 143 | 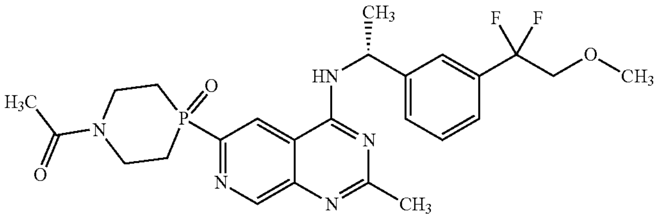 [SMILES: COCC(F)(F)c1cccc([C@@H](C)Nc2nc(C)nc3cnc(P4(=O)CCN(C(C)=O)CC4)cc23)c1]<br>1-acetyl-4-[4-({(1R)-1-[3-(1,1-difluoro-2-methoxyethyl)phenyl]ethyl}amino)-2-methylpyrido[3,4-d]pyrimidin-6-yl]-1,4lambda$^5$-azaphosphinan-4-one<br>$^1$H-NMR (400 MHz, DMSO-d6) δ [ppm]: 1.615 (5.17), 1.633 (5.15), 1.902 (0.42), 2.052 |

TABLE 9-continued

| Ex. | Examples<br>Structure; IUPAC-Name; Analytical Data; Starting Materials; Yield |
|---|---|
| | (0.45), 2.114 (16.00), 2.253 (0.44), 2.265 (0.45), 2.276 (0.44), 2.378 (0.44), 2.389 (0.43), 2.402 (0.42), 2.472 (15.05), 2.518 (2.87), 2.523 (1.93), 3.287 (15.25), 3.697 (0.42), 3.736 (0.43), 3.821 (0.40), 3.830 (0.44), 3.853 (2.59), 3.887 (4.23), 3.922 (1.87), 4.028 (0.41), 5.634 (0.76), 5.652 (1.14), 5.670 (0.75), 7.399 (0.89), 7.419 (1.89), 7.442 (1.38), 7.461 (2.00), 7.481 (0.82), 7.599 (1.46), 7.618 (1.16), 7.667 (2.29), 8.973 (1.71), 8.990 (1.71), 9.107 (4.63), 9.225 (1.23), 9.245 (1.19).<br>LC-MS (Method 2): $R_t$ = 0.99 min; MS (ESIpos): m/z = 518 $[M + H]^+$<br>Intermediate 192<br>73.9 mg (99% purity, 64% yield) |
| 144 | 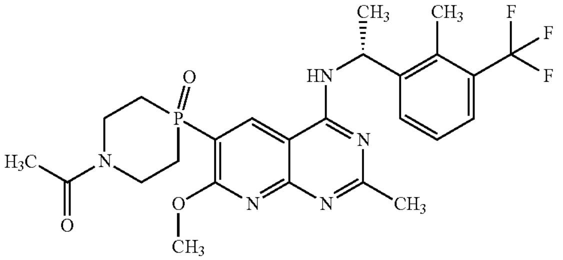 [SMILES: COc1nc2nc(C)nc(N[C@H](C)c3cccc(C(F)(F)F)c3C)c2cc1P1(=O)CCN(C(C)=O)CC1]<br>1-acetyl-4-[7-methoxy-2-methyl-4-({(1R)-1-[2-methyl-3-(trifluoromethyl)phenyl]ethyl}amino)pyrido[2,3-d]pyrimidin-6-yl]-1,4lambda$^5$-azaphosphinan-4-one<br>$^1$H-NMR (400 MHz, DMSO-d6) δ [ppm]: 1.542 (4.32), 1.560 (4.36), 1.978 (0.44), 2.124 (16.00), 2.318 (0.73), 2.323 (1.38), 2.327 (1.94), 2.332 (1.56), 2.337 (0.97), 2.356 (7.41), 2.432 (0.44), 2.455 (0.47), 2.518 (6.12), 2.523 (4.35), 2.611 (5.59), 2.660 (0.47), 2.665 (1.11), 2.669 (1.57), 2.673 (1.06), 2.679 (0.46), 3.974 (15.38), 5.697 (0.41), 5.706 (0.57), 5.715 (0.56), 7.343 (0.63), 7.362 (1.36), 7.381 (0.80), 7.535 (1.41), 7.554 (1.15), 7.779 (1.23), 7.799 (1.11), 9.128 (0.87), 9.136 (0.91), 9.161 (1.06), 9.169 (1.04).<br>LC-MS (Method 1): $R_t$ = 0.90 min; MS (ESIpos): m/z = 536 $[M + H]^+$<br>Intermediate 199<br>52.0 mg (95% purity, 38% yield) |
| 145 | 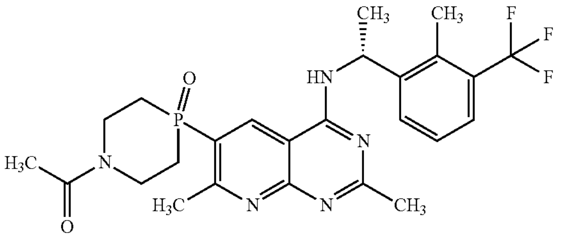 [SMILES: CC(=O)N1CCP(=O)(c2cc3c(N[C@H](C)c4cccc(C(F)(F)F)c4C)nc(C)nc3nc2C)CC1]<br>1-acetyl-4-[2,7-dimethyl-4-({(1R)-1-[2-methyl-3-(trifluoromethyl)phenyl]ethyl}amino)pyrido[2,3-d]pyrimidin-6-yl]-1,4lambda$^5$-azaphosphinan-4-one<br>$^1$H-NMR (400 MHz, DMSO-d6) δ [ppm]: 1.296 (1.94), 1.313 (1.97), 1.572 (2.56), 1.577 (2.70), 1.590 (2.66), 1.595 (2.60), 1.816 (5.50), 2.100 (16.00), 2.164 (0.43), 2.300 (0.41), 2.318 (0.87), 2.323 (1.51), 2.327 (2.07), 2.331 (1.67), 2.336 (1.14), 2.365 (9.16), 2.367 (9.34), 2.404 (2.00), 2.407 (1.95), 2.444 (0.43), 2.518 (5.63), 2.523 (4.06), 2.608 (5.56), 2.660 (0.44), 2.665 (1.01), 2.669 (1.41), 2.673 (0.98), 2.678 (0.43), 2.866 (10.77), 3.391 (0.56), 3.421 (0.53), 3.754 (0.41), 5.713 (0.42), 5.723 (0.61), 5.730 (0.60), 5.740 (0.42), 7.348 (0.62), 7.367 (1.41), 7.388 (0.90), 7.546 (1.49), 7.566 (1.24), 7.607 (0.41), 7.738 (0.72), 7.747 (0.73), 7.758 (0.66), 7.766 (0.64), 8.790 (0.87), 8.796 (0.87), 8.822 (0.88), 8.829 (0.84), 9.010 (0.68), 9.017 (0.73), 9.026 (0.73), 9.034 (0.65).<br>LC-MS (Method 2): $R_t$ = 1.06 min; MS (ESIneg): m/z = 518 $[M - H]^-$<br>Intermediate 200<br>35.9 mg (90% purity, 45% yield) |

TABLE 9-continued

| Examples | |
|---|---|
| Ex. | Structure; IUPAC-Name; Analytical Data; Starting Materials; Yield |
| 146 | 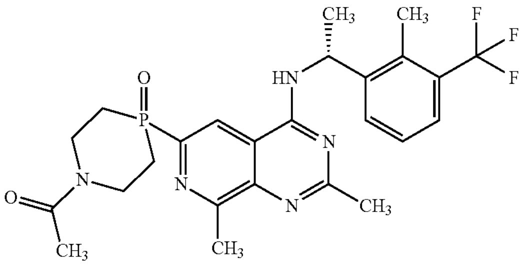 [SMILES: CC(=O)N1CCP(=O)(c2cc3c(N[C@H](C)c4cccc(C(F)(F)F)c4C)nc(C)nc3c(C)n2)CC1]<br>(R)-1-(4-(2,8-dimethyl-4-((1-(2-methyl-3-(trifluoromethyl)phenyl)ethyl)amino)pyrido[3,4-d]pyrimidin-6-yl)-4-oxido-1,4-azaphosphinan-1-yl)ethan-1-one<br>$^1$H NMR (400 MHz, DMSO-d6) δ ppm 1.58 (d, J=6.84 Hz, 3 H) 1.78-2.09 (m, 2 H) 2.12 (s, 3 H) 2.20-2.40 (m, 2 H) 2.43 (s, 3 H) 2.62 (s, 3 H) 2.77 (s, 3 H) 3.62-4.11 (m, 4 H) 5.58-5.80 (m, 1 H) 7.29-7.44 (m, 1 H) 7.51-7.61 (m, 1 H) 7.71-7.83 (m, 1 H) 8.77-8.88 (m, 1 H) 9.18-9.31 (m, 1 H).<br>Intermediate 201<br>74.3 mg (95% purity, 62% yield) |
| 147 | 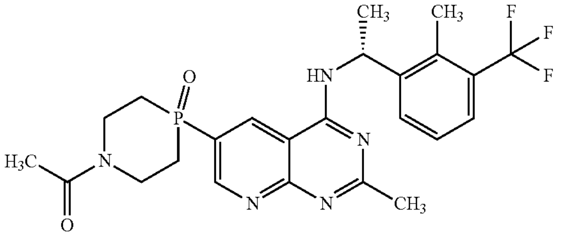 [SMILES: CC(=O)N1CCP(=O)(c2cnc3nc(C)nc(N[C@H](C)c4cccc(C(F)(F)F)c4C)c3c2)CC1]<br>1-acetyl-4-[2-methyl-4-({(1R)-1-[2-methyl-3-(trifluoromethyl)phenyl]ethyl}amino)pyrido[2,3-d]pyrimidin-6-yl]-1,4lambda$^5$-azaphosphinan-4-one<br>$^1$H-NMR (400 MHz, DMSO-d6) δ [ppm]: 1.574 (4.94), 1.591 (4.90), 2.000 (0.44), 2.117 (16.00), 2.318 (0.74), 2.323 (1.11), 2.327 (1.44), 2.331 (1.07), 2.337 (0.57), 2.403 (15.42), 2.518 (4.85), 2.523 (3.44), 2.620 (6.24), 2.660 (0.41), 2.665 (0.88), 2.669 (1.21), 2.673 (0.83), 3.471 (0.51), 3.500 (0.51), 3.751 (0.47), 3.782 (0.52), 5.714 (0.77), 5.731 (1.19), 5.749 (0.76), 7.349 (0.64), 7.369 (1.41), 7.388 (0.81), 7.547 (1.68), 7.566 (1.36), 7.771 (1.28), 7.790 (1.16), 9.226 (0.80), 9.232 (0.92), 9.239 (1.72), 9.244 (2.62), 9.250 (2.13), 9.255 (2.02), 9.260 (1.33), 9.291 (1.08).<br>LC-MS (Method 2): $R_t$ = 1.06 min; MS (ESIpos): m/z = 506 [M + H]$^+$<br>Intermediate 203<br>52.2 mg (95% purity, 69% yield) |

The examples shown in Table 10 were prepared according to General Procedure 8 from the respective amine derivatives.

TABLE 10

| Examples | |
|---|---|
| Ex. | Structure; IUPAC-Name; Analytical Data; Starting Materials; Yield |
| 149 | 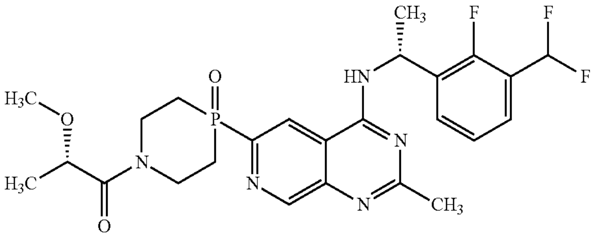 [SMILES: CO[C@@H](C)C(=O)N1CCP(=O)(c2cc3c(N[C@H](C)c4cccc(C(F)F)c4F)nc(C)nc3cn2)CC1]<br>4-[4-{{(1R)-1-[3-(difluoromethyl)-2-fluorophenyl]ethyl}amino)-2-methylpyrido[3,4-d]pyrimidin-6-yl]-1-[(2S)-2-methoxypropanoyl]-1,4lambda$^5$-azaphosphinan-4-one |

TABLE 10-continued

| Examples | |
|---|---|
| Ex. | Structure; IUPAC-Name; Analytical Data; Starting Materials; Yield |
| | $^1$H-NMR (500 MHz, DMSO-d6) δ [ppm]: 1.253 (10.99), 1.266 (10.60), 1.626 (7.20), 1.640 (7.17), 1.957 (0.65), 2.040 (0.56), 2.361 (1.54), 2.447 (16.00), 2.514 (3.86), 2.518 (3.22), 2.522 (2.38), 2.635 (1.27), 3.252 (9.56), 3.258 (8.52), 3.888 (0.91), 3.913 (0.85), 4.301 (0.80), 4.314 (2.84), 4.327 (2.71), 4.340 (0.77), 5.796 (1.04), 5.811 (1.55), 5.825 (1.00), 7.133 (1.62), 7.241 (3.34), 7.297 (1.37), 7.312 (2.87), 7.328 (1.62), 7.350 (1.44), 7.509 (1.01), 7.521 (1.77), 7.536 (0.92), 7.700 (0.91), 7.713 (1.62), 7.729 (0.86), 9.036 (1.48), 9.048 (1.50), 9.115 (2.34), 9.121 (2.21).<br>LC-MS (Method 2): $R_t$ = 1.05 min; MS (ESIpos): m/z = 537 [M + H]$^+$<br>Example 9<br>52.0 mg (95% purity, 44% yield) |
| 150 | 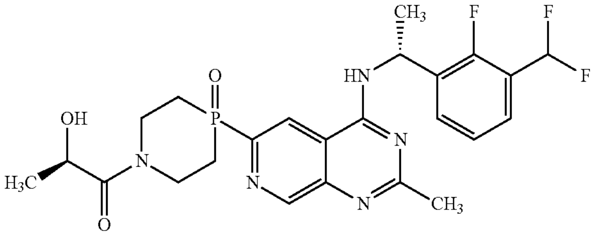 [SMILES: Cc1nc(N[C@H](C)c2cccc(C(F)F)c2F)c2cc(P3(=O)CCN(C(=O)[C@@H](C)O)CC3)ncc2n1]<br>4-[4-{{(1R)-1-[3-(difluoromethyl)-2-fluorophenyl]ethyl}amino)-2-methylpyrido[3,4-d]pyrimidin-6-yl]-1-[(2R)-2-hydroxypropanoyl]-1,4lambda$^5$-azaphosphinan-4-one<br>$^1$H-NMR (400 MHz, DMSO-d6) δ [ppm]: 1.226 (5.79), 1.242 (5.81), 1.303 (0.46), 1.369 (0.44), 1.619 (5.36), 1.636 (5.37), 1.931 (0.42), 1.957 (0.41), 2.318 (0.52), 2.323 (0.89), 2.327 (1.19), 2.331 (0.91), 2.336 (0.53), 2.401 (0.54), 2.432 (16.00), 2.518 (4.76), 2.523 (3.14), 2.665 (0.75), 2.669 (1.05), 2.673 (0.74), 3.875 (0.44), 3.897 (0.57), 3.930 (0.44), 4.492 (0.56), 4.508 (0.83), 4.524 (0.54), 5.194 (0.75), 5.211 (0.79), 5.227 (0.68), 5.244 (0.58), 5.782 (0.88), 5.800 (1.34), 5.817 (0.86), 7.106 (1.39), 7.241 (2.92), 7.287 (1.03), 7.306 (2.24), 7.325 (1.27), 7.377 (1.22), 7.499 (0.80), 7.516 (1.36), 7.533 (0.67), 7.690 (0.75), 7.709 (1.35), 7.726 (0.68), 9.020 (1.62), 9.036 (1.63), 9.114 (4.32), 9.276 (0.47), 9.295 (0.57), 9.306 (0.68), 9.324 (0.55).<br>LC-MS (Method 2): Rt = 1.00 min; MS (ESIpos): m/z = 523 [M + H]$^+$<br>Example 9<br>47.0 mg (95% purity, 41% yield) |
| 151 | 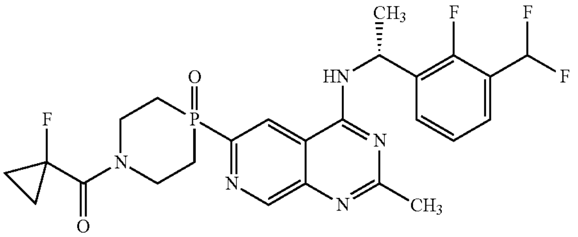 [SMILES: Cc1nc(N[C@H](C)c2cccc(C(F)F)c2F)c2cc(P3(=O)CCN(C(=O)C4(F)CC4)CC3)ncc2n1]<br>4-[4-{{(1R)-1-[3-(difluoromethyl)-2-fluorophenyl]ethyl}amino)-2-methylpyrido[3,4-d]pyrimidin-6-yl]-1-(1-fluorocyclopropane-1-carbonyl)-1,4lambda$^5$-azaphosphinan-4-one<br>$^1$H-NMR (400 MHz, DMSO-d6) δ [ppm]: 1.237 (2.53), 1.260 (2.47), 1.289 (1.22), 1.300 (1.82), 1.324 (0.72), 1.337 (0.96), 1.351 (1.66), 1.629 (7.89), 1.646 (7.90), 2.074 (1.67), 2.318 (0.94), 2.392 (0.95), 2.457 (16.00), 2.518 (11.56), 2.523 (7.58), 2.659 (0.82), 4.165 (0.93), 5.801 (1.15), 5.819 (1.76), 5.836 (1.11), 7.107 (2.01), 7.243 (4.22), 7.297 (1.42), 7.316 (3.11), 7.336 (1.78), 7.378 (1.76), 7.509 (1.10), 7.526 (2.04), 7.545 (1.15), 7.565 (0.45), 7.595 (0.54), 7.612 (0.43), 7.621 (0.54), 7.624 (0.52), 7.700 (1.01), 7.718 (1.85), 7.736 (0.91), 9.054 (2.20), 9.070 (2.21), 9.137 (6.40).<br>LC-MS (Method 2): $R_t$ = 1.13 min; MS (ESIpos): m/z = 537 [M + H]$^+$<br>Example 6<br>38.0 mg (90% purity, 31% yield) |

TABLE 10-continued

| Examples | |
|---|---|
| Ex. | Structure; IUPAC-Name; Analytical Data; Starting Materials; Yield |
| 152 | 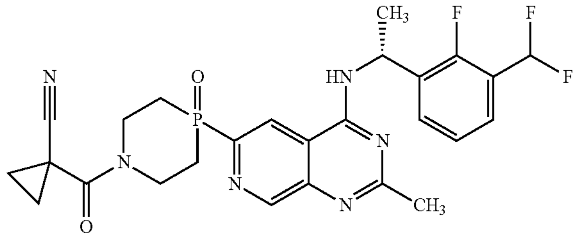 [SMILES: Cc1nc(N[C@H](C)c2cccc(C(F)F)c2F)c2cc(P3(=O)CCN(C(=O)C4(C#N)CC4)CC3)ncc2n1]<br>1-{4-[4-{{(1R)-1-[3-(difluoromethyl)-2-fluorophenyl]ethyl}amino)-2-methylpyrido[3,4-d]pyrimidin-6-yl]-4-oxo-1,4lambda5-azaphosphinane-1-carbonyl}cyclopropane-1-carbonitrile<br>$^1$H-NMR (400 MHz, DMSO-d6) δ [ppm]: 1.586 (2.87), 1.632 (8.32), 1.650 (11.20), 2.074 (2.14), 2.142 (0.52), 2.318 (0.65), 2.359 (0.41), 2.461 (16.00), 2.518 (8.22), 2.523 (5.56), 2.659 (0.61), 2.888 (0.45), 3.696 (0.48), 3.707 (0.80), 3.710 (0.65), 3.715 (0.45), 4.116 (0.52), 5.805 (1.11), 5.823 (1.71), 5.840 (1.10), 7.108 (1.92), 7.244 (3.96), 7.299 (1.35), 7.319 (2.95), 7.338 (1.69), 7.379 (1.70), 7.512 (1.04), 7.529 (1.86), 7.547 (1.07), 7.704 (0.97), 7.721 (1.75), 7.740 (0.90), 8.132 (0.51), 9.060 (2.13), 9.076 (2.14), 9.143 (6.29).<br>LC-MS (Method 2): $R_t$ = 1.09 min; MS (ESIpos): m/z = 544 $[M + H]^+$<br>Example 9<br>34.0 mg (90% purity, 27% yield) |
| 153 | 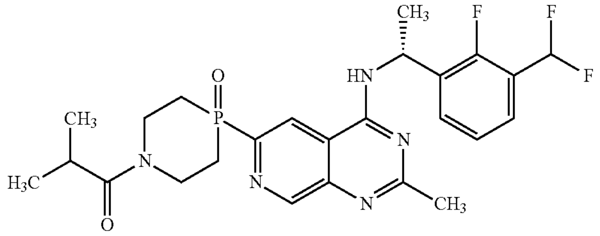 [SMILES: Cc1nc(N[C@H](C)c2cccc(C(F)F)c2F)c2cc(P3(=O)CCN(C(=O)C(C)C)CC3)ncc2n1]<br>4-[4-({(1R)-1-[3-(difluoromethyl)-2-fluorophenyl]ethyl}amino)-2-methylpyrido[3,4-d]pyrimidin-6-yl]-1-(2-methylpropanoyl)-1,4lambda$^5$-azaphosphinan-4-one<br>$^1$H-NMR (400 MHz, DMSO-d6) δ [ppm]: 1.033 (5.86), 1.049 (9.78), 1.063 (5.90), 1.626 (7.85), 1.643 (7.88), 1.928 (0.59), 1.976 (0.49), 2.028 (0.60), 2.074 (0.53), 2.275 (0.57), 2.318 (1.09), 2.354 (0.61), 2.451 (16.00), 2.518 (11.60), 2.523 (7.61), 2.678 (0.85), 2.941 (0.66), 2.958 (1.68), 2.974 (2.29), 2.991 (1.65), 3.008 (0.64), 3.730 (0.55), 3.760 (0.56), 3.901 (0.52), 3.926 (0.59), 3.961 (0.65), 4.009 (0.90), 4.051 (0.72), 5.796 (1.05), 5.813 (1.60), 5.831 (1.03), 7.106 (1.96), 7.242 (4.14), 7.294 (1.39), 7.313 (3.03), 7.333 (1.73), 7.377 (1.73), 7.507 (1.06), 7.525 (1.81), 7.542 (0.95), 7.565 (0.41), 7.595 (0.47), 7.621 (0.49), 7.624 (0.45), 7.696 (0.96), 7.714 (1.75), 7.733 (0.87), 9.038 (2.27), 9.054 (2.25), 9.123 (6.54).<br>LC-MS (Method 2): $R_t$ = 1.10 min; MS (ESIpos): m/z = 521 $[M + H]^+$<br>Example 9<br>26.0 mg (90% purity, 22% yield) |
| 154 | 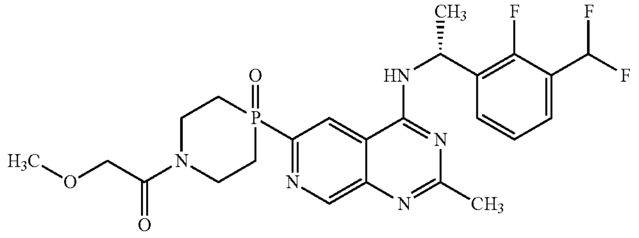 [SMILES: COCC(=O)N1CCP(=O)(c2cc3c(N[C@H](C)c4cccc(C(F)F)c4F)nc(C)nc3cn2)CC1]<br>4-[4-{{(1R)-1-[3-(difluoromethyl)-2-fluorophenyl]ethyl}amino)-2-methylpyrido[3,4-d]pyrimidin-6-yl]-1-(methoxyacetyl)-1,4lambda$^5$-azaphosphinan-4-one<br>$^1$H-NMR (500 MHz, DMSO-d6) δ [ppm]: 1.624 (2.71), 1.638 (2.67), 2.441 (6.19), 2.515 (1.08), 2.518 (1.07), 2.522 (0.84), 3.325 (16.00), 3.339 (3.58), 4.197 (2.60), 4.201 (2.62), 5.806 (0.51), 7.133 (0.61), 7.241 (1.24), 7.294 (0.48), 7.310 (1.04), 7.325 (0.57), 7.350 (0.54), 7.520 (0.57), 7.711 (0.56), 9.023 (0.80), 9.036 (0.79), 9.117 (2.10).<br>LC-MS (Method 2): $R_t$ = 1.02 min; MS (ESIpos): m/z = 523 $[M + H]^+$<br>Example 9<br>35.0 mg (95% purity, 31% yield) |

TABLE 10-continued

| Examples | |
|---|---|
| Ex. | Structure; IUPAC-Name; Analytical Data; Starting Materials; Yield |
| 155 | 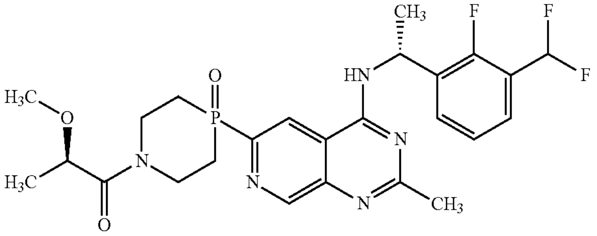 [SMILES: CO[C@H](C)C(=O)N1CCP(=O)(c2cc3c(N[C@H](C)c4cccc(C(F)F)c4F)nc(C)nc3cn2)CC1]<br>4-[4-{{(1R)-1-[3-(difluoromethyl)-2-fluorophenyl]ethyl}amino)-2-methylpyrido[3,4-d]pyrimidin-6-yl]-1-[(2R)-2-methoxypropanoyl]-1,4lambda$^5$-azaphosphinan-4-one<br>$^1$H-NMR (400 MHz, DMSO-d6) δ [ppm]: 1.251 (13.31), 1.268 (13.27), 1.624 (6.91), 1.642 (6.91), 1.957 (0.66), 1.997 (0.63), 2.037 (0.55), 2.074 (0.41), 2.284 (0.43), 2.318 (0.87), 2.322 (1.50), 2.327 (1.97), 2.331 (1.49), 2.336 (0.85), 2.381 (0.45), 2.445 (13.85), 2.518 (6.96), 2.523 (4.62), 2.659 (0.55), 2.665 (1.18), 2.669 (1.69), 2.673 (1.23), 2.678 (0.55), 3.255 (16.00), 3.882 (0.97), 3.925 (1.10), 3.940 (0.96), 3.992 (0.56), 4.296 (0.89), 4.313 (3.45), 4.329 (3.38), 4.346 (0.85), 5.791 (0.93), 5.808 (1.43), 5.826 (0.92), 7.106 (1.92), 7.242 (3.96), 7.292 (1.29), 7.311 (2.83), 7.331 (1.62), 7.377 (1.67), 7.504 (1.04), 7.521 (1.72), 7.539 (0.84), 7.693 (0.94), 7.712 (1.72), 7.730 (0.85), 9.033 (2.33), 9.050 (2.31), 9.116 (3.04).<br>LC-MS (Method 2): $R_t$ = 1.04 min; MS (ESIpos): m/z = 537 [M + H]$^+$<br>Example 9<br>44.0 mg (95% purity, 37% yield) |
| 156 | 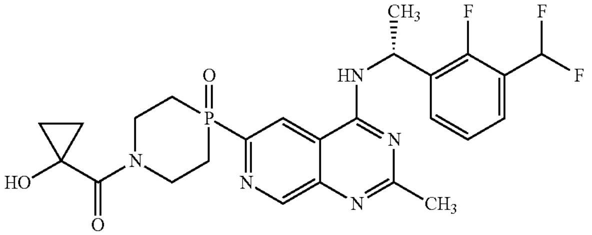 [SMILES: Cc1nc(N[C@H](C)c2cccc(C(F)F)c2F)c2cc(P3(=O)CCN(C(=O)C4(O)CC4)CC3)ncc2n1]<br>4-[4-{{(1R)-1-[3-(difluoromethyl)-2-fluorophenyl]ethyl}amino)-2-methylpyrido[3,4-d]pyrimidin-6-yl]-1-(1-hydroxycyclopropane-1-carbonyl)-1,4lambda$^5$-azaphosphinan-4-one<br>$^1$H-NMR (400 MHz, DMSO-d6) δ [ppm]: 0.795 (0.96), 0.809 (2.86), 0.814 (2.99), 0.826 (1.33), 0.975 (3.60), 0.982 (3.08), 1.226 (0.66), 1.616 (5.77), 1.633 (5.72), 2.003 (0.51), 2.396 (0.60), 2.429 (16.00), 2.518 (4.04), 5.779 (0.95), 5.797 (1.46), 5.815 (0.93), 6.532 (5.95), 7.102 (1.30), 7.238 (2.69), 7.283 (1.04), 7.303 (2.26), 7.322 (1.30), 7.374 (1.17), 7.495 (0.85), 7.511 (1.42), 7.530 (0.70), 7.688 (0.78), 7.707 (1.42), 7.725 (0.72), 9.018 (2.04), 9.034 (2.02), 9.114 (5.09), 9.296 (1.59), 9.314 (1.53).<br>LC-MS (Method 2): $R_t$ = 1.03 min; MS (ESIpos): m/z = 535 [M + H]$^+$<br>Example 9<br>34.0 mg (95% purity, 29% yield) |
| 157 | 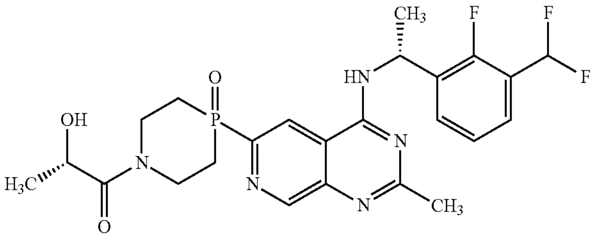 [SMILES: Cc1nc(N[C@H](C)c2cccc(C(F)F)c2F)c2cc(P3(=O)CCN(C(=O)[C@H](C)O)CC3)ncc2n1]<br>4-[4-{{(1R)-1-[3-(difluoromethyl)-2-fluorophenyl]ethyl}amino)-2-methylpyrido[3,4-d]pyrimidin-6-yl]-1-[(2S)-2-hydroxypropanoyl]-1,4lambda$^5$-azaphosphinan-4-one<br>$^1$H-NMR (400 MHz, DMSO-d6) δ [ppm]: 1.226 (6.07), 1.242 (6.02), 1.619 (5.29), 1.636 (5.26), 1.931 (0.43), 2.318 (0.75), 2.323 (1.36), 2.327 (1.89), 2.331 (1.41), 2.336 (0.76), 2.401 (0.59), 2.404 (0.59), 2.432 (16.00), 2.518 (7.12), 2.523 (4.77), 2.659 (0.55), 2.665 (1.21), 2.669 (1.72), 2.673 (1.21), 2.678 (0.54), 3.623 (0.43), 3.896 |

TABLE 10-continued

| Examples | |
|---|---|
| Ex. | Structure; IUPAC-Name; Analytical Data; Starting Materials; Yield |
| | (0.58), 3.931 (0.45), 4.493 (0.55), 4.508 (0.79), 4.522 (0.53), 5.196 (0.54), 5.211 (0.63), 5.227 (0.57), 5.244 (0.45), 5.782 (0.86), 5.800 (1.32), 5.817 (0.85), 7.106 (1.42), 7.241 (2.98), 7.287 (1.04), 7.306 (2.25), 7.325 (1.29), 7.377 (1.25), 7.499 (0.79), 7.516 (1.36), 7.535 (0.66), 7.690 (0.75), 7.709 (1.33), 7.726 (0.66), 9.020 (1.60), 9.036 (1.59), 9.114 (4.11), 9.278 (0.47), 9.295 (0.57), 9.307 (0.69), 9.325 (0.56).<br>LC-MS (Method 2): $R_t$ = 0.99 min; MS (ESIpos): m/z = 523 $[M + H]^+$<br>Example 9<br>35.0 mg (95% purity, 31% yield) |
| 158 | 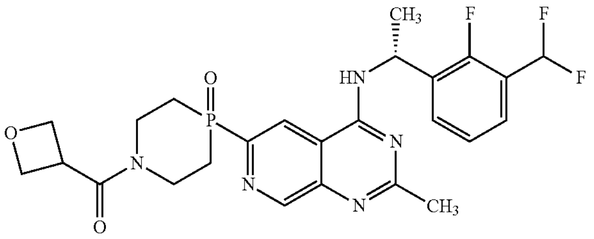 [SMILES: Cc1nc(N[C@H](C)c2cccc(C(F)F)c2F)c2cc(P3(=O)CCN(C(=O)C4COC4)CC3)ncc2n1]<br>4-[4-{{(1R)-1-[3-(difluoromethyl)-2-fluorophenyl]ethyl}amino)-2-methylpyrido[3,4-d]pyrimidin-6-yl]-1-(oxetane-3-carbonyl)-1,4lambda$^5$-azaphosphinan-4-one<br>$^1$H-NMR (400 MHz, DMSO-d6) δ [ppm]: 1.617 (6.38), 1.635 (6.38), 1.963 (0.73), 2.002 (0.83), 2.118 (0.54), 2.318 (2.06), 2.323 (3.26), 2.327 (4.33), 2.331 (3.32), 2.336 (1.87), 2.432 (16.00), 2.518 (14.87), 2.523 (9.79), 2.659 (1.08), 2.665 (2.47), 2.669 (3.50), 2.673 (2.50), 2.678 (1.13), 3.592 (0.85), 3.638 (0.88), 3.805 (0.50), 3.836 (0.50), 4.039 (0.49), 4.231 (0.80), 4.236 (0.89), 4.253 (1.63), 4.271 (0.95), 4.274 (1.04), 4.292 (0.45), 4.670 (0.92), 4.683 (3.32), 4.695 (4.78), 4.700 (3.24), 4.708 (1.63), 4.715 (5.30), 4.729 (2.24), 4.737 (2.40), 4.752 (1.08), 5.782 (0.76), 5.799 (1.14), 5.813 (0.73), 7.105 (1.64), 7.241 (3.51), 7.286 (1.22), 7.306 (2.66), 7.325 (1.55), 7.377 (1.45), 7.500 (0.92), 7.517 (1.55), 7.535 (0.77), 7.685 (0.83), 7.704 (1.52), 7.721 (0.76), 9.005 (2.21), 9.022 (2.24), 9.107 (5.91), 9.269 (1.48), 9.286 (1.48).<br>LC-MS (Method 2): $R_t$ = 0.98 min; MS (ESIpos): m/z = 534 $[M + H]^+$<br>Example 9<br>18.0 mg (95% purity, 15% yield) |
| 159 | 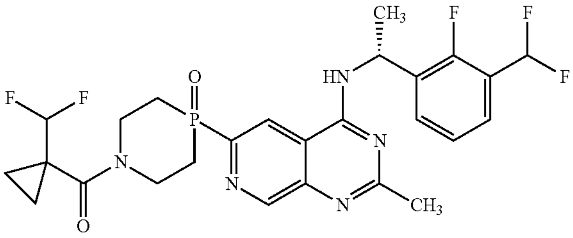 [SMILES: Cc1nc(N[C@H](C)c2cccc(C(F)F)c2F)c2cc(P3(=O)CCN(C(=O)C4(C(F)F)CC4)CC3)ncc2n1]<br>1-[1-(difluoromethyl)cyclopropane-1-carbonyl]-4-[4-{{(1R)-1-[3-(difluoromethyl)-2-fluorophenyl]ethyl}amino)-2-methylpyrido[3,4-d]pyrimidin-6-yl]-1,4lambda$^5$-azaphosphinan-4-one<br>$^1$H-NMR (500 MHz, DMSO-d6) δ [ppm]: 1.101 (8.69), 1.633 (11.90), 1.647 (11.75), 2.050 (1.58), 2.074 (12.49), 2.354 (2.99), 2.358 (4.72), 2.361 (5.85), 2.365 (4.43), 2.463 (16.00), 2.515 (13.36), 2.518 (13.47), 2.522 (10.65), 2.628 (1.48), 2.631 (3.14), 2.635 (4.51), 2.639 (3.26), 2.642 (1.47), 2.687 (0.61), 2.729 (0.49), 2.888 (0.65), 3.927 (1.05), 4.099 (1.47), 5.809 (1.48), 5.823 (2.25), 5.837 (1.50), 5.867 (2.51), 5.979 (4.89), 6.091 (2.20), 7.134 (3.13), 7.242 (6.31), 7.303 (2.14), 7.319 (4.49), 7.334 (2.54), 7.351 (2.71), 7.515 (1.58), 7.529 (2.74), 7.540 (2.01), 7.549 (2.00), 7.556 (1.63), 7.560 (0.99), 7.564 (1.84), 7.570 (1.71), 7.596 (1.65), 7.600 (2.35), 7.614 (2.06), 7.617 (1.91), 7.621 (2.12), 7.623 (2.12), 7.627 (1.91), 7.631 (1.28), 7.637 (1.45), 7.705 (1.55), 7.719 (2.83), 7.735 (1.41), 8.132 (1.89), 9.054 (2.46), 9.066 (2.45), 9.139 (7.71).<br>LC-MS (Method 2): $R_t$ = 1.11 min; MS (ESIpos): m/z = 569 $[M + H]^+$<br>Example 9<br>47.0 mg (90% purity, 36% yield) |

TABLE 10-continued

| Ex. | Examples<br>Structure; IUPAC-Name; Analytical Data; Starting Materials; Yield |
|---|---|
| 160 | 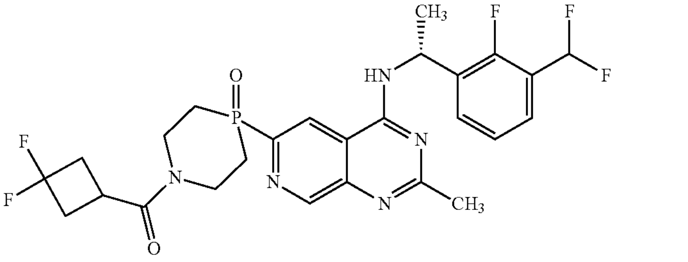 [SMILES: Cc1nc(N[C@H](C)c2cccc(C(F)F)c2F)c2cc(P3(=O)CCN(C(=O)C4CC(F)(F)C4)CC3)ncc2n1]<br>1-(3,3-difluorocyclobutane-1-carbonyl)-4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one<br>$^1$H-NMR (400 MHz, DMSO-d6) δ [ppm]: 1.619 (7.28), 1.637 (7.28), 1.988 (0.65), 2.002 (0.68), 2.041 (0.74), 2.081 (0.43), 2.299 (0.61), 2.323 (2.16), 2.327 (2.74), 2.331 (2.25), 2.336 (1.51), 2.357 (0.86), 2.396 (0.45), 2.434 (16.00), 2.518 (8.79), 2.523 (5.89), 2.660 (0.68), 2.665 (1.52), 2.669 (2.10), 2.673 (1.51), 2.678 (0.67), 2.769 (0.72), 2.796 (1.70), 2.819 (2.10), 2.830 (1.91), 2.836 (2.29), 2.858 (2.09), 2.881 (0.81), 3.352 (1.05), 3.359 (0.92), 3.374 (1.12), 3.380 (1.11), 3.395 (0.69), 3.402 (0.66), 3.799 (0.89), 3.816 (1.69), 3.828 (1.39), 3.841 (1.36), 3.856 (1.64), 3.870 (1.05), 3.990 (0.54), 5.783 (0.80), 5.801 (1.19), 5.815 (0.79), 7.106 (1.74), 7.241 (3.70), 7.287 (1.28), 7.306 (2.79), 7.326 (1.61), 7.377 (1.52), 7.500 (0.95), 7.517 (1.62), 7.535 (0.80), 7.687 (0.86), 7.705 (1.58), 7.724 (0.79), 9.012 (2.47), 9.028 (2.46), 9.111 (6.36), 9.268 (1.74), 9.286 (1.68).<br>LC-MS (Method 2): $R_t$ = 1.14 min; MS (ESIpos): m/z = 569 $[M + H]^+$<br>Example 9<br>32.0 mg (95% purity, 26% yield) |
| 161 | 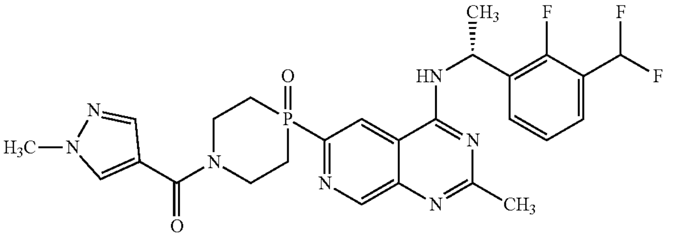 [SMILES: Cc1nc(N[C@H](C)c2cccc(C(F)F)c2F)c2cc(P3(=O)CCN(C(=O)c4cnn(C)c4)CC3)ncc2n1]<br>4-[4-({(1R)-1-[3-(difluoromethyl)-2-fluorophenyl]ethyl}amino)-2-methylpyrido[3,4-d]pyrimidin-6-yl]-1-(1-methyl-1H-pyrazole-4-carbonyl)-1,4lambda$^5$-azaphosphinan-4-one<br>$^1$H-NMR (500 MHz, DMSO-d6) δ [ppm]: 1.627 (4.20), 1.641 (4.10), 2.045 (0.64), 2.074 (0.70), 2.357 (1.22), 2.361 (1.64), 2.365 (1.39), 2.368 (0.83), 2.382 (0.68), 2.392 (0.65), 2.449 (8.07), 2.514 (3.96), 2.518 (3.85), 2.522 (3.06), 2.631 (0.93), 2.634 (1.29), 2.638 (0.93), 2.642 (0.43), 3.867 (16.00), 4.170 (0.58), 5.798 (0.60), 5.812 (0.91), 5.827 (0.57), 7.133 (0.95), 7.242 (1.99), 7.297 (0.74), 7.313 (1.57), 7.329 (0.88), 7.350 (0.84), 7.509 (0.54), 7.522 (0.90), 7.537 (0.46), 7.700 (0.50), 7.714 (0.92), 7.730 (0.50), 7.743 (4.22), 7.744 (4.12), 8.159 (4.00), 9.048 (1.08), 9.061 (1.05), 9.128 (3.23).<br>LC-MS (Method 2): $R_t$ = 1.01 min; MS (ESIpos): m/z = 559 $[M + H]^+$<br>Example 9<br>56.0 mg (95% purity, 46% yield) |
| 162 | 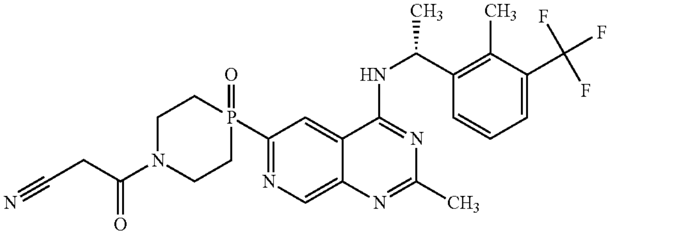 [SMILES: Cc1nc(N[C@H](C)c2cccc(C(F)(F)F)c2C)c2cc(P3(=O)CCN(C(=O)CC#N)CC3)ncc2n1]<br>3-{4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinan-1-yl}-3-oxopropanenitrile<br>$^1$H-NMR (400 MHz, DMSO-d6) δ [ppm]: 1.052 (0.43), 1.156 (1.28), 1.174 (2.77), 1.192 (1.30), 1.231 (0.62), 1.241 (1.34), 1.256 (1.75), 1.272 (0.90), 1.576 (6.27), 1.593 (6.27), 1.973 (0.53), 2.130 (0.64), 2.171 (0.40), 2.306 (0.62), 2.318 (0.99), 2.323 |

TABLE 10-continued

| Ex. | Examples<br>Structure; IUPAC-Name; Analytical Data; Starting Materials; Yield |
|---|---|
| | (1.63), 2.327 (2.17), 2.331 (1.76), 2.424 (16.00), 2.518 (7.34), 2.523 (5.11), 2.624 (8.68), 2.660 (0.62), 2.665 (1.29), 2.669 (1.76), 2.673 (1.27), 2.678 (0.58), 3.079 (0.60), 3.091 (0.62), 3.097 (0.62), 3.109 (0.61), 3.760 (0.90), 3.776 (1.55), 3.789 (1.24), 3.801 (1.21), 3.816 (1.69), 4.018 (0.50), 4.155 (0.68), 4.202 (4.67), 4.217 (4.92), 4.265 (0.77), 5.711 (0.70), 5.724 (1.01), 5.729 (1.02), 5.741 (0.69), 5.759 (1.53), 7.350 (0.95), 7.369 (2.08), 7.389 (1.21), 7.545 (2.32), 7.564 (1.87), 7.787 (2.06), 7.806 (1.87), 9.016 (2.18), 9.033 (2.16), 9.095 (6.08), 9.380 (0.98), 9.396 (0.97).<br>LC-MS (Method 2): $R_t$ = 1.16 min; MS (ESIpos): m/z = 532 $[M + H]^+$<br>Example 6<br>25.0 mg (90% purity, 25% yield) |
| 163 | 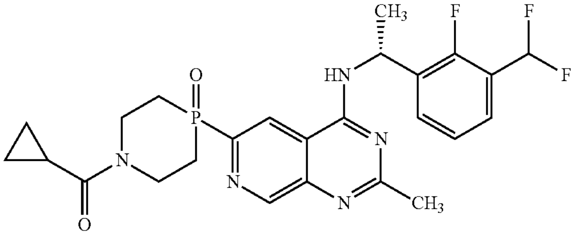 [SMILES: Cc1nc(N[C@H](C)c2cccc(C(F)F)c2F)c2cc(P3(=O)CCN(C(=O)C4CC4)CC3)ncc2n1]<br>1-(cyclopropanecarbonyl)-4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one<br>$^1$H-NMR (400 MHz, DMSO-d6) δ [ppm]: 0.754 (1.18), 0.761 (3.20), 0.781 (5.35), 0.794 (3.17), 1.623 (6.70), 1.641 (6.71), 1.913 (0.46), 2.036 (0.47), 2.069 (0.65), 2.074 (0.71), 2.081 (1.04), 2.088 (1.02), 2.100 (1.47), 2.113 (0.78), 2.119 (0.74), 2.284 (0.49), 2.318 (0.67), 2.445 (16.00), 2.518 (6.48), 2.523 (4.44), 3.719 (0.42), 3.745 (0.42), 4.071 (0.70), 4.229 (0.42), 5.791 (0.95), 5.808 (1.46), 5.826 (0.94), 7.106 (1.64), 7.242 (3.43), 7.291 (1.16), 7.311 (2.49), 7.330 (1.45), 7.378 (1.43), 7.504 (0.91), 7.521 (1.50), 7.536 (0.86), 7.547 (0.44), 7.565 (0.41), 7.595 (0.48), 7.621 (0.48), 7.624 (0.46), 7.693 (0.80), 7.712 (1.45), 7.731 (0.72), 9.034 (2.10), 9.050 (2.08), 9.127 (5.66).<br>LC-MS (Method 2): $R_t$ = 1.07 min; MS (ESIpos): m/z = 519 $[M + H]^+$<br>Example 9<br>55.0 mg (90% purity, 46% yield) |
| 164 | 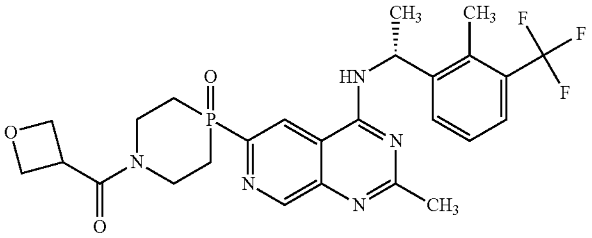 [SMILES: Cc1nc(N[C@H](C)c2cccc(C(F)(F)F)c2C)c2cc(P3(=O)CCN(C(=O)C4COC4)CC3)ncc2n1]<br>4-[2-methyl-4-{{(1R)-1-[2-methyl-3-(trifluoromethyl)phenyl]ethyl}amino)pyrido[3,4-d]pyrimidin-6-yl]-1-(oxetane-3-carbonyl)-1,4lambda$^5$-azaphosphinan-4-one<br>$^1$H-NMR (400 MHz, DMSO-d6) δ [ppm]: 0.852 (0.50), 1.232 (1.55), 1.353 (0.50), 1.573 (5.95), 1.591 (5.89), 2.000 (0.96), 2.117 (0.52), 2.292 (0.99), 2.318 (1.83), 2.323 (3.04), 2.327 (4.02), 2.331 (3.00), 2.391 (0.42), 2.421 (16.00), 2.518 (11.39), 2.523 (7.56), 2.622 (8.69), 2.660 (1.12), 2.665 (2.39), 2.669 (3.23), 2.673 (2.30), 2.678 (1.02), 3.599 (0.95), 3.640 (1.11), 3.796 (0.50), 3.818 (0.51), 4.057 (0.50), 4.235 (0.83), 4.252 (1.51), 4.274 (0.92), 4.291 (0.40), 4.670 (0.86), 4.684 (2.98), 4.693 (4.75), 4.702 (2.68), 4.715 (4.11), 4.729 (1.85), 4.738 (2.31), 4.752 (1.08), 5.708 (0.73), 5.725 (1.02), 5.738 (0.68), 7.349 (0.91), 7.368 (2.00), 7.388 (1.16), 7.545 (2.32), 7.563 (1.85), 7.783 (2.01), 7.802 (1.81), 9.003 (1.84), 9.019 (1.85), 9.087 (5.62), 9.362 (1.12), 9.375 (1.13).<br>LC-MS (Method 2): $R_t$ = 1.14 min; MS (ESIpos): m/z = 548 $[M + H]^+$<br>Example 6<br>27.0 mg (95% purity, 31% yield) |

TABLE 10-continued

| Examples | |
|---|---|
| Ex. | Structure; IUPAC-Name; Analytical Data; Starting Materials; Yield |
| 165 | 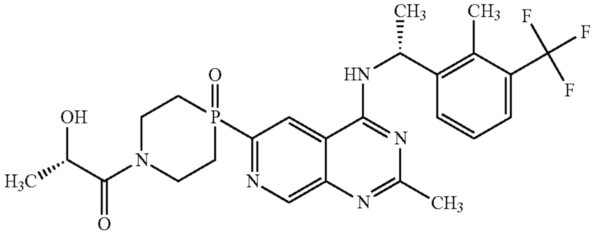 [SMILES: Cc1nc(N[C@H](C)c2cccc(C(F)(F)F)c2C)c2cc(P3(=O)CCN(C(=O)[C@H](C)O)CC3)ncc2n1]<br>1-[(2S)-2-hydroxypropanoyl]-4-[2-methyl-4-{{(1R)-1-[2-methyl-3-(trifluoromethyl)phenyl]ethyl}amino)pyrido[3,4-d]pyrimidin-6-yl]-1,4lambda$^5$-azaphosphinan-4-one<br>$^1$H-NMR (400 MHz, DMSO-d6) δ [ppm]: 1.225 (6.98), 1.242 (7.04), 1.282 (0.46), 1.303 (0.72), 1.320 (0.54), 1.353 (0.93), 1.369 (0.78), 1.575 (5.61), 1.593 (5.62), 1.960 (0.46), 2.336 (1.16), 2.421 (16.00), 2.518 (11.20), 2.523 (7.48), 2.625 (8.10), 2.673 (2.32), 2.678 (1.05), 3.891 (0.52), 4.492 (0.57), 4.509 (0.83), 4.524 (0.55), 5.190 (0.90), 5.208 (0.91), 5.228 (0.74), 5.245 (0.67), 5.708 (0.90), 5.725 (1.39), 5.743 (0.90), 7.350 (0.89), 7.370 (1.87), 7.389 (1.08), 7.545 (2.15), 7.564 (1.72), 7.788 (1.86), 7.808 (1.65), 9.017 (1.48), 9.033 (1.48), 9.095 (4.51), 9.361 (0.50), 9.378 (0.57), 9.394 (0.72), 9.410 (0.60).<br>LC-MS (Method 2): $R_t$ = 1.13 min; MS (ESIpos): m/z = 536 [M + H]$^+$<br>Example 6<br>39.0 mg (95% purity, 46% yield) |
| 166 | 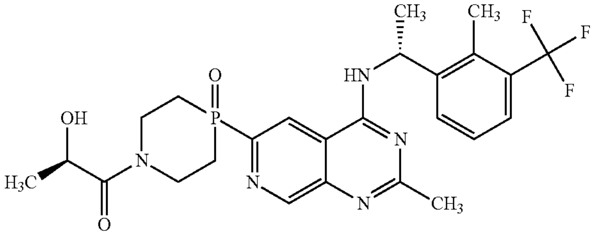 [SMILES: Cc1nc(N[C@H](C)c2cccc(C(F)(F)F)c2C)c2cc(P3(=O)CCN(C(=O)[C@@H](C)O)CC3)ncc2n1]<br>1-[(2R)-2-hydroxypropanoyl]-4-[2-methyl-4-{{(1R)-1-[2-methyl-3-(trifluoromethyl)phenyl]ethyl}amino)pyrido[3,4-d]pyrimidin-6-yl]-1,4lambda$^5$-azaphosphinan-4-one<br>$^1$H-NMR (400 MHz, DMSO-d6) δ [ppm]: 1.225 (6.94), 1.241 (6.84), 1.574 (5.34), 1.592 (5.37), 1.956 (0.43), 2.074 (0.55), 2.323 (0.99), 2.327 (1.32), 2.331 (1.00), 2.336 (0.54), 2.421 (16.00), 2.518 (4.47), 2.523 (2.66), 2.624 (7.58), 2.660 (0.41), 2.665 (0.84), 2.669 (1.16), 2.673 (0.84), 3.305 (0.52), 3.863 (0.42), 3.889 (0.53), 3.918 (0.41), 4.491 (0.56), 4.507 (0.80), 4.522 (0.53), 5.193 (0.61), 5.210 (0.66), 5.230 (0.57), 5.247 (0.47), 5.706 (0.86), 5.724 (1.30), 5.741 (0.84), 7.350 (0.82), 7.369 (1.77), 7.389 (1.02), 7.544 (2.01), 7.563 (1.62), 7.789 (1.75), 7.808 (1.57), 9.017 (1.54), 9.034 (1.55), 9.094 (4.38), 9.366 (0.48), 9.383 (0.56), 9.397 (0.68), 9.414 (0.56).<br>LC-MS (Method 2): $R_t$ = 1.13 min; MS (ESIpos): m/z = 536 [M + H]$^+$<br>Example 6<br>38.0 mg (95% purity, 45% yield) |
| 167 | 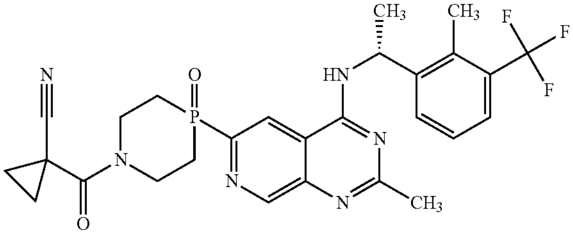 [SMILES: Cc1nc(N[C@H](C)c2cccc(C(F)(F)F)c2C)c2cc(P3(=O)CCN(C(=O)C4(C#N)CC4)CC3)ncc2n1]<br>1-{4-[2-methyl-4-{{(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carbonyl}cyclopropane-1-carbonitrile<br>$^1$H-NMR (400 MHz, DMSO-d6) δ [ppm]: 1.578 (6.84), 1.596 (6.13), 1.648 (2.52), 2.331 (1.07), 2.336 (0.55), 2.427 (16.00), 2.518 (5.21), 2.523 (3.39), 2.626 (6.94), 2.673 (1.01), 5.713 (0.84), 5.730 (1.28), 5.748 (0.82), 7.353 (0.80), 7.372 (1.69), 7.391 |

TABLE 10-continued

| Examples | |
|---|---|
| Ex. | Structure; IUPAC-Name; Analytical Data; Starting Materials; Yield |
| | (0.99), 7.547 (1.87), 7.566 (1.51), 7.791 (1.64), 7.811 (1.48), 9.033 (1.89), 9.049 (1.85), 9.108 (4.92), 9.376 (1.39), 9.393 (1.34).<br>LC-MS (Method 2): $R_t$ = 1.23 min; MS (ESIpos): m/z = 557 $[M + H]^+$<br>Example 6<br>45.0 mg (95% purity, 52% yield) |
| 168 | 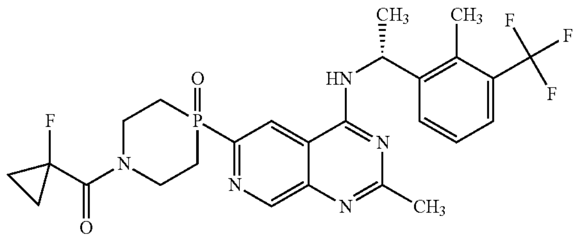 [SMILES: Cc1nc(N[C@H](C)c2cccc(C(F)(F)F)c2C)c2cc(P3(=O)CCN(C(=O)C4(F)CC4)CC3)ncc2n1]<br>1-(1-fluorocyclopropane-1-carbonyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one<br>$^1$H-NMR (400 MHz, DMSO-d6) δ [ppm]: 1.236 (1.74), 1.259 (1.65), 1.286 (0.84), 1.298 (1.23), 1.335 (0.62), 1.351 (1.13), 1.576 (5.35), 1.593 (5.36), 2.074 (0.92), 2.327 (1.88), 2.331 (1.45), 2.392 (0.80), 2.424 (16.00), 2.518 (8.02), 2.523 (4.80), 2.625 (7.36), 2.673 (1.29), 4.172 (0.66), 5.709 (0.86), 5.727 (1.32), 5.744 (0.84), 7.351 (0.80), 7.370 (1.76), 7.390 (1.01), 7.545 (1.93), 7.564 (1.55), 7.790 (1.71), 7.809 (1.55), 9.028 (1.93), 9.044 (1.93), 9.102 (4.90), 9.385 (1.31), 9.402 (1.28).<br>LC-MS (Method 2): $R_t$ = 1.26 min; MS (ESIpos): m/z = 550 $[M + H]^+$<br>Example 6<br>57.0 mg (95% purity, 66% yield) |
| 169 | 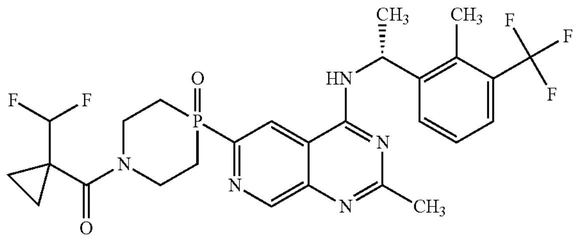 [SMILES: Cc1nc(N[C@H](C)c2cccc(C(F)(F)F)c2C)c2cc(P3(=O)CCN(C(=O)C4(C(F)F)CC4)CC3)ncc2n1]<br>1-[1-(difluoromethyl)cyclopropane-1-carbonyl]-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one<br>$^1$H-NMR (400 MHz, DMSO-d6) δ [ppm]: 1.101 (4.81), 1.576 (5.75), 1.593 (5.73), 2.040 (0.88), 2.323 (2.02), 2.327 (2.49), 2.331 (2.11), 2.391 (0.55), 2.424 (16.00), 2.522 (4.97), 2.624 (8.21), 2.665 (1.21), 2.669 (1.59), 2.673 (1.20), 3.929 (0.60), 4.111 (0.82), 5.709 (0.95), 5.726 (1.43), 5.744 (0.94), 5.842 (1.12), 5.981 (2.20), 6.121 (0.98), 7.350 (0.90), 7.370 (1.91), 7.389 (1.14), 7.545 (2.13), 7.564 (1.72), 7.787 (1.92), 7.807 (1.72), 9.020 (2.10), 9.036 (2.07), 9.101 (5.20), 9.366 (1.58), 9.383 (1.51).<br>LC-MS (Method 2): $R_t$ = 1.24 min; MS (ESIpos): m/z = 582 $[M + H]^+$<br>Example 6<br>39.0 mg (95% purity, 43% yield) |
| 170 | 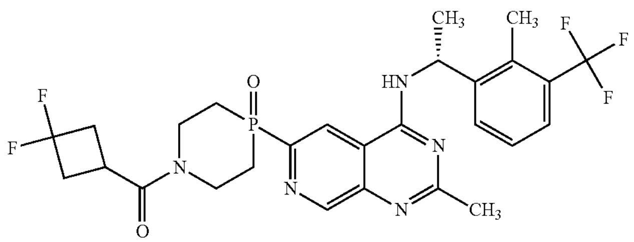 [SMILES: Cc1nc(N[C@H](C)c2cccc(C(F)(F)F)c2C)c2cc(P3(=O)CCN(C(=O)C4CC(F)(F)C4)CC3)ncc2n1]<br>1-(3,3-difluorocyclobutane-1-carbonyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one<br>$^1$H-NMR (400 MHz, DMSO-d6) δ [ppm]: 1.575 (6.73), 1.592 (6.62), 1.983 (0.66), 1.999 (0.64), 2.037 (0.72), 2.074 (1.21), 2.294 (0.61), 2.323 (1.54), 2.327 (1.89), 2.331 (1.58), 2.349 (0.85), 2.368 (0.60), 2.390 (0.59), 2.422 (16.00), 2.518 (4.27), 2.523 (2.66), 2.623 (9.30), 2.665 (0.88), 2.669 (1.20), 2.673 (0.87), 2.768 (0.73), 2.793 |

TABLE 10-continued

| Ex. | Examples<br>Structure; IUPAC-Name; Analytical Data; Starting Materials; Yield |
|---|---|
| | (1.62), 2.814 (1.96), 2.819 (2.04), 2.836 (2.19), 2.858 (1.98), 2.881 (0.82), 3.351 (1.09), 3.358 (0.92), 3.373 (1.11), 3.379 (1.08), 3.395 (0.67), 3.402 (0.63), 3.820 (1.68), 3.833 (1.33), 3.851 (1.35), 3.861 (1.42), 4.006 (0.54), 5.710 (0.75), 5.723 (1.06), 5.727 (1.09), 5.740 (0.72), 7.350 (1.03), 7.369 (2.25), 7.389 (1.30), 7.545 (2.41), 7.564 (1.97), 7.784 (2.21), 7.803 (1.97), 9.009 (2.17), 9.025 (2.15), 9.090 (6.36), 9.359 (1.28), 9.371 (1.23).<br>LC-MS (Method 2): $R_t$ = 1.27 min; MS (ESIpos): m/z = 582 [M + H]$^+$<br>Example 6<br>55.0 mg (95% purity, 60% yield) |
| 171 | 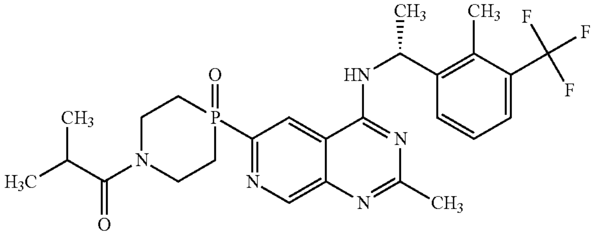<br>4-[2-methyl-4-{{(1R)-1-[2-methyl-3-(trifluoromethyl)phenyl]ethyl}amino)pyrido[3,4-d]pyrimidin-6-yl]-1-(2-methylpropanoyl)-1,4lambda$^5$-azaphosphinan-4-one<br>$^1$H-NMR (400 MHz, DMSO-d6) δ [ppm]: 1.033 (3.78), 1.047 (6.22), 1.062 (3.74), 1.574 (5.24), 1.591 (5.31), 2.322 (0.53), 2.327 (0.69), 2.332 (0.58), 2.336 (0.40), 2.354 (0.40), 2.420 (16.00), 2.518 (1.51), 2.523 (1.01), 2.622 (6.71), 2.669 (0.50), 2.955 (1.08), 2.973 (1.43), 2.989 (1.04), 4.016 (0.56), 4.059 (0.43), 5.705 (0.70), 5.723 (1.07), 5.741 (0.69), 5.758 (5.72), 7.348 (0.79), 7.367 (1.69), 7.387 (0.97), 7.543 (1.82), 7.561 (1.46), 7.786 (1.61), 7.806 (1.45), 9.015 (1.85), 9.031 (1.81), 9.089 (4.93), 9.370 (1.18), 9.387 (1.13).<br>LC-MS (Method 2): $R_t$ = 1.23 min; MS (ESIpos): m/z = 534 [M + H]$^+$<br>Example 6<br>25.0 mg (95% purity, 30% yield) |
| 172 | 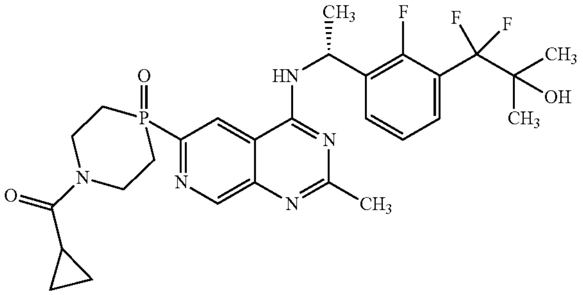 [SMILES: Cc1nc(N[C@H](C)c2cccc(C(F)(F)C(C)(C)O)c2F)c2cc(P3(=O)CCN(C(=O)C4CC4)CC3)ncc2n1]<br>1-(cyclopropanecarbonyl)-4-[4-{{(1R)-1-[3-(1, 1-difluoro-2-hydroxy-2-methylpropyl)-2-fluorophenyl]ethyl}amino)-2-methylpyrido[3,4-d]pyrimidin-6-yl]-1,4lambda$^5$-azaphosphinan-4-one<br>$^1$H-NMR (400 MHz, DMSO-d6) δ [ppm]: 0.754 (0.86), 0.762 (2.22), 0.781 (3.76), 0.794 (2.27), 1.203 (6.04), 1.227 (6.25), 1.596 (4.30), 1.614 (4.27), 2.068 (0.45), 2.081 (0.72), 2.088 (0.72), 2.100 (0.99), 2.112 (0.53), 2.119 (0.51), 2.419 (13.10), 2.518 (4.88), 2.523 (3.28), 4.072 (0.56), 5.340 (6.30), 5.758 (16.00), 5.775 (0.69), 5.793 (1.04), 5.811 (0.65), 7.207 (0.69), 7.226 (1.63), 7.245 (1.05), 7.306 (0.73), 7.323 (1.06), 7.339 (0.49), 7.609 (0.58), 7.625 (1.04), 7.641 (0.53), 9.031 (1.64), 9.047 (1.62), 9.116 (4.28), 9.283 (1.24), 9.301 (1.18).<br>LC-MS (Method 2): $R_t$ = 1.02 min; MS (ESIpos): m/z = 576 [M + H]$^+$<br>Intermediate 228<br>40.6 mg (95% purity, 55% yield) |
| 173 | 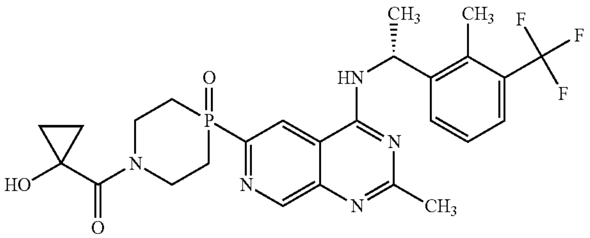 [SMILES: Cc1nc(N[C@H](C)c2cccc(C(F)(F)F)c2C)c2cc(P3(=O)CCN(C(=O)C4(O)CC4)CC3)ncc2n1] |

TABLE 10-continued

| Ex. | Examples<br>Structure; IUPAC-Name; Analytical Data; Starting Materials; Yield |
|---|---|
| | 1-(1-hydroxycyclopropane-1-carbonyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one<br>$^1$H-NMR (400 MHz, DMSO-d6) δ [ppm]: 0.799 (0.78), 0.812 (2.21), 0.818 (2.32), 0.830 (1.06), 0.979 (2.99), 0.986 (2.43), 1.576 (4.90), 1.593 (4.91), 2.318 (0.68), 2.323 (1.31), 2.327 (1.79), 2.331 (1.35), 2.336 (0.72), 2.423 (16.00), 2.518 (5.21), 2.523 (3.52), 2.625 (6.24), 2.660 (0.52), 2.665 (1.16), 2.669 (1.60), 2.673 (1.12), 2.678 (0.50), 5.708 (0.78), 5.725 (1.19), 5.743 (0.77), 6.532 (7.20), 7.351 (0.71), 7.370 (1.57), 7.390 (0.91), 7.545 (1.71), 7.563 (1.37), 7.792 (1.50), 7.811 (1.35), 9.018 (1.72), 9.034 (1.69), 9.098 (4.63), 9.382 (1.29), 9.399 (1.24).<br>LC-MS (Method 2): $R_t$ = 1.17 min; MS (ESIpos): m/z = 548 [M + H]$^+$<br>Example 6<br>35.0 mg (95% purity, 35% yield) |
| 174 | 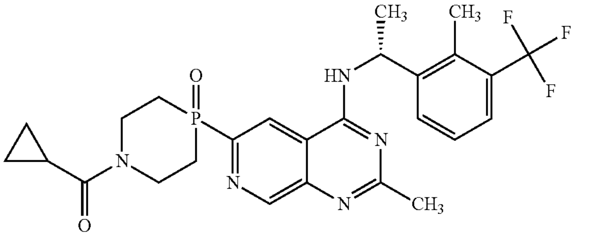 [SMILES: Cc1nc(N[C@H](C)c2cccc(C(F)(F)F)c2C)c2cc(P3(=O)CCN(C(=O)C4CC4)CC3)ncc2n1]<br>1-(cyclopropanecarbonyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one<br>$^1$H-NMR (400 MHz, DMSO-d6) δ [ppm]: 0.761 (2.91), 0.780 (4.77), 0.792 (2.97), 1.575 (5.54), 1.593 (5.51), 1.908 (0.47), 2.029 (0.48), 2.067 (0.62), 2.080 (0.91), 2.086 (0.91), 2.099 (1.23), 2.111 (0.72), 2.118 (0.66), 2.262 (0.52), 2.331 (0.92), 2.423 (16.00), 2.625 (7.76), 2.673 (0.80), 3.706 (0.42), 4.058 (0.69), 4.092 (0.63), 4.233 (0.44), 5.708 (0.85), 5.725 (1.28), 5.743 (0.83), 7.350 (0.87), 7.369 (1.84), 7.388 (1.08), 7.544 (2.01), 7.564 (1.64), 7.788 (1.81), 7.808 (1.66), 9.020 (2.07), 9.036 (2.05), 9.100 (4.96), 9.379 (1.46), 9.396 (1.39).<br>LC-MS (Method 2): $R_t$ = 1.21 min; MS (ESIpos): m/z = 532 [M + H]$^+$<br>Example 6<br>55.0 mg (95% purity, 56% yield) |
| 175 | 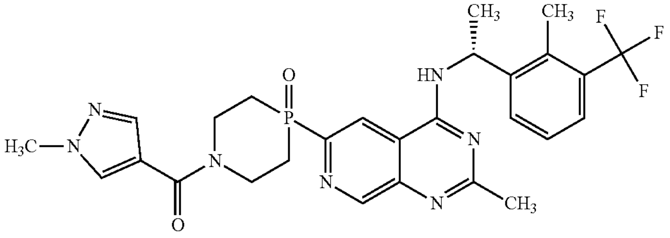 [SMILES: Cc1nc(N[C@H](C)c2cccc(C(F)(F)F)c2C)c2cc(P3(=O)CCN(C(=O)c4cnn(C)c4)CC3)ncc2n1]<br>4-[2-methyl-4-{{(1R)-1-[2-methyl-3-(trifluoromethyl)phenyl]ethyl}amino)pyrido[3,4-d]pyrimidin-6-yl]-1-(1-methyl-1H-pyrazole-4-carbonyl)-1,4lambda$^5$-azaphosphinan-4-one<br>$^1$H-NMR (400 MHz, DMSO-d6) δ [ppm]: 1.575 (4.07), 1.593 (4.10), 2.037 (0.65), 2.331 (0.86), 2.337 (0.54), 2.370 (0.70), 2.394 (0.68), 2.422 (13.30), 2.518 (3.48), 2.523 (2.32), 2.625 (5.33), 2.673 (0.74), 3.866 (16.00), 4.137 (0.41), 4.183 (0.58), 5.708 (0.65), 5.725 (1.01), 5.743 (0.64), 7.350 (0.61), 7.369 (1.31), 7.389 (0.76), 7.545 (1.45), 7.563 (1.15), 7.742 (4.56), 7.744 (4.61), 7.789 (1.28), 7.809 (1.15), 8.160 (3.97), 9.028 (1.48), 9.043 (1.43), 9.097 (3.95), 9.382 (1.08), 9.399 (1.03).<br>LC-MS (Method 2): $R_t$ = 1.15 min; MS (ESIpos): m/z = 572 [M + H]$^+$<br>Example 6<br>58.0 mg (95% purity, 55% yield) |
| 176 | 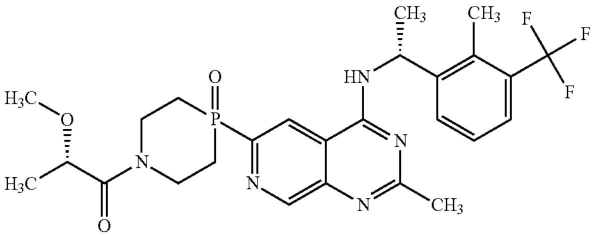 [SMILES: CO[C@@H](C)C(=O)N1CCP(=O)(c2cc3c(N[C@H](C)c4cccc(C(F)(F)F)c4C)nc(C)nc3cn2)CC1] |

TABLE 10-continued

| Examples | |
|---|---|
| Ex. | Structure; IUPAC-Name; Analytical Data; Starting Materials; Yield |
| | 1-[(2S)-2-methoxypropanoyl]-4-[2-methyl-4-{{(1R)-1-[2-methyl-3-(trifluoromethyl)phenyl]ethyl}amino)pyrido[3,4-d]pyrimidin-6-yl]-1,4lambda$^5$-azaphosphinan-4-one<br>$^1$H-NMR (400 MHz, DMSO-d6) δ [ppm]: 1.250 (7.71), 1.267 (7.67), 1.574 (4.82), 1.592 (4.75), 2.318 (0.49), 2.323 (0.89), 2.327 (1.18), 2.331 (0.88), 2.336 (0.48), 2.421 (16.00), 2.518 (4.09), 2.523 (2.88), 2.624 (6.38), 2.665 (0.78), 2.669 (1.07), 2.673 (0.75), 3.250 (6.35), 3.257 (5.68), 3.882 (0.50), 3.905 (0.55), 3.935 (0.59), 4.295 (0.53), 4.311 (1.95), 4.327 (1.92), 4.344 (0.50), 5.706 (0.72), 5.724 (1.12), 5.741 (0.72), 7.350 (0.73), 7.369 (1.55), 7.389 (0.89), 7.544 (1.72), 7.562 (1.38), 7.787 (1.40), 7.807 (1.26), 9.017 (1.21), 9.033 (1.19), 9.085 (1.80), 9.092 (1.62), 9.359 (0.46), 9.376 (0.55), 9.387 (0.61), 9.404 (0.50).<br>LC-MS (Method 2): $R_t$ = 1.14 min; MS (ESIpos): m/z = 550 $[M + H]^+$<br>Example 6<br>31.9 mg (95% purity, 51% yield) |
| 177 | 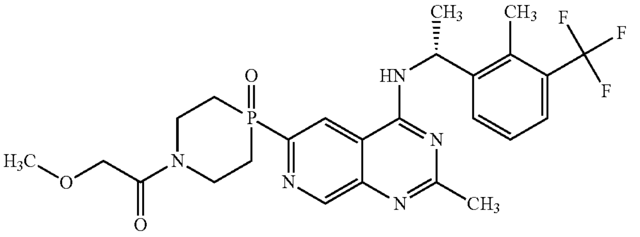<br>1-(methoxyacetyl)-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one<br>$^1$H-NMR (400 MHz, DMSO-d6) δ [ppm]: 1.574 (3.04), 1.591 (3.06), 2.318 (0.43), 2.322 (0.67), 2.327 (0.85), 2.331 (0.67), 2.421 (8.96), 2.522 (4.84), 2.623 (4.17), 2.664 (0.55), 2.669 (0.74), 2.673 (0.57), 3.299 (0.42), 3.305 (0.62), 3.313 (1.62), 3.324 (16.00), 3.370 (1.32), 3.377 (0.68), 3.810 (0.41), 3.823 (0.41), 4.198 (3.69), 5.705 (0.42), 5.723 (0.63), 5.740 (0.43), 7.349 (0.47), 7.368 (1.01), 7.388 (0.60), 7.543 (1.10), 7.562 (0.90), 7.785 (0.99), 7.805 (0.90), 9.009 (1.04), 9.026 (1.04), 9.090 (2.81), 9.370 (0.72), 9.387 (0.72).<br>LC-MS (Method 2): $R_t$ = 1.11 min; MS (ESIpos): m/z = 545 $[M + H]^+$<br>Example 6<br>29.6 mg (95% purity, 49% yield) |
| 178 | 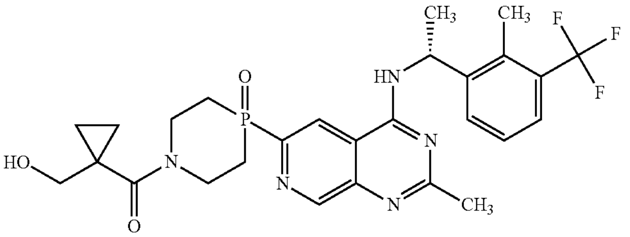 [SMILES: Cc1nc(N[C@H](C)c2cccc(C(F)(F)F)c2C)c2cc(P3(=O)CCN(C(=O)C4(CO)CC4)CC3)ncc2n1]<br>1-[1-(hydroxymethyl)cyclopropane-1-carbonyl]-4-[2-methyl-4-{{(1R)-1-[2-methyl-3-(trifluoromethyl)phenyl]ethyl}amino)pyrido[3,4-d]pyrimidin-6-yl]-1,4lambda$^5$-azaphosphinan-4-one<br>$^1$H-NMR (400 MHz, DMSO-d6) δ [ppm]: 0.716 (2.83), 0.807 (2.14), 1.575 (4.95), 1.593 (4.95), 2.011 (0.57), 2.323 (1.25), 2.327 (1.55), 2.332 (1.23), 2.336 (0.84), 2.422 (16.00), 2.518 (3.60), 2.523 (2.63), 2.623 (6.36), 2.665 (0.71), 2.669 (1.00), 2.673 (0.68), 3.304 (0.40), 3.310 (0.58), 3.365 (0.41), 3.476 (1.99), 3.490 (1.99), 4.110 (0.42), 4.958 (1.16), 4.972 (2.72), 4.987 (1.13), 5.707 (0.78), 5.725 (1.19), 5.742 (0.77), 7.349 (0.75), 7.369 (1.59), 7.388 (0.92), 7.544 (1.73), 7.562 (1.39), 7.787 (1.54), 7.806 (1.38), 9.011 (1.73), 9.026 (1.69), 9.095 (4.86), 9.097 (4.50), 9.361 (1.32), 9.378 (1.26).<br>LC-MS (Method 2): $R_t$ = 1.09 min; MS (ESIpos): m/z = 562 $[M + H]^+$<br>Example 6<br>41.9 mg (95% purity, 66% yield) |

TABLE 10-continued

| Examples | |
|---|---|
| Ex. | Structure; IUPAC-Name; Analytical Data; Starting Materials; Yield |
| 179 | 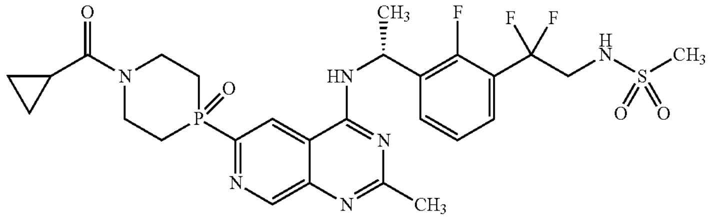<br>N-(2-{3-[(1R)-1-({6-[1-(cyclopropanecarbonyl)-4-oxo-1,4lambda$^5$-azaphosphinan-4-yl]-2-methylpyrido[3,4-d]pyrimidin-4-yl}amino)ethyl]-2-fluorophenyl}-2,2-difluoroethyl)methanesulfonamide<br>$^1$H-NMR (400 MHz, DMSO-d6) δ [ppm]: 0.754 (0.61), 0.761 (1.59), 0.781 (2.68), 0.794 (1.59), 1.107 (16.00), 1.609 (3.16), 1.626 (3.18), 2.081 (0.51), 2.088 (0.50), 2.100 (0.72), 2.119 (0.42), 2.442 (10.30), 2.518 (4.01), 2.523 (2.63), 2.830 (11.35), 3.729 (0.49), 3.747 (0.56), 3.770 (0.75), 3.786 (0.70), 4.191 (1.48), 5.785 (0.49), 5.803 (0.75), 5.820 (0.48), 7.272 (0.62), 7.291 (1.36), 7.311 (0.79), 7.429 (0.48), 7.445 (0.78), 7.679 (0.42), 7.696 (0.75), 7.766 (0.49), 7.783 (1.06), 7.800 (0.47), 9.025 (1.17), 9.041 (1.14), 9.120 (3.17), 9.276 (0.91), 9.294 (0.86).<br>LC-MS (): $R_t$ = min; MS (): m/z =<br>Intermediate 232<br>41.4 mg (95% purity, 62% yield) |
| 180 | 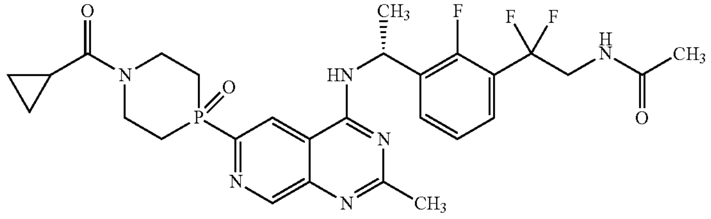<br>N-(2-{3-[(1R)-1-({6-[1-(cyclopropanecarbonyl)-4-oxo-1,4lambda$^5$-azaphosphinan-4-yl]-2-methylpyrido[3,4-d]pyrimidin-4-yl}amino)ethyl]-2-fluorophenyl}-2,2-difluoroethyl)acetamide<br>$^1$H-NMR (400 MHz, DMSO-d6) δ [ppm]: 0.753 (0.47), 0.761 (1.26), 0.781 (2.08), 0.793 (1.24), 1.106 (16.00), 1.607 (2.46), 1.625 (2.47), 1.791 (9.04), 2.100 (0.55), 2.327 (0.46), 2.441 (7.35), 2.518 (1.41), 2.523 (1.04), 2.669 (0.40), 4.192 (1.69), 5.800 (0.58), 7.239 (0.46), 7.258 (1.01), 7.277 (0.60), 7.400 (0.61), 7.667 (0.58), 8.344 (0.76), 9.024 (0.92), 9.040 (0.91), 9.118 (2.38), 9.269 (0.70), 9.287 (0.67).<br>LC-MS (): $R_t$ = min; MS (): m/z =<br>Intermediate 233<br>42.8 mg (95% purity, 52% yield) |
| 181 | 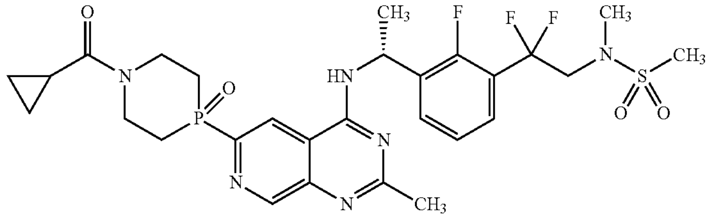<br>N-(2-{3-[(1R)-1-({6-[1-(cyclopropanecarbonyl)-4-oxo-1,4lambda$^5$-azaphosphinan-4-yl]-2-methylpyrido[3,4-d]pyrimidin-4-yl}amino)ethyl]-2-fluorophenyl}-2,2-difluoroethyl)-N-methylmethanesulfonamide<br>$^1$H-NMR (400 MHz, DMSO-d6) δ [ppm]: 0.761 (1.00), 0.781 (1.67), 0.794 (1.01), 1.106 (16.00), 1.602 (2.01), 1.620 (2.02), 2.100 (0.45), 2.431 (6.17), 2.518 (1.02), 2.523 (0.63), 2.857 (10.46), 4.191 (1.54), 5.784 (0.48), 7.287 (0.86), 7.307 (0.50), 7.454 (0.49), 7.686 (0.47), 9.030 (0.75), 9.047 (0.74), 9.119 (2.02), 9.276 (0.58), 9.294 (0.55).<br>LC-MS (): $R_t$ = min; MS (): m/z =<br>Intermediate 234<br>60.6 mg (95% purity, 67% yield) |

TABLE 10-continued

| Examples | |
|---|---|
| Ex. | Structure; IUPAC-Name; Analytical Data; Starting Materials; Yield |
| 182 | 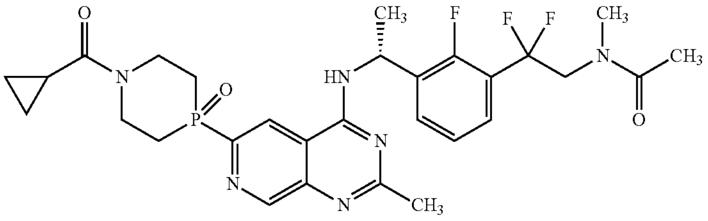 N-(2-{3-[(1R)-1-({6-[1-(cyclopropanecarbonyl)-4-oxo-1,4lambda$^5$-azaphosphinan-4-yl]-2-methylpyrido[3,4-d]pyrimidin-4-yl}amino)ethyl]-2-fluorophenyl}-2,2-difluoroethyl)-N-methylacetamide<br>$^1$H-NMR (500 MHz, DMSO-d6) δ [ppm]: 0.763 (0.56), 0.778 (0.66), 0.793 (0.50), 1.107 (16.00), 1.607 (0.73), 1.616 (0.71), 1.621 (0.79), 1.630 (0.63), 1.917 (1.72), 1.926 (2.44), 2.429 (1.94), 2.434 (2.17), 2.515 (0.53), 2.518 (0.53), 2.522 (0.42), 2.841 (1.25), 3.022 (1.64), 4.189 (1.60), 9.033 (0.45), 9.046 (0.45), 9.119 (0.65), 9.122 (0.57).<br>LC-MS (): $R_t$ = min; MS (): m/z =<br>Intermediate 235<br>43.7 mg (95% purity, 63% yield) |

The examples shown in Table 11 were prepare according to General Procedure trom the respective amine derivatives and the respective isocyanates.

TABLE 11

| Examples | |
|---|---|
| Ex. | Structure; IUPAC-Name; Analytical Data; Starting Materials; Yield |
| 183 | 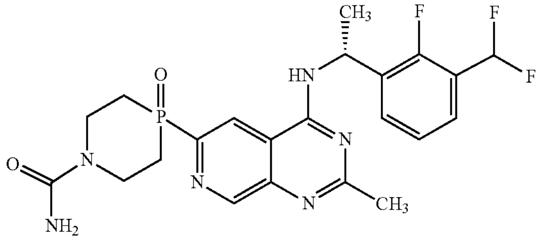 4-[4-({(1R)-1-[3-(difluoromethyl)-2-fluorophenyl]ethyl}amino)-2-methylpyrido[3,4-d]pyrimidin-6-yl]-4-oxo-1,4lambda$^5$-azaphosphinane-1-carboxamide<br>$^1$H-NMR (400 MHz, DMSO-d6) δ [ppm]: 0.932 (0.90), 0.948 (0.85), 1.616 (5.09), 1.634 (5.11), 1.791 (0.47), 1.831 (0.87), 1.871 (0.46), 2.290 (0.79), 2.322 (2.72), 2.327 (3.49), 2.331 (2.68), 2.336 (1.40), 2.430 (14.52), 2.518 (16.00), 2.522 (9.74), 2.660 (1.01), 2.665 (2.19), 2.669 (3.10), 2.673 (2.28), 2.678 (1.08), 3.630 (0.80), 3.664 (0.86), 3.692 (0.42), 3.833 (0.54), 3.879 (0.75), 5.779 (0.80), 5.797 (1.26), 5.814 (0.78), 6.242 (3.60), 7.105 (1.19), 7.241 (2.46), 7.285 (0.91), 7.305 (1.99), 7.324 (1.16), 7.377 (1.04), 7.498 (0.70), 7.514 (1.16), 7.532 (0.58), 7.687 (0.64), 7.705 (1.18), 7.724 (0.61), 8.996 (1.71), 9.012 (1.68), 9.121 (4.35), 9.284 (1.28), 9.302 (1.26). LC-MS (Method 2): $R_t$ = 0.96 min; MS (ESIpos): m/z = 494 $[M + H]^+$<br>Intermediate 226 57.0 mg (95% purity, 53% yield) |

TABLE 11-continued

Examples

| Ex. | Structure; IUPAC-Name; Analytical Data; Starting Materials; Yield |
| --- | --- |
| 184 | 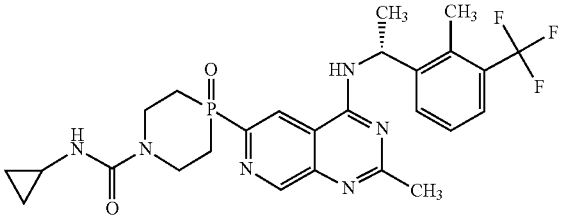 N-cyclopropyl-4-[2-methyl-4-({(1R)-1-[2-methyl-3-(trifluoromethyl)phenyl]ethyl}amino)pyrido[3,4-d]pyrimidin-6-yl]-4-oxo-1,4lambda$^5$-azaphosphinane-1-carboxamide<br><br>$^1$H-NMR (400 MHz, DMSO-d6) δ [ppm]: 0.391 (0.72), 0.403 (2.11), 0.408 (2.20), 0.412 (2.31), 0.418 (2.58), 0.429 (0.96), 0.551 (0.94), 0.561 (2.13), 0.568 (2.63), 0.579 (2.78), 0.585 (1.85), 0.597 (0.74), 1.571 (5.00), 1.588 (5.02), 1.831 (0.82), 1.870 (0.45), 2.218 (0.40), 2.242 (0.83), 2.258 (0.70), 2.265 (0.77), 2.327 (0.95), 2.332 (0.67), 2.419 (16.00), 2.518 (3.62), 2.523 (2.72), 2.563 (1.05), 2.572 (1.03), 2.580 (0.79), 2.589 (0.49), 2.621 (6.41), 2.669 (0.98), 2.673 (0.68), 3.636 (0.76), 3.644 (0.72), 3.668 (0.79), 3.697 (0.42), 3.816 (0.52), 3.862 (0.75), 5.703 (0.80), 5.720 (1.23), 5.738 (0.78), 6.846 (1.80), 6.853 (1.77), 7.346 (0.73), 7.365 (1.61), 7.385 (0.93), 7.542 (1.74), 7.559 (1.41), 7.784 (1.55), 7.803 (1.40), 8.990 (1.77), 9.005 (1.76), 9.089 (4.72), 9.366 (1.37), 9.383 (1.32). LC-MS (Method 2): $R_t$ = 1.17 min; MS (ESIpos): m/z = 547 $[M + H]^+$ Example 6 46.7 mg (95% purity, 69% yield) |
| 185 | 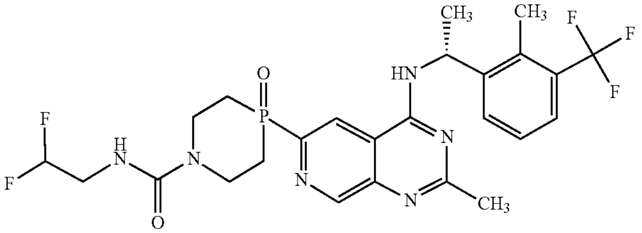 N-(2,2-difluoroethyl)-4-[2-methyl-4-({(1R)-1-[2-methyl-3-(trifluoromethyl)-phenyl]ethyl}amino)pyrido[3,4-d]pyrimidin-6-yl]-4-oxo-1,4lambda$^5$-azaphosphinane-1-carboxamide<br><br>$^1$H-NMR (400 MHz, DMSO-d6) δ [ppm]: 1.573 (4.76), 1.590 (4.75), 1.883 (0.74), 1.921 (0.41), 2.273 (0.77), 2.296 (0.69), 2.318 (0.80), 2.322 (1.44), 2.327 (1.84), 2.332 (1.38), 2.336 (0.60), 2.420 (16.00), 2.518 (6.29), 2.523 (4.45), 2.622 (5.98), 2.660 (0.52), 2.664 (1.13), 2.669 (1.65), 2.673 (1.17), 2.678 (0.51), 3.420 (0.56), 3.433 (0.44), 3.447 (0.78), 3.461 (1.07), 3.471 (0.79), 3.486 (0.41), 3.498 (0.53), 3.715 (0.66), 3.724 (0.65), 3.749 (0.68), 3.776 (0.40), 3.855 (0.48), 3.898 (0.72), 5.706 (0.75), 5.723 (1.16), 5.740 (0.74), 5.866 (0.62), 5.997 (0.55), 6.006 (1.28), 6.017 (0.59), 6.148 (0.56), 7.204 (0.70), 7.218 (1.46), 7.232 (0.68), 7.348 (0.70), 7.367 (1.51), 7.386 (0.87), 7.543 (1.64), 7.561 (1.32), 7.785 (1.46), 7.804 (1.32), 9.000 (1.69), 9.015 (1.64), 9.091 (4.53), 9.093 (4.44), 9.366 (1.28), 9.384 (1.23). LC-MS (Method 2): $R_t$ = 1.19 min; MS (ESIpos): m/z = 571 $[M + H]^+$ Example 6 44.9 mg (95% purity, 64% yield) |
| 186 | 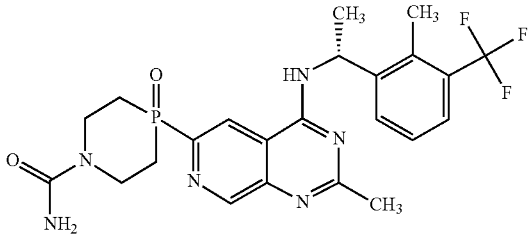 4-[2-methyl-4-({(1R)-1-[2-methyl-3-(trifluoromethyl)phenyl]ethyl}-amino)pyrido[3,4-d]pyrimidin-6-yl]-4-oxo-1,4lambda$^5$-azaphosphinane-1-carboxamide |

TABLE 11-continued

| Ex. | Examples<br>Structure; IUPAC-Name; Analytical Data; Starting Materials; Yield |
|---|---|
| | $^1$H-NMR (400 MHz, DMSO-d6) δ [ppm]: 1.572 (5.07), 1.590 (5.03), 1.829 (0.79), 1.866 (0.44), 2.258 (0.47), 2.282 (0.77), 2.304 (0.76), 2.318 (0.91), 2.323 (1.29), 2.327 (1.64), 2.331 (1.19), 2.336 (0.69), 2.418 (16.00), 2.518 (4.69), 2.523 (3.24), 2.622 (6.60), 2.660 (0.43), 2.665 (0.90), 2.669 (1.25), 2.673 (0.84), 3.297 (0.58), 3.627 (0.75), 3.659 (0.79), 3.842 (0.55), 3.877 (0.68), 3.889 (0.72), 3.927 (0.42), 5.703 (0.80), 5.720 (1.23), 5.738 (0.78), 6.242 (3.45), 7.347 (0.77), 7.367 (1.65), 7.386 (0.94), 7.542 (1.79), 7.561 (1.45), 7.786 (1.57), 7.805 (1.41), 8.993 (1.64), 9.008 (1.64), 9.098 (4.88), 9.372 (1.30), 9.389 (1.19). LC-MS (Method 2): $R_t$ = 1.05 min; MS (ESIpos): m/z = 507 $[M + H]^+$ Example 6 39.5 mg (95% purity, 69% yield) |

The examples shown in Table 12 were prepared according to General Procedure 10 from the respective amine derivatives and the respective isocyanates.

TABLE 12

| Ex | Examples<br>Structure; IUPAC-Name; Analytical Data; Starting Materials; Yield |
|---|---|
| 187 | 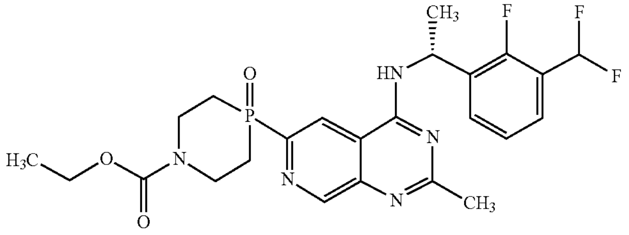<br>ethyl 4-[4-({(1R)-1-[3-(difluoromethyl)-2-fluorophenyl]ethyl}amino)-2-methyl-pyrido[3,4-d]pyrimidin-6-yl]-4-oxo-1,4lambda$^5$-azaphosphinane-1-carboxylate<br>$^1$H-NMR (400 MHz, DMSO-d6) δ [ppm]: 1.203 (5.63), 1.220 (12.70), 1.238 (6.01), 1.616 (5.37), 1.633 (5.40), 1.916 (0.40), 1.956 (0.84), 1.995 (0.48), 2.293 (0.82), 2.318 (0.99), 2.323 (1.23), 2.327 (1.36), 2.331 (1.03), 2.336 (0.69), 2.432 (16.00), 2.518 (3.02), 2.523 (2.03), 2.665 (0.53), 2.669 (0.76), 2.673 (0.52), 3.742 (0.62), 3.898 (0.57), 3.945 (0.80), 3.980 (0.42), 4.085 (0.63), 4.103 (1.64), 4.120 (1.58), 4.136 (0.58), 5.779 (0.79), 5.797 (1.20), 5.815 (0.77), 7.105 (1.29), 7.240 (2.67), 7.284 (0.97), 7.304 (2.10), 7.323 (1.21), 7.376 (1.14), 7.498 (0.72), 7.514 (1.23), 7.533 (0.72), 7.547 (0.45), 7.565 (0.50), 7.573 (0.44), 7.595 (0.65), 7.612 (0.54), 7.621 (0.63), .624 (0.63), 7.687 (0.66), 7.705 (1.21), 7.724 (0.60), 9.012 (1.87), 9.028 (1.84), 9.112 (4.63), 9.290 (1.33), 9.307 (1.28). LC-MS (Method 2): $R_t$ = 1.14 min; MS (ESIpos): m/z = 523 $[M + H]^+$ Intermediate 226 73.0 mg (95% purity, 64% yield) |
| 188 | 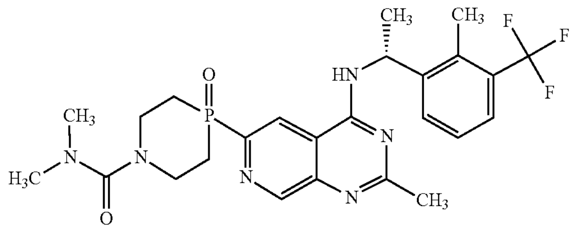<br>N,N-dimethyl-4-[2-methyl-4-({(1R)-1-[2-methyl-3-(trifluoromethyl)-phenyl]ethyl}amino)pyrido[3,4-d]pyrimidin-6-yl]-4-oxo-1,4lambda$^5$-azaphosphinane-1-carboxamide<br>LC-MS (Method 2): $R_t$ = 1.19 min; MS (ESIpos): m/z = 535 $[M + H]^+$ Example 6 22.4 mg (95% purity, 34% yield) |

TABLE 12-continued

| Examples | |
|---|---|
| Ex | Structure; IUPAC-Name; Analytical Data; Starting Materials; Yield |
| 189 | 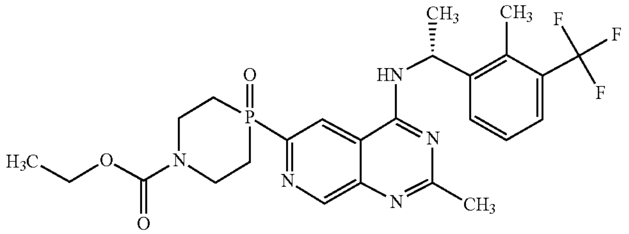<br>ethyl 4-[2-methyl-4-({(1R)-1-[2-methyl-3-(trifluoromethyl)phenyl]ethyl}amino)-pyrido[3,4-d]pyrimidin-6-yl]-4-oxo-1,4lambda$^5$-azaphosphinane-1-carboxylate<br><br>$^1$H-NMR (400 MHz, DMSO-d6) δ [ppm]: 1.202 (5.63), 1.220 (12.21), 1.237 (5.81), 1.571 (5.27), 1.589 (5.24), 1.918 (0.41), 1.952 (0.85), 1.990 (0.49), 2.263 (0.48), 2.286 (0.96), 2.298 (0.74), 2.309 (0.88), 2.323 (1.17), 2.327 (1.25), 2.331 (0.98), 2.420 (16.00), 2.518 (3.51), 2.523 (2.33), 2.622 (6.92), 2.665 (0.63), 2.669 (0.87), 2.673 (0.62), 3.159 (4.56), 3.171 (4.80), 3.737 (0.63), 3.908 (0.61), 3.922 (0.48), 3.943 (0.80), 3.956 (0.85), 3.992 (0.44), 4.086 (1.02), 4.099 (2.55), 4.112 (1.88), 4.118 (1.60), 4.136 (0.58), 5.703 (0.83), 5.720 (1.27), 5.738 (0.81), 7.346 (0.78), 7.366 (1.70), 7.386 (0.98), 7.542 (1.86), 7.561 (1.50), 7.784 (1.66), 7.804 (1.49), 9.007 (1.94), 9.024 (1.90), 9.092 (4.86), 9.373 (1.44), 9.390 (1.37). LC-MS (Method 2): $R_t$ = 1.28 min; MS (ESIpos): m/z = 536 $[M + H]^+$ Example 9 35.9 mg (95% purity, 54% yield) |

The examples shown in Table 13 were prepared according to General Procedure 7 from the respective amine derivatives.

TABLE 13

| Examples | |
|---|---|
| Ex. | Structure; IUPAC-Name; Analytical Data; Starting Materials; Yield |
| 190 | 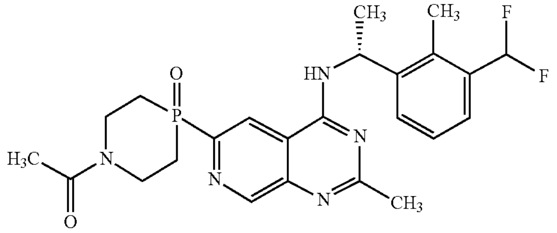<br>1-acetyl-4-[4-({(1R)-1-[3-(difluoromethyl)-2-methylphenyl]ethyl}-amino)-2-methylpyrido[3,4-d]pyrimidin-6-yl]-1,4lambda$^5$-azaphosphinan-4-one<br><br>$^1$H-NMR (500 MHz, DMSO-d6) δ [ppm]: 1.559 (5.62), 1.573 (5.64), 1.907 (0.43), 2.056 (0.46), 2.115 (15.60), 2.259 (0.47), 2.278 (0.44), 2.358 (0.57), 2.361 (0.77), 2.365 (0.64), 2.389 (0.45), 2.402 (0.44), 2.441 (16.00), 2.515 (1.73), 2.518 (1.77), 2.522 (1.43), 2.631 (0.44), 2.635 (0.63), 2.639 (0.43), 3.703 (0.43), 3.729 (0.44), 3.829 (0.41), 3.836 (0.41), 3.848 (0.43), 3.859 (0.57), 3.876 (0.58), 3.884 (0.52), 3.906 (0.47), 4.031 (0.41), 4.040 (0.43), 5.742 (0.59), 5.756 (0.87), 5.767 (0.57), 7.109 (1.01), 7.219 (2.16), 7.289 (0.88), 7.305 (2.03), 7.320 (1.28), 7.329 (0.89), 7.391 (1.91), 7.406 (1.37), 7.674 (1.60), 7.690 (1.44), 9.012 (1.89), 9.025 (1.84), 9.092 (4.70), 9.326 (0.99), 9.337 (0.96). LC-MS (Method 2): $R_t$ = 1.03 min; MS (ESIpos): m/z = 489 $[M + H]^+$ Intermediate 227 91.0 mg (95% purity, 41% yield) |

TABLE 13-continued

| Ex. | Structure; IUPAC-Name; Analytical Data; Starting Materials; Yield |
|---|---|
| | Examples |
| 191 | 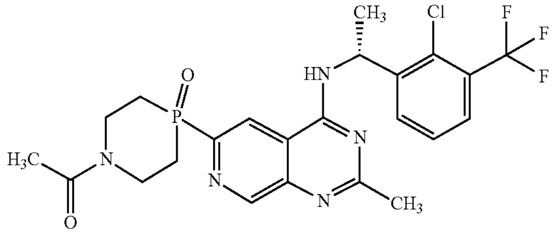<br>1-acetyl-4-[4-({(1R)-1-[2-chloro-3-(trifluoromethyl)phenyl]ethyl}-amino)-2-methylpyrido[3,4-d]pyrimidin-6-yl]-1,4lambda$^5$-azaphosphinan-4-one<br>$^1$H-NMR (400 MHz, DMSO-d6) δ [ppm]: 1.600 (4.69), 1.618 (4.68), 2.121 (16.00), 2.280 (0.40), 2.323 (0.47), 2.327 (0.64), 2.332 (0.44), 2.389 (10.08), 2.409 (0.40), 2.518 (2.12), 2.523 (1.55), 2.665 (0.40), 2.669 (0.57), 3.868 (0.47), 3.891 (0.44), 5.866 (0.46), 5.870 (0.48), 5.883 (0.70), 5.887 (0.70), 5.900 (0.47), 5.904 (0.45), 7.495 (0.75), 7.514 (1.62), 7.533 (0.92), 7.733 (1.35), 7.750 (1.10), 7.855 (1.23), 7.874 (1.12), 9.038 (1.58), 9.054 (1.55), 9.117 (4.10), 9.407 (1.18), 9.423 (1.12). LC-MS (Method 2): $R_t$ = 1.12 min; MS (ESIpos): m/z = 526 [M + H]$^+$ Intermediate 237 63.8 mg (95% purity, 67% yield) |
| 192 | 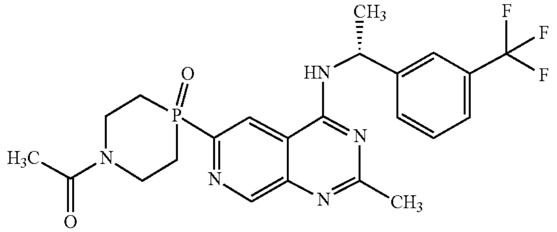<br>1-acetyl-4-[2-methyl-4-({(1R)-1-[3-(trifluoromethyl)phenyl]ethyl}-amino)pyrido[3,4-d]pyrimidin-6-yl-1,4lambda$^5$-azaphosphinan-4-one<br>$^1$H-NMR (400 MHz, DMSO-d6) δ [ppm]: 1.627 (4.94), 1.644 (4.99), 2.116 (16.00), 2.273 (0.40), 2.464 (14.00), 2.475 (0.97), 2.518 (3.73), 2.523 (2.64), 3.309 (0.58), 3.856 (0.52), 3.869 (0.53), 3.881 (0.46), 5.645 (0.68), 5.663 (1.04), 5.681 (0.67), 7.555 (0.49), 7.575 (1.53), 7.593 (1.88), 7.601 (1.99), 7.621 (0.55), 7.766 (1.28), 7.784 (1.01), 7.850 (2.04), 8.963 (1.57), 8.979 (1.55), 9.112 (4.23), 9.235 (0.99), 9.254 (0.95). LC-MS (Method 2): $R_t$ = 1.06 min; MS (ESIpos): m/z = 492 [M + H]$^+$ Intermediate 238 56.8 mg (95% purity, 60% yield) |
| 193 | 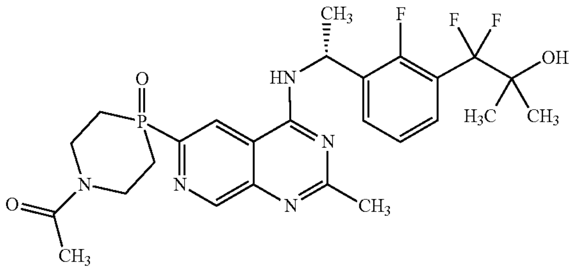<br>(R)-1-(4-(4-((1-(3-(1,1-difluoro-2-hydroxy-2-methylpropyl)-2-fluorophenyl)ethyl)amino)-2-methylpyrido[3,4-d]pyrimidin-6-yl)-4-oxido-1,4-azaphosphinan-1-yl)ethan-1-one<br>$^1$H NMR (400 MHz, DMSO-d6) δ ppm 1.21 (d, J = 9.89 Hz, 6 H) 1.60 (d, J = 7.10 Hz, 3 H) 1.79-2.10 (m, 2 H) 2.12 (s, 3 H) 2.19-2.31 (m, 1 H) 2.42 (s, 3 H) 3.60-4.14 (m, 4 H) 5.34 (s, 1 H) 5.67-5.89 (m, 1 H) 7.14-7.27 (m, |

TABLE 13-continued

| Ex. | Structure; IUPAC-Name; Analytical Data; Starting Materials; Yield |
|---|---|
| | 1 H) 7.29-7.38 (m, 1 H) 7.58-7.67 (m, 1 H) 8.99-9.07 (m, 1 H) 9.09-9.15 (m, 1 H) 9.22-9.35 (m, 1 H). LC-MS (Method 2): $R_t$ = 0.94 min; MS (ESIpos): m/z = 550.5 $[M + H]^+$ Intermediate 228 36.7 mg (95% purity, 51% yield) |
| 194 | 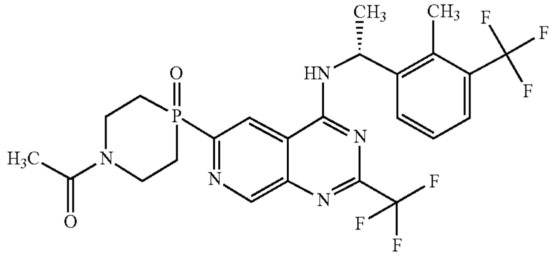 1-acetyl-4-[4-({(1R)-1-[2-methyl-3-(trifluoromethyl)phenyl]ethyl}-amino)-2-(trifluoromethyl)pyrido[3,4-d]pyrimidin-6-yl]-1,4lambda$^5$-azaphosphinan-4-one $^1$H-NMR (400 MHz, DMSO-d6) δ [ppm]: 1.618 (4.76), 1.636 (4.71), 1.953 (0.40), 1.962 (0.40), 2.124 (16.00), 2.273 (0.49), 2.287 (0.65), 2.297 (0.44), 2.406 (0.51), 2.429 (0.48), 2.518 (0.51), 2.594 (6.44), 3.892 (0.62), 3.906 (0.51), 3.918 (0.41), 3.934 (0.44), 5.662 (0.56), 5.679 (0.82), 5.694 (0.55), 7.340 (0.74), 7.359 (1.60), 7.379 (0.92), 7.536 (1.72), 7.555 (1.39), 7.764 (1.56), 7.783 (1.40), 9.176 (1.72), 9.193 (1.70), 9.333 (4.61), 10.065 (0.92), 10.078 (0.89). LC-MS (Method 1): $R_t$ = 1.26 min; MS (ESIpos): m/z = 561 $[M + H]^+$ Intermediate 229 260 mg (100% purity, 63% yield) |
| 195 | 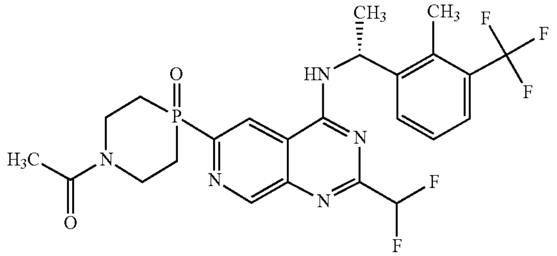 1-acetyl-4-[2-(difluoromethyl)-4-({(1R)-1-[2-methyl-3-(trifluoro-methyl)phenyl]ethyl}amino)pyrido[3,4-d]pyrimidin-6-yl]-1,4lambda$^5$-azaphosphinan-4-one LC-MS (Method 1): $R_t$ = 1.18 min; MS (ESIpos): m/z = 543 $[M + H]^+$ Intermediate 230 110 mg (100% purity, 58% yield) |
| 196 | 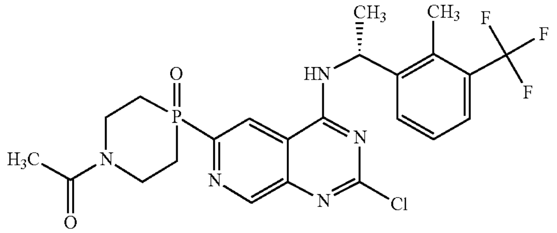 1-acetyl-4-[2-chloro-4-({(1R)-1-[2-methyl-3-(trifluoromethyl)-phenyl]ethyl}amino)pyrido[3,4-d]pyrimidin-6-yl]-1,4lambda$^5$-azaphosphinan-4-one $^1$H-NMR (400 MHz, DMSO-d6) δ [ppm]: 1.592 (5.09), 1.609 (5.10), 1.920 (0.42), 2.074 (0.67), 2.118 (16.00), 2.242 (0.46), 2.266 (0.42), 2.331 (0.84), 2.337 (0.47), 2.373 (0.46), 2.397 (0.44), 2.518 (4.05), 2.523 (2.80), 2.600 (6.71), 2.673 (0.75), 3.702 (0.40), 3.735 (0.41), 3.853 (0.41), 3.865 (0.50), 3.889 (0.60), 3.900 (0.48), 3.929 (0.44), 4.062 (0.41), 5.634 (0.63), 5.651 (0.94), 5.667 (0.62), 7.379 (0.77), |

TABLE 13-continued

| Examples | |
|---|---|
| Ex. | Structure; IUPAC-Name; Analytical Data; Starting Materials; Yield |
| | 7.399 (1.69), 7.419 (0.98), 7.578 (1.82), 7.596 (1.46), 7.776 (1.63), 7.795 (1.46), 9.083 (1.85), 9.100 (1.86), 9.134 (5.00), 9.934 (0.98), 9.949 (0.94). LC-MS (Method 2): $R_t$ = 1.18 min; MS (ESIpos): m/z = 526 $[M + H]^+$ Intermediate 231 31.0 mg (98% purity, 21% yield) |
| 197 | 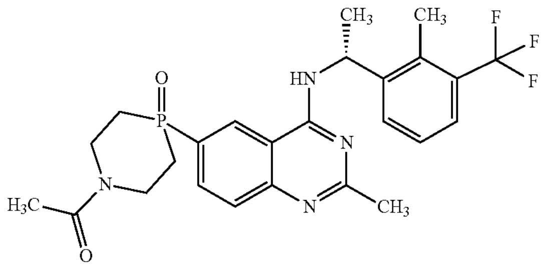 1-acetyl-4-[2-methyl-4-({(1R)-1-[2-methyl-3-(trifluoromethyl)-phenyl]ethyl}amino)quinazolin-6-yl]-1,4lambda$^5$-azaphosphinan-4-one <br> $^1$H-NMR (400 MHz, DMSO-d6) δ [ppm]: 1.576 (5.53), 1.594 (5.58), 1.953 (0.60), 1.996 (0.52), 2.040 (0.53), 2.115 (15.75), 2.258 (0.46), 2.273 (0.51), 2.283 (0.42), 2.337 (0.68), 2.358 (16.00), 2.386 (0.55), 2.399 (0.57), 2.411 (0.49), 2.518 (7.58), 2.523 (5.24), 2.630 (6.98), 2.673 (1.24), 2.678 (0.56), 3.299 (0.57), 3.307 (0.76), 3.311 (1.00), 3.379 (1.62), 3.386 (1.06), 3.393 (0.68), 3.398 (0.50), 3.461 (0.62), 3.487 (0.58), 3.742 (0.52), 3.773 (0.60), 5.719 (0.85), 5.736 (1.31), 5.754 (0.84), 7.337 (0.71), 7.357 (1.55), 7.376 (0.90), 7.531 (1.86), 7.549 (1.50), 7.659 (1.49), 7.666 (1.51), 7.681 (1.67), 7.687 (1.60), 7.787 (1.46), 7.806 (1.32), 8.044 (0.84), 8.047 (0.85), 8.069 (1.61), 8.090 (0.74), 8.094 (0.75), 8.829 (1.31), 8.860 (1.32), 8.957 (0.78), 8.965 (0.91), 8.974 (0.87), 8.983 (0.78). LC-MS (Method 2): $R_t$ = 1.13 min; MS (ESIneg): m/z = 503 $[M - H]^-$ Intermediate 239 34.8 mg (95% purity, 76% yield) |
| 198 | 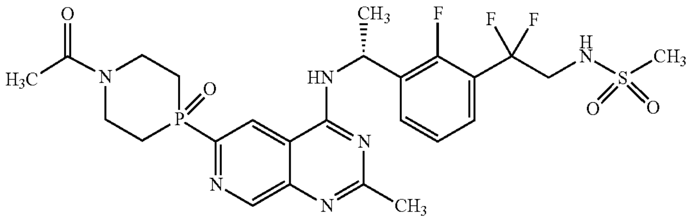 N-(2-{3-[(1R)-1-{[6-(1-acetyl-4-oxo-1,4lambda$^5$-azaphosphinan-4-yl)-2-methyl-pyrido[3,4-d]pyrimidin-4-yl]amino}ethyl]-2-fluorophenyl}-2,2-difluoroethyl)-methanesulfonamide <br> $^1$H-NMR (400 MHz, DMSO-d6) δ [ppm]: 1.106 (16.00), 1.608 (3.19), 1.626 (3.24), 2.118 (12.03), 2.441 (8.61), 2.518 (3.37), 2.523 (2.01), 2.830 (10.92), 3.742 (0.59), 3.771 (0.73), 3.785 (0.60), 3.826 (0.42), 3.850 (0.41), 3.865 (0.55), 4.192 (1.55), 5.803 (0.58), 7.272 (0.65), 7.291 (1.41), 7.310 (0.83), 7.428 (0.49), 7.445 (0.80), 7.677 (0.43), 7.695 (0.78), 7.783 (0.79), 9.015 (1.23), 9.032 (1.21), 9.116 (3.24), 9.267 (0.93), 9.286 (0.89). LC-MS (): $R_t$ = min; MS (): m/z = Intermediate 232 36.8 mg (95% purity, 57% yield) |

TABLE 13-continued

| Examples | |
|---|---|
| Ex. | Structure; IUPAC-Name; Analytical Data; Starting Materials; Yield |
| 199 | 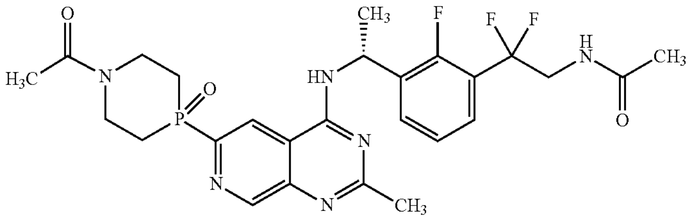<br>N-(2-{3-[(1R)-1-{[6-(1-acetyl-4-oxo-1,4lambda$^5$-azaphosphinan-4-yl)-2-methylpyrido[3,4-d]pyrimidin-4-yl]amino}ethyl]-2-fluorophenyl}-2,2-difluoroethyl)acetamide<br>$^1$H-NMR (400 MHz, DMSO-d6) δ [ppm]: 1.106 (16.00), 1.607 (3.49), 1.624 (3.50), 1.790 (13.84), 2.117 (13.05), 2.322 (0.56), 2.327 (0.76), 2.331 (0.54), 2.440 (9.20), 2.518 (3.19), 2.523 (2.07), 2.665 (0.48), 2.669 (0.70), 2.673 (0.50), 3.837 (0.48), 3.848 (0.60), 3.864 (0.72), 3.877 (0.72), 3.885 (0.65), 3.894 (0.62), 3.920 (0.60), 3.934 (0.41), 4.192 (1.47), 5.782 (0.41), 5.799 (0.61), 5.814 (0.41), 7.239 (0.68), 7.258 (1.49), 7.277 (0.89), 7.383 (0.53), 7.400 (0.86), 7.417 (0.40), 7.648 (0.45), 7.666 (0.81), 7.683 (0.42), 8.328 (0.52), 8.344 (1.08), 8.360 (0.50), 9.015 (1.33), 9.030 (1.32), 9.114 (3.56), 9.260 (0.96), 9.278 (0.93). LC-MS (): $R_t$ = min; MS (): m/z =<br>Intermediate 205 53.9 mg (95% purity, 68% yield) |
| 200 | 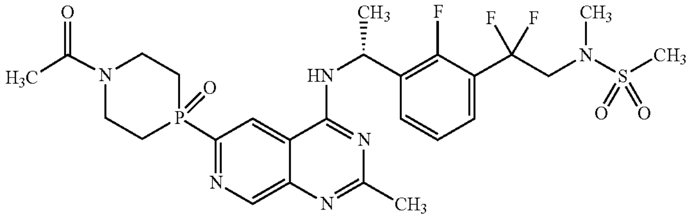<br>N-(2-{3-[(1R)-1-{[6-(1-acetyl-4-oxo-1,4lambda$^5$-azaphosphinan-4-yl)-2-methyl-pyrido[3,4-d]pyrimidin-4-yl]amino}ethyl]-2-fluorophenyl}-2,2-difluoroethyl)-N-methanesulfonamide<br>$^1$H-NMR (500 MHz, DMSO-d6) δ [ppm]: 1.107 (16.00), 1.604 (1.73), 1.618 (1.75), 2.118 (6.31), 2.431 (4.17), 2.515 (0.59), 2.518 (0.58), 2.522 (0.46), 2.856 (8.31), 3.872 (0.40), 4.190 (1.42), 7.288 (0.73), 7.303 (0.41), 9.023 (0.61), 9.036 (0.61), 9.117 (1.55), 9.268 (0.48), 9.282 (0.45). LC-MS (): $R_t$ = min; MS (): m/z =<br>Intermediate 234 59.0 mg (95% purity, 68% yield) |
| 201 | 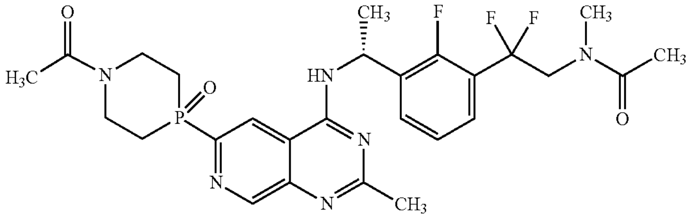<br>N-(2-{3-[(1R)-1-{[6-(1-acetyl-4-oxo-1,4lambda$^5$-azaphosphinan-4-yl)-2-methyl-pyrido[3,4-d]pyrimidin-4-yl]amino}ethyl]-2-fluorophenyl}-2,2-difluoroethyl)-N-methylacetamide<br>$^1$H-NMR (500 MHz, DMSO-d6) δ [ppm]: 1.107 (16.00), 1.607 (1.14), 1.616 (1.08), 1.621 (1.23), 1.630 (0.96), 1.916 (2.72), 1.926 (3.90), 2.118 (6.15), 2.428 (2.50), 2.434 (2.79), 2.515 (1.12), 2.518 (1.09), 2.522 (0.86), 2.840 (1.96), 3.021 (2.50), 4.191 (0.57), 7.249 (0.45), 9.024 (0.71), 9.037 (0.70), 9.116 (1.00), 9.119 (0.87). LC-MS (): $R_t$ = min; MS (): m/z =<br>Intermediate 41.2 mg (95% purity, 62% yield) |

TABLE 13-continued

| Ex. | Structure; IUPAC-Name; Analytical Data; Starting Materials; Yield |
|---|---|
| 202 | 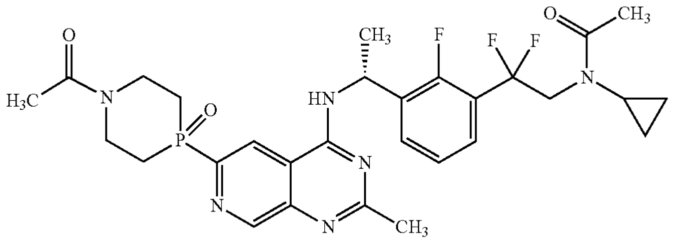<br>N-(2-{3-[(1R)-1-{[6-(1-acetyl-4-oxo-1,4lambda$^5$-azaphosphinan-4-yl)-2-methyl-pyrido[3,4-d]pyrimidin-4-yl]amino}ethyl]-2-fluorophenyl}-2,2-difluoroethyl)-N-cyclopropylacetamide<br>$^1$H-NMR (400 MHz, DMSO-d6) δ [ppm]: 0.735 (3.46), 0.748 (3.38), 0.798 (0.46), 0.834 (0.46), 0.851 (0.80), 1.035 (0.86), 1.052 (1.68), 1.070 (0.85), 1.232 (6.50), 1.616 (5.24), 1.634 (5.31), 1.883 (3.02), 1.956 (0.58), 2.022 (11.62), 2.075 (0.53), 2.116 (16.00), 2.292 (0.50), 2.323 (2.67), 2.327 (3.49), 2.331 (2.74), 2.357 (0.45), 2.415 (14.98), 2.522 (11.64), 2.665 (2.21), 2.669 (3.02), 2.673 (2.24), 3.452 (0.46), 3.492 (0.63), 3.518 (0.61), 3.756 (0.59), 3.787 (0.65), 3.925 (0.47), 3.969 (0.47), 4.004 (0.76), 4.040 (0.81), 4.185 (0.55), 4.221 (1.08), 4.257 (1.03), 5.784 (0.85), 5.801 (1.31), 5.819 (0.83), 7.240 (0.72), 7.258 (1.57), 7.279 (0.96), 7.409 (0.71), 7.426 (1.18), 7.444 (0.63), 7.636 (0.61), 7.655 (1.05), 7.672 (0.59), 9.119 (1.18), 9.137 (1.18), 9.255 (1.33), 9.260 (2.13), 9.266 (1.78), 9.271 (2.37), 9.307 (1.23). LC-MS (): $R_t$ = min; MS (): m/z =<br>Intermediate 156 6.20 mg (95% purity, 94% yield) |

The examples shown in Table 14 were prepared from the respective amine derivatives according to General Procedure 11.

TABLE 14

| Ex. | Structure; IUPAC-Name; Analytical Data; Starting Materials; Yield |
|---|---|
| 203 | 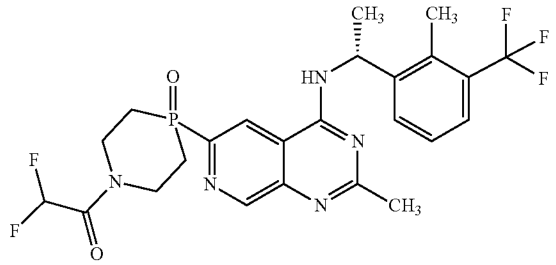<br>1-(difluoroacetyl)-4-[2-methyl-4-({(1R)-1-[2-methyl-3-(trifluoro-methyl)phenyl]ethyl}amino)pyrido[3,4-d]pyrimidin-6-yl]-1,4lambda$^5$-azaphosphinan-4-one<br>$^1$H-NMR (400 MHz, DMSO-d6) δ [ppm]: 1.231 (0.87), 1.576 (5.67), 1.593 (5.73), 2.043 (0.49), 2.085 (0.52), 2.120 (0.52), 2.318 (1.14), 2.323 (2.35), 2.327 (3.17), 2.331 (2.49), 2.336 (1.40), 2.357 (0.51), 2.424 (16.00), 2.518 (9.40), 2.523 (6.29), 2.624 (7.56), 2.660 (0.93), 2.665 (2.02), 2.669 (2.85), 2.673 (1.98), 2.678 (0.87), 3.807 (0.47), 3.841 (0.47), 3.908 (0.43), 3.942 (0.55), 3.968 (0.69), 4.009 (0.48), 4.122 (0.46), 5.710 (0.67), 5.728 (1.00), 5.742 (0.68), 6.720 (1.31), 6.851 (2.86), 6.982 (1.11), 7.350 (0.88), 7.370 (1.90), 7.389 (1.08), 7.546 (2.08), 7.564 (1.64), 7.787 (1.82), 7.807 (1.63), 9.027 (2.03), 9.044 (1.99), 9.099 (5.47), 9.385 (1.20), 9.402 (1.15). LC-MS (Method 2): $R_t$ = 1.22 min; MS (ESIpos): m/z = 542 [M + H]$^+$<br>Intermediate 231 19.0 mg (95% purity, 23% yield) |

TABLE 14-continued

| Ex. | Structure; IUPAC-Name; Analytical Data; Starting Materials; Yield |
|---|---|
| 204 | 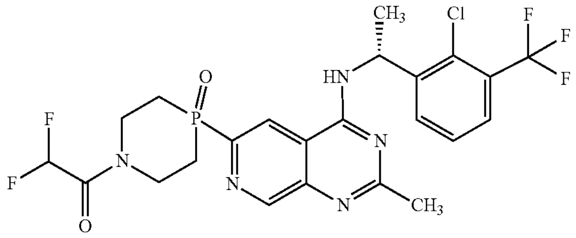 4-[4-({(1R)-1-[2-chloro-3-(trifluoromethylphenyl]ethyl}amino)-2-methylpyrido[3,4-d]pyrimidin-6-yl]-1-(difluoroacetyl)-1,4lambda$^5$-azaphosphinan-4-one $^1$H-NMR (400 MHz, DMSO-d6) δ [ppm]: 1.601 (7.23), 1.619 (7.32), 2.051 (0.59), 2.089 (0.62), 2.129 (0.62), 2.323 (1.29), 2.327 (1.72), 2.332 (1.37), 2.336 (1.02), 2.349 (0.62), 2.361 (0.63), 2.391 (16.00), 2.454 (0.94), 2.459 (0.91), 2.518 (6.68), 2.523 (4.38), 2.665 (0.98), 2.669 (1.37), 2.673 (0.97), 3.297 (0.45), 3.812 (0.58), 3.848 (0.63), 3.876 (0.41), 3.914 (0.55), 3.924 (0.53), 3.948 (0.67), 3.962 (0.58), 3.975 (0.83), 4.020 (0.61), 4.128 (0.56), 5.872 (0.84), 5.886 (1.24), 5.903 (0.84), 6.724 (1.52), 6.855 (3.20), 6.986 (1.28), 7.496 (1.22), 7.515 (2.63), 7.535 (1.50), 7.735 (2.31), 7.751 (1.86), 7.855 (2.07), 7.874 (1.88), 9.053 (2.53), 9.070 (2.50), 9.120 (6.44), 9.418 (1.90), 9.435 (1.84). LC-MS (Method 1): $R_t$ = 1.14 min; MS (ESIpos): m/z = 562 [M + H]$^+$ Intermediate 237 51.7 mg (95% purity, 51% yield) |
| 205 | 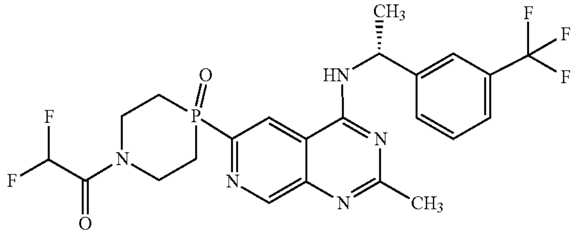 1-(difluoroacetyl)-4-[2-methyl-4-({(1R)-1-[3-(trifluoromethyl)phenyl]ethyl}amino)pyrido[3,4-d]pyrimidin-6-yl]-1,4lambda$^5$-azaphoxphinan-4-one $^1$H-NMR (400 MHz, DMSO-d6) δ [ppm]: 1.627 (5.59), 1.645 (5.62), 2.041 (0.43), 2.080 (0.46), 2.118 (0.45), 2.318 (0.59), 2.323 (0.89), 2.327 (1.31), 2.332 (1.01), 2.336 (0.63), 2.352 (0.42), 2.444 (0.58), 2.465 (16.00), 2.518 (4.14), 2.523 (2.82), 2.665 (0.67), 2.669 (0.93), 2.673 (0.66), 3.806 (0.42), 3.840 (0.44), 3.938 (0.50), 3.950 (0.48), 3.964 (0.62), 4.006 (0.46), 4.117 (0.40), 5.647 (0.74), 5.665 (1.13), 5.683 (0.74), 6.717 (1.15), 6.849 (2.37), 6.980 (0.98), 7.556 (0.56), 7.575 (1.73), 7.594 (2.14), 7.602 (2.31), 7.622 (0.66), 7.766 (1.49), 7.784 (1.20), 7.851 (2.46), 8.978 (1.70), 8.995 (1.68), 9.114 (4.83), 9.248 (1.14), 9.266 (1.12). LC-MS (Method 1): $R_t$ = 1.04 min; MS (ESIpos): m/z = 528 [M + H]$^+$ Intermediate 238 56.2 mg (95% purity, 55% yield) |
| 206 | 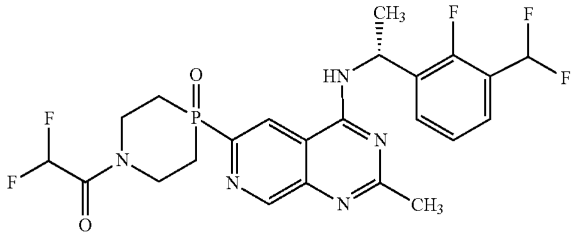 1-(difluoroacetyl)-4-[4-({(1R)-1-[3-(difluoromethyl)-2-fluorophenyl]ethyl}amino)-2-methylpyrido[3,4-d]pyrimidin-6-yl]-1,4lambda$^5$-azaphosphinan-4-one |

TABLE 14-continued

| Ex. | Structure; IUPAC-Name; Analytical Data; Starting Materials; Yield |
|---|---|
| | $^{1}$H-NMR (400 MHz, DMSO-d6) δ [ppm]: 1.233 (0.66), 1.620 (6.16), 1.637 (6.13), 2.044 (0.49), 2.085 (0.53), 2.123 (0.48), 2.337 (1.36), 2.436 (16.00), 2.518 (10.02), 2.523 (6.74), 2.674 (2.08), 2.679 (0.91), 3.812 (0.48), 3.848 (0.49), 3.910 (0.46), 3.945 (0.68), 4.004 (0.51), 4.104 (0.44), 5.784 (0.79), 5.801 (1.18), 5.819 (0.80), 6.720 (1.40), 6.851 (3.00), 6.982 (1.20), 7.106 (1.52), 7.242 (3.30), 7.288 (1.14), 7.307 (2.49), 7.326 (1.40), 7.377 (1.34), 7.501 (0.82), 7.517 (1.38), 7.535 (0.68), 7.689 (0.76), 7.706 (1.38), 7.726 (0.69), 9.029 (2.18), 9.046 (2.14), 9.119 (5.76), 9.294 (1.51), 9.311 (1.45). LC-MS (Method 2): $R_t$ = 1.09 min; MS (ESIneg): m/z = 526[M − H]$^-$ Intermediate 226 15.0 mg (95 % purity, 81 % yield) |
| 207 | 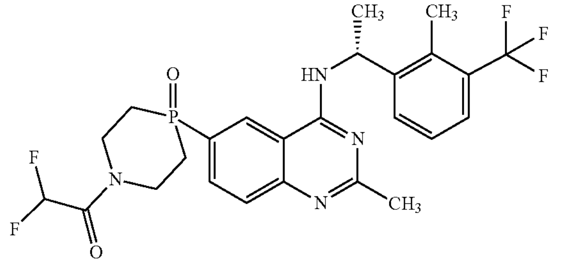 1-(difluoroacetyl)-4-[2-methyl-4-({(1R)-1-[2-methyl-3-(trifluoromethyl)phenyl]ethyl}amino)quinazolin-6-yl]-1,4lambda$^5$-azaphosphinan-4-one $^{1}$H-NMR (400 MHz, DMSO-d6) δ [ppm]: 1.576 (6.11), 1.594 (6.08), 2.060 (0.70), 2.066 (0.67), 2.074 (1.12), 2.095 (0.74), 2.337 (0.72), 2.361 (16.00), 2.389 (0.62), 2.401 (0.65), 2.415 (0.64), 2.430 (0.70), 2.443 (0.73), 2.518 (5.95), 2.523 (4.12), 2.630 (7.76), 2.678 (0.47), 3.579 (0.65), 3.608 (0.65), 3.650 (0.58), 3.812 (0.51), 3.843 (0.59), 4.014 (0.41), 5.720 (0.90), 5.737 (1.37), 5.755 (0.88), 6.686 (0.85), 6.817 (1.73), 6.949 (0.80), 7.336 (0.84), 7.356 (2.17), 7.364 (1.02), 7.376 (1.04), 7.531 (2.10), 7.550 (1.68), 7.666 (1.53), 7.673 (1.67), 7.688 (1.71), 7.695 (1.62), 7.790 (1.53), 7.811 (1.28), 8.057 (0.82), 8.079 (1.43), 8.101 (0.72), 8.139 (2.01), 8.851 (1.37), 8.883 (1.37), 8.986 (1.16), 9.003 (1.13). LC-MS (Method 1): $R_t$ = 0.98 min; MS (ESIpos): m/z = 541 [M + H]$^+$ Example 6 68.5 mg (95% purity, 70% yield) |

Experimental Section—Biological Assays

Examples were tested in selected biological assays one or more times. When tested more than once, data are reported as either average values or as median values, wherein

- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Biochemical Assay: hK-RasG12C Interaction Assay with hSOS1

This assay quantifies the equilibrium interaction of human SOS1 (SOS1) with human K-Ras$^{G}$12$^{C}$ (K-RasG12C). Detection of the interaction is achieved by measuring homogenous time-resolved fluorescence resonance energy transfer (HTRF) from antiGST-Europium (FRET donor) bound to GST-K-RasG12C to anti-6His-XL665 bound to His-tagged hSOS1 (FRET-acceptor).

The assay buffer containes 5 mM HEPES pH 7.4 (Applichem), 150 mM NaCl (Sigma), 10 mM EDTA (Promega), 1 mM DTT (Thermofisher), 0.05% BSA Fraction V, pH 7.0, (ICN Biomedicals), 0.0025% (v/v) Igepal (Sigma) and 100 mM KF (FLUKA).

The expression and purification of N-terminally GST-tagged human K-RasG12C (termed GST-hK-RasG12C) and N-terminally His-tagged human SOS1 (termed His10-hSOS1) is described in WO 2019/201848, page 220 line 12-34 and page 222, line 13-25 (expression) and page 222, line 26 to page 223, line 17 (purification). Concentrations of protein batches used are optimized to be within the linear range of the HTRF signal. A Ras working solution is prepared in assay buffer containing typically 10 nM GST-hK-RasG12C and 2 nM antiGST-Eu(K) (Cisbio, France). A SOS1 working solution is prepared in assay buffer containing typically 20 nM His-hSOS1 and 10 nM anti-6His-XL665 (Cisbio, France). An inhibitor control solution is prepared in assay buffer containing nM anti-6His-XL665 without SOS1.

Fifty nl of a 100-fold concentrated solution of the test compound in DMSO are transferred into a black microtiter test plate (384 or 1536, Greiner Bio-One, Germany). For this, either a Hummingbird liquid handler (Digilab, MA, USA) or an Echo acoustic system (Labcyte, CA, USA) is used.

All steps of the assay are performed at 20° C. A volume of 2.5 µl of the Ras working solution is added to all wells of the test plate using a Multidrop dispenser (Thermo Labsystems). After 2 min preincubation, 2.5 µl of the SOS1 working solution are added to all wells except for those wells at the side of the test plate that are subsequently filled with 2.5 µl of the inhibitor control solution. After 60 min incubation the fluorescence is measured with a Pherastar (BMG, Germany) using the HTRF module (excitation 337 nm, emission 1: 620 nm, emission 2: 665 nm).

The ratiometric data (emission 2 divided by emission 1) are normalized using the controls (DMSO=0% inhibition, inhibition control wells with inhibitor control solution=100% inhibition). Compounds are tested in duplicates at up to 11 concentrations (for 20 µM, 5,7 µM, 1,6 µM, 0.47 µM, 0.13 µM, 38 nM, 11 nM, 3.1 nM, 0.89 nM, 0.25 nM and 0.073 nM). IC50 values are calculated by 4-Parameter fitting using a commercial software package (Genedata Screener, Switzerland).

-continued

| Example | K-RasG12C - SOS interaction assay $IC_{50}$ - [mol/l] (mean) |
|---|---|
| 1 | 2.06E−8 |
| 2 | 5.08E−8 |
| 3 | 1.91E−8 |
| 4 | 1.28E−8 |
| 5 | 2.61E−7 |
| 6 | n.d. |
| 7 | 6.24E−9 |
| 8 | 9.40E−8 |
| 9 | 2.23E−8 |
| 10 | 7.80E−9 |
| 11 | 5.29E−8 |
| 12 | 5.94E−8 |
| 13 | 1.63E−8 |
| 14 | 9.78E−9 |
| 15 | 4.71E−8 |
| 16 | 1.06E−8 |
| 17 | 1.06E−8 |
| 18 | 2.77E−8 |
| 19 | 1.43E−8 |
| 20 | 7.21E−9 |
| 21 | 1.21E−7 |
| 22 | 1.87E−8 |
| 23 | 1.24E−8 |
| 24 | ! 2.00E−5 |
| 25 | 4.85E−6 |
| 26 | 9.18E−9 |
| 30 | 1.36E−6 |
| 31 | 6.37E−9 |
| 32 | 1.22E−8 |
| 33 | 7.06E−9 |
| 34 | 7.28E−8 |
| 35 | 2.15E−8 |
| 36 | 1.67E−8 |
| 37 | 9.69E−9 |
| 38 | 1.07E−8 |
| 39 | 1.11E−8 |
| 40 | 1.83E−8 |
| 41 | 1.74E−7 |
| 42 | 4.87E−9 |
| 43 | 3.75E−7 |
| 44 | 1.59E−8 |
| 45 | 1.70E−8 |
| 46 | 6.10E−9 |
| 47 | 1.38E−8 |
| 48 | 2.93E−8 |
| 49 | 8.75E−8 |
| 50 | 1.56E−7 |
| 51 | 8.63E−8 |
| 52 | 3.55E−8 |
| 53 | 6.54E−8 |
| 54 | 2.25E−8 |
| 55 | 2.62E−8 |
| 56 | 7.41E−8 |
| 57 | 1.93E−8 |
| 58 | 6.33E−9 |
| 59 | 7.06E−9 |
| 60 | 1.35E−8 |
| 61 | 9.82E−9 |
| 62 | 1.35E−8 |
| 63 | 1.01E−8 |
| 64 | 1.78E−8 |
| 65 | 1.05E−8 |
| 66 | 2.51E−8 |
| 67 | 6.69E−8 |
| 68 | 2.82E−8 |
| 69 | 1.95E−8 |
| 70 | 2.76E−8 |
| 71 | 3.54E−8 |
| 72 | 2.43E−8 |
| 73 | 1.13E−8 |
| 74 | 2.46E−8 |
| 75 | 1.53E−8 |
| 76 | 2.13E−8 |
| 77 | 1.78E−8 |
| 78 | 2.18E−8 |
| 79 | 1.23E−8 |
| 80 | 5.88E−9 |
| 81 | 1.02E−8 |
| 82 | 2.45E−8 |
| 83 | 3.10E−8 |
| 84 | 2.41E−8 |
| 85 | 1.20E−8 |
| 86 | 3.66E−8 |
| 87 | 2.86E−9 |
| 89 | 6.06E−9 |
| 90 | 2.66E−8 |
| 91 | 2.86E−7 |
| 92 | 7.72E−8 |
| 93 | 3.70E−8 |
| 94 | 4.65E−8 |
| 95 | 2.39E−8 |
| 96 | 5.02E−8 |
| 97 | 1.36E−8 |
| 98 | 1.39E−7 |
| 99 | 3.21E−8 |
| 100 | 4.89E−9 |
| 101 | 1.75E−8 |
| 102 | 8.02E−8 |
| 103 | 1.42E−8 |
| 104 | 1.88E−8 |
| 105 | 1.17E−7 |
| 106 | 1.61E−8 |
| 107 | 2.05E−8 |
| 108 | 1.53E−7 |
| 109 | 3.33E−8 |
| 110 | 5.68E−8 |
| 111 | 2.15E−8 |
| 112 | 1.12E−8 |
| 113 | 7.85E−9 |
| 114 | 6.65E−8 |
| 115 | 8.03E−8 |
| 116 | 5.76E−8 |
| 117 | 5.69E−8 |
| 118 | 5.65E−8 |
| 119 | 4.29E−8 |
| 120 | 3.67E−8 |
| 121 | 8.71E−8 |
| 122 | 6.26E−8 |
| 123 | 5.90E−8 |
| 124 | 1.67E−8 |
| 125 | 4.43E−8 |
| 126 | 9.24E−9 |
| 127 | 2.34E−8 |
| 128 | 2.09E−8 |
| 129 | 1.32E−7 |

-continued

| Example | K-RasG12C - SOS interaction assay $IC_{50}$ - [mol/l] (mean) |
|---|---|
| 130 | 1.61E−8 |
| 131 | 1.15E−8 |
| 132 | 1.17E−8 |
| 134 | 2.52E−8 |
| 135 | 1.70E−8 |
| 136 | 3.89E−8 |
| 137 | 4.04E−9 |
| 138 | 6.01E−9 |
| 139 | 5.40E−9 |
| 140 | 1.14E−8 |
| 141 | 1.28E−8 |
| 142 | 6.30E−9 |
| 143 | 1.26E−8 |
| 144 | 1.97E−9 |
| 145 | 4.35E−9 |
| 146 | 8.10E−8 |
| 147 | 4.51E−9 |
| 149 | 1.80E−8 |
| 150 | 4.76E−9 |
| 151 | 1.22E−8 |
| 152 | 1.27E−8 |
| 153 | 7.40E−9 |
| 154 | 6.15E−9 |
| 155 | 1.11E−8 |
| 156 | 1.14E−8 |
| 157 | 5.04E−9 |
| 158 | 7.89E−9 |
| 159 | 1.27E−8 |
| 160 | 7.87E−9 |
| 161 | 1.34E−8 |
| 162 | 2.72E−7 |
| 163 | 4.77E−9 |
| 164 | 7.01E−9 |
| 165 | 4.37E−9 |
| 166 | 4.83E−9 |
| 167 | 1.27E−8 |
| 168 | 1.20E−8 |
| 169 | 9.55E−9 |
| 170 | 1.13E−8 |
| 171 | 6.76E−9 |
| 172 | 4.78E−9 |
| 173 | 5.62E−9 |
| 174 | 3.89E−9 |
| 175 | 9.07E−9 |
| 176 | 6.82E−9 |
| 177 | 5.01E−9 |
| 178 | 7.94E−9 |
| 179 | 3.68E−9 |
| 180 | 4.60E−9 |
| 181 | 2.95E−9 |
| 182 | 3.95E−9 |
| 183 | 8.38E−9 |
| 184 | 5.62E−9 |
| 185 | 3.86E−9 |
| 186 | 4.71E−9 |
| 187 | 1.20E−8 |
| 188 | 6.34E−9 |
| 189 | 2.06E−8 |
| 190 | 5.90E−9 |
| 191 | 8.09E−9 |
| 192 | 1.17E−8 |
| 193 | 4.10E−9 |
| 194 | 1.21E−8 |
| 195 | 6.56E−9 |
| 196 | 2.38E−9 |
| 197 | 7.40E−9 |
| 198 | 4.61E−9 |
| 199 | 4.61E−9 |
| 200 | 3.95E−9 |
| 201 | 5.81E−9 |
| 202 | 3.89E−9 |

-continued

| Example | K-RasG12C - SOS interaction assay $IC_{50}$ - [mol/l] (mean) |
|---|---|
| 203 | 5.65E−9 |
| 204 | 5.96E−9 |
| 205 | 9.64E−9 |
| 206 | 3.77E−9 |
| 207 | 6.84E−9 |

The invention claimed is:

1. A compound of formula (I)

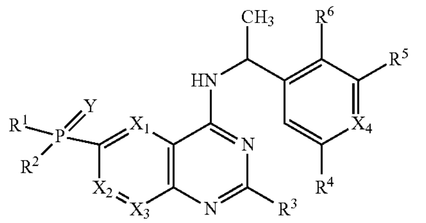

(I)

in which $X_1$ represents CH or N;

$X_2$ represents $CR^a$ or N $X_3$ represents $CR^a$ or N $X_4$ represents CH or N Y represents O or S;

$R^1$, $R^2$ is independently of each other selected from $C_{1-4}$ alkyl, $OR^b$ or $NR^cR^d$, or $R^1$, $R^2$ together with the phosphorus atom they are attached to form a 4-7 membered heterocycloalkyl in which one or more carbon atom can be replaced by —O—, —$NR^c$—, —S—, —S(O)—, $S(O)_2$— or —S(O)$NR^f$—; and in which each remaining carbon atom can optionally be substituted by one or two —$CH_3$ or by one —$CH_2$—$CH_3$, $R^3$ is selected from —H, —OH, —$CH_3$, —CN, —$NR^pR^q$, or $C_{1-2}$-alkyl optionally substituted with —OH, —$CH_3$, —CN or halogen $R^4$ is selected from —H, —F, —Cl, —Br, —OH, —$NH_2$, —$N(CH_3)H$, —$CH_3$ or —$CF_2H$;

$R^5$ represents -A-B-E in which

A represents —$CR^jR^k$— or is absent, and

B represents —$CR^lR^m$— or is absent, and

E represents —H, —F, —OH, —$OCH_3$, —$NH_2$, —NH—$CH_3$, —$N(CH_3)_2$, —$N(CH_3)$—$OCH_3$, —CN, —$SO_2$—$CH_3$, —NH—$SO_2$—$CH_3$, —$N(CH_3)$—$SO_2$—$CH_3$, —NH—C(O)—$CH_3$, —$N(CH_3)$—C(O)—$CH_3$, —S(═NH)(═O)—$CH_3$, —S(═N—$CH_3$)(═O)—$CH_3$, —C(O)—$NH_2$, —C(O)—$NH(CH_3)$, —C(O)—$N(CH_3)_2$, or $R^5$ represents —$SO_2$—$NR^nR^o$, $R^6$ is selected from —H, halogen or —$CH_3$;

$R^a$ is selected from —H, halogen, —OH, —$OCH_3$, —CN, cyclopropyl, —$NH_2$, —$NH(CH_3)$, —$N(CH_3)_2$, or $C_{1-2}$ alkyl optionally substituted one or more times by halogen, —OH or —$OCH_3$, —$CH_3$, —$CF_3$, —$NH_2$, —$NH(CH_3)$, —$N(CH_3)_2$, or —CN $R^b$ is selected from —H (under the condition, that if $R^1$ and $R^2$ are both $OR^b$ only one $R^b$ can be —H), —$CH_3$, —$CH_2$—$CH_3$, —$CH(CH_3)_2$ or cyclopropyl, $R^c$ is selected from —$CH_3$, —$CH_2$—$CH_3$, —$CH(CH_3)_2$ or cyclopropyl, $R^d$ is selected from —H, —$CH_3$, —$CH_2$—$CH_3$, —CH$(CH_3)_2$ or cyclopropyl, $R^e$ is selected from —H, $C_{1-3}$-alkyl optionally substituted by one or more —F, cyclopropyl, —C(O)—$R^g$, —$SO_2$—$CH_3$ or 5 membered heteroaryl optionally substituted by —$CH_3$, halogen, —$CF_3$ or —$CF_2H$ $R^f$ is selected from —H, —$CH_3$, or —$CH_2$—$CH_3$, $R^g$ is selected from $C_{1-4}$ alkyl optionally substituted by —OH, —$OCH_3$, —$CH_3$, halogen; or is selected from 5-membered heteroaryl optionally substituted by —$CH_3$, —$CH_2CH_3$, $CF_2H$, $CF_3$ or halogen; or is selected from $NR^hR^i$, $R^h$ is selected from —H or —$CH_3$, and $R^i$ is selected from $C_{1-3}$ alkyl optionally substituted by halogen or from cyclopropyl, $R^j$ and $R^k$ are independently of each other selected from —H, —F or —$CH_3$, or form together with the carbon atom they are attached to cyclopropyl;

$R^l$ and $R^m$ are independently of each other selected from —H, Deuterium, or —$CH_3$, —$CH_2$—$CH_3$, cyclopropyl;

or form together with the carbon atom they are attached to cyclopropyl; or $R^n$ and $R^o$ are independently selected from —H or $C_{1-4}$ alkyl optionally substituted by —OH, —$OCH_3$, or $R^n$ and $R^o$ form together with the nitrogen atom they are attached to a 4 to 7 membered heterocycloalkyl optionally containing further heteroatoms selected from N or O, in which carbon atoms of this heterocycloalkyl can be optionally substituted by H or $C_{1-4}$ alkyl and where this $C_{1-4}$ alkyl can again be substituted by halogen, =O, —OH, —$OCH_3$, —$NH_2$, —NH—$CH_3$ or —$N(CH_3)_2$, and in which nitrogen atoms of this heterocycloalkyl can be optionally substituted by —C(O)-cyclopropyl or —C(O)—$C_{1-4}$-alkyl, both optionally substituted one or more times with —F;

$R^p$ and $R^q$ are independently selected from —H, —$CH_3$ or —$CH_2$—$CH_3$;

or a stereoisomer, a tautomer, an N-oxide, a hydrate, a solvate, or a salt thereof.

2. The compound according to claim 1 of formula (I) in which $X_1$ represents CH;

$X_2$ represents $CR^a$ or N $X_3$ represents $CR^a$ or N $X_4$ represents CH or N Y represents O;

$R^1$, $R^2$ is independently of each other selected from —$CH_3$, —$CH_2$—$CH_3$ or —$CH(CH_3)_2$; or $R^1$, $R^2$ together with the phosphorus atom they are attached to form

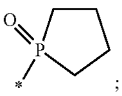 ; 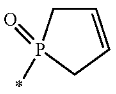 or 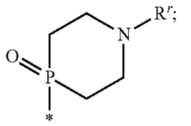

$R^3$ is selected from —$CH_3$, —$CHF_2$, or —$CF_3$;

$R^4$ is selected from —H, —$NH_2$ or —$CH_3$;

$R^5$ is selected from

—Br, $CF_2$—H, —$CF_2$—F, —$CF_2$—$CH_3$, —$CF_2$—$CH_2$—OH, —$CF_2$—$CD_2$—OH, —$CF_2$—$CH_2$—$OCH_3$, —$CF_2$—$CH(CH_3)$—OH, —$CF_2$—CH($CH_2$—$CH_3$)—OH, —$CF_2$—$C(CH_3)_2$—OH, $CF_2$—C($CH_3$)2—$OCH_3$, —$CF_2$—CH($CH(CH_3)_2$)—OH, —$CF_2$—CH($C(CH_3)_3$)—OH, —$CF_2$—C($CH_3$)($CH_2$—$CH_2$—$CH_2$—$CH_3$)—OH, $CF_2$—C(=O)—$CH(CH_3)_2$, —$CF_2$—C(=O)—C$(CH_3)_3$, $CF_2$—C(=O)—OH, —$CF_2$—C(=O)—$NH_2$, —$CF_2$—C(=O)—$N(CH_3)_2$, —$CF_2$—C(=O)—NH—$CH_3$, —$CF_2$—C(=O)—NH—$CH_2$—$CH_3$, —$CF_2$—C(=O)—NH—cyclopropyl, $CF_2$—$CH_2$—NH—$SO_2$—$CH_3$, —$CF_2$—$CH_2$—N$(CH_3)$—$SO_2$—$CH_3$, —$CF_2$—$CH_2$—NH—C(=O)—$CH_3$ or —$CF_2$—$CH_2$—$N(CH_3)$;

$R^6$ is selected from —H, —$CH_3$, —F or —Cl;

$R^a$ is selected from —H, —$CH_3$, —$CH_2$—$CH_3$, —$CF_3$, —$CHF_2$, —$CH_2$—OH, —$CH_2$—O—$CH_3$, —OH, —$OCH_3$ or cyclopropyl, $R^r$ is selected from —H, —$CH_3$, —$CH(CH_3)_2$, —C(=O)—H, —C(=O)—$CH_3$, —C(=O)—$CH_2F$, —C(=O)—$CH(CH_3)_2$, —C(=O)—$CH(CH_3)$—OH, —C(=O)—$CH(CH_3)$—O—$CH_3$,

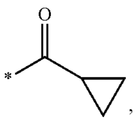 , 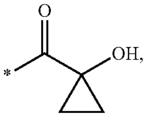 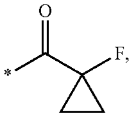

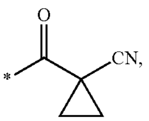 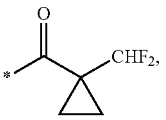 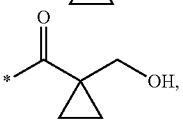

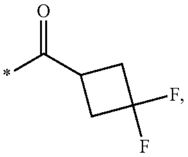 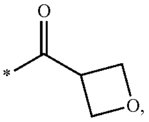

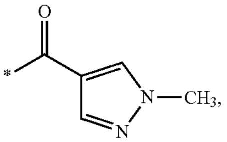

C(=O)—$CH_2$—CN, —C(=O)—$CH_2$—O—$CH_3$, —C(=O)—O—$C(CH_3)_3$, —C(=O)—O—$CH_2$—$CH_3$,

—C(=O)—$NH_2$, —C(=O)—$N(CH_3)_2$, —C(=O)—$CH_2$—$CHF_2$, —C(=O)—NH—cyclopropyl, —C(=S)—$CH_3$, —$SO_2$—$CH_3$,

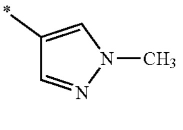 or 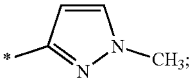

or a stereoisomer, a tautomer, an N-oxide, a hydrate, a solvate, or a salt thereof.

3. The compound according to claim 1, wherein only one of $X_1$, $X_2$, $X_3$ or $X_4$ is N or a stereoisomer, a tautomer, an N-oxide, a hydrate, a solvate, or a salt thereof.

4. The compound according to claim 1, wherein Y represents O or a stereoisomer, a tautomer, an N-oxide, a hydrate, a solvate, or a salt thereof.

5. The compound according to claim 1, wherein $R^1$ and $R^2$ are selected from $C_{1-4}$ alkyl or a stereoisomer, a tautomer, an N-oxide, a hydrate, a solvate, or a salt thereof.

6. The compound according to claim 1, wherein $R^3$ is selected from $C_{1-2}$-alkyl optionally substituted with 1 to 3 —F or a stereoisomer, a tautomer, an N-oxide, a hydrate, a solvate, or a salt thereof.

7. The compound according to claim 1, wherein $R^6$ is selected from —F, —Cl, —H or —$CH_3$ or a stereoisomer, a tautomer, an N-oxide, a hydrate, a solvate, or a salt thereof.

8. The compound according to claim 1, wherein Ra is selected from —H, —Cl, —$CH_3$, —$CF_3$ or —$CF_2H$ or a stereoisomer, a tautomer, an N-oxide, a hydrate, a solvate, or a salt thereof.

9. The compound according to claim 1, wherein $R^j$ and $R^k$ form together with the carbon atom they are attached to cyclopropyl or are selected from either both —F, both —$CH_3$, or a stereoisomer, a tautomer, an N-oxide, a hydrate, a solvate, or a salt thereof.

10. The compound according to claim 1, wherein both $R^1$ and $R^2$ are —$CH_3$ or a stereoisomer, a tautomer, an N-oxide, a hydrate, a solvate, or a salt thereof.

11. The compound according to claim 1, wherein $R^5$ is —$CF_3$ and $R^6$ is —F or a stereoisomer, a tautomer, an N-oxide, a hydrate, a solvate, or a salt thereof.

12. The compound according to claim 1, wherein $X^2$ is N and $X^3$ is CH or a stereoisomer, a tautomer, an N-oxide, a hydrate, a solvate, or a salt thereof.

13. The compound according to claim 1, wherein $R^n$ and $R^o$ form together with the nitrogen atom they are attached to morpholine or N-acetylpiperazine both optionally substituted with 1 or 2—$CH_3$, —$CF_3$ or —$CF_2H$ or a stereoisomer, a tautomer, an N-oxide, a hydrate, a solvate, or a salt thereof.

14. The compound according to claim 1, which is 1-acetyl-4-[2-methyl-4-({(1R)-1-[2-methyl-3-(trifluoromethyl)phenyl]ethyl}amino)pyrido[3,4-d]pyrimidin-6-yl]-1,4lambda$^5$-azaphosphinan-4-one according to the formula

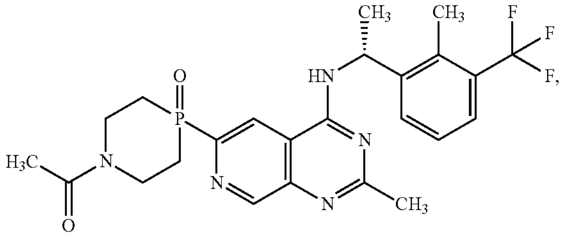 [SMILES: CC(=O)N1CCP(=O)(c2cc3c(N[C@H](C)c4cccc(C(F)(F)F)c4C)nc(C)nc3cn2)CC1]

or a stereoisomer, a tautomer, an N-oxide, a hydrate, a solvate, or a salt thereof.

15. A method for treating a hyperproliferative disorder in a subject in need thereof, comprising administering to the subject a therapeutically effective amount of a compound according to claim 1.

16. The method of claim 15, wherein the hyperproliferative disorder is cancer.

17. The method of claim 16, wherein the cancer is selected from the group consisting of lung cancer, colorectal cancer, and pancreatic cancer.

18. The method of claim 15, further comprising administering a second active ingredient, wherein the second active ingredient is an anti-cancer agent.

19. The method of claim 18, wherein the anti-cancer agent is selected from the group consisting of pemetrexed, osimertinib, and cetuximab.

* * * * *